United States Patent
Deziel et al.

(10) Patent No.: US 9,193,749 B2
(45) Date of Patent: Nov. 24, 2015

(54) DIBENZO[B,F][1,4]OXAZEPIN-11-YL-N-HYDROXYBENZAMIDES AS HDAC INHIBITORS

(71) Applicants: Forum Pharmaceuticals, Inc., Watertown, MA (US); MethylGene, Inc., Montreal (CA)

(72) Inventors: Robert Deziel, Mount-Royal (CA); Silvana Leit, Kirkland (CA); Patrick Beaulieu, Laval (CA); Yves Andre Chantigny, Pincourt (CA); John Mancuso, Vaudreuil (CA); Pierre Tessier, Hawkesbury (CA); Gideon Shapiro, Gainesville, FL (US); Richard Chesworth, Boston, MA (US); David Smil, Montreal (CA)

(73) Assignees: Forum Pharmaceuticals, Inc., Waltham, MA (US); MethylGene, Inc., Montreal, Quebec (CA)

( * ) Notice: Subject to any disclaimer, the term of this patent is extended or adjusted under 35 U.S.C. 154(b) by 232 days.

(21) Appl. No.: 13/767,478

(22) Filed: Feb. 14, 2013

(65) Prior Publication Data

US 2014/0011988 A1    Jan. 9, 2014

Related U.S. Application Data

(62) Division of application No. 11/925,151, filed on Oct. 26, 2007, now Pat. No. 8,399,452.

(60) Provisional application No. 60/863,347, filed on Oct. 28, 2006, provisional application No. 60/884,287, filed on Jan. 10, 2007.

(51) Int. Cl.
| | |
|---|---|
| *C07D 491/00* | (2006.01) |
| *C07H 13/10* | (2006.01) |
| *C07D 209/02* | (2006.01) |
| *C07D 209/08* | (2006.01) |
| *C07D 209/52* | (2006.01) |
| *C07D 209/94* | (2006.01) |
| *C07D 221/12* | (2006.01) |
| *C07D 223/16* | (2006.01) |
| *C07D 223/20* | (2006.01) |
| *C07D 223/22* | (2006.01) |
| *C07D 223/26* | (2006.01) |
| *C07D 223/28* | (2006.01) |

(Continued)

(52) U.S. Cl.
CPC .............. *C07H 13/10* (2013.01); *C07D 209/02* (2013.01); *C07D 209/08* (2013.01); *C07D 209/52* (2013.01); *C07D 209/94* (2013.01); *C07D 221/12* (2013.01); *C07D 223/16* (2013.01); *C07D 223/20* (2013.01); *C07D 223/22* (2013.01); *C07D 223/26* (2013.01); *C07D 223/28* (2013.01); *C07D 225/08* (2013.01); *C07D 239/28* (2013.01); *C07D 239/34* (2013.01); *C07D 239/42* (2013.01); *C07D 243/24* (2013.01); *C07D 243/38* (2013.01); *C07D 265/38* (2013.01); *C07D 267/14* (2013.01); *C07D 267/18* (2013.01); *C07D 267/20* (2013.01); *C07D 279/22* (2013.01); *C07D 279/26* (2013.01); *C07D 281/16* (2013.01); *C07D 285/36* (2013.01); *C07D 291/08* (2013.01); *C07D 295/155* (2013.01); *C07D 313/12* (2013.01); *C07D 401/14* (2013.01); *C07D 403/04* (2013.01); *C07D 403/14* (2013.01); *C07D 413/06* (2013.01); *C07D 413/12* (2013.01); *C07D 471/04* (2013.01); *C07D 471/08* (2013.01); *C07D 487/04* (2013.01); *C07D 487/08* (2013.01); *C07D 487/14* (2013.01); *C07D 491/08* (2013.01); *C07D 495/04* (2013.01); *C07D 498/04* (2013.01); *C07D 513/04* (2013.01)

(58) Field of Classification Search
None
See application file for complete search history.

(56) References Cited

U.S. PATENT DOCUMENTS

| | | |
|---|---|---|
| 3,956,295 A | 5/1976 | Biere et al. |
| 5,189,033 A | 2/1993 | Tucker |

(Continued)

FOREIGN PATENT DOCUMENTS

| | | |
|---|---|---|
| CH | 620 891 | 12/1980 |
| EP | 0 030 254 | 6/1981 |

(Continued)

OTHER PUBLICATIONS

Marks et al., Expert Opinion on Investigational Drugs, 2005 14(12):1497-1511.

(Continued)

*Primary Examiner* — Noble Jarrell
(74) *Attorney, Agent, or Firm* — Jones Day

(57) ABSTRACT

This invention relates to compounds for the inhibition of histone deacetylase. More particularly, the invention provides for compounds of formula (I)

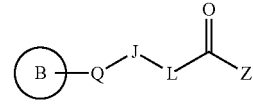

wherein

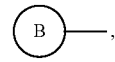

Q, J, L and Z are as defined in the specification.

2 Claims, No Drawings

(51) Int. Cl.

| | | |
|---|---|---|
| *C07D 225/08* | (2006.01) |
| *C07D 239/28* | (2006.01) |
| *C07D 239/34* | (2006.01) |
| *C07D 239/42* | (2006.01) |
| *C07D 243/24* | (2006.01) |
| *C07D 243/38* | (2006.01) |
| *C07D 265/38* | (2006.01) |
| *C07D 267/14* | (2006.01) |
| *C07D 267/18* | (2006.01) |
| *C07D 267/20* | (2006.01) |
| *C07D 279/22* | (2006.01) |
| *C07D 279/26* | (2006.01) |
| *C07D 285/36* | (2006.01) |
| *C07D 291/08* | (2006.01) |
| *C07D 313/12* | (2006.01) |
| *C07D 401/14* | (2006.01) |
| *C07D 403/04* | (2006.01) |
| *C07D 403/14* | (2006.01) |
| *C07D 413/06* | (2006.01) |
| *C07D 413/12* | (2006.01) |
| *C07D 471/04* | (2006.01) |
| *C07D 471/08* | (2006.01) |
| *C07D 487/04* | (2006.01) |
| *C07D 487/08* | (2006.01) |
| *C07D 487/14* | (2006.01) |
| *C07D 491/08* | (2006.01) |
| *C07D 495/04* | (2006.01) |
| *C07D 498/04* | (2006.01) |
| *C07D 513/04* | (2006.01) |
| *C07D 281/16* | (2006.01) |
| *C07D 295/155* | (2006.01) |

(56) References Cited

U.S. PATENT DOCUMENTS

| | | |
|---|---|---|
| 6,117,869 A | 9/2000 | Picard et al. |
| 8,399,452 B2 | 3/2013 | Deziel et al. |
| 2005/0026991 A1 | 2/2005 | Cholody et al. |
| 2005/0165040 A1 | 7/2005 | Kuki et al. |
| 2005/0250753 A1 | 11/2005 | Fink et al. |
| 2005/0250784 A1 | 11/2005 | Anandan et al. |
| 2006/0074124 A1 | 4/2006 | Napper et al. |
| 2011/0196147 A1 | 8/2011 | Deziel et al. |

FOREIGN PATENT DOCUMENTS

| | | |
|---|---|---|
| EP | 1 147 080 | 10/2001 |
| EP | 0 938 471 | 12/2001 |
| WO | 96/33983 | 10/1996 |
| WO | 01/12592 | 2/2001 |
| WO | 02/085883 | 10/2002 |
| WO | 03/076401 | 9/2003 |
| WO | 2006/010751 | 2/2006 |
| WO | 2006/031894 | 3/2006 |
| WO | 2006/074124 | 4/2006 |
| WO | 2006/097449 | 9/2006 |
| WO | 2006/123121 | 11/2006 |
| WO | 2007/022214 | 2/2007 |
| WO | 2007/118137 | 10/2007 |

OTHER PUBLICATIONS

Brodrick et al., Journal of the Chemical Society, 1953, 1079-80.
Sadri-Vakili et al., Nature Clinical Practice, 2006, 2(6):330-338.
Iwata et al., PNAS, 2005, 102(37):12135-13140.
Huntington's Disease, 2010 http://www.healthscout.com/ency/68/275/main.html, accessed Aug. 18, 2010.
Harfenist et al., J. Med. Chem., 40(16):2466-2483, 1997.
Remiszewski et al., J. Med. Chem., 46:4609-4627, 2003.
Miller, T.A., "Patent Status of Histone Deacetylase Inhibitors," Expert Opinion on Therapeutic Patents, 14(6), 2004, 791-804.
Hamblett et al., "The discovery of 6-amino nicotinamides as potent and selective histone deacetylase inhibitors," Bioorg. Med. Chem. Lett., 2007, 17:5300-5309.

DIBENZO[B,F][1,4]OXAZEPIN-11-YL-N-HYDROXYBENZAMIDES AS HDAC INHIBITORS

CROSS REFERENCE TO RELATED APPLICATIONS

This application is a divisional of U.S. application Ser. No. 11/925,151, filed Oct. 26, 2007, now U.S. Pat. No. 8,399,452 issued on Mar. 19, 2013, and each of the above-noted applications claim the benefit of both U.S. provisional application 60/884,287, filed Jan. 10, 2007, and U.S. provisional application 60/863,347, filed Oct. 28, 2006. The foregoing related applications, in their entirety, are incorporated herein by reference.

BACKGROUND OF THE INVENTION

1. Field of the Invention

This invention relates to compounds for the inhibition of histone deacetylase.

2. Description of Related Art

In eukaryotic cells, nuclear DNA associates with histones to form a compact complex called chromatin. The histones constitute a family of basic proteins which are generally highly conserved across eukaryotic species. The core histones, termed H2A, H2B, H3, and H4, associate to form a protein core. DNA winds around this protein core, with the basic amino acids of the histones interacting with the negatively charged phosphate groups of the DNA. Approximately 146 base pairs of DNA wrap around a histone core to make up a nucleosome particle, the repeating structural motif of chromatin.

Csordas, *Biochem. J.*, 286: 23-38 (1990) teaches that histones are subject to posttranslational acetylation of the N-terminal lysine residues, a reaction that is catalyzed by histone acetyl transferase (HAT1). Acetylation neutralizes the positive charge of the lysine side chain, and is thought to impact chromatin structure. Indeed, Taunton et al., *Science*, 272: 408-411 (1996), teaches that access of transcription factors to chromatin templates is enhanced by histone hyperacetylation. Taunton et al. further teaches that an enrichment in underacetylated histone H4 has been found in transcriptionally silent regions of the genome.

Histone acetylation is a reversible modification, with deacetylation being catalyzed by a family of enzymes termed histone deacetylases (HDACs). The molecular cloning of gene sequences encoding proteins with HDAC activity has established the existence of a set of discrete HDAC enzyme isoforms. Grozinger et al., *Proc. Natl. Acad. Sci. USA*, 96:4868-4873 (1999), teaches that HDACs may be divided into two classes, the first represented by yeast Rpd3-like proteins, and the second represented by yeast Hd1-like proteins. Grozinger et al. also teaches that the human HDAC-1, HDAC-2, and HDAC-3 proteins are members of the first class of HDACs, and discloses new proteins, named HDAC-4, HDAC-5, and HDAC-6, which are members of the second class of HDACs. Kao et al., *Gene & Development* 14:55-66 (2000), discloses an additional member of this second class, called HDAC-7. More recently, Hu, E. et al. *J. Bio. Chem.* 275:15254-13264 (2000) disclosed another member of the first class of histone deacetylases, HDAC-8. Zhou et al., *Proc. Natl. Acad. Sci. U.S.A.*, 98: 10572-10577 (2001) teaches the cloning and characterization of a new histone deacetylase, HDAC-9. Kao et al., *J. Biol. Chem.*, 277:187-93 (2002) teaches the isolation and characterization of mammalian HDAC10, a novel histone deacetylase. Gao et al, *J. Biol. Chem.* (In press) teaches the cloning and functional characterization of HDAC11, a novel member of the human histone deacetylase family. Shore, *Proc. Natl. Acad. Sci. U.S.A.* 97: 14030-2 (2000) discloses another class of deacetylase activity, the Sir2 protein family. It has been unclear what roles these individual HDAC enzymes play.

Studies utilizing known HDAC inhibitors have established a link between acetylation and gene expression. Numerous studies have examined the relationship between HDAC and gene expression. Taunton et al., *Science* 272:408-411 (1996), discloses a human HDAC that is related to a yeast transcriptional regulator. Cress et al., *J. Cell. Phys.* 184:1-16 (2000), discloses that, in the context of human cancer, the role of HDAC is as a corepressor of transcription. Ng et al., *TIBS* 25: March (2000), discloses HDAC as a pervasive feature of transcriptional repressor systems. Magnaghi-Jaulin et al., *Prog. Cell Cycle Res.* 4:41-47 (2000), discloses HDAC as a transcriptional co-regulator important for cell cycle progression.

Richon et al., *Proc. Natl. Acad. Sci. USA*, 95: 3003-3007 (1998), discloses that HDAC activity is inhibited by trichostatin A (TSA), a natural product isolated from *Streptomyces hygroscopicus*, which has been shown to inhibit histone deacetylase activity and arrest cell cycle progression in cells in the G1 and G2 phases (Yoshida et al., *J. Biol. Chem.* 265: 17174-17179, 1990; Yoshida et al., *Exp. Cell Res.* 177: 122-131, 1988), and by a synthetic compound, suberoylanilide hydroxamic acid (SAHA). Yoshida and Beppu, *Exper. Cell Res.*, 177: 122-131 (1988), teaches that TSA causes arrest of rat fibroblasts at the $G_1$ and $G_2$ phases of the cell cycle, implicating HDAC in cell cycle regulation. Indeed, Finnin et al., *Nature*, 401: 188-193 (1999), teaches that TSA and SAHA inhibit cell growth, induce terminal differentiation, and prevent the formation of tumors in mice. Suzuki et al., U.S. Pat. No. 6,174,905, EP 0847992 and JP 258863/96, disclose benzamide derivatives that induce cell differentiation and inhibit HDAC. Delorme et al., WO 01/38322 and WO 2001/070675, disclose additional compounds that serve as HDAC inhibitors. Other inhibitors of histone deacetylase activity, including trapoxin, depudecin, FR901228 (Fujisawa Pharmaceuticals), and butyrate, have been found to similarly inhibit cell cycle progression in cells (Taunton et al., *Science* 272: 408-411, 1996; Kijima et al., *J. Biol. Chem.* 268(30): 22429-22435, 1993; Kwon et al., *Proc. Natl. Acad. Sci. USA* 95(7):3356-61, 1998).

Research in the past decade has uncovered a new classification of inherited neurodegenerative diseases, the polyglutamine (polyQ) expansion diseases. In each, the underlying mutation is an expansion of a CAG trinucleotide repeat that encodes polyQ in the respective disease protein. All are progressive, ultimately fatal disorders that typically begin in adulthood and progress over 10 to 30 years. The clinical features and pattern of neuronal degeneration differ among the diseases, yet increasing evidence suggests that polyQ diseases share important pathogenic features. In particular, abnormal protein conformations promoted by polyQ expansion seem to be central to pathogenesis. This class of PolyQ expansion neurodegenerative disease are Huntington's Disease (HD), Dentatorubralpallidoluysian atrophy (DRPLA), spinal and bulbar muscular atrophy (SBMA), and five spinocerebellar ataxias (SCA1, SCA2, SCA3/MJD (Machado-Joseph Disease), SCA6 and SCA7).

It is known that certain HDAC inhibitors, for example SAHA, CBHA and pryoxiamide can cross the blood brain barrier at sufficient amounts to significantly inhibit HDAC activity causing the accumulation of acetylated histones in the brain (WO 03/032921). This discovery therefore provides for the use of HDAC inhibitors for inhibiting HDAC in the brain, for the treatment of polyglutamine (polyQ) expansion diseases.

The art provides data that HDAC inhibitors are promising novel therapeutics for polyglutamine expansion diseases. Other data support a therapeutic benefit of HDAC inhibitors for Huntington's disease. Sadri-Vakili and Cha (Nature Clinical Practice Neurology, 2006, 2(6):330-338), and references cited therein, for example, review the current state of knowledge regarding the status of histones in Huntington's Disease and teach that recent studies have shown a therapeutic role for hisone deacetylase inhibitors in a number of Huntington's Disease models. In vivo, HDAC inhibitors arrest ongoing progressive neuronal degeneration induced by polygluatmine repeat expansion, and they reduce lethality in two *Drosophila* models of polyglutamine disease (Steffan et al., 2001, Nature 413: 739-743). Similar findings were observed with sodium butyrate and TSA (Zhao et al., 2005, J. Expt. Biol., 208:697-705). Gardian et al. (2005, J. Biol. Chem., 280:556-563) showed that phenylbutyrate is capable of improving survival and attenuating brain atrophy in the N171-82Q transgenic mouse model of Huntington's Disease. In the R6/2 model of Huntington's Disease, sodium butyrate extended survival, improved motor deficits and delayed neuropathological sequelae (Ferrante et al., 2003, J. Neurosci., 23:9418-9427). In that same model, suberoylanilide hydroxamic acid (SAHA) was also active in improving the motor impairment (Hockly, 2003, Proc. Natl. Acad. Sci. USA, 100:2041-0246). Ying et al. (2005, J. Biol. Chem., 281:12580-12586) showed that sodium butyrate improved life span and motor deficits in a mouse model for DRPLA. Bates et al. (2006, The Journal of Neuroscience, 26(10):2830-2838) reported that in *Caenorhabditis elegans* expressing a human huntingtin fragment with an expanded polyglutamine tract (Htn-Q150), knockdown of *C. elegans* hda-3 suppressed Htn-Q150 toxicity. Neuronal expression of hda-3 restored Htn-Q150 toxicity and suggested that *C. elegans* HDAC3 acts within neurons to promote degeneration in response to Htn-Q 150.

These findings suggest that inhibition of HDAC activity represents a novel approach for intervening in cell cycle regulation and that HDAC inhibitors have great therapeutic potential in the treatment of polyglutamine (polyQ) expansion diseases, such as Huntington's Disease. It would be highly desirable to have novel inhibitors of histone deacetylase.

SUMMARY OF THE INVENTION

The present invention provides compounds for the inhibition of histone deacetylase.

In a first aspect, the present invention provides compounds that are useful as inhibitors of histone deacetylase that have the formula (I) and racemic mixtures, diastereomers and enantiomers thereof and N-oxides, hydrates, solvates, pharmaceutically acceptable salts, prodrugs and complexes thereof,

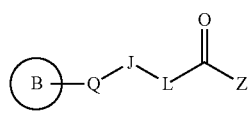
(I)

wherein

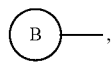

Q, J, L and Z are as defined below.

In a second aspect, the invention provides a composition comprising a compound according to the first aspect and a pharmaceutically acceptable carrier.

In a third aspect, the invention provides a method of inhibiting histone deacetylase, the method comprising contacting the histone deacetylase or a cell containing histone deacetylase, with a histone deacetylase inhibiting amount of a compound according to the first aspect or a composition according to second aspect.

The foregoing merely summarizes various aspects of the invention and is not intended to be limiting in nature. These aspects and other aspects and embodiments are described more fully below. The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

DETAILED DESCRIPTION OF THE INVENTION

The present invention provides compounds that are useful as inhibitors of histone deacetylase.

In one aspect, the invention provides compound of the formula (I)

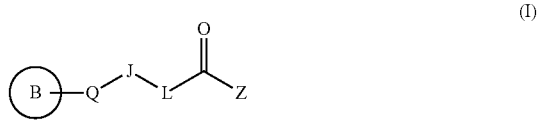
(I)

and racemic mixtures, diastereomers and enantiomers thereof and N-oxides, hydrates, solvates, pharmaceutically acceptable salts, prodrugs and complexes thereof, wherein groups

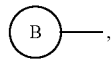

Q, J, L and Z are as defined herein.

In the second aspect, the invention provides a composition comprising a compound according to the first aspect or a preferred embodiment thereof and a pharmaceutically acceptable carrier.

In the third aspect, the invention provides a method of inhibiting histone deacetylase. In one embodiment, the method comprises contacting the histone deacetylase with a histone deacetylase inhibiting amount of a compound according to the first aspect or a preferred embodiment thereof. In a further embodiment of the third aspect, the method comprises contacting the histone deacetylase with a histone deacetylase inhibiting amount of a composition according to the second aspect. In yet another embodiment, the method comprises inhibiting histone deacetylase in a cell comprising contacting the cell with a histone deacetylase inhibiting amount of compound according to the first aspect or a preferred embodiment thereof. In still another embodiment, the method comprises inhibiting histone deacetylase in a cell comprising contacting the cell with a histone deacetylase inhibiting amount of a composition according to the second aspect.

In a particularly preferred embodiment of the third aspect, compounds according to the first aspect are able to cross the blood brain barrier and inhibit a histone deacetylase in a cell thereacross. In a preferred embodiment, the cell is a cell of the central nervous system, more preferably a brain cell, more preferably a cortical cell.

In another aspect, the present invention provides a method of inhibiting HDAC in the brain of an individual. The method comprises administering to the individual a HDAC inhibiting amount of a histone deacetylase inhibitor according to the present invention, or a composition thereof.

In another aspect, the present invention provides a method of treating a polyglutamine (polyQ) expansion disease, comprising administering to an individual in need of treatment a therapeutically effective amount of a compound according to the present invention, or a composition thereof.

In certain preferred embodiments, the disease is selected from the group consisting of Huntington's Disease (HD), Dentatorubralpallidoluysian atrophy (DRPLA), spinal and bulbar muscular atrophy (SBMA), and five spinocerebellar ataxias (SCA1, SCA2, SCA3/MJD (Machado-Joseph Disease), SCA6 and SCA7).

In a preferred embodiment, the disease is Huntington's Disease.

In preferred embodiments, the individual is a mammal, preferably a primate, more preferably a human.

For purposes of the present invention, the following definitions will be used (unless expressly stated otherwise).

The terms "treating", "treatment", or the like, as used herein covers the treatment of a disease-state in an animal and includes at least one of: (i) preventing the disease-state from occurring, in particular, when such animal is predisposed to the disease-state but has not yet developed symptoms of having it; (ii) inhibiting the disease-state, i.e., partially or completely arresting its development; (iii) relieving the disease-state, i.e., causing regression of symptoms of the disease-state, or ameliorating a symptom of the disease; and (iv) reversal or regression of the disease-state, preferably eliminating or curing of the disease. In a preferred embodiment the terms "treating", "treatment", or the like, covers the treatment of a disease-state in an animal and includes at least one of (ii), (iii) and (iv) above. In a preferred embodiment of the present invention the animal is a mammal, preferably a primate, more preferably a human. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

As used herein, the terms "histone deacetylase" and "HDAC" are intended to refer to any one of a family of enzymes that remove acetyl groups from a protein, such as for example, the e-amino groups of lysine residues at the N-terminus of a histone. Unless otherwise indicated by context, the term "histone" is meant to refer to any histone protein, including H1, H2A, H2B, H3, H4, and H5, from any species. Preferred histone deacetylases include class I and class II enzymes. Other preferred histone deacetylases include class III enzymes. Preferably the histone deacetylase is a human HDAC, including, but not limited to, HDAC-1, HDAC-2, HDAC-3, HDAC-4, HDAC-5, HDAC-6, HDAC-7, HDAC-8, HDAC-9, HDAC-10 and HDAC-11. In some other preferred embodiments, the histone deacetylase is derived from a protozoal or fungal source.

The terms "histone deacetylase inhibitor" and "inhibitor of histone deacetylase" are intended to mean a compound having a structure as defined herein, which is capable of interacting with a histone deacetylase and inhibiting its enzymatic activity.

The term "inhibiting histone deacetylase enzymatic activity" is intended to mean reducing the ability of a histone deacetylase to remove an acetyl group from a protein, such as a histone. The concentration of inhibitor which reduces the activity of a histone deacetylase to 50% of that of the uninhibited enzyme is determined as the $IC_{50}$ value. In some preferred embodiments, such reduction of histone deacetylase activity is at least 50%, more preferably at least about 75%, and still more preferably at least about 905. In other preferred embodiments, histone deacetylase activity is reduced by at least 95% and more preferably by at least 99%.

Preferably, such inhibition is specific, i.e., the histone deacetylase inhibitor reduces the ability of a histone deacetylase to remove an acetyl group from a protein, such as a histone, at a concentration that is lower than the concentration of the inhibitor that is required to produce another, unrelated biological effect. Preferably, the concentration of the inhibitor required for histone deacetylase inhibitory activity is at least 2-fold lower, more preferably at least 5-fold lower, even more preferably at least 10-fold lower, and most preferably at least 20-fold lower than the concentration required to produce an unrelated biological effect.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as $(A)_a$-B—, wherein a is 0 or 1. In such instances, when a is 0 the moiety is B— and when a is 1 the moiety is A-B—.

For simplicity, reference to a "$C_n$-$C_m$" heterocyclyl or "$C_n$-$C_m$" heteroaryl means a heterocyclyl or heteroaryl having from "n" to "m" annular atoms, where "n" and "m" are integers. Thus, for example, a $C_8$-$C_6$-heterocyclyl is a 5- or 6-membered ring having at least one heteroatom, and includes pyrrolidinyl ($C_5$) and piperidinyl ($C_6$); $C_6$-heteroaryl includes, for example, pyridyl and pyrimidyl.

The term "hydrocarbyl" refers to a straight, branched, or cyclic alkyl, alkenyl, or alkynyl, each as defined herein. A "$C_0$" hydrocarbyl is used to refer to a covalent bond. Thus, "$C_0$-$C_3$-hydrocarbyl" includes a covalent bond, methyl, ethyl, ethenyl, ethynyl, propyl, propenyl, propynyl, and cyclopropyl.

The term "alkyl" is intended to mean a straight or branched chain aliphatic group having from 1 to 12 carbon atoms, preferably 1-8 carbon atoms, and more preferably 1-6 carbon atoms. Other preferred alkyl groups have from 2 to 12 carbon atoms, preferably 2-8 carbon atoms and more preferably 2-6 carbon atoms. Preferred alkyl groups include, without limitation, methyl, ethyl, propyl, isopropyl, butyl, isobutyl, sec-butyl, tert-butyl, pentyl, and hexyl. A "$C_0$" alkyl (as in "$C_0$-$C_3$-alkyl") is a covalent bond.

The term "alkenyl" is intended to mean an unsaturated straight or branched chain aliphatic group with one or more carbon-carbon double bonds, having from 2 to 12 carbon atoms, preferably 2-8 carbon atoms, and more preferably 2-6 carbon atoms. Preferred alkenyl groups include, without limitation, ethenyl, propenyl, butenyl, pentenyl, and hexenyl.

The term "alkynyl" is intended to mean an unsaturated straight or branched chain aliphatic group with one or more carbon-carbon triple bonds, having from 2 to 12 carbon atoms, preferably 2-8 carbon atoms, and more preferably 2-6 carbon atoms. Preferred alkynyl groups include, without limitation, ethynyl, propynyl, butynyl, pentynyl, and hexynyl.

The terms "alkylene," "alkenylene," or "alkynylene" as used herein are intended to mean an alkyl, alkenyl, or alkynyl group, respectively, as defined hereinabove, that is positioned between and serves to connect two other chemical groups. Preferred alkylene groups include, without limitation, methylene, ethylene, propylene, and butylene. Preferred alkenylene groups include, without limitation, ethenylene, propenylene, and butenylene. Preferred alkynylene groups include, without limitation, ethynylene, propynylene, and butynylene.

The term "cycloalkyl" is intended to mean a saturated or unsaturated mono-, bi, tri- or poly-cyclic hydrocarbon group having about 3 to 15 carbons, preferably having 3 to 12 carbons, preferably 3 to 8 carbons, and more preferably 3 to 6 carbons. In certain preferred embodiments, the cycloalkyl group is fused to an aryl, heteroaryl or heterocyclic group. Preferred cycloalkyl groups include, without limitation, cyclopenten-2-enone, cyclopenten-2-enol, cyclohex-2-enone, cyclohex-2-enol, cyclopropyl, cyclobutyl, cyclopentyl, cyclopentenyl, cyclohexyl, cyclohexenyl, cycloheptyl, and cyclooctyl.

In certain preferred embodiments, the cycloalkyl group is a bridged cycloalkyl group, preferably a $C_5$-$C_{10}$ bridged bicyclic group. In certain preferred embodiments, the bridged cycloalkyl group is a $C_5$ bridged bicyclic group. In certain preferred embodiments, the bridged cycloalkyl group is a $C_6$ bridged bicyclic group. In certain preferred embodiments, the bridged cycloalkyl group is a $C_7$ bridged bicyclic group. In certain preferred embodiments, the bridged cycloalkyl group is a $C_8$ bridged bicyclic group. In certain preferred embodiments, the bridged cycloalkyl group is a $C_9$ bridged bicyclic. In certain preferred embodiments, the bridged cycloalkyl group has a bridge of 0, 1, 2 or 3 carbon atoms. A bridge of 0 carbon atoms is a bond, and equates to a cycloalkyl group fused to another ring structure. In certain preferred embodiments, the bridged cycloalkyl group has a bridge of 0, 1 or 3 carbon atoms. In certain preferred embodiments, the bridged cycloalkyl group has a bridge of 1 or 3 carbon atoms. In certain preferred embodiments, the bridged cycloalkyl group has a bridge of 1 carbon atom. In certain preferred embodiments, the bridged cycloalkyl group has a bridge of 2 carbon atoms. In certain preferred embodiments, the bridged cycloalkyl group has a bridge of 3 carbon atoms. If a bridged cycloalkyl group is described as "optionally substituted", it is intended to be optionally substituted on any position, including the bridge. The bridged cycloalkyl group is not limited to any particular stereochemistry.

The term "heteroalkyl" is intended to mean a saturated or unsaturated, straight or branched chain aliphatic group, wherein one or more carbon atoms in the chain are independently replaced by a heteroatom selected from the group consisting of O, $S(O)_{0-2}$, N and $N(R^{33})$.

The term "aryl" is intended to mean a mono-, bi-, tri- or polycyclic $C_6$-$C_{14}$ aromatic moiety, preferably comprising one to three aromatic rings. Preferably, the aryl group is a $C_6$-$C_{10}$ aryl group, more preferably a $C_6$ aryl group. Preferred aryl groups include, without limitation, phenyl, naphthyl, anthracenyl, and fluorenyl.

The terms "aralkyl" or "arylalkyl" is intended to mean a group comprising an aryl group covalently linked to an alkyl group. If an aralkyl group is described as "optionally substituted", it is intended that either or both of the aryl and alkyl moieties may independently be optionally substituted or unsubstituted. Preferably, the aralkyl group is $(C_1$-$C_6)$alk$(C_6$-$C_{10})$aryl, including, without limitation, benzyl, phenethyl, and naphthylmethyl. For simplicity, when written as "aralkyl" this term, and terms related thereto, is intended to indicate the order of groups in a compound as "aryl-alkyl". Similarly, "alkyl-aryl" is intended to indicate the order of the groups in a compound as "alkyl-aryl".

The terms "heterocyclyl", "heterocyclic" or "heterocycle" are intended to mean a group which is a mono-, bi-, or polycyclic structure having from about 3 to about 14 atoms, wherein one or more atoms are independently selected from the group consisting of N, O, and S. The ring structure may be saturated, unsaturated or partially unsaturated. In certain preferred embodiments, the heterocyclic group is non-aromatic. In a bicyclic or polycyclic structure, one or more rings may be aromatic; for example one ring of a bicyclic heterocycle or one or two rings of a tricyclic heterocycle may be aromatic, as in indan and 9,10-dihydro anthracene. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl, heteroaryl, or cycloalkyl group. Examples of such fused heterocycles include, without limitation, tetrahydroquinoline and dihydrobenzofuran. Specifically excluded from the scope of this term are compounds where an annular O or S atom is adjacent to another O or S atom.

In certain preferred embodiments, the heterocyclic group is a bridged heterocyclic group, preferably a $C_6$-$C_{10}$ bridged bicyclic group, wherein one or more carbon atoms are independently replaced by a heteroatom selected from the group consisting of N, O and S. In certain preferred embodiments, the bridged heterocyclic group is a $C_6$ bridged bicyclic group. In certain preferred embodiments, the bridged heterocyclic group is a $C_7$ bridged bicyclic group. In certain preferred embodiments, the bridged heterocyclic group is a $C_8$ bridged bicyclic group. In certain preferred embodiments, the bridged heterocyclic group is a $C_9$ bridged bicyclic. In certain preferred embodiments, the bridged heterocyclic group has a bridge of 0, 1, 2 or 3 carbon atoms. In certain preferred embodiments, the bridged heterocyclic group has a bridge of 0, 1 or 3 carbon atoms. A bridge of 0 carbon atoms is a bond, and equates to a heterocyclic group fused to another ring structure. In certain preferred embodiments, the bridged heterocyclic group has a bridge of 1 or 3 carbon atoms. In certain preferred embodiments, the bridged heterocyclic group has a bridge of 1 carbon atom. In certain preferred embodiments, the bridged heterocyclic group has a bridge of 2 carbon atoms. In certain preferred embodiments, the bridged heterocyclic group has a bridge of 3 carbon atoms. If a bridged heterocyclic group is described as "optionally substituted", it is intended to be optionally substituted on any position, including the bridge. The bridged heterocyclic group is not limited to any particular stereochemistry.

In certain preferred embodiments, the heterocyclic group is a heteroaryl group. As used herein, the term "heteroaryl" is intended to mean a mono-, bi-, tri- or polycyclic group having 5 to 14 ring atoms, preferably 5, 6, 9, or 10 ring atoms; having 6, 10, or 14 pi electrons shared in a cyclic array; and having, in addition to carbon atoms, between one or more heteroatoms independently selected from the group consisting of N, O, and S. For example, a heteroaryl group may be pyrimidinyl, pyridinyl, benzimidazolyl, thienyl, benzothiazolyl, benzofuranyl and indolinyl. Preferred heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl.

The terms "arylene," "heteroarylene," or "heterocyclylene" are intended to mean an aryl, heteroaryl, or heterocyclyl group, respectively, as defined hereinabove, that is positioned between and serves to connect two other chemical groups.

Preferred heterocyclyls and heteroaryls include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, thiadiazolyl (e.g., 1,2,3-thiadiazolyl, 1,2,4-thiadiazolyl, 1,2,5-thiadiazolyl, 1,3,4-thiadiazolyl), thianthrenyl, thiazolyl, thienyl, thienothiazolyl, thienooxazolyl, thienoimidazolyl, thiophenyl, triazinyl, triazolyl (e.g., 1,2,3-triazolyl, 1,2,4-triazolyl, 1,2,5-triazolyl, 1,3,4-triazolyl), and xanthenyl.

Aromatic polycycles include, but are not limited to, bicyclic and tricyclic fused ring systems, including for example naphthyl.

Non-aromatic polycycles include, but are not limited to, bicyclic and tricyclic fused ring systems where each ring can be 4-9 membered and each ring can containing zero, 1 or more double and/or triple bonds. Suitable examples of non-aromatic polycycles include, but are not limited to, decalin, octahydroindene, perhydrobenzocycloheptene and perhydrobenzo-[f]-azulene.

Polyheteroaryl groups include bicyclic and tricyclic fused rings systems where each ring can independently be 5 or 6 membered and contain one or more heteroatom, for example, 1, 2, 3 or 4 heteroatoms, independently chosen from O, N and S such that the fused ring system is aromatic. Suitable examples of polyheteroaryl ring systems include quinoline, isoquinoline, pyridopyrazine, pyrrolopyridine, furopyridine, indole, benzofuran, benzothiofuran, benzindole, benzoxazole, pyrroloquinoline, and the like.

Non-aromatic polyheterocyclic groups include but are not limited to bicyclic and tricyclic ring systems where each ring can be 4-9 membered, contain one or more heteratom, for example 1, 2, 3 or 4 heteratoms, independently chosen from O, N and S, and contain zero, or one or more C—C double or triple bonds. Suitable examples of non-aromatic polyheterocycles include but are not limited to, hexitol, cis-perhydrocyclohepta[b]pyridinyl, decahydro-benzo[f][1,4]oxazepinyl, 2,8-dioxabicyclo[3.3.0]octane, hexahydro-thieno[3,2-b]thiophene, perhydropyrrolo[3,2-b]pyrrole, perhydronaphthyridine, perhydrop-1H-dicyclopenta[b,e]pyran.

Mixed aryl and non-aryl polyheterocycle groups include but are not limited to bicyclic and tricyclic fused ring systems where each ring can be 4-9 membered, contain one or more heteroatom independently chosen from O, N and S and at least one of the rings must be aromatic. Suitable examples of mixed aryl and non-aryl polyheteorcycles include 2,3-dihydroindole, 1,2,3,4-tetrahydroquinoline, 5,11-dihydro-10H-dibenz[b,e][1,4]diazepine, 5H-dibenzo[b,e][1,4]diazepine, 1,2-dihydropyrrolo[3,4-b][1,5]benzodiazepine, 1,5-dihydropyrido[2,3-b][1,4]diazepin-4-one, 1,2,3,4,6,11-hexhydrobenzo[b]pyrido[2,3-e][1,4]diazepine-5-one, methylenedioxyphenyl, bis-methylenedioxyphenyl, 1,2,3,4-tetrahydronaphthalene, dibenzosuberane dihydroanthracene and 9H-fluorene.

As employed herein, and unless stated otherwise, when a moiety (e.g., alkyl, heteroalkyl, cycloalkyl, aryl, heteroaryl, heterocyclyl, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—) nitro, halohydrocarbyl, hydrocarbyl, alkyl, cycloalkyl, heterocyclyl, aryl, heteroaryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, (b) $C_1$-$C_5$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$ alkylsulfinyl, arylalkylsulfinyl, arylsulfinyl, $C_1$-$C_8$ alkylsulfonyl, arylalkylsulfonyl, arylsulfonyl, $C_0$-$C_6$ N-alkyl carbamoyl, $C_2$-$C_{15}$ N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, $C_5$-$C_{15}$ heteroaryl or any of these rings fused or spiro-fused to a cycloalkyl, heterocyclyl, or aryl, wherein each of the foregoing is further optionally substituted with one more moieties listed in (a), above; and (c) —$(CR^{32}R^{33a})_s$—$NR^{30}R^{31}$, wherein s is from 0 (in which case the nitrogen is directly bonded to the moiety that is substituted) to 6, $R^{32}$ and $R^{33a}$ are each independently hydrogen, halo, hydroxyl or $C_1$-$C_4$alkyl, and $R^{30}$ and $R^{31}$ are each independently hydrogen, cyano, oxo, hydroxyl, —$C_1$-$C_8$ alkyl, $C_1$-$C_8$ heteroalkyl, $C_1$-$C_8$ alkenyl, carboxamido, $C_1$-$C_3$ alkyl-carboxamido, carboxamido-$C_1$-$C_3$ alkyl, amidino, $C_2$-$C_8$hydroxyalkyl, $C_1$-$C_3$ alkylaryl, aryl-$C_1$-$C_3$ alkyl, $C_1$-$C_3$ alkylheteroaryl, heteroaryl-$C_1$-$C_3$ alkyl, $C_1$-$C_3$ alkylheterocyclyl, heterocyclyl-$C_1$-$C_3$ alkyl $C_1$-$C_3$ alkylcycloalkyl, cycloalkyl-$C_1$-$C_3$ alkyl, $C_2$-$C_8$ alkoxy, $C_2$-$C_8$ alkoxy-$C_1$-$C_4$alkyl, $C_1$-$C_8$ alkoxycarbonyl, aryloxycarbonyl, aryl-$C_1$-$C_3$ alkoxycarbonyl, heteroaryloxycarbonyl, heteroaryl-$C_1$-$C_3$ alkoxycarbonyl, $C_1$-$C_8$ acyl, $C_0$-$C_8$ alkyl-carbonyl, aryl-$C_0$-$C_8$ alkyl-carbonyl, heteroaryl-$C_0$-$C_8$ alkyl-carbonyl, cycloalkyl-$C_0$-$C_8$ alkyl-carbonyl, $C_0$-$C_8$ alkyl-NH-carbonyl, aryl-$C_0$-$C_8$ alkyl-NH-carbonyl, heteroaryl-$C_0$-$C_8$ alkyl-NH-carbonyl, cycloalkyl-$C_0$-$C_8$ alkyl-NH-carbonyl, $C_0$-$C_8$ alkyl-O-carbonyl, aryl-$C_0$-$C_8$ alkyl-O-carbonyl, heteroaryl-$C_0$-$C_8$ alkyl-O-carbonyl, cycloalkyl-$C_0$-$C_8$ alkyl-O-carbonyl, $C_1$-$C_8$ alkylsulfonyl, arylalkylsulfonyl, arylsulfonyl, heteroarylalkylsulfonyl, heteroarylsulfonyl, $C_1$-$C_8$ alkyl-NH-sulfonyl, arylalkyl-NH-sulfonyl, aryl-NH-sulfonyl, heteroarylalkyl-NH-sulfonyl, heteroaryl-NH-sulfonyl aroyl, aryl, cycloalkyl, heterocyclyl, heteroaryl, aryl-$C_1$-$C_3$ alkyl-, cycloalkyl-$C_1$-$C_3$ alkyl-, heterocyclyl-$C_1$-$C_3$ alkyl-, heteroaryl-$C_1$-$C_3$ alkyl-, or protecting group, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents selected from the group consisting of (a) above, a protecting group, and ($X^{30}$—$Y^{31}$—), wherein said heterocyclyl may also be bridged (forming a bicyclic moiety with a methylene, ethylene or propylene bridge); wherein $X^{30}$ is selected from the group consisting of $C_1$-$C_8$alkyl, $C_2$-$C_8$alkenyl-, $C_2$-$C_8$alkynyl-, —$C_0$-$C_3$alkyl —$C_2$-$C_8$alkenyl-$C_0$-$C_3$alkyl, $C_0$-$C_3$alkyl-$C_2$-$C_8$alkynyl-$C_0$-$C_3$alkyl, $C_0$-$C_3$alkyl-O—$C_0$-$C_3$alkyl-, HO—$C_0$-$C_3$alkyl-, $C_0$-$C_4$alkyl-N($R^{30}$)—$C_0$-$C_3$alkyl-, N($R^{30}$)($R^{31}$)—$C_0$-$C_3$alkyl-, N($R^{30}$)($R^{31}$)—$C_0$-$C_3$alkynyl-, N($R^{30}$)($R^{31}$)—$C_0$-$C_3$alkyl-, (N($R^{30}$)($R^{31}$))$_2$—C=N—, $C_0$-$C_3$alkyl-S(O)$_{0-2}$—$C_0$-$C_3$alkyl-, $CF_3$—$C_0$-$C_3$alkyl-, $C_1$-$C_8$heteroalkyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, N($R^{30}$)($R^{31}$)-heterocyclyl-$C_1$-$C_3$alkyl-, wherein the aryl, cycloalkyl, heteroaryl and heterocycyl are optionally substituted with 1 to 3 substituents from (a); and $Y^{31}$ is selected from the group consisting of a direct bond, —O—, —N($R^{30}$)—, —C(O)—, —O—C(O)—, —C(O)—O—, —N($R^{30}$)—C(O)—, —C(O)—N($R^{30}$)—, —N($R^{30}$)—C(S)—, —C(S)—N($R^{30}$)—, —N($R^{30}$)—C(O)—N($R^{31}$)—, —N($R^{30}$)—C(N$R^{30}$)—N($R^{31}$)—, —N($R^{30}$)—C(N$R^{31}$)—, —C(N$R^{31}$)—N($R^{30}$), —N($R^{30}$)—C(S)—N($R^{31}$)—, —N($R^{30}$)—C(O)—O—, —O—C(O)—N($R^{31}$)—, —N($R^{30}$)—C(S)—O—, —O—C(S)—N($R^{31}$)—, —S(O)$_{0-2}$—, —SO$_2$N($R^{31}$)—, —N($R^{31}$)—SO$_2$— and —N($R^{30}$)—SO$_2$N($R^{31}$)—.

As a non-limiting example, substituted phenyls include 2-fluorophenyl, 3,4-dichlorophenyl, 3-chloro-4-fluoro-phenyl, 2-fluoro-3-propylphenyl. As another non-limiting example, substituted n-octyls include 2,4-dimethyl-5-ethyl-octyl and 3-cyclopentyl-octyl. Included within this definition are methylenes (—$CH_2$—) substituted with oxygen to form carbonyl —CO—.

When there are two optional substituents bonded to adjacent atoms of a ring structure, such as for example phenyl, thiophenyl, or pyridinyl, the substituents, together with the atoms to which they are bonded, optionally form a 5- or 6-membered cycloalkyl or heterocycle having 1, 2, or 3 annular heteroatoms.

In a preferred embodiment, hydrocarbyl, alkyl, alkenyl, alkynyl, heteroalkyl, cycloalkyl, heterocyclic, aryl, heteroaryl, aromatic polycycle, non-aromatic polycycle, polyheteroaryl, non-aromatic polyheterocyclic and mixed aryl and non-aryl polyheterocycle groups are unsubstituted.

In other preferred embodiments, hydrocarbyl, alkyl, alkenyl, alkynyl, heteroalkyl, cycloalkyl, heterocyclic, aryl, heteroaryl, aromatic polycycle, non-aromatic polycycle, polyheteroaryl, non-aromatic polyheterocyclic and mixed aryl and non-aryl polyheterocycle groups are substituted with from 1 to 3 independently selected substituents.

Preferred substituents on alkyl groups include, but are not limited to, hydroxyl, halogen (e.g., a single halogen substituent or multiple halo substituents; in the latter case, groups such as $CF_3$ or an alkyl group bearing more than one Cl), cyano, nitro, alkyl, cycloalkyl, alkenyl, cycloalkenyl, alkynyl, heterocycle, aryl, —$OR^u$, —$SR^u$, —$S(=O)R^y$, —$S(=O)_2R^y$, —$P(=O)_2R^y$, —$S(=O)_2OR^y$, —$P(=O)_2OR^y$, —$NR'R^w$, —$NR'S(=O)_2R^y$, —$NR'P(=O)_2R^y$, —$S(=O)_2NR'R^w$, —$P(=O)_2NR'R^w$, —$C(=O)OR^y$, —$C(=O)R^u$, —$C(=O)NR'R^w$, —$OC(=O)R^u$, —$OC(=O)$ $NR'R^w$, —$NR'C(=O)OR^y$, —$NR^xC(=O)NR'R^w$, —$NR^xS(=O)_2NR'R^w$, —$NR^xP(=O)_2NR'R^w$, —$NR'C(=O)R^u$ or —$NR'P(=O)_2R^y$, wherein $R^{11}$ is hydrogen, alkyl, cycloalkyl, alkenyl, cycloalkenyl, alkynyl, heterocycle or aryl; $R^v$, $R^w$ and $R^x$ are independently hydrogen, alkyl, cycloalkyl, heterocycle or aryl, or said $R^v$ and $R^w$ together with the N to which they are bonded optionally form a heterocycle; and $R^y$ is alkyl, cycloalkyl, alkenyl, cycloalkenyl, alkynyl, heterocycle or aryl. In the aforementioned exemplary substituents, groups such as alkyl, cycloalkyl, alkenyl, alkynyl, cycloalkenyl, heterocycle and aryl can themselves be optionally substituted.

Preferred substituents on alkenyl and alkynyl groups include, but are not limited to, alkyl or substituted alkyl, as well as those groups recited as preferred alkyl substituents.

Preferred substituents on cycloalkyl groups include, but are not limited to, nitro, cyano, alkyl or substituted alkyl, as well as those groups recited about as preferred alkyl substituents. Other preferred substituents include, but are not limited to, spiro-attached or fused cyclic substituents, preferably spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

Preferred substituents on cycloalkenyl groups include, but are not limited to, nitro, cyano, alkyl or substituted alkyl, as well as those groups recited as preferred alkyl substituents. Other preferred substituents include, but are not limited to, spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

Preferred substituents on aryl groups include, but are not limited to, nitro, cycloalkyl or substituted cycloalkyl, cycloalkenyl or substituted cycloalkenyl, cyano, alkyl or substituted alkyl, as well as those groups recited above as preferred alkyl substituents. Other preferred substituents include, but are not limited to, fused cyclic groups, especially fused cycloalkyl, fused cycloalkenyl, fused heterocycle, or fused aryl, where the aforementioned cycloalkyl, cylcoalkenyl, heterocycle and aryl substituents can themselves be optionally substituted. Still other preferred substituents on aryl groups (phenyl, as a non-limiting example) include, but are not limited to, haloalkyl and those groups recited as preferred alkyl substituents.

Preferred substituents on heterocylic groups include, but are not limited to, cycloalkyl, substituted cycloalkyl, cycloalkenyl, substituted cycloalkenyl, nitro, oxo (i.e., =O), cyano, alkyl, substituted alkyl, as well as those groups recited as preferred alkyl substituents. Other preferred substituents on heterocyclic groups include, but are not limited to, spiro-attached or fused cylic substituents at any available point or points of attachment, more preferably spiro-attached cycloalkyl, spiro-attached cycloalkenyl, spiro-attached heterocycle (excluding heteroaryl), fused cycloalkyl, fused cycloakenyl, fused heterocycle and fused aryl, where the aforementioned cycloalkyl, cycloalkenyl, heterocycle and aryl substituents can themselves be optionally substituted.

In a preferred embodiment, a heterocyclic group is substituted on carbon, nitrogen and/or sulfur at one or more positions. Preferred substituents on nitrogen include, but are not limited to N-oxide, alkyl, aryl, aralkyl, alkylcarbonyl, alkylsulfonyl, arylcarbonyl, arylsulfonyl, alkoxycarbonyl, or aralkoxycarbonyl. Preferred substituents on sulfur include, but are not limited to, oxo and $C_{1-6}$alkyl. In certain preferred embodiments, nitrogen and sulfur heteroatoms may independently be optionally oxidized and nitrogen heteroatoms may independently be optionally quaternized.

Especially preferred substituents on alkyl groups include halogen and hydroxy.

Especially preferred substituents on ring groups, such as aryl, heteroaryl, cycloalkyl and heterocyclyl, include halogen, alkoxy and alkyl.

Preferred substituents on aromatic polycycles include, but are not limited to, oxo, $C_1$-$C_6$alkyl, cycloalkylalkyl (e.g. cyclopropylmethyl), oxyalkyl, halo, nitro, amino, alkylamino, aminoalkyl, alkyl ketones, nitrile, carboxyalkyl, alkylsulfonyl, arylsulfonyl, aminosulfonyl and $OR^{aa}$, such as alkoxy, wherein $R^{aa}$ is selected from the group consisting of H, $C_1$-$C_6$alkyl, $C_4$-$C_9$cycloalkyl, $C_4$-$C_9$heterocycloalkyl, aryl, heteroaryl, arylalkyl, heteroarylalkyl and $(CH_2)_{0-6}Z^aR^{bb}$, wherein $Z^a$ is selected from the group consisting of O, $NR^{cc}$, S and S(O), and $R^{bb}$ is selected from the group consisting of H, $C_1$-$C_6$alkyl, $C_4$-$C_9$cycloalkyl, $C_4$-$C_9$heterocycloalkyl, $C_4$-$C_9$heterocycloalkylalkyl, aryl, mixed aryl and non-aryl polycycle, heteroaryl, arylalkyl, (e.g. benzyl), and heteroarylalkyl (e.g. pyridylmethyl); and $R^{cc}$ is selected from the group consisting of H, $C_1$-$C_6$alkyl, $C_4$-$C_9$cycloalkyl, $C_4$-$C_9$heterocycloalkyl, aryl, heteroaryl, arylalkyl (e.g. benzyl), heteroarylalkyl (e.g. pyridylmethyl) and amino acyl.

Preferred substituents on non-aromatic polycycles include, but are not limited to, oxo, $C_3$-$C_9$cycloalkyl, such as cyclopropyl, cyclobutyl, cyclopentyl, cyclohexyl and the like. Unless otherwise noted, non-aromatic polycycle substituents include both unsubstituted cycloalkyl groups and cycloalkyl groups that are substituted by one or more suitable substituents, including but not limited to, $C_1$-$C_6$alkyl, oxo, halo, hydroxy, aminoalkyl, oxyalkyl, alkylamino and $OR^{aa}$, such as alkoxy. Preferred substituents for such cycloalkyl groups include halo, hydroxy, alkoxy, oxyalkyl, alkylamino and aminoalkyl.

Preferred substituents on carbon atoms of polyheteroaryl groups include but are not limited to, straight and branched optionally substituted $C_1$-$C_6$alkyl, unsaturation (i.e., there are one or more double or triple C—C bonds), acyl, oxo, cycloalkyl, halo, oxyalkyl, alkylamino, aminoalkyl, acylamino, $OR^{aa}$ (for example alkoxy), and a substituent of the formula —O—$(CH_2CH=CH(CH_3)(CH_2))_{1-3}H$. Examples of suitable straight and branched $C_1$-$C_6$alkyl substituents include but are not limited to methyl, ethyl, n-propyl, 2-propyl, n-butyl, sec-butyl, t-butyl and the like. Preferred substituents include halo, hydroxy, alkoxy, oxyalkyl, alkylamino and aminoalkyl. Preferably substitutions on nitrogen atoms include, for example by N-oxide or Rec. Preferred substituents on nitrogen atoms include H, $C_1$-$C_4$alkyl, acyl, aminoacyl and sulfonyl. Preferably sulfur atoms are unsubstituted. Preferred substituents on sulfur atoms include but are not limited to oxo and lower alkyl.

Preferred substituents on carbon atoms of non-aromatic polyheterocyclic groups include but are not limited to straight and branched optionally substituted $C_1$-$C_6$alkyl, unsaturation (i.e., there are one or more double or triple C—C bonds), acyl, oxo, cycloalkyl, halo, oxyalkyl, alkylamino, aminoalkyl, acylamino and $OR^{aa}$, for example alkoxy. Examples of suitable straight and branched $C_1$-$C_6$alkyl substituents include but are not limited to methyl, ethyl, n-propyl, 2-propyl, n-butyl, sec-butyl, t-butyl and the like. Preferred substituents include halo, hydroxy, alkoxy, oxyalkyl, alkylamino and aminoalkyl. Preferably substitutions on nitrogen atoms include, for example, N-oxide or $R^{cc}$. Preferred N substituents include H, $C_1$-$C_4$ alkyl, acyl, aminoacyl and sulfonyl. Preferably, sulfur atoms are unsubstituted. Preferred S substituents include oxo and lower alkyl.

Preferred substituents on mixed aryl and non-aryl polyheterocycle groups include, but are not limited to, nitro or as described above for non-aromatic polycycle groups. Preferred substituents on carbon atoms include, but are not limited to, —N—OH, =N—OH, optionally substituted alkyl, unsaturation (i.e., there are one or more double or triple C—C bonds), oxo, acyl, cycloalkyl, halo, oxyalkyl, alkylamino, aminoalkyl, acylamino and $OR^{aa}$, for example alkoxy. Preferably substitutions on nitrogen atoms include, for example, N-oxide or $R^{cc}$. Preferred N substituents include H, $C_{1-4}$alkyl, acyl aminoacyl and sulfonyl. Preferably sulfur atoms are unsubstituted. Preferred S substituents include oxo and lower alkyl.

A "halohydrocarbyl" is a hydrocarbyl moiety in which from one to all hydrogens have been replaced with one or more halo.

The term "halogen" or "halo" is intended to mean chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., $NH_2$—CO—). The nitrogen atom of an acylamino or carbamoyl substituent is additionally optionally substituted. The term "sulfonamido" refers to a sulfonamide substituent attached by either the sulfur or the nitrogen atom. The term "amino" is meant to include $NH_2$, alkylamino, arylamino, and cyclic amino groups. The term "ureido" as employed herein refers to a substituted or unsubstituted urea moiety.

The term "radical" is intended to mean a chemical moiety comprising one or more unpaired electrons.

Where optional substituents are chosen from "one or more" groups it is to be understood that this definition includes all substituents being chosen from one of the specified groups or the substituents being chosen from two or more of the specified groups.

In addition, substituents on cyclic moieties (i.e., cycloalkyl, heterocyclyl, aryl, heteroaryl) include 5-6 membered mono- and 9-14 membered bi-cyclic moieties fused to the parent cyclic moiety to form a bi- or tri-cyclic fused ring system. Substituents on cyclic moieties also include 5-6 membered mono- and 9-14 membered bi-cyclic moieties attached to the parent cyclic moiety by a covalent bond to form a bi- or tri-cyclic bi-ring system. For example, an optionally substituted phenyl includes, but is not limited to, the following:

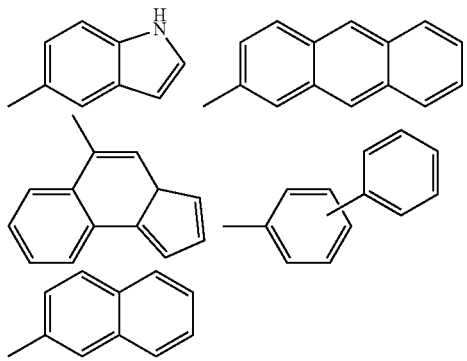

An "unsubstituted" moiety (e.g., unsubstituted cycloalkyl, unsubstituted heteroaryl, etc.) means that moiety as defined above that does not have an optional substituent. Thus, for example, "unsubstituted aryl" does not include phenyl substituted with a halo.

The term "protecting group" is intended to mean a group used in synthesis to temporarily mask the characteristic chemistry of a functional group because it interferes with another reaction. A good protecting group should be easy to put on, easy to remove and in high yielding reactions, and inert to the conditions of the reaction required. A protecting group or protective group is introduced into a molecule by chemical modification of a functional group in order to obtain chemoselectivity in a subsequent chemical reaction. One skilled in the art will recognize that during any of the processes for preparation of the compounds in the present invention, it may be necessary and/or desirable to protect sensitive or reactive groups on any of the molecules concerned. This may be achieved by means of conventional protecting groups, such as but not limited to, Bn— (or —CH$_2$Ph), —CHPh$_2$, alloc (or CH$_2$=CH—CH$_2$—O—C(O)—), BOC—, -Cbz (or Z—), —F-moc, —C(O)—CF$_3$, N-Phthalimide, 1-Adoc-, TBDMS-, TBDPS-, TMS-, TIPS-, IPDMS-, —SiR$_3$, SEM-, t-Bu-, Tr-, THP- and Allyl-. These protecting groups may be removed at a convenient stage using methods known from the art.

The term "therapeutically effective amount" as that term is used herein refers to an amount which elicits the desired therapeutic effect. The therapeutic effect is dependent upon the disease being treated and the results desired. As such, the therapeutic effect can be a decrease in the severity of symptoms associated with the disease and/or inhibition (partial or complete) of progression of the disease. Further, the therapeutic effect can be inhibition of HDAC in the brain. The amount needed to elicit the therapeutic response can be determined based on the age, health, size and sex of the patient. Optimal amounts can also be determined based on monitoring of the patient's response to treatment. Administration may be by any route, including, without limitation, parenteral, oral, sublingual, transdermal, topical, intranasal, intratracheal, or intrarectal. In certain particularly preferred embodiments, compounds of the invention are administered intravenously in a hospital setting. In certain other preferred embodiments, administration may preferably be by the oral route.

Some compounds of the invention may have one or more chiral centers and/or geometric isomeric centers (E- and Z-isomers), and it is to be understood that the invention encompasses all such optical, diastereoisomers and geometric isomers. The invention also comprises all tautomeric forms of the compounds disclosed herein.

The present invention also includes prodrugs of compounds of the invention. The term "prodrug" is intended to represent covalently bonded carriers, which are capable of releasing the active ingredient when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of the invention include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (I)), amides (e.g., trifluoroacetylamino, acetylamino, and the like), and the like.

The compounds of the invention may be administered as is or as a prodrug, for example in the form of an in vivo hydrolyzable ester or in vivo hydrolyzable amide. An in vivo hydrolyzable ester of a compound of the invention containing carboxy or hydroxy group is, for example, a pharmaceutically acceptable ester which is hydrolyzed in the human or animal body to produce the parent acid or alcohol. Suitable pharmaceutically acceptable esters for carboxy include C$_{1-6}$-alkoxymethyl esters (e.g., methoxymethyl), C$_{1-6}$-alkanoyloxymethyl esters (e.g., for example pivaloyloxymethyl), phthalidyl esters, C$_{3-8}$-cycloalkoxycarbonyloxyC$_{1-6}$-alkyl esters (e.g., 1-cyclohexylcarbonyloxyethyl); 1,3-dioxolen-2-onylmethyl esters (e.g., 5-methyl-1,3-dioxolen-2-onylmethyl; and C$_{1-6}$-alkoxycarbonyloxyethyl esters (e.g., 1-methoxycarbonyloxyethyl) and may be formed at any appropriate carboxy group in the compounds of this invention.

An in vivo hydrolyzable ester of a compound of the invention containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolyzable ester forming groups for hydroxy include alkanoyl, benzoyl, phenylacetyl and substituted benzoyl and phenylacetyl, alkoxycarbonyl (to give alkyl carbonate esters), dialkylcarbamoyl and N—(N,N-dialkylaminoethyl)-N-alkylcarbamoyl (to give carbamates), N,N-dialkylaminoacetyl and carboxyacetyl. Examples of substituents on benzoyl include morpholino and piperazino linked from a ring nitrogen atom via a methylene group to the 3- or 4-position of the benzoyl ring. A suitable value for an in vivo hydrolyzable amide of a compound of the invention containing a carboxy group is, for example, a N—C$_{1-6}$-alkyl or N,N-di-C$_{1-6}$-alkyl amide such as N-methyl, N-ethyl, N-propyl, N,N-dimethyl, N-ethyl-N-methyl or N,N-diethyl amide.

For simplicity, and unless stated otherwise, a moiety is written in the direction corresponding to the order given in Formula (I). For example, if moiety J is —C$_{0-6}$alkyl-aryl-C$_{2-6}$heteroalkyl-, it is meant that the —C$_{0-6}$alkyl-portion is attached to Q and the —C$_{2-6}$heteroalkyl-portion is attached to L.

The foregoing merely summarizes some aspects and preferred embodiments thereof and is not intended to be limiting in nature. These aspects and preferred embodiments thereof are described more fully below.

Compounds

In a first aspect, the invention provides novel inhibitors of histone deacetylase. In a first embodiment, the novel inhibitors of histone deacetylase are represented by Formula (I):

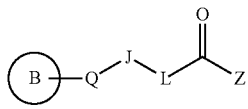
(I)

and N-oxides, hydrates, solvates, pharmaceutically acceptable salts, prodrugs and complexes thereof, and racemic mixtures, diastereomers and enantiomers thereof, wherein Z is selected from the group consisting of —N(R₁)OR² and H;

L is selected from the group consisting of a covalent bond and —N(OR²)—;

wherein, when L is —N(OR²)—, Z is H; and wherein, when Z is H, L is —N(OR²)—;

J is selected from the group consisting of a covalent bond, =CH—, —C₁-C₈alkyl-, —C₀-C₃alkyl-C₁-C₈heteroalkyl-C₀-C₃alkyl-, —C₀-C₃alkyl-C₂-C₈alkenyl-C₀-C₃alkyl-, —C₀-C₃alkyl-C₂-C₈alkynyl-C₀-C₃alkyl-, —C₀-C₆alkyl-aryl-C₀-C₆alkyl-, —C₀-C₆alkyl-aryl-C₂-C₆heteroalkyl-, —C₀-C₃alkyl-C₁-C₆heteroalkyl-aryl-C₀-C₆alkyl-, —C₀-C₃alkyl-C₁-C₆heteroalkyl-heteroaryl-C₀-C₆alkyl-, —C₀-C₆alkyl-cycloalkyl-C₀-C₆alkyl-, —C₀-C₆alkyl-heterocyclyl-C₀-C₆alkyl-, —C₄-C₆heterocyclyl-aryl-C₀-C₆alkyl-, —C₄-C₆heterocyclyl-aryl-C₀-C₆heteroalkyl-, —C₀-C₆alkyl-C₄-C₆heterocyclyl-C₀-C₆alkyl-, —C₀-C₆alkyl-heteroaryl-C₀-C₆alkyl-, —C₀-C₆alkylheteroaryl-C₀-C₆heteroalkyl-, —C₄-C₆heterocyclyl-heteroaryl-C₀-C₆alkyl-, —C₀-C₆alkyl-aryl-C₂-C₆alkynyl-, —C₀-C₆alkyl-heteroaryl-C₂-C₆alkynyl-, —C₀-C₆alkyl-aryl-C₂-C₆alkynyl-C₂-C₆alkenyl-, —C₀-C₆alkyl-aryl-C₂-C₆alkenyl-, —C₀-C₆alkyl-heteroaryl-C₂-C₆alkenyl-, —C₀-C₃alkyl-C₂-C₆alkenyl-aryl-C₀-C₆alkyl-, —C₀-C₃alkyl-C₂-C₆alkenyl-heteroaryl-C₀-C₆alkyl-, —C₀-C₃alkyl-C₂-C₆alkynyl-aryl-C₀-C₆alkyl-, —C₀-C₃alkyl-C₂-C₆alkynyl-heteroaryl-C₀-C₆alkyl-, —C₀-C₆alkylaryl-aryl-C₀-C₆alkyl-, —C₀-C₆alkylaryl-heteroaryl-C₀-C₆alkyl-, —C₀-C₃alkyl-heteroaryl-heteroaryl-C₀-C₃alkyl-, —C₀-C₃alkyl-heteroaryl-aryl-C₀-C₃alkyl-, —C₀-C₃alkyl-aryl-heteroaryl-C₀-C₃alkyl-, —C₀-C₃alkyl-aryl-aryl-C₀-C₃alkyl-, and —C₀-C₆alkyl-C₃-C₆cycloalkyl-C₀-C₆alkyl-, wherein each alkyl, alkenyl, alkynyl, heteroalkyl, aryl, heteroaryl, heterocyclyl, and cycloalkyl moiety is optionally substituted, and wherein when J is =CH—, Q is a covalent bond and B is attached through a carbon sp² to J;

Q is selected from the group consisting of an optionally substituted:

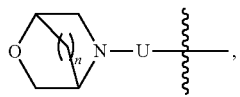
(a-1)

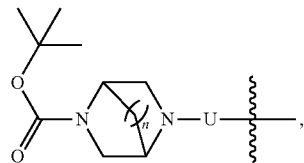
(a-2)

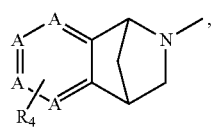
(a-3)

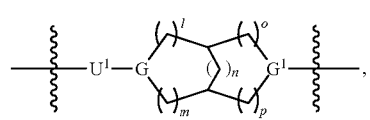
(a-4)

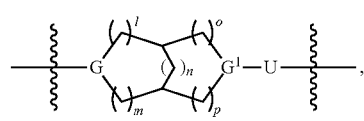
(a-5)

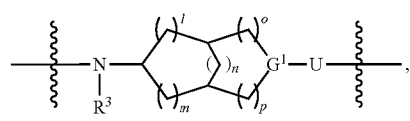
(a-6)

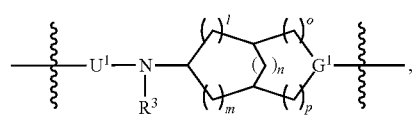
(a-7)

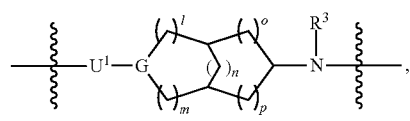
(a-8)

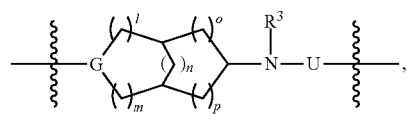
(a-9)

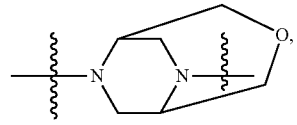
(a-10)

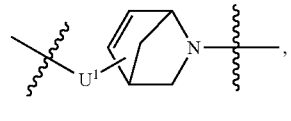
(a-11)

(a-12)

-continued

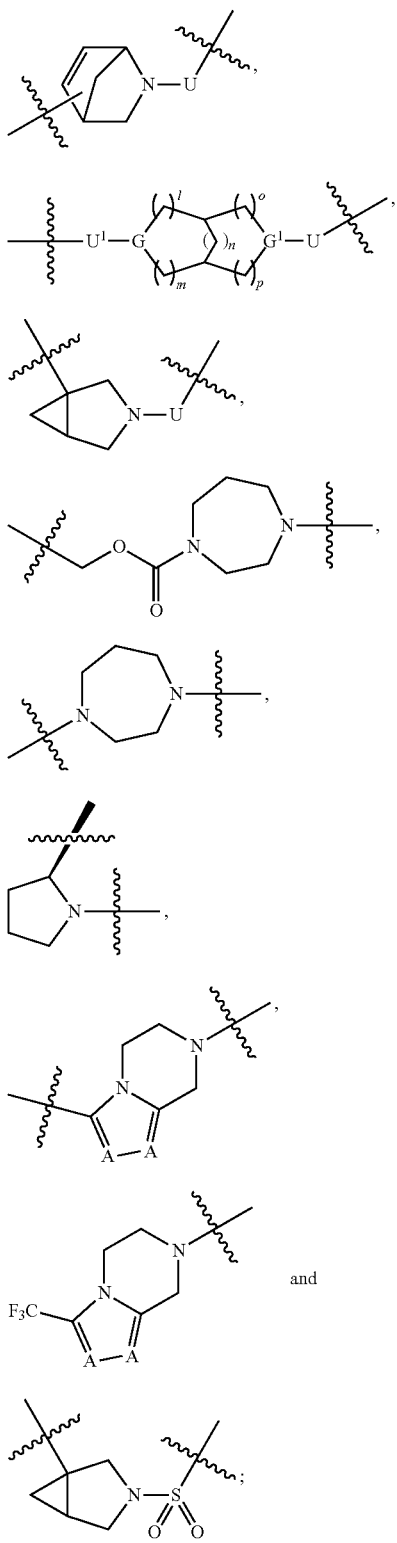

or where possible, an (R,R) or (S,S) enantiomer or a mixture of enantiomers thereof,
wherein G and $G^1$ are independently selected from carbon and N; the variables I, m, n, o and p denote numbers that are each independently selected from 0, 1, 2 or 3 provided that the sum total of l, m, n, o and p is 4, 5, 6 or 7, such that the group represented by Q comprises a 6, 7, 8 or 9 membered bridged or fused heterocyclyl, respectively, and further provided that when G and $G^1$ are both N then the sum total of l/and o is not zero, and the sum total of m and p is not zero, and wherein n is an integer ranging from 0 to 3; (preferably, Q comprises a 7 or 8-membered ring; in one particular embodiment, n is zero, such that Q comprises a fused bicyclic ring);

U is selected from the group consisting of —$C_0$-$C_8$alkyl-C(O)—$C_0$-$C_3$alkyl-, —$C_1$-$C_8$alkyl-, —$C_0$-$C_8$alkyl-N($R^3$)—C(O)—$C_0$-$C_3$alkyl-, —$C_0$-$C_8$alkyl-O—C(O)—$C_0$-$C_3$alkyl-, —$C_0$-$C_8$alkyl-N($R^3$)—C(S)—$C_0$-$C_3$alkyl-, —$C_0$-$C_8$alkyl-O—C(S)—$C_0$-$C_3$alkyl-, —$C_0$-$C_8$alkyl-N($R^3$)—S(O)$_2$—$C_0$-$C_3$alkyl-, —$C_0$-$C_8$alkyl-heterocyclyl-$C_0$-$C_3$alkyl-, a covalent bond and —O—$C_2$-$C_4$alkyl-; and $U^1$ is selected from the group consisting of H, —C($R^1$)($R^2$)—, —$C_0$-$C_8$alkyl-C(O)—$C_0$-$C_3$alkyl-, —$C_1$-$C_8$alkyl-, —$C_0$-$C_8$alkyl-N($R^3$)—C(O)—$C_0$-$C_3$alkyl-, —C($R^1$)($R^2$)—N($R^3$)—C(O)—$C_0$-$C_3$alkyl-, —C($R^1$)($R^2$)—C(O)—$C_0$-$C_3$alkyl-, —$C_0$-$C_8$alkyl-O—C(O)—$C_0$-$C_3$alkyl-, —C($R^1$)($R^2$)—O—C(O)—$C_0$-$C_3$alkyl-, —$C_0$-$C_8$alkyl-N($R^3$)—C(S)—$C_0$-$C_3$alkyl-, —$C_0$-$C_8$alkyl-O—C(S)—$C_0$-$C_3$alkyl-, —$C_0$-$C_8$alkyl-N($R^3$)—S(O)$_2$—$C_0$-$C_3$alkyl-, —$C_0$-$C_8$alkyl-heterocyclyl-$C_0$-$C_3$alkyl-, a covalent bond, ($R^3$)($R^{3a}$)N—$C_2$-$C_4$alkyl-, —O—$C_2$-$C_4$alkyl-, and $R^3$—O—$C_2$-$C_4$alkyl-; or Q is selected from the group consisting of a covalent bond, —$C_1$-$C_8$alkyl-, —$C_1$-$C_8$alkyl-, —$C_1$-$C_8$heterocyclyl-, =N—O—, —$C_0$-$C_6$alkyl-N($R^3$)—$C_0$-$C_3$alkyl-, —$C_0$-$C_6$alkyl-O—$C_0$-$C_3$alkyl-, —$C_0$-$C_6$alkyl-S(O)$_{0-2}$—$C_0$-$C_3$alkyl-, —$C_0$-$C_6$alkyl-heterocyclyl-$C_0$-$C_3$alkyl-, —$C_0$-$C_6$alkyl-C(O)—$C_0$-$C_3$alkyl-, —$C_0$-$C_6$alkyl-O—$C_0$-$C_3$alkyl-, —$C_0$-$C_6$alkyl-cycloalkyl-$C_0$-$C_3$alkyl-, —$C_0$-$C_6$alkyl-N($R^3$)—C(O)-cycloalkyl-$C_0$-$C_3$alkyl-, —$C_0$-$C_6$alkyl-N($R^3$)-cycloalkyl-$C_0$-$C_3$alkyl-, —$C_0$-$C_6$alkyl-S(O)$_{0-2}$—N($R^3$)-cycloalkyl-$C_0$-$C_3$alkyl-, —$C_0$-$C_6$alkyl-N($R^3$)—C(O)—N($R^3$)-cycloalkyl-$C_0$-$C_3$alkyl-, —$C_0$-$C_6$alkyl-O—C(O)-β-cycloalkyl-$C_0$-$C_3$alkyl-, —$C_0$-$C_6$alkyl-N($R^3$)—C(O)—O-cycloalkyl-$C_0$-$C_3$alkyl-, —$C_0$-$C_6$alkyl-(CR$^3$=CR$^3$)$_{1-2}$—$C_0$-$C_6$alkyl-, —$C_0$-$C_6$alkyl-(C≡C)$_{1-2}$—$C_0$-$C_6$alkyl-, —$C_0$-$C_6$alkyl-N($R^3$)—C(O)—$C_0$-$C_3$alkyl-, —$C_0$-$C_6$alkyl-N($R^3$)—C(O)-alkenyl-$C_0$-$C_4$alkyl-, —$C_0$-$C_6$alkyl-C(O)—N($R^3$)—$C_0$-$C_4$alkyl-, —$C_0$-$C_6$alkyl-SO$_2$—N($R^3$)—$C_0$-$C_3$alkyl-, —$C_0$-$C_6$alkyl-N($R^3$)—SO$_2$—$C_3$alkyl-, —$C_0$-$C_3$alkyl-N($R^3$)—S(O)$_2$—N($R^3$)—$C_0$-$C_3$alkyl-, —$C_0$-$C_6$alkyl-S—$C_0$-$C_3$alkyl-, —$C_0$-$C_6$alkyl-S(O)—$C_0$-$C_3$alkyl-, —$C_0$-$C_6$alkyl-S(O)$_2$—$C_0$-$C_3$alkyl-, —$C_0$-$C_6$alkyl-N($R^3$)—C(O)—N($R^3$)—$C_0$-$C_3$alkyl-, =N—O—$C_0$-$C_3$alkyl-, -heterocyclyl-$C_0$-$C_3$alkyl-heterocyclyl-$C_0$-$C_3$alkyl-, —SO$_2$—$C_0$-$C_6$alkyl-heterocyclyl-$C_0$-$C_3$alkyl-, —C(O)—$C_0$-$C_6$alkyl-bridged heterocyclyl-$C_0$-$C_3$alkyl-, —N($R^3$)—C(O)—$C_0$-$C_6$alkyl-heterocyclyl-$C_0$-$C_3$alkyl-, —O—C(O)—$C_0$-$C_6$alkyl-heterocyclyl-$C_0$-$C_3$alkyl-, —N($R^3$)—C(S)—$C_0$-$C_6$alkyl-heterocyclyl-$C_0$-$C_3$alkyl-, —O—C(S)—$C_0$-$C_6$alkyl-heterocyclyl-$C_0$-$C_3$alkyl-, —N($R^3$)—S(O)$_2$—$C_0$-$C_6$alkyl-heterocyclyl-$C_0$-$C_3$alkyl-, —$C_0$-$C_6$alkyl-heterocyclyl-$C_0$-$C_3$alkyl-SO$_2$—N($R^3$)—, —$C_0$-$C_6$alkyl-heterocyclyl-$C_0$-$C_3$alkyl-C(O)—N($R^3$)— and —$C_0$-$C_6$alkyl-heterocyclyl-$C_0$-$C_3$alkyl-C(O)—O—, wherein each alkyl, alkenyl, alkynyl, heteroalkyl, cycloalkyl, heterocyclyl, aryl and heteroaryl moiety is optionally substituted; wherein

Ⓑ— is selected from the group consisting of b-1a to b-1k and b-1 to b-125, and wherein when Q is attached to

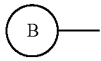

via =N—O—, or =N—O—$C_{0-3}$alkyl, it is attached through carbon Sola-Penna et al.[2] in

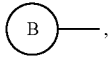

and wherein each alkyl, heteroalkyl, cycloalkyl, heterocyclyl and alkenyl moiety is optionally substituted; and wherein when Q is a covalent bond and J is attached to

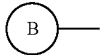

via =CH—, then it is attached through carbon sp$^2$ in

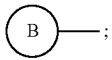

or
when

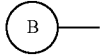

is selected from the group consisting of b-1 to b-121 and is attached to Q via a N in

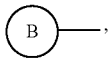

then Q is selected from the group consisting of a covalent bond, —C(O)—$C_1$-$C_3$alkyl-O—, —$C_1$-$C_8$alkyl-, —$C_2$-$C_6$alkyl-N($R^3$)—$C_0$-$C_3$alkyl-, —$C_0$-$C_6$alkyl-heterocyclyl-$C_0$-$C_3$alkyl-, —$C_0$-$C_6$alkyl-C(O)—$C_0$-$C_3$alkyl-, —$C_0$-$C_6$alkyl-O—$C_0$-$C_3$alkyl-, —$C_1$-$C_6$alkyl-(CR$^3$=CR$^3$)$_{1-2}$-$C_0$-$C_6$alkyl-, —$C_1$-$C_6$alkyl-(C≡C)$_{1-2}$-$C_0$-$C_6$alkyl-, —$C_2$-$C_6$alkyl-N($R^3$)—C(O)—$C_0$-$C_3$alkyl, —$C_2$-$C_6$alkyl-N($R^3$)—C(O)-alkenyl-$C_0$-$C_3$alkyl, —$C_0$-$C_6$alkyl-C(O)—N($R^3$)—$C_0$-$C_4$alkyl-, —C(O)—O—$C_0$-$C_4$alkyl-, —$C_0$-$C_6$alkyl-S(O)$_2$—N($R^3$)—$C_0$-$C_3$alkyl, —$C_2$-$C_6$alkyl-N($R^3$)—S(O)$_2$—$C_0$-$C_3$alkyl, —$C_2$-$C_3$alkyl-N($R^3$)—S(O)$_2$—N($R^3$)—$C_0$-$C_3$alkyl-, —$C_2$-$C_6$alkyl-S—$C_0$-$C_3$alkyl, —$C_2$-$C_6$alkyl-S(O)—$C_0$-$C_3$alkyl, —$C_0$-$C_6$alkyl-S(O)$_2$—$C_0$-$C_3$alkyl, —$C_2$-$C_6$alkyl-N($R^3$)—C(O)—N($R^3$)—$C_0$-$C_3$alkyl, —$C_2$-$C_3$alkyl-C=N—O—$C_0$-$C_3$alkyl, —SO$_2$—$C_0$-$C_6$alkyl-heterocyclyl-$C_0$-$C_3$alkyl-, —C(O)—$C_0$-$C_6$alkyl-heterocyclyl-$C_0$-$C_3$alkyl-, —$C_2$-$C_4$alkyl-N($R^3$)—C(O)—$C_0$-$C_6$alkyl-heterocyclyl-$C_0$-$C_3$alkyl-, —$C_2$-$C_4$alkyl-O—C(O)—$C_0$-$C_6$alkyl-heterocyclyl-$C_0$-$C_3$alkyl-, —$C_2$-$C_4$alkyl-N($R^3$)—C(S)—$C_0$-$C_6$alkyl-heterocyclyl-$C_0$-$C_3$alkyl-, —$C_2$-$C_4$alkyl-O—C(S)—$C_0$-$C_6$alkyl-heterocyclyl-$C_0$-$C_3$alkyl-, —$C_2$-$C_4$alkyl-N($R^3$)—S(O)$_2$—$C_0$-$C_6$alkyl-heterocyclyl-$C_0$-$C_3$alkyl-, —$C_0$-$C_6$alkyl-heterocyclyl-$C_0$-$C_3$alkyl-S(O)$_2$—N($R^3$)—, —$C_0$-$C_6$alkyl-heterocyclyl-$C_0$-$C_3$alkyl-C(O)—N($R^3$)— and —$C_0$-$C_6$alkyl-heterocyclyl-$C_0$-$C_3$alkyl-C(O)—O—, wherein each alkyl, heterocyclyl and alkenyl moiety is optionally substituted, and wherein the heterocyclyl moiety is optionally bridged with —(CH$_2$)$_{0-3}$—;

$R^1$ and $R^2$ are independently selected from the group consisting of —H, $C_1$-$C_6$alkyl, aryl, heteroaryl, heterocyclyl, cycloalkyl and a protecting group;

each $R^3$ is independently selected from the group consisting of —H, alkyl, $C_0$-$C_3$alkyl-heterocyclyl, $C_1$-$C_3$alkyl-$C_2$-$C_6$alkenyl, $C_1$-$C_3$alkyl-$C_2$-$C_3$alkynyl, —$C_2$-$C_4$alkyl-OR$^1$, —$C_2$-$C_4$alkyl-NR$^{3b}$R$^{3c}$, —$C_2$-$C_4$alkyl-NR$^1$R$^2$, heteroalkyl, $C_0$-$C_6$alkylheteroaryl, C(O)CF$_3$, —C(O)—NH$_2$, —C(O)—NR$^{3b}$R$^{3c}$, —C(O)—NR$^1$R$^2$, —C(O)—OR$^1$, —S(O)$_2$—NR$^1$R$^2$, —S(O)$_2$—R$^1$, —C(O)—R$^1$, —$C_3$-$C_6$cycloalkyl, —$C_0$-$C_3$alkyl-$C_3$-$C_7$cycloalkyl, —$C_1$-$C_6$alkylaryl, aryl, $C_0$-$C_3$alkyl-heteroaryl and heteroaryl, wherein each alkyl, alkenyl, alkynyl, heteroalkyl, cycloalkyl, heterocyclyl, aryl and heteroaryl moiety is optionally substituted with from one to three independently selected substituents;

each $R^{3a}$ is independently selected from the group consisting of —H, alkyl, heterocyclyl, $C_2$-$C_6$alkenyl, $C_2$-$C_3$alkynyl, $C_2$-$C_4$alkyl-OR$^1$, heteroalkyl, heteroaryl, $C_0$-$C_6$alkylheteroaryl, C(O)CF$_3$, —C(O)—NH$_2$, —$C_3$-$C_6$cycloalkyl, -alkyl-$C_3$-$C_6$cycloalkyl, —$C_1$-$C_6$alkylaryl, aryl, alkylheteroaryl and heteroaryl, covalent bond, wherein each alkyl, alkenyl, alkynyl, heteroalkyl, cycloalkyl, heterocyclyl, aryl and heteroaryl moiety is optionally substituted;

wherein $R^3$ and $R^{3a}$, together with the atom to which they are attached, optionally form a heterocyclic ring, wherein the heterocyclyl moiety is optionally substituted;

wherein $R^{3b}$ and $R^{3c}$, together with the atom to which they are attached, optionally form a heterocyclic ring, wherein the heterocyclyl moiety is optionally substituted;

provided that

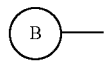

is absent when Q is structure (a-1), (a-2), (a-3), (a-20) or when $U^1$ is H, N($R^3$)($R^{3a}$)—$C_2$-$C_4$alkyl- or $R^3$—O—$C_2$-$C_4$alkyl-;

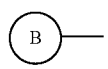

is selected from the group consisting of hydrogen, aryl, arylalkyl-, heteroaryl, heteroaryl-alkyl-, heterocyclyl, cycloalkyl, heterocyclyl-alkyl, cycloalkyl-alkyl, $C_1$-$C_{10}$alkyl, (aryl)$_2$-CH—$C_0$-$C_6$alkyl-, (aryl)(heteroaryl)CH—$C_0$-$C_6$alkyl- and (heteroaryl)$_2$CH—$C_0$-$C_6$alkyl-, each of which is optionally substituted; or

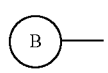

is a radical selected from the group consisting of
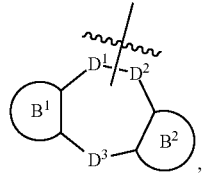 (b-1a)
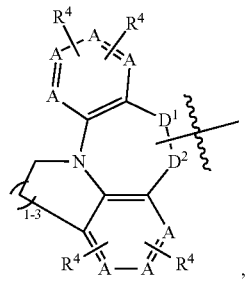 (b-1b)
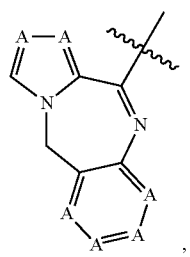 (b-1c)
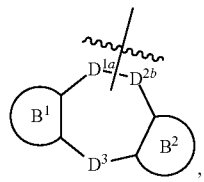 (b-1d)
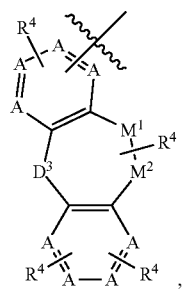 (b-1e)
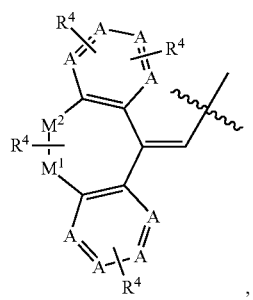 (b-1f)
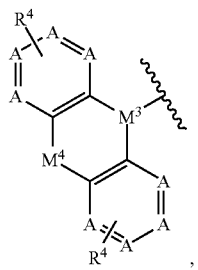 (b-1g)
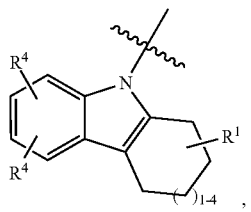 (b-1h)
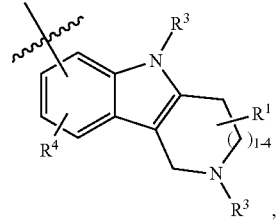 (b-1i)
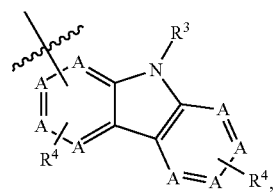 (b-1j)
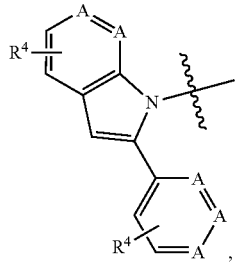 (b-1k)
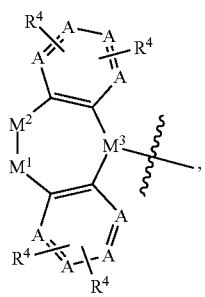 (b-1l)

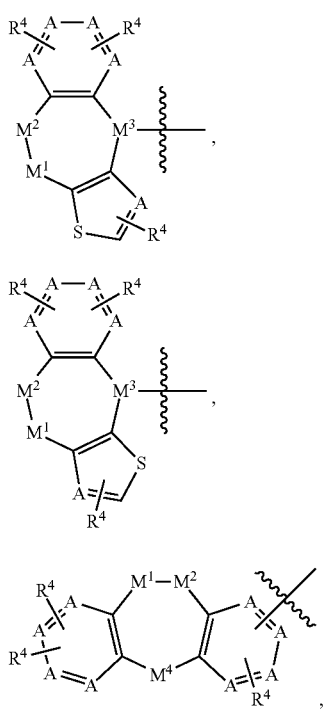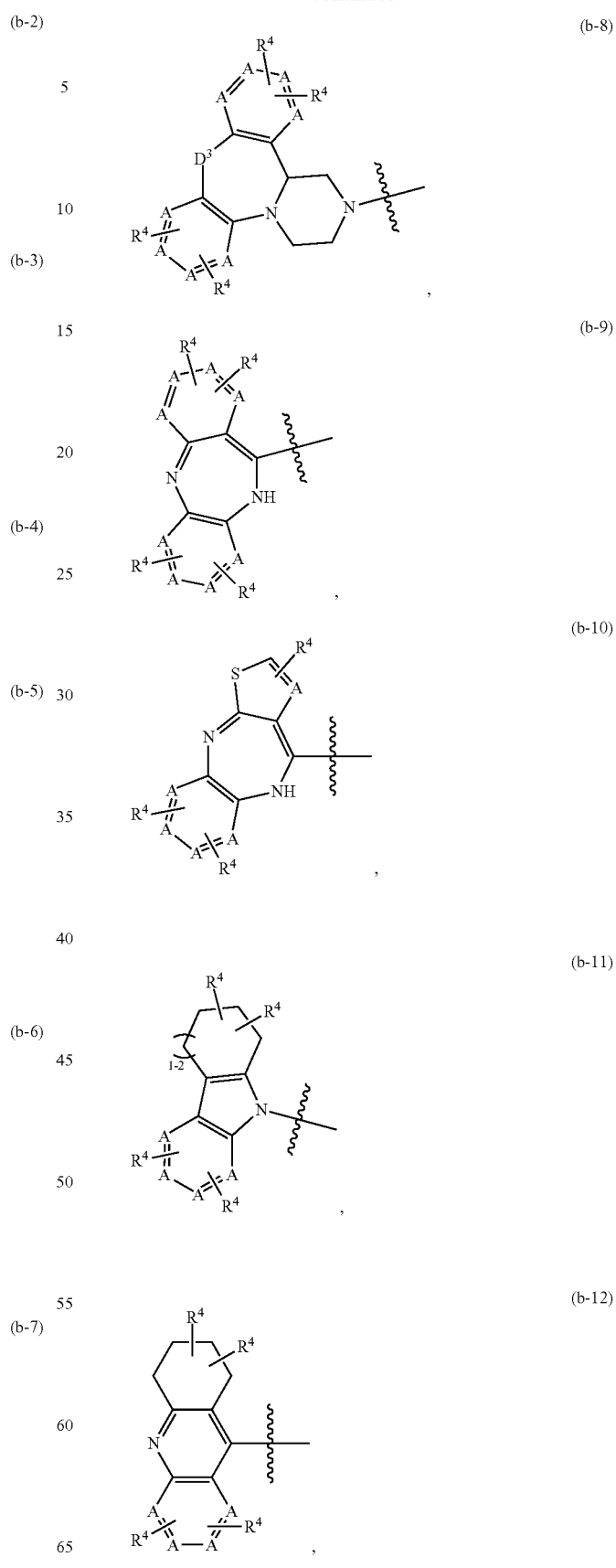

-continued
(b-13)
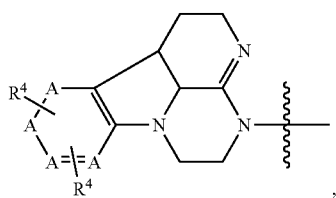
(b-14)
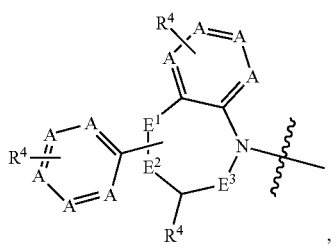
(b-15)
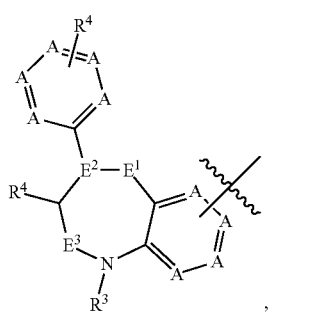
(b-16)
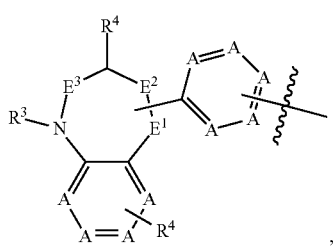
(b-17)
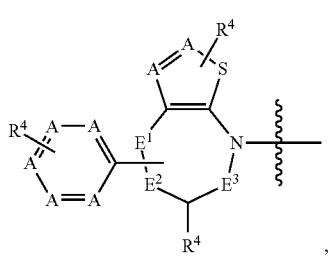
(b-18)
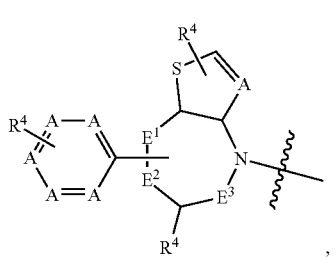
(b-19)
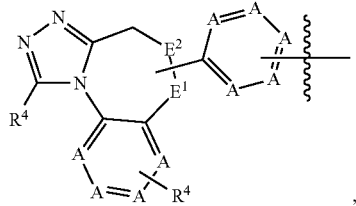
(b-20)
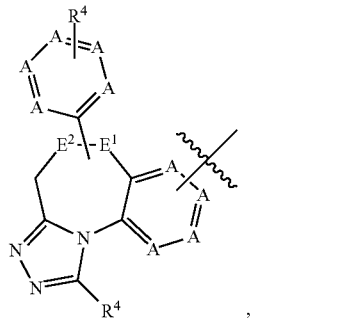
(b-21)
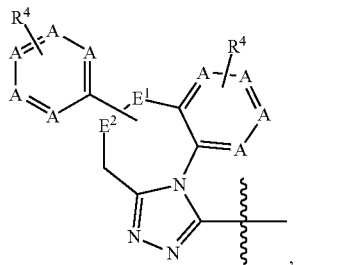
(b-22)
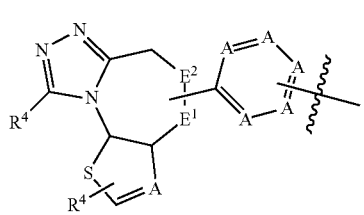
(b-23)
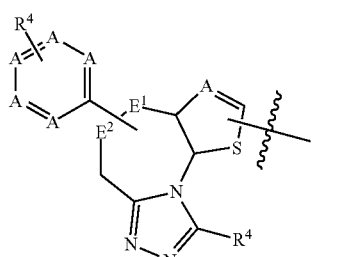
(b-24)
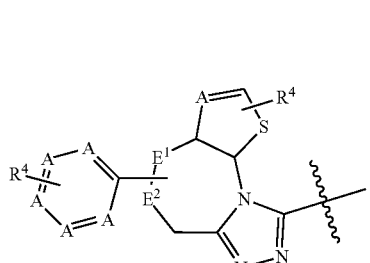

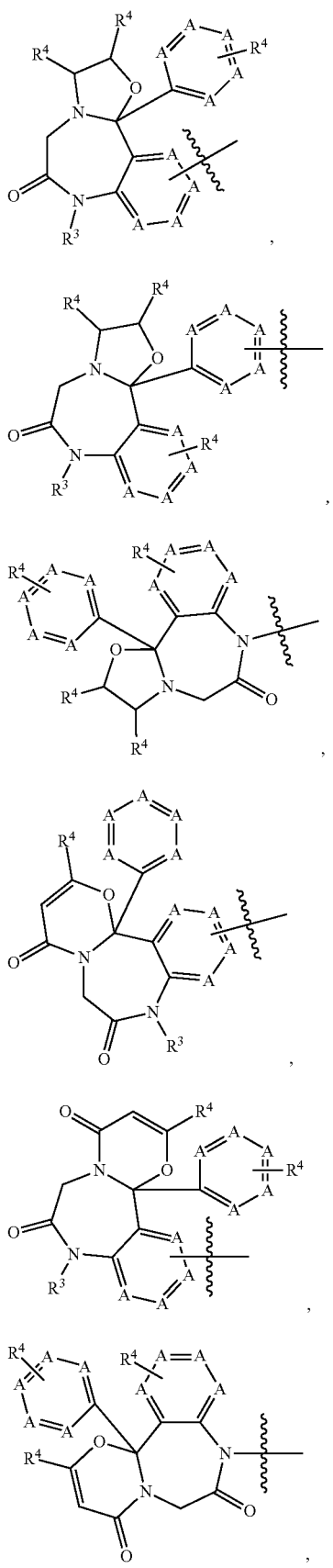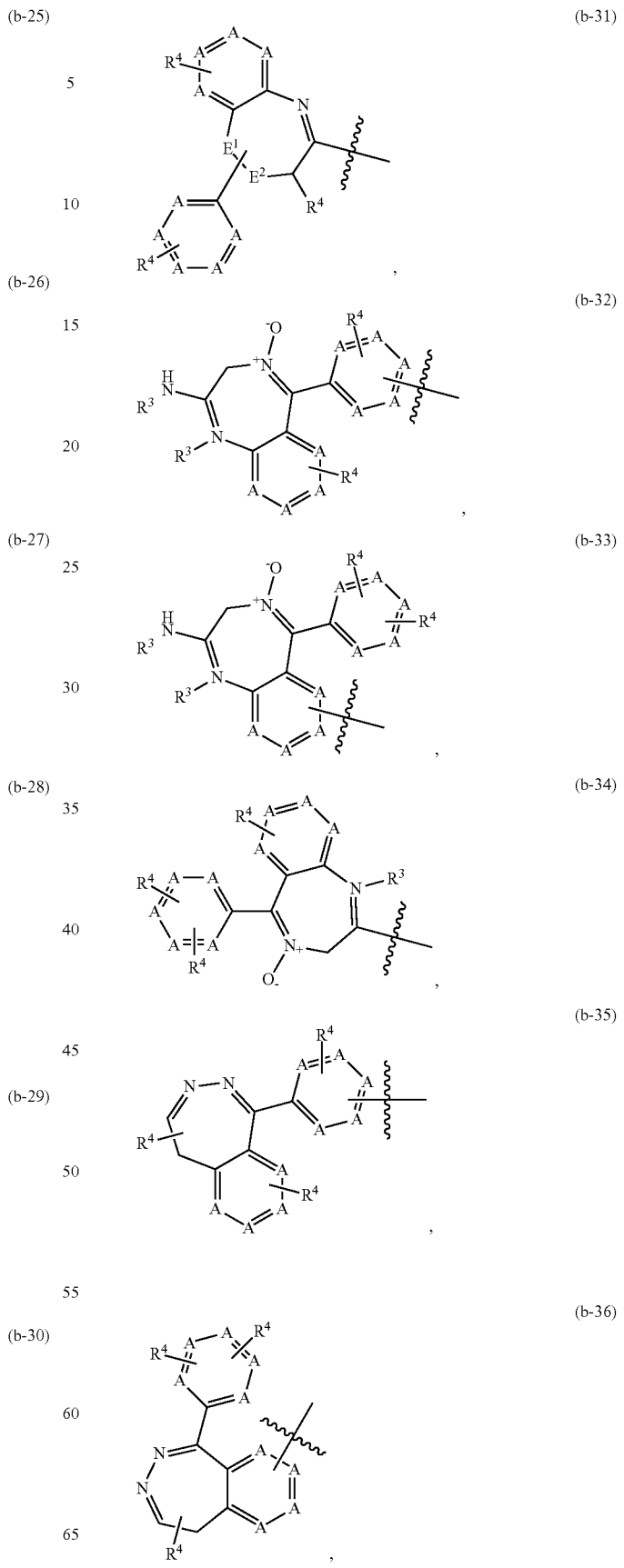

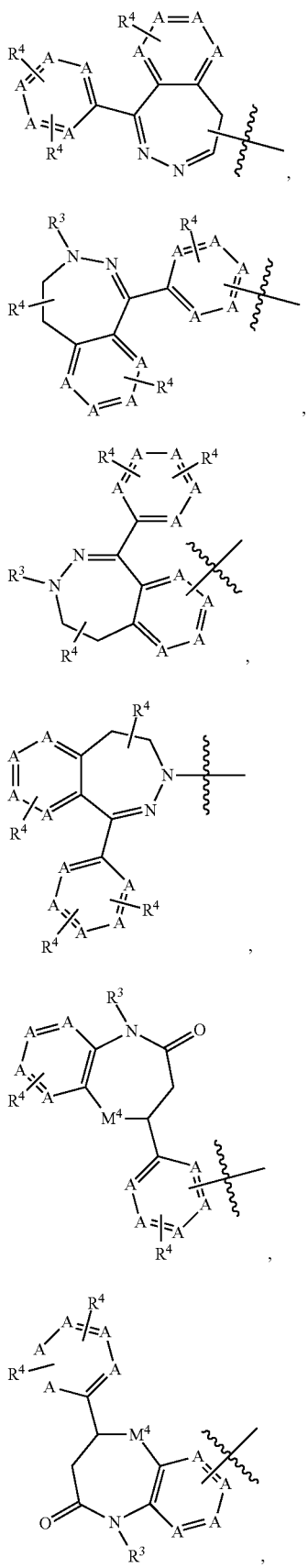
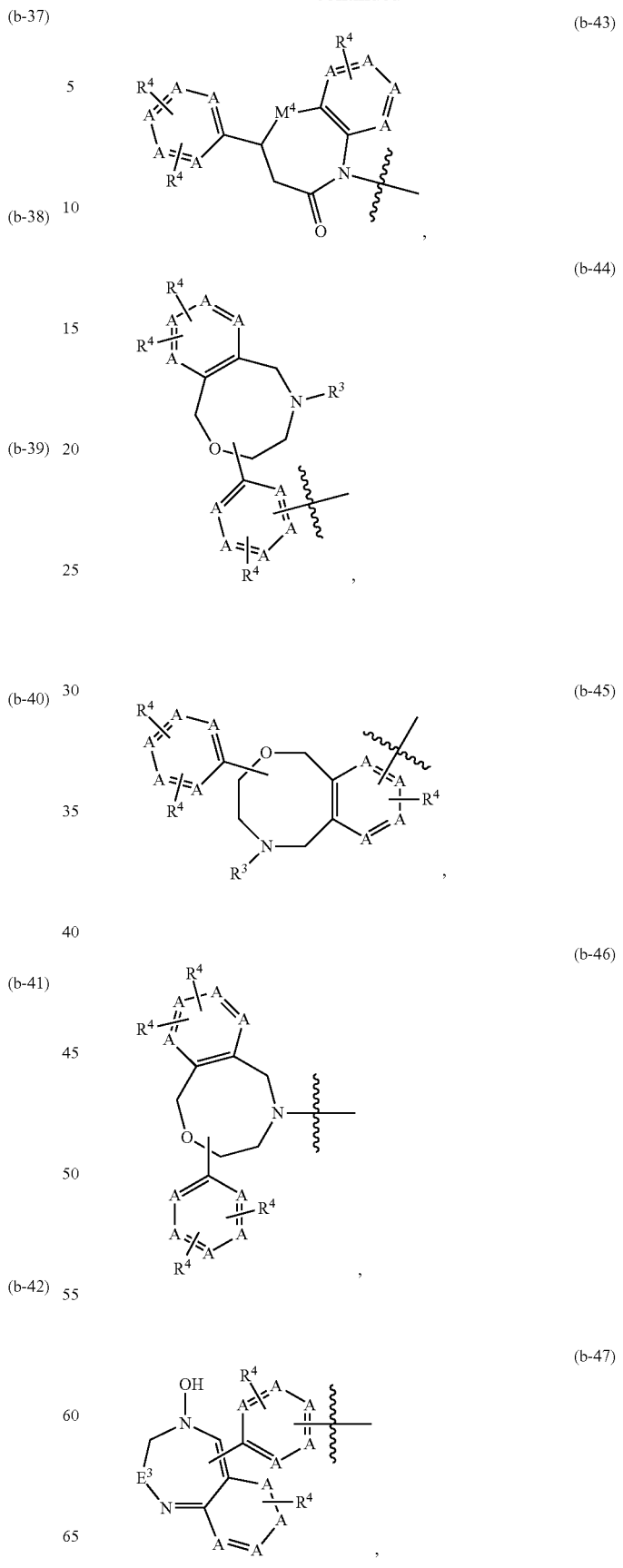

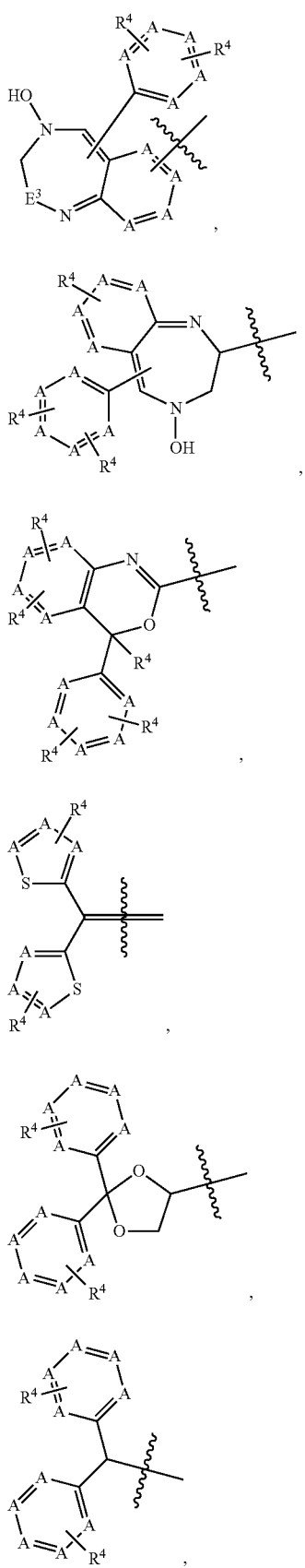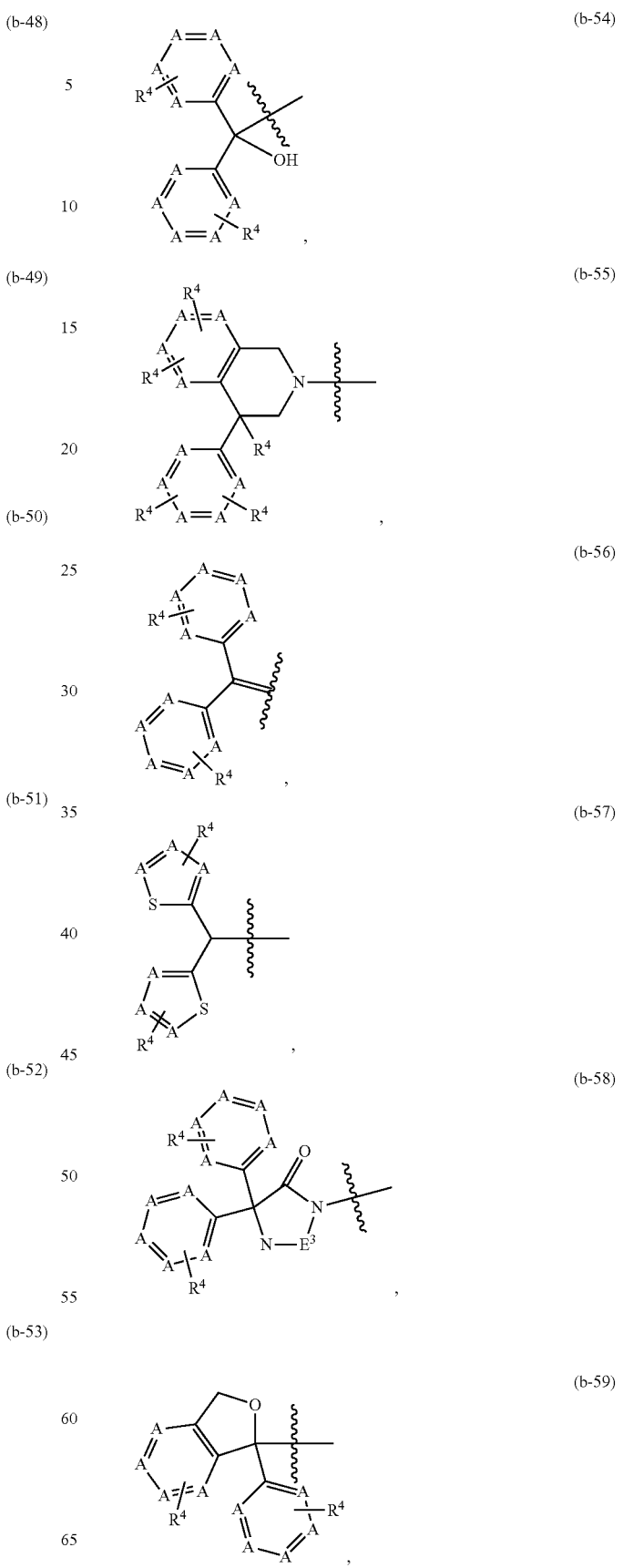

(b-60) 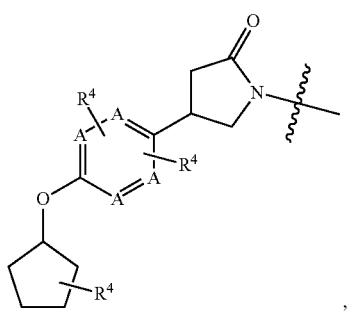
(b-61) 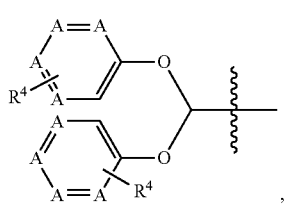
(b-62) 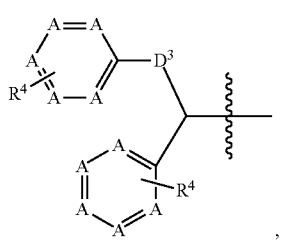
(b-63) 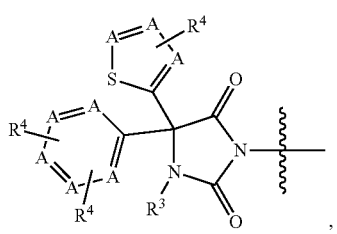
(b-64) 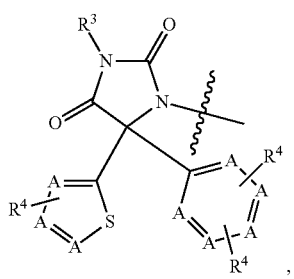
(b-65) 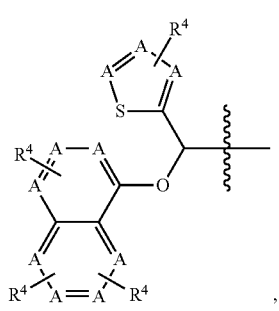
(b-66) 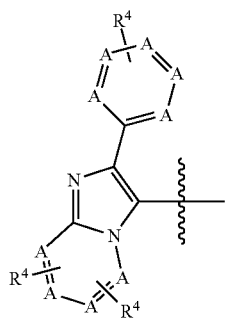
(b-67) 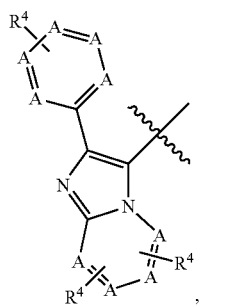
(b-68) 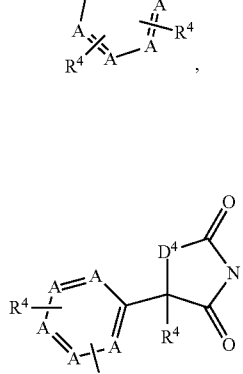
(b-69) 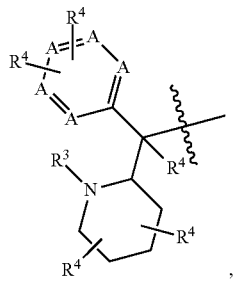
(b-70) 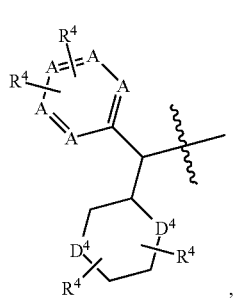

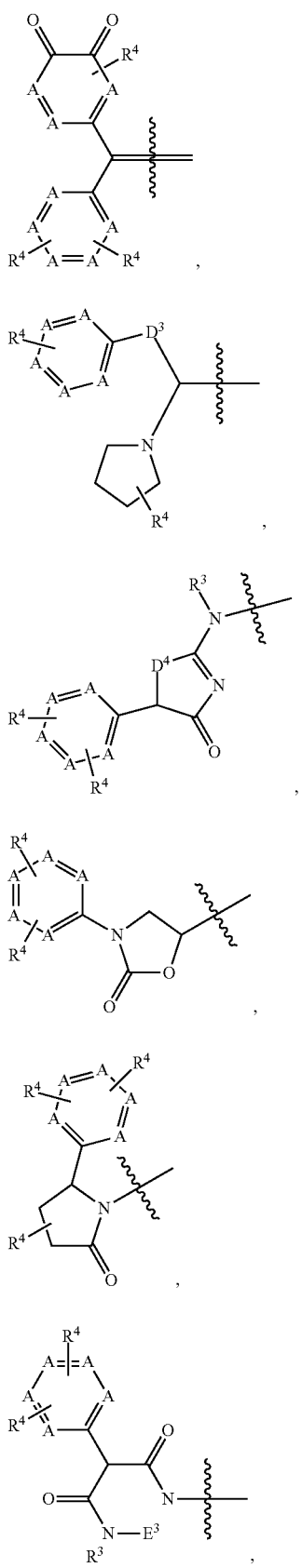
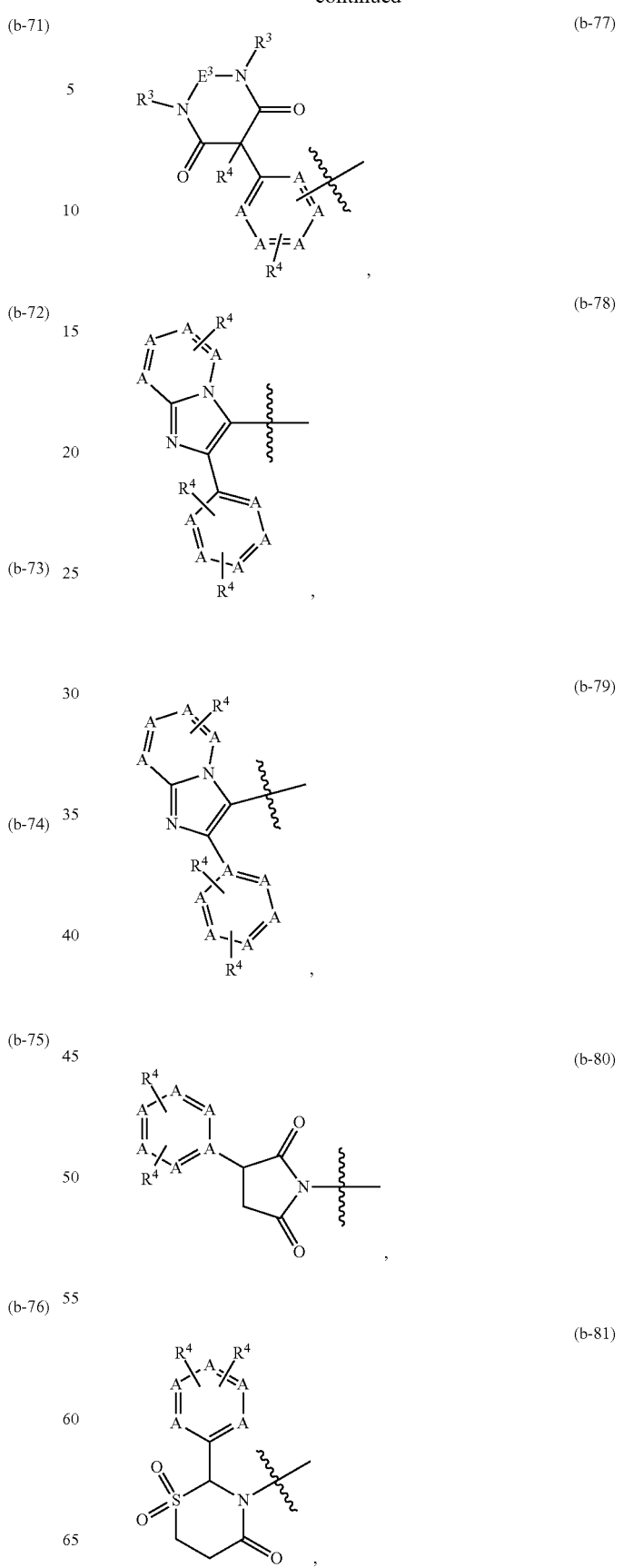

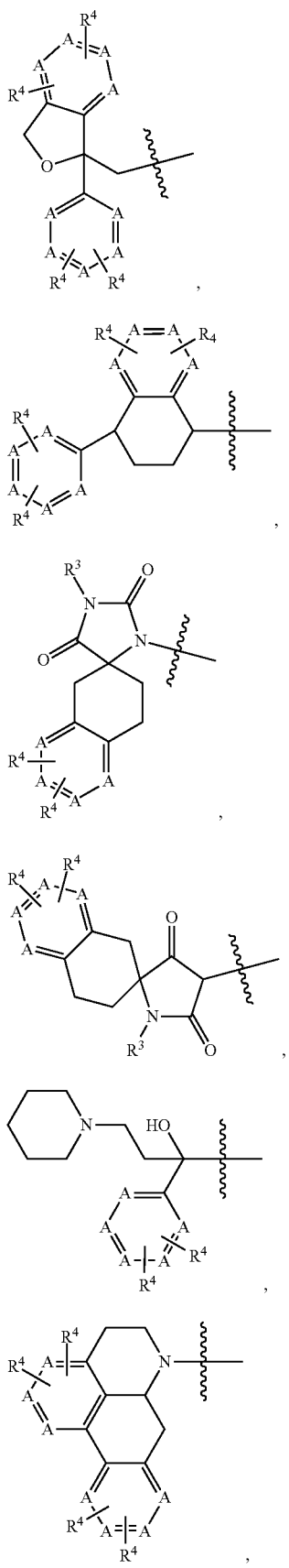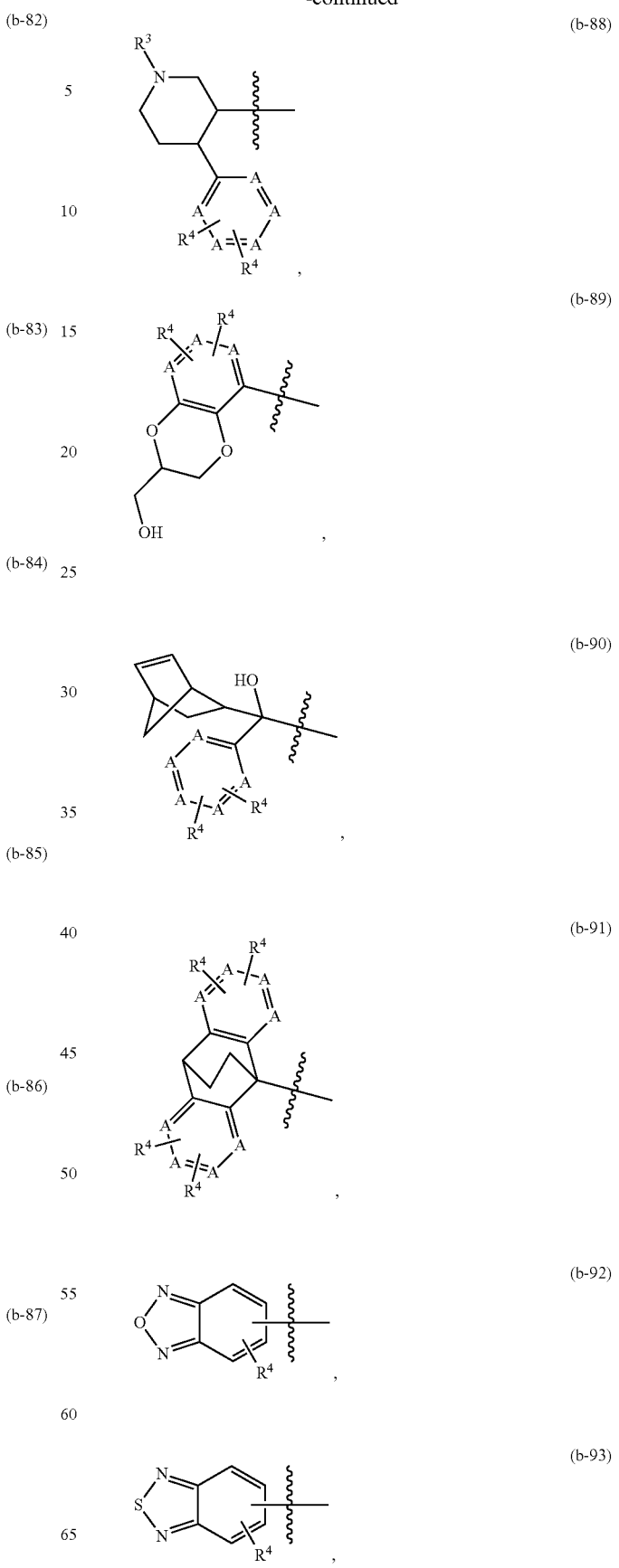

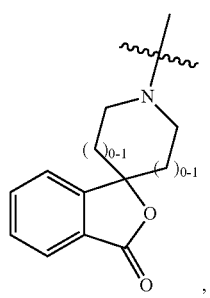
(b-94)
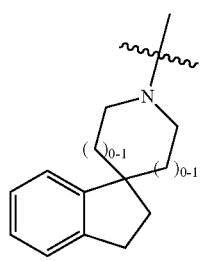
(b-95)
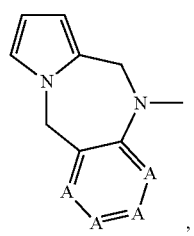
(b-96)
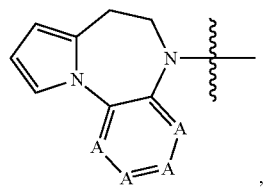
(b-97)
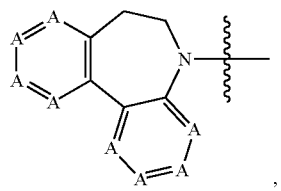
(b-98)
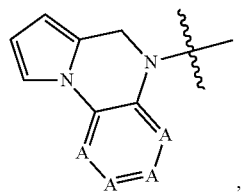
(b-99)
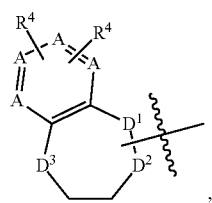
(b-100)
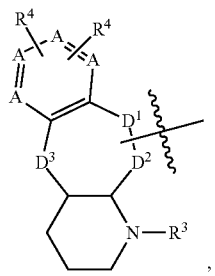
(b-101)
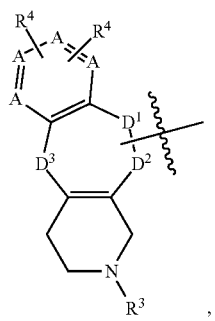
(b-102)
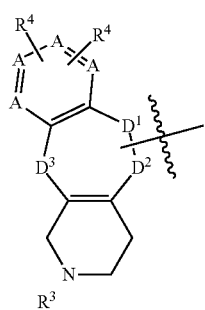
(b-103)
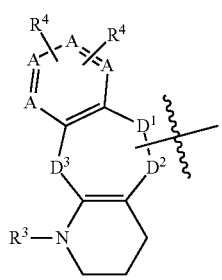
(b-104)
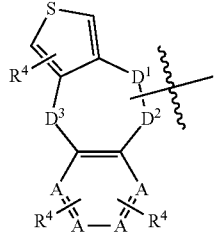
(b-105)

(b-106) 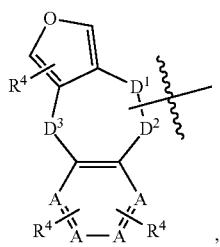
(b-107) 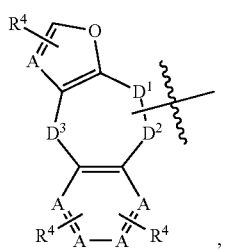
(b-108) 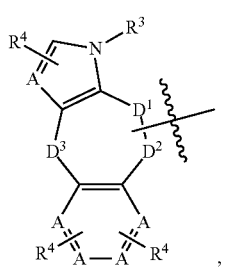
(b-109) 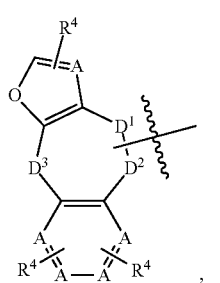
(b-110) 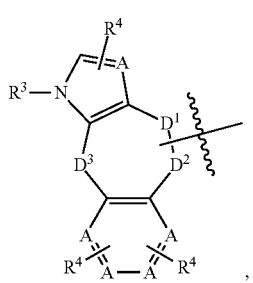
(b-111) 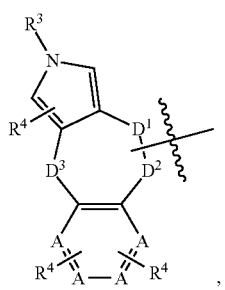
(b-112) 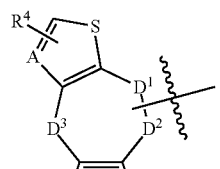
(b-113) 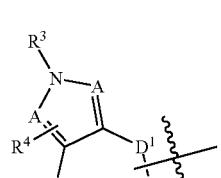
(b-114) 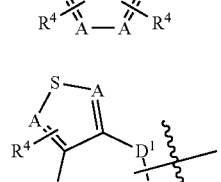
(b-115) 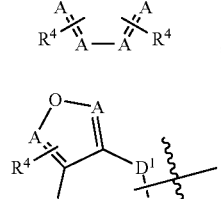
(b-116) 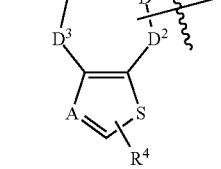
(b-117) 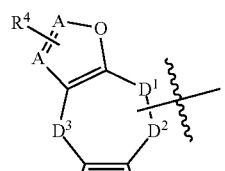

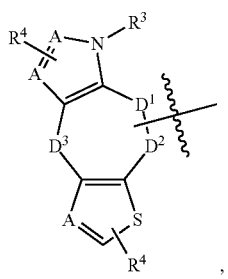
(b-118)

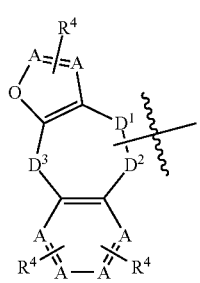
(b-119)

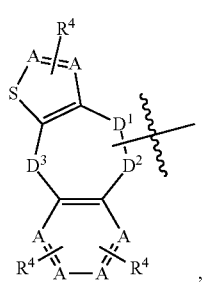
(b-120)

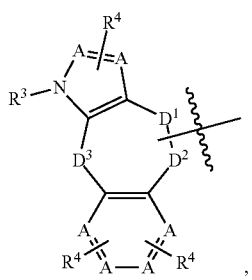
(b-121)

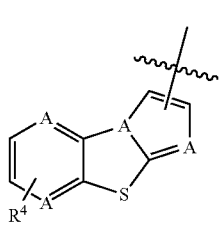
(b-122)

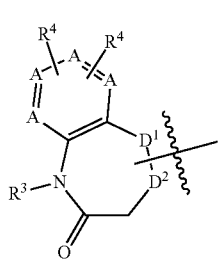
(b-123)

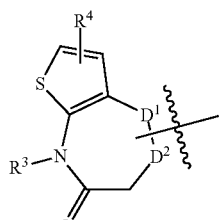
(b-124)

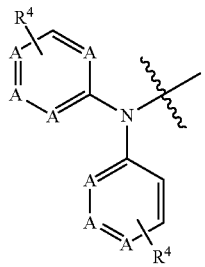
(b-125)

wherein

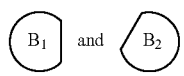

are independently selected from phenyl, a 5- or 6-membered heteroaryl and heterocyclyl, each of which is optionally substituted with one to three independently selected substituents; provided that when

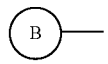

is selected from the group consisting of hydrogen, aryl, aryl-alkyl-, heteroaryl, heteroaryl-alkyl-, heterocyclyl, cycloalkyl, heterocyclyl-alkyl, cycloalkyl-alkyl, $C_1$-$C_{10}$alkyl, (aryl)$_2$CH—$C_0$-$C_6$alkyl-, (aryl)(heteroaryl)CH—$C_0$-$C_6$alkyl- and (heteroaryl)$_2$CH—$C_0$-$C_6$alkyl-, each of which is optionally substituted, then Q is selected from the group consisting of a-3, a-4, a-5, a-6, a-7, a-8, a-9, a-10, a-11, a-12, a-13 and a-14, wherein
each A is independently selected from the group consisting of N, —N-oxide, —CH═ and —C($R^4$)═, wherein no more than two A per 5 or 6 membered ring are N in a

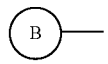

group, and wherein no more than one A is —N-oxide;
the group $M^1$-$M^2$ is selected from the group consisting of a covalent bond, —N($R^3$)$CH_2$—, —$CH_2$N($R^3$)—, —S(O)$_{0-2}$—$CH_2$—, —$CH_2$S(O)$_{0-2}$—, —O—$CH_2$—, —$CH_2$—O—, —C(O)N($R^3$)—, —C(O)—O—, —C(O)—$CH_2$—, —CH(OH)—$CH_2$—, —CH(F)—$CH_2$—, —$CH_2$—C(O)—, —$CH_2$—CH(OH)—, —$CH_2$—CH(F)—, —N($R^3$)—C(O)—, —$SO_2$N($R^3$)—, —N($R^3$)$SO_2$—, —CH($R^4$)$CH_2$—, —$CH_2$CH($R^4$)—, —N═C($R^4$)—, —C($R^4$)═N—, —$CH_2$—$CH_2$—, —CH═CH—, —CH($R^3$)—CH($R^3$)—, —C($R^3$)═C($R^3$)—, —C($R^4$)═C($R^4$)—, —CF═CH—, —CH═CF—,

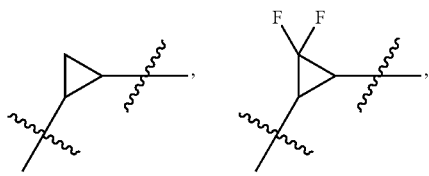 [SMILES: *C1CC1* ; *C1C(*)C1(F)F]

—CH$_2$—, —C(R$^3$)(R$^{3a}$)—, —S(O)$_{0-2}$—, —N(R$^3$)—, or absent;

M$^3$ is selected from the group consisting of

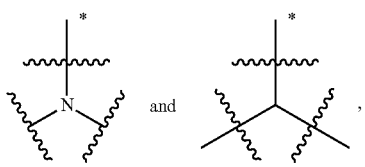

or M$^3$ is

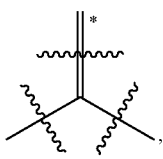

wherein Q is attached to

via =N—O—, or =N—O—C$_{0-3}$alkyl, or J is attached to

via =CH—,
wherein * represents the point of attachment to Q;
M$^4$ is selected from the group consisting of

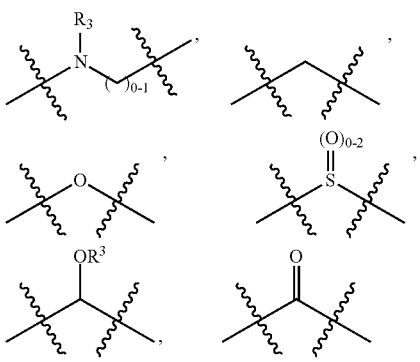

and covalent bond;

wherein, when M$^1$-M$^2$ is a covalent bond, M$^4$ is selected from the group consisting of

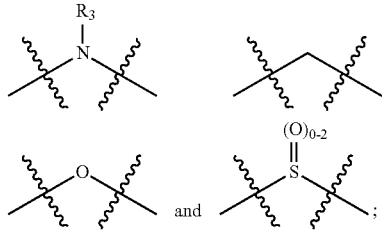

the groups D$^1$-D$^2$ and D$^{1a}$-D$^{2a}$ are selected from the group consisting of

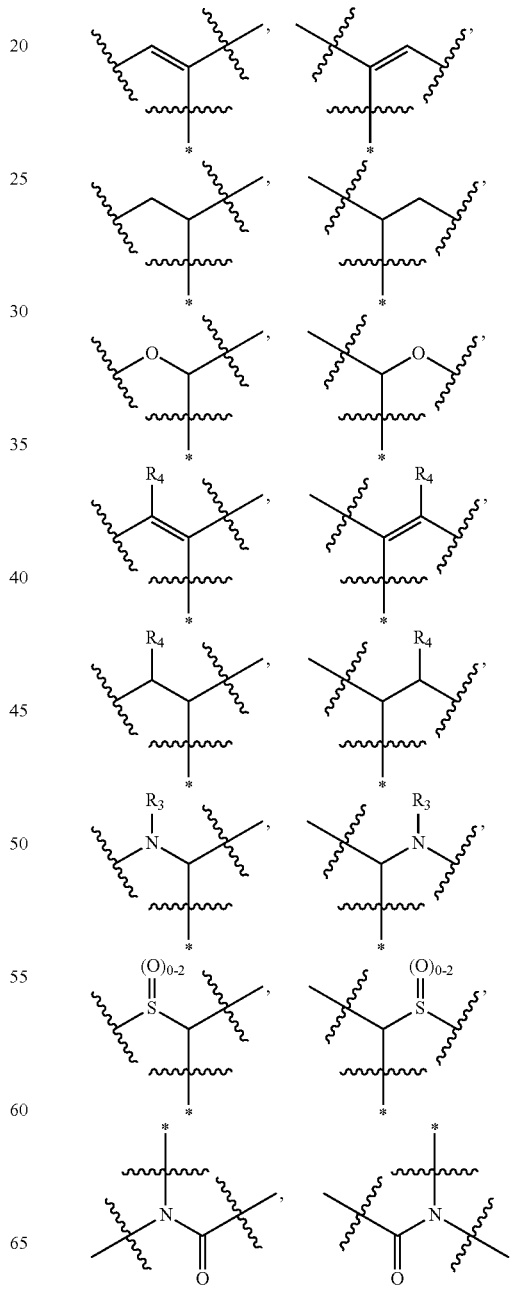

-continued

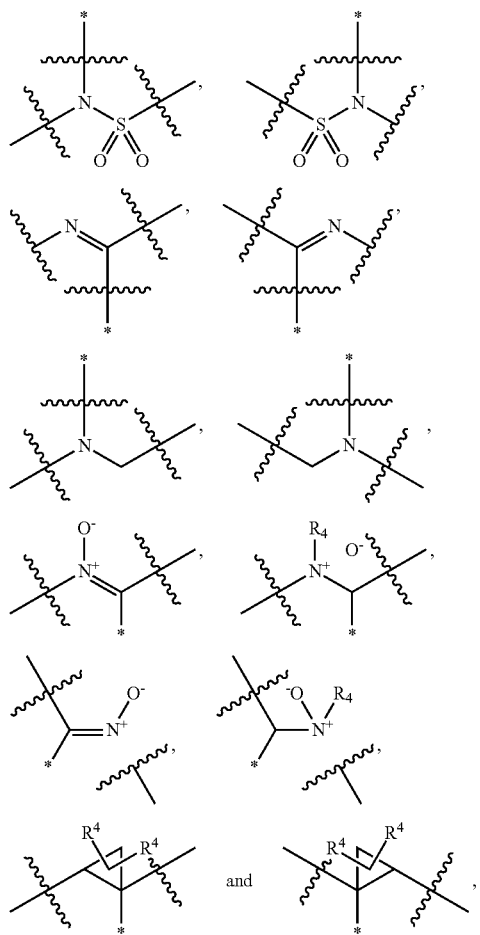

wherein, * represents the point of attachment to Q;
D³ is selected from the group consisting of a covalent bond,

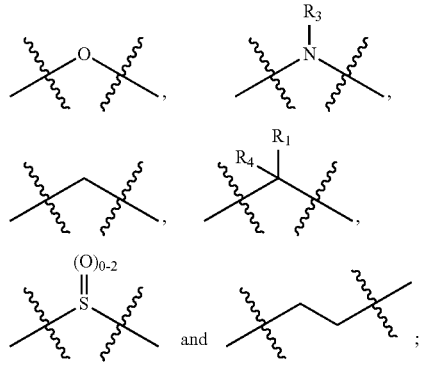

wherein the

and

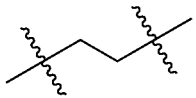 [SMILES: *CC*]

are optionally substituted;
D⁴ is selected from the group consisting of

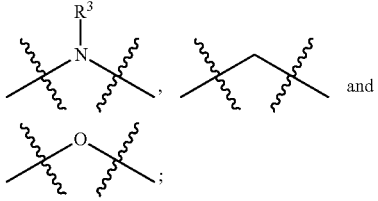

wherein the

is optionally substituted;
the group E¹-E² is selected from the group consisting of

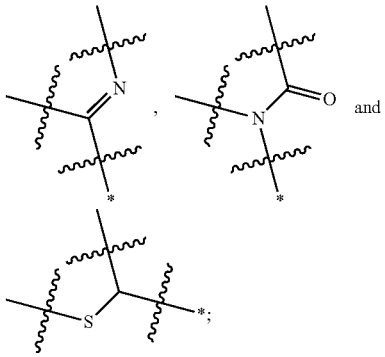

wherein * represents the point of attachment to Q; and
E³ is selected from the group consisting of —C(O)—, —C(S)—, —CH₂—, —C(OH)₂— and —C=N(R³)—; and
R⁴ is independently selected from the group consisting of —H, $C_1$-$C_6$alkyl, $C_2$-$C_6$alkenyl, $C_2$-$C_6$alkynyl, $C_1$-$C_6$alkyl-R³, —$C_0$-$C_6$alkyl-OR³, —$C_0$-$C_6$alkyl-OR¹, —$C_0$-$C_6$alkyl-C(O)—OR³, —$C_0$-$C_6$alkyl-C(O)NR³, $R^{3a}$, —CH=CH—C(O)—OR³, —CH=CH—C(O)—N(R³)($R^{3a}$), —N(R³)—C(O)—CF³, —N(R³)—$C_2$-$C_6$alkyl-N(R³)($R^{3a}$), —$C_0$-$C_6$alkyl-N(R³)($R^{3a}$), —N(R³)—C(O)—$C_1$-$C_6$alkyl-R³, —N(R³)—S(O)₂—$C_1$-$C_6$alkyl-R³, —S(O)₂—N(R³)$R^{3a}$, —O—$C_2$-$C_6$alkyl-N(R³)($R^{3a}$), —O—$C_2$-$C_6$alkyl-OR¹, —S—R³, —S(O)—$C_1$-$C_6$alkyl-R³, —S(O)₂—$C_1$-$C_6$alkyl-R³, $C_3$-$C_6$cycloalkyl, heterocyclyl, $C_4$-$C_7$heterocyclyl-R³, —O—$C_2$-$C_4$alkyl-heterocyclyl, —O-heterocyclyl-C(O)—OR³, —O—$C_0$-$C_4$alkyl-aryl, —O—$C_0$-$C_4$alkyl-heteroaryl, —O—C(O)—NR³—$C_0$-$C_4$alkyl-aryl, —O—C(O)—NR³—$C_0$-$C_4$alkyl-heteroaryl, —O—$C_0$-$C_4$alkyl-heterocyclylaryl, —O—$C_0$-$C_4$alkyl-heterocyclyl-heteroaryl, —N(R³)—$C_2$-$C_4$alkyl-heterocyclyl, —N(R³)C(O)N(R³)—$C_0$-$C_4$alkyl-heterocyclyl-R³, —$C_0$-$C_4$alkyl-OC(O)—R³, —$C_0$-$C_4$alkyl-N $(R^3)C(O)-O-R^3$, $-C_0-C_4$alkyl-heterocyclyl-C(O)-O-$R^3$, $-N(R^3)-C_2-C_4$alkyl-heterocyclyl, F, Cl, Br, I, $NO_2$, $-CF_3$, $-OCF_3$, $-OCHF_2$, $-SCF_3$, $-SF_5$, $-SO_3H$, $-CN$, $-C_1-C_6$ alkylaryl, aryl, heteroaryl, cycloalkyl, $-C_1-C_6$ alkylheteroaryl, wherein each alkyl, alkenyl, alkynyl, cycloalkyl, heterocyclyl, aryl and heteroaryl moiety of the aforementioned $R^4$ is optionally substituted;
or

is selected from the group consisting of structures b-1a to b-1k and (b-1) to (b-125) and Q-J-L taken together is selected from the group consisting of $-C_3-C_8$alkyl-, $-C(O)-C_3-C_8$alkyl-, $-C_0-C_3$alkyl-O-$C_3-C_8$alkyl-, $-C_0-C_3$alkyl-$C_1-C_4$alkenyl-$C_0-C_3$alkyl-, $=N-O-C_1-C_8$alkyl, $=N-O-C_0-C_3$alkyl-aryl-$C_0-C_3$alkyl-, $=N-O-C_0-C_3$alkyl-aryl-$C_0-C_3$alkenyl-, $=N-O-C_0-C_3$alkyl-aryl-$C_0-C_3$alkynyl-, $=N-O-C_0-C_3$alkyl-heteroaryl-$C_0-C_3$alkyl-, $=N-O-C_0-C_3$alkyl-heteroaryl-$C_0-C_3$alkenyl-, $=N-O-C_0-C_3$alkyl-heteroaryl-$C_0-C_3$alkynyl-, $-C_0-C_3$alkyl-aryl-$C_0-C_3$alkyl-, $-C_0-C_3$alkyl-aryl-$C_2-C_4$alkenyl-, $-C_0-C_3$alkyl-aryl-$C_2-C_4$alkynyl-, $-C_0-C_3$alkyl-heteroaryl-$C_0-C_3$alkyl-, $-C_0-C_3$alkyl-heteroaryl-$C_1-C_3$alkenyl-, $-C_0-C_3$alkyl-heteroaryl-$C_1-C_3$alkynyl-, $-C_0-C_3$alkyl-N(R^3)-$C_0-C_3$alkyl-aryl-$C_0-C_3$alkyl-, $-C_0-C_3$alkyl-N(R^3)-$C_0-C_3$alkyl-aryl-$C_2-C_3$alkenyl-, $-C_0-C_3$alkyl-N(R^3)-$C_0-C_3$alkyl-aryl-$C_2-C_3$alkynyl-, $-C_0-C_3$alkyl-N(R^3)-$C_0-C_3$alkyl-heteroaryl-$C_0-C_3$alkyl-, $-C_0-C_3$alkyl-N(R^3)-$C_0-C_3$alkyl-heteroaryl-$C_2-C_3$alkenyl-, $-C_0-C_3$alkyl-N(R^3)-$C_0-C_3$alkyl-heteroaryl-$C_2-C_3$alkynyl-, $-C_0-C_3$alkyl-C(O)-N(R^3)-$C_0-C_3$alkyl-aryl-$C_0-C_3$alkyl-, $-C_0-C_3$alkyl-N(R^3)-C(O)-$C_0-C_3$alkyl-aryl-$C_0-C_3$alkyl-, $-C_0-C_3$alkyl-C(O)-N(R^3)-$C_0-C_3$alkyl-aryl-$C_2-C_3$alkenyl-, $-C_0-C_3$alkyl-N(R^3)-C(O)-$C_0-C_3$alkyl-aryl-$C_2-C_3$alkenyl-, $-C_0-C_3$alkyl-C(O)-N(R^3)-$C_0-C_3$alkyl-aryl-$C_2-C_3$alkynyl-, $-C_0-C_3$alkyl-N(R^3)-C(O)-$C_0-C_3$alkyl-aryl-$C_2-C_3$alkynyl-, $-C_0-C_3$alkyl-C(O)-N(R^3)-$C_0-C_3$alkyl-heteroaryl-$C_0-C_3$alkyl-, $-C_0-C_3$alkyl-N(R^3)-C(O)-$C_0-C_3$alkyl-heteroaryl-$C_0-C_3$alkyl-, $-C_0-C_3$alkyl-C(O)-N(R^3)-$C_0-C_3$alkyl-heteroaryl-$C_2-C_3$alkenyl-, $-C_0-C_3$alkyl-N(R^3)-C(O)-$C_0-C_3$alkyl-heteroaryl-$C_2-C_3$alkenyl-, $-C_0-C_3$alkyl-C(O)-N(R^3)-$C_0-C_3$alkyl-heteroaryl-$C_2-C_3$alkynyl-, $-C_0-C_3$alkyl-N(R^3)-C(O)-$C_0-C_3$alkyl-heteroaryl-$C_2-C_3$alkynyl-, $-C_0-C_3$alkyl-heteroaryl-$C_0-C_3$alkyl-aryl-$C_0-C_3$alkyl-, $-C_0-C_3$alkyl-C(O)-heterocyclyl-$C_0-C_3$alkyl-aryl-$C_0-C_3$alkyl-, $-C_0-C_3$alkyl-N(R^3)-C(O)-heterocyclyl-$C_0-C_3$alkyl-aryl-$C_0-C_3$alkyl-, $-C_0-C_3$alkyl-O-C(O)-heterocyclyl-$C_0-C_3$alkyl-aryl-$C_0-C_3$alkyl-, $-C_0-C_3$alkyl-heterocyclyl-$C_0-C_3$alkyl-aryl-$C_2-C_4$alkenyl-, $-C_0-C_3$alkyl-C(O)-heterocyclyl-$C_0-C_3$alkyl-aryl-$C_2-C_4$alkenyl-, $-C_0-C_3$alkyl-N(R^3)-C(O)-heterocyclyl-$C_0-C_3$alkyl-aryl-$C_2-C_4$alkenyl-, $-C_0-C_3$alkyl-O-C(O)-heterocyclyl-$C_0-C_3$alkyl-aryl-$C_2-C_4$alkenyl-, $-C_0-C_3$alkyl-heterocyclyl-$C_0-C_3$alkyl-aryl-$C_2-C_4$alkynyl-, $-C_0-C_3$alkyl-C(O)-heterocyclyl-$C_0-C_3$alkyl-aryl-$C_2-C_4$alkynyl-, $-C_0-C_3$alkyl-N(R^3)-C(O)-heterocyclyl-$C_0-C_3$alkyl-aryl-$C_2-C_4$alkynyl-, $-C_0-C_3$alkyl-O-C(O)-heterocyclyl-$C_0-C_3$alkyl-aryl-$C_2-C_4$alkynyl-, $-C_0-C_3$alkyl-heterocyclyl-$C_0-C_3$alkyl-heteroaryl-$C_0-C_3$alkyl, $-C_0-C_3$alkyl-C(O)-heterocyclyl-$C_0-C_3$alkyl-heteroaryl-$C_0-C_3$alkyl, $-C_0-C_3$alkyl-N(R^3)-C(O)-heterocyclyl-$C_0-C_3$alkyl-heteroaryl-$C_0-C_3$alkyl, $-C_0-C_3$alkyl-O-C(O)-heterocyclyl-$C_0-C_3$alkyl-heteroaryl-$C_0-C_3$alkyl, $-C_0-C_3$alkyl-heterocyclyl-$C_1-C_3$alkyl-heteroaryl-$C_2-C_3$alkenyl-, $-C_0-C_3$alkyl-C(O)-heterocyclyl-$C_1-C_3$alkyl-heteroaryl-$C_2-C_3$alkenyl-, $-C_0-C_3$alkyl-N(R^3)-C(O)-heterocyclyl-$C_1-C_3$alkyl-heteroaryl-$C_2-C_3$alkenyl-, $-C_0-C_3$alkyl-O-C(O)-heterocyclyl-$C_1-C_3$alkyl-heteroaryl-$C_2-C_3$alkenyl-, $-C_0-C_3$alkyl-heterocyclyl-$C_1-C_3$alkyl-heteroaryl-$C_2-C_3$alkynyl-, $-C_0-C_3$alkyl-C(O)-heterocyclyl-$C_1-C_3$alkyl-heteroaryl-$C_2-C_3$alkynyl-, $-C_0-C_3$alkyl-N(R^3)-C(O)-heterocyclyl-$C_1-C_3$alkyl-heteroaryl-$C_2-C_3$alkynyl-, $-C_0-C_3$alkyl-O-C(O)-heterocyclyl-$C_1-C_3$alkyl-heteroaryl-$C_2-C_3$alkynyl-, $-C_2-C_4$alkyl-O-$C_0-C_3$alkyl-aryl-, $-C_2-C_4$alkyl-O-$C_0-C_3$alkyl-aryl-$C_0-C_3$alkyl-, $-C_2-C_4$alkyl-O-$C_0-C_3$alkyl-aryl-$C_2-C_4$alkenyl, $-C_2-C_4$alkyl-O-$C_0-C_3$alkyl-aryl-$C_2-C_4$alkynyl, $-C_2-C_4$alkyl-O-$C_0-C_3$alkyl-heteroaryl-$C_0-C_3$alkyl, $-C_2-C_4$alkyl-O-$C_1-C_3$alkyl-heteroaryl-$C_2-C_3$alkenyl-, $-C_2-C_4$alkyl-O-$C_1-C_3$alkyl-heteroaryl-$C_2-C_3$alkynyl-, $-C_0-C_6$alkyl-U-bridged heterocyclyl-heteroaryl-$C_0-C_6$alkyl-, $-C_0-C_6$alkyl-U-bridged heterocyclyl-N(R^3)-heteroaryl-$C_0-C_6$alkyl-, $-C_0-C_6$alkyl-U-N(R^3)-bridged heterocyclyl-heteroaryl-$C_0-C_6$alkyl-, $-C_0-C_6$alkyl-U-bridged heterocyclyl-aryl-$C_0-C_6$alkyl-, $-C_0-C_6$alkyl-U-bridged heterocyclyl-N(R^3)-aryl-$C_0-C_6$alkyl-, $-C_0-C_6$alkyl-U-N(R^3)-bridged heterocyclyl-aryl-$C_0-C_6$alkyl-, $-C_0-C_6$alkyl-U-bridged heterocyclyl-aryl-$C_2-C_6$alkenyl-, $-C_0-C_6$alkyl-U-bridged heterocyclyl-N(R^3)-aryl-$C_2-C_6$alkenyl-, $-C_0-C_6$alkyl-U-N(R^3)-bridged heterocyclyl-aryl-$C_2-C_6$alkenyl-, $-C_0-C_6$alkyl-U-bridged heterocyclyl-heteroaryl-$C_2-C_6$alkenyl-, $-C_0-C_6$alkyl-U-bridged heterocyclyl-N(R^3)-heteroaryl-$C_2-C_6$alkenyl-, $-C_0-C_6$alkyl-U-N(R^3)-bridged heterocyclyl-heteroaryl-$C_2-C_6$alkenyl-, $-C_0-C_6$alkyl-bridged heterocyclyl-U-heteroaryl-$C_0-C_6$alkyl-, $-C_0-C_6$alkyl-N(R^3)-bridged heterocyclyl-U-heteroaryl-$C_0-C_6$alkyl-, $-C_0-C_6$alkyl-bridged heterocyclyl-N(R^3)-U-heteroaryl-$C_0-C_6$alkyl-, $-C_0-C_6$alkyl-bridged heterocyclyl-U-aryl-$C_0-C_6$alkyl-, $-C_0-C_6$alkyl-N(R^3)-bridged heterocyclyl-U-aryl-$C_0-C_6$alkyl-, $-C_0-C_6$alkyl-bridged heterocyclyl-N(R^3)-U-aryl-$C_0-C_6$alkyl-, $-C_0-C_6$alkyl-bridged heterocyclyl-U-aryl-$C_2-C_6$alkenyl-, $-C_0-C_6$alkyl-N(R^3)-bridged heterocyclyl-U-aryl-$C_2-C_6$alkenyl-, $-C_0-C_6$alkyl-bridged heterocyclyl-N(R^3)-U-aryl-$C_2-C_6$alkenyl-, $-C_0-C_6$alkyl-bridged heterocyclyl-U-heteroaryl-$C_2-C_6$alkenyl-, $-C_0-C_6$alkyl-N(R^3)-bridged heterocyclyl-U-heteroaryl-$C_2-C_6$alkenyl-, and $-C_0-C_6$alkyl-bridged heterocyclyl-N(R^3)-U-heteroaryl-$C_2-C_6$alkenyl-, wherein each alkyl, alkenyl, aryl, alkynyl, heteroaryl and heterocyclyl moiety is optionally substituted; and wherein the bridge is methylene or propylene;

provided that Formula (I) excludes those compounds wherein -Q-J-L-C(O)Z is optionally substituted $-C_1-C_{13}$alkyl-N(R^3)-$C_0-C_6$alkyl-aryl-$C_2$alkenyl-C(O)NHOH; and

is selected from the group consisting of aromatic polycycles, non-aromatic polycycles, mixed aryl and non-arylpolycycles, polyheteroaryl, non-aromatic polyheterocycles, and mixed aryl and non-aryl polyheterocycles, each of which is optionally substituted;
and
provided that Formula (I) excludes compounds of Formula (A)

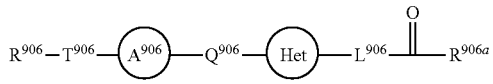

wherein $R^{906}$ is selected from the group consisting of aryl and heteroaryl;

$T^{906}$ is selected from the group consisting of —$C_{0-6}$alkyl-S(O)$_2$—$C_{0-6}$alkyl-, —$C_{0-6}$alkyl-C(O)—$C_0$-$C_6$alkyl- and $C_{1-3}$alkyl, wherein $T^{906}$ is substituted at the carbon atom attached to $R^{906}$ with a moiety selected from the group consisting of; aryl, heteroaryl, cycloalkyl and heterocycle;

$A^{906}$ is an optionally substituted unbridged heterocycle;

$Q^{906}$ is a bond;

Het is an optionally substituted 5-membered aryl ring;

$L^{906}$ is a bond or —$C_{1-4}$alkyl-; and $R^{906a}$ is —N($R^{906b}$)OH, wherein $R^{906b}$ is selected from the group consisting of H, optionally substituted alkyl and optionally substituted aryl;

and provided that Formula (I) excludes those compounds wherein -Q-J-L-C(O)Z is optionally substituted —$C_0$-$C_4$alkyl-X—$C_1$-$C_4$alkyl-phenyl-$C_2$alkenyl-C(O)NHOH;

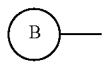

is a 5- or 6-membered aromatic heterocyclic group condensed with a carbon ring or other heterocyclic ring, which

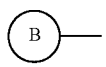

is substituted with 1 to 4 substituents selected from phenyl, another 5- or 6-membered aromatic heterocyclic group and a heterocyclic group, said heterocyclic group being optionally substituted with $C_{1-4}$alkyl, a benzyl group or a pyridylmethyl group; and X is a moiety having a structure selected from the group consisting of —C(O)N($R^{A1}$)—, —O—C(O)—N($R^{A1}$)—, —SO$_2$—, —N($R^{A2}$)SO$_2$—, wherein $R^{A1}$ and $R^{A2}$ are independently —H or optionally substituted $C_1$-$C_4$alkyl;

and provided that Formula (I) excludes compounds wherein B-Q- is

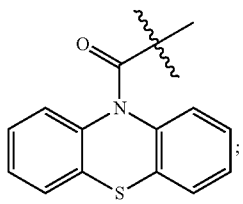 [SMILES: *C(=O)N1c2ccccc2Sc2ccccc21]

and
-J-L- is

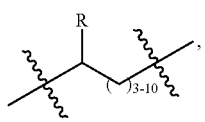

wherein R is directly attached or attached through a linker, and is selected from the group consisting of substituted or unsubstituted aryl, cycloalkyl, cycloalkylamino, naphtha, pyridineamino, piperidino, 9-purine-6-amine, thiazoleamino group, hydroxyl, branched or unbranched alkyl, alkenyl, alkyoxy, aryloxy, arylalkyloxy and pyridine group, wherein the linker is selected from the group consisting of an amide moiety, —O—, —S—, —NH— and —CH$_2$—; and provided that Formula (I) excludes compounds of Formula (B)

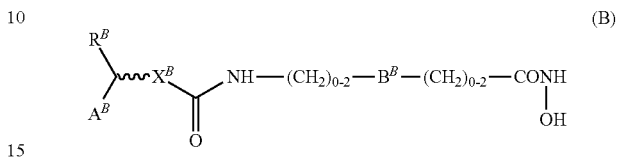

wherein $R^B$ is H or phenyl;

$A^B$ is a bi- or tricyclic residue optionally partially or totally unsaturated, and which optionally contains one or more heteroatoms selected from the group consisting of N, S and O, and optionally substituted by hydroxy, alkanoyloxy, primary, secondary or tertiary amino, amino$C_1$-$C_4$alkyl, mono- or di($C_1$-$C_4$)alkyl-amino$C_1$-$C_4$alkyl, halogen, $C_1$-$C_4$alkyl and tri($C_1$-$C_4$)alkylammonium$C_1$-$C_4$alkyl;

⁓⁓⁓ is a chain of 1 to 5 carbon atoms optionally containing a double bond or an NR group, wherein R is H or $C_1$-$C_4$alkyl;

$X^B$ is absent, an oxygen atom or an NR group, wherein R is H or $C_1$-$C_4$alkyl; and $B^B$ is a phenylene or cyclohexylene ring;

and provided that Formula (I) excludes compounds of Formula (D)

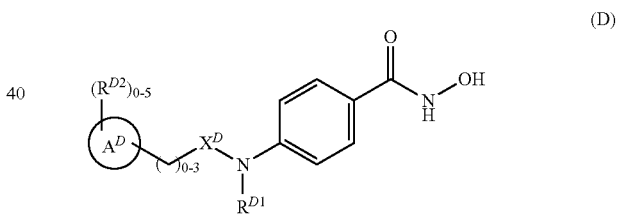

wherein $A^D$ is selected from the group consisting of a 4- to 10-membered aromatic or non-aromatic heterocyclyl;

$X^D$ is C=O or S(O)$_2$;

$R^{D1}$ is H or $C_1$-$C_6$alkyl;

$R^{D2}$ is independently selected from the group consisting of oxo, (C=O)—NH$_2$, $C_1$-$C_6$alkyl-aryl and heterocyclyl, when $A^D$ is a non-aromatic heterocycle, wherein said alkyl, and aryl moieties are optionally substituted with one to three $R^b$; or $R^{D2}$ is independently selected from the group consisting of OH, NO$_2$, (C=O)$_{0-1}$—$C_{0-1}$-$C_1$-$C_6$alkyl, CN, (C=O)$_{0-1}$—$C_{0-1}$-$C_3$-$C_{10}$cycloakyl, halogen, (C=O)$_{0-1}$—N($R^a$)$_2$, CF$_3$, NH—S(O)$_{0-2}$—$R^a$, (C=O)$_{0-1}$—O$_{0-1}$-heterocyclyl, (C=O)$_{0-1}$—O$_{0-1}$-aryl, S(O)$_{0-2}$—$R^a$, NH(C=O)$R^a$, $C_1$-$C_6$alkyl-aryl and heterocyclyl, when $A^D$ is an aromatic heterocyclyl, wherein said alkyl, cycloalkyl, aryl and heterocyclyl are optionally substituted with one to three $R^b$;

$R^a$ is independently H or $C_1$-$C_6$alkyl; and $R^b$ is independently selected from the group consisting of oxo, NO$_2$, N($R^a$)$_2$, OH, CN, halogen, CF$_3$ and $C_1$-$C_6$alkyl;

and
provided that Formula (I) excludes compounds of Formula (E)

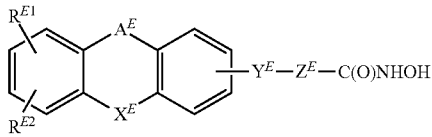

(E)

wherein
$A^E$ is selected from the group consisting of —CH$_2$—O—, —CH$_2$—S—, —CH$_2$—CH$_2$— and —NH—CO—;
$X^E$ is selected from the group consisting of —N(R$^{E3}$)—, =C(O) and —CH(OH)—;
$Y^E$ is selected from the group consisting of O, S and —N(R$^{E4}$)—;
$Z^E$ is selected from the group consisting of a straight chain C4-C8alkylene, wherein one CH$_2$ group may be replaced by an oxygen or a sulfur atom, or wherein 2 carbon atoms form a C=C double bond, and which is either unsubstituted or substituted by one or two substituents selected from C$_1$-C$_4$alkyl and halogen;
$R^{E1}$ and $R^{E2}$ are independently selected from the group consisting of H, halogen, C$_1$-C$_4$alkyl, trifluoromethyl, hydroxy, C$_1$-C$_4$alkoxy, benzyloxy, C$_1$-C$_3$alkylenedioxy, nitro, amino, C$_1$-C$_4$alkylamino, di[(C$_1$-C$_4$)alkyl]-amino, and C$_1$-C$_4$alkanoylamino; and
$R^{E3}$ and $R^{E4}$ are independently selected from H and C$_1$-C$_4$alkyl; and
provided that Formula (I) excludes compounds of Formula (F)

$A^F$-Q$^{1F}$-J$^F$-Q$^{2F}$-C(O)—NH—OH    (F)

wherein
$A^F$ is a C$_5$-C$_{20}$ aryl group or a 5-20 membered heteroaryl group, each having one ring or two or more fused rings, wherein at least one ring is aromatic, said ary and heteroaryl groups being optionally substituted;
$Q^{1F}$ is a linker group having a backbone length of at least 2 carbon atoms, the linker being optionally substituted;
$J^F$ is —N(R$^F$)—C(O)— or —C(O)—N(R$^F$)—;
$Q^{2F}$ is selected from the group consisting of C$_1$-C$_{10}$alkyl, C$_5$-C$_{20}$aryl, 5 to 20 membered heteroaryl, C$_5$-C$_{20}$aryl-C$_1$-C$_{10}$alkyl, 5 to 20 membered heteroaryl-C$_1$-C$_{10}$alkyl, C$_1$-C$_{10}$alkyl-O$_5$—C$_{20}$aryl and C$_1$-C$_{10}$alkyl-5 to 20 membered heteroaryl, each of which is optionally substituted; and
$R^F$ is selected from the group consisting of H, C$_1$-C$_7$alkyl, C$_3$-C$_{20}$heterocyclyl and C$_5$-C$_{20}$aryl, each of which is optionally substituted; and
provided that Formula (I) excludes compounds wherein Z is —N(R$^1$)(OR$^2$);

$R^1$ and $R^2$ are independently selected from the group consisting of H, C$_1$-C$_6$alkyl, aryl and heteroaryl;
L is a bond; and

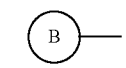

is selected from the group consisting of hydrogen, aryl, arylalkyl-, heteroaryl, heteroaryl-alkyl-, heterocyclyl, cycloalkyl, heterocyclyl-alkyl, cycloalkyl-alkyl, C$_1$-C$_{10}$alkyl, (aryl)$_2$-CH—C$_0$-C$_6$alkyl-, (aryl)(heteroaryl)CH—C$_0$-C$_6$alkyl- and (heteroaryl)$_2$CH—C$_0$-C$_6$alkyl-, each of which is optionally substituted; and
Q comprises a ring selected from the group consisting of

and

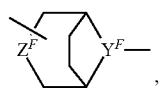

wherein $Y^u$ is nitrogen or —CH<, and $Z^F$ is oxygen, NH or —CH$_2$— if $Z^F$ is not bonded to

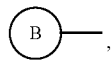

or $Z^u$ is nitrogen or —CH< if $Z^F$ is bonded to

through a covalent bond or a radical group selected from the group consisting of H, —C(R$^1$)(R$^2$)—, —C$_0$-C$_8$alkyl-C(O)—C$_0$-C$_3$alkyl-, —C$_1$-C$_8$alkyl-, —C$_0$-C$_8$alkyl-N(R$^3$)—C(O)—C$_0$-C$_3$alkyl-, —C(R$^1$)(R$^2$)—N(R$^3$)—C(O)—C$_0$-C$_3$alkyl-, —C(R$^1$)(R$^2$)—C(O)—C$_0$-C$_3$alkyl-, —C$_0$-C$_8$alkyl-β-C(O)—C$_0$-C$_3$alkyl-, —C(R$^1$)(R$^2$)—O—C(O)—C$_0$-C$_3$alkyl-, —C$_0$-C$_8$alkyl-N(R$^3$)—C(S)—C$_0$-C$_3$alkyl-, —C$_0$-C$_8$alkyl-O—C(S)—C$_0$-C$_3$alkyl-, —C$_0$-C$_8$alkyl-N(R$^3$)—S(O)$_2$—C$_0$-C$_3$alkyl-, —C$_0$-C$_8$alkyl-heterocyclyl-C$_0$-C$_3$alkyl-, a covalent bond, (R$^3$)(R$^{3a}$)N—C$_2$-C$_4$alkyl-, —O—C$_2$-C$_4$alkyl-, and R$^3$—O—C$_2$-C$_4$alkyl-; or

is selected from the group consisting of b-53, b-62 (wherein D$^3$ is

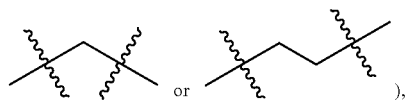

), b-69 (wherein R$^4$ is H), b-70, b-72 (wherein D$^3$ is

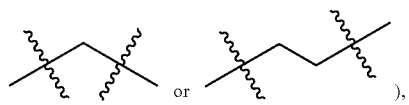

), b-92 and b-93; and

Q-J is selected from the group consisting of —$X^F$—$C_{0-4}$alkyl-aryl-$C_{0-4}$alkyl-, —$X^F$—$C_{0-4}$alkyl-heteroaryl-$C_{0-4}$alkyl-, and —$X^F$—$C_{0-4}$alkyl-heterocyclyl-$C_{0-4}$alkyl-, wherein said alkyl, aryl, heteroaryl, and heterocyclyl are optionally substituted, and wherein said heterocyclyl is a mono- or bi-saturated or mono- or bi-unsaturated heterocyclic ring, and wherein $X^F$ is selected from the group consisting of

[chemical structures]

wherein the left side attaches to

[structure with B]

and wherein r and s are each independently 0, 1, 2, 3, 4 or 5, wherein r and s cannot be both 0 and when r or s are 0 then a direct bound in intended; each r' is independently 0, 1, 3, 3 or 4 and r' cannot be 0 when s is 0; $R^{4A}$ is H, $C_{1-6}$alkyl or phenyl; $Y^F$ is nitrogen or —CH<, and $Z^F$ is oxygen, NH or —$CH_2$— if $Z^F$ is not bonded to

[structure with B]

or $Z^F$ is nitrogen or —CH< if $Z^F$ is bonded to

[structure with B]

and provided that Formula (I) excludes those compounds having the following structure:

[chemical structure]

wherein $X^9$ is selected from the group consisting of CO, $SO_2$ and $CH_2$;

$Y^9$ is selected from the group consisting of N—$R^{9f}$, CH—$OR^{9f}$, CH—$NR^{9f}R^{9i}$ and C=CH—CO—$R^{9g}$;

$A^9$ and $B^9$ are independently selected from 5- or 6-membered rings;

$R^{9a}$, $R^{9b}$, $R^{9c}$ and $R^{9d}$ are independently selected from the group consisting of H, halogen, $CF_3$, $NO_2$, $NR^{9i}R^{9j}$, CN, COOH, $(CH_2)_{0-2}$—$CONR^{9i}R^{9j}$, $C_{1-6}$alkyl, OH, O—$C_{1-6}$alkyl, O-cyclopropyl, O—$(CH_2)_2$—O—$C_{1-6}$alkyl, O—$(CH_2)_2$—$NR^{9i}R^{9j}$, O—$CONHR^{9i}$, $CH_2$—$Z^9$—$R^{9b}$, $COR^{9i}$, $CR^{9i}R^{9m}R^{9a}$, $SR^{9i}$, $SO_2R^{9i}$, $CR^{9i}NOR^{9i}$, $CR^{9i}NNR^{9i}R^{9j}$, a $Q^9$-$(CH_2)_{2-9}$CONHOH group, furan, thiophene, pyrrole, oxazole, thiazole, imidazole, pyrazole, isoxazole, isothiazole, 1,2,3-oxathiazole, 1,2,3-triazole, pyridine, pyridazine, pyrimidine, pyrazine, morpholine thiomorpholine, piperidine and pyrrolidine;

$R^{9e}$ and $R^{9f}$ are $Q^{9a}$-$(CH_2)_{2-9}$CONHOH;

$R^{9g}$ is NH—$(CH_2)_{2-9}$CONHOH;

$R^{9h}$ is a $(CH_2)P$—$R^{9k}$ group, wherein $R^{9k}$ can be methyl or hydroxyl;

$Z^9$ is selected from the group consisting of O, $NR^{9L}$ and S;

$Q^9$ is selected from the group consisting of a chemical bond, —O—, —S—, —$NR^{9L}$—, —$NR^{9i}CO$—, —$CONR^{9i}$—, —$W^9$—, —$COW^9$—, wherein $W^9$ is piperidine or pyrrolidine;

$Q^{9a}$ is a bond or a —CO—;

$R^{9i}$ and $R^{9j}$ are independently H or a $C_{1-6}$alkyl;

$R^{9L}$ is H or $R^{9h}$;

$R^{9m}$ and $R^{9n}$ can either be a fluorine atom or oxygen atoms linked together by an alkyl chain consisting of 2 or 3 $CH_2$; and $R^{9o}$ is a $C_{1-6}$alkyl; provided that (1) only one $(CH_2)_{2-9}$CONHOH is present in the molecule and (2) when $X^9$ is CO and $A^9$ and $B^9$ are both benzene then $R^{9c}$ and $R^{9d}$ cannot signify $Q^9$-$(CH_2)_{2-9}$CONHOH.

In a preferred embodiment of the present invention,

[structures B₁ and B₂] and are independently selected from the group consisting of phenyl, heteroaryl and heterocyclyl, wherein each phenyl, heteroaryl and heterocyclyl is optionally substituted with one to three substituents independently selected from the group consisting of halo, —$CF_3$, —$OCF_3$, —$NO_2$, —CN, —$C_1$-$C_6$alkoxyl, —O—$C_2$-$C_6$alkyl-O—$R^{53}$, —O—$R^{53}$, —$C_0$-$C_6$alkyl-S(O)$_{0-2}$—$R^{53}$, —$C_0$-$C_6$alkyl-C(O)—$R^{53}$, —$C_0$-

C₆alkyl-C(O)NR⁵⁰R⁵¹, —C₀-C₆alkyl-NR⁵²C(O)—R⁵³, —C₀-C₆alkyl-S(O)₂NR⁵⁰R⁵¹, —C₀-C₆alkyl-NR⁵²S(O)₂—R⁵³, —C₀-C₆alkyl-OC(O)NR⁵⁰R⁵¹, —C₀-C₆alkyl-NR⁵²C(O)O—R⁵³, —C₀-C₆alkyl-NR⁵²C(O)NR⁵⁰R⁵¹, —C₀-C₆alkyl-C(O)O—R⁵³, —C₀-C₆alkyl-OC(O)—R⁵³, —C₀-C₆alkyl-aryl, —C₀-C₆alkyl-heteroaryl, —C₀-C₆alkyl-C₃-C₇cycloalkyl, —C₀-C₆alkyl-heterocyclyl, —C₀-C₆alkyl-NR⁵⁰R⁵¹, —O—C₂-C₆alkyl-NR⁵⁰R⁵¹, —NR⁵³—C₂-C₆alkyl-NR⁵⁰R⁵¹ and —O-heterocyclyl-R⁵³.

In a preferred embodiment of the present invention,

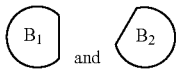

are independently selected from the group consisting of phenyl, heteroaryl and heterocyclyl, wherein each phenyl, heteroaryl and heterocyclyl is optionally substituted with one to three substituents independently selected from the group consisting of R⁴.

In a preferred embodiment of the compounds of the present invention, J-Q is selected from the group consisting of —C₁-C₉alkyl, —C₁-C₉heteroalkyl, phenyl, aryl, heteroaryl, —C₁-C₄alkyl-phenyl, —C₁-C₄alkyl-aryl, —C₁-C₄alkyl-heteroaryl, —NR³³aryl, —NR³³—C₁-C₄alkyl-aryl, —NR³³heteroaryl and NR³³—C₁-C₄alkyl-heteroaryl, wherein each alkyl and heteroalkyl is optionally substituted with one or three substituents independently selected from the group consisting of F, —OH and oxo, and wherein each phenyl, aryl and heteroaryl is optionally substituted with one or two substituents independently selected from the group consisting of halo, —OH, —OR⁵³, —C₁-C₄alkyl, —C₁-C₄alkoxyl, —O—C₂-C₄alkyl-O—C₁-C₆alkyl, —CN, —CF₃, —OCF₃, —NO₂, —C₁-C₆alkyl-S(O)₀₋₂R⁵³, —NH₂, —NR⁵⁰R⁵¹, —C₁-C₆alkyl-NR⁵⁰R⁵¹ and —N(C₁-C₆alkyl)₂, wherein R³³ is independently selected from the group consisting of —H, —C₁-C₆alkyl, —C₀-C₆alkyl-C₃-C₇cycloalkyl and —C₀-C₄alkyl-phenyl, wherein each phenyl and cycloalkyl is optionally substituted with one or three substituents independently selected from the group consisting of halo, —OH, —NO₂, —CF₃, —OCF₃, amino, —N(C₁-C₆alkyl)₂, —C₁-C₆alkyl-S(O)₀₋₂R⁵³, —C₁-C₄alkoxyl-CN, —O—C₂alkyl-O—CH₃, —NR⁵⁰R⁵¹, —C₁-C₆alkyl-NR⁵⁰R⁵¹ or —C₁-C₄alkyl.

In a preferred embodiment, embodiment A, of the compounds of the present invention, Q comprises a bridged heterocycle,

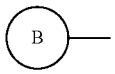

comprises a first ring structure, said first ring structure attached via a covalent bond to said bridged heterocycle and J comprises a second ring structure, said second ring structure attached via a covalent bond to said bridged heterocycle, each of which is optionally substituted. In another preferred embodiment, L is a covalent bond.

In another preferred embodiment, embodiment B, of the compounds according to the present invention, L is a covalent bond, Q is a heterocycle comprising a one or three carbon bridge, and J is heteroaryl, wherein each of

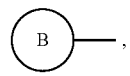

Q and J are optionally substituted.

In another preferred embodiment, embodiment B-2, of the compounds according to the present invention, L is a covalent bond, Q comprises a heterocycle comprising an unsubstituted methylene, ethylene or propylene bridge, and J is heteroaryl, wherein each of

Q and J are otherwise optionally substituted.

In another preferred embodiment, embodiment B-3, of the compounds according to the present invention, L is a covalent bond, Q comprises a heterocycle comprising an unsubstituted methylene, ethylene or propylene bridge, and J is aryl, wherein each of

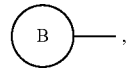

Q and J are otherwise optionally substituted.

In another preferred embodiment, embodiment C, of the compounds according to the present invention, L is a covalent bond, Q is a heterocycle comprising a one or three carbon bridge, and J is pryimidine, wherein each of

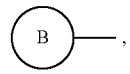

Q and J are optionally substituted.

In another preferred embodiment, embodiment D, of the compounds according to the present invention, L is a covalent bond, Q is a heterocycle comprising an unsubstituted methylene bridge, and J is pryimidine, wherein each of

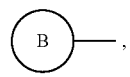

Q and J are otherwise optionally substituted.

In another preferred embodiment, embodiment E, of the compounds according to the present invention, L is a covalent bond, Q is a heterocycle comprising a three carbon bridge; and J is pryimidine, wherein each of

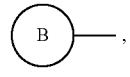

Q and J are optionally substituted.

In another preferred embodiment, embodiment F, of the compounds according to the present invention, L is a covalent bond, Q is a 2,5-diazabicyclo[2.2.1]heptane, and J is pryimidine, wherein each of

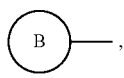,

Q and J are optionally substituted.

In a preferred embodiment, embodiment G, of each of the forgoing,

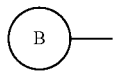

is an optionally substituted aryl or heteroary, preferably aryl, more preferably phenyl.

In another preferred embodiment, embodiment G-1, of each of the embodiments A to F,

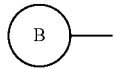

is an optionally substituted heteroary, preferably pyridine.

In a preferred embodiment, embodiment H, of the compounds of the present invention,

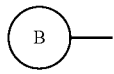

is a radical selected from the group consisting of

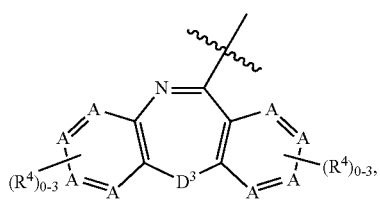

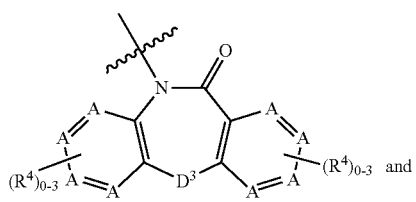

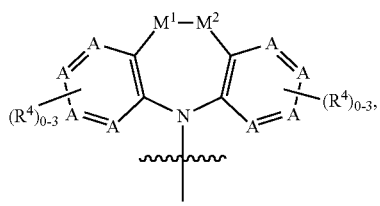

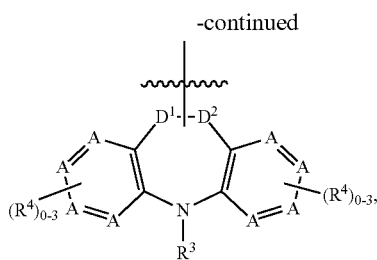

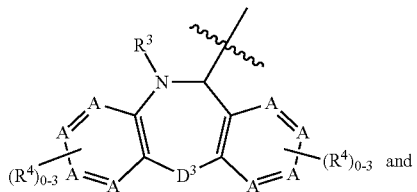

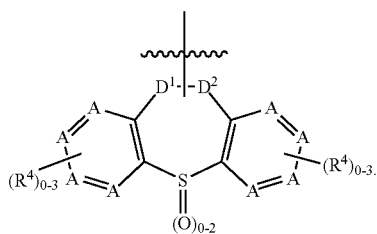
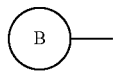

In another preferred embodiment, embodiment I, of the compounds according to the present invention,

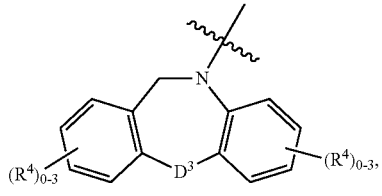

is a radical selected from the group consisting of

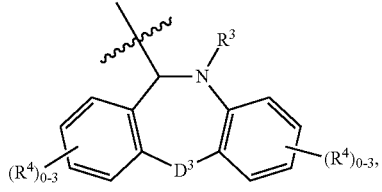

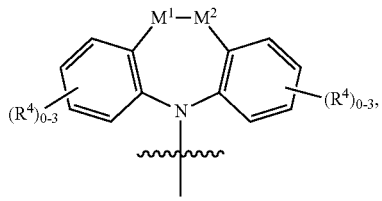

-continued
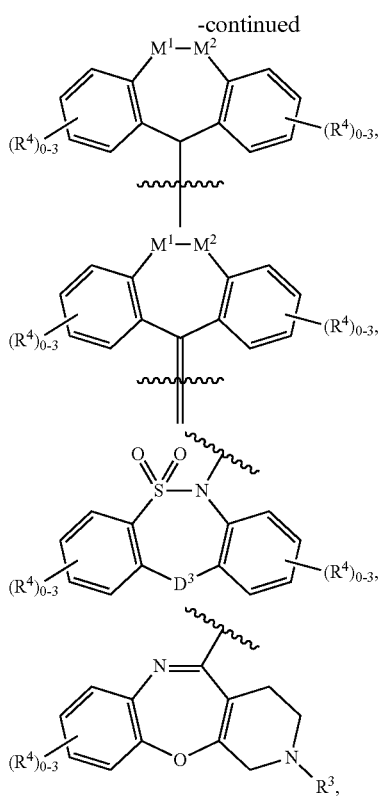
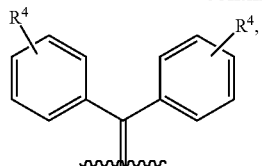
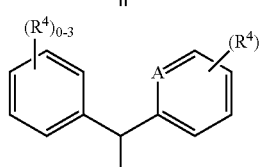
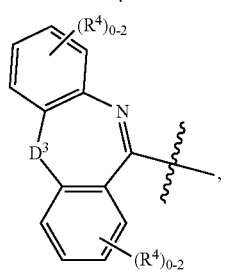
wherein when
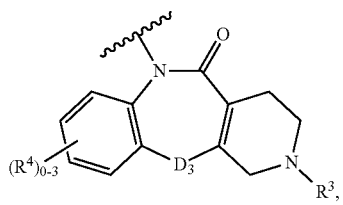 is
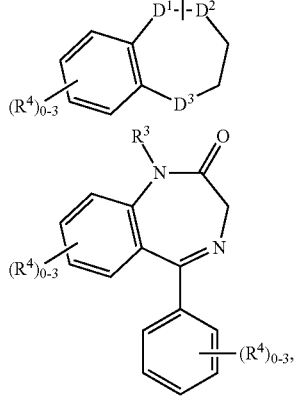
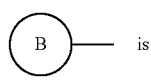 or
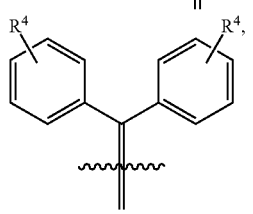
Q is attached via
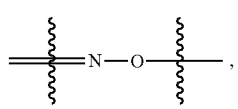 [SMILES: *ON=*],
and wherein when
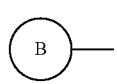

is

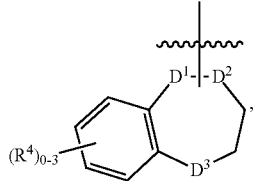

Q is attached via $D^1$-$D^2$.

In another preferred embodiment, embodiment J, of the compounds according to the present invention

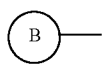

is a radical selected from the group consisting of

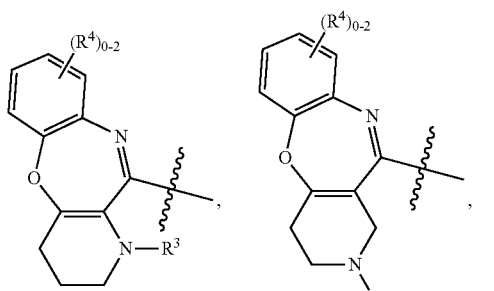

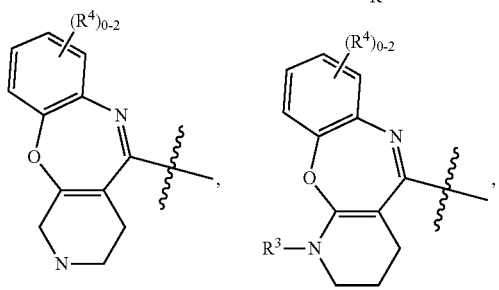

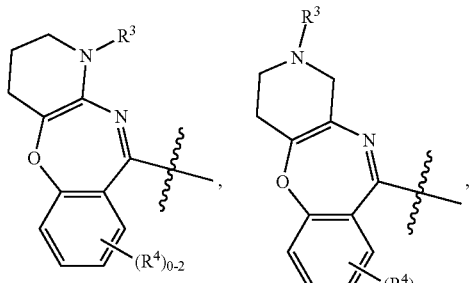

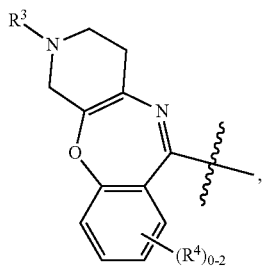

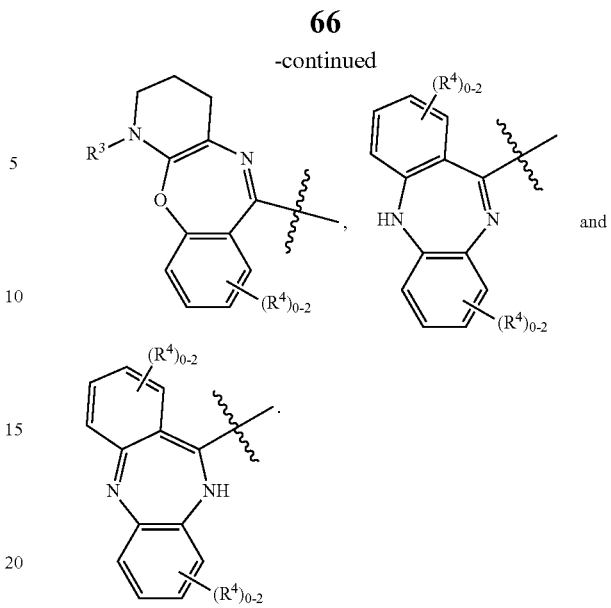

In another preferred embodiment, embodiment K, of the compounds according to the present invention, Q is an optionally substituted moiety selected from the group consisting of

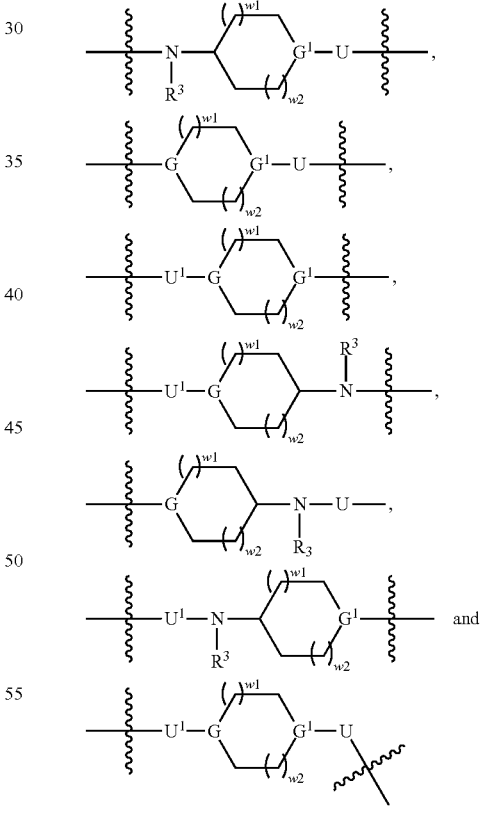

or where possible, an (R,R) or (S,S) enantiomer or a mixture of enantiomers, preferably an (R,R) enantiomer, more preferably an (S,S) enantiomer thereof, wherein G and $G^1$ are independently selected from —CH— and N; w1 and w2 are independently 0, 1, 2 or 3, provided that when both G and $G^1$ are N, then w1 and W2 are independently 1, 2 or 3; and wherein each ring structure includes a 0 (i.e., a bond), 1, 2 or 3 carbon bridge between two non-adjacent carbon atoms, provided that

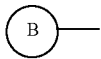

is absent when $U^1$ is H, $N(R^3)(R^{3a})$—$C_2$-$C_4$alkyl- or $R^3$—O—$C_2$-$C_4$alkyl-. Preferably the ring size is 6, 7, 8 or 9 ring atoms, excluding any bridge atoms.

In another preferred embodiment, embodiment L, of the compounds according to the present invention, Q is an optionally substituted moiety selected from the group consisting of

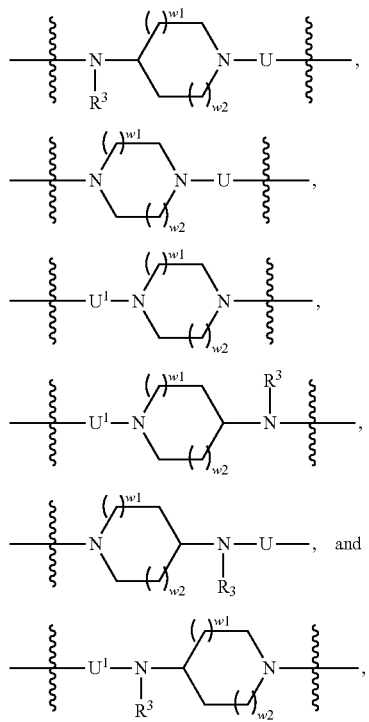

or where possible, an (R,R) or (S,S) enantiomer or a mixture of enantiomers, preferably an (R,R) enantiomer, more preferably an (S,S) enantiomer thereof, wherein w1 and w2 are independently 0, 1, 2 or 3, provided that when the ring includes two N atoms, then w1 and w2 are independently 1, 2 or 3; and wherein each ring structure includes a 0 (i.e., a bond), 1, 2 or 3 carbon bridge between two non-adjacent carbon atoms, provided that

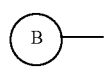

is absent when $U^1$ is H, $N(R^3)(R^{3a})$—$C_2$-$C_4$alkyl- or $R^3$—O—$C_2$-$C_4$alkyl-.

In another preferred embodiment, embodiment M, of the compounds according to the present invention, Q is an optionally substituted moiety, selected from the group consisting of

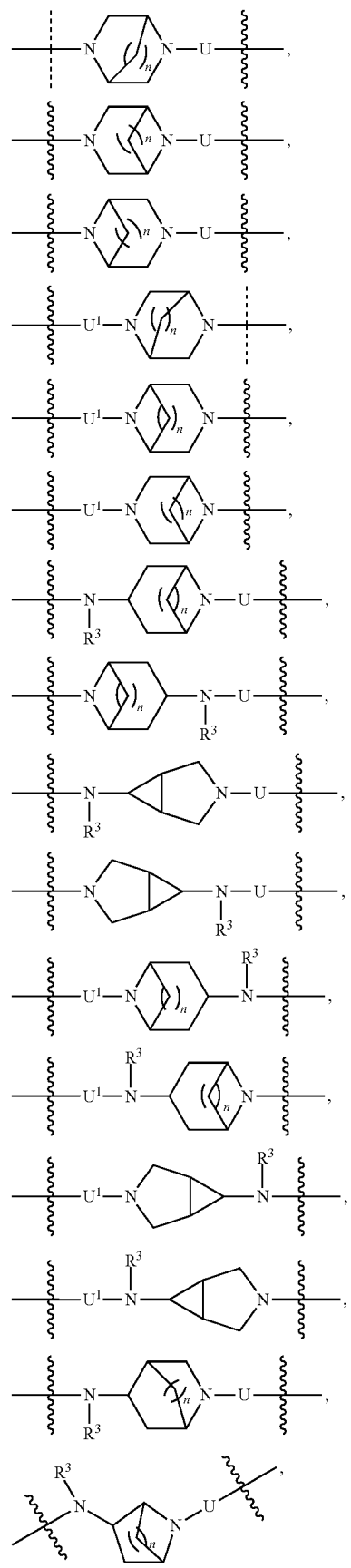

-continued

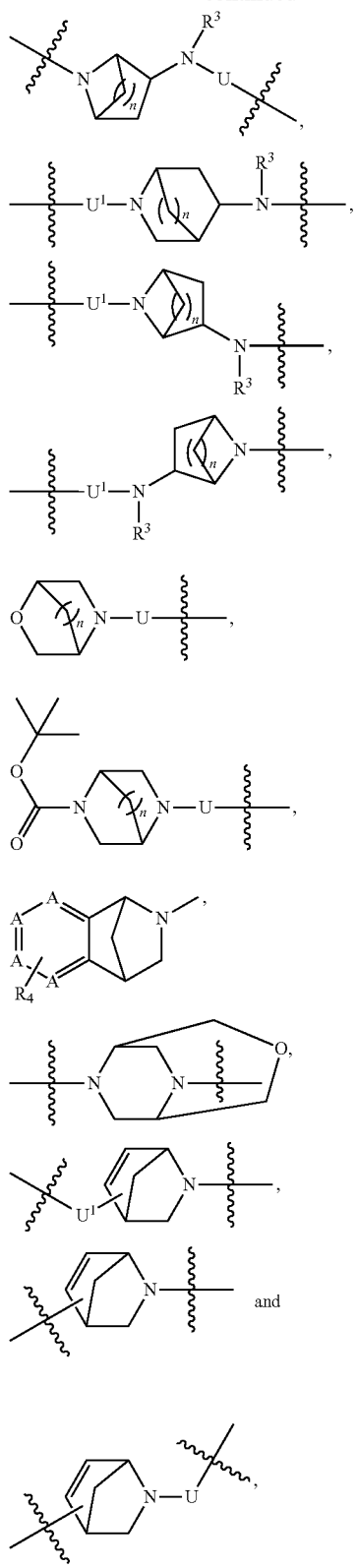

or wherein possible, a (R,R) or (S,S) enantiomer or a mixture of enantiomers, preferably an (R,R) enantiomer, more preferably an (S,S) enantiomer thereof, wherein n is 1, 2 or 3, and wherein

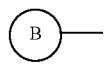

is absent when Q is structure (a-1), (a-2), (a-3) or when $U^1$ is H, $N(R^3)(R^{3a})$—$C_2$-$C_4$alkyl- or $R^3$—O—$C_2$-$C_4$alkyl-.

In another preferred embodiment, embodiment N, of the compounds according to the present invention, Q is an optionally substituted moiety selected from the group consisting of

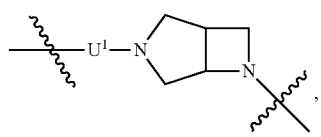

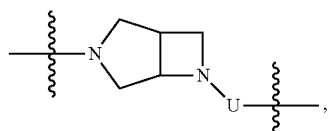

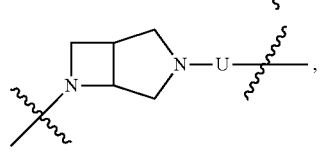

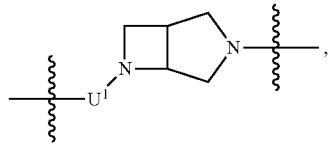

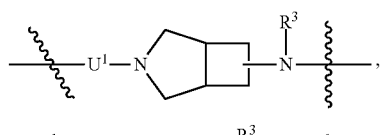

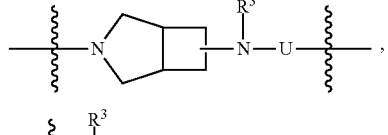

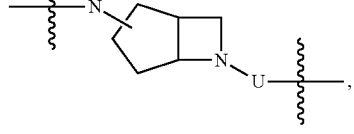

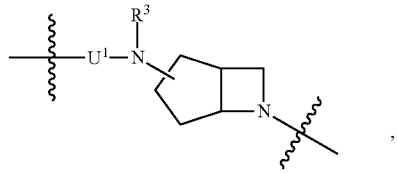

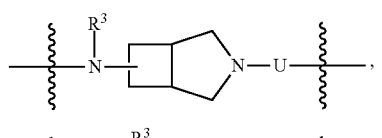

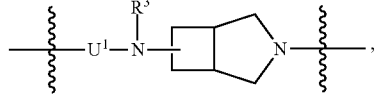

71
-continued
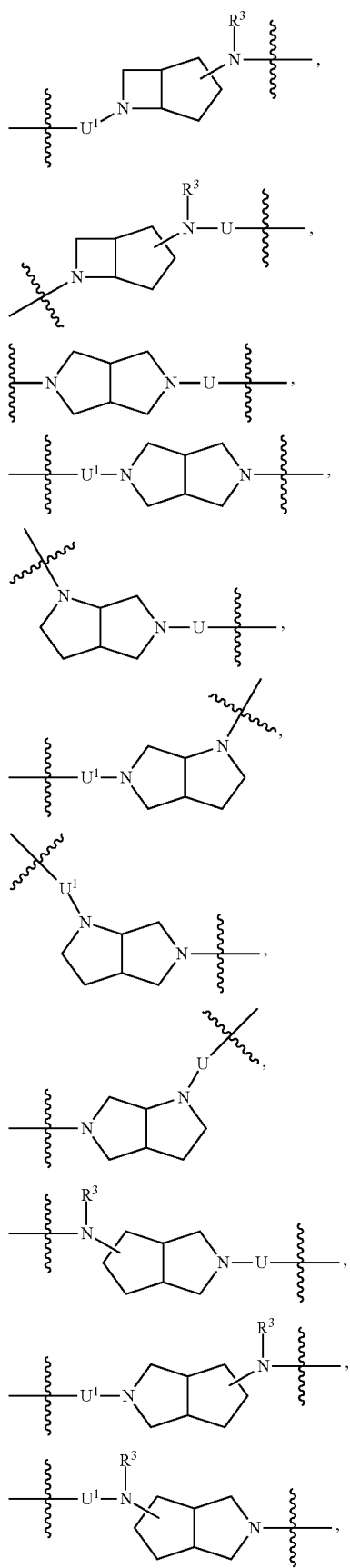
72
-continued
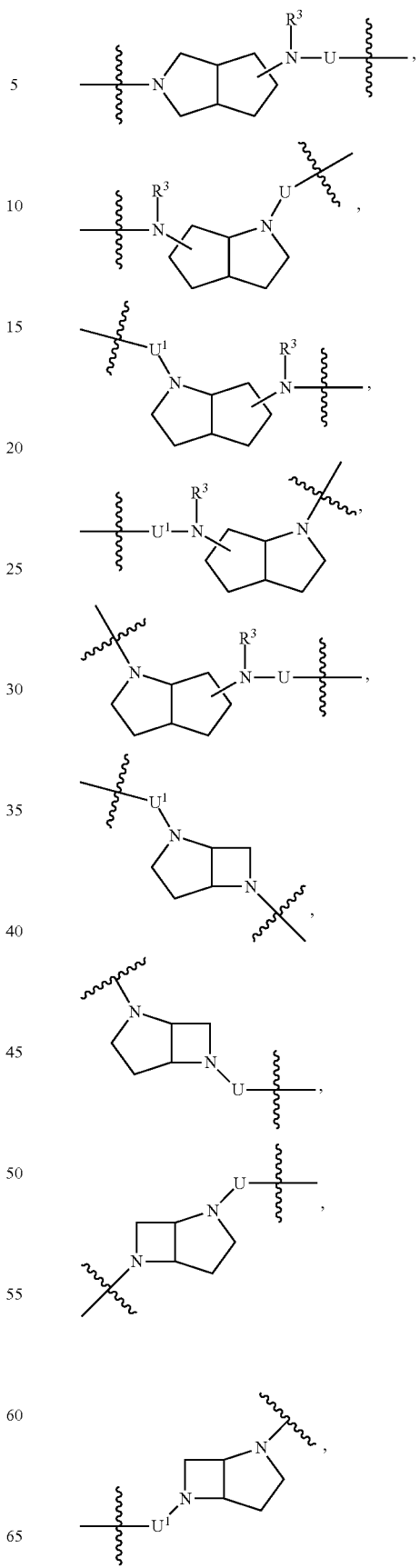

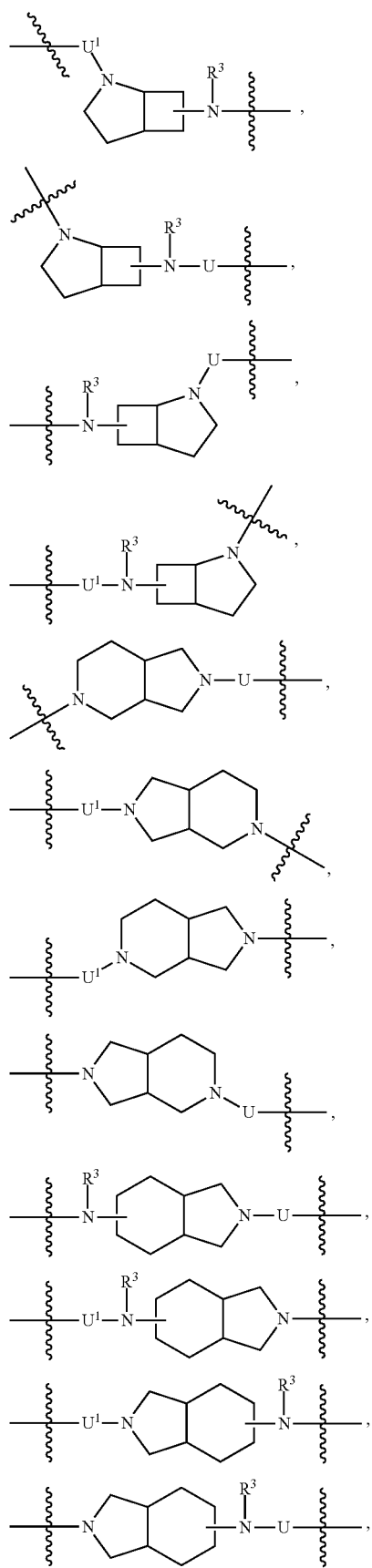
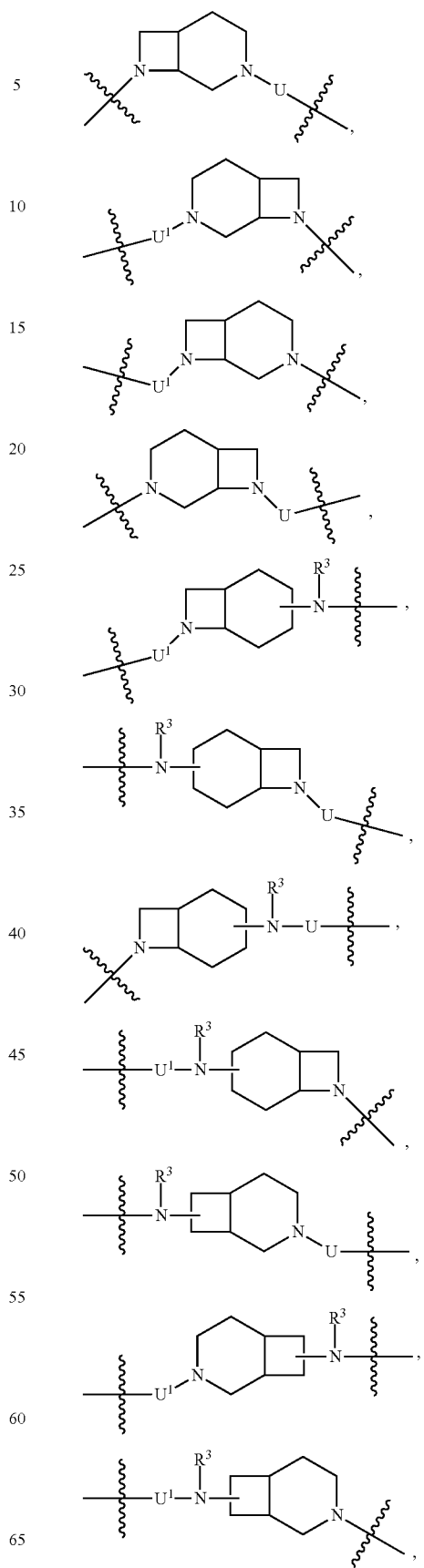

-continued

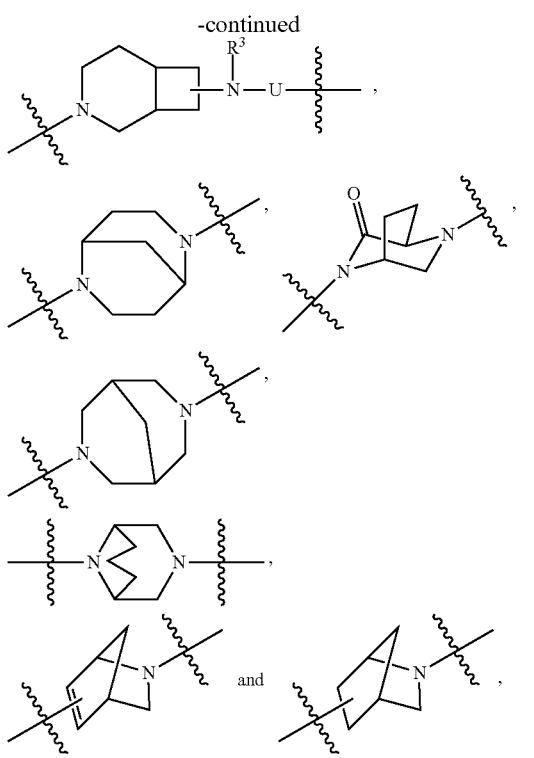

and or wherein possible, a (R,R) or (S,S) enantiomer or a mixture of enantiomers, preferably an (R,R) enantiomer, more preferably an (S,S) enantiomer thereof, wherein

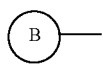

is absent when $U^1$ is H, $N(R^3)(R^{3a})$—$C_2$-$C_4$alkyl- or $R^3$—O—$C_2$-$C_4$alkyl-.

In a preferred embodiment, embodiment 0, of the compounds of the present invention, Z is —$N(R^1)(OR^2)$;

L is a covalent bond;

J is selected from the group consisting of a covalent bond, =CH—, —$C_1$-$C_8$alkyl-, —$C_0$-$C_3$alkyl-$C_1$-$C_8$heteroalkyl-$C_0$-$C_3$alkyl-, —$C_0$-$C_3$alkyl-$C_2$-$C_8$alkenyl-$C_0$-$C_3$alkyl-, —$C_0$-$C_3$alkyl-$C_2$-$C_8$alkynyl-$C_0$-$C_3$alkyl-, —$C_0$-$C_6$alkyl-aryl-$C_0$-$C_6$alkyl-, —$C_0$-$C_6$alkyl-aryl-$C_2$-$C_6$heteroalkyl-, —$C_0$-$C_6$alkyl-cycloalkyl-$C_0$-$C_6$alkyl-, —$C_4$-$C_6$heterocyclyl-aryl-$C_0$-$C_6$alkyl-, —$C_4$-$C_6$heterocyclyl-aryl-$C_0$-$C_6$heteroalkyl-, —$C_0$-$C_6$alkyl-$C_4$-$C_6$heterocyclyl-$C_0$-$C_6$alkyl-, —$C_0$-$C_6$alkyl-heteroaryl-$C_0$-$C_6$alkyl-, —$C_0$-$C_6$alkyl-heteroaryl-$C_0$-$C_6$heteroalkyl-, —$C_4$-$C_6$heterocyclyl-heteroaryl-$C_0$-$C_6$alkyl-, —$C_0$-$C_6$alkyl-aryl-$C_2$-$C_6$alkynyl-, —$C_0$-$C_6$alkyl-heteroaryl-$C_2$-$C_6$alkynyl-, —$C_0$-$C_6$alkyl-aryl-$C_2$-$C_6$alkynyl-$C_2$-$C_6$alkenyl-, —$C_0$-$C_6$alkyl-aryl-$C_2$-$C_6$alkenyl-, —$C_0$-$C_6$alkyl-heteroaryl-$C_2$-$C_6$alkenyl-, —$C_2$-$C_6$alkenyl-aryl-$C_0$-$C_6$alkyl-, —$C_2$-$C_6$alkenyl-heteroaryl-$C_0$-$C_6$alkyl-, —$C_0$-$C_6$alkylaryl-aryl-$C_0$-$C_6$alkyl-, —$C_0$-$C_6$alkylaryl-heteroaryl-$C_0$-$C_6$alkyl- and —$C_0$-$C_6$alkyl-$C_3$-$C_6$cycloalkyl-$C_0$-$C_6$alkyl-, wherein each alkyl, alkenyl, alkynyl, heteroalkyl, aryl, heteroaryl, heterocyclyl, and cycloalkyl moiety is optionally substituted, wherein when J is =CH—, Q is a covalent bond and B is attached through a carbon $sp^2$ to J;

Q is a moiety selected from the group consisting of

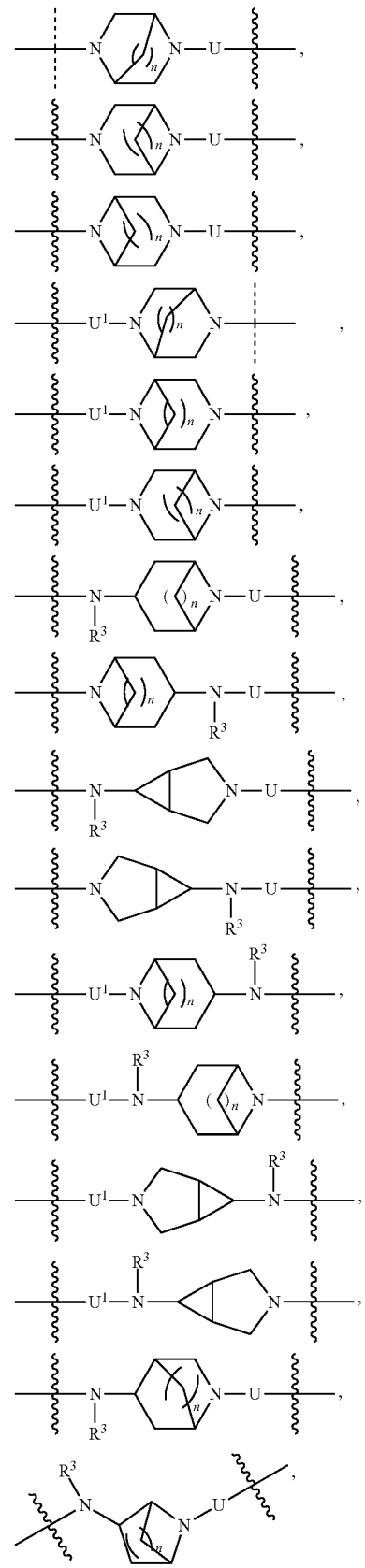

-continued

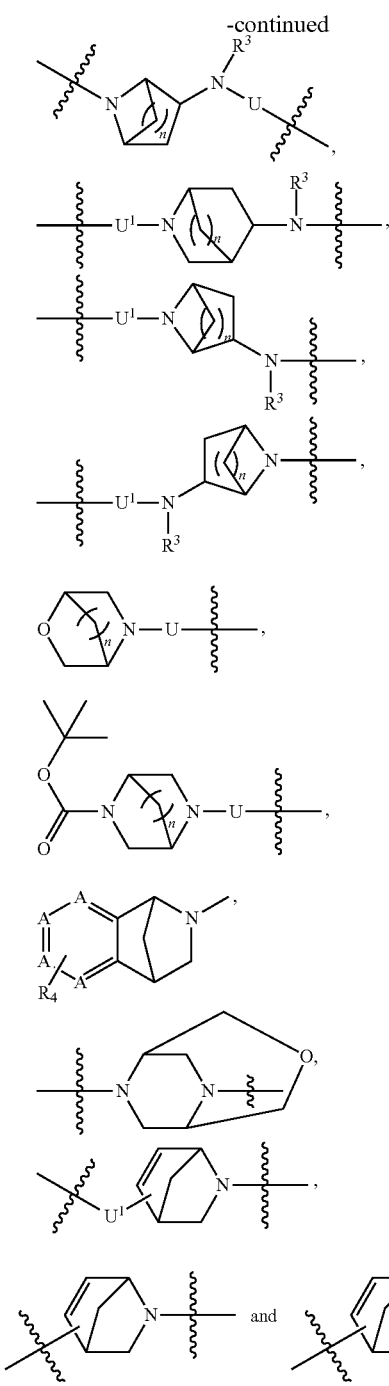

(a-1)

(a-2)

(a-3)

or an optionally substituted (R,R) or (S,S) enantiomer or a mixture of enantiomers, preferably an (R,R) enantiomer, more preferably an (S,S) enantiomer thereof, wherein n is 0, 1, 2 or 3; and U is selected from the group consisting of —$C_0$-$C_8$alkyl-C(O)—$C_0$-$C_3$alkyl-, —$C_1$-$C_8$alkyl-, —$C_0$-$C_8$alkyl-N($R^3$)—C(O)—$C_0$-$C_3$alkyl-, —$C_0$-$C_8$alkyl-O—C(O)—$C_0$-$C_3$alkyl-, —$C_0$-$C_8$alkyl-N($R^3$)—C(S)—$C_0$-$C_3$alkyl-, —$C_0$-$C_8$alkyl-O—C(S)—$C_0$-$C_3$alkyl-, —$C_0$-$C_8$alkyl-N($R^3$)—S(O)$_2$—$C_0$-$C_3$alkyl-, —$C_0$-$C_8$alkyl-heterocyclyl-$C_0$-$C_3$alkyl-, a covalent bond and —O—$C_2$-$C_4$alkyl-; and $U^1$ is selected from the group consisting of H, —$C_0$-$C_8$alkyl-C(O)—$C_0$-$C_3$alkyl-, —$C_1$-$C_8$alkyl-, —$C_0$-$C_8$alkyl-N($R^3$)—C(O)—$C_0$-$C_3$alkyl-, —$C_0$-$C_8$alkyl-O—C(O)—$C_0$-$C_3$alkyl-, —$C_0$-$C_8$alkyl-N($R^3$)—C(S)—$C_0$-$C_3$alkyl-, —$C_0$-$C_8$alkyl-O—C(S)—$C_0$-$C_3$alkyl-, —$C_0$-$C_8$alkyl-N($R^3$)—S(O)$_2$—$C_0$-$C_3$alkyl-, —$C_0$-$C_8$alkyl-heterocyclyl-$C_0$-$C_3$alkyl-, a covalent bond, ($R^3$)($R^{3a}$)N—$C_2$-$C_4$alkyl-, —O—$C_2$-$C_4$alkyl-, and $R^3$—O—$C_2$-$C_4$alkyl-;

wherein

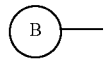

is absent when Q is structure (a-1), (a-2), (a-3) or when $U^1$ is H, N($R^3$)($R^{3a}$)—$C_2$-$C_4$alkyl- or $R^3$—O—$C_2$-$C_4$alkyl-.

In a preferred embodiment of embodiment O, embodiment O-1, of the compounds according to the present invention, J is selected from the group consisting of a —$C_0$-$C_3$alkyl-$C_1$-$C_8$heteroalkyl-$C_0$-$C_3$alkyl-, —$C_0$-$C_6$alkyl-aryl-$C_0$-$C_6$alkyl-, —$C_0$-$C_6$alkyl-aryl-$C_2$-$C_6$heteroalkyl-, —$C_0$-$C_6$alkyl-cycloalkyl-$C_0$-$C_6$alkyl-, —$C_4$-$C_6$heterocyclyl-aryl-$C_0$-$C_6$alkyl-, —$C_4$-$C_6$heterocyclyl-aryl-$C_0$-$C_6$heteroalkyl-, —$C_0$-$C_6$alkyl-$C_4$-$C_6$heterocyclyl-$C_0$-$C_6$alkyl-, —$C_0$-$C_6$alkyl-heteroaryl-$C_0$-$C_6$alkyl-, —$C_0$-$C_6$alkyl-heteroaryl-$C_0$-$C_6$heteroalkyl-, —$C_4$-$C_6$heterocyclyl-heteroaryl-$C_0$-$C_6$alkyl-, —$C_0$-$C_6$alkyl-aryl-$C_2$-$C_6$alkynyl-, —$C_0$-$C_6$alkyl-heteroaryl-$C_2$-$C_6$alkynyl-, —$C_0$-$C_6$alkyl-aryl-$C_2$-$C_6$alkynyl-$C_2$-$C_6$alkenyl-, —$C_0$-$C_6$alkyl-aryl-$C_2$-$C_6$alkenyl-, —$C_0$-$C_6$alkyl-heteroaryl-$C_2$-$C_6$alkenyl-, —$C_2$-$C_6$alkenyl-aryl-$C_0$-$C_6$alkyl-, —$C_2$-$C_6$alkenyl-heteroaryl-$C_0$-$C_6$alkyl-, —$C_0$-$C_6$alkylaryl-aryl-$C_0$-$C_6$alkyl-, —$C_0$-$C_6$alkylaryl-heteroaryl-$C_0$-$C_6$alkyl- and —$C_0$-$C_6$alkyl-$C_3$-$C_6$cycloalkyl-$C_0$-$C_6$alkyl-, wherein each alkyl, alkenyl, alkynyl, heteroalkyl, aryl, heteroaryl, heterocyclyl, and cycloalkyl moiety is optionally substituted.

In a preferred embodiment of embodiment O-1, embodiment O-2, J is —$C_0$-$C_6$alkyl-heteroaryl-$C_0$-$C_6$alkyl- or —$C_0$-$C_6$alkyl-aryl-$C_0$-$C_6$alkyl-.

In a preferred embodiment of embodiment O-2, embodiment O-3, Q is selected from the group consisting of

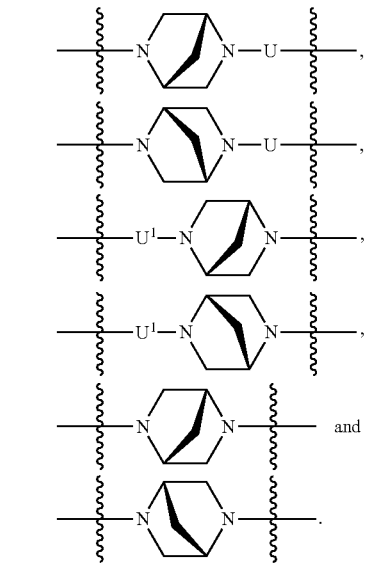

In a preferred embodiment of embodiment O-3, embodiment O-4, U and $U^1$ are a covalent bond.

In a preferred embodiment of embodiment O-3 embodiment O-5, U and U$^1$ are —C(O)—.

In another preferred embodiment of embodiment O-3, embodiment O-6, moiety U is —C(O)—O—C$_0$-C$_3$alkyl-.

In another preferred embodiment of embodiment O-3, embodiment O-7, U$^1$ is —C$_0$-C$_3$alkyl-O—C(O)—.

In another preferred embodiment, embodiment P of the compounds according to the present invention
J is selected from the group consisting of —C$_1$-C$_8$alkyl-, —C$_0$-C$_6$alkyl-aryl-C$_0$-C$_3$alkyl-C$_2$alkenyl-C$_0$-C$_3$alkyl, —C$_0$-C$_6$alkyl-heteroaryl-C$_0$-C$_3$alkyl-C$_2$alkenyl-C$_0$-C$_3$alkyl, —C$_0$-C$_6$alkyl-aryl-C$_0$-C$_6$alkyl- and —C$_0$-C$_6$alkyl-heteroaryl-C$_0$-C$_6$alkyl-, wherein each is optionally substituted;

Q is selected from the group consisting of a covalent bond, —C$_1$-C$_8$alkyl-, =N—O—, —C$_0$-C$_6$alkyl-N(R$^3$)—C$_0$-C$_3$alkyl-, —C$_0$-C$_6$alkyl-heterocyclyl-C$_0$-C$_3$alkyl-, —C$_0$-C$_6$alkyl-C(O)—C$_0$-C$_3$alkyl-, —C$_0$-C$_6$alkyl-O—C$_0$-C$_3$alkyl-, —C$_0$-C$_6$alkyl-(CR$^3$=CR$^3$)$_{1-2}$—C$_0$-C$_6$alkyl-, —C$_0$-C$_6$alkyl-(C≡C)$_{1-2}$—C$_0$-C$_6$alkyl-, —C$_0$-C$_6$alkyl-N(R$^3$)—C(O)—C$_0$-C$_3$alkyl-, wherein each alkyl and heterocyclyl moiety is optionally substituted;
or
Q is selected from the group consisting of:

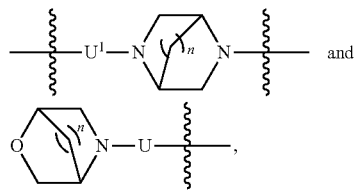
and wherein
U$^1$ is selected from the group consisting of —C$_0$-C$_8$alkyl-C(O)—C$_0$-C$_3$alkyl-, —C$_1$-C$_8$alkyl-, —C$_0$-C$_8$alkyl-O—C(O)—C$_0$-C$_3$alkyl- and a covalent bond;
wherein, when B is attached to Q via a N in B, then Q is selected from the group consisting of a covalent bond, —C(O)—C$_1$-C$_3$alkyl-O—, —C$_1$-C$_8$alkyl-, —C$_0$-C$_6$alkyl-C(O)—C$_0$-C$_3$alkyl-, —C$_2$-C$_6$alkyl-O—C$_0$-C$_3$alkyl-, —C$_1$-C$_6$alkyl-(CR$^3$=CR$^3$)$_{1-2}$—C$_0$-C$_6$alkyl- and —C$_1$-C$_6$alkyl-(C≡C)$_{1-2}$—C$_0$-C$_6$alkyl-, wherein each alkyl moiety is optionally substituted;
provided that

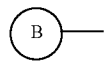

is absent when Q is

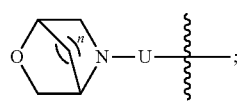

and

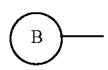

is selected from the group consisting of hydrogen, aryl, cycloalkyl, heterocyclyl, heteroaryl, heteroarylalkyl, arylalkyl-, (heteroaryl)$_2$-CH—C$_0$-C$_6$alkyl- and (aryl)$_2$-CH—C$_0$-C$_6$alkyl-, each of which is optionally substituted, provided that Q is

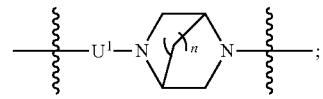

or

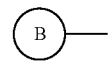

is a radical selected from the group consisting of

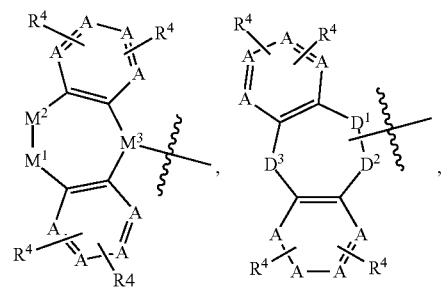

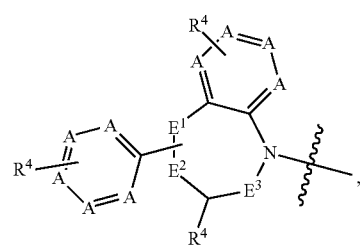

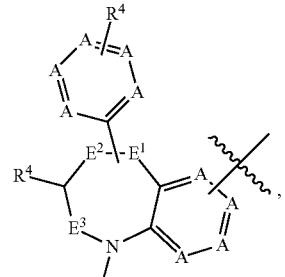

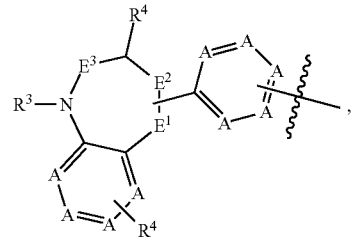

-continued
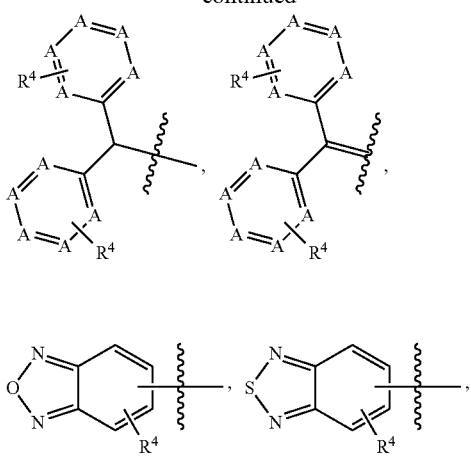
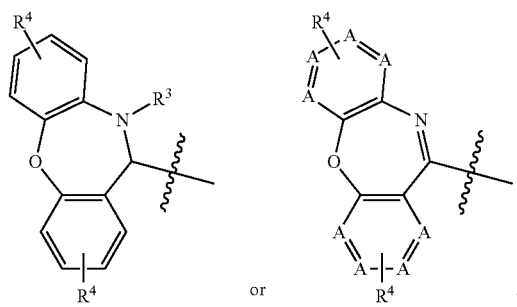
is
In another preferred embodiment, embodiment Q, of the compounds according to the present invention, the compound has a structure selected from the group consisting of
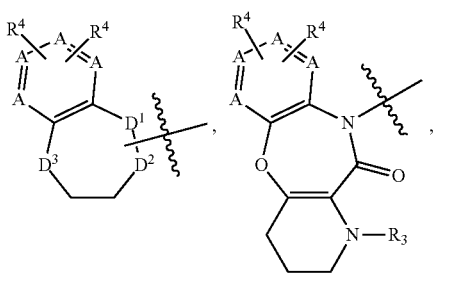
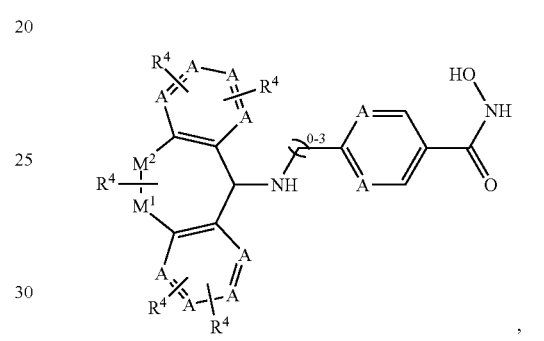
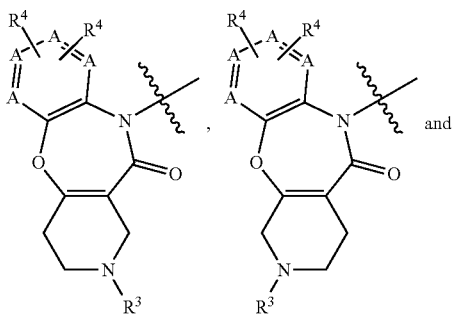
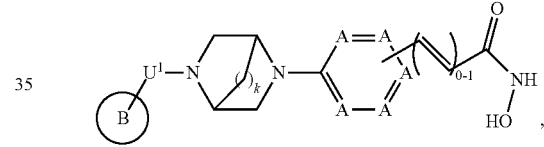
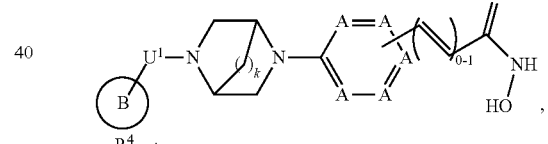
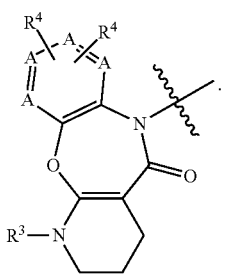
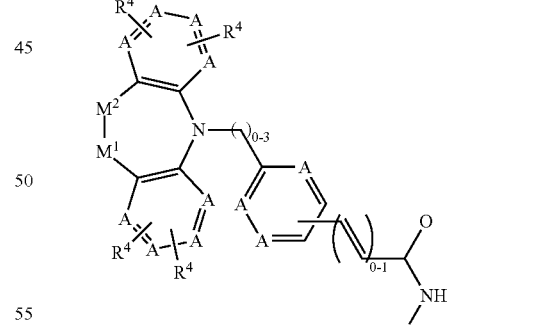
In a preferred embodiment of embodiment P, embodiment P-1,
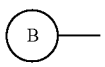
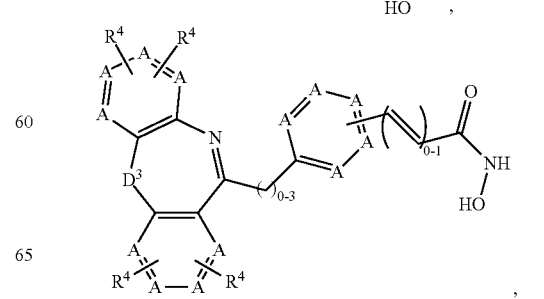

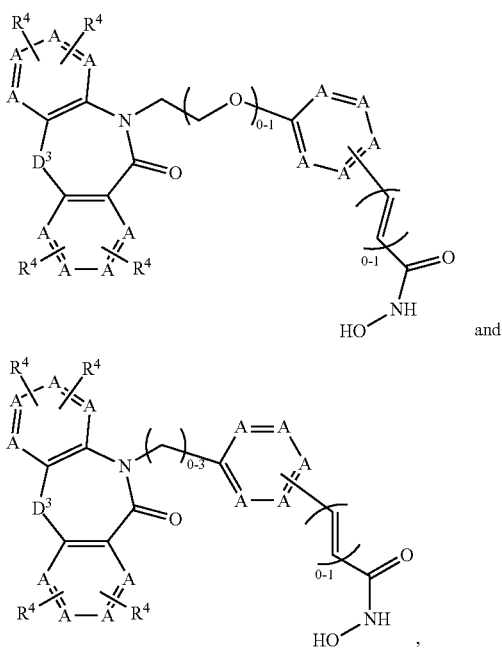

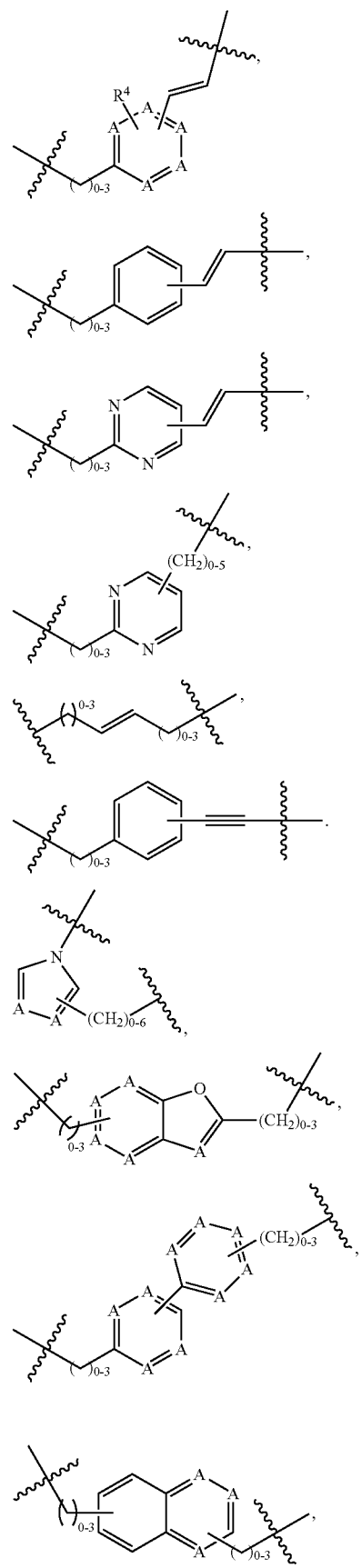

wherein k is 0 or 3.

In another preferred embodiment, embodiment R, of the compounds according to the present invention, Z is —NR$^1$OR$^2$, R$^1$ and R$^2$ are H, and L is a covalent bond.

In another preferred embodiment, embodiment S, of the compounds according to the present invention, Z is H and L is —N(OH).

In another preferred embodiment, embodiment T, of the compounds according to the present invention, J is selected from the group consisting of —C$_1$-C$_8$alkyl-, —C$_0$-C$_3$alkyl-C$_1$-C$_8$alkenyl-C$_0$-C$_3$-alkyl, —C$_0$-C$_6$alkyl-aryl-C$_0$-C$_6$alkyl-, —C$_0$-C$_6$alkyl-aryl-C$_2$-C$_6$alkenyl, —C$_0$-C$_6$alkyl-heteroaryl-C$_0$-C$_6$alkyl- and —C$_0$-C$_6$alkyl-heterocyclyl-heteroaryl-C$_0$-C$_6$alkyl-.

In another preferred embodiment, embodiment U, of the compounds according to the present invention, J is selected from the group consisting of -continued

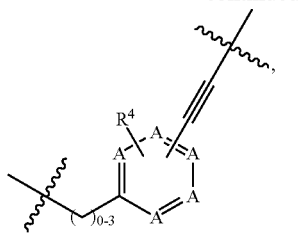

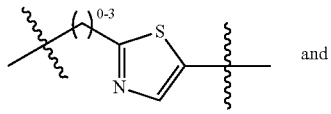 and

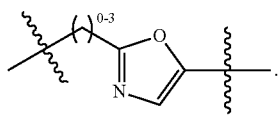

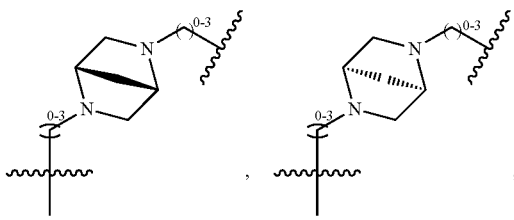

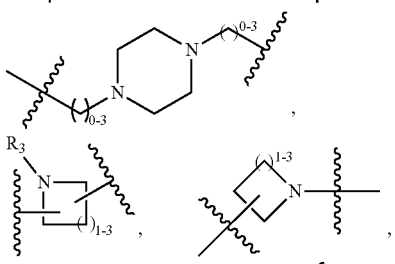

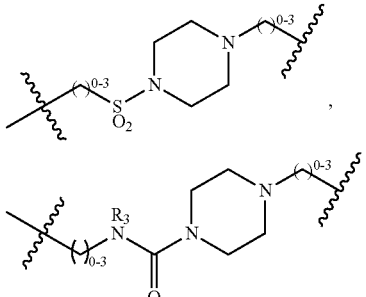

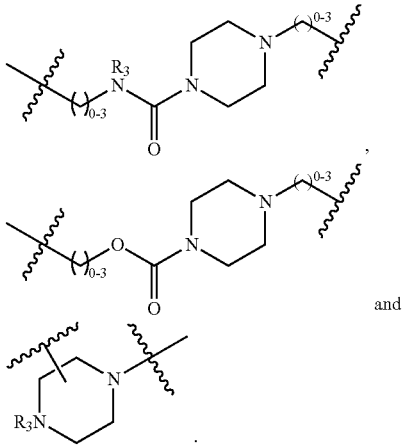

In another preferred embodiment, embodiment V, of the compounds according to the present invention, Q is selected from the group consisting of a covalent bond, —$C_1$-$C_8$alkyl-, =N—O—, —$C_0$-$C_6$alkyl-N($R^3$)—$C_0$-$C_3$alkyl-, —$C_0$-$C_6$alkyl-heterocyclyl-$C_0$-$C_3$alkyl-, —$C_0$-$C_6$alkyl-C(O)—$C_0$-$C_3$alkyl-, —$C_0$-$C_6$alkyl-O—$C_0$-$C_3$alkyl-, —$C_0$-$C_6$alkyl-($CR^3$=$CR^3$)$_{1-2}$—$C_0$-$C_6$alkyl-, —$C_0$-$C_6$alkyl-(C≡C)$_{1-2}$—$C_0$-$C_6$alkyl-, —$C_0$-$C_6$alkyl-N($R^3$)—C(O)—$C_0$-$C_3$alkyl-, —$C_0$-$C_6$alkyl-N($R^3$)—C(O)-alkenyl-$C_0$-$C_4$alkyl-, —$C_0$-$C_6$alkyl-C(O)—N($R^3$)—$C_0$-$C_4$alkyl-, —$C_0$-$C_6$alkyl-$SO_2$—N($R^3$)—$C_0$-$C_3$alkyl-, —$C_0$-$C_6$alkyl-N($R^3$)—$SO_2$—$C_0$-$C_3$alkyl-, —$C_0$-$C_3$alkyl-N($R^3$)—S(O)$_2$—N($R^3$)—$C_0$-$C_3$alkyl-, —$C_0$-$C_6$alkyl-S—$C_0$-$C_3$alkyl-, —$C_0$-$C_6$alkyl-S(O)—$C_0$-$C_3$alkyl-, —$C_0$-$C_6$alkyl-S(O)$_2$—$C_0$-$C_3$alkyl-, —$C_0$-$C_6$alkyl-N($R^3$)—C(O)—N($R^3$)—$C_0$-$C_3$alkyl-, —$C_0$-$C_3$alkyl-C=N—O—$C_0$-$C_3$alkyl-, -heterocyclyl-$C_0$-$C_3$alkyl-heterocyclyl-$C_0$-$C_3$alkyl-, —$SO_2$—$C_0$-$C_6$alkyl-heterocyclyl-$C_0$-$C_3$alkyl-, —C(O)—$C_0$-$C_6$alkyl-bridged heterocyclyl-$C_0$-$C_3$alkyl-, —N($R^3$)—C(O)—$C_0$-$C_6$alkyl-heterocyclyl-$C_0$-$C_3$alkyl-, —O—C(O)—$C_0$-$C_6$alkyl-heterocyclyl-$C_0$-$C_3$alkyl-, —N($R^3$)—C(S)—$C_0$-$C_6$alkyl-heterocyclyl-$C_0$-$C_3$alkyl-, —O—C(S)—$C_0$-$C_6$alkyl-heterocyclyl-$C_0$-$C_3$alkyl-, —N($R^3$)—S(O)$_2$—$C_0$-$C_6$alkyl-heterocyclyl-$C_0$-$C_3$alkyl-, —$C_0$-$C_6$alkyl-heterocyclyl-$C_0$-$C_3$alkyl-$SO_2$—N($R^3$)—, —$C_0$-$C_6$ alkyl-heterocyclyl-$C_0$-$C_3$alkyl-C(O)—N($R^3$)— and —$C_0$-$C_6$alkyl-heterocyclyl-$C_0$-$C_3$alkyl-C(O)—O—, wherein each alkyl, heterocyclyl and alkenyl moiety is optionally substituted.

In another preferred embodiment, embodiment W, of the compounds according to the present invention, Q is selected from the group consisting of covalent bond, =N—O—, —$C_1$-$C_8$ alkyl-, —$C_0$-$C_6$ alkyl-N($R_3$)—$C_0$-$C_3$ alkyl-, —$C_0$-$C_6$alkyl-C(O)—$C_0$-$C_3$ alkyl-, —$C_0$-$C_6$ alkyl-C(O)N$R_3$—$C_0$-$C_3$ alkyl-, —$C_0$-$C_6$ alkyl-O—$C_0$-$C_3$ alkyl- and —$C_0$-$C_3$alkyl-heterocyclyl-$C_0$-$C_3$-alkyl.

In another preferred embodiment, embodiment X, of the compounds according to the present invention, Q is selected from the group consisting of In another preferred embodiment, embodiment Y, of the compounds according to the present invention,

is selected from the group consisting of aryl, aryl-alkyl-, heteroaryl, heteroaryl-alkyl-, (aryl)$_2$-CH—$C_0$-$C_6$alkyl-, (aryl)(heteroaryl)CH—$C_0$-$C_6$alkyl-, (heteroaryl)$_2$CH—$C_0$-$C_6$alkyl- and (aryl)$_2$-CH—$C_0$-$C_6$alkyl-C(O)—, wherein each group is optionally substituted with 1, 2, 3 or 4 substituents independently selected from the group consisting of hydroxy, amino, halo, $C_1$-$C_6$alkyl, nitro, cyano, $C_2$-$C_6$alkoxy, $C_1$-$C_6$alkylamino and $CF_3$.

In another preferred embodiment, embodiment Z, of the compounds according to the present invention,

is selected from the group consisting of
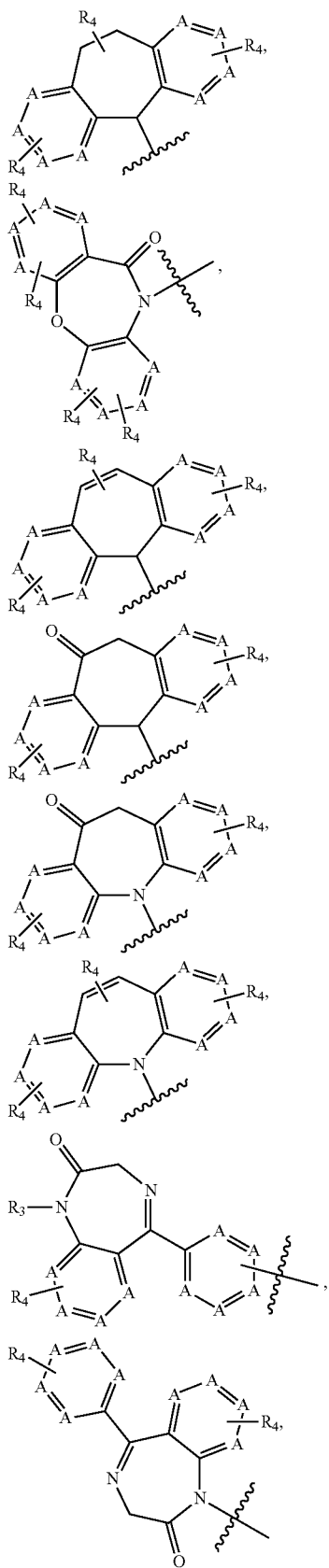
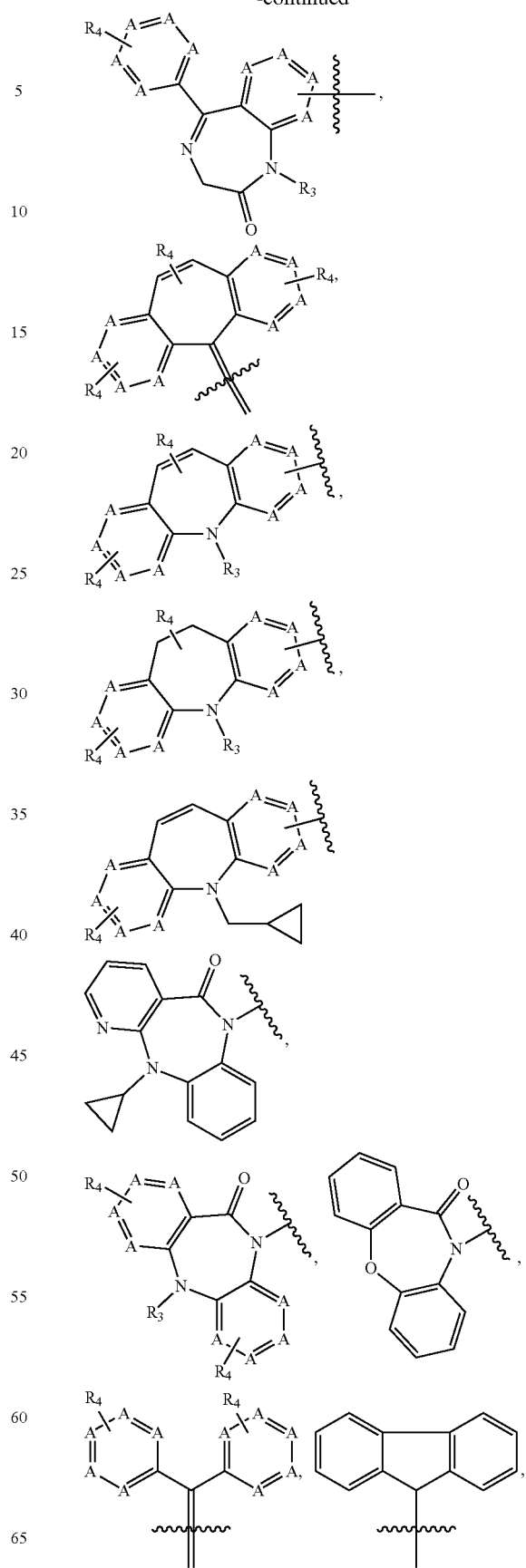

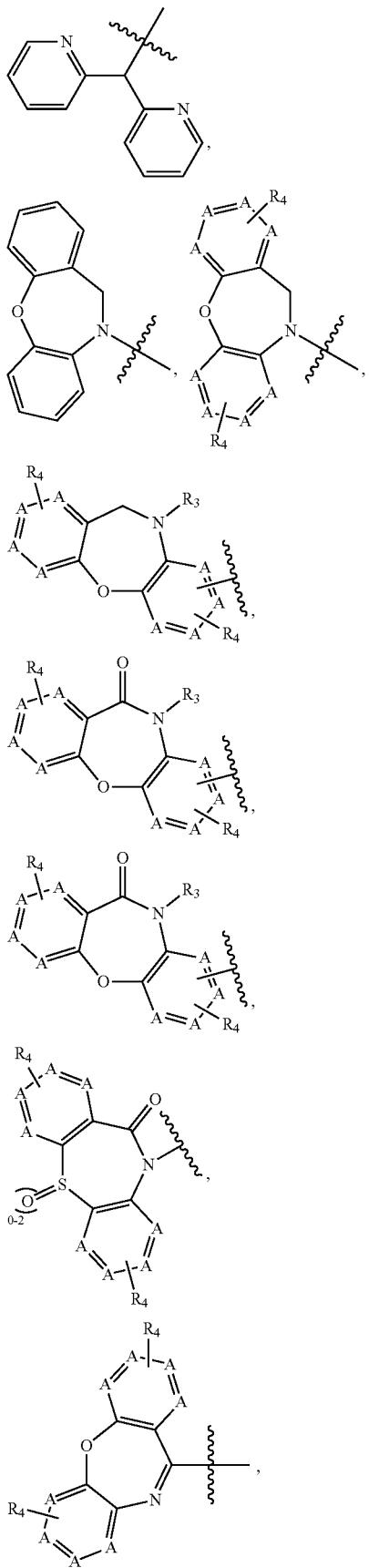
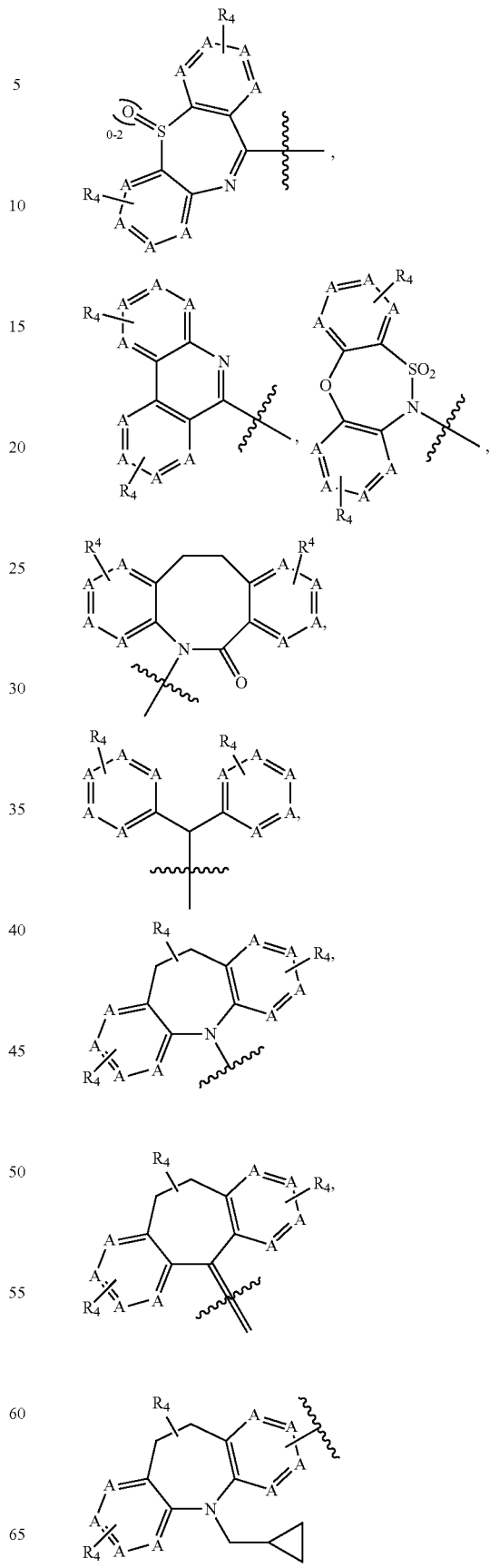

-continued

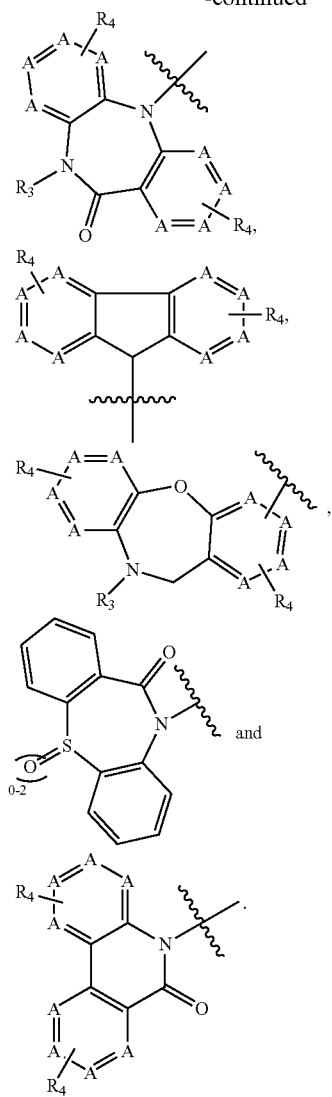

In another preferred embodiment, embodiment AA, of the compounds according to the present invention, each alkyl, alkenyl, alkynyl, heteroalkyl, aryl, heteroaryl, heterocyclyl, and cycloalkyl moiety of J is optionally substituted with from one to three substituents independently selected from the group consisting of alkyl, heterocyclyl, $C_2$-$C_6$alkenyl, $C_2$-$C_3$alkynyl, $C_2$-$C_4$alkyl-$OR^1$, heteroalkyl, heteroaryl, $C_0$-$C_6$alkylheteroaryl, C(O)CF$_3$, —C(O)—NH$_2$, —$C_3$-$C_6$cycloalkyl, -alkyl-$C_3$-$C_6$cycloalkyl, —$C_1$-$C_6$alkylaryl, aryl, alkylheteroaryl and heteroaryl.

In another preferred embodiment, embodiment BB, of the compounds according to the present invention, Q is selected from the group consisting of a covalent bond, —$C_1$-$C_8$alkyl-, =N—O—, —$C_0$-$C_6$alkyl-N($R^3$)—$C_0$-$C_3$alkyl-, —$C_0$-$C_6$alkyl-heterocyclyl-$C_0$-$C_3$alkyl-,—$C_0$-$C_6$alkyl-C(O)—$C_0$-$C_3$alkyl-, —$C_0$-$C_6$alkyl-O—$C_0$-$C_3$alkyl-, —$C_0$-$C_6$alkyl-(CR$^3$=CR$^3$)$_{1-2}$—$C_0$-$C_6$alkyl-, —$C_0$-$C_6$alkyl-(C≡C)$_{1-2}$—$C_0$-$C_6$alkyl-, —$C_0$-$C_6$alkyl-N($R^3$)—C(O)—$C_0$-$C_3$alkyl-, —$C_0$-$C_6$alkyl-N($R^3$)—C(O)-alkenyl-$C_0$-$C_4$alkyl-, —$C_0$-$C_6$alkyl-C(O)—N($R^3$)—$C_0$-$C_4$alkyl-, —$C_0$-$C_6$alkyl-SO$_2$—N($R^3$)—$C_0$-$C_3$alkyl-, —$C_0$-$C_6$alkyl-N($R^3$)—SO$_2$—$C_0$-$C_3$alkyl-, —$C_0$-$C_3$alkyl-N($R^3$)—S(O)$_2$—N($R^3$)—$C_0$-$C_3$alkyl-, —$C_0$-$C_6$alkyl-S—$C_0$-$C_3$alkyl-, —$C_0$-$C_6$alkyl-S(O)—$C_0$-$C_3$alkyl-, —$C_0$-$C_6$alkyl-S(O)$_2$—$C_0$-$C_3$alkyl-, —$C_0$-$C_6$alkyl-N($R^3$)—C(O)—N($R^3$)—$C_0$-$C_3$alkyl-, —$C_0$-$C_3$alkyl-C=N—O—$C_0$-$C_3$alkyl-, -heterocyclyl-$C_0$-$C_3$alkyl-heterocyclyl-$C_0$-$C_3$alkyl-, —SO$_2$—$C_0$-$C_6$alkyl-heterocyclyl-$C_0$-$C_3$alkyl-, —C(O)—$C_0$-$C_6$alkyl-bridged heterocyclyl-$C_0$-$C_3$alkyl-, —N($R^3$)—C(O)—$C_0$-$C_6$alkyl-heterocyclyl-$C_0$-$C_3$alkyl-, —O—C(O)—$C_0$-$C_6$alkyl-heterocyclyl-$C_0$-$C_3$alkyl-, —N($R^3$)—C(S)—$C_0$-$C_6$alkyl-heterocyclyl-$C_0$-$C_3$alkyl-, —O—C(S)—$C_0$-$C_6$alkyl-heterocyclyl-$C_0$-$C_3$alkyl-, —N($R^3$)—S(O)$_2$—$C_0$-$C_6$alkyl-heterocyclyl-$C_0$-$C_3$alkyl-, —$C_0$-$C_6$alkyl-heterocyclyl-$C_0$-$C_3$alkyl-SO$_2$—N($R^3$)—, —$C_0$-$C_6$ alkyl-heterocyclyl-$C_0$-$C_3$alkyl-C(O)—N($R^3$)— and —$C_0$-$C_6$alkyl-heterocyclyl-$C_0$-$C_3$alkyl-C(O)—O—, wherein each alkyl, heterocyclyl and alkenyl moiety is optionally substituted with from one to three substituents independently selected from the group consisting of alkyl, heterocyclyl, $C_2$-$C_6$alkenyl, $C_2$-$C_3$alkynyl, $C_2$-$C_4$alkyl-$OR^1$, heteroalkyl, heteroaryl, $C_0$-$C_6$alkylheteroaryl, C(O)CF$_3$, —C(O)—NH$_2$, —$C_3$-$C_6$cycloalkyl, -alkyl-$C_3$-$C_6$cycloalkyl, —$C_1$-$C_6$alkylaryl, aryl, alkylheteroaryl and heteroaryl.

In another preferred embodiment, embodiment CC, of the compounds according to the present invention, Q is an optionally substituted (1R,4R) or (1S,4S) 2,5-diazabicyclo[2.2.1] heptane enantiomer or a mixture of enantiomers, preferably an (1R,4R) enantiomer, more preferably an (1S,4S) enantiomer, selected from the group consisting of

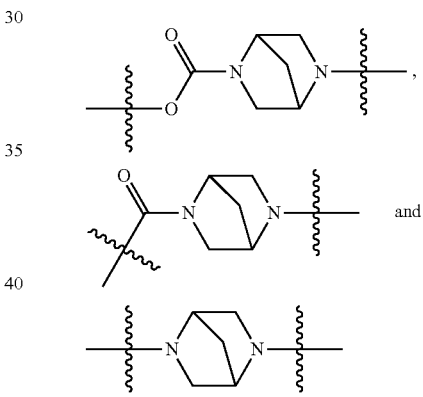

or

Q is

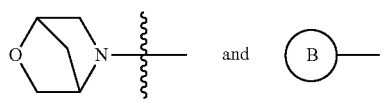

is absent; or

Q is

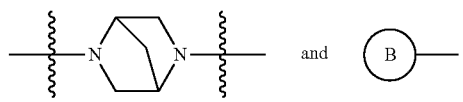

is H.

In another preferred embodiment, embodiment DD, of the compounds according to the present invention, when

is attached to Q via a N in

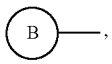, then Q is selected from the group consisting of —$C_1$-$C_8$alkyl-, —$C_2$-$C_6$alkyl-N($R^3$)—$C_0$-$C_3$alkyl-, —$C_0$-$C_6$alkyl-heterocyclyl-$C_0$-$C_3$alkyl-, —$C_0$-$C_6$alkyl-C(O)—$C_0$-$C_3$alkyl-, —$C_2$-$C_6$alkyl-O—$C_0$-$C_3$alkyl-, —$C_1$-$C_6$alkyl-(C$R^3$=C$R^3$)$_{1-2}$—$C_0$-$C_6$alkyl-, —$C_1$-$C_6$alkyl-(C≡C)$_{1-2}$—$C_0$-$C_6$alkyl-, —$C_2$-$C_6$alkyl-N($R^3$)—C(O)—$C_0$-$C_3$alkyl, —$C_2$-$C_6$alkyl-N($R^3$)—C(O)-alkenyl-$C_0$-$C_3$alkyl, —$C_0$-$C_6$alkyl-C(O)—N($R^3$)—$C_0$-$C_4$alkyl-, —C(O)—O—$C_0$-$C_4$alkyl, —$C_0$-$C_6$alkyl-S(O)$_2$—N($R^3$)—$C_0$-$C_3$alkyl, —$C_2$-$C_6$alkyl-N($R^3$)—S(O)$_2$—$C_0$-$C_3$alkyl, —$C_2$-$C_3$alkyl-N($R^3$)—S(O)$_2$—N($R^3$)—$C_0$-$C_3$alkyl-, —$C_2$-$C_6$alkyl-S—$C_0$-$C_3$alkyl, —$C_2$-$C_6$alkyl-S(O)—$C_0$-$C_3$alkyl, —$C_0$-$C_6$alkyl-S(O)$_2$—$C_0$-$C_3$alkyl, —$C_2$-$C_6$alkyl-N($R^3$)—C(O)—N($R^3$)—$C_0$-$C_3$alkyl, —$C_2$-$C_3$alkyl-C=N—O—$C_0$-$C_3$alkyl, —SO$_2$—$C_0$-$C_6$alkyl-heterocyclyl-$C_0$-$C_3$alkyl-, —C(O)—$C_0$-$C_6$alkyl-heterocyclyl-$C_0$-$C_3$alkyl-, —N($R^3$)—C(O)—$C_0$-$C_6$alkyl-heterocyclyl-$C_0$-$C_3$alkyl-, —O—C(O)—$C_0$-$C_6$alkyl-heterocyclyl-$C_0$-$C_3$alkyl-, —N($R^3$)—C(S)—$C_0$-$C_6$alkyl-heterocyclyl-$C_0$-$C_3$alkyl-, —O—C(S)—$C_0$-$C_6$alkyl-heterocyclyl-$C_0$-$C_3$alkyl-, —N($R^3$)—S(O)$_2$—$C_0$-$C_6$alkyl-heterocyclyl-$C_0$-$C_3$alkyl-, —$C_0$-$C_6$alkyl-heterocyclyl-$C_0$-$C_3$alkyl-S(O$_2$)—N($R^3$)—, —$C_0$-$C_6$alkyl-heterocyclyl-$C_0$-$C_3$alkyl-C(O)—N($R^3$)— and —$C_0$-$C_6$alkyl-heterocyclyl-$C_0$-$C_3$alkyl-C(O)—O—, wherein each alkyl, heterocyclyl and alkenyl moiety is optionally substituted with from one to three substituents independently selected the group consisting of alkyl, heterocyclyl, $C_2$-$C_6$alkenyl, $C_2$-$C_3$alkynyl, $C_2$-$C_4$alkyl-O$R^1$, heteroalkyl, heteroaryl, $C_0$-$C_6$alkylheteroaryl, C(O)CF$_3$, —C(O)—NH$_2$, —$C_3$-$C_6$cycloalkyl, -alkyl-$C_3$-$C_6$cycloalkyl, —$C_1$-$C_6$alkylaryl, aryl, alkylheteroaryl and heteroaryl, and wherein the heterocyclyl moiety optionally has a bridge of —(CH$_2$)$_{0-3}$—.

In another preferred embodiment, embodiment EE, of the compounds according to the present invention, each $R_3$ is independently selected from the group consisting of —H, alkyl, heterocyclyl, $C_2$-$C_6$alkenyl, $C_2$-$C_3$alkynyl, $C_2$-$C_4$alkyl-O$R^1$, heteroalkyl, heteroaryl, $C_0$-$C_6$alkylheteroaryl, C(O)CF$_3$, —C(O)—NH$_2$, —$C_3$-$C_6$cycloalkyl, -alkyl-$C_3$-$C_6$cycloalkyl, —$C_1$-$C_6$alkylaryl, aryl, alkylheteroaryl, heteroaryl and a covalent bond, wherein each alkyl, alkenyl, alkynyl, heteroalkyl, cycloalkyl, heterocyclyl, aryl and heteroaryl moiety is optionally substituted with from one to three substituents independently selected from the group consisting of alkyl, heterocyclyl, $C_2$-$C_6$alkenyl, $C_2$-$C_3$alkynyl, $C_2$-$C_4$alkyl-O$R^1$, heteroalkyl, heteroaryl, $C_0$-$C_6$alkylheteroaryl, C(O)CF$_3$, —C(O)—NH$_2$, —$C_3$-$C_6$cycloalkyl, -alkyl-$C_3$-$C_6$cycloalkyl, —$C_1$-$C_6$alkylaryl, aryl, alkylheteroaryl and heteroaryl.

In another preferred embodiment, embodiment FF, of the compounds according to the present invention, Q-J-L is selected from the group consisting of —$C_3$-$C_8$alkyl-, —C(O)—$C_3$-$C_8$alkyl-, —$C_0$-$C_3$alkyl-O—$C_3$-$C_8$alkyl-, —$C_0$-$C_3$alkyl-$C_1$-$C_4$alkenyl-$C_0$-$C_3$alkyl-, =N—O—$C_1$-$C_8$alkyl-, =N—O—$C_0$-$C_3$alkyl-aryl-$C_0$-$C_3$alkyl-, =N—O—$C_0$-$C_3$alkyl-aryl-$C_0$-$C_3$alkenyl-, =N—O—$C_0$-$C_3$alkyl-aryl-$C_0$-$C_3$alkynyl-, =N—O—$C_0$-$C_3$alkyl-heteroaryl-$C_0$-$C_3$alkyl-, =N—O—$C_0$-$C_3$alkyl-heteroaryl-$C_0$-$C_3$alkenyl-, =N—O—$C_0$-$C_3$alkyl-heteroaryl-$C_0$-$C_3$alkynyl-, —$C_0$-$C_3$alkyl-aryl-, —$C_0$-$C_3$alkyl-aryl-$C_0$-$C_3$alkyl-, —$C_0$-$C_3$alkyl-aryl-$C_2$-$C_4$alkenyl-, —$C_0$-$C_3$alkyl-aryl-$C_2$-$C_4$alkynyl-, —$C_0$-$C_3$alkyl-heteroaryl-$C_0$-$C_3$alkyl-, —$C_1$-$C_3$alkyl-heteroaryl-$C_1$-$C_3$alkenyl-, —$C_1$-$C_3$alkyl-heteroaryl-$C_1$-$C_3$alkynyl-, —$C_0$-$C_3$alkyl-N($R^3$)—$C_0$-$C_3$alkyl-aryl-$C_0$-$C_3$alkyl-, —$C_0$-$C_3$alkyl-N($R^3$)—$C_0$-$C_3$alkyl-aryl-$C_2$-$C_3$alkenyl-, —$C_0$-$C_3$alkyl-N($R^3$)—$C_0$-$C_3$alkyl-aryl-$C_2$-$C_3$alkynyl-, —$C_0$-$C_3$alkyl-N($R^3$)—$C_0$-$C_3$alkyl-heteroaryl-$C_0$-$C_3$alkyl-, —$C_0$-$C_3$alkyl-N($R^3$)—$C_0$-$C_3$alkyl-heteroaryl-$C_2$-$C_3$alkenyl-, —$C_0$-$C_3$alkyl-N($R^3$)—$C_0$-$C_3$alkyl-heteroaryl-$C_2$-$C_3$alkynyl-, —$C_0$-$C_3$alkyl-C(O)—N($R^3$)—$C_0$-$C_3$alkyl-aryl-$C_0$-$C_3$alkyl-, —$C_0$-$C_3$alkyl-C(O)—N($R^3$)—$C_0$-$C_3$alkyl-aryl-$C_2$-$C_3$alkenyl-, —$C_0$-$C_3$alkyl-C(O)—N($R^3$)—$C_0$-$C_3$alkyl-aryl-$C_2$-$C_3$alkynyl-, —$C_0$-$C_3$alkyl-C(O)—N($R^3$)—$C_0$-$C_3$alkyl-heteroaryl-$C_0$-$C_3$alkyl-, —$C_0$-$C_3$alkyl-C(O)—N($R^3$)—$C_0$-$C_3$alkyl-heteroaryl-$C_2$-$C_3$alkenyl-, —$C_0$-$C_3$alkyl-C(O)—N($R^3$)—$C_0$-$C_3$alkyl-heteroaryl-$C_2$-$C_3$alkynyl-, —$C_0$-$C_3$alkyl-heterocyclyl-$C_0$-$C_3$alkyl-aryl-, —$C_0$-$C_3$alkyl-heterocyclyl-$C_0$-$C_3$alkyl-aryl-$C_0$-$C_3$alkyl-, —$C_0$-$C_3$alkyl-heterocyclyl-$C_0$-$C_3$alkyl-aryl-$C_2$-$C_4$alkenyl-, —$C_0$-$C_3$alkyl-heterocyclyl-$C_0$-$C_3$alkyl-aryl-$C_2$-$C_4$alkynyl-, —$C_0$-$C_3$alkyl-heterocyclyl-$C_0$-$C_3$alkyl-heteroaryl-$C_0$-$C_3$alkyl, —$C_0$-$C_3$alkyl-heterocyclyl-$C_1$-$C_3$alkyl-heteroaryl-$C_2$-$C_3$alkenyl-, —$C_0$-$C_3$alkyl-heterocyclyl-$C_1$-$C_3$alkyl-heteroaryl-$C_2$-$C_3$alkynyl-, —$C_2$-$C_4$alkyl-O—$C_0$-$C_3$alkyl-aryl-, —$C_2$-$C_4$alkyl-O—$C_0$-$C_3$alkyl-aryl-$C_0$-$C_3$alkyl-, —$C_2$-$C_4$alkyl-O—$C_0$-$C_3$alkyl-aryl-$C_2$-$C_4$alkenyl, —$C_2$-$C_4$alkyl-O—$C_0$-$C_3$alkyl-aryl-$C_2$-$C_4$alkynyl, —$C_2$-$C_4$alkyl-O—$C_0$-$C_3$alkyl-heteroaryl-$C_0$-$C_3$alkyl, —$C_2$-$C_4$alkyl-O—$C_1$-$C_3$alkyl-heteroaryl-$C_2$-$C_3$alkenyl- and —$C_2$-$C_4$alkyl-O—$C_1$-$C_3$alkyl-heteroaryl-$C_2$-$C_3$alkynyl-, wherein each alkyl, alkenyl, aryl, alkynyl, heteroaryl and heterocyclyl moiety is optionally substituted with from one to three substituents independently selected from the group consisting of alkyl, heterocyclyl, $C_2$-$C_6$alkenyl, $C_2$-$C_3$alkynyl, $C_2$-$C_4$alkyl-O$R^1$, heteroalkyl, heteroaryl, $C_0$-$C_6$alkylheteroaryl, C(O)CF$_3$, —C(O)—NH$_2$, —$C_3$-$C_6$cycloalkyl, -alkyl-$C_3$-$C_6$cycloalkyl, —$C_1$-$C_6$alkylaryl, aryl, alkylheteroaryl and heteroaryl.

In another preferred embodiment, embodiment GG, of the compounds according to the present invention,

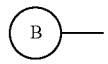

is selected from the group consisting of hydrogen, aryl, arylalkyl-, heteroaryl, heteroaryl-alkyl-, (aryl)$_2$-CH—$C_0$-$C_6$alkyl-, (aryl)(heteroaryl)CH—$C_0$-$C_6$alkyl-, (heteroaryl)$_2$CH—$C_0$-$C_6$alkyl- and (aryl)$_2$-CH—$C_0$-$C_6$alkyl-C(O)—, each of which is optionally substituted with from one to three substituents independently selected from the group consisting of alkyl, heterocyclyl, $C_2$-$C_6$alkenyl, $C_2$-$C_3$alkynyl, $C_2$-$C_4$alkyl-O$R^1$, heteroalkyl, heteroaryl, $C_0$-$C_6$alkylheteroaryl, C(O)CF$_3$, —C(O)—NH$_2$, —$C_3$-$C_6$cycloalkyl, -alkyl-$C_3$-$C_6$cycloalkyl, —$C_1$-$C_6$alkylaryl, aryl, alkylheteroaryl and heteroaryl, provided that variable n of Q is 0, 1 or 3.

In another preferred embodiment, embodiment HH,

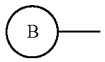

is selected from the group consisting of structures (b-1) to (b-121) and Q-J-L taken together is selected from the group consisting of —$C_3$-$C_8$alkyl-, —C(O)—$C_3$-$C_8$alkyl-, —$C_0$-$C_3$alkyl-O—$C_3$-$C_8$alkyl-, —$C_0$-$C_3$alkyl-$C_1$-$C_4$alkenyl-$C_0$-$C_3$alkyl-, =N—O—$C_1$-$C_8$alkyl-, =N—O—$C_0$-$C_3$alkyl-aryl-$C_0$-$C_3$alkyl-, =N—O—$C_0$-$C_3$alkyl-aryl-$C_0$-$C_3$alkenyl-, =N—O—$C_0$-$C_3$alkyl-aryl-$C_0$-$C_3$alkynyl-, =N—O—$C_0$-$C_3$alkyl-heteroaryl-$C_0$-$C_3$alkyl-, =N—O—$C_0$-$C_3$alkyl-heteroaryl-$C_0$-$C_3$alkenyl-, =N—O—$C_0$-$C_3$alkyl-heteroaryl-$C_0$-$C_3$alkynyl-, —$C_0$-$C_3$alkyl-aryl-$C_0$-$C_3$alkyl-, —$C_0$-$C_3$alkyl-aryl-$C_2$-$C_4$alkenyl-, —$C_0$-$C_3$alkyl-aryl-$C_2$-$C_4$alkynyl-, —$C_0$-$C_3$alkyl-heteroaryl-$C_0$-$C_3$alkyl-, —$C_0$-$C_3$alkyl-heteroaryl-$C_1$-$C_3$alkenyl-, —$C_0$-$C_3$alkyl-heteroaryl-$C_1$-$C_3$alkynyl-, —$C_0$-$C_3$alkyl-N($R^3$)—$C_0$-$C_3$alkyl-aryl-$C_0$-$C_3$alkyl-, —$C_0$-$C_3$alkyl-N($R^3$)—$C_0$-$C_3$alkyl-aryl-$C_2$-$C_3$alkenyl-, —$C_0$-$C_3$alkyl-N($R^3$)—$C_0$-$C_3$alkyl-aryl-$C_2$-$C_3$alkynyl-, —$C_0$-$C_3$alkyl-N($R^3$)—$C_0$-$C_3$alkyl-heteroaryl-$C_0$-$C_3$alkyl-, —$C_0$-$C_3$alkyl-N($R^3$)—$C_0$-$C_3$alkyl-heteroaryl-$C_2$-$C_3$alkenyl-, —$C_0$-$C_3$alkyl-N($R^3$)—$C_0$-$C_3$alkyl-heteroaryl-$C_2$-$C_3$alkynyl-, —$C_0$-$C_3$alkyl-C(O)—N($R^3$)—$C_0$-$C_3$alkyl-aryl-$C_0$-$C_3$alkyl-, —$C_0$-$C_3$alkyl-N($R^3$)—C(O)—$C_0$-$C_3$alkyl-aryl-$C_0$-$C_3$alkyl-, —$C_0$-$C_3$alkyl-C(O)—N($R^3$)—$C_0$-$C_3$alkyl-aryl-$C_2$-$C_3$alkenyl-, —$C_0$-$C_3$alkyl-N($R^3$)—C(O)—$C_0$-$C_3$alkyl-aryl-$C_2$-$C_3$alkenyl-, —$C_0$-$C_3$alkyl-C(O)—N($R^3$)—$C_0$-$C_3$alkyl-aryl-$C_2$-$C_3$alkynyl-, —$C_0$-$C_3$alkyl-N($R^3$)—C(O)—$C_0$-$C_3$alkyl-aryl-$C_2$-$C_3$alkynyl-, —$C_0$-$C_3$alkyl-C(O)—N($R^3$)—$C_0$-$C_3$alkyl-heteroaryl-$C_0$-$C_3$alkyl-, —$C_0$-$C_3$alkyl-N($R^3$)—C(O)—$C_0$-$C_3$alkyl-heteroaryl-$C_0$-$C_3$alkyl-, —$C_0$-$C_3$alkyl-C(O)—N($R^3$)—$C_0$-$C_3$alkyl-heteroaryl-$C_2$-$C_3$alkenyl-, —$C_0$-$C_3$alkyl-N($R^3$)—C(O)—$C_0$-$C_3$alkyl-heteroaryl-$C_2$-$C_3$alkenyl-, —$C_0$-$C_3$alkyl-C(O)—N($R^3$)—$C_0$-$C_3$alkyl-heteroaryl-$C_2$-$C_3$alkynyl-, —$C_0$-$C_3$alkyl-N($R^3$)—C(O)—$C_0$-$C_3$alkyl-heteroaryl-$C_2$-$C_3$alkynyl-, —$C_0$-$C_3$alkyl-heterocyclyl-$C_0$-$C_3$alkyl-aryl-$C_0$-$C_3$alkyl-, —$C_0$-$C_3$alkyl-C(O)-heterocyclyl-$C_0$-$C_3$alkyl-aryl-$C_0$-$C_3$alkyl-, —$C_0$-$C_3$alkyl-N($R^3$)—C(O)-heterocyclyl-$C_0$-$C_3$alkyl-aryl-$C_0$-$C_3$alkyl-, —$C_0$-$C_3$alkyl-O—C(O)-heterocyclyl-$C_0$-$C_3$alkyl-aryl-$C_0$-$C_3$alkyl-, —$C_0$-$C_3$alkyl-heterocyclyl-$C_0$-$C_3$alkyl-aryl-$C_2$-$C_4$alkenyl, —$C_0$-$C_3$alkyl-C(O)-heterocyclyl-$C_0$-$C_3$alkyl-aryl-$C_2$-$C_4$alkenyl, —$C_0$-$C_3$alkyl-N($R^3$)—C(O)-heterocyclyl-$C_0$-$C_3$alkyl-aryl-$C_2$-$C_4$alkenyl-, —$C_0$-$C_3$alkyl-O—C(O)-heterocyclyl-$C_0$-$C_3$alkyl-aryl-$C_2$-$C_4$alkenyl-, —$C_0$-$C_3$alkyl-heterocyclyl-$C_0$-$C_3$alkyl-aryl-$C_2$-$C_4$alkynyl-, —$C_0$-$C_3$alkyl-C(O)-heterocyclyl-$C_0$-$C_3$alkyl-aryl-$C_2$-$C_4$alkynyl-, —$C_0$-$C_3$alkyl-N($R^3$)—C(O)-heterocyclyl-$C_0$-$C_3$alkyl-aryl-$C_2$-$C_4$alkynyl-, —$C_0$-$C_3$alkyl-O—C(O)-heterocyclyl-$C_0$-$C_3$alkyl-aryl-$C_2$-$C_4$alkynyl-, —$C_0$-$C_3$alkyl-heterocyclyl-$C_0$-$C_3$alkyl-heteroaryl-$C_0$-$C_3$alkyl, —$C_0$-$C_3$alkyl-C(O)-heterocyclyl-$C_0$-$C_3$alkyl-heteroaryl-$C_0$-$C_3$alkyl, —$C_0$-$C_3$alkyl-N($R^3$)—C(O)-heterocyclyl-$C_0$-$C_3$alkyl-heteroaryl-$C_0$-$C_3$alkyl, —$C_0$-$C_3$alkyl-O—C(O)-heterocyclyl-$C_0$-$C_3$alkyl-heteroaryl-$C_0$-$C_3$alkyl, —$C_0$-$C_3$alkyl-heterocyclyl-$C_1$-$C_3$alkyl-heteroaryl-$C_2$-$C_3$alkenyl-, —$C_0$-$C_3$alkyl-C(O)-heterocyclyl-$C_1$-$C_3$alkyl-heteroaryl-$C_2$-$C_3$alkenyl-, —$C_0$-$C_3$alkyl-N($R^3$)—C(O)-heterocyclyl-$C_1$-$C_3$alkyl-heteroaryl-$C_2$-$C_3$alkenyl-, —$C_0$-$C_3$alkyl-O—C(O)-heterocyclyl-$C_1$-$C_3$alkyl-heteroaryl-$C_2$-$C_3$alkenyl-, —$C_0$-$C_3$alkyl-heterocyclyl-$C_1$-$C_3$alkyl-heteroaryl-$C_2$-$C_3$alkynyl-, —$C_0$-$C_3$alkyl-C(O)-heterocyclyl-$C_1$-$C_3$alkyl-heteroaryl-$C_2$-$C_3$alkynyl-, —$C_0$-$C_3$alkyl-N($R^3$)—C(O)-heterocyclyl-$C_1$-$C_3$alkyl-heteroaryl-$C_2$-$C_3$alkynyl-, —$C_0$-$C_3$alkyl-O—C(O)-heterocyclyl-$C_1$-$C_3$alkyl-heteroaryl-$C_2$-$C_3$alkynyl-, —$C_0$-$C_3$alkyl-O—$C_0$-$C_3$alkyl-aryl-$C_0$-$C_3$alkyl-, —$C_2$-$C_4$alkyl-O—$C_0$-$C_3$alkyl-aryl-$C_0$-$C_3$alkyl-, —$C_2$-$C_4$alkyl-O—$C_0$-$C_3$alkyl-aryl-$C_2$-$C_4$alkenyl, —$C_2$-$C_4$alkyl-O—$C_0$-$C_3$alkyl-aryl-$C_2$-$C_4$alkynyl-, —$C_2$-$C_4$alkyl-O—$C_0$-$C_3$alkyl-heteroaryl-$C_0$-$C_3$alkyl, —$C_2$-$C_4$alkyl-O—$C_1$-$C_3$alkyl-heteroaryl-$C_2$-$C_3$alkenyl-, —$C_2$-$C_4$alkyl-O—$C_1$-$C_3$alkyl-heteroaryl-$C_2$-$C_3$alkynyl-, —$C_0$-$C_6$alkyl-U-bridged heterocyclyl-heteroaryl-$C_0$-$C_6$alkyl-, —$C_0$-$C_6$alkyl-U-bridged heterocyclyl-N($R^3$)-heteroaryl-$C_0$-$C_6$alkyl-, —$C_0$-$C_6$alkyl-U—N($R^3$)-bridged heterocyclyl-heteroaryl-$C_0$-$C_6$alkyl-, —$C_0$-$C_6$alkyl-U-bridged heterocyclyl-aryl-$C_0$-$C_6$alkyl-, —$C_0$-$C_6$alkyl-U-bridged heterocyclyl-N($R^3$)-aryl-$C_0$-$C_6$alkyl-, —$C_0$-$C_6$alkyl-U—N($R^3$)-bridged heterocyclyl-aryl-$C_0$-$C_6$alkyl-, —$C_0$-$C_6$alkyl-U-bridged heterocyclyl-aryl-$C_2$-$C_6$alkenyl-, —$C_0$-$C_6$alkyl-U-bridged heterocyclyl-N($R^3$)-aryl-$C_2$-$C_6$alkenyl-, —$C_0$-$C_6$alkyl-U—N($R^3$)-bridged heterocyclyl-aryl-$C_2$-$C_6$alkenyl-, —$C_0$-$C_6$alkyl-U-bridged heterocyclyl-heteroaryl-$C_2$-$C_6$alkenyl-, —$C_0$-$C_6$alkyl-U-bridged heterocyclyl-N($R^3$)-heteroaryl-$C_2$-$C_6$alkenyl-, —$C_0$-$C_6$alkyl-U—N($R^3$)-bridged heterocyclyl-heteroaryl-$C_2$-$C_6$alkenyl-, —$C_0$-$C_6$alkyl-bridged heterocyclyl-U-heteroaryl-$C_0$-$C_6$alkyl-, —$C_0$-$C_6$alkyl-N($R^3$)-bridged heterocyclyl-U-heteroaryl-$C_0$-$C_6$alkyl-, —$C_0$-$C_6$alkyl-bridged heterocyclyl-N($R^3$)—U-heteroaryl-$C_0$-$C_6$alkyl-, —$C_0$-$C_6$alkyl-bridged heterocyclyl-U-aryl-$C_0$-$C_6$alkyl-, —$C_0$-$C_6$alkyl-N($R^3$)-bridged heterocyclyl-U-aryl-$C_0$-$C_6$alkyl-, —$C_0$-$C_6$alkyl-bridged heterocyclyl-N($R^3$)—U-aryl-$C_0$-$C_6$alkyl-, —$C_0$-$C_6$alkyl-bridged heterocyclyl-U-aryl-$C_2$-$C_6$alkenyl-, —$C_0$-$C_6$alkyl-N($R^3$)-bridged heterocyclyl-U-aryl-$C_2$-$C_6$alkenyl-, —$C_0$-$C_6$alkyl-bridged heterocyclyl-N($R^3$)—U-aryl-$C_2$-$C_6$alkenyl-, —$C_0$-$C_6$alkyl-bridged heterocyclyl-U-heteroaryl-$C_2$-$C_6$alkenyl-, —$C_0$-$C_6$alkyl-N($R^3$)-bridged heterocyclyl-U-heteroaryl-$C_2$-$C_6$alkenyl-, and —$C_0$-$C_6$alkyl-bridged heterocyclyl-N($R^3$)—U-heteroaryl-$C_2$-$C_6$alkenyl-, wherein each alkyl, alkenyl, aryl, alkynyl, heteroaryl and heterocyclyl moiety is optionally substituted; and wherein the bridge is methylene or propylene.

In another preferred embodiment, embodiment II, of the compounds according to the present invention B-Q-J-L- are taken together, wherein each such B-Q-J-L group is optionally substituted with up to 4 substituents independently selected from the group consisting of hydroxy, amino, halo, $C_1$-$C_6$alkyl, nitro, cyano, $C_2$-$C_6$alkoxy, $C_1$-$C_6$-amino and $CF_3$, heterocyclyl, $C_2$-$C_6$alkenyl, $C_2$-$C_3$alkynyl, $C_2$-$C_4$alkyl-$OR^1$, heteroalkyl, heteroaryl, $C_0$-$C_6$alkylheteroaryl, C(O)$CF_3$, —C(O)—$NH_2$, —$C_3$-$C_6$cycloalkyl, -alkyl-$C_3$-$C_6$cycloalkyl, —$C_1$-$C_6$alkylaryl, aryl and alkylheteroaryl.

In another preferred embodiment, embodiment JJ, of the compounds according to the present invention, $R^4$ is independently selected from the group consisting of —H, $C_1$-$C_6$alkyl, $C_2$-$C_6$alkenyl, $C_2$-$C_6$alkynyl, $C_1$-$C_6$alkyl-$R^3$, —$C_0$-$C_6$alkyl-$OR^3$, —$C_0$-$C_6$alkyl-$OR^1$, —$C_0$-$C_6$alkyl-C(O)—$OR^3$, —$C_0$-$C_6$alkyl-C(O)$NR^3$, $R^{3a}$, —CH=CH—C(O)—$OR^3$, —CH=CH—C(O)—N($R^3$)($R^{3a}$), —N($R^3$)—C(O)—$CF^3$, —N($R^3$)—$C_2$-$C_6$alkyl-N($R^3$)($R^{3a}$), —$C_0$-$C_6$alkyl-N($R^3$)($R^{3a}$), —N($R^3$)—C(O)—$C_1$-$C_6$alkyl-$R^3$, —N($R^3$)—S(O)$_2$—$C_1$-$C_6$alkyl-$R^3$, —S(O)$_2$—N($R^3$)$R^{3a}$, —O—$C_2$-$C_6$alkyl-N($R^3$)($R^{3a}$), —S—$R^3$, —S(O)—$C_1$-$C_6$alkyl-$R^3$, —S(O)$_2$—$C_1$-$C_6$alkyl-$R^3$, $C_3$-$C_6$cycloalkyl, heterocyclyl, $C_4$-$C_7$heterocyclyl-$R^3$, —O—$C_2$-$C_4$alkyl-heterocyclyl, —O-heterocyclyl-C(O)—$OR^3$, —O—$C_0$-$C_4$alkyl-aryl, —O—$C_0$-$C_4$alkyl-heteroaryl, —O—C(O)—$NR^3$—$C_0$-$C_4$alkyl-aryl, —O—C(O)—$NR^3$—$C_0$-$C_4$alkyl-heteroaryl, —O—$C_0$-$C_4$alkyl-heterocyclylaryl, —O—$C_0$-$C_4$alkyl-heterocyclyl-heteroaryl, —N($R^3$)—$C_2$-$C_4$alkyl-heterocyclyl, —N(R³)C(O)N(R³)—C₀-C₄alkyl-heterocyclyl-R³, —C₀-C₄alkyl-OC(O)—R³, —C₀-C₄alkyl-N(R³)C(O)—O—R³, —C₀-C₄alkyl-heterocyclyl-C(O)—O—R³, —N(R³)—C₂-C₄alkyl-heterocyclyl, F, Cl, Br, I, NO₂, —CF₃, —SO₃H, —CN, —C₁-C₆ alkylaryl, aryl, heteroaryl, —C₁-C₆ alkylheteroaryl, wherein each alkyl, alkenyl, alkynyl, cycloalkyl, heterocyclyl, aryl and heteroaryl moeity of the aformentioned R⁴ is optionally substituted with from one to three substituents independently selected from the group consisting of alkyl, heterocyclyl, C₂-C₆alkenyl, C₂-C₃alkynyl, C₂-C₄alkyl-OR¹, heteroalkyl, heteroaryl, C₀-C₆alkylheteroaryl, C(O)CF₃, —C(O)—NH₂, —C₃-C₆cycloalkyl, -alkyl-C₃-C₆cycloalkyl, —C₁-C₆alkylaryl, aryl, alkylheteroaryl and heteroaryl.

In another preferred embodiment, embodiment KK, of the compounds according to the present invention, R³ᵃ is independently selected from the group consisting of —H, alkyl, heterocyclyl, C₂-C₆alkenyl, C₂-C₃alkynyl, C₂-C₄alkyl-OR¹, heteroalkyl, heteroaryl, C₀-C₆alkylheteroaryl, C(O)CF₃, —C(O)—NH₂, —C₃-C₆cycloalkyl, -alkyl-C₃-C₆cycloalkyl, —C₁-C₆alkylaryl, aryl, alkylheteroaryl and heteroaryl, covalent bond, wherein each alkyl, alkenyl, alkynyl, heteroalkyl, cycloalkyl, heterocyclyl, aryl and heteroaryl moiety is optionally substituted with from one to three substituents independently selected from the group consisting of alkyl, heterocyclyl, C₂-C₆alkenyl, C₂-C₃alkynyl, C₂-C₄alkyl-OR¹, heteroalkyl, heteroaryl, C₀-C₆alkylheteroaryl, C(O)CF₃, —C(O)—NH₂, —C₃-C₆cycloalkyl, -alkyl-C₃-C₆cycloalkyl, —C₁-C₆alkylaryl, aryl, alkylheteroaryl and heteroaryl.

In another preferred embodiment, embodiment LL, of the compounds according to the present invention, Q is selected from the group consisting of

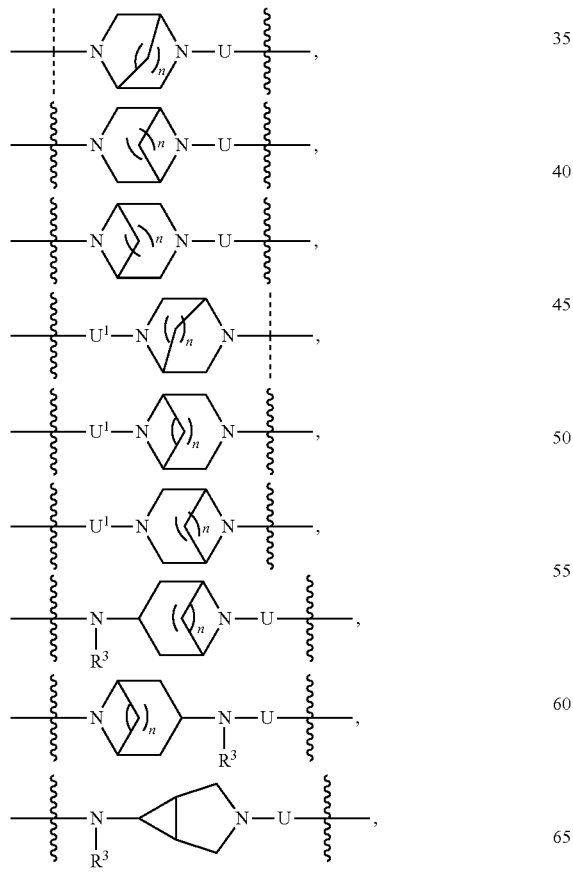

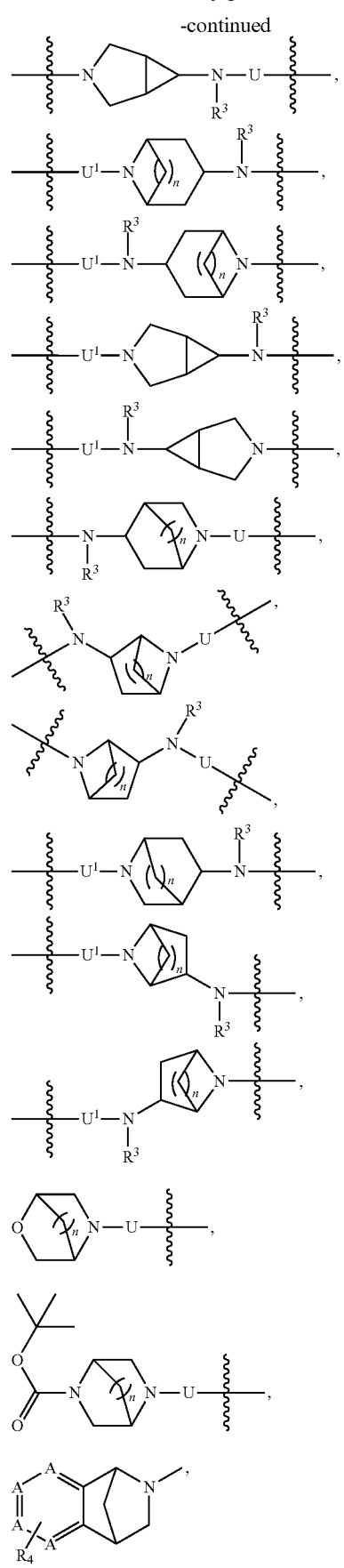

(a-1)

(a-2)

(a-3)

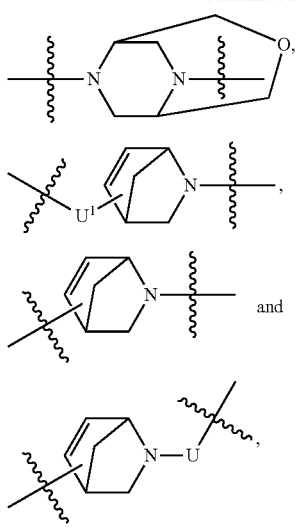

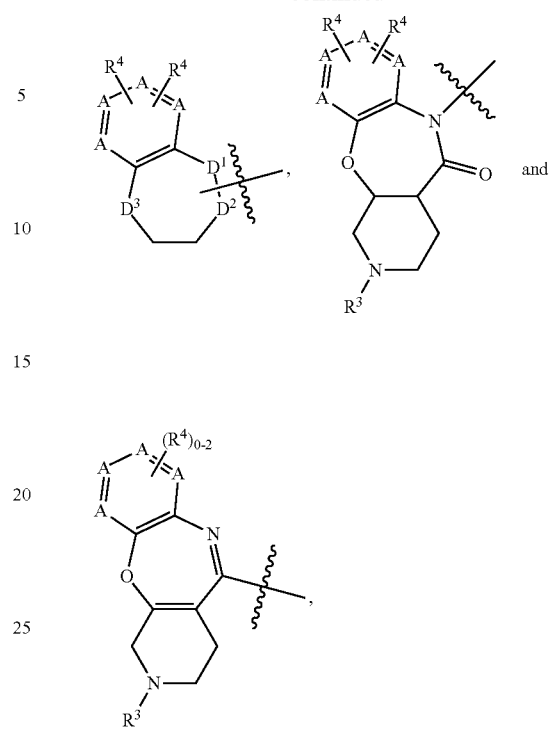

or an optionally substituted (R,R) or (S,S) enantiomer or a mixture of enantiomers, preferably an (R,R) enantiomer, more preferably an (S,S) enantiomer thereof, each of which is optionally substituted with a substituent selected from the group consisting of halo, alkyl and aryl.

In another preferred embodiment, embodiment MM, of the compounds according to the present invention,

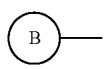

is selected from the group consisting of

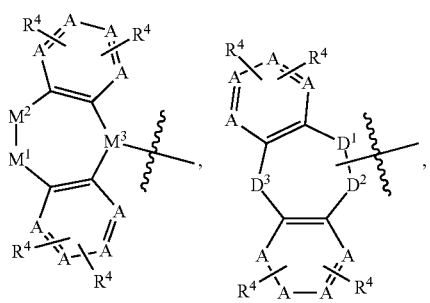

wherein $M^1$-$M^2$- is —CH=CH— or —CH$_2$—CH$_2$—;

A is selected from the group consisting of N, C(R$^4$) and CH;

Z is —NHOH;

L is covalent bond;

J is selected from the group consisting of —C$_1$-C$_8$alkyl-, —C$_0$-C$_6$alkyl-aryl-C$_0$-C$_6$alkyl-, —C$_0$-C$_6$alkyl-aryl-C$_2$-C$_6$alkenyl-, —C$_0$-C$_6$alkyl-heteroaryl-C$_0$-C$_6$alkyl- and —CH=; and Q is selected from the group consisting of covalent bond, =N—O—, —C$_0$-C$_6$alkyl-N(R$^3$)—C$_0$-C$_3$alkyl-, —C$_0$-C$_6$alkyl-N(R$^3$)—C(O)—C$_0$-C$_3$alkyl- and —C$_0$-C$_6$alkyl-C(O)—C$_0$-C$_3$alkyl-.

In preferred embodiment of embodiment MM, embodiment MM-1,

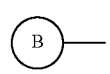

is further selected from the group consisting of

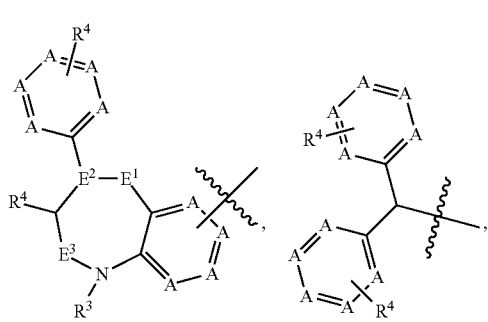

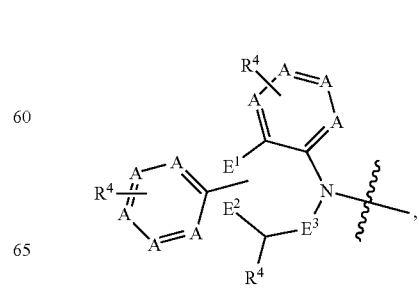

-continued

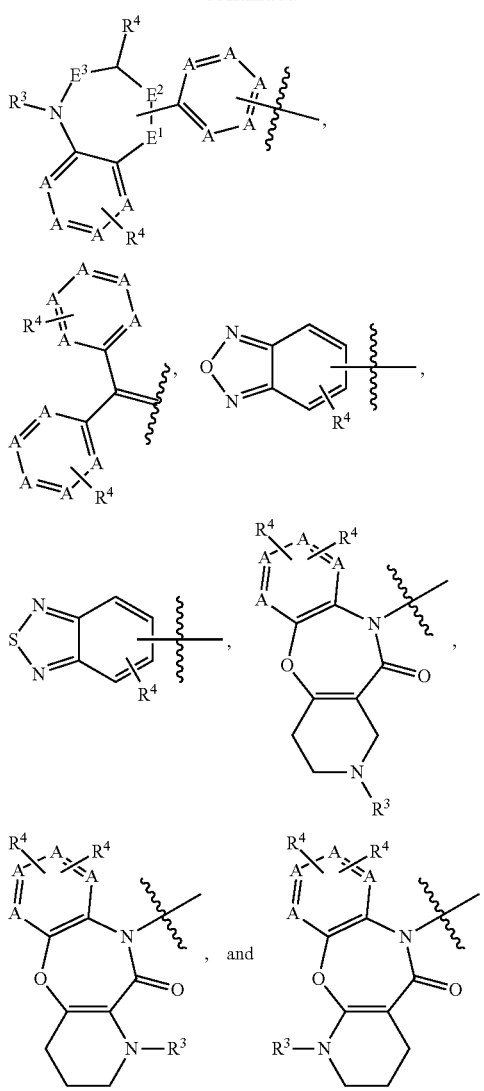

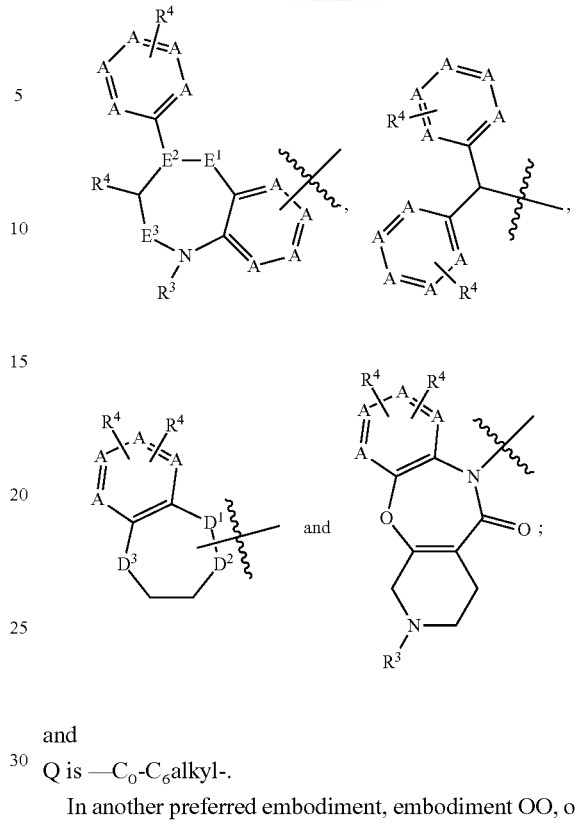

and

Q is —C₀-C₆alkyl-.

In another preferred embodiment, embodiment OO, of the compounds according to the present invention,

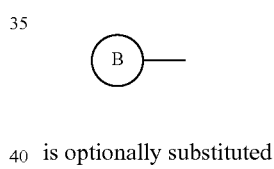

is optionally substituted

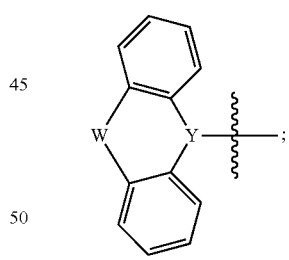

W is —CH=CH— or —CH₂—CH₂—;
Y is selected from the group consisting of N, C(R⁴) and CH;
Z is —NHOH;
L is covalent bond;
J is selected from the group consisting of —C₁-C₈alkyl-, —C₀-C₆alkyl-aryl-C₀-C₆alkyl-, —C₀-C₆alkyl-aryl-C₂-C₆alkenyl-, —C₀-C₆alkyl-heteroaryl-C₀-C₆alkyl- and —CH=; and Q is selected from the group consisting of covalent bond, =N—O—, —C₀-C₆alkyl-N(R³)—C₀-C₃alkyl-, —C₀-C₆alkyl-N(R³)—C(O)—C₀-C₃alkyl- and —C₀-C₆alkyl-C(O)—C₀-C₃alkyl-.

In another preferred embodiment, embodiment NN, of the compounds according to the present invention,

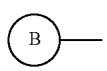

is selected from the group consisting of

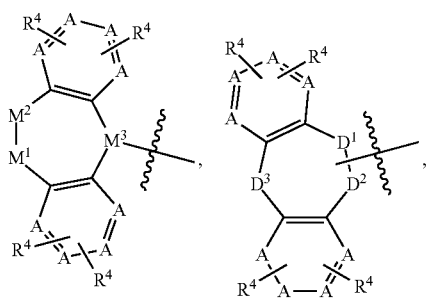

In another preferred embodiment, embodiment PP, of the compounds of the present invention,

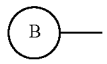

is selected from the group consisting of

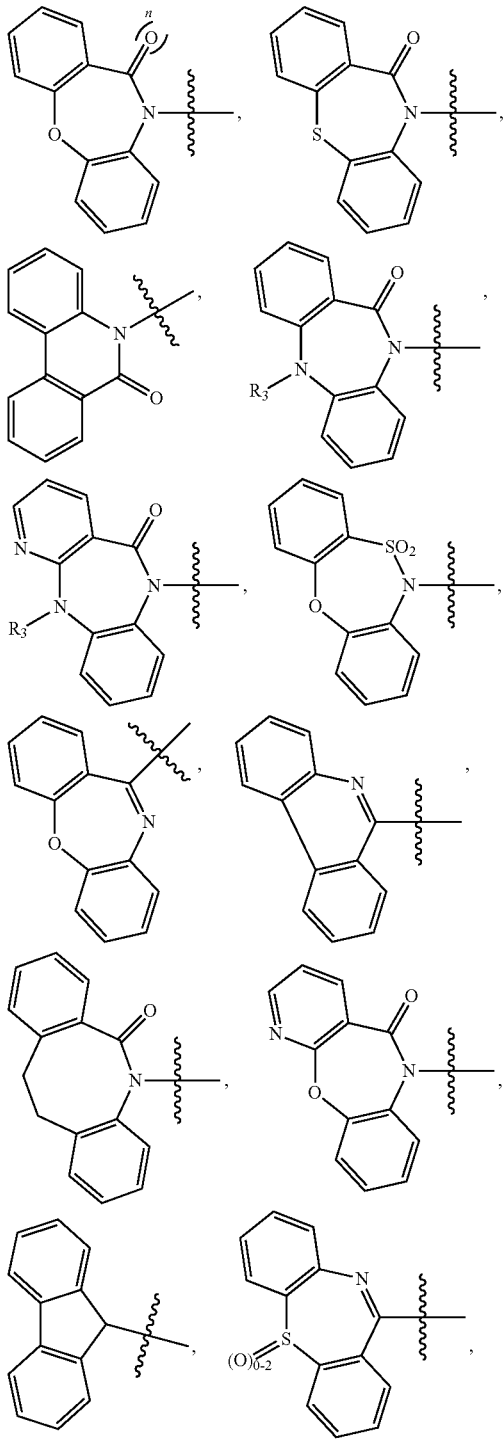

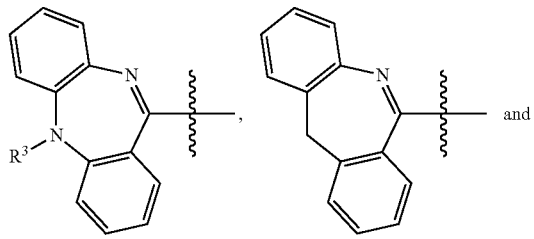

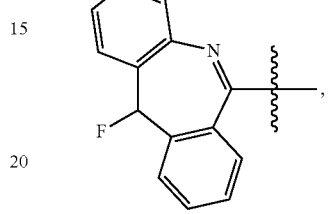

each of which is optionally substituted on a phenyl ring with one or two $R^4$;

Z is —$NR^1OR^2$ or H;

$R^1$ and $R^2$ are —H;

L is covalent bond or —N(OH)—;

J is —$C_1$-$C_8$alkyl-, —$C_0$-$C_6$alkyl-aryl-$C_0$-$C_6$alkyl-, —$C_0$-$C_6$alkyl-heteroaryl-$C_0$-$C_6$alkyl-, —$C_0$-$C_3$alkyl-$C_2$-$C_6$alkenyl-$C_0$-$C_3$alkyl-, —$C_0$-$C_6$alkyl-aryl-$C_2$-$C_6$alkenyl- and —$C_2$-$C_6$alkenyl-aryl-$C_0$-$C_6$alkyl-;

Q is selected from the group consisting of covalent bond, —$C_1$-$C_3$alkyl-(C)—$C_0$-$C_3$alkyl, —$C_0$-$C_6$alkyl-, —$C_1$-$C_3$alkyl-(CH=CH)—$C_0$-$C_3$alkyl-, —$C_2$-$C_6$alkyl-O—$C_0$-$C_3$alkyl-, —$C_2$-$C_6$alkyl-C(O)—$C_0$-$C_3$alkyl- and —$C_2$-$C_6$alkyl-heterocyclyl-$C_0$-$C_3$alkyl-; or Q is selected from the group consisting of a covalent bond, —$C_1$-$C_3$alkyl-(C≡C)—$C_0$-$C_3$alkyl, —$C_0$-$C_6$alkyl-, —$C_1$-$C_3$alkyl-(CH=CH)—$C_0$-$C_3$alkyl-, —$C_0$-$C_6$alkyl-O—$C_0$-$C_3$alkyl-, —$C_0$-$C_6$alkyl-C(O)—$C_0$-$C_3$alkyl- and —$C_0$-$C_6$alkyl-heterocyclyl-$C_0$-$C_3$alkyl- when

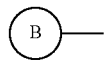

is

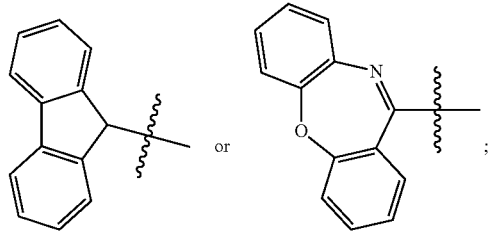 [SMILES: *C1c2ccccc2-c2ccccc21 ; *C1=Nc2ccccc2Oc2ccccc21]

and $R^3$ is H or cycloalkyl.

In another preferred embodiment, embodiment QQ, of the compounds according to the present invention,

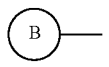

is selected from the group consisting of (aryl)$_2$-CH—C$_0$-C$_6$alkyl-, (aryl)$_2$-C$_1$-C$_6$alkyl- and (heteroaryl)$_2$-C$_1$-C$_6$alkyl-, wherein each aryl, alkyl and heteroaryl moiety is optionally substituted;
Z is NHOH;
Q is selected from the group consisting of —C$_0$-C$_6$alkyl-heteroaryl-C$_0$-C$_6$alkyl-, =N—O—, —C$_0$-C$_6$alkyl-heterocyclyl-C$_0$-C$_3$alkyl and —C$_0$-C$_6$alkyl-O—C$_0$-C$_3$alkyl;
J is —C$_0$-C$_6$alkyl-heteroaryl-C$_0$-C$_6$alkyl; and
L is a covalent bond.

In another preferred embodiment, embodiment RR, of the compounds according to the present invention,

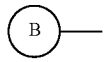

is selected from the group consisting of aryl and (aryl)$_2$-alkyl, each of which is optionally substituted and H;
Q is selected from the group consisting of —C$_0$-C$_6$alkyl-bridged heterocyclyl-C$_0$-C$_3$alkyl- and

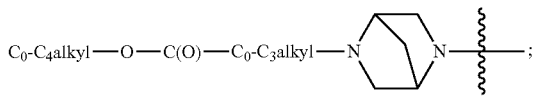

J is —C$_0$-C$_6$alkyl-heteroaryl-C$_0$-C$_6$alkyl;
L is a covalent bond; and
Z is NHOH.

In another preferred embodiment, embodiment SS, of the compounds according to the present invention,

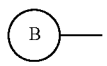

is

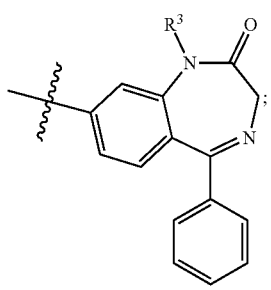

Z is —NHOH;
R$^3$ is H or alkyl;
L is covalent bond;
J is —C$_1$-C$_8$alkyl- or —C$_0$-C$_3$alkyl-C$_1$-C$_8$alkenyl-C$_0$-C$_3$alkyl-; and
Q is covalent bond.

In another preferred embodiment, embodiment TT, of the compounds according to the present invention,

is

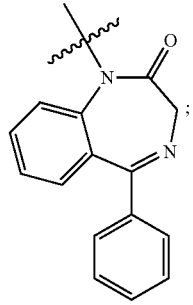 [SMILES: *N1C(=O)CN=C(c2ccccc2)c2ccccc21]

Z is —NHOH;
L is a covalent bond;
J is —C$_1$-C$_8$alkyl- or —C$_0$-C$_6$alkyl-aryl-C$_2$-C$_6$alkenyl-; and
Q is a covalent bond.

In another preferred embodiment, embodiment UU, of the compounds according to the present invention, the compound is selected from one of the following structures:

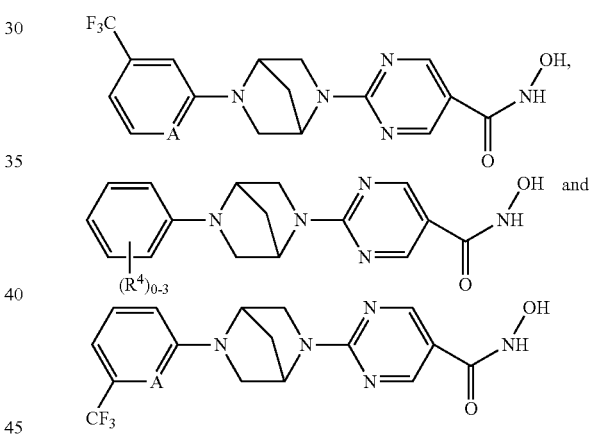

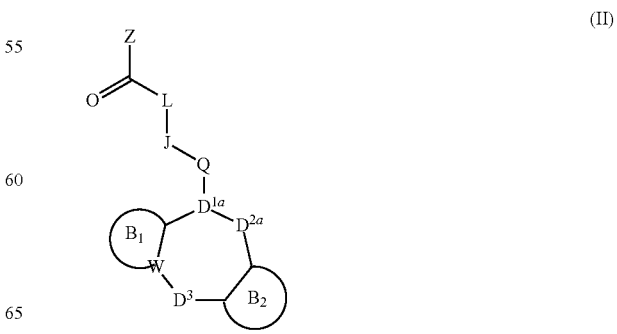

wherein R$^4$ is as defined for embodiment (A), and A is selected from the group consisting of N and —CH=.

In another preferred embodiment, embodiment VV, of the compounds according to the present invention, the compounds are represented by the Formula II:

(II)

and N-oxides, hydrates, solvates, pharmaceutically acceptable salts, prodrugs, polymorphs and complexes thereof, and racemic and scalemic mixtures, diastereomers and enantiomers thereof, wherein Z is selected from the group consisting of —N($R^1$)$OR^2$ and H;

L is selected from the group consisting of a covalent bond and —N($OR^2$)—;

wherein, when L is —N($OR^2$)—, then Z is H; and wherein, when Z is H, then L is —N($OR^2$)—;

$R^1$ and $R^2$ are independently selected from the group consisting of —H and $C_1$-$C_6$alkyl;

W is nitrogen or carbon;

$D^{1a}$-$D^{2a}$ is selected from the group consisting of

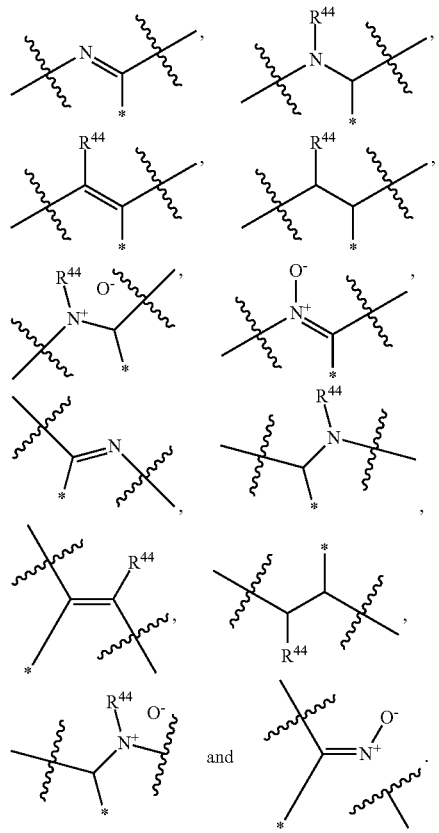

wherein, * represents the point of attachment to Q;

$D^3$ is independently selected from the group consisting of —C($R^{55}$)($R^{66}$)—, —C($R^{55}$)(OH)—, —C(O)—, —O—, —N($R^{77}$)— and —S(O)$_{0-2}$—;

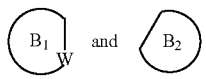

are independently selected from the group consisting of phenyl, heteroaryl and heterocyclyl, wherein each phenyl, heteroaryl and heterocyclyl is optionally substituted with one to three substituents independently selected from the group consisting of halo, —$CF_3$, —$OCF_3$, —$NO_2$, —CN, —$C_1$-$C_6$alkyl, —$C_1$-$C_6$alkoxyl, —O—$C_2$-$C_6$alkyl-O—$R^{53}$, —O—$R^{53}$, —$C_0$-$C_6$alkyl-S(O)$_{0-2}$—$R^{53}$, —$C_0$-$C_6$alkyl-C(O)—$R^{53}$, —$C_0$-$C_6$alkyl-C(O)N$R^{50}R^{51}$, —$C_0$-$C_6$alkyl-N$R^{52}$C(O)—$R^{53}$, —$C_0$-$C_6$alkyl-S(O)$_2$N$R^{50}R^{51}$, —$C_0$-$C_6$alkyl-N$R^{52}$S(O)$_2$—$R^{53}$, —$C_0$-$C_6$alkyl-OC(O)N$R^{50}R^{51}$, —$C_1$-$C_6$alkyl-N$R^{52}$C(O)O—$R^{53}$, —$C_0$-$C_6$alkyl-N$R^{52}$C(O)N$R^{50}R^{51}$, —$C_0$-$C_6$alkyl-C(O)O—$R^{53}$, —$C_0$-$C_6$alkyl-OC(O)—$R^{53}$, —$C_0$-$C_6$alkyl-aryl, —$C_0$-$C_6$alkyl-heteroaryl, —$C_0$-$C_6$alkyl-$C_3$-$C_7$cycloalkyl, —$C_0$-$C_6$alkyl-heterocyclyl, —$C_0$-$C_6$alkyl-N$R^{50}R^{51}$, —O—$C_2$-$C_6$alkyl-N$R^{50}R^{51}$, —N$R^{53}$—$C_2$-$C_6$alkyl-N$R^{50}R^{51}$ and —O-heterocyclyl-$R^{53}$;

$R^{44}$ is independently selected from the group consisting of —H, —$C_1$-$C_6$alkyl, —$C_0$-$C_6$alkyl-$C_3$-$C_7$cycloalkyl and —$C_0$-$C_4$alkyl-heterocyclyl;

$R^{50}$ and $R^{51}$ are independently selected from the group consisting of H, —$C_1$-$C_6$alkyl, —$C_2$-$C_6$alkyl-O—$C_1$-$C_6$alkyl, —$C_0$-$C_6$alkyl-$C_3$-$C_7$cycloalkyl, wherein each alkyl and cycloalkyl is optionally substituted with one or more substituents independently selected from the group consisting of halo, —OH, amino, —CN or —$C_1$-$C_4$alkyl; or $R^{50}$ and $R^{51}$, together with the N atom to which they are attached, optionally form a 3-10 membered heterocyclic ring, wherein the heterocyclyl is optionally substituted with one to three substituents independently selected from the group consisting of halo, —OH, amino, —CN or —$C_1$-$C_4$alkyl;

$R^{52}$ is independently selected from the group consisting of —H, —$C_1$-$C_6$alkyl, —$C_2$-$C_6$alkyl-O—$C_1$-$C_6$alkyl, —$C_0$-$C_6$alkyl-$C_3$-$C_7$cycloalkyl, wherein each alkyl and cycloalkyl is optionally substituted with one or more substituents independently selected from the group consisting of halo, —OH, amino, —CN or —$C_1$-$C_4$alkyl;

$R^{53}$ is independently selected from the group consisting of —$C_1$-$C_6$alkyl, —$C_0$-$C_4$alkyl-$C_3$-$C_2$cycloalkyl, —$C_0$-$C_4$alkyl-aryl, —$C_0$-$C_4$alkyl-heteroaryl and —$C_0$-$C_4$alkyl-heterocyclyl, wherein each alkyl, aryl, heteroaryl and heterocyclyl is optionally substituted with one or three substituents independently selected from the group consisting of halo, —OH, amino, —CN or —$C_1$-$C_4$alkyl;

$R^{55}$ and $R^{66}$ are independently selected from the group consisting of —H, —$C_1$-$C_6$alkyl, —$C_1$-$C_6$alkoxyl, —$C_0$-$C_4$alkyl-$C_3$-$C_7$cycloalkyl and —$C_0$-$C_4$alkyl-heterocyclyl; or $R^{55}$ and $R^{66}$, together with the atom to which they are attached, optionally form a 3-7 membered cycloalkyl or heterocyclic ring, wherein each cycloalkyl and heterocyclyl is optionally substituted with one to three substituents independently selected from the group consisting of halo, —OH, amino, —CN or —$C_1$-$C_4$alkyl;

$R^{77}$ is independently selected from the group consisting of —H, —$C_1$-$C_6$alkyl, —$C_1$-$C_6$heteroalkyl, —$C_3$-$C_7$cycloalkyl, —C(O)—$R^{53}$, —C(O)O—$R^{53}$, -cycloalkyl, —$C_1$-$C_4$alkyl-cycloalkyl, phenyl, —$C_1$-$C_4$alkyl-phenyl, -heterocyclyl, —$C_1$-$C_4$alkyl-heterocyclyl and —$C_2$-$C_6$alkyl-N$R^{88}R^{99}$, wherein each alkyl and heteroalkyl is optionally substituted with one or three substituents independently selected from the group consisting of F, —OH and oxo, wherein each phenyl, cycloalkyl and heterocyclyl is optionally substituted with one or two substituents independently selected from the group consisting of halo, —CN, —$C_1$-$C_4$alkyl, —$C_1$-$C_4$alkoxyl, —O—$C_2$-$C_4$alkyl-O—$C_1$-$C_4$alkyl, —$CF_3$, —$OCF_3$, —$NO_2$, —$C_1$-$C_6$alkyl-S(O)$_{0-2}R^{53}$, —$NH_2$, —N$R^{50}R^{51}$, —$C_1$-$C_6$alkyl-N$R^{50}R^{51}$ and —N($C_1$-$C_6$alkyl)$_2$;

or $R^{77}$ together with the N to which it is attached may form a ring with

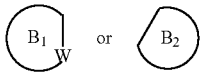

wherein the ring is a 5-7 membered heterocyclic ring, and $R^{88}$ and $R^{99}$ are independently selected from the group consisting of —H, —$C_1$-$C_6$alkyl, —$C_2$-$C_6$alkyl-O—$C_1$-$C_6$alkyl and —$C_0$-$C_4$alkyl-$C_3$-$C_2$cycloalkyl, wherein each cycloalkyl and alkyl is optionally substituted with one to three substituents independently selected from the group consisting of halo, —OH, amino, —CN or —$C_1$-$C_6$alkyl-aryl;
or
$R^{88}$ and $R^{99}$, together with the N atom to which they are attached, optionally form a 3-10 membered heterocyclic ring, wherein an heterocyclyl is optionally substituted with one to three substituents independently selected from the group consisting of halo, —OH, amino or —CN In a preferred embodiment of embodiment VV, embodiment VV-1, of the compounds of the present invention,
J-Q is selected from the group consisting of —$C_1$-$C_9$alkyl, —$C_1$-$C_9$heteroalkyl, phenyl, aryl, heteroaryl, —$C_1$-$C_4$alkyl-phenyl, —$C_1$-$C_4$alkyl-aryl, —$C_1$-$C_4$alkyl-heteroaryl, —$NR^{33}$aryl, —$NR^{33}$—$C_1$-$C_4$alkyl-aryl, —$NR^{33}$heteroaryl and $NR^{33}$—$C_1$-$C_4$alkyl-heteroaryl, wherein each alkyl and heteroalkyl is optionally substituted with one or three substituents independently selected from the group consisting of F, —OH and oxo, wherein each phenyl, aryl and heteroaryl is optionally substituted with one or two substituents independently selected from the group consisting of halo, —OH, —$OR^{53}$, —$C_1$-$C_4$alkyl, —$C_1$-$C_4$alkoxyl, —O—$C_2$-$C_4$alkyl-O—$C_1$-$C_6$alkyl, —CN, —$CF_3$, —$OCF_3$, —$NO_2$, —$C_1$-$C_6$alkyl-S(O)$_{0-2}R^{53}$, —$NH_2$, —$NR^{50}R^{51}$, —$C_1$-$C_6$alkyl-$NR^{50}R^{51}$ and —N($C_1$-$C_6$alkyl)$_2$, wherein $R^{33}$ is independently selected from the group consisting of —H, —$C_1$-$C_6$alkyl, —$C_0$-$C_6$alkyl-$C_3$-$C_2$cycloalkyl and —$C_0$-$C_4$alkyl-phenyl, wherein each phenyl and cycloalkyl is optionally substituted with one or three substituents independently selected from the group consisting of halo, —OH, —$NO_2$, —$CF_3$, —$OCF_3$, amino, —N($C_1$-$C_6$alkyl)$_2$, —$C_1$-$C_6$alkyl-S(O)$_{0-2}R^{53}$, —$C_1$-$C_4$alkoxyl —CN, —O—$C_2$alkyl-O—$CH_3$, —$NR^{50}R^{51}$, —$C_1$-$C_6$alkyl-$NR^{50}R^{51}$ or —$C_1$-$C_4$alkyl.

In a preferred embodiment of embodiment VV, embodiment VV-2, of the compounds of the present invention, the moiety

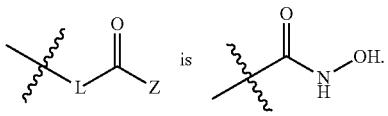

In a preferred embodiment of embodiment VV, embodiment VV-3, of the compounds of the present invention,
J-Q is selected from the group consisting of 5- or 6-membered heteroaryl.

In a preferred embodiment of embodiment VV, embodiment VV-4, of the compounds of the present invention, the compounds are represented by the Formula (III):

(III)

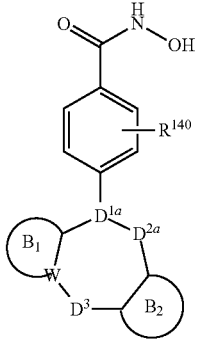

wherein $R^{140}$ is selected from the group consisting of H, —OH, halo, —CN, —$C_1$-$C_4$alkyl, —$C_1$-$C_4$alkoxyl, —O—$C_2$-$C_4$alkyl-O—$C_1$-$C_4$alkyl, —$CF_3$, —$OCF_3$, —$NO_2$, —$C_1$-$C_6$alkyl-S(O)$_{0-2}R^{53}$, —$NH_2$, —$NR^{50}R^{51}$, —$C_1$-$C_6$alkyl-$NR^{50}R^{51}$ and —N($C_1$-$C_6$alkyl)$_2$.

In a preferred embodiment of embodiment VV-4, embodiment VV-5, of the compounds of the present invention, $D^{1a}$-$D^{2a}$ is selected from the group consisting of

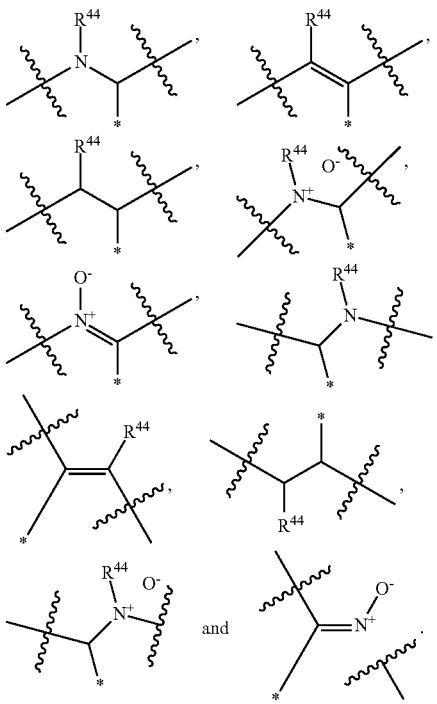

In a preferred embodiment of embodiment VV-4, embodiment VV-6, of the compounds of the present invention, $D^{1a}$-$D^{2a}$ is

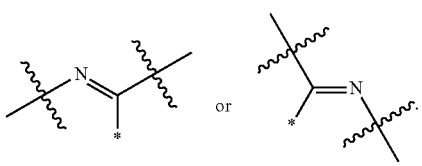 [SMILES: *N=C(*)* ; *N=C(*)*]

In a preferred embodiment of embodiment VV-4, embodiment VV-7, of the compounds of the present invention, $D^{1a}$-$D^{2a}$ is

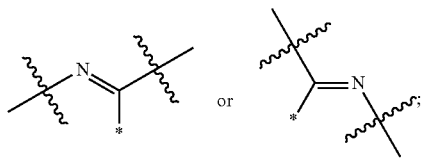 [SMILES: *N=C(*)* ; *N=C(*)*]

and
$D^3$ is selected from the group consisting of —C($R^{55}$)($R^{66}$)—, —C($R^{55}$)(OH)—, —C(O)—, —O—, —N($R^{77}$)— and —S(O)$_{0-2}$.

In a preferred embodiment of embodiment VV-4, embodiment VV-8, of the compounds of the present invention, $D^{1a}$-$D^{2a}$ is

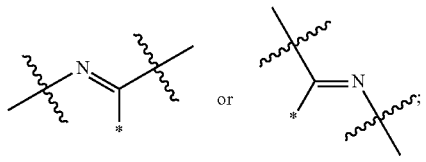 [SMILES: *N=C(*)* ; *N=C(*)*]

and
$D^3$ is —N($R^{77}$)—.

In a preferred embodiment of embodiment VV-4, embodiment VV-9, of the compounds of the present invention, $D^{1a}$-$D^{2a}$ is

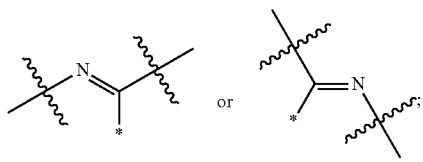 [SMILES: *N=C(*)* ; *N=C(*)*]

and
$D^3$ is —O—.

In a preferred embodiment of embodiment VV-4, embodiment VV-10, of the compounds of the present invention, $D^{1a}$-$D^{2a}$ is

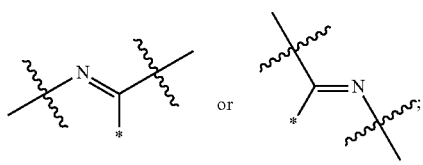 [SMILES: *N=C(*)* ; *N=C(*)*]

$D^3$ is —O—; and

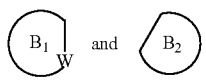

are independently selected from the group consisting of phenyl, pyridyl, pyrimidyl, thienyl, pyrazolyl, thiazyl and oxazyl.

In a preferred embodiment of embodiment VV-4, embodiment VV-11, of the compounds of the present invention, $D^{1a}$-$D^{2a}$ is

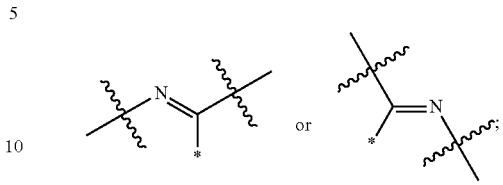

$D^3$ is —O—; and

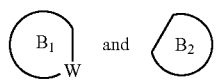

are independently selected from the group consisting of phenyl, pyridyl, pyrimidyl, thienyl, pyrazolyl, thiazyl and oxazyl, wherein at least one of

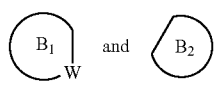

is phenyl, wherein the phenyl, pyridyl, pyrimidyl, thienyl, pyrazolyl, thiazyl and oxazyl are independently optionally substituted.

In a preferred embodiment of embodiment VV-4, embodiment VV-12, of the compounds of the present invention, $D^{1a}$-$D^{2a}$ is

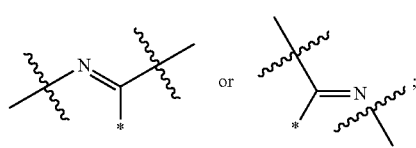

$D^3$ is —N($R^{77}$)—; and

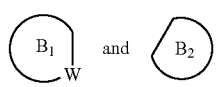

are independently selected from the group consisting of phenyl, pyridyl, pyrimidyl and thienyl.

In a preferred embodiment of embodiment VV-4, embodiment VV-13, of the compounds of the present invention, $D^{1a}$-$D^{2a}$ is

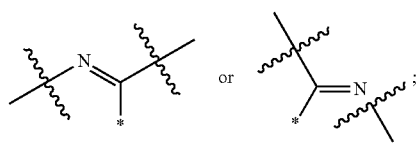

$D^3$ is —N($R^{22}$)—; and

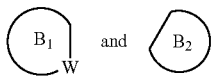

are independently selected from the group consisting of phenyl, pyridyl, pyrimidyl and thienyl, wherein at least one of

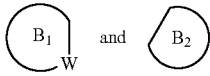

is phenyl, wherein said phenyl, pyridyl, pyrimidyl and thienyl are independently optionally substituted.

In a preferred embodiment of embodiment VV, embodiment VV-14, of the compounds of the present invention, the compounds are represented by the Formula (IV):

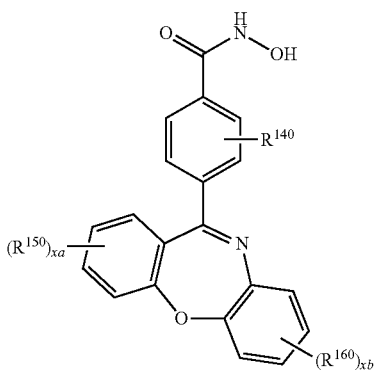

(IV)

wherein $R^{140}$, is as defined in Formula III;
xa and xb denote numbers that are each independently selected from 0, 1 and 2; and
$R^{150}$ and $R^{160}$ are independently selected from the group consisting of H, halo, —CN, —$CF_3$, —$OCF_3$, —$C_1$-$C_6$alkyl, —$C_1$-$C_6$alkoxyl, —O—$C_2$-$C_6$alkyl-O—$R^{53}$, —$OR^{53}$, —$C_0$-$C_6$alkyl-S(O)$_{0-2}$—$R^{53}$, —$C_0$-$C_6$alkyl-C(O)—$R^{53}$, —$C_0$-$C_6$alkyl-C(O)NR$^{50}$R$^{51}$, —$C_0$-$C_6$alkyl-NR$^{52}$C(O)—$R^{53}$, —$C_0$-$C_6$alkyl-S(O)$_2$NR$^{50}$R$^{51}$, —$C_0$-$C_6$alkyl-NR$^{52}$S(O)$_2$—$R^{53}$, —$C_0$-$C_6$alkyl-OC(O)NR$^{50}$R$^{51}$, —$C_0$-$C_6$alkyl-NR$^{52}$C(O)O—$R^{53}$, —$C_0$-$C_6$alkyl-NR$^{52}$C(O)NR$^{50}$R$^{51}$, —$C_0$-$C_6$alkyl-C(O)O—$R^{53}$, —$C_0$-$C_6$alkyl-OC(O)—$R^{53}$, —$C_0$-$C_6$alkyl-aryl, —$C_0$-$C_6$alkyl-heteroaryl, —$C_0$-$C_6$alkyl-cycloalkyl, —$C_0$-$C_6$alkyl-heterocyclyl, —$NH_2$, —NR$^{50}$R$^{51}$, —O—$C_2$-$C_6$alkyl-NR$^{50}$R$^{51}$, —NR$^{53}$—$C_2$-$C_6$alkyl-NR$^{50}$R$^{51}$ and —O-heterocyclyl-$R^{53}$, wherein each alkyl and heteroalkyl is optionally substituted with one or three substituents independently selected from the group consisting of F, —OH and oxo, and wherein each aryl, heteroaryl, cycloalkyl and heterocyclyl is optionally substituted with one or two substituents independently selected from the group consisting of halo, —CN, —$C_1$-$C_4$alkyl, —$C_1$-$C_4$alkoxyl, —O—$C_2$-$C_4$alkyl-O—$C_1$-$C_4$alkyl, —$CF_3$, —$OCF_3$, —$NO_2$, —$C_1$-$C_6$alkyl-S(O)$_{0-2}$R$^{53}$, —$NH_2$, —NR$^{50}$R$^{51}$, —$C_1$-$C_6$alkyl-NR$^{50}$R$^{51}$ and —N($C_1$-$C_6$alkyl)$_2$;

In a preferred embodiment of embodiment VV, embodiment VV-15, of the compounds of the present invention, the compounds are represented by the Formula (V):

(V)

wherein $R^{140}$ is as defined in Formula III, and xb, $R^{150}$ and $R^{160}$ are as defined in Formula IV;
xc is 0 or 1; and
$R^{170}$ is selected from the group consisting of H, halo, —CN, —$CF_3$, —$OCF_3$, —$C_1$-$C_6$alkyl, —$C_1$-$C_0$alkoxyl, —O—$C_2$-$C_6$alkyl-O—$R^{53}$, —$OR^{53}$, —$C_0$-$C_6$alkyl-S(O)$_{0-2}$—$R^{53}$, —$C_0$-$C_6$alkyl-C(O)—$R^{53}$, —$C_0$-$C_6$alkyl-C(O)NR$^{50}$R$^{51}$, —$C_0$-$C_6$alkyl-NR$^{52}$C(O)—$R^{53}$, —$C_0$-$C_6$alkyl-S(O)$_2$NR$^{50}$R$^{51}$, —$C_0$-$C_6$alkyl-NR$^{52}$S(O)$_2$—$R^{53}$, —$C_0$-$C_6$alkyl-OC(O)NR$^{50}$R$^{51}$, —$C_0$-$C_6$alkyl-NR$^{52}$C(O)O—$R^{53}$, —$C_0$-$C_6$alkyl-NR$^{52}$C(O)NR$^{50}$R$^{51}$, —$C_0$-$C_6$alkyl-C(O)O—$R^{53}$, —$C_0$-$C_6$alkyl-OC(O)—$R^{53}$, —$C_0$-$C_6$alkyl-aryl, —$C_0$-$C_6$alkyl-heteroaryl, —$C_0$-$C_6$alkyl-cycloalkyl, —$C_0$-$C_6$alkyl-heterocyclyl, —$NH_2$, —NR$^{50}$R$^{51}$, —$C_1$-$C_6$alkyl-NR$^{50}$R$^{51}$, —O—$C_2$-$C_6$alkyl-NR$^{50}$R$^{51}$, —NR$^{53}$—$C_2$-$C_6$alkyl-NR$^{50}$R$^{51}$ and —O-heterocyclyl-$R^{53}$, wherein each alkyl and heteroalkyl is optionally substituted with one or three substituents independently selected from the group consisting of F, —OH and oxo, wherein each aryl, heteroaryl, cycloalkyl and heterocyclyl is optionally substituted with one or two substituents independently selected from the group consisting of halo, —CN, —$C_1$-$C_4$alkyl, —$C_1$-$C_4$alkoxyl, —O—$C_2$-$C_4$alkyl-O—$C_1$-$C_4$alkyl, —$CF_3$, —$OCF_3$, —$NO_2$, —$C_1$-$C_6$alkyl-S(O)$_{0-2}$R$^{53}$, —$NH_2$, —NR$^{50}$R$^{51}$, —$C_1$-$C_6$alkyl-NR$^{50}$R$^{51}$ and —N($C_1$-$C_6$alkyl)$_2$.

In a preferred embodiment of embodiment VV, embodiment VV-16, of the compounds of the present invention, the compounds represented by the Formula (VI):

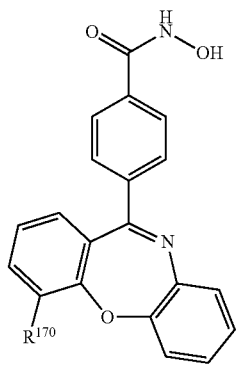

(VI)

wherein $R^{170}$ is as defined in Formula V.

In a preferred embodiment of embodiment VV, embodiment VV-17, of the compounds of the present invention, the compounds are represented by the Formula (VII):

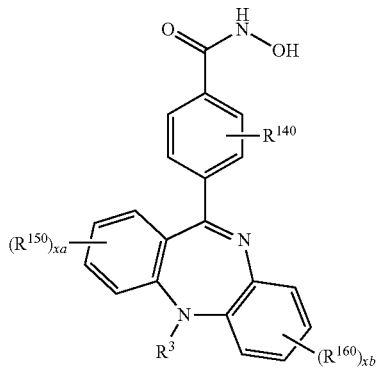

(VII)

wherein $R^{140}$ is as defined in Formula III, xa, xb, $R^{150}$ and $R^{160}$ are as defined in Formula IV; and $R^3$ is as defined in Formula I.

In a preferred embodiment of embodiment VV, embodiment VV-18, of the compounds of the present invention, $R^3$ is $R^{180}$, wherein $R^{180}$ is selected from the group consisting of H, —$C_1$-$C_6$alkyl, —$C_1$-$C_6$alkenyl, —$C_1$-$C_6$alkynyl, —$C_2$-$C_6$alkoxyl, —$C_2$-$C_6$alkyl-O—$R^{53}$, —$OR^{53}$, —$C_2$-$C_6$alkyl-S(O)$_{0-2}$—$R^{53}$, —$C_2$-$C_6$alkyl-C(O)—$R^{53}$, —$C_2$-$C_6$alkyl-C(O)NR$^{50}$R$^{51}$, —$C_2$-$C_6$alkyl-NR$^{52}$C(O)—$R^{53}$, —$C_2$-$C_6$alkyl-S(O)$_2$NR$^{50}$R$^{51}$, —$C_2$-$C_6$alkyl-NR$^{52}$S(O)$_2$—$R^{53}$, —$C_2$-$C_6$alkyl-OC(O)NR$^{50}$R$^{51}$, —$C_2$-$C_6$alkyl-NR$^{52}$C(O)O—$R^{53}$, —$C_2$-$C_6$alkyl-NR$^{52}$C(O)NR$^{50}$R$^{51}$, —$C_2$-$C_6$alkyl-C(O)O—$R^{53}$, —$C_2$-$C_6$alkyl-OC(O)—$R^{53}$, —$C_0$-$C_6$alkyl-heterocyclyl-$R^{53}$, —$C_0$-$C_6$alkyl-heterocyclyl-O—$R^{53}$, —$C_0$-$C_6$alkyl-heterocyclyl-S(O)$_{0-2}$—$R^{53}$, —$C_0$-$C_6$alkyl-heterocyclyl-C(O)—$R^{53}$, —$C_0$-$C_6$alkyl-heterocyclyl-C(O)NR$^{50}$R$^{51}$, —$C_0$-$C_6$alkyl-heterocyclyl-NR$^{52}$C(O)—$R^{53}$, —$C_0$-$C_6$alkyl-heterocyclyl-S(O)$_2$NR$^{50}$R$^{51}$, —$C_0$-$C_6$alkyl-heterocyclyl-NR$^{52}$S(O)$_2$—$R^{53}$, —$C_0$-$C_6$alkyl-heterocyclyl-OC(O)NR$^{50}$R$^{51}$, —$C_0$-$C_6$alkyl-heterocyclyl-NR$^{52}$C(O)O—$R^{53}$, —$C_0$-$C_6$alkyl-heterocyclyl-NR$^{52}$C(O)NR$^{50}$R$^{51}$, —$C_0$-$C_6$alkyl-heterocyclyl-C(O)O—$R^{53}$, —$C_0$-$C_6$alkyl-heterocyclyl-OC(O)—$R^{53}$, —$C_0$-$C_6$alkyl-cycloalkyl-$R^{53}$, —$C_0$-$C_6$alkyl-cycloalkyl —O—$R^{53}$, —$C_0$-$C_6$alkyl-cycloalkyl —S(O)$_{0-2}$—$R^{53}$, —$C_0$-$C_6$alkyl-cycloalkyl-C(O)—$R^{53}$, —$C_0$-$C_6$alkyl-cycloalkyl —C(O)NR$^{50}$R$^{51}$, —$C_0$-$C_6$alkyl-cycloalkyl-NR$^{52}$C(O)—$R^{53}$, —$C_0$-$C_6$alkyl-cycloalkyl-S(O)$_2$NR$^{50}$R$^{51}$, —$C_0$-$C_6$alkyl-cycloalkyl-NR$^{52}$S(O)$_2$—$R^{53}$, —$C_0$-$C_6$alkyl-cycloalkyl-OC(O)NR$^{50}$R$^{51}$, —$C_0$-$C_6$alkyl-cycloalkyl-NR$^{52}$C(O)O—$R^{53}$, —$C_0$-$C_6$alkyl-cycloalkyl-NR$^{52}$C(O)NR$^{50}$R$^{51}$, —$C_0$-$C_6$alkyl-cycloalkyl-C(O)O—$R^{53}$, —$C_0$-$C_6$alkyl-cycloalkyl-OC(O)—$R^{53}$, —$C_0$-$C_6$alkyl-heteroaryl-$R^{53}$, —$C_0$-$C_6$alkyl-heteroaryl —O—$R^{53}$, —$C_0$-$C_6$alkyl-heteroaryl —S(O)$_{0-2}$—$R^{53}$, —$C_0$-$C_6$alkyl-heteroaryl —C(O)—$R^{53}$, —$C_0$-$C_6$alkyl-heteroaryl —C(O)NR$^{50}$R$^{51}$, —$C_0$-$C_6$alkyl-heteroaryl —NR$^{52}$C(O)—$R^{53}$, —$C_0$-$C_6$alkyl-heteroaryl —S(O)$_2$NR$^{50}$R$^{51}$, —$C_0$-$C_6$alkyl-heteroaryl —NR$^{52}$S(O)$_2$—$R^{53}$, —$C_0$-$C_6$alkyl-heteroaryl —OC(O)NR$^{50}$R$^{51}$, —$C_0$-$C_6$alkyl-heteroaryl-NR$^{52}$C(O)O—$R^{53}$, —$C_0$-$C_6$alkyl-heteroaryl —NR$^{52}$C(O)NR$^{50}$R$^{51}$, —$C_0$-$C_6$alkyl-heteroaryl —C(O)O—$R^{53}$, —$C_0$-$C_6$alkyl-heteroaryl —OC(O)—$R^{53}$, —$C_0$-$C_6$alkyl-aryl-$R^{53}$, —$C_0$-$C_6$alkyl-aryl —O—$R^{53}$, —$C_0$-$C_6$alkyl-aryl —S(O)$_{0-2}$—$R^{53}$, —$C_0$-$C_6$alkyl-aryl —C(O)—$R^{53}$, —$C_0$-$C_6$alkyl-aryl —C(O)NR$^{50}$R$^{51}$, —$C_0$-$C_6$alkyl-aryl —NR$^{52}$C(O)—$R^{53}$, —$C_0$-$C_6$alkyl-aryl —S(O)$_2$NR$^{50}$R$^{51}$, —$C_0$-$C_6$alkyl-aryl —NR$^{52}$S(O)$_2$—$R^{53}$, —$C_0$-$C_6$alkyl-aryl —OC(O)NR$^{50}$R$^{51}$, —$C_0$-$C_6$alkyl-aryl-NR$^{52}$C(O)O—$R^{53}$, —$C_0$-$C_6$alkyl-aryl —NR$^{52}$C(O)NR$^{50}$R$^{51}$, —$C_0$-$C_6$alkyl-aryl —C(O)O—$R^{53}$, —$C_0$-$C_6$alkyl-aryl —OC(O)—$R^{53}$, —$C_0$-$C_6$alkyl-aryl, —$C_0$-$C_6$alkyl-heteroaryl, —$C_0$-$C_6$alkyl-cycloalkyl, —$C_0$-$C_6$alkyl-heterocyclyl and —$C_2$-$C_6$alkyl-NR$^{50}$R$^{51}$, wherein each alkyl and heteroalkyl is optionally substituted with one to three substituents independently selected from the group consisting of F, —OH and oxo, wherein each aryl, heteroaryl, cycloalkyl and heterocyclyl is optionally substituted with one or two substituents.

In a preferred embodiment of embodiment VV, embodiment VV-19, the compound is selected from the group consisting of:

(Z)-4-(dibenzo[b,f][1,4]oxazepin-11-yl)-N-hydroxybenzamide, (Z)-4-(dibenzo[b,f][1,4]thiazepin-11-yl)-N-hydroxybenzamide, 4-(10,11-dihydrodibenzo[b,f][1,4]oxazepin-11-yl)-N-hydroxybenzamide, N-hydroxy-4-(10-methyl-10,11-dihydrodibenzo[b,f][1,4]oxazepin-11-yl)benzamide, (Z)-4-(8-chloro-5H-dibenzo[b,e][1,4]diazepin-11-yl)-N-hydroxybenzamide, (Z)-4-(benzo[b]pyrido[3,2-f][1,4]oxazepin-5-yl)-N-hydroxybenzamide, (Z)-4-(2-fluorodibenzo[b,f][1,4]oxazepin-11-yl)-N-hydroxybenzamide, (Z)—N-hydroxy-4-(2-methoxydibenzo[b,f][1,4]oxazepin-11-yl)benzamide, (Z)-4-(benzo[b]pyrido[4,3-f][1,4]oxazepin-5-yl)-N-hydroxybenzamide, (Z)-4-(2-(2-(dimethylamino)ethoxy)dibenzo[b,f][1,4]oxazepin-11-yl)-N-hydroxybenzamide, (Z)—N-hydroxy-4-(8-(trifluoromethyl)dibenzo[b,f][1,4]oxazepin-11-yl)benzamide, (Z)-4-(dibenzo[b,f][1,4]oxazepin-11-yl)-2-fluoro-N-hydroxybenzamide, (Z)-5-(4-(hydroxycarbamoyl)phenyl)benzo[b]pyrido[4,3-f][1,4]oxazepine 2-oxide, (Z)—N-hydroxy-4-(3-methoxydibenzo[b,f][1,4]oxazepin-11-yl)benzamide, (Z)-3-(dibenzo[b,f][1,4]oxazepin-11-yl)-N-hydroxybenzamide, (Z)—N-hydroxy-4-(8-methyldibenzo[b,f][1,4]oxazepin-11-yl)benzamide, (Z)—N-hydroxy-4-(4-methoxydibenzo[b,f][1,4]oxazepin-11-yl)benzamide, (Z)-4-(9-fluorodibenzo[b,f][1,4]oxazepin-11-yl)-N-hydroxybenzamide, (Z)—N-hydroxy-4-(7-(trifluoromethyl)dibenzo[b,f][1,4]oxazepin-11-yl)benzamide, (Z)-4-(7-chlorodibenzo[b,f][1,4]oxazepin-11-yl)-N-hydroxybenzamide, (Z)-4-(2-chlorodibenzo[b,f][1,4]oxazepin-11-yl)-N-hydroxybenzamide, (Z)-4-(8-cyanodibenzo[b,f][1,4]oxazepin-11-yl)-N-hydroxybenzamide, (Z)—N-hydroxy-4-(4-methyldibenzo[b,f][1,4]oxazepin-11-yl)benzamide, (Z)—N-hydroxy-4-(3-methyldibenzo[b,f][1,4]oxazepin-11-yl)benzamide, (Z)-4-(benzo[b]thieno[2,3-f][1,4]oxazepin-10-yl)-N-hydroxybenzamide, (Z)-4-(3-fluorodibenzo[b,f][1,4]oxazepin-11-yl)-N-hydroxybenzamide, (Z)-4-(8-chlorodibenzo[b,f][1,4]oxazepin-11-yl)-N-hydroxybenzamide,
(Z)—N-hydroxy-4-(3-(trifluoromethyl)dibenzo[b,f][1,4]oxazepin-11-yl)benzamide,
(Z)-4-(6-fluorodibenzo[b,f][1,4]oxazepin-11-yl)-N-hydroxybenzamide,
(Z)-4-(7-cyanodibenzo[b,f][1,4]oxazepin-11-yl)-N-hydroxybenzamide,
(Z)—N-hydroxy-4-(4-hydroxydibenzo[b,f][1,4]oxazepin-11-yl)benzamide,
(Z)—N-hydroxy-4-(1-methoxydibenzo[b,f][1,4]oxazepin-11-yl)benzamide,
(Z)—N-hydroxy-4-(4-(2-methoxyethoxy)dibenzo[b,f][1,4]oxazepin-11-yl)benzamide,
(Z)-4-(1-fluorodibenzo[b,f][1,4]oxazepin-11-yl)-N-hydroxybenzamide,
(Z)—N-hydroxy-4-(2-(trifluoromethyl)benzo[f]pyrido[2,3-b][1,4]oxazepin-6-yl)benzamide,
(Z)-4-(11-cyclopropyl-11H-benzo[b]pyrido[2,3-e][1,4]diazepin-5-yl)-N-hydroxybenzamide,
(Z)-4-(5-cyclopropyl-5H-dibenzo[b,e][1,4]diazepin-11-yl)-N-hydroxybenzamide,
(Z)-4-(5H-dibenzo[b,e][1,4]diazepin-11-yl)-N-hydroxybenzamide,
(Z)—N-hydroxy-4-(4-(2-morpholinoethoxy)dibenzo[b,f][1,4]oxazepin-11-yl)benzamide,
(Z)-4-(benzo[f]pyrido[2,3-b][1,4]oxazepin-6-yl)-N-hydroxybenzamide,
(Z)-4-(2-fluoro-4-methoxydibenzo[b,f][1,4]oxazepin-11-yl)-N-hydroxybenzamide,
(Z)—N-hydroxy-4-(4-(methylthio)dibenzo[b,f][1,4]oxazepin-11-yl)benzamide,
(Z)—N-hydroxy-4-(4-(trifluoromethyl)dibenzo[b,f][1,4]oxazepin-11-yl)benzamide,
(Z)—N-hydroxy-4-(4-(methylsulfinyl)dibenzo[b,f][1,4]oxazepin-11-yl)benzamide,
(Z)-4-(5H-benzo[e]pyrrolo[1,2-a][1,4]diazepin-11-yl)-N-hydroxybenzamide,
(Z)—N-hydroxy-4-(4-(methylsulfonyl)dibenzo[b,f][1,4]oxazepin-11-yl)benzamide,
(E)-4-((dibenzo[b,f][1,4]oxazepin-11-ylamino)methyl)-N-hydroxybenzamide,
(Z)—N-hydroxy-4-(4-methoxy-8-(trifluoromethyl)dibenzo[b,f][1,4]oxazepin-11-yl)benzamide,
(Z)—N-hydroxy-4-(3-morpholinodibenzo[b,f][1,4]oxazepin-11-yl)benzamide,
(Z)—N-hydroxy-4-(4-propyldibenzo[b,f][1,4]oxazepin-11-yl)benzamide,
(Z)—N-hydroxy-4-(4-(trifluoromethoxy)dibenzo[b,f][1,4]oxazepin-11-yl)benzamide,
(Z)—N-hydroxy-4-(6-methyldibenzo[b,f][1,4]oxazepin-11-yl)benzamide,
(E)-4-(dibenzo[b,f][1,4]oxazepin-11-yl)-3-fluoro-N-hydroxybenzamide,
(E)-6-(dibenzo[b,f][1,4]oxazepin-11-yl)-N-hydroxynicotinamide,
(E)-5-(dibenzo[b,f][1,4]oxazepin-11-yl)-N-hydroxyfuran-2-carboxamide,
(E)-5-(dibenzo[b,f][1,4]oxazepin-11-yl)-N-hydroxythiophene-2-carboxamide,
(Z)-4-(5-ethyl-5H-dibenzo[b,e][1,4]diazepin-11-yl)-N-hydroxybenzamide,
(Z)-4-(5-cyclopropyl-5H-dibenzo[b,e][1,4]diazepin-11-yl)-N-hydroxy-N-methylbenzamide,
(Z)—N-hydroxy-4-(5-isopropyl-5H-dibenzo[b,e][1,4]diazepin-11-yl)benzamide,
(E)-4-((5-cyclopropyl-5H-dibenzo[b,e][1,4]diazepin-11-ylamino)methyl)-N-hydroxybenzamide,
(Z)-4-(4-fluorodibenzo[b,f][1,4]oxazepin-11-yl)-N-hydroxybenzamide,
(Z)—N-hydroxy-4-(5-(2-methoxyethyl)-5H-dibenzo[b,e][1,4]diazepin-11-yl)benzamide,
(E)-4-(2-(dibenzo[b,f][1,4]oxazepin-11-ylamino)ethyl)-N-hydroxybenzamide,
(Z)-4-(11-ethyl-11H-benzo[b]pyrido[2,3-e][1,4]diazepin-5-yl)-N-hydroxybenzamide,
(Z)-4-(5-cyclopropyl-2-fluoro-5H-dibenzo[b,e][1,4]diazepin-11-yl)-N-hydroxybenzamide,
(Z)—N-hydroxy-4-(11-isopropyl-11H-benzo[b]pyrido[2,3-e][1,4]diazepin-5-yl)benzamide,
(Z)-4-(benzo[f]thieno[2,3-b][1,4]oxazepin-5-yl)-N-hydroxybenzamide,
(Z)-6-(4-(dibenzo[b,f][1,4]oxazepin-11-yl)benzamidooxy)-3,4,5-trihydroxytetrahydro-2H-pyran-2-carboxylic acid,
(Z)—N-hydroxy-4-(1143-morpholinopropyl)-11H-benzo[b]pyrido[2,3-e][1,4]diazepin-5-yl)benzamide,
(Z)—N-hydroxy-4-(11-(2-morpholinoethyl)-11H-benzo[b]pyrido[2,3-e][1,4]diazepin-5-yl)benzamide,
(Z)-4-(11-(cyclopropylmethyl)-11H-benzo[b]pyrido[2,3-e][1,4]diazepin-5-yl)-N-hydroxybenzamide,
(Z)—N-hydroxy-4-(5-(2-morpholinoethyl)-5H-dibenzo[b,e][1,4]diazepin-11-yl)benzamide,

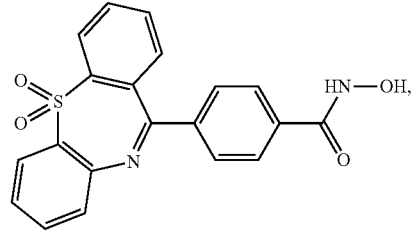

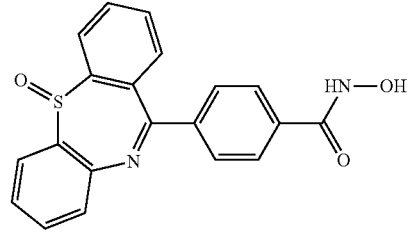
and

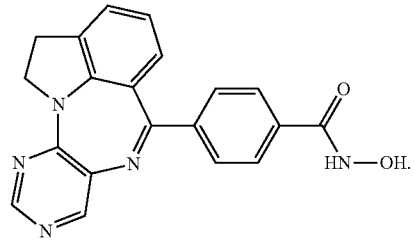

In a preferred embodiment, embodiment WW, of the compounds according to the present invention, the compounds are represented by the Formula VIII:

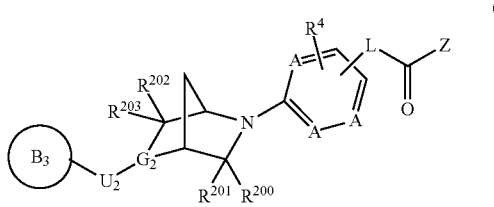
(VIII)

and N-oxides, hydrates, solvates, pharmaceutically acceptable salts, prodrugs, polymorphs and complexes thereof, and racemic and scalemic mixtures, diastereomers and enantiomers thereof, wherein wherein $R^4$ and A are as defined in Formula I;

Z is —N($R^1$)O$R^2$ or H;

L is a covalent bond or —$C_0$-$C_3$alkyl-N(O$R^2$)—;

wherein, when L is $C_0$-$C_3$alkyl-N(O$R^2$)—, then Z is H; and wherein, when Z is H, then L is —$C_0$-$C_3$alkyl-N(O$R^2$)—;

$G^2$ is carbon or N;

$U^2$ is selected from the group consisting of a covalent bond, —$C_1$-$C_8$alkyl-, —C($R^{300}$)($R^{400}$)—, —C(O)—C($R^{301}$)($R^{401}$)—, —$C_0$-$C_2$alkyl-C(O)—O—$C_0$-$C_4$alkyl-, —$C_0$-$C_2$alkyl-C(O)—$C_0$-$C_4$alkyl-, —$C_0$-$C_2$alkyl-C(O)—N$R^3$—$C_0$-$C_4$alkyl-, —C(O)—O—C($R^{301}$)($R^{401}$)—, —C(O)—C($R^{301}$)($R^{401}$)— and —C(O)—N$R^3$—C($R^{300}$)($R^{400}$)—, wherein $R^3$ and $R^{3a}$ are as defined in Formula I;

$R^{300}$ and $R^{400}$ are independently selected from the group consisting of —H, —F, —$C_1$-$C_6$alkyl, aryl, heteroaryl, heterocyclyl and cycloalkyl;

$R^{301}$ and $R^{401}$ are independently selected from the group consisting of —H, F, O$R^1$, —N$R^3R^{3a}$—, —$C_1$-$C_6$alkyl, aryl, heteroaryl, heterocyclyl and cycloalkyl;

$R^{200}$, $R^{201}$, $R^{202}$ and $R^{203}$ are independently selected from the group consisting of —H, —$C_1$-$C_6$alkyl, aryl, heteroaryl, heterocyclyl and cycloalkyl; and

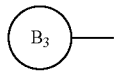

is selected from the group consisting of hydrogen, aryl, heteroaryl, alkyl, heterocyclyl, cycloalkyl, wherein each aryl, heteroaryl, cycloalkyl and heterocyclyl is optionally substituted with one to three substituents independently selected from the group consisting of halo, —$CF_3$, —$OCF_3$, —$SCF_3$, —$SF_5$, —$NO_2$, —CN, —$C_1$-$C_6$alkyl, —$C_1$-$C_6$alkoxyl, —O—$C_2$-$C_6$alkyl-O—$R^1$, —O—$R^1$, —$OCF_2$H, —$C_0$-$C_6$alkyl-S(O)$_{0-2}$—$R^1$, —$C_0$-$C_6$alkyl-C(O)—$R^1$, —$C_0$-$C_6$alkyl-C(O)N$R^3R^{3a}$, —$C_0$-$C_6$alkyl-N$R^3$C(O)—$R^2$, —$C_0$-$C_6$alkyl-S(O)$_2$N$R^3R^{3a}$, —$C_0$-$C_6$alkyl-N$R^3$S(O)$_2$—$R^2$, —$C_0$-$C_6$alkyl-OC(O)N$R^3R^{3a}$, —$C_0$-$C_6$alkyl-N$R^3$C(O)O—$R^1$, —$C_0$-$C_6$alkyl-N$R^1$C(O)N$R^3R^{3a}$, —$C_0$-$C_6$alkyl-C(O)O—$R^1$, —$C_0$-$C_6$alkyl-OC(O)—$R^1$, —$C_0$-$C_6$alkyl-aryl, —$C_0$-$C_6$alkyl-heteroaryl, —$C_0$-$C_6$alkyl-$C_3$-$C_7$cycloalkyl, —$C_0$-$C_6$alkyl-heterocyclyl, —$C_0$-$C_6$alkyl-N$R^3R^{3a}$ and —O—$C_2$-$C_6$alkyl-N$R^3R^{3a}$;

In a preferred embodiment of embodiment WW, embodiment WW-1, the moiety

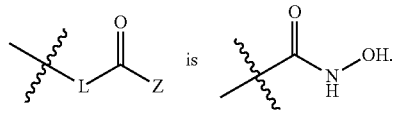

In a preferred embodiment of embodiment WW, embodiment WW-2, the moiety

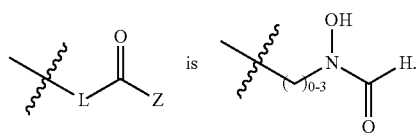

In a preferred embodiment of embodiment WW, embodiment WW-3, the moiety

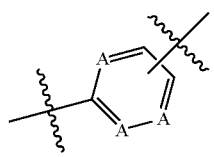

is a radical selected from the group consisting of

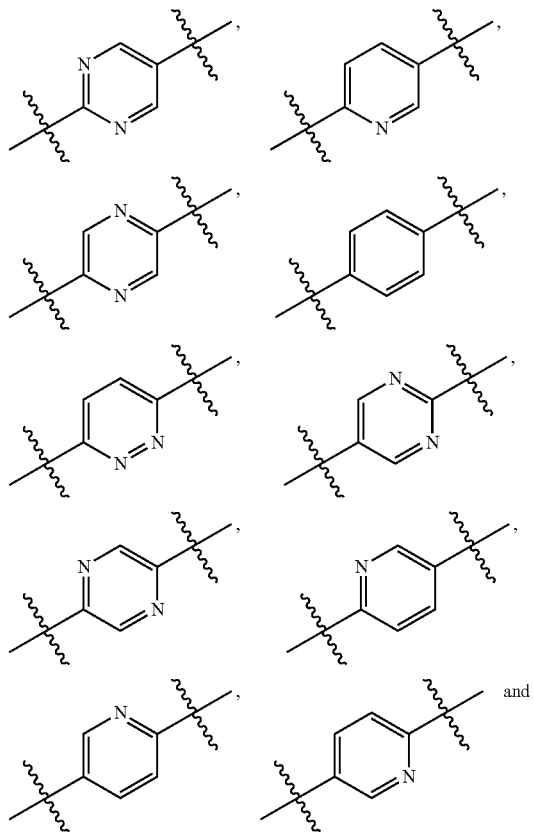

-continued

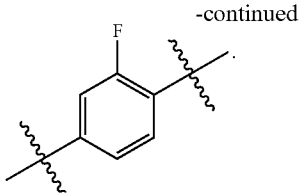

In a preferred embodiment of embodiment WW, embodiment WW-4, the moiety

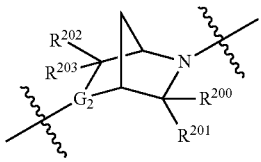

is a radical

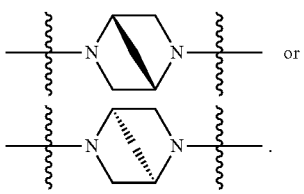

or an enantiomer thereof, a scalemic thereof, or a mixture of enantiomers thereof.

In a preferred embodiment of embodiment WW, embodiment WW-5, $U^2$ is a covalent bond.

In a preferred embodiment of embodiment WW, embodiment WW-6, $U^2$ is selected from the group consisting of a —$C_1$-$C_4$alkyl, —CH(aryl)-, —CH(heteroaryl)-, —C(O)—, —C(O)—CH(aryl)-, —C(O)—CH(heteroaryl)-, —C(O)O—$C_1$-$C_2$alkyl-, —C(O)O— and —C(O)NH—.

In a preferred embodiment of embodiment WW, embodiment WW-7, the moiety

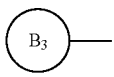

is a radical selected from the group consisting of H, alkyl, aryl, heteroaryl, cycloalkyl and heterocyclyl, wherein each aryl, heteroaryl, cycloalkyl and heterocyclyl is optionally substituted with one to three substituents independently selected from the group consisting of halo, —$CF_3$, —$OCF_3$, —$SCF_3$, —$SF_5$, —CN, —$C_1$-$C_6$alkyl, —O—$C_2$-$C_6$alkyl-O—$R^1$, —O—$R^1$, —$OCF_2H$, —$C_0$-$C_6$alkyl-S(O)$_{0-2}$—$R^1$, —$C_0$-$C_6$alkyl-C(O)$NR^3R^{3a}$, —$C_0$-$C_6$alkyl-$NR^3$C(O)—$R^2$, —$C_0$-$C_6$alkyl-S(O)$_2NR^3R^{3a}$, —$C_0$-$C_6$alkyl-$NR^3$S(O)$_2$—$R^2$, —$C_0$-$C_6$alkyl-OC(O)$NR^3R^{3a}$, —$C_0$-$C_6$alkyl-$NR^3$C(O)O—$R^1$, —$C_0$-$C_6$alkyl-$NR^1$C(O)$NR^3R^{3a}$, —$C_0$-$C_6$alkyl-C(O)O—$R^1$, —$C_0$-$C_6$alkyl-OC(O)—$R^1$, —$C_0$-$C_6$alkyl-aryl, —$C_0$-$C_6$alkyl-heteroaryl, —$C_0$-$C_6$alkyl-$C_3$-$C_7$cycloalkyl, —$C_0$-$C_6$alkyl-heterocyclyl, —$C_0$-$C_6$alkyl-$NR^3R^{3a}$ and —O—$C_2$-$C_6$alkyl-$NR^3R^{3a}$.

In a preferred embodiment of embodiment WW, embodiment WW-8, the moiety

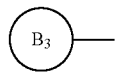

is a radical selected from the group consisting of

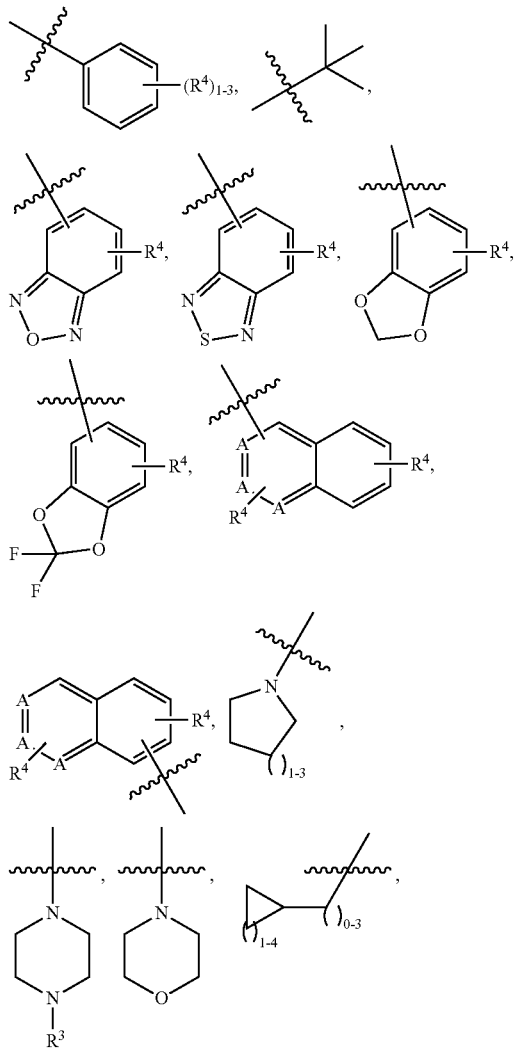

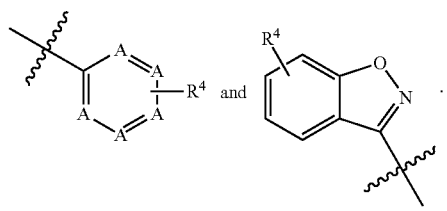

In a preferred embodiment of embodiment WW, embodiment WW-9, the compounds are represented by the Formula (IX):

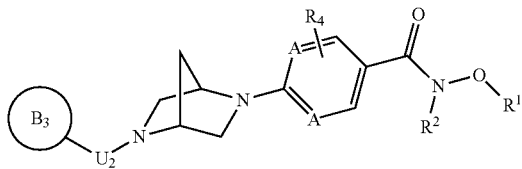

(IX)

or where possible, a (R,R) or (S,S) enantiomer, scalemic or a mixture of enantiomers thereof,
wherein

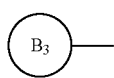

and $U_2$ are as defined in Formula (VIII); and
A, $R^1$, $R^2$ and $R^4$ are as defined in Formula I.

In a preferred embodiment of embodiment WW, embodiment WW-10, the compounds are represented by the Formula (X):

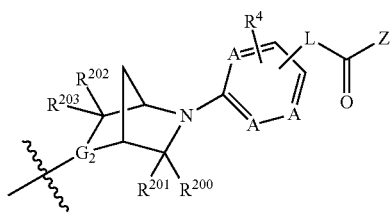

(X)

or where possible, a (R,R) or (S,S) enantiomer, scalemic or a mixture of enantiomers thereof, wherein

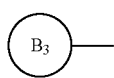

is as defined in Formula (VIII); and
A and $R^4$ are as defined in Formula I.

In a preferred embodiment of embodiment WW, embodiment WW-11, the moiety is a radical selected from the group consisting of

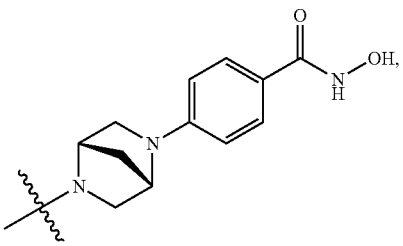

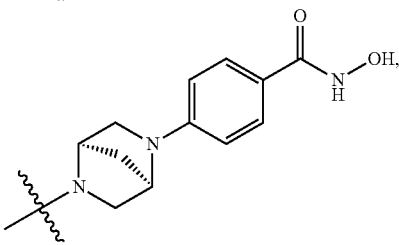

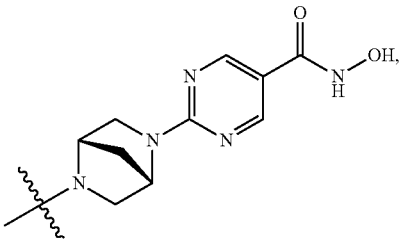

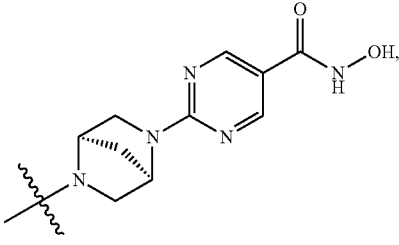

and

In a preferred embodiment of embodiment WW, embodiment WW-12, the compound is selected from the group consisting of:
2-((1S,4S)-5-benzyl-2,5-diazabicyclo[2.2.1]heptan-2-yl)-N-hydroxypyrimidine-5-carboxamide,
N-hydroxy-2-((1S,4S)-5-p-tolyl-2,5-diazabicyclo[2.2.1]heptan-2-yl)pyrimidine-5-carboxamide,
2-((1S,4S)-5-benzhydryl-2,5-diazabicyclo[2.2.1]heptan-2-yl)-N-hydroxypyrimidine-5-carboxamide, 2-((1S,4S)-5-(4-chlorophenyl)-2,5-diazabicyclo[2.2.1]heptan-2-yl)-N-hydroxypyrimidine-5-carboxamide,
(1S,4S)-tert-butyl 5-(5-(hydroxycarbamoyl)pyrimidin-2-yl)-2,5-diazabicyclo[2.2.1]heptane-2-carboxylate,
2-((1S,4S)-5-(3-fluorophenyl)-2,5-diazabicyclo[2.2.1]heptan-2-yl)-N-hydroxypyrimidine-5-carboxamide,
2-((1S,4S)-5-(4-fluorophenyl)-2,5-diazabicyclo[2.2.1]heptan-2-yl)-N-hydroxypyrimidine-5-carboxamide,
2-((1S,4S)-2,5-diazabicyclo[2.2.1]heptan-2-yl)-N-hydroxypyrimidine-5-carboxamide,
N-hydroxy-2-((1S,4S)-5-o-tolyl-2,5-diazabicyclo[2.2.1]heptan-2-yl)pyrimidine-5-carboxamide,
N-hydroxy-2-((1S,4S)-5-phenyl-2,5-diazabicyclo[2.2.1]heptan-2-yl)pyrimidine-5-carboxamide,
2-((1S,4S)-5-benzoyl-2,5-diazabicyclo[2.2.1]heptan-2-yl)-N-hydroxypyrimidine-5-carboxamide,
N-hydroxy-2-((1S,4S)-5-(3-(trifluoromethyl)phenyl)-2,5-diazabicyclo[2.2.1]heptan-2-yl)pyrimidine-5-carboxamide,
2-((1S,4S)-5-(2-fluoro-4-(trifluoromethyl)phenyl)-2,5-diazabicyclo[2.2.1]heptan-2-yl)-N-hydroxypyrimidine-5-carboxamide,
N-hydroxy-2-((1S,4S)-5-(2-(trifluoromethyl)phenyl)-2,5-diazabicyclo[2.2.1]heptan-2-yl)pyrimidine-5-carboxamide,
N-hydroxy-2-((1S,4S)-5-(4-(trifluoromethyl)phenyl)-2,5-diazabicyclo[2.2.1]heptan-2-yl)pyrimidine-5-carboxamide,
2-((1S,4S)-5-(benzo[c][1,2,5]oxadiazol-5-yl)-2,5-diazabicyclo[2.2.1]heptan-2-yl)-N-hydroxypyrimidine-5-carboxamide,
2-((1S,4S)-5-(benzo[c][1,2,5]thiadiazol-5-yl)-2,5-diazabicyclo[2.2.1]heptan-2-yl)-N-hydroxypyrimidine-5-carboxamide,
N-hydroxy-2-((1S,4S)-5-(3-(trifluoromethyl)benzoyl)-2,5-diazabicyclo[2.2.1]heptan-2-yl)pyrimidine-5-carboxamide,
2-((1S,4S)-5-(benzo[d][1,3]dioxol-5-yl)-2,5-diazabicyclo[2.2.1]heptan-2-yl)-N-hydroxypyrimidine-5-carboxamide,
2-((1S,4S)-5-(cyclohexanecarbonyl)-2,5-diazabicyclo[2.2.1]heptan-2-yl)-N-hydroxypyrimidine-5-carboxamide,
2-((1S,4S)-5-(2,2-diphenylacetyl)-2,5-diazabicyclo[2.2.1]heptan-2-yl)-N-hydroxypyrimidine-5-carboxamide,
N-hydroxy-4-((1S,4S)-5-p-tolyl-2,5-diazabicyclo[2.2.1]heptan-2-yl)benzamide,
(1S,4S)-benzyl 5-(5-(hydroxycarbamoyl)pyrimidin-2-yl)-2,5-diazabicyclo[2.2.1]heptane-2-carboxylate,
(1S,4S)-isobutyl 5-(5-(hydroxycarbamoyl)pyrimidin-2-yl)-2,5-diazabicyclo[2.2.1]heptane-2-carboxylate,
N-hydroxy-2-((1S,4S)-5-(3-(trifluoromethoxy)phenyl)-2,5-diazabicyclo[2.2.1]heptan-2-yl)pyrimidine-5-carboxamide,
2-((1S,4S)-5-(2,2-difluorobenzo[d][1,3]dioxol-5-yl)-2,5-diazabicyclo[2.2.1]heptan-2-yl)-N-hydroxypyrimidine-5-carboxamide,
N-hydroxy-2-((1S,4S)-5-(3-(trifluoromethylthio)phenyl)-2,5-diazabicyclo[2.2.1]heptan-2-yl)pyrimidine-5-carboxamide,
N-hydroxy-2-((1S,4S)-5-(4-(trifluoromethyl)pyridin-2-yl)-2,5-diazabicyclo[2.2.1]heptan-2-yl)pyrimidine-5-carboxamide,
N-hydroxy-2-((1S,4S)-5-(2-(trifluoromethyl)quinolin-4-yl)-2,5-diazabicyclo[2.2.1]heptan-2-yl)pyrimidine-5-carboxamide,
2-((1S,4S)-5-(3-(difluoromethoxy)phenyl)-2,5-diazabicyclo[2.2.1]heptan-2-yl)-N-hydroxypyrimidine-5-carboxamide,
N-hydroxy-2-((1S,4S)-5-(6-(trifluoromethyl)pyridin-2-yl)-2,5-diazabicyclo[2.2.1]heptan-2-yl)pyrimidine-5-carboxamide,
(1S,4S)-cyclopentyl 5-(5-(hydroxycarbamoyl)pyrimidin-2-yl)-2,5-diazabicyclo[2.2.1]heptane-2-carboxylate,
2-((1S,4S)-5-(benzo[c][1,2,5]oxadiazol-4-yl)-2,5-diazabicyclo[2.2.1]heptan-2-yl)-N-hydroxypyrimidine-5-carboxamide,
N-hydroxy-2-((1S,4S)-5-(5-(trifluoromethyl)pyridin-3-yl)-2,5-diazabicyclo[2.2.1]heptan-2-yl)pyrimidine-5-carboxamide,
N-hydroxy-2-((1R,4R)-5-p-tolyl-2,5-diazabicyclo[2.2.1]heptan-2-yl)pyrimidine-5-carboxamide,
(1S,4S)-isopropyl 5-(5-(hydroxycarbamoyl)pyrimidin-2-yl)-2,5-diazabicyclo[2.2.1]heptane-2-carboxylate,
(1S,4S)-pyridin-3-ylmethyl 5-(5-(hydroxycarbamoyl)pyrimidin-2-yl)-2,5-diazabicyclo[2.2.1]heptane-2-carboxylate,
(1S,4S)-cyclopropylmethyl 5-(5-(hydroxycarbamoyl)pyrimidin-2-yl)-2,5-diazabicyclo[2.2.1]heptane-2-carboxylate,
(1S,4S)-tetrahydro-2H-pyran-4-yl 5-(5-(hydroxycarbamoyl)pyrimidin-2-yl)-2,5-diazabicyclo[2.2.1]heptane-2-carboxylate,
2-((1S,4S)-5-(3,5-bis(trifluoromethyl)phenyl)-2,5-diazabicyclo[2.2.1]heptan-2-yl)-N-hydroxypyrimidine-5-carboxamide,
2-((1S,4S)-5-(benzo[d]isoxazol-3-yl)-2,5-diazabicyclo[2.2.1]heptan-2-yl)-N-hydroxypyrimidine-5-carboxamide,
2-((1S,4S)-5-(3-(dimethylcarbamoyl)phenyl)-2,5-diazabicyclo[2.2.1]heptan-2-yl)-N-hydroxypyrimidine-5-carboxamide,
2-((1S,4S)-5-(3-((dimethylamino)methyl)phenyl)-2,5-diazabicyclo[2.2.1]heptan-2-yl)-N-hydroxypyrimidine-5-carboxamide,
N-hydroxy-2-((1S,4S)-5-(3-methoxyphenyl)-2,5-diazabicyclo[2.2.1]heptan-2-yl)pyrimidine-5-carboxamide,
N-hydroxy-2-((1S,4S)-5-m-tolyl-2,5-diazabicyclo[2.2.1]heptan-2-yl)pyrimidine-5-carboxamide,
N-hydroxy-6-(5-p-tolyl-2,5-diazabicyclo[2.2.1]heptan-2-yl)nicotinamide,
N-hydroxy-5-((1S,4S)-5-(3-(trifluoromethyl)phenyl)-2,5-diazabicyclo[2.2.1]heptan-2-yl)pyrazine-2-carboxamide,
2-fluoro-N-hydroxy-4-((1S,4S)-5-(3-(trifluoromethyl)phenyl)-2,5-diazabicyclo[2.2.1]heptan-2-yl)benzamide,
N-hydroxy-2-((1S,4S)-5-(pyrrolidine-1-carbonyl)-2,5-diazabicyclo[2.2.1]heptan-2-yl)pyrimidine-5-carboxamide,
N-hydroxy-2-((1S,4S)-5-(4-(trifluoromethyl)pyrimidin-2-yl)-2,5-diazabicyclo[2.2.1]heptan-2-yl)pyrimidine-5-carboxamide,
N-hydroxy-6-((1S,4S)-5-(3-(trifluoromethyl)phenyl)-2,5-diazabicyclo[2.2.1]heptan-2-yl)pyridazine-3-carboxamide,
N-hydroxy-2-((1R,4R)-5-(4-(trifluoromethyl)pyridin-2-yl)-2,5-diazabicyclo[2.2.1]heptan-2-yl)pyrimidine-5-carboxamide,
N-hydroxy-2-((1R,4R)-5-m-tolyl-2,5-diazabicyclo[2.2.1]heptan-2-yl)pyrimidine-5-carboxamide,
2-(5-(3-cyanophenyl)-2,5-diazabicyclo[2.2.1]heptan-2-yl)-N-hydroxypyrimidine-5-carboxamide,
N-hydroxy-4-(5-(3-methoxyphenyl)-2,5-diazabicyclo[2.2.1]heptan-2-yl)benzamide, N-hydroxy-4-(5-m-tolyl-2,5-diazabicyclo[2.2.1]heptan-2-yl)benzamide,
N-hydroxy-4-((1S,4S)-5-(3-(trifluoromethyl)phenyl)-2,5-diazabicyclo[2.2.1]heptan-2-yl)benzamide,
N-hydroxy-4-((1S,4S)-5-(4-(trifluoromethyl)pyridin-2-yl)-2,5-diazabicyclo[2.2.1]heptan-2-yl)benzamide,
4-((1S,4S)-5-(3-cyanophenyl)-2,5-diazabicyclo[2.2.1]heptan-2-yl)-N-hydroxybenzamide,
N-hydroxy-4-((1R,4R)-5-m-tolyl-2,5-diazabicyclo[2.2.1]heptan-2-yl)benzamide,
N-hydroxy-4-((1R,4R)-5-(4-(trifluoromethyl)pyridin-2-yl)-2,5-diazabicyclo[2.2.1]heptan-2-yl)benzamide,
N-hydroxy-4-((1S,4S)-5-(4-(trifluoromethyl)pyrimidin-2-yl)-2,5-diazabicyclo[2.2.1]heptan-2-yl)benzamide,
N-hydroxy-N-methyl-4-((1S,4S)-5-p-tolyl-2,5-diazabicyclo[2.2.1]heptan-2-yl)benzamide and

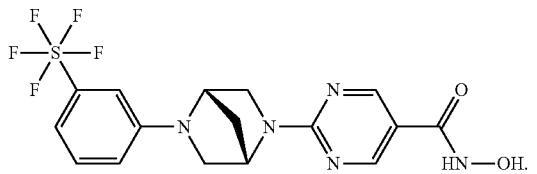 [SMILES: O=C(NO)c1cnc(N2C[C@@H]3C[C@H]2CN3c2cccc(S(F)(F)(F)(F)F)c2)nc1]

In a preferred embodiment of the compounds according to the present invention, embodiment XX, the compounds are represented by the Formula (XI):

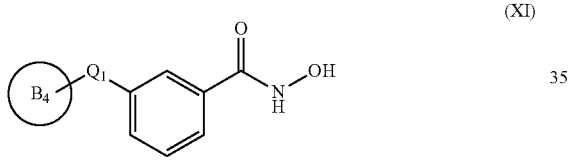

(XI)

and N-oxides, hydrates, solvates, pharmaceutically acceptable salts, prodrugs, polymorphs and complexes thereof, and racemic and scalemic mixtures, diastereomers and enantiomers thereof,
wherein

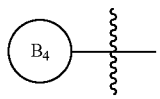

is

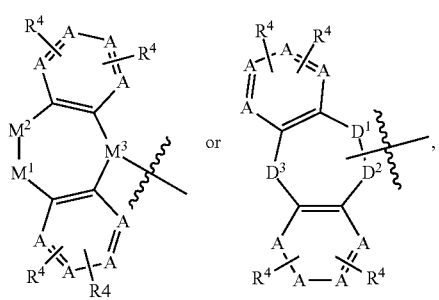

$Q^1$ is selected from the group consisting of —$C_1$-$C_6$alkyl, covalent bond, —$C_0$-$C_6$alkyl-O—$C_0$-$C_6$alkyl-, —$C_0$-$C_6$alkyl-$NR_3$—$C_0$-$C_6$alkyl-, —$C_0$-$C_6$alkyl-$S(O)_{0-2}$—$C_0$-$C_6$alkyl-, —$C_0$-$C_6$alkyl-$NR_3C(O)$—$C_0$-$C_6$alkyl-, —$C_0$-$C_6$alkyl-$C(O)NR_3$—$C_0$-$C_6$alkyl- and —$C_0$-$C_6$alkyl-$OC(O)NR_3$—$C_0$-$C_6$alkyl-; and $R^3$, $R^4$, $M^1$-$M^2$, $M^3$, A, $D^1$-$D^2$, $D^3$ are as defined in Formula I.

In a preferred embodiment of embodiment XX, embodiment XX-1, the moiety

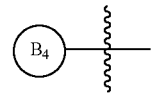

is selected from a radical consisting of

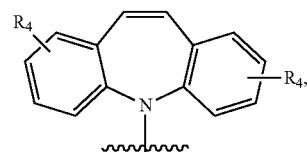

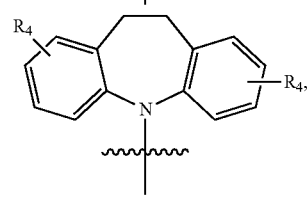

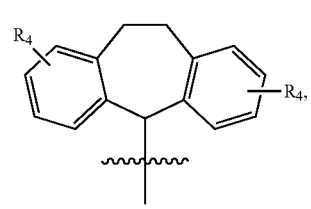

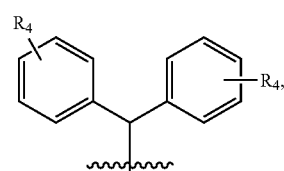

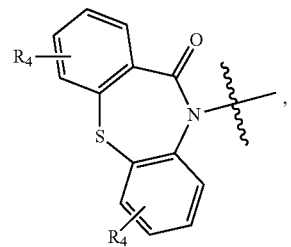

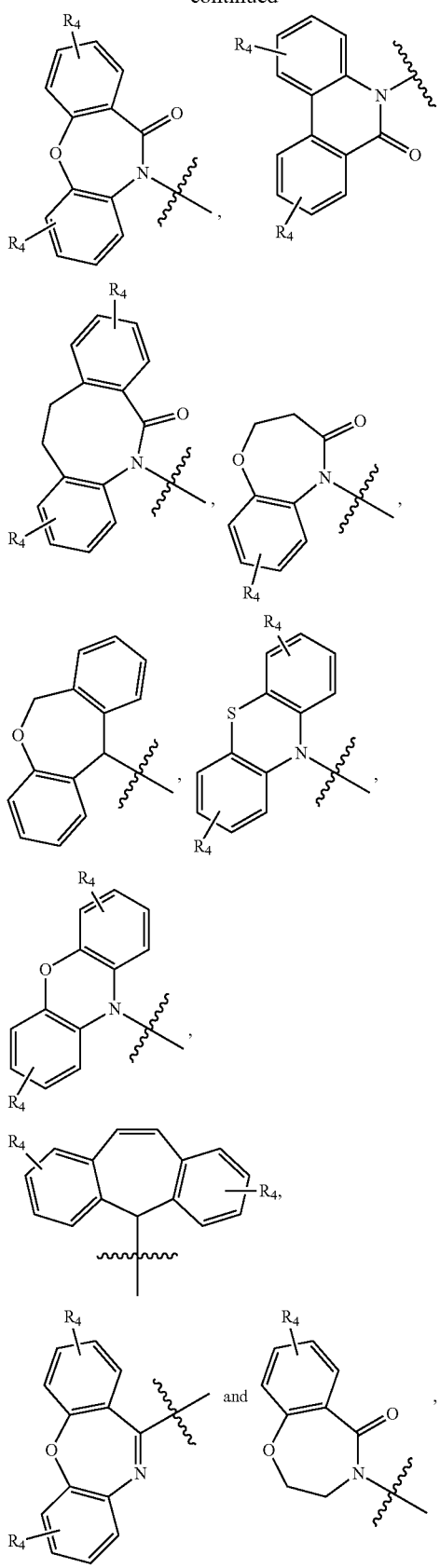

wherein R⁴ is as defined in Formula I.

In a preferred embodiment, embodiment YY, of the compounds according to the present invention, the compounds are represented by the Formula (XII):

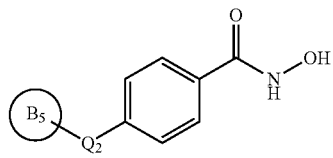

(XII)

and N-oxides, hydrates, solvates, pharmaceutically acceptable salts, prodrugs, polymorphs and complexes thereof, and racemic and scalemic mixtures, diastereomers and enantiomers thereof, wherein

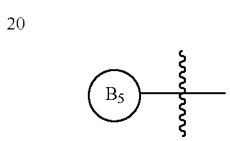

is

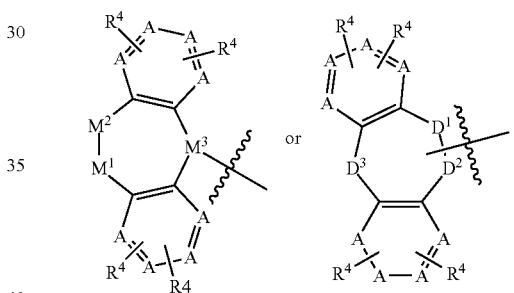

or $Q^2$ is selected from the group consisting of —$C_1$-$C_6$alkyl, covalent bond, —$C_0$-$C_6$alkyl-O—$C_0$-$C_6$alkyl-, —$C_0$-$C_6$alkyl-$NR_3$—$C_0$-$C_6$alkyl-, —$C_0$-$C_6$alkyl-$S(O)_{0-2}$—$C_0$-$C_6$alkyl-, —$C_0$-$C_6$alkyl-$NR_3$C(O)—$C_0$-$C_6$alkyl-, —$C_0$-$C_6$alkyl-C(O)$NR_3$—$C_0$-$C_6$alkyl- and —$C_0$-$C_6$alkyl-OC(O)$NR_3$—$C_0$-$C_6$alkyl-; and $R^3$, $R^4$, $M^1$-$M^2$, $M^3$, A, $D^1$-$D^2$, $D^3$ are as defined in Formula I;

In a preferred embodiment of embodiment YY, embodiment YY-1, the moiety

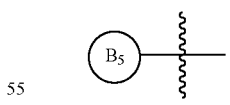

is selected from a radical consisting of

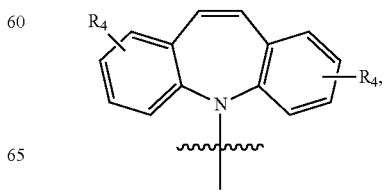

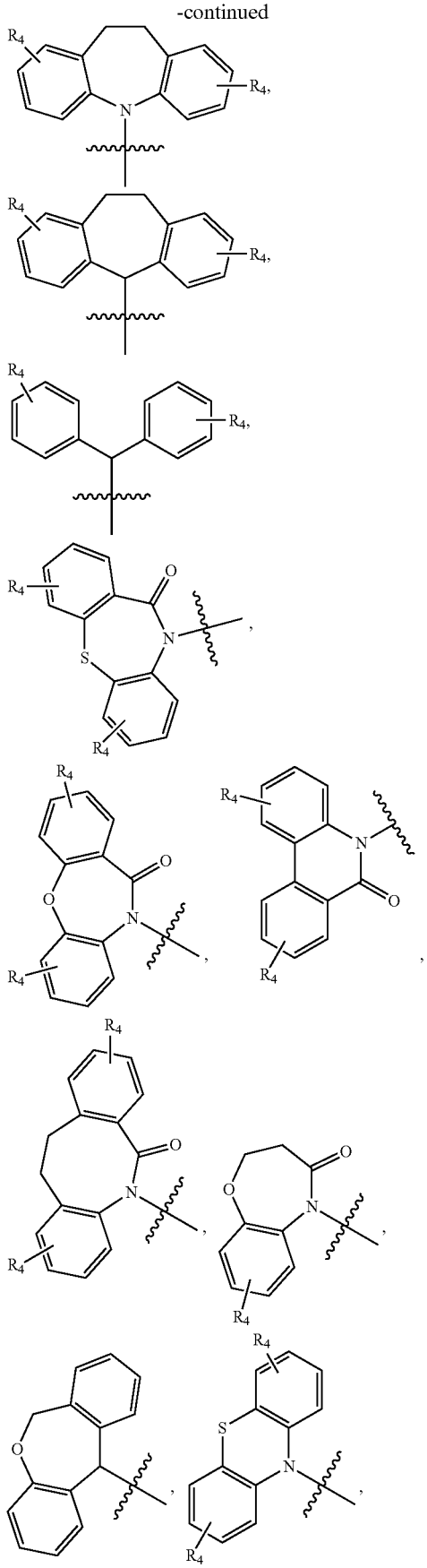
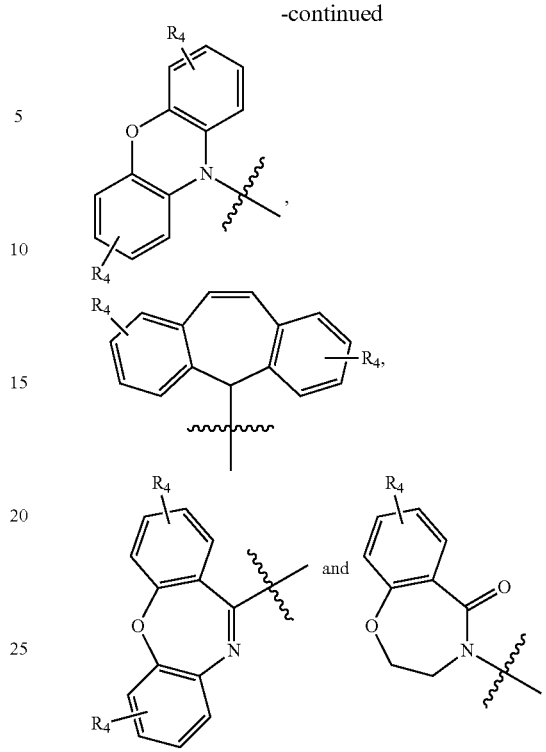

wherein $R^4$ is as defined in Formula I.

In a preferred embodiment, embodiment ZZ, of the compounds according to the present invention, the compounds are represented by the Formula (XIII):

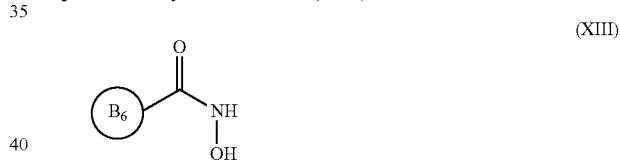

(XIII)

and N-oxides, hydrates, solvates, pharmaceutically acceptable salts, prodrugs, polymorphs and complexes thereof, and racemic and scalemic mixtures, diastereomers and enantiomers thereof, wherein

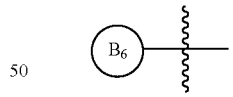

is a radical selected from the group consisting of

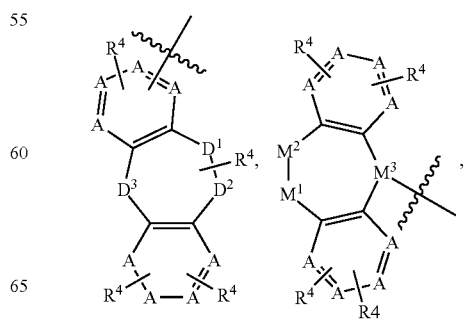

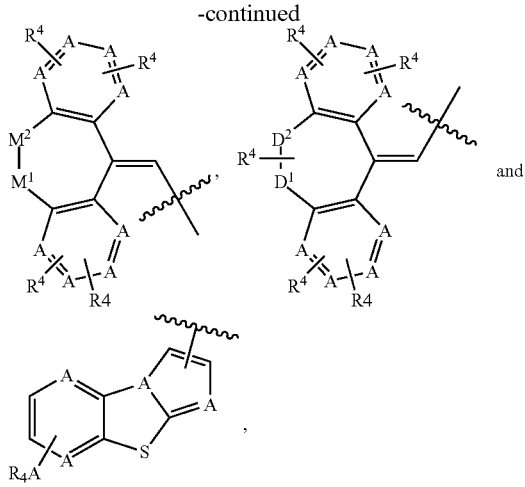

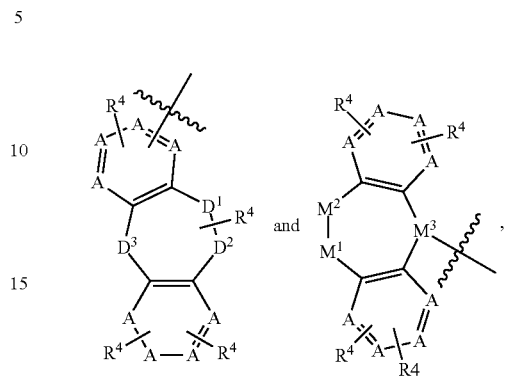

wherein each aryl, heteroaryl, cycloalkyl and heterocyclyl is optionally substituted; and wherein Q, $R^4$, $M^1$-$M^2$, $M^3$, A, $D^1$-$D^2$, $D^3$ are as defined in Formula I.

and
$R^4$, $M^1$-$M^2$, $M^3$, A, $D^1$-$D^2$, $D^3$ are as defined in Formula I.

In a preferred embodiment, embodiment AAA, of the compounds according to the present invention, the compounds are represent by the Formula (XIV):

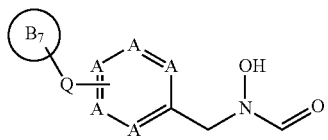

(XIV)

and N-oxides, hydrates, solvates, pharmaceutically acceptable salts, prodrugs, polymorphs and complexes thereof, and racemic and scalemic mixtures, diastereomers and enantiomers thereof,
wherein

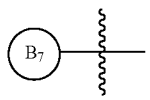

Some examples of the compounds according to the first aspect of the invention are given below. These examples merely serve to exemplify some of the compounds of the first aspect of the invention and do not limit the scope of the invention:

Synthetic Schemes and Experimental Procedures

The compounds of the invention can be prepared according to the reaction schemes for the examples illustrated below utilizing methods known to one of ordinary skill in the art. These schemes serve to exemplify some procedures that can be used to make the compounds of the invention. One skilled in the art will recognize that other general synthetic procedures may be used. The compounds of the invention can be prepared from starting components that are commercially available. Any kind of substitutions can be made to the starting components to obtain the compounds of the invention according to procedures that are well known to those skilled in the art.

Scheme 1

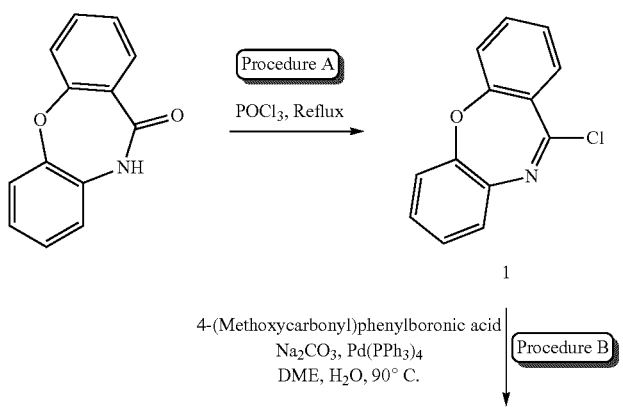

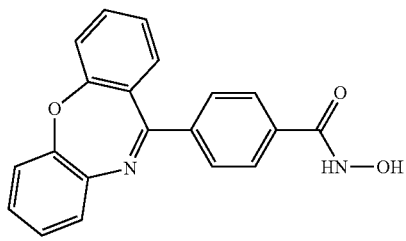

3: Example 1

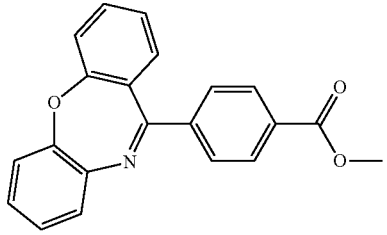

2

Example 1

(Z)-4-(Dibenzo[b,f][1,4]oxazepin-11-yl)-N-hydroxybenzamide (3)

Step 1: (E)-11-Chlorodibenz[b,f][1,4]oxazepine (1)

A solution of 10,11-dihydrodibenz[b,f][1,4]oxazepin-11-one (1.00 g, 4.74 mmol) and phosphorus oxychloride (40 mL) was stirred for 5 h at reflux. The reaction mixture was then cooled to room temperature and concentrated under reduced pressure. The residue was dissolved into AcOEt and washed with water and brine. The organic layer was dried ($Na_2SO_4$), filtered and concentrated to give an orange oil. The residue was purified by silica gel column chromatography with EtOAc (10%) in Hexanes to afford 1 (939 mg, 86%) as a yellow solid. LRMS (ESI): (calc) 229.0. (found) 230.1 $(MH)^+$.

Step 2: (Z)-Methyl 4-(dibenzo[b,f][1,4]oxazepin-11-yl)benzoate (2)

To a solution of 1 (229 mg, 1.00 mmol) in DME (3 mL) was added 4-methoxycarbonylphenylboronic acid (216 mg, 1.20 mmol), $Pd(PPh_3)_4$ (0.065 mg, 0.056 mmol) and 2 N $Na_2CO_{3(aq)}$ (1.5 mL, 3.0 mmol). The reaction mixture was stirred for 2 h at 90° C. The solution was then cooled at room temperature and poured into AcOEt. The organic layer was washed with water, brine and dried ($Na_2SO_4$), filtered and concentrated to give a yellow oil. The residue was purified by silica gel column chromatography with EtOAc (15%) in Hexanes to afford 2 (327 mg, 99%) as a yellow foam. LRMS (ESI): (calc) 329.1. (found) 330.3 $(MH)^+$.

Step 3: (Z)-4-(Ddibenzo[b,f][1,4]oxazepin-11-yl)-N-hydroxybenzamide (3)

To a stirring solution of ester 2 (327 mg, 1.00 mmol) in MeOH (4.0 mL) and THF (4.0 mL) was added hydroxylamine (1.2 mL, excess, 50% in water) followed by KOH (212 mg, 4.00 mmol) and the reaction mixture was stirred at room temperature for 15 min. The reaction mixture was concentrated under vacuum. 3N HCl was added to the residue to reach pH=7-8. The mixture was extracted with ethyl acetate (3×). The combined organic phases were washed with water (2×) and brine, dried over sodium sulfate and concentrate in vacuo to one third volume. Hexane was added to the mixture and the solid was filtered. The crude product was purified by flash eluting with 75% ethyl acetate in hexanes to afford the title compound (3) as a yellow solid (35 mg, 11%). $^1$H NMR (DMSO-$d_6$) δ (ppm): 11.37 (br s, 1H), 9.14 (br s, 1H), 7.86 (d, J=8.8 Hz, 2H), 7.81 (d, J=8.8 Hz, 2H), 7.66-7.62 (m, 1H), 7.43-7.39 (m, 2H), 7.32-7.25 (m, 4H), 7.17 (dd, J=8.0, 1.6 Hz, 1H). LRMS (ESI): (calc) 330.1. (found) 331.4 $(MH)^+$.

Scheme 2

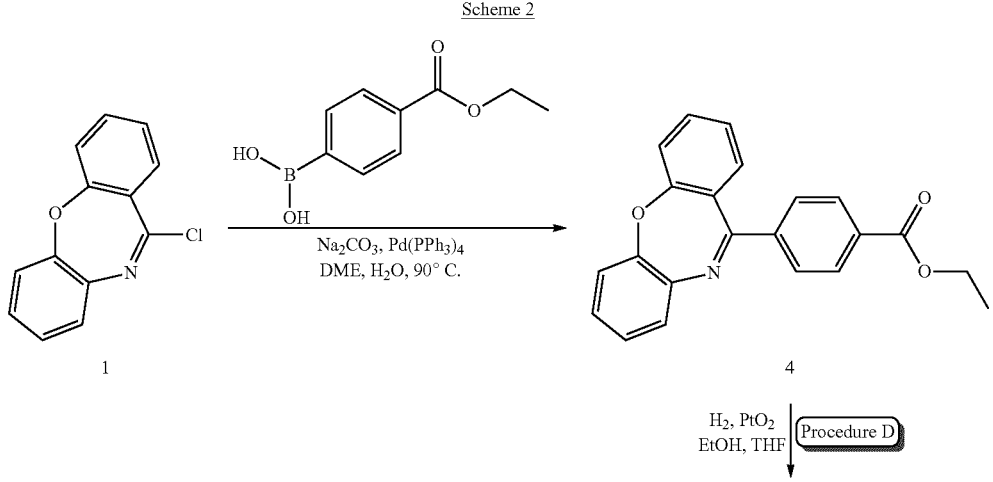

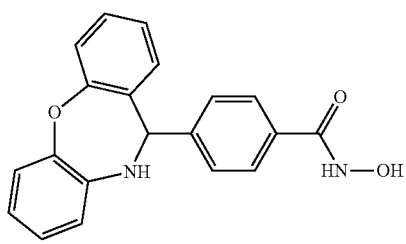 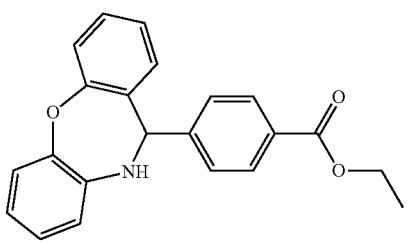

6: Example 2    5

Example 2

4-(10,11-dihydrodibenzo[b,f][1,4]oxazepin-11-yl)-N-hydroxybenzamide (6)

Step 1: (Z)-ethyl 4-(dibenzo[b,f][1,4]oxazepin-11-yl)benzoate (4)

Using Procedure B (Table 1) with compound 1 and 4-(ethoxycarbonyl)phenylboronic acid the title compound 4 was obtained (2.76 g, 83%) as a yellow foam. LRMS (ESI): (calc) 343.12. (found) 344.3 (MH)$^+$.

Step 2: ethyl 4-(10,11-dihydrodibenzo[b,f][1,4]oxazepin-11-yl)benzoate (5)

Title compound 4 was dissolved in ethanol (25 mL) and THF (5 mL). Platinum (IV) oxide (0.075 g, 10% wt) was added. The mixture was stirred at room temperature for 3 h under 1 atmosphere of hydrogen. The catalyst was filtered and the filtrate was concentrated under reduced pressure to one third volume. The precipitate was filtered to afford title compound 5 (510 mg, 67%) as a white solid. LRMS (ESI): (calc) 345.14. (found) 346.3 (MH)$^+$. $^1$H NMR (400 MHz, DMSO-$d_6$) δ (ppm): 7.88 (d, J=8.4 Hz, 2H), 7.48 (dd, J=7.5, 1.7 Hz, 1H), 7.39 (d, J=8.0 Hz, 2H), 7.33 (td, J=7.7, 1.8 Hz, 1H), 7.19 (td, J=7.4, 1.2 Hz, 1H), 7.11 (dd, J=8.0, 1.2 Hz, 1H), 6.90-6.83 (m, 3H), 6.77 (dd, J=7.9, 1.4 Hz, 1H), 6.50 (td, J=7.3, 1.6 Hz, 1H), 5.55 (d, J=6.1 Hz, 1H), 4.28 (q, J=7.0 Hz, 2H), 1.28 (t, J=7.0 Hz, 3H).

Step 3: 4-(10,11-dihydrodibenzo[b,f][1,4]oxazepin-11-yl)-N-hydroxybenzamide (6)

Using Procedure C (Table 1) with compound 5 the title compound 6 was obtained (133 mg, 66%) as a white solid. $^1$H NMR (DMSO-d6) δ (ppm): 11.12 (s, 1H), 8.99 (s, 1H), 7.65 (d, J=8.4 Hz, 2H), 7.45 (dd, J=7.6, 1.8 Hz, 1H), 7.35-7.30 (m, 3H), 7.18 (td, J=7.4, 1.2 Hz, 1H), 7.10 (dd, J=8.0, 1.4 Hz, 1H), 6.89-6.75 (m, 4H), 6.52-6.48 (m, 1H), 5.51 (d, J=6.0 Hz, 1H). LRMS (ESI): (calc) 332.12. (found) 333.19 (MH)$^+$.

Scheme 3

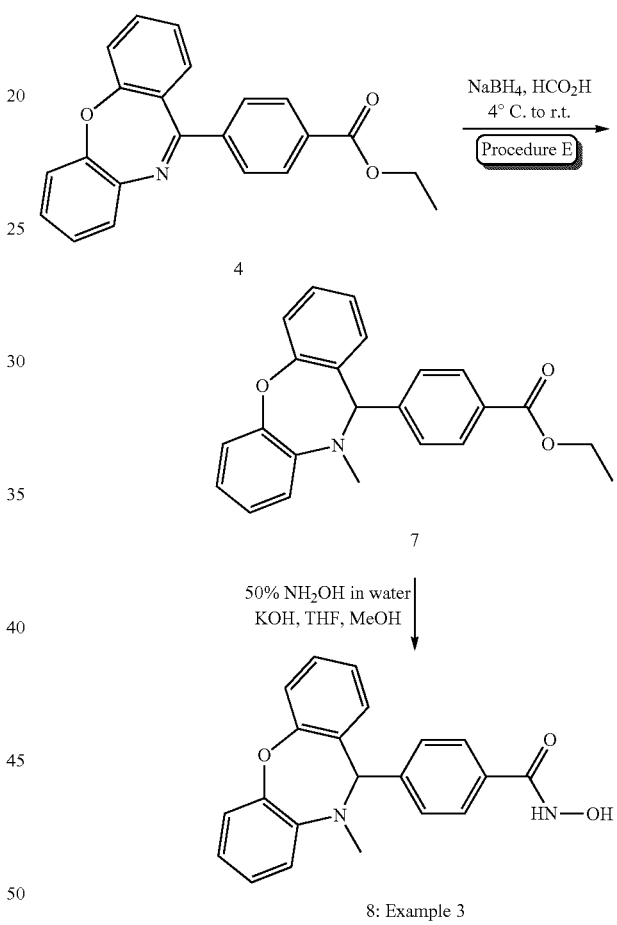

8: Example 3

Example 3

N-hydroxy-4-(10-methyl-10,11-dihydrodibenzo[b,f][1,4]oxazepin-11-yl)benzamide (8)

Step 1: ethyl 4-(10-methyl-10,11-dihydrodibenzo[b,f][1,4]oxazepin-11-yl)benzoate (7)

Title compound 4 (0.508 g, 1.48 mmol) was dissolved in formic acid (5.0 mL) and the mixture was cooled at 4° C. Sodium borohydride (0.502 g) was added and the reaction mixture was stirred at room temperature for 90 min. The mixture was diluted in water (50 mL) and solid sodium bicarbonate was added until alkaline (pH=8-9). This mixture was extracted twice with ethyl acetate. The combined organic extracts were washed with water and brine, dried over sodium sulfate and evaporated. The crude was purified by flash chromatography with 10% ethyl acetate in hexanes to afford title compound 7 (408 mg, 77%) as a colorless oil. LRMS (ESI): (calc) 359.15. (found) 360.3 (MH)+.

Step 2: N-hydroxy-4-(10-methyl-10,11-dihydrodibenzo[b,f][1,4]oxazepin-11-yl)benzamide Using Procedure C (Table 1) with compound 7 the title compound 8 (175 mg, 44%) was obtained as an off-white solid. $^1$H NMR (MeOD-d$_4$) δ (ppm): 7.60 (d, J=8.4 Hz, 2H), 7.43-7.39 (m, 1H), 7.35-7.29 (m, 2H), 7.20-7.13 (m, 5H), 7.09-7.05 (m, 1H), 6.94 (dd, J=8.0 Hz, 1.6 Hz, 1H), 6.02 (s, 1H), 3.27 (s, 3H). LRMS (ESI): (calc) 346.13. (found) 347.28 (MH)+.

directly to the column eluting with 10% to 50% ethyl acetate in hexanes to afford the title compound 9 (1.42 g, 76%) as a purple solid.

Step 2: (E)-8,11-dichloro-5H-dibenzo[b,e][1,4]diazepine (10)

A mixture of amide 9 (1.39 g, 5.70 mmol), phosphorus oxychloride (1.6 mL, 17.1 mmol) and N-dimethylaniline (2.9 mL, 22.8 mmol) in benzene (10 mL) was heated at reflux for 2 hours. The reaction mixture was then cooled to room temperature and excess of phosphorus oxychloride, N-dimethylaniline and benzene were removed at reduced pressure. The resulting residue was dissolved in dioxane (20 mL) and 2 M Na$_2$CO$_3$ (30 mL 0.06 mol) and then heated at 80° C. for 1 hour. The reaction mixture was cooled to room temperature Scheme 4

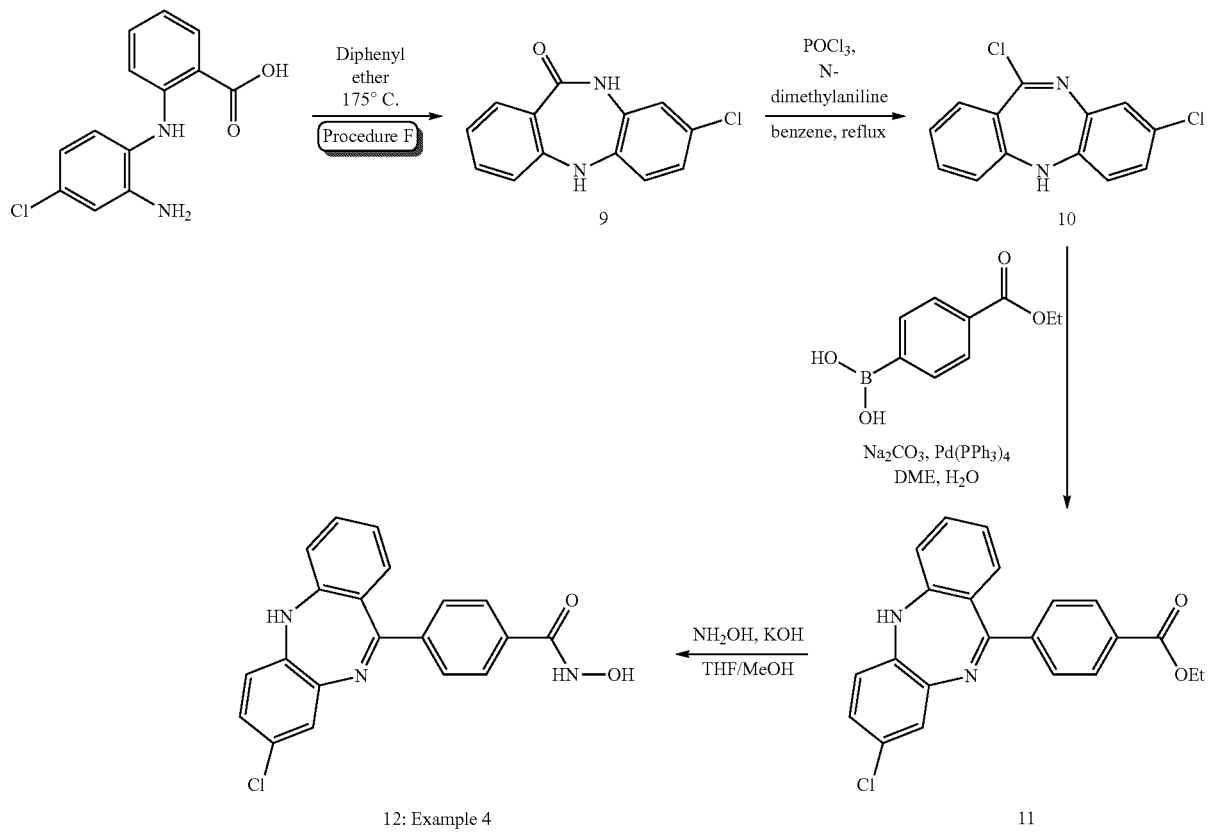

Example 4

(Z)-4-(7-chloro-5H-dibenzo[b,e][1,4]diazepin-11-yl)-N-hydroxybenzamide (12)

Step 1: 8-chloro-5H-dibenzo[b,e][1,4]diazepin-11(10H)-one (9)

The 2-(2-amino-4-chlorophenylamino)benzoic acid (2.00 g, 7.63 mmol) was mixed with diphenyl ether (5 mL). The reaction mixture was stirred at 175° C. for 2 hours. The mixture was cooled down to room temperature and put and dioxane was removed at reduced pressure and the resulting aqueous solution was extracted with EtOAc (30 mL). The organic phase was washed with water, brine, dried (Na$_2$SO$_4$), filtered and solvent evaporated. The resulting crude residue was purified by column chromatography (10% ethyl acetate in hexanes) to afford title compound 10 (869 mg, 58%) as an orange solid. LRMS (ESI): (calc) 262.01. (found) 263.1 (MH)+.

Step 3: (Z)-ethyl 4-(8-chloro-5H-dibenzo[b,e][1,4]diazepin-11-yl)benzoate (11)

Using Procedure B (Table 1) with compound 10 the title compound 11 (610 mg, 49%) was obtained as a red foam.

LRMS (ESI): (calc) 376.10. (found) 377.2 (MH)+. ¹H NMR (400 MHz, DMSO-d₆) δ (ppm): 8.03, (d, J=8.2 Hz, 2H), 7.73 Hz, 1H), 7.01-6.90 (m, 3H), 6.85 (dd, J=7.6, 1.6 Hz, 1H). LRMS (ESI): (calc) 363.08. (found) 364.2 (MH)+.

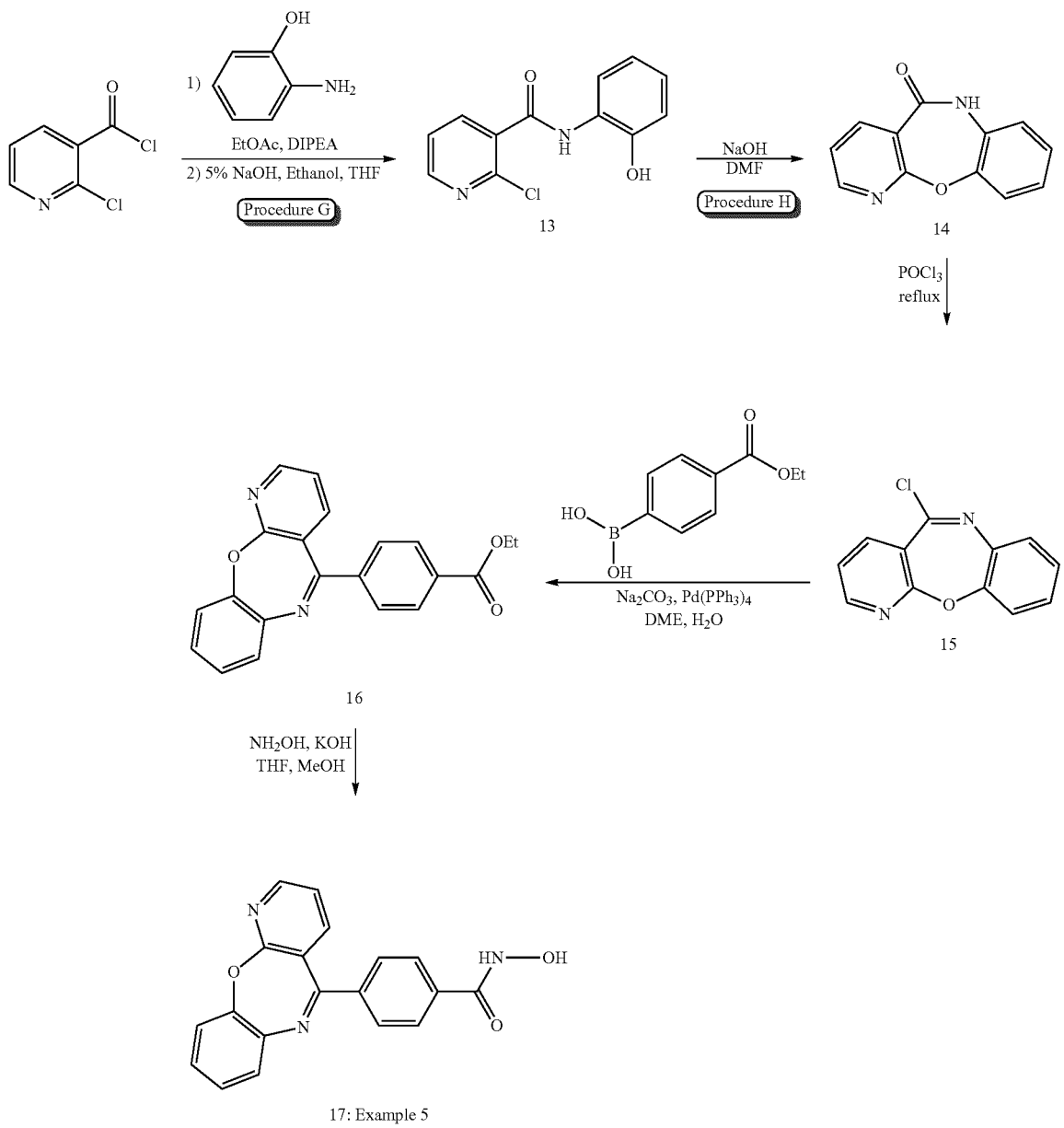

Scheme 5

17: Example 5

(d, J=8.2 Hz, 2H), 7.50 (s, 1H), 7.40 (t, J=7.6 Hz, 1H), 7.21 (s, 1H), 7.13 (d, J=8.4 Hz, 1H), 7.02 (d, J=7.8 Hz, 1H), 6.95 (t, J=7.6 Hz, 2H), 6.85 (d, J=6.1 Hz, 1H), 4.35 (q, J=7.0 Hz, 2H), 1.34 (t, J=7.0 Hz, 3H).

Step 4: (Z)-4-(8-chloro-5H-dibenzo[b,e][1,4]diazepin-11-yl)-N-hydroxybenzamide (12)

Using Procedure C (Table 1) with compound 11 the title compound 12 (48 mg, 20%) was obtained as an orange solid. ¹H NMR (DMSO-d6) δ (ppm): 11.33 (s, 1H), 9.12 (s, 1H), 7.80 (d, J=8.4 Hz, 2H), 7.64 (d, J=8.4 Hz, 2H), 7.46 (s, 1H), 7.40-7.36 (m, 1H), 7.19 (d, J=2.4 Hz, 1H), 7.10 (dd, J=8.8, 2.8

Example 5

Z)-4-(benzo[b]pyrido[3,2-f][1,4]oxazepin-5-yl)-N-hydroxybenzamide (17)

Step 1: 2-chloro-N-(2-hydroxyphenyl)nicotinamide (13)

A solution of 2-chloronicotinoyl chloride (2.91 g, 16.6 mmol) in ethyl acetate (50 mL) was added to a mixture of 2-aminophenol (2.00 g, 18.3 mmol) and DIPEA (4.8 mL, 27.5 mmol) in ethyl acetate (50 mL) at 4° C. The reaction mixture was stirred for 1 hour. The organic mixture was washed with water and brine then concentrated under reduced pressure. The residue was dissolved in ethanol/THF 1:1 (75 mL) and 15% sodium hydroxide (25 mL) and the mixture was stirred at 50° C. for 45 min. The mixture was cooled down to room temperature and concentrated in vacuo to one third volume and then acidified to pH=2 with 3M HCl. The solid was filtered, washed with water and dried to afford title compound 13 (3.69 g, 81%) as a beige solid. LRMS (ESI): (calc) 248.04. (found) 249.2 (MH)+.

Step 2:
benzo[b]pyrido[3,2-f][1,4]oxazepin-5(6H)-one (14)

Title compound 13 (3.65 g, 14.7 mmol) was dissolved in DMF (25.0 mL) and sodium hydroxide (0.706 g, 17.7 mmol) was added. The reaction mixture was stirred at 130° C. for 5 hours. The mixture was cooled down to room temperature and an ice/water mixture was added. The precipitate was filtered then triturated in ethanol to afford title compound 14 (1.798 g, 58%) as a white solid. LRMS (ESI): (calc) 212.06. (found) 213.2 (MH)+.

Step 3:
(E)-5-chlorobenzo[b]pyrido[3,2-f][1,4]oxazepine (15)

Using Procedure A (Table 1) with compound 14 the title compound 15 (741 mg) was obtained as a yellow oil. LRMS (ESI): (calc) 230.02. (found) 231.2 (MH)+.

Step 4: (Z)-ethyl 4-(benzo[b]pyrido[3,2-f][1,4]oxazepin-5-yl)benzoate (16)

Using Procedure B (Table 1) with compound 15 the title compound 16 (675 mg, 69% for 2 steps) was obtained as a yellow foam. LRMS (ESI): (calc) 344.12. (found) 345.2 (MH)+.

Step 5: (Z)-4-(benzo[b]pyrido[3,2-f][1,4]oxazepin-5-yl)-N-hydroxybenzamide (17)

Using Procedure C (Table 1) with compound 16 the title compound 17 (80 mg, 36%) was obtained as a yellow solid. $^1$H NMR (DMSO-d6) δ (ppm): 11.39 (s, 1H), 9.16 (s, 1H), 8.52 (dd, J=5.2, 2.0 Hz, 1H), 7.88 (d, J=8.4 Hz, 2H), 7.84 (d, J=8.4 Hz, 2H), 7.75 (dd, J=8.0, 2.0 Hz, 1H), 7.48-7.41 (m, 2H), 7.34-7.30 (m, 3H). LRMS (ESI): (calc) 331.12 (found) 332.18 (MH)+.

Scheme 6

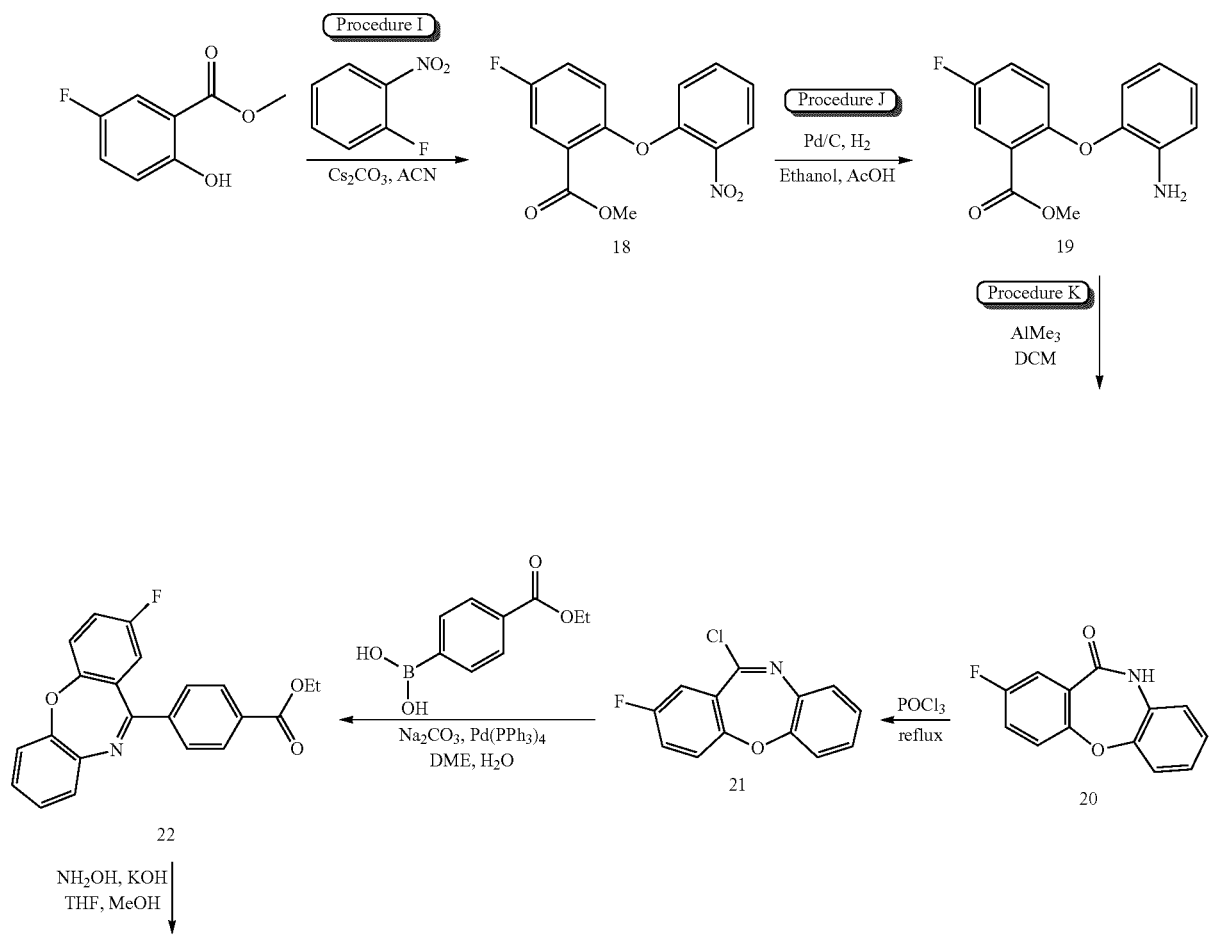

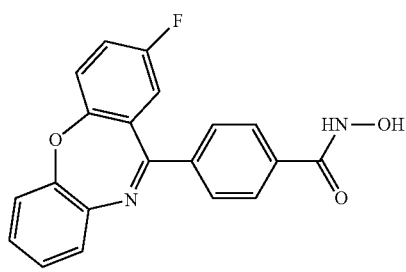

23: Example 6

Example 6

(Z)-4-(2-fluorodibenzo[b,f][1,4]oxazepin-11-yl)-N-hydroxybenzamide (23)

Step 1: methyl 5-fluoro-2-(2-nitrophenoxy)benzoate (18)

Methyl 5-fluoro-2-hydroxybenzoate (2.65 g, 15.6 mmo.) and 1-fluoro-2-nitrobenzene (2.02 g, 14.2 mmol) were dissolved in acetonitrile (30 mL) and cesium carbonate (6.10 g, 18.7 mmol) was added. The reaction mixture was stirred at 80° C. for 60 hours. The mixture was cooled down to room temperature and poured into ethyl acetate. This organic mixture was washed with water and brine, dried over sodium sulfate, filtered and evaporated. The crude was purified by flash chromatography with 10-20% ethyl acetate in hexanes and triturated in ethanol to afford the title compound 18 (3.49 g, 84%) as white solid. LRMS (ESI): (calc) 291.05. (found) 292.2 (MS)+.

Step 2: methyl 2-(2-aminophenoxy)-5-fluorobenzoate (19)

To a stirring solution of title compound 18 (3.48 g, 11.9 mmol) in ethanol (30 mL), acetic acid (1.0 mL) and THF (10 mL) was added palladium on charcoal 10% (0.37 g, 10% w/w). The reaction mixture was stirred under hydrogen atmosphere for 20 hours. The catalyst was filtered and the filtrate was concentrated in vacuo. The residue was diluted with ether and this organic mixture was washed with a saturated aqueous solution of bicarbonate, water and brine then solvent evaporated to afford title compound 19 (2.95 g, 95%) as a beige solid. LRMS (ESI): (calc) 261.08. (found) 262.3 (MS)+.

Step 3: 2-fluorodibenzo[b,f][1,4]oxazepin-11(10H)-one (20)

Title compound 19 (802 mg, 3.07 mmol) was dissolved in DCM (10 mL) and the mixture was cooled to 0° C. Trimethylaluminum 2M in toluene (1.8 mL, 3.69 mmol) was added dropwise and the reaction mixture was allowed to warm to room temperature. The mixture was then heated to 45° C. for 45 h. The mixture was cooled to room temperature for the slow addition of water. The solution was extracted with ethyl acetate then washed twice with HCl (10%), water and saturated solution of bicarbonate. The organic layer was then dried over sodium sulfate and concentrated in vacuo until the product precipitated. The solid was filtered and dried to afford title compound 20 (511 mg, 73%) as a white solid. LRMS (ESI): (calc) 229.05. (found) 230.1 (MS)+.

Step 4: (E)-11-chloro-2-fluorodibenzo[b,f][1,4]oxazepine (21)

Using Procedure A (Table 1) with compound 20 the title compound 21 was obtained (545 mg, 65%) as a yellow solid. LRMS (ESI): (calc) 247.02. (found) 248.0 (MS)+.

Step 5: (Z)-ethyl 4-(2-fluorodibenzo[b,f][1,4]oxazepin-11-yl)benzoate (22)

Using Procedure B (Table 1) with compound 21 the title compound 22 was obtained (680 mg, 86%) as a yellow foam. LRMS (ESI): (calc) 361.11. (found) 362.2 (MS)+.

Step 6: (Z)-4-(2-fluorodibenzo[b,f][1,4]oxazepin-11-yl)-N-hydroxybenzamide (23)

Using Procedure C (Table 1) with compound 22 the title compound 23 was obtained (341 mg, 52%) as a yellow solid. $^1$H NMR (400 MHZ, DMSO-d6) δ (ppm): 11.39 (s, 1H), 9.16 (s, 1H), 7.88 (d, J=8.8 Hz, 2H), 7.85 (d, J=8.8 Hz, 2H), 7.53-7.40 (m, 3H), 7.34-7.25 (m, 3H), 6.99 (dd, J=8.6, 2.4 Hz, 1H). LRMS (ESI): (calc) 348.09. (found) 349.19 (MH)+.

Scheme 7

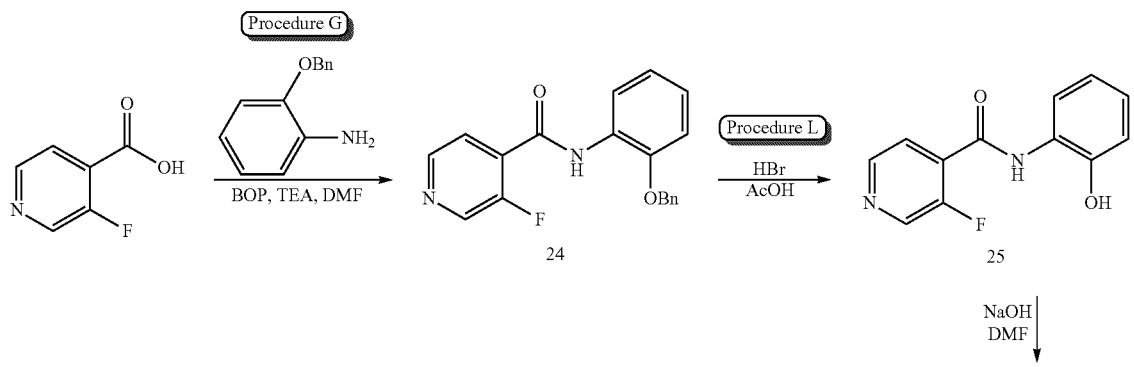

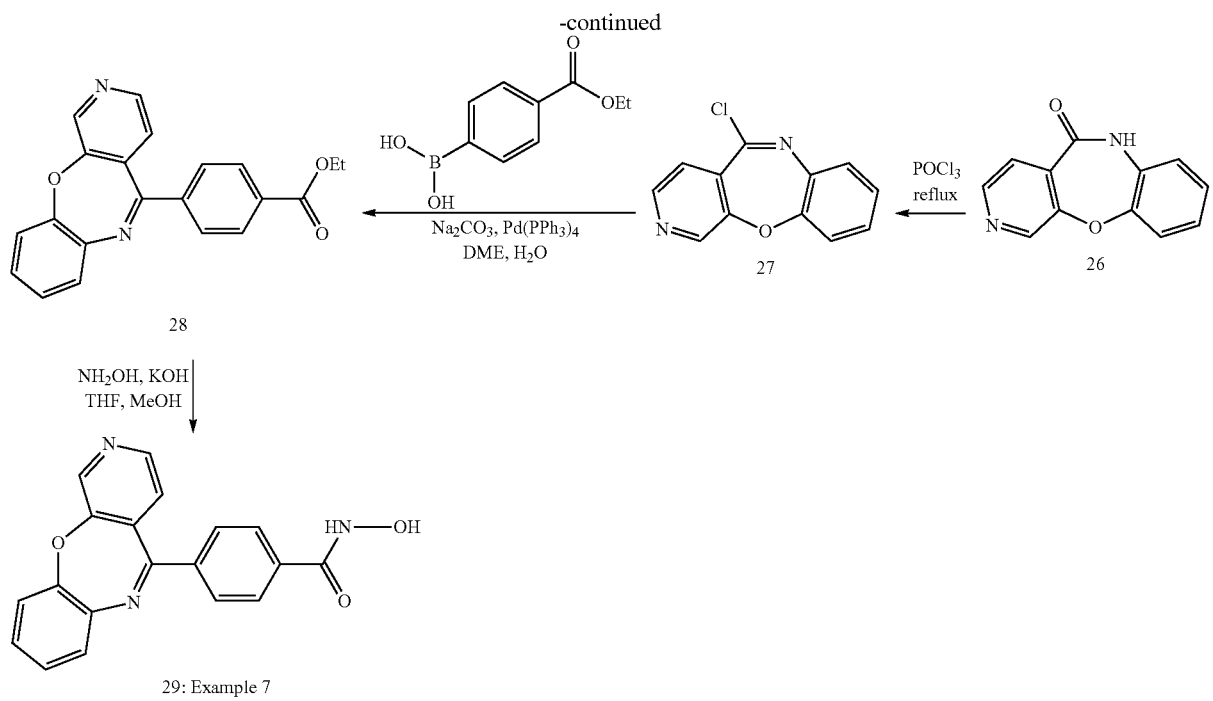

Example 7

(Z)-4-(benzo[b]pyrido[4,3-f][1,4]oxazepin-5-yl)-N-hydroxybenzamide (29)

Step 1: N-(2-(benzyloxy)phenyl)-3-fluoroisonicotinamide (24)

To a mixture of 3-fluoroisonicotinic acid (2.20 g, 15.6 mmol), 2-(benzyloxy)aniline (2.84 g, 14.2 mmol) and BOP (6.94 g, 15.6 mmol) in DMF (20.0 mL) was added TEA (4.4 mL, 31.2 mmol). The reaction mixture was stirred at room temperature for 20 min and poured into water. The aqueous layer was extracted with ethyl acetate (2×). The combined organic extracts were washed with water and brine, dried over sodium sulfate and concentrated in vacuo to a quarter volume. The resulting solid was found to be the desired compound. The filtrate was concentrated in vacuo to dryness. The residue was triturated in 30% ethyl acetate in hexanes and the 2 solids were combined to afford compound 24 (4.45 g, 97%) as a white solid. LRMS (ESI): (calc) 322.11. (found) 323.2 (MH)+.

Step 2: 3-fluoro-N-(2-hydroxyphenyl)isonicotinamide (25)

Title compound 24 (4.40 g, 13.6 mmol) was dissolved in 33% HBr in AcOH (30 mL) and the reaction mixture was stirred at room temperature for 2 hours. The mixture was diluted with water and solid sodium bicarbonate (until alkaline) then extracted twice with ethyl acetate. The combined organic extracts were washed with water and brine, dried over sodium sulfate and concentrated in vacuo. The crude was triturated in 30% ethyl acetate in hexanes to afford the title compound 25 (2.36 g, 75%) as a beige solid. LRMS (ESI): (calc) 232.06. (found) 233.1 (MH)+.

Step 3: benzo[b]pyrido[4,3-f][1,4]oxazepin-5(6H)-one (26)

Using Procedure H (Table 1) with compound 25 the title compound 26 was obtained (1.86 g, 88%) as a brown solid. LRMS (ESI): (calc) 212.06. (found) 213.1 (MH)+. $^1$H NMR (400 MHz, DMSO-$d_6$) δ (ppm): 10.86 (s, 1H), 8.71 (s, 1H), 8.55 (d, J=4.9 Hz, 1H), 7.70 (dd, J=4.9, 0.6 Hz, 1H), 7.40-7.37 (m, 1H), 7.25-7.15 (m, 3H).

Step 4: (E)-5-chlorobenzo[b]pyrido[4,3-f][1,4]oxazepine (27)

Using Procedure A (Table 1) with compound 26 the title compound 27 was obtained (1.79 g, 92%) as a light yellow solid. LRMS (ESI): (calc) 230.02. (found) 231.1 (MH)+.

Step 5: (Z)-ethyl 4-(benzo[b]pyrido[4,3-f][1,4]oxazepin-5-yl)benzoate (28)

Using Procedure B (Table 1) with compound 27 the title compound 28 was obtained (2.39 g, 92%) as a light yellow solid. LRMS (ESI): (calc) 344.12. (found) 345.0 (MH)+.

Step 6: (Z)-4-(benzo[b]pyrido[4,3-f][1,4]oxazepin-5-yl)-N-hydroxybenzamide (29)

Using Procedure C (Table 1) with compound 28 the title compound 29 was obtained (18 mg, 7%) as a yellow solid. (DMSO-d6) d(ppm) 1H, 11.41 (s, 1H), 9.19 (s, 1H), 8.78 (d, J=0.4 Hz, 1H), 8.55 (d, J=4.8 Hz, 1H), 7.92-7.87 (m, 4H), 7.50-7.48 (m, 1H), 7.42-7.31 (m, 3H), 7.22 (dd, J=4.8, 0.4 Hz, 1H). LRMS (ESI): (calc) 331.32. (found) 332.15.

Scheme 8
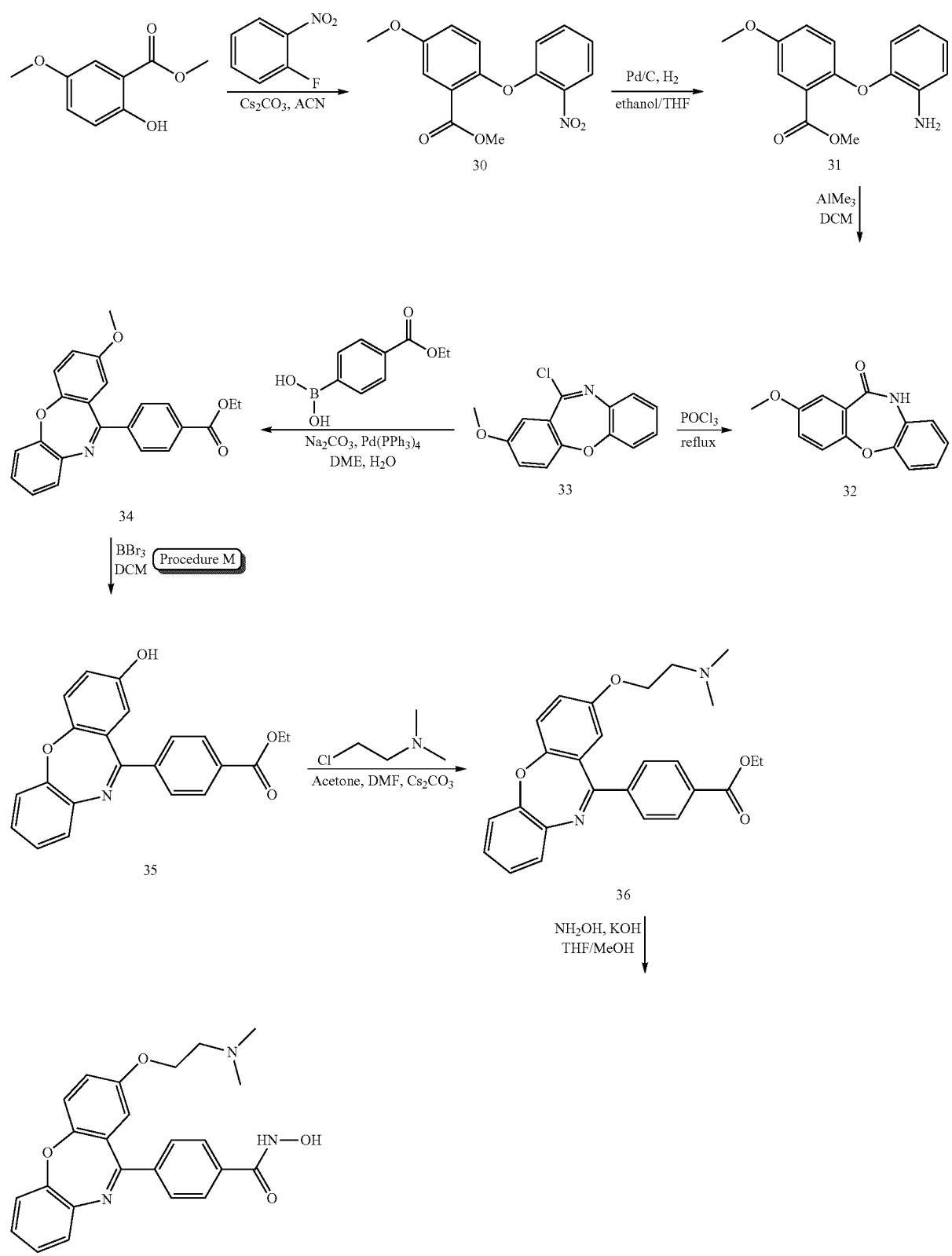
37: Example 8

Example 8

(Z)-4-(2-(2-(dimethylamino)ethoxy)dibenzo[b,f][1,4]oxazepin-11-yl)-N-hydroxybenzamide

Step 1: methyl 5-methoxy-2-(2-nitrophenoxy)benzoate (30)

Using Procedure I (Table 1) with methyl 2-hydroxy-5-methoxybenzoate and 1-fluoro-2-nitrobenzene the title compound 30 was obtained (4.20 g, 95%) as a yellow solid. LRMS (ESI): (calc) 303.07. (found) 304.1 (MH)+. $^1$H NMR (400 MHz, DMSO-$d_6$) δ (ppm): 8.02 (dd, J=8.1 Hz, 1H), 7.57 (ddd, J=8.6, 7.4, 1.8 Hz, 1H), 7.42 (dd, J=2.1, 1.4 Hz, 1H), 7.30-7.29 (m, 2H), 7.23 (ddd, J=8.4, 7.4, 1.1 Hz, 1H), 6.77 (dd, J=8.5, 1.1 Hz, 1H), 3.83 (s, 3H), 3.64 (s, 3H).

Step 2: methyl 2-(2-aminophenoxy)-5-methoxybenzoate (31)

Using Procedure J (Table 1) with compound 30 the title compound 31 was obtained (3.71 g, 100%) as a white solid. LRMS (ESI): (calc) 273.10. (found) 274.1 (MH)+. $^1$H NMR (400 MHz, DMSO-$d_6$) δ (ppm): 7.27 (d, J=3.3 Hz, 1H), 7.11 (dd, J=9.1, 3.2 Hz, 1H), 6.88-6.83 (m, 2H), 6.78 (dd, J=7.9, 1.7 Hz, 1H), 6.63 (dd, J=8.0, 1.4 Hz, 1H), 6.50 (ddd, J=8.0, 7.2, 1.7 Hz, 1H), 4.97 (s, 2H), 3.77 (s, 3H), 3.76 (s, 3H).

Step 3: 2-methoxydibenzo[b,f][1,4]oxazepin-11(10H)-one (32)

Using Procedure K (Table 1) with compound 31 the title compound 32 was obtained (3.00 g, 92%) as a white solid. LRMS (ESI): (calc) 241.07. (found) 242.0 (MH)+. $^1$H NMR (400 MHz, DMSO-$d_6$) δ (ppm): 10.55 (s, 1H), 7.34-7.26 (m, 2H), 7.22 (d, J=3.1 Hz, 1H), 7.19-7.09 (m, 4H), 3.76 (s, 3H).

Step 4: (E)-11-chloro-2-methoxydibenzo[b,f][1,4]oxazepine (33)

Using Procedure A (Table 1) with compound 32 the title compound 33 was obtained (1.83 g, 84%) as a light yellow solid. LRMS (ESI): (calc) 259.04. (found) 260.1 (MH)+.

Step 5: (Z)-ethyl 4-(2-methoxydibenzo[b,f][1,4]oxazepin-11-yl)benzoate (34)

Using Procedure B (Table 1) with compound 33 the title compound 34 was obtained (2.23 g, 85%) as a yellow foam. LRMS (ESI): (calc) 373.40. (found) 374.1 (MH)+.

Step 6: (Z)-ethyl 4-(2-hydroxydibenzo[b,f][1,4]oxazepin-11-yl)benzoate (35)

To a stirring solution of compound 34 (1.57 g, 4.21 mmol) in DCM (30 mL) was added BBr$_3$ (1M in DCM, 13.0 mL, 13.0 mmol) at 4° C. drop wise and the reaction mixture was stirred for 2 h. Ethanol (20 mL) was added and the mixture was stirred at room temperature for 30 min. Enough MeOH to get everything soluble was added and this mixture was poured into ethyl acetate (600 mL). This organic phase was washed with water and brine, dried over sodium sulfate, filtered and evaporated. The crude product was purified by flash chromatography with 30% ethyl acetate in hexanes to afford title compound 35 (453 mg, 30%) as a beige solid. LRMS (ESI): (calc) 359.12. (found) 360.2 (MH)+.

Step 7: (Z)-ethyl 4-(2-(2-(dimethylamino)ethoxy)dibenzo[b,f][1,4]oxazepin-11-yl)benzoate (36)

Using Procedure I (Table 1) with compound 35 the title compound 36 was obtained (445 mg, 83%) as yellow oil. LRMS (ESI): (calc) 430.19. (found) 431.4 (MH)+. $^1$H NMR (400 MHz, CD$_3$OD) δ (ppm): 8.15-8.12 (m, 2H), 7.91-7.88 (m, 2H), 7.41-7.39 (m, 1H), 7.28-7.16 (m, 5H), 6.63 (d, J=2.9 Hz, 1H), 4.41 (q, J=7.1 Hz, 2H), 3.95 (t, J=5.4 Hz, 2H), 2.66 (t, J=5.4 Hz, 2H), 2.25 (s, 6H), 1.41 (t, J=7.1 Hz, 3H).

Step 8: (Z)-4-(2-(2-(dimethylamino)ethoxy)dibenzo[b,f][1,4]oxazepin-11-yl)-N-hydroxybenzamide (37)

Using Procedure C (Table 1) with compound 36 the title compound 37 was obtained (38 mg, 27%) as yellow solid. 1H NMR (400 MHz, MeOH-d4) δ (ppm): 7.91-7.86 (m, 4H), 7.42-7.39 (m, 1H), 7.32-7.21 (m, 5H), 6.70 (d, J=3.2 Hz, 1H), 4.11 (t, J=5.2 Hz, 2H), 3.12 (t, J=5.2 Hz, 2H), 2.61 (s, 6H) LRMS (ESI): (calc) 417.17. (found) 418.47 (MH)+.

Scheme 9

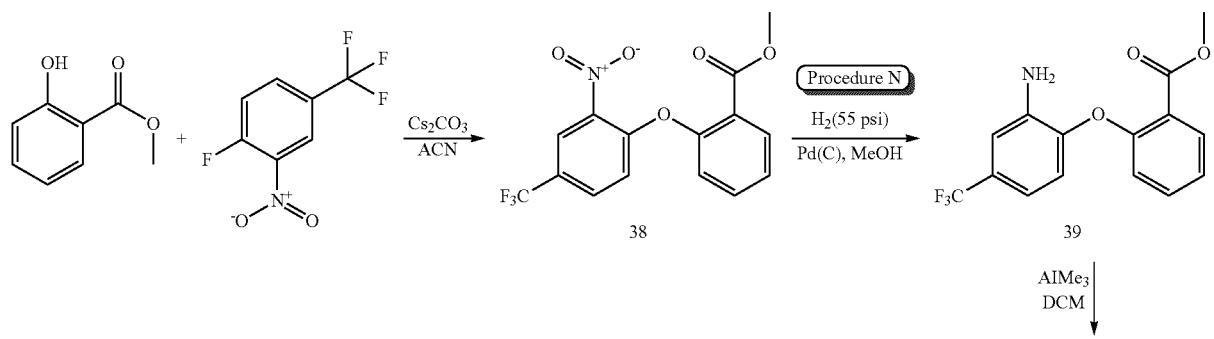

AlMe$_3$
DCM

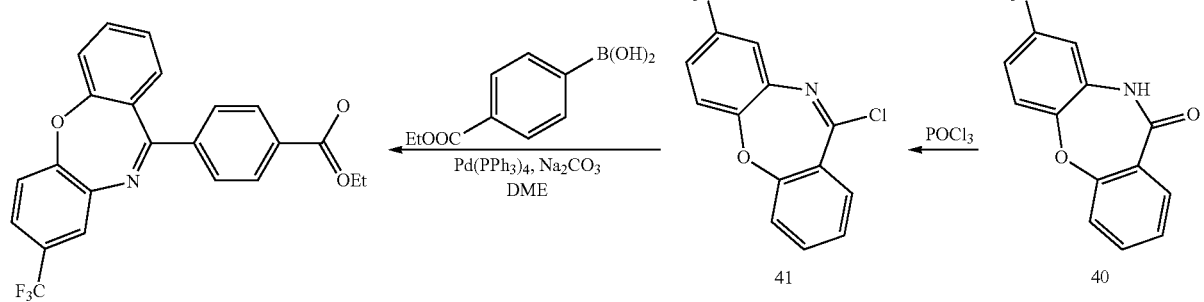

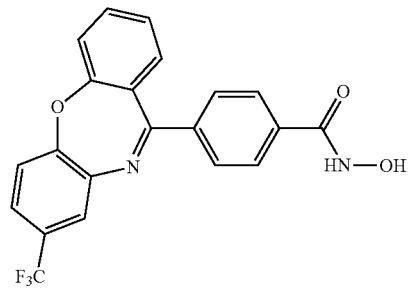

43: Example 9

Example 9

(Z)—N-hydroxy-4-(8-(trifluoromethyl)dibenzo[b,f][1,4]oxazepin-11-yl)benzamide (43)

Step 1: methyl 2-(2-nitro-4-(trifluoromethyl)phenoxy)benzoate (38)

Using Procedure I (Table 1) with methyl 2-hydroxybenzoate and 1-fluoro-2-nitro-4-(trifluoromethyl)benzene the title compound 38 was obtained (1.70 g, 52%). LRMS (ESI): (calc) 341.05. (found) 342.0 (MH)+.

Step 2: methyl 2-(2-amino-4-(trifluoromethyl)phenoxy)benzoate (39)

Title compound 38 (1.70 g, 1.98 mmol), Pd (C) 10% (0.17 g, 10% w/w) and MeOH were put in a Parr-Shaker apparatus and the reaction mixture was pressurized to 55 PSI of $H_2$. The mixture was agitated over night. The catalyst was filtered and the filtrate was concentrated to afford title compound 39 (1.55 g, 100%) as a clear oil. LRMS (ESI): (calc) 311.08. (found) 312.1 (MH)+.

Step 3: 8-(trifluoromethyl)dibenzo[b,f][1,4]oxazepin-11(10H)-one (40)

Using Procedure K (Table 1) with compound 39 the title compound 40 was obtained (1.20 g, 86%). LRMS (ESI): (calc) 279.05. (found) 280.1 (MH)+. $^1$H NMR (400 MHz, DMSO-$d_6$) δ (ppm): 10.73 (s, 1H), 7.80 (dd, J=7.6, 1.8 Hz, 1H), 7.66 (ddd, J=8.1, 7.3, 1.8 Hz, 1H), 7.58-7.51 (m, 3H), 7.41 (dd, J=8.2, 1.0 Hz, 1H), 7.36 (td, J=7.5, 1.2 Hz, 1H).

Step 4: (E)-11-chloro-8-(trifluoromethyl)dibenzo[b,f][1,4]oxazepine (41)

Using Procedure A (Table 1) with compound 40 the title compound 41 was obtained (0.83 g, 65%). LRMS (ESI): (calc) 297.02. (found) 298.1 (MH)+.

Step 5: (Z)-ethyl 4-(8-(trifluoromethyl)dibenzo[b,f][1,4]oxazepin-11-yl)benzoate (42)

Using Procedure B (Table 1) with compound 41 the title compound 42 was obtained (0.82 g, 72%). LRMS (ESI): (calc) 411.11. (found) 412.4 (MH)+.

Step 6: (Z)—N-hydroxy-4-(8-(trifluoromethyl)dibenzo[b,f][1,4]oxazepin-11-yl)benzamide (43)

Using Procedure C (Table 1) with compound 42 the title compound 43 was obtained (0.166 g, 43%). 1H NMR (400 MHz, DMSO-$d_6$) δ (ppm): 11.38 (s, 1H), 9.17 (s, 1H), 7.95-7.84 (m, 4H), 7.76 (d, J=1.6 Hz, 1H), 7.72-7.64 (m, 2H), 7.55 (d, J=8.5 Hz, 1H), 7.48 (d, J=7.8 Hz, 1H), 7.33 (t, J=7.6 Hz, 1H), 7.21 (dd, J=7.7 and 1.4 Hz, 1H) LRMS (ESI): (calc.) 398.1. (found) 399.2 (MH)+.

Scheme 10

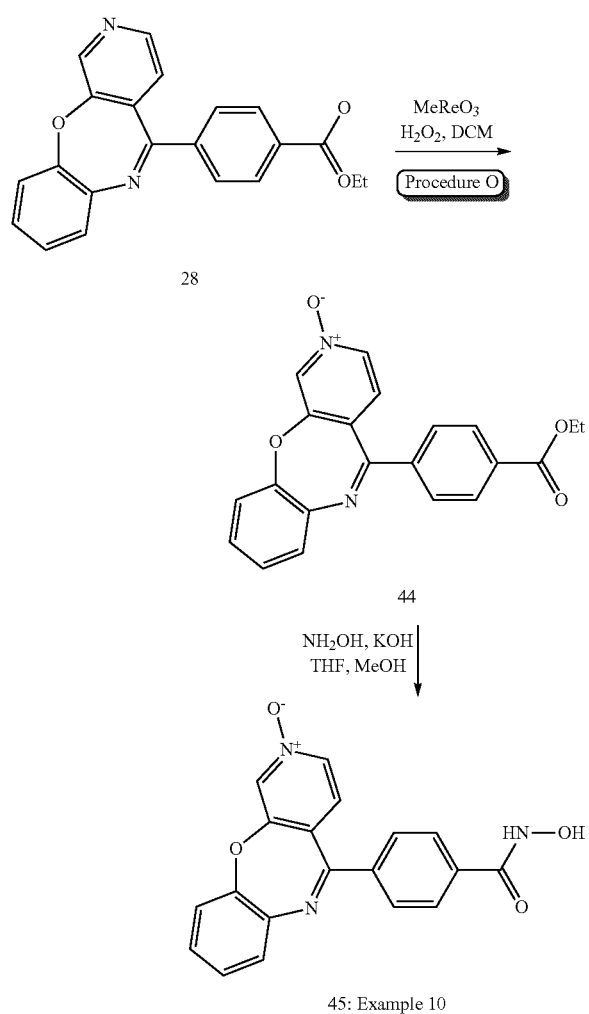

Example 10

(Z)-5-(4-(hydroxycarbamoyl)phenyl)benzo[b]pyrido[4,3-f][1,4]oxazepine 2-oxide (45)

Step 1:
N-(2-(benzyloxy)phenyl)-3-fluoroisonicotinamide (44)

To a stirring solution of compound 28 (0.37 g, 1.08 mmol) in DCM (5.0 mL) was added methyltrioxorhenium (0.027 g, 0.107 mmol) and the mixture was stirred for 5 min. Hydrogen peroxide (35% w, 0.11 mL, 1.29 mmol) was added and the reaction mixture was stirred at room temperature for 2 h. The mixture was concentrated in vacuo and the crude was purified by flash chromatography with 75% ethyl acetate in hexanes to afford title compound 44 (0.132 g, 34%) as a yellow oil. LRMS (ESI): (calc) 360.11. (found) 361.3 (MH)+. $^1$H NMR (400 MHz, CD$_3$OD) δ (ppm): 8.50-8.49 (m, 1H), 8.17-8.12 (m, 3H), 7.92-7.89 (m, 2H), 7.49-7.46 (m, 1H), 7.36-7.29 (m, 3H), 7.24-7.22 (m, 1H), 4.40 (q, J=7.1 Hz, 2H), 1.41 (t, J=7.1 Hz, 3H).

Step 2: (Z)-5-(4-(hydroxycarbamoyl)phenyl)benzo[b]pyrido[4,3-f][1,4]oxazepine 2-oxide (45)

Using Procedure C (Table 1) with compound 44 the title compound 45 was obtained (13 mg, 35%). $^1$H NMR (400 MHz, MeOH-d$_4$) δ (ppm): 8.51 (d, J=1.8 Hz, 1H), 8.18 (dd, J=6.8, 1.8 Hz, 1H), 7.94-7.89 (m, 4H), 7.51-7.49 (m, 1H), 7.37-7.31 (m, 3H), 7.26 (d, J=6.7 Hz, 1H). LRMS (ESI): (calc) 347.09. (found) 348.1 (MH)+.

Scheme 11

Example 11

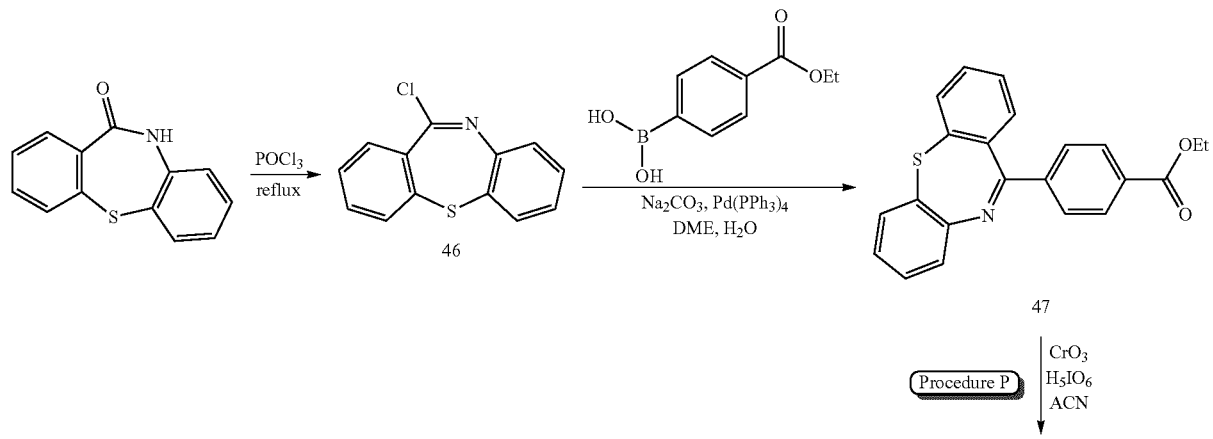

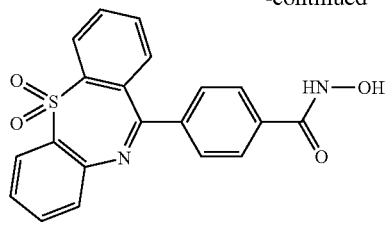

49: Example 11

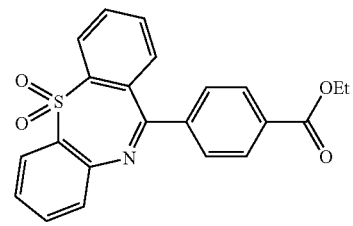

48

Step 1: (E)-11-chlorodibenzo[b,f][1,4]thiazepine (46)

Using Procedure A (Table 1) with dibenzo[b,f][1,4]thiazepin-11(10H)-one the title compound 46 was obtained.

Step 2: (Z)-ethyl 4-(dibenzo[b,f][1,4]thiazepin-11-yl)benzoate (47)

Using Procedure B (Table 1) with compound 46 the title compound 47 was obtained (1.60 g, 81%) as a yellow foam. LRMS (ESI): (calc) 359.10. (found) 360.3 (MH)+.

Step 3: (48)

Periodic acid (1.30 g, 5.71 mmol) was added to acetonitrile (30 mL) and the mixture was stirred for 30 min. Chromium (VI) oxide (0.091 g, 0.91 mmol) was added and the mixture was stirred for 5 min. This above mixture was added to a solution of compound 47 (0.684 g, 1.90 mmol) in acetonitrile (20 mL). The reaction mixture was stirred at room temperature for 1 h. The solid was filtered and washed with acetonitrile. The filtrate was concentrated to a volume of 20 mL and ethyl acetate was added. This organic phase was washed with water and brine, dried over sodium sulfate, filtered and concentrated. The crude was purified by flash chromatography with 10% to 30% ethyl acetate in hexanes to afford title compound 48 (545 mg, 73%) as a yellow solid. LRMS (ESI): (calc) 391.09. (found) 392.2 (MH)+. $^1$H NMR (400 MHz, DMSO-$d_6$) δ (ppm): 8.13-8.10 (m, 3H), 8.01 (dd, J=8.0, 1.4 Hz, 1H), 7.94-7.78 (m, 5H), 7.65 (dd, J=8.0, 1.0 Hz, 1H), 7.57 (dd, J=7.5, 1.3 Hz, 1H), 7.52 (ddd, J=8.3, 7.2, 1.4 Hz, 1H), 4.37 (q, J=7.0 Hz, 2H), 1.35 (t, J=7.0 Hz, 3H).

Step 4: (49)

Using Procedure C (Table 1) with compound 48 the title compound 49 was obtained (365 mg, 71%) as a light yellow solid. $^1$H NMR (400 MHz, DMSO-$d_6$) δ (ppm): 11.42 (s, 1H), 9.20 (s, 1H), 8.13-8.10 (m, 1H), 7.99 (dd, J=8.0, 1.2 Hz, 1H), 7.93-7.83 (m, 6H), 7.81-7.77 (m, 1H), 7.63 (dd, J=8.0, 0.8 Hz, 1H), 7.59-7.57 (m, 1H), 7.53-7.49 (m, 1H). LRMS (ESI): (calc) 378.40. (found) 379.1 (MH)+.

Scheme 12

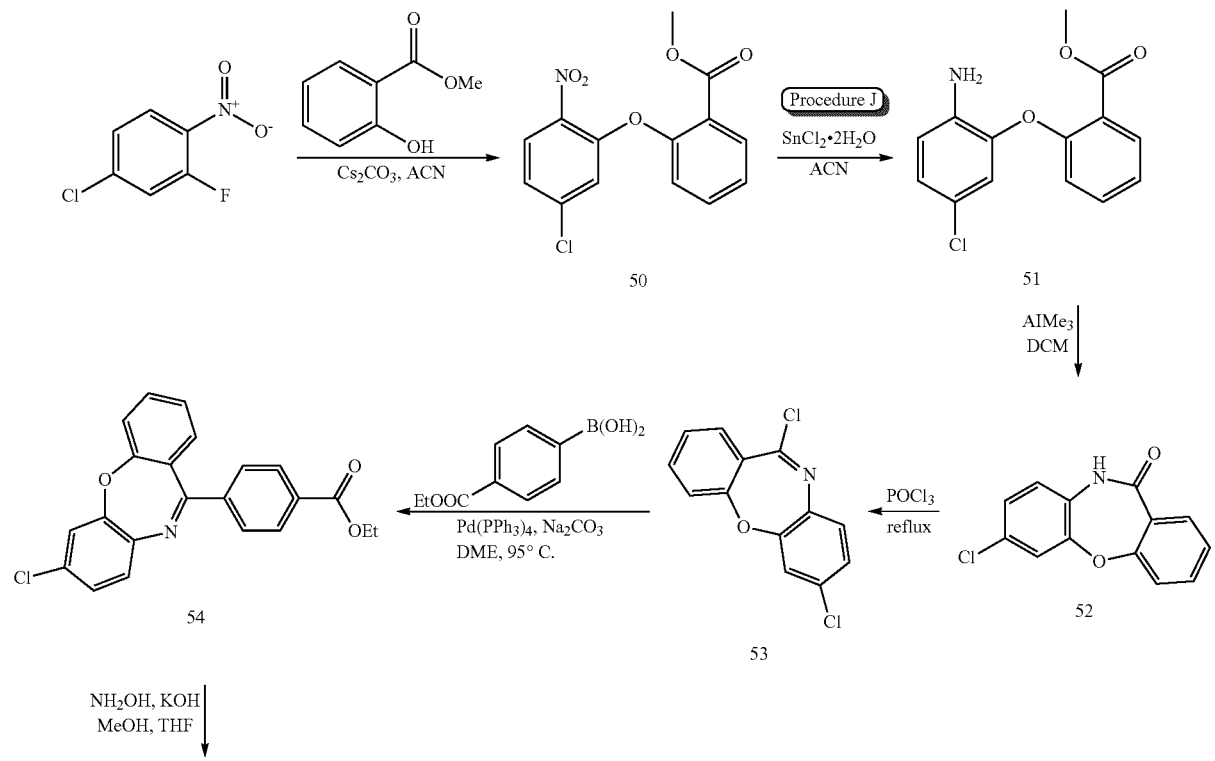

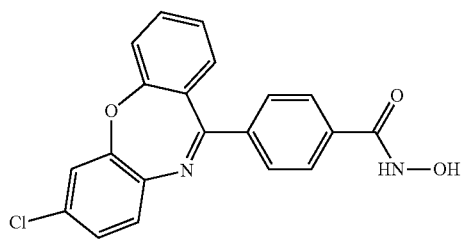

55: Example 12

Example 12

(Z)-4-(7-chlorodibenzo[b,f][1,4]oxazepin-11-yl)-N-hydroxybenzamide (55)

Step 1: methyl 2-(5-chloro-2-nitrophenoxy)benzoate (50)

Using Procedure I (Table 1) with 4-chloro-2-fluoro-1-nitrobenzene and methyl 2-hydroxybenzoate the title compound 50 was obtained (4.40 g, 100%) as red oil. LRMS (ESI): (calc) 307.02. (found) 308.2 (MH)+.

Step 2: methyl 2-(2-amino-5-chlorophenoxy)benzoate (51)

A mixture of compound 50 (4.40 g, 14.30 mmol) and SnCl$_2$.2H$_2$O (16.13 g, 71.5 mmol) in ethanol (100 mL) was stirred at 80° C. for 3 h. Water and saturated bicarbonate solution (~250 ml) was added (very effervescent). The reaction mixture was diluted with ethyl acetate and then Celite® was added and the mixture was stirred for 15 min then filtered. The filtrate was extracted with ethyl acetate twice, and the organic extract was dried over Na$_2$SO$_4$, filtered and concentrated. The crude was purified by flash chromatography, dry loaded with THF onto 80 g SiO$_2$ and eluted with 0% to 50% ethyl acetate in hexanes to afford title compound 51 (2.10 g, 51%) as a beige solid. LRMS (ESI): (calc) 277.05. (found) 278.2 (MH)+. $^1$H NMR (400 MHz, CDCl$_3$) δ (ppm): 7.89 (dd, J=7.9, 1.7 Hz, 1H), 7.46 (ddd, J=7.9, 7.4, 1.8 Hz, 1H), 7.17 (td, J=7.6, 1.2 Hz, 1H), 6.97 (dd, J=8.3, 0.9 Hz, 1H), 6.94 (dd, J=8.4, 2.3 Hz, 1H), 6.79 (d, J=2.3 Hz, 1H), 6.73 (d, J=8.4 Hz, 1H), 4.05 (s, 2H), 3.87 (s, 3H).

Step 3: 7-chlorodibenzo[b,f][1,4]oxazepin-11(10H)-one (52)

Using Procedure K (Table 1) with compound 51 the title compound 52 was obtained (1.60 g, 86%). LRMS (ESI): (calc) 245.02. (found) 246.0 (MH)+.

Step 4: (E)-7,11-dichlorodibenzo[b,f][1,4]oxazepine (53)

Using Procedure A (Table 1) with compound 52 the title compound 53 was obtained (1.00 g, 93%) as a white solid.

Step 5: (Z)-ethyl 4-(7-chlorodibenzo[b,f][1,4]oxazepin-11-yl)benzoate (54)

Using Procedure B (Table 1) with compound 53 the title compound 54 was obtained (0.50 g, 39%). LRMS (ESI): (calc) 377.08. (found) 377.7 (MH)+.

Step 6: (Z)-4-(7-chlorodibenzo[b,f][1,4]oxazepin-11-yl)-N-hydroxybenzamide (55)

Using Procedure C (Table 1) with compound 54 the title compound 55 was obtained (0.21 g, 82%). $^1$H NMR (400 MHz, DMSO-d$_6$) δ (ppm): 11.37 (s, 1H), 9.16 (s, 1H), 7.87 (d, J=8.3 Hz, 2H), 7.82 (d, J=8.2 Hz, 2H), 7.70-7.64 (m, 1H), 7.52-7.41 (m, 3H), 7.38-7.28 (m, 2H), 7.22-7.17 (m, 1H). LRMS (ESI): (calc) 364.06. (found) 365.1 (MH)+.

Scheme 13

Example 13

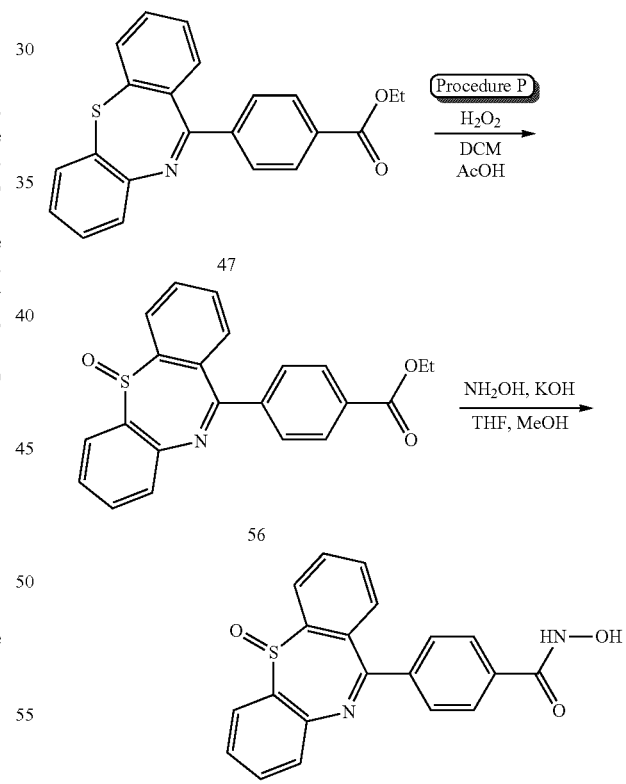

57: Example 13

Compound (57)

Step 1: Compound (56)

To a stirring solution of title compound 47 (0.359 g, 1.0 mmol) in DCM (5.0 mL) was added AcOH (5.0 mL) and oxygen peroxide (2.5 mL, excess) and the reaction mixture was stirred 20 h at room temperature. The reaction mixture was cooled to room temperature and diluted with ethyl acetate. This organic phase was washed with a saturated solution of bicarbonate (2 times) and brine (1 time), dried over sodium sulfate, filtered and evaporated. The crude product was purified by flash chromatography with 20-30% ethyl acetate in hexanes to afford title compound 56 (345 mg, 92%) as yellow solid. LRMS (ESI): (calc) 375.09. (found) 376.4 (MH)+.

Step 2: (57)

Using Procedure C (Table 1) with compound 56 the title compound 57 was obtained (27 mg, 16%) as yellow solid. $^1$H NMR (400 MHz, DMSO-$d_6$) δ (ppm): 11.42 (s, 1H), 9.20 (s, 1H), 7.91-7.80 (m, 6H), 7.64-7.47 (m, 4H), 7.41 (d, J=7.6 Hz, 1H), 7.37 (d, J=8.0 Hz, 1H). LRMS (ESI): (calc) 362.07. (found) 363.3 (MH)+.

Scheme 14

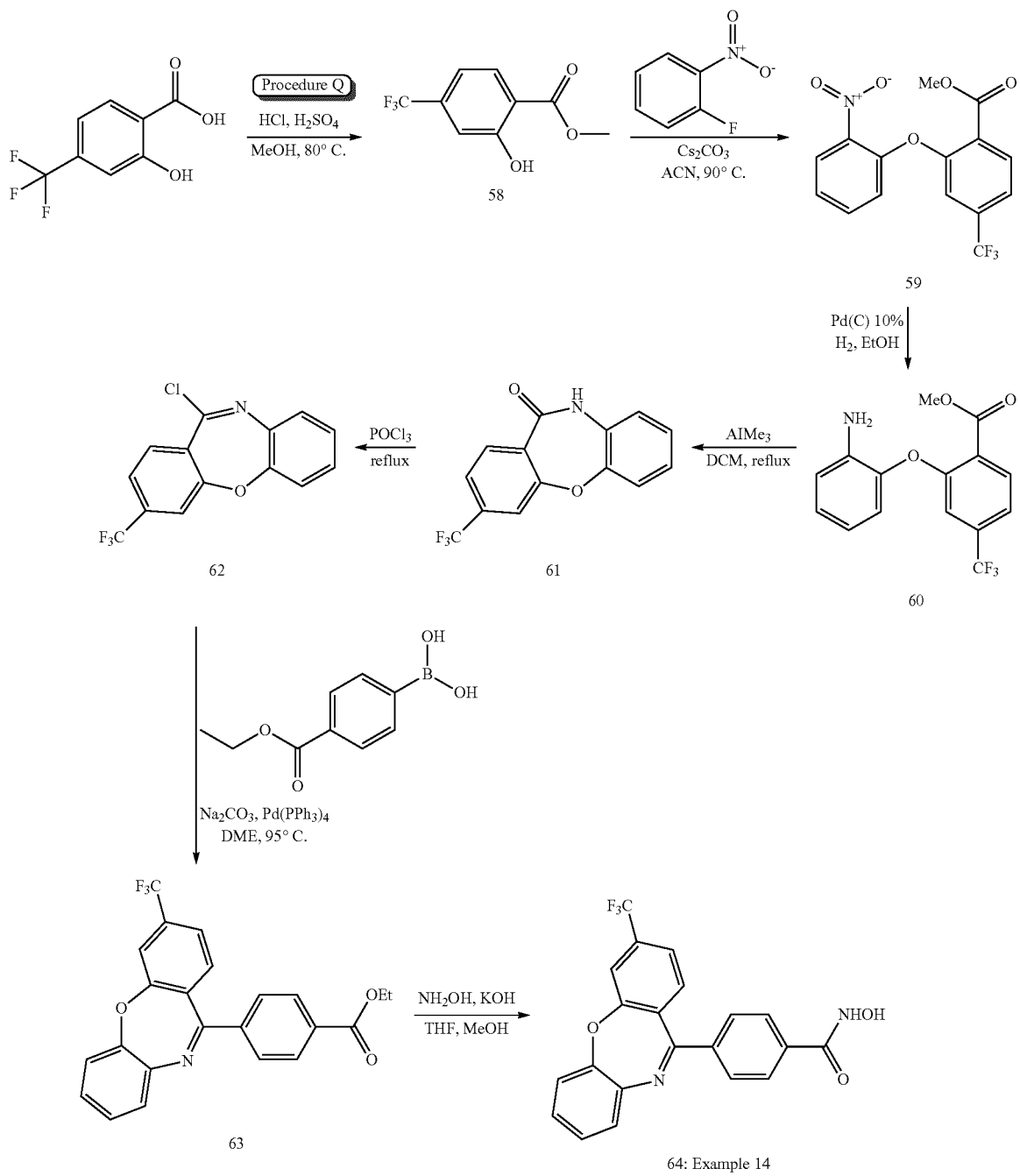

Example 14

(Z)—N-hydroxy-4-(3-(trifluoromethyl)dibenzo[b,f] [1,4]oxazepin-11-yl)benzamide (64)

Step 1: methyl 2-hydroxy-4-(trifluoromethyl)benzoate (58)

2-Hydroxy-4-(trifluoromethyl)benzoic acid (5.0 g, 24.26 mmol), hydrochloric acid (0.2 mL, 2.40 mmol), sulfuric acid (1.5 mL, 28.1 mmol) and methanol (40 mL) were mixed together and the reaction mixture was stirred at 80° C. overnight. The mixture was concentrated and reloaded, stirred at 100° C. overnight. More $H_2SO_4$ was added (heated to 100° C. overnight). The mixture was concentrated and ether was added. The organic layer was washed with water twice, saturated solution of bicarbonate then brine, dried over $Na_2SO_4$, filtered and concentrated. The residue was dissolved in 20 ml $Et_2O$ and filtered (to remove starting material) and the filtrate was evaporated to afford title compound 58 (3.9 g, 73%) as a clear oil.

Step 2: methyl 2-(2-nitrophenoxy)-4-(trifluoromethyl)benzoate (59)

Using Procedure I (Table 1) with compound 58 the title compound 59 was obtained (4.8 g, 87%) as white solid. LRMS (ESI): (calc) 341.05. (found) 342.3 (MH)+.

Step 3: methyl 2-(2-aminophenoxy)-4-(trifluoromethyl)benzoate (60)

Using Procedure J (Table 1) with compound 59 the title compound 60 was obtained (3.9 g, 89%) as brown oil. LRMS (ESI): (calc) 311.08. (found) 312.3 (MH)+.

Step 4: 3-(trifluoromethyl)dibenzo[b,f][1,4]oxazepin-11(10H)-one (61)

Using Procedure K (Table 1) with compound 60 the title compound 61 was obtained (2.7 g, 77%) as white solid. LRMS (ESI): (calc) 279.05. (found) 280.2 (MH)+.

Step 5: (E)-11-chloro-3-(trifluoromethyl)dibenzo[b,f][1,4]oxazepine (62)

Using Procedure A (Table 1) with compound 61 the title compound 62 was obtained (1.1 g, 72%) as yellow solid. LRMS (ESI): (calc) 297.02. (found) 298.2 (MH)+.

Step 6: (Z)-ethyl 4-(3-(trifluoromethyl)dibenzo[b,f][1,4]oxazepin-11-yl)benzoate (63)

Using Procedure B (Table 1) with compound 62 the title compound 63 was obtained (1.0 g, 66%). LRMS (ESI): (calc) 411.11. (found) 412.4 (MH)+.

Step 7: (Z)—N-hydroxy-4-(3-(trifluoromethyl)dibenzo[b,f][1,4]oxazepin-11-yl)benzamide (64)

Using Procedure C (Table 1) with compound 63 the title compound 64 was obtained (0.38 g, 75%) as a white solid. $^1$H NMR (400 MHz, DMSO-$d_6$) δ (ppm): 11.39 (s, 1H), 9.17 (s, 1H), 7.94-7.82 (m, 5H), 7.66 (d, J=7.8 HZ, 1H), 7.48-7.39 (m, 3H), 7.36-7.28 (m, 2H). LRMS (ESI): (calc) 398.09. (found) 399.4 (MH)+.

Scheme 15

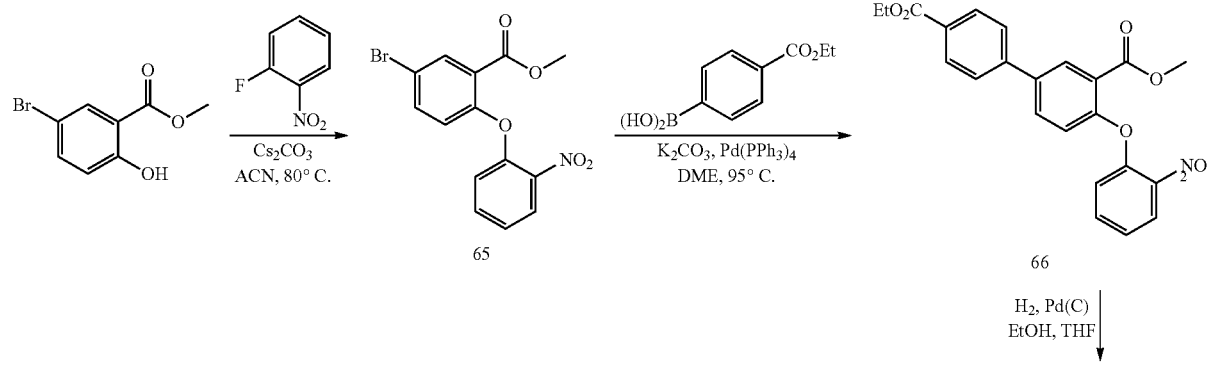

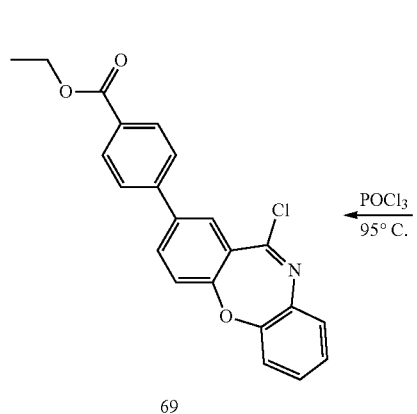
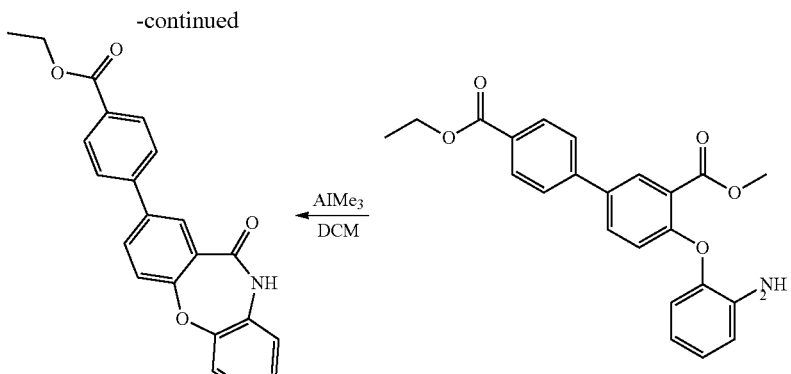
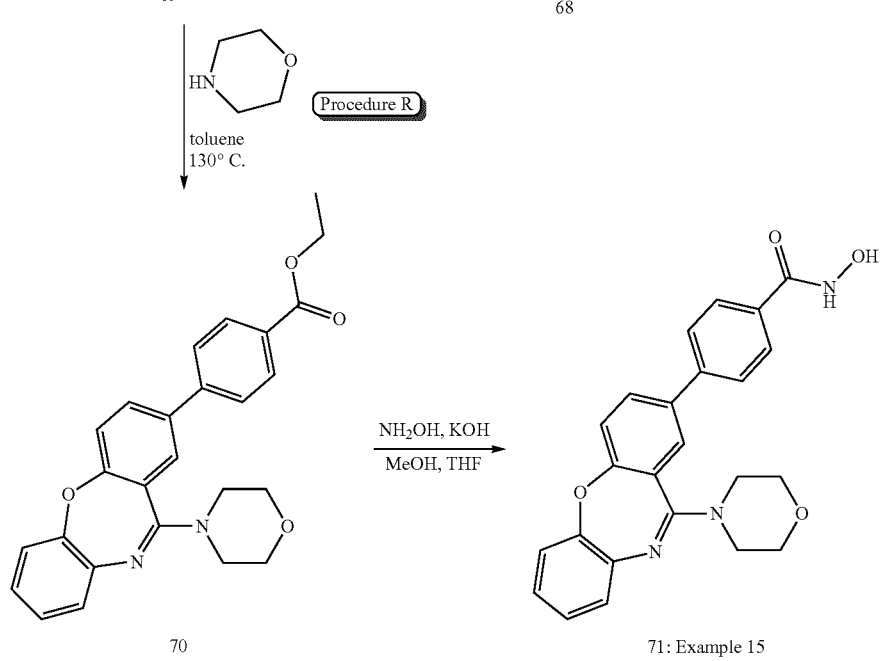

Example 15

(E)-N-hydroxy-4-(11-morpholinodibenzo[b,f][1,4]oxazepin-2-yl)benzamide (71)

Step 1: methyl 5-bromo-2-(2-nitrophenoxy)benzoate (65)

Using Procedure I (Table 1) with methyl 5-bromo-2-hydroxybenzoate and 1-fluoro-2-nitrobenzene the title compound 65 was obtained (3.12 g, 67%) as a yellow oil. LRMS (ESI): (calc) 350.97. (found) 354.2 (MH)+.

Step 2: 4'-ethyl 3-methyl 4-(2-nitrophenoxy)biphenyl-3,4'-dicarboxylate (66)

Using Procedure B (Table 1) with compound 65 the title compound 66 was obtained (2.16 g, 58%) as a beige solid. LRMS (ESI): (calc) 421.12. (found) 422.4 (MH)+.

Step 3: 4'-ethyl 3-methyl 4-(2-aminophenoxy)biphenyl-3,4'-dicarboxylate (67)

Using Procedure J (Table 1) with compound 66 the title compound 67 was obtained (1.98 g, 100%) as a yellow oil. LRMS (ESI): (calc) 391.14. (found) 392.5 (MH)+.

Step 4: ethyl 4-(11-oxo-10,11-dihydrodibenzo[b,f][1,4]oxazepin-2-yl)benzoate (68)

Using Procedure K (Table 1) with compound 67 the title compound 68 was obtained (0.58 g, 26%) as a beige solid. LRMS (ESI): (calc) 359.12. (found) 360.4 (MH)+.

Step 5: (E)-ethyl 4-(11-chlorodibenzo[b,f][1,4]oxazepin-2-yl)benzoate (69)

Using Procedure A (Table 1) with compound 68 the title compound 69 was obtained and used crude for next step.

Step 6: (E)-ethyl 4-(11-morpholinodibenzo[b,f][1,4]oxazepin-2-yl)benzoate (70)

To a stirring solution of title compound 69 (285 mg, 0.754 mmol) in toluene (5.0 mL) was added morpholine (1.00 g, 11.48 mmol) and the reaction mixture was stirred at 130° C. for 4 h. It was cooled to room temperature and diluted with ethyl acetate. The organic layer was washed with water and brine, dried over sodium sulfate, filtered and concentrated in vacuo. The crude was purified by flash chromatography with 10%-30% ethyl acetate in hexanes to afford title compound 70 (223 mg, 69%) as a white solid. LRMS (ESI): (calc) 428.17. (found) 429.5 (MH)+. $^1$H NMR (400 MHz, CD$_3$OD) δ (ppm): 8.09 (d, J=8.6 Hz, 2H), 7.84 (dd, J=8.4, 2.3 Hz, 1H), 7.71-7.69 (m, 3H), 7.40 (d, J=8.4 Hz, 1H), 7.17-7.01 (m, 4H), 4.38 (q, J=7.1 Hz, 2H), 3.90-3.75 (m, 4H), 3.60-3.48 (m, 4H), 1.40 (t, J=7.1 Hz, 3H).

Step 7: (E)-N-hydroxy-4-(11-morpholinodibenzo[b,f][1,4]oxazepin-2-yl)benzamide (71)

Using Procedure C (Table 1) with compound 70 the title compound 71 was obtained (74 mg, 35%) as a white solid. 1H NMR (400 MHz, DMSO-d$_6$) δ (ppm): 11.28 (s, 1H), 9.08 (s, 1H), 7.90 (dd, J=8.4, 2.0 Hz, 1H), 7.83 (d, J=8.6 Hz, 2H), 7.73 (d, J=8.6 Hz, 2H), 7.68 (d, J=2.4 Hz, 1H), 7.47 (d, J=8.4 Hz, 1H), 7.22 (dd, J=8.0, 1.2 Hz, 1H), 7.12-7.06 (m, 2H), 7.03-6.99 (m, 1H), 3.08-3.07 (m, 4H), 3.55-3.54 (m, 4H). LRMS (ESI): (calc) 415.15. (found) 416.6 (MH)+.

Example 16

(Z)—N-hydroxy-4-(2-(trifluoromethyl)benzo[f]pyrido[2,3-b][1,4]oxazepin-6-yl)benzamide (77)

Step 1: 2-(benzyloxy)-N-(2-chloro-6-(trifluoromethyl)pyridin-3-yl)benzamide (72)

To a stirring solution of 2-(benzyloxy)benzoic acid (2.55 g, 11.19 mmol) and oxalyl chloride (2.84 g, 22.39 mmol) in THF (20 mL) was added a few drops of DMF (0.012 mL, 0.153 mmol) at 0° C. The reaction mixture was allowed to warm to room temperature and further stirred 30 minutes, diluted with toluene and then solvent evaporated. The residue was taken up in THF (20 mL) and to this solution was added 2-chloro-6-(trifluoromethyl)pyridin-3-amine (2.0 g, 10.18 mmol) at 0° C. followed by the addition of triethylamine (4.68 mL, 33.6 mmol). The reaction mixture was allowed to stir 3 days at room temperature then quenched with saturated bicarbonate solution, extracted with EtOAc and solvent evaporated to afford title compound 72 (3.0 g, 73% yield) after Scheme 16

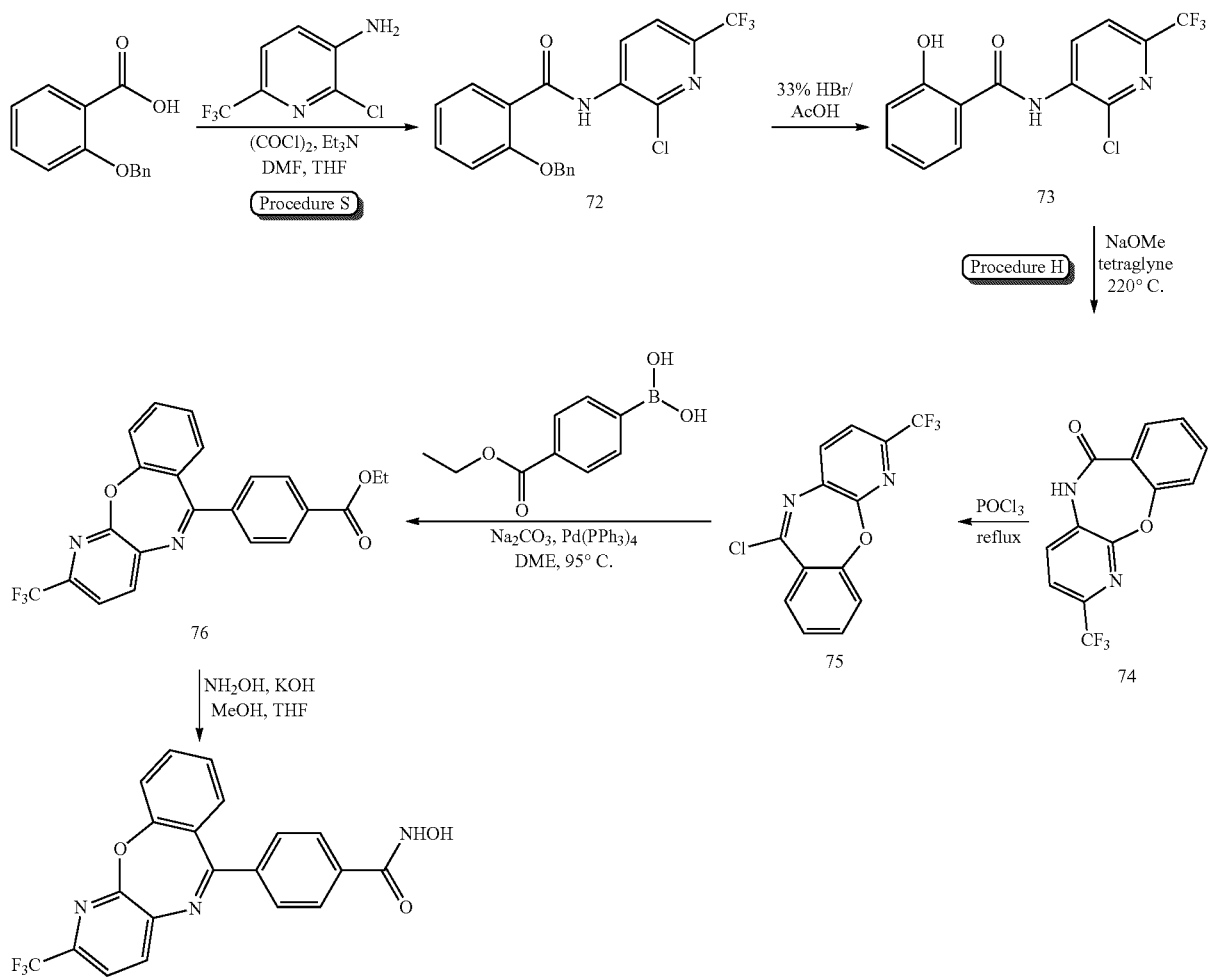

77: Example 16 purification by flash chromatography (0 to 100% ethyl acetate in hexane). LRMS (ESI): (calc) 406.07. (found) 407.4 (MH)+.

Step 2: N-(2-chloro-6-(trifluoromethyl)pyridin-3-yl)-2-hydroxybenzamide (73)

Using Procedure L (Table 1) with compound 72 the title compound 73 was obtained (1.54 g, 82%) as a white solid. LRMS (ESI): (calc) 316.02. (found) 317.2 (MH)+.

Step 3: 2-(trifluoromethyl)benzo[f]pyrido[2,3-b][1,4]oxazepin-6(5H)-one (74)

To a stirring solution of title compound 73 (0.76 g, 2.4 mmol) in tetraglyne (10 mL) was added sodium methoxide (0.220 g, 4.08 mmol) and the reaction mixture was stirred at 220° C. for 3 h. The reaction mixture was cooled to room temperature diluted with water (25 mL), stirred for 20 min then filtered to give a light brown solid which was purified by flash chromatography (0% to 60% ethyl acetate in hexanes) to afford title compound 74 (0.37 g, 55%). LRMS (ESI): (calc) 280.05. (found) 281.3 (MH)+.

Step 4: (E)-6-chloro-2-(trifluoromethyl)benzo[f]pyrido[2,3-b][1,4]oxazepine (75)

Using Procedure A (Table 1) with compound 74 the title compound 75 (0.32 g, 50%) was obtained as a yellowish solid.

Step 5: (Z)-ethyl 4-(2-(trifluoromethyl)benzo[f]pyrido[2,3-b][1,4]oxazepin-6-yl)benzoate (76)

Using Procedure B (Table 1) with compound 75 the title compound 76 (220 mg, 25%) was obtained as a yellow solid. LRMS (ESI): (calc) 412.10. (found) 413.4 (MH)+.

Step 6: (Z)—N-hydroxy-4-(2-(trifluoromethyl)benzo[f]pyrido[2,3-b][1,4]oxazepin-6-yl)benzamide (77)

Using Procedure C (Table 1) with compound 76 the title compound 77 (31 mg, 13%) was obtained as a yellow solid. $^1$H NMR (400 MHz, DMSO-d$_6$) δ (ppm): 11.43 (s, 1H), 9.20 (s, 1H), 8.18 (d, J=8.1 Hz, 1H), 7.97-7.86 (m, 5H), 7.78-7.72 (m, 1H), 7.55 (d, J=8.0 Hz, 1H), 7.40 (t, J=7.6 Hz, 1H), 7.29 (d, J=6.6 Hz, 1H). LRMS (ESI): (calc) 399.08. (found) 400.4 (MH)+.

Scheme 17

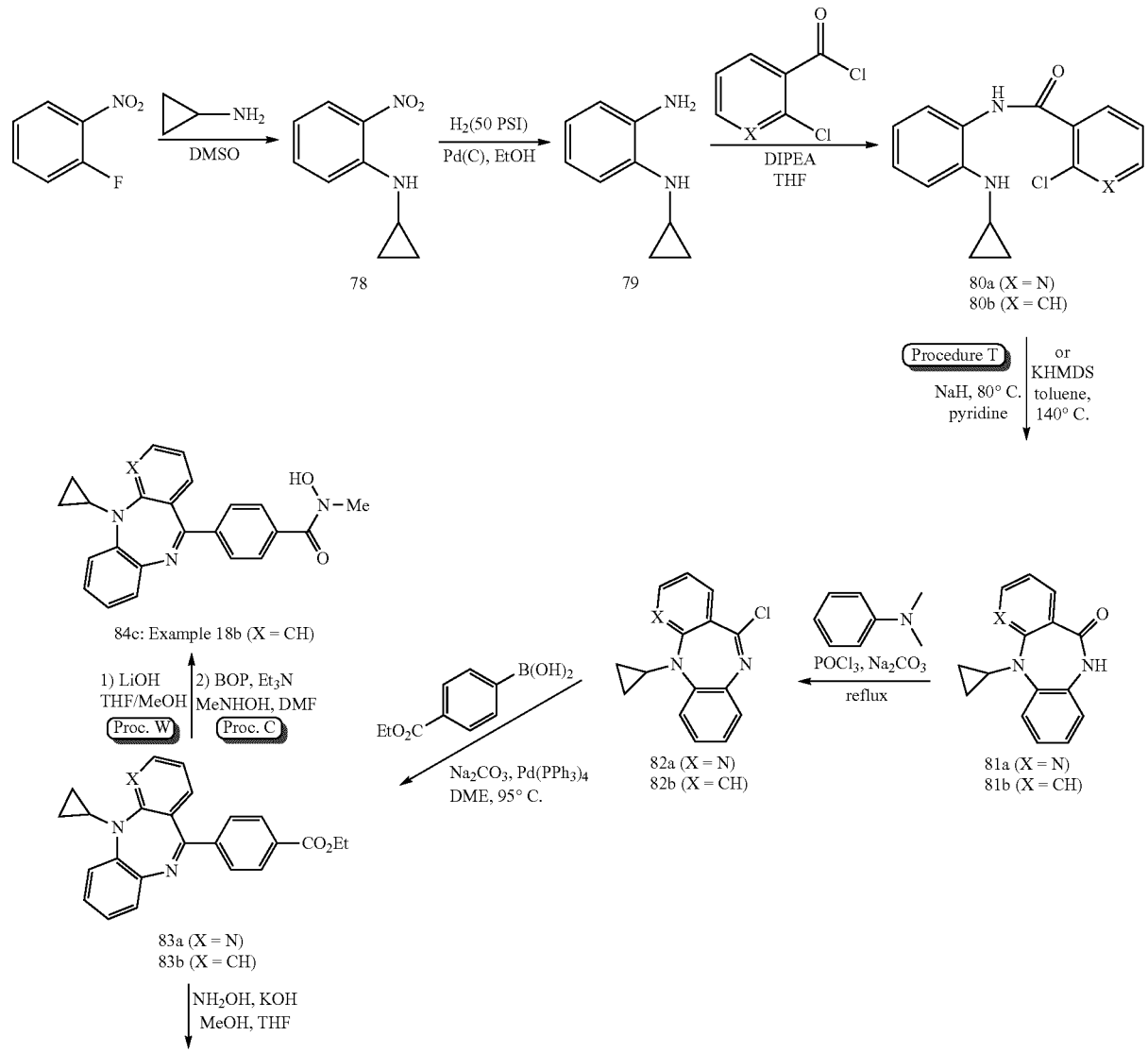

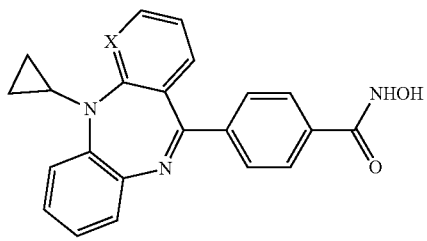

84a: Example 17 (X = N)
84b: Example 18a (X = CH)

Example 17

(Z)-4-(11-cyclopropyl-11H-benzo[b]pyrido[2,3-e][1,4]diazepin-5-yl)-N-hydroxybenzamide (84a)

Example 18b (Z)-4-(5-cyclopropyl-5H-dibenzo[b,e][1,4]diazepin-11-yl)-N-hydroxy-N-methylbenzamide (84c)

Step 1: N-cyclopropyl-2-nitroaniline (78)

Using Procedure I (Table 1) with 1-fluoro-2-nitrobenzene the title compound 78 (18 g, 100%) was obtained as an orange oil.

Step 2: N1-cyclopropylbenzene-1,2-diamine (79)

Using Procedure N (Table 1) with compound 78 the title compound 79 (1.9 g, 76%) was obtained as a dark brown oil.

Step 3: 2-chloro-N-(2-(cyclopropylamino)phenyl)nicotinamide (80a)

Using Procedure G (Table 1) with compound 79 the title compound 80a (1.7 g, 55%) was obtained as a white solid. LRMS (ESI): (calc) 287.08. (found) 288.1 (MH)+.

Step 4: 11-cyclopropyl-6,11-dihydro-5H-benzo[b]pyrido[2,3-e][1,4]diazepin-5-one (81a)

To a solution of title compound 80a (1.9 g, 6.6 mmol) in pyridine (60 mL) was added washed sodium hydride (0.8 g, 19.8 mmol, 60% in oil). Bubbling occurred and the clear solution turn yellow. The mixture was heated to 80° C. for 1 h and overnight at room temperature. It was then heated to 120° C. for 1 h (the mixture turned black). The mixture was cooled down to room temperature and 1N HCl (20 mL) was added slowly. This mixture was extracted with DCM (2×). The combined organic extracts were dried over sodium sulfate, filtered and concentrated. The crude was purified by flash chromatography (SiO2, 0% to 50% ethyl acetate in hexanes over 20 min then 50% for 10 min) to afford the title compound 81a (1.12 g, 68%) as a beige solid.

Step 5: (E)-5-chloro-11-cyclopropyl-11H-benzo[b]pyrido[2,3-e][1,4]diazepine (82a)

Using Procedure A (Table 1) with compound 81a the title compound 82a (0.25 g, 93%) was obtained. LRMS (ESI): (calc) 269.07. (found) 270.2 (MH)+.

Step 6: (Z)-ethyl 4-(11-cyclopropyl-11H-benzo[b]pyrido[2,3-e][1,4]diazepin-5-yl)benzoate (83a)

Using Procedure B (Table 1) with compound 82a the title compound 83a (164 mg, 62%) was obtained as a yellow solid. LRMS (ESI): (calc) 383.16. (found) 384.4 (MH)+.

Step 7: (Z)-4-(11-cyclopropyl-11H-benzo[b]pyrido[2,3-e][1,4]diazepin-5-yl)-N-hydroxybenzamide (84a)

Using Procedure C (Table 1) with compound 83a the title compound 84a (31 mg, 13%) was obtained as a yellow solid. $^1$H NMR (400 MHz, DMSO-$d_6$) δ (ppm): 11.33 (s, 1H), 9.16 (s, 1H), 8.50-8.46 (m, 1H), 7.83 (d, J=8.2 Hz, 2H), 7.68 (d, J=8.2 Hz, 2H), 7.45-7.41 (m, 1H), 7.36 (d, J=8.0 Hz, 1H), 7.27-7.21 (m, 2H), 7.20-7.11 (m, 2H), 3.05-3.48 (m, 1H), 0.95-0.80 (m, 2H), 0.51-0.45 (m, 1H), 0.31-0.23 (m, 1H). LRMS (ESI): (calc) 370.14. (found) 371.2 (MH)+.

Step 8: (Z)-4-(5-cyclopropyl-5H-dibenzo[b,e][1,4]diazepin-11-yl)-N-hydroxy-N-methylbenzamide (84c)

To a solution of title compound 83b (0.5 g, 1.307 mmol) in THF (5 mL) and MeOH (5 mL) was added an aqueous solution of lithium hydroxide (2.5 mL, 5 mmol). The mixture was stirred for 2 h at room temperature then diluted with DCM and 1N HCl and extracted with DCM. The combined organic layers were dried over $Na_2SO_4$, filtered and solvent evaporated to afford the acid intermediate. LRMS (ESI): (calc) 354.14. (found) 355.4 (MH)+.

To a solution of the acid intermediate (0.3 g, 0.846 mmol) in DMF (5 mL) was added BOP (0.412 g, 0.931 mmol) and triethylamine (0.354 mL, 2.54 mmol). The mixture was stirred for 15 min then N-methylhydroxylamine hydrochloride (0.106 g, 1.270 mmol) was added. The mixture was stirred for 1 h, poured into water and the resulting solid was filtered then purified by Phenomenex column (50 to 100% MeOH in $H_2O$) to afford title compound 84c (92 mg, 28%). $^1$H NMR (400 MHz, DMSO-$d_6$) δ (ppm): 10.10 (s, 1H), 7.66 (d, J=8.4 Hz, 2H), 7.63 (d, J=8.4 Hz, 2H), 7.52 (t, J=7.2 Hz, 1H), 7.45 (d, J=8.0 Hz, 1H), 7.32 (d, J=7.8 Hz, 1H), 7.23 to 7.15 (m, 2H), 7.14 to 7.06 (m, 2H), 6.94 (d, J=7.8 Hz, 1H), 3.44 to 3.35 (m, 1H), 0.9 to 0.6 (m, 2H), 0.50 to 0.40 (m, 1H), 0.35 to 0.27 (m, 1H). LRMS (ESI): (calc) 354.14. (found) 355.4 (MH)+.

Example 18a (Z)-4-(5-cyclopropyl-5H-dibenzo[b,e][1,4]diazepin-11-yl)-N-hydroxybenzamide (84b)

Following the same procedures as for compound 84a (example 17) except for step 4.

Step 4: 5-cyclopropyl-5H-dibenzo[b,e][1,4]diazepin-11(10H)-one (81b)

A solution of compound 83b (0.84 g, 3.11 mmol) and KHMDS (13.67 g, 6.84 mmol, 0.5M in toluene) was heated to 140° C. overnight. The mixture was cooled to room temperature and water was added. This mixture was extracted with a mixture of ethyl acetate and THF twice. The organics were washed with brine and dried over $Na_2SO_4$, filtered and evaporated. The residue was triturated with DCM then purified by flash chromatography ($SiO_2$, 0% to 50% ethyl acetate in hexanes over 30 min) to afford title compound 81b (0.45 g, 57%) as a beige solid. LRMS (ESI): (calc) 369.15. (found) 370.5 (MH)+.

80%) was obtained as a light brown solid. LRMS (ESI): (calc) 244.04. (found) 245.2 (MH)+.

Step 2: 5H-dibenzo[b,e][1,4]diazepin-11(10H)-one (86)

A suspension of title compound 85 (1.75 g, 7.15 mmol) in a solution of sodium formate (2.43 g, 35.8 mmol) in water (32 mL) was stirred at 50° C. for 8 hours and then at room temperature. The reaction mixture was filtered and the resulting solid was dissolved in THF (20 mL), diluted with ethyl acetate (200 mL) then filtered through Celite® and concentrated. The crude residue was triturated in 30% ethyl acetate in hexanes to afford title compound 86 (1.17 g, 78%) as a yellow solid. LRMS (ESI): (calc) 210.08. (found) 211.2 (MH)+. $^1$H NMR (400 MHz, DMSO-$d_6$) δ (ppm): 9.84 (s, 1H), 7.84 (s, 1H), 7.67 (dd, J=7.9, 1.7 Hz, 1H), 7.33 (ddd, J=8.1, 7.2, 1.8 Hz, 1H), 7.00-6.86 (m, 6H).

Scheme 18

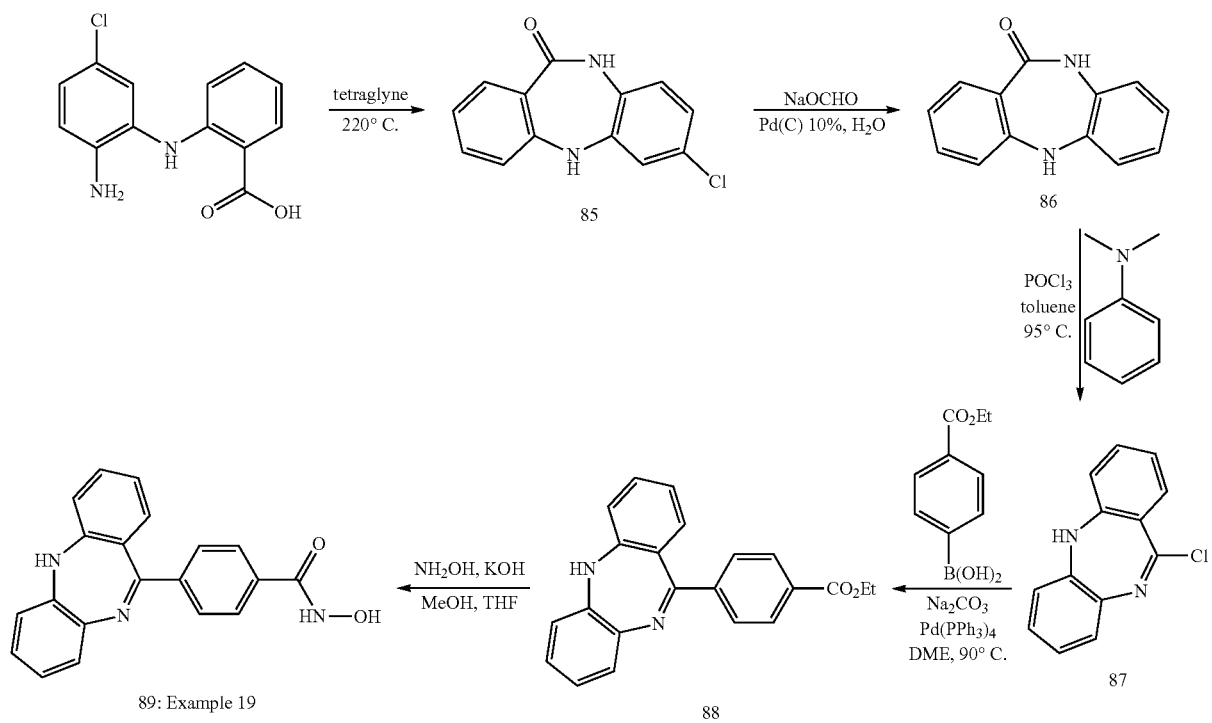

Example 19

(Z)-4-(5H-dibenzo[b, e][1,4]diazepin-11-yl)-N-hydroxybenzamide (89)

Step 1: 7-chloro-5H-dibenzo[b,e][1,4]diazepin-11(10H)-one (85)

Using Procedure F (Table 1) with 2-(2-amino-5-chlorophenylamino)benzoic acid the title compound 85 (7.45 g,

Step 3: (E)-11-chloro-5H-dibenzo[b,e][1,4]diazepine (87)

Using Procedure A (Table 1) with 86 the title compound 87 (1.125 g, 90%) was obtained as an orange oil. LRMS (ESI): (calc) 228.05. (found) 229.2 (MH)+.

Step 4: (Z)-ethyl 4-(5H-dibenzo[b][1,4]diazepin-11-yl)benzoate (88)

Using Procedure B (Table 1) with 87 the title compound 88 (0.954 g, 57%) was obtained as an orange solid. LRMS (ESI): (calc) 342.14. (found) 343.5 (MH)+.

Step 5: (Z)-4-(5H-dibenzo[b,e][1,4]diazepin-11-yl)-N-hydroxybenzamide (89)
Using Procedure C (Table 1) with 88 the title compound 89 (14 mg, 3%) was obtained as an orange solid. $^1$H NMR (400 MHz, DMSO-d$_6$) δ (ppm): 11.33 (s, 1H), 9.13 (s, 1H), 7.81 (d, J=8.4 Hz, 2H), 7.65 (d, J=8.4 Hz, 2H), 7.39-7.34 (m, 2H), 7.16 (dd, J=7.6, 1.6 Hz, 1H), 7.09-6.91 (m, 5H), 7.85 (dd, J=7.6, 1.2 Hz, 1H). LRMS (ESI): (calc) 329.12. (found) 330.4 (MH)+.
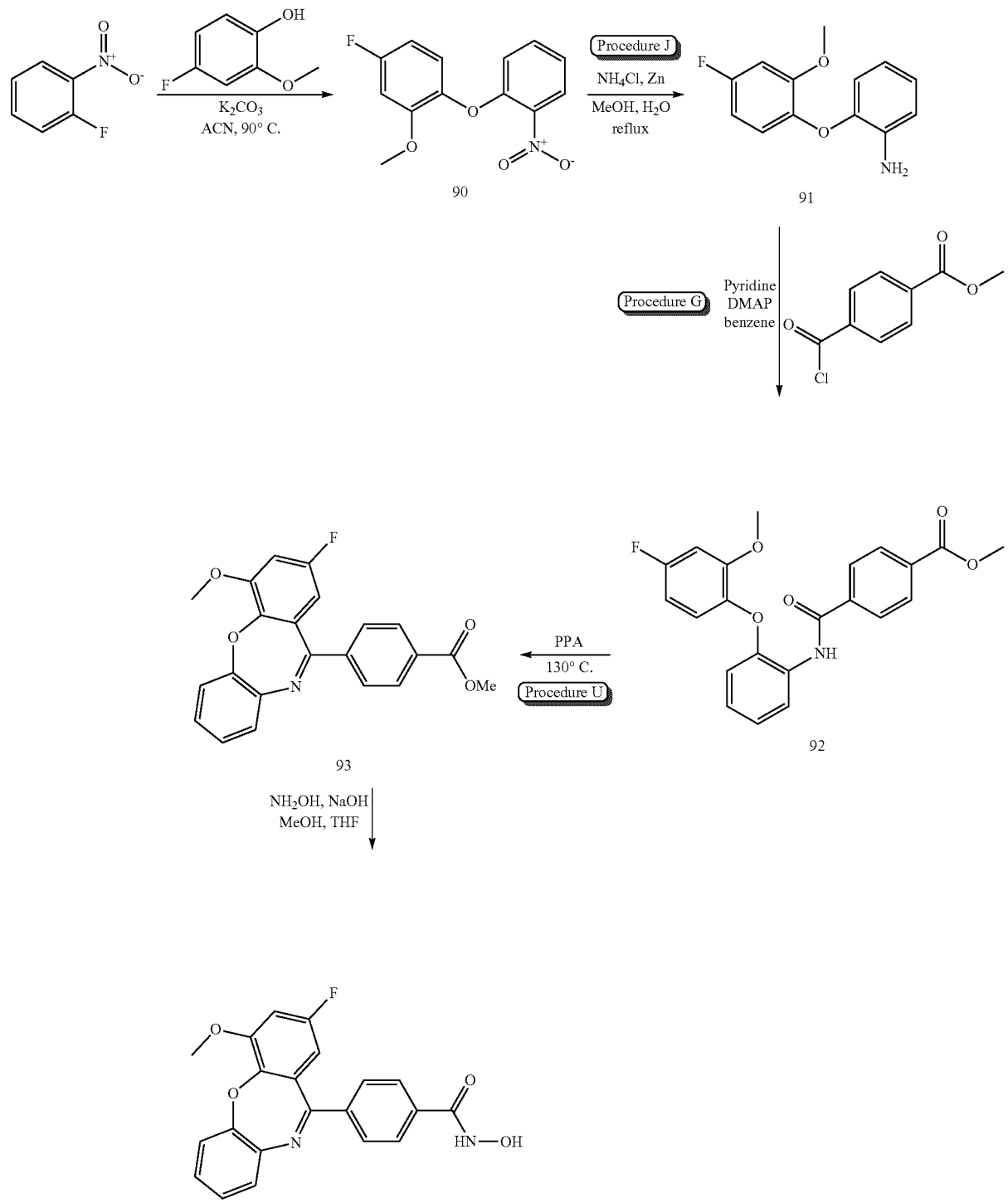
Scheme 19

Example 20

(Z)-4-(2-fluoro-4-methoxydibenzo[b,f][1,4]oxazepin-11-yl)-N-hydroxybenzamide (94)

Step 1:
4-fluoro-2-methoxy-1-(2-nitrophenoxy)benzene (90)

Using Procedure I (Table 1) with 1-fluoro-2-nitrobenzene and 4-fluoro-2-methoxyphenol the title compound 90 (9.32 g, 100%) was obtained as yellow oil. LRMS (ESI): (calc) 263.06. (found) 264.3 (MH)+.

Step 2: 2-(4-fluoro-2-methoxyphenoxy)aniline (91)

To a solution of title compound 90 (9.32 g, 35.4 mmol) in MeOH (30 mL) and water (5 mL) was added ammonium chloride (3.79 g, 70.8 mmol) and zinc chloride (20.83 g, 319 mmol) and the reaction mixture was heated to reflux for 2 hours. The mixture was cooled to room temperature and filtered and the solvent removed. The residue was diluted with ethyl acetate and water and the organic phase was washed well with water, dried over $Na_2SO_4$, filtered and concentrated to afford title compound 91 (8.3 g, 100%). LRMS (ESI): (calc) 233.09. (found) 234.1 (MH)+.

Step 3: methyl 4-(2-(4-fluoro-2-methoxyphenoxy)phenylcarbamoyl)benzoate (92)

To a slurry of title compound 91 (4 g, 17.15 mmol) and methyl 4-(chlorocarbonyl)benzoate (3.58 g, 18.01 mmol) in benzene (60 mL) at 0° C. was added pyridine (4.85 mL, 60.0 mmol) drop wise followed by a single crystal of DMAP. The temperature was raised to room temperature and the reaction mixture was left to stir for 1 h. The reaction mixture was filtered and the filtrate was diluted with 5% aq HCl and ethyl acetate. The organic layer was washed with 5% aq HCl, water and brine then left in the fridge over the weekend. The precipitated solid was filtered, washed with water and hexanes to afford title compound 92 (6.38 g, 94%) as an off-white solid. LRMS (ESI): (calc) 395.12. (found) 396.4 (MH)+.

Step 4: (Z)-methyl 4-(2-fluoro-4-methoxydibenzo[b,f][1,4]oxazepin-11-yl)benzoate (93)

A stirring mixture of title compound 92 (2 g, 5.06 mmol) in polyphosphoric acid (4.76 ml, 41.7 mmol) was heated at 130° C. for 3 h. The reaction mixture was cooled, diluted with dichloromethane and water and stirred overnight. The layers were separated and the aqueous layer was extracted with dichloromethane. The combined organic layers were washed with brine, dried over $MgSO_4$, filtered and solvent evaporated. The crude residue was purified via ISCO (0-25% Hex/EtOAc; 40 g silica gel column) to afford title compound 93 (125 mg, 6.5%) as a light yellow solid. LRMS (ESI): (calc) 377.11. (found) 378.4 (MH)+.

Step 5: (Z)-4-(2-fluoro-4-methoxydibenzo[b,f][1,4]oxazepin-11-yl)-N-hydroxybenzamide (94)

Using Procedure C (Table 1) with compound 93 the title compound 94 (102 mg, 81%) was obtained as yellow solid. $^1$H NMR (400 MHz, $CD_3OD$) δ (ppm): 7.88 (s, 4H), 7.41 (m, 1H), 7.26 (m, 3H), 7.11 (dd, J=2.8 Hz, 10.4 Hz, 1H), 6.38 (dd, J=2.8 Hz, 8.4 Hz, 1H), 3.97 (s, 3H). LRMS (ESI): (calc) 378.10. (found) 377.3 (MH)−.

Scheme 20

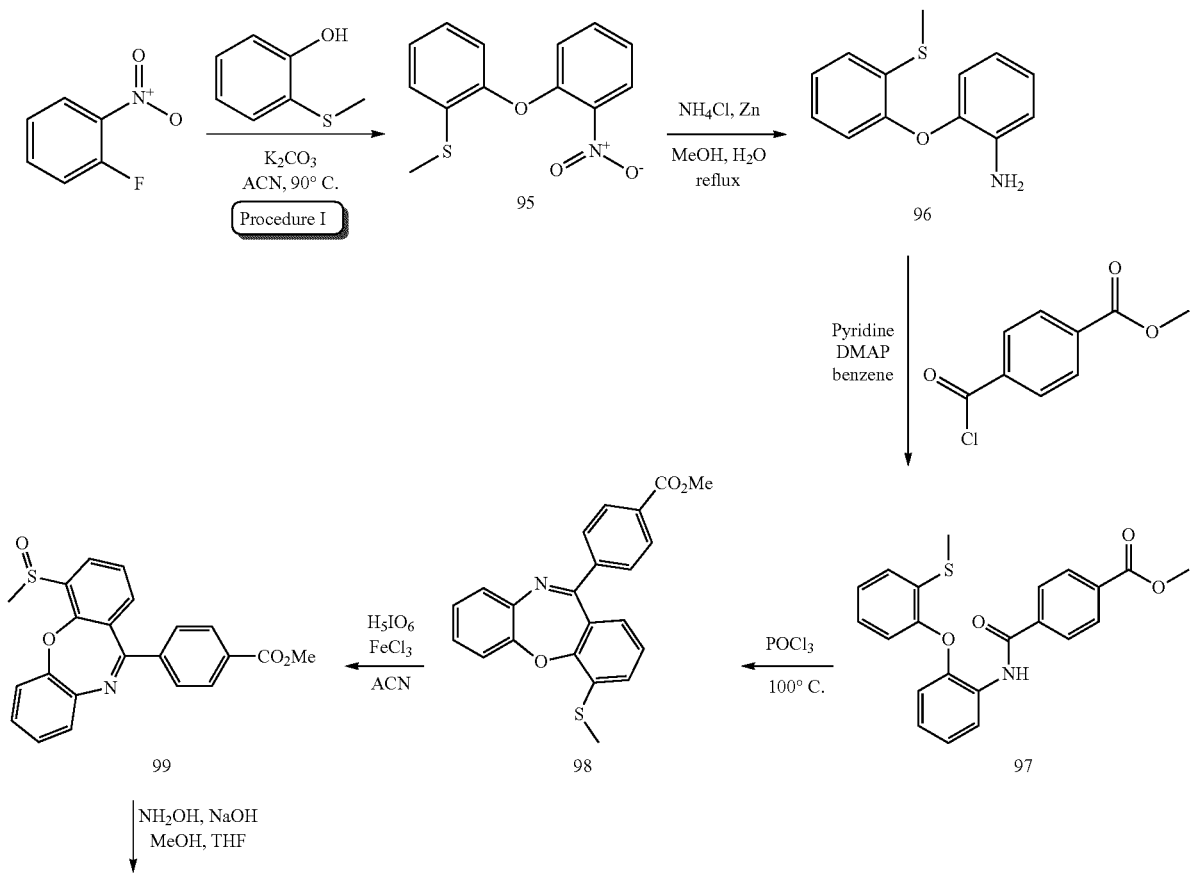

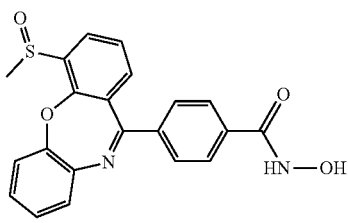

100: Example 21

Example 21

(Z)—N-hydroxy-4-(4-(methylsulfinyl)dibenzo[b,f][1,4]oxazepin-11-yl)benzamide (100)

Step 1: methyl(2-(2-nitrophenoxy)phenyl)sulfane (95)

Using Procedure I (Table 1) with 1-fluoro-2-nitrobenzene and 2-(methylthio)phenol the title compound 95 (9.25 g, 100%) was obtained as yellow oil.

Step 2: 2-(2-(methylthio)phenoxy)aniline (96)

Using Procedure J (Table 1) with compound 95 the title compound 96 (5.82 g, 71%) was obtained as yellow oil. LRMS (ESI): (calc) 231.07. (found) 232.2 (MH)+.

Step 3: methyl 4-(2-(2-(methylthio)phenoxy)phenylcarbamoyl)benzoate (97)

Using Procedure G (Table 1) with compound 96 the title compound 97 (6.77 g, 100%) was obtained as white solid. LRMS (ESI): (calc) 393.10. (found) 394.5 (MH)+.

Step 4: (Z)-methyl 4-(4-(methylthio)dibenzo[b,f][1,4]oxazepin-11-yl)benzoate (98)

Using Procedure U (Table 1) with compound 97 the title compound 98 (341 mg, 36%) was obtained as yellow solid. LRMS (ESI): (calc) 375.09. (found) 376.4 (MH)+.

Step 5: (Z)-methyl 4-(4-(methylsulfinyl)dibenzo[b,f][1,4]oxazepin-11-yl)benzoate (99)

To a stirring suspension of compound 98 (100 mg, 0.266 mmol) and iron (III) chloride (1.296 mg, 7.99 µmol) in acetonitrile (2 mL) after 5 minutes was added periodic acid (66.8 mg, 0.293 mmol) in one portion. The reaction mixture was left to stir at room temperature overnight then quenched with saturated sodium thiosulfate solution and diluted with ethyl acetate. The organic layer was washed with water, brine, dried over MgSO$_4$, filtered and solvent evaporated. Purification via ISCO (0-40% EtOAc/Hexanes; 40 g silica gel column) afforded title compound 99 (60 mg, 57%) as a yellow solid. LRMS (ESI): (calc) 391.09. (found) 392.4 (MH)+.

Step 6: (Z)—N-hydroxy-4-(4-(methylsulfinyl)dibenzo[b,f][1,4]oxazepin-11-yl)benzamide (100)

Using Procedure C (Table 1) with compound 99 the title compound 100 (53 mg, 88%) was obtained as yellow solid. $^1$H NMR (400 MHz, CD$_3$OD) δ (ppm): 8.00 (d, J=7.6 Hz, 1H), 7.87 (s, 4H), 7.52 (t, J=8 Hz, 1H), 7.46 (m, 1H), 7.37 (d, J=7.6 Hz, 1H), 7.31 (m, 3H), 3.06 (s, 3H). LRMS (ESI): (calc) 392.08. (found) 391.4 (MH)−.

Scheme 21

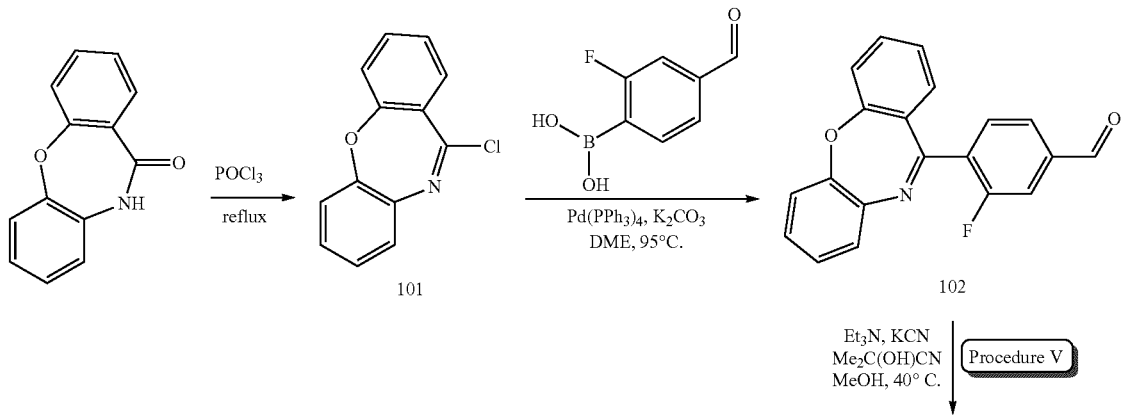

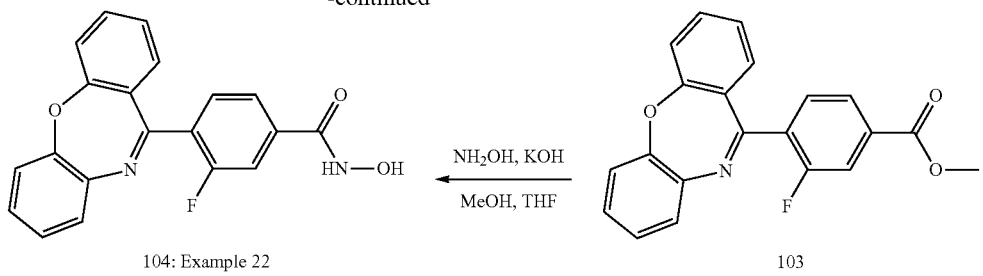

Example 22

(E)-4-(dibenzo[b,f][1,4]oxazepin-11-yl)-3-fluoro-N-hydroxybenzamide (104)

Step 1: (E)-11-chlorodibenzo[b,f][1,4]oxazepine (101)

Using Procedure A (Table 1) with dibenzo[b,f][1,4]oxazepin-11(10H)-one the title compound 101 (2.20 g, 100%) was obtained.

Step 2: (E)-4-(dibenzo[b,f][1,4]oxazepin-11-yl)-3-fluorobenzaldehyde (102)

Using Procedure B (Table 1) with compound 101 the title compound 102 (1.21 g, 87%) was obtained as a yellow foam. LRMS (ESI): (calc) 317.09. (found) 318.4 (MH)+.

Step 3: (E)-methyl 4-(dibenzo[b,f][1,4]oxazepin-11-yl)-3-fluorobenzoate (103)

A mixture of compound 102 (0.59 g, 1.90 mmol), triethylamine (1.6 mL, 11.48 mmol), potassium cyanide (0.061 g, 0.93) and 2-hydroxy-2-methylpropanenitrile (1 mL, 10.93) in methanol (15 mL) was stirred at 40° C. for 24 h then solvent evaporated. The resulting crude residue was purified on ISCO (0-100% EtOAc in Hexanes) to afford title compound 103 (0.364 g, 56%) as a yellow solid. LRMS (ESI): (calc) 347.10. (found) 348.4 (MH)+.

Step 4: (E)-4-(dibenzo[b,f][1,4]oxazepin-11-yl)-3-fluoro-N-hydroxybenzamide (104)

Using Procedure C (Table 1) with compound 103 the title compound 104 (0.357 g, 55%) was obtained as a white solid. $^1$H NMR (400 MHz, DMSO-$d_6$) δ (ppm): 11.47 (s, 1H), 9.28 (s, 1H), 7.93 (t, J=7.6 Hz, 1H), 7.79 (dd, J=8.4, 1.6, 1H), 7.66-7.60 (m, 2H), 7.44-7.39 (m, 2H), 7.35-7.22 (m, 4H), 7.08 (d, J=7.6 Hz, 1H). LRMS (ESI): (calc) 348.09. (found) 349.3 (MH)+.

Scheme 22

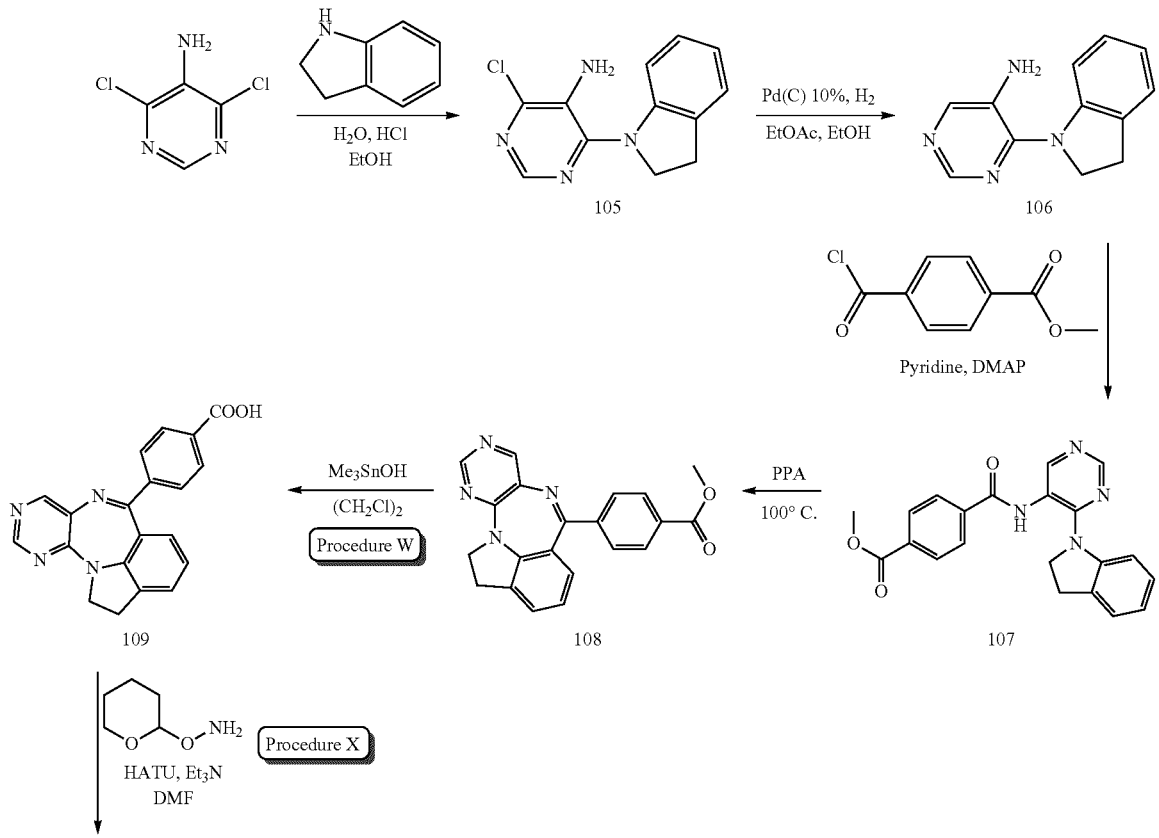

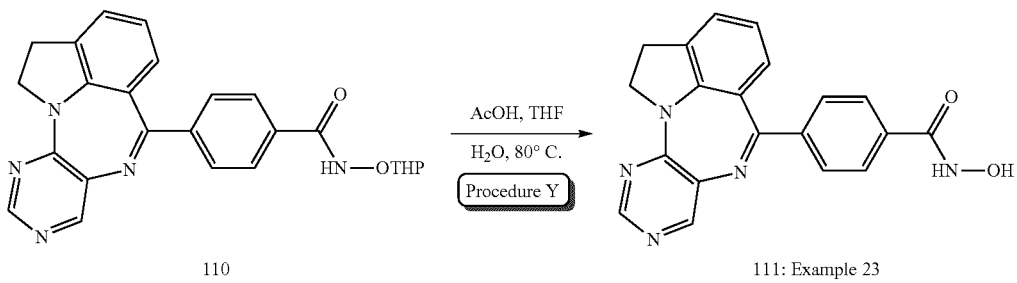

110 → 111: Example 23

Example 23

Compound (111)

Step 1: 4-chloro-6-(indolin-1-yl)pyrimidin-5-amine (105)

To a stirring slurry of 5-amino-4,6-dichloropyrimidine (3 g, 18.29 mmol) and indoline (2.057 mL, 18.29 mmol) in ethanol (7 mL) and water (43 mL) was added concentrated aqueous HCl (600 µL) and the mixture was refluxed for 3 h and left to stir at room temperature overnight. The reaction mixture was extracted with ethyl acetate, washed with water, brine, dried over MgSO4 and solvent evaporated. The resulting residue was triturated in 25% ethyl acetate in hexanes for 1 h then filtered to afford title compound 105 (1.55 g, 34%) as a tan solid. LRMS (ESI): (calc) 246.07. (found) 247.2 (MH)+.

Step 2: 4-(indolin-1-yl)pyrimidin-5-amine (106)

Using Procedure J (Table 1) with compound 105 the title compound 106 (1.33 g, 100%) was obtained. LRMS (ESI): (calc) 212.11. (found) 213.1 (MH)+.

Step 3: methyl 4-(4-(indolin-1-yl)pyrimidin-5-ylcarbamoyl)benzoate (107)

Using Procedure G (Table 1) with compound 106 the title compound 107 (1.40 g, 60%) was obtained as a light brown solid. LRMS (ESI): (calc) 374.14. (found) 375.4 (MH)+.

Step 4: Compound (108)

Using Procedure U (Table 1) with compound 107 the title compound 108 (282 mg, 47%) was obtained as a red solid. LRMS (ESI): (calc) 356.13. (found) 357.4 (MH)+.

Step 5: Compound (109)

A stirring suspension of compound 108 (282 mg, 0.791 mmol) and trimethyltin hydroxide (858 mg, 4.75 mmol) in dichloroethane (5 mL) was heated at 90° C. overnight. The mixture was cooled, diluted with ethyl acetate and washed with 5% aq HCl. The product precipitated out of the aqueous layer therefore it was filtered and dried to afford title compound 109 (155 mg, 57%) as a dark red powder. LRMS (ESI): (calc) 342.11. (found) 343.4 (MH)+.

Step 6: Compound (110)

To a stirring solution of compound 109 (155 mg, 0.453 mmol) in dry DMF (15 mL) was added HATU (207 mg, 0.543 mmol) and the suspension was stirred for 10 min at room temperature. O-(tetrahydro-2H-pyran-2-yl)hydroxylamine (106 mg, 0.906 mmol) was added and the resulting clear red solution was stirred for 20 min before triethylamine (0.150 mL, 1.076 mmol) was added. The mixture was stirred for 16 h at room temperature, quenched with water and extracted with dichloromethane. The combined organic layers were washed with water, brine, dried over MgSO$_4$, filtered and solvent evaporated. The crude residue was purified via ISCO (50-100% EtOAc/Hexanes) to afford title compound 110 (87 mg, 43%) as a dark red solid. LRMS (ESI): (calc) 441.18. (found) 442.5 (MH)+.

Step 7: Compound (111)

To a stirring solution of compound 110 (87 mg, 0.197 mmol) in THF (1.0 mL) and water (0.5 mL) was added AcOH (1 mL). The reaction was then heated at 80° C. overnight and then cooled to room temperature. The product precipitated out and was filtered off to afford title compound III (16 mg, 23%) as a red powder. $^1$H NMR (400 MHz, DMSO-d$_6$) δ (ppm): 11.3 (bs, 1H), 9.12 (bs, 1H), 8.29 (s, 1H), 8.02 (s, 1H), 7.78 (d, J=8.4 Hz, 2H), 7.51 (d, J=8.4 Hz, 2H), 7.25 (d, J=7.2 Hz, 1H), 6.78 (t, J=7.6 Hz, 1H), 6.52 (d, J=7.6 Hz, 1H), 4.00 (t, J=8.4 Hz, 2H), 2.94 (t, J=8.4 Hz, 2H). LRMS (ESI): (calc) 357.12 (found) 356.4 (MH)+.

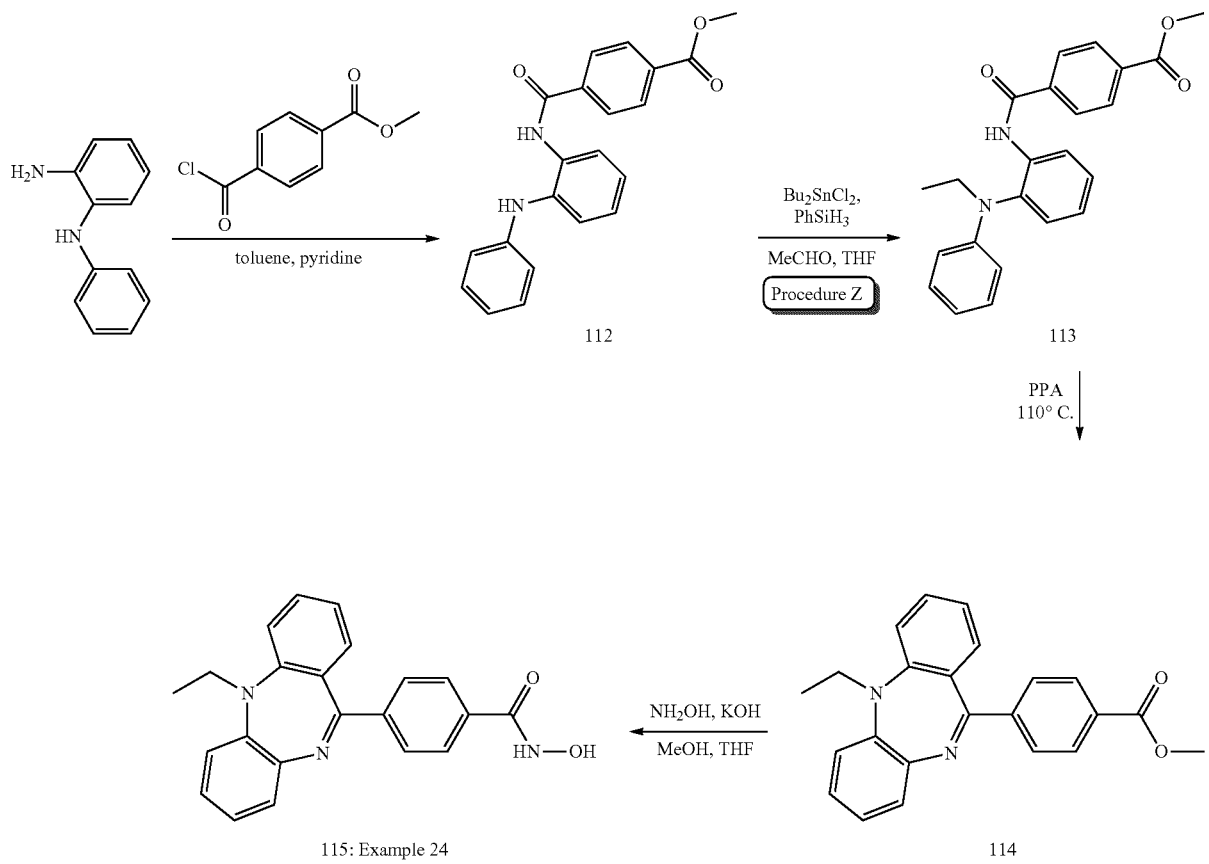

Scheme 23

Example 24

(Z)-4-(5-ethyl-5H-dibenzo[b,e][1,4]diazepin-11-yl)-N-hydroxybenzamide (115)

Step 1: methyl 4-(2-(phenylamino)phenylcarbamoyl)benzoate (112)

Using Procedure G (Table 1) with N1-phenylbenzene-1,2-diamine and methyl 4-(chlorocarbonyl)benzoate the title compound 112 (3.46 g, 92%) was obtained as a red solid. LRMS (ESI): (calc) 346.13. (found) 347.4 (MH)+.

Step 2: methyl 4-(2-(ethyl(phenyl)amino)phenylcarbamoyl)benzoate (113)

To a stirring solution of compound 112 (1.00 g, 2.89 mmol) in THF was added dibutyltin dichloride (0.175 g, 0.577 mmol) and acetaldehyde (1.182 g, 26.8 mmol) and the reaction mixture was stirred 15 minutes. Phenylsilane (0.375 g, 3.46 mmol) was added and the reaction mixture was stirred at room temperature 60 h then solvent evaporated. The resulting crude product was purified by Isco (80 g column, 10%-50%) to afford title compound 113 (1.145 g, 100%) as a yellowish oil. LRMS (ESI): (calc) 374.16. (found) 375.4 (MH)+.

Step 3: (Z)-methyl 4-(5-ethyl-5H-dibenzo[b,e][1,4]diazepin-11-yl)benzoate (114)

Using Procedure U (Table 1) with compound 113 the title compound 114 (353 mg, 54%) was obtained as an orange foam. LRMS (ESI): (calc) 356.15. (found) 357.5 (MH)+.

Step 4: (Z)-4-(5-ethyl-5H-dibenzo[b,e][1,4]diazepin-11-yl)-N-hydroxybenzamide (115)

Using Procedure C (Table 1) with compound 114 the title compound 115 (248 mg, 72%) was obtained as a yellow solid. $^1$H NMR (400 MHz, MeOH-$d_4$) δ (ppm): 7.83 (d, J=8.8 Hz, 2H), 7.77 (d, J=8.8 Hz, 2H), 7.49 (ddd, J=8.2, 7.2, 1.6 Hz, 1H), 7.26 (dd, J=1.6 Hz, 1H), 7.23-7.18 (m, 2H), 7.13-7.03 (m, 3H), 7.96 (dd, J=7.6, 1.2, 1H), 3.83-3.68 (m, 2H), 1.24 (t, J=6.8 Hz, 3H). LRMS (ESI): (calc) 357.15. (found) 358.3 (MH)+.

Scheme 24

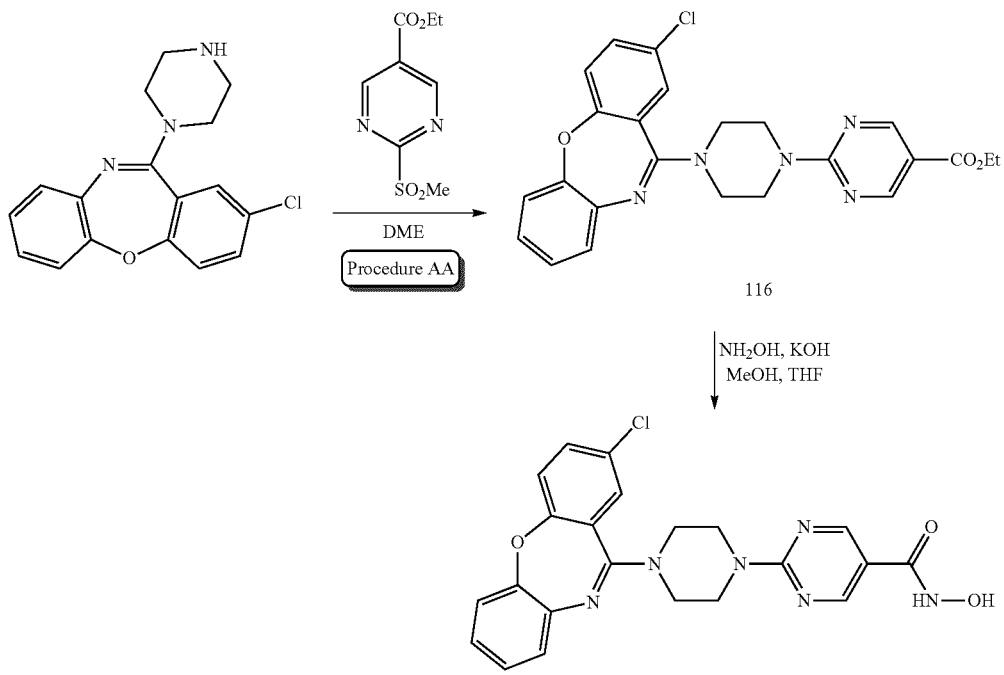

Example 25

(E)-2-(4-(2-chlorodibenzo[b,f][1,4]oxazepin-11-yl) piperazin-1-yl)-N-hydroxypyrimidine-5-carboxamide (117)

Step 1: (E)-ethyl 2-(4-(2-chlorodibenzo[b,f][1,4] oxazepin-11-yl)piperazin-1-yl)pyrimidine-5-carboxylate (116)

A solution of (E)-2-chloro-11-(piperazin-1-yl)dibenzo[b,f][1,4]oxazepine (0.25 g, 0.8 mmol) and ethyl 2-(methylsulfonyl)pyrimidine-5-carboxylate (0.13 g, 0.57 mmol) in DME was stirred at room temperature for 1 h. The reaction mixture was diluted with water and extracted with ethyl acetate. The organic extract was washed with saturated aqueous solution of bicarbonate, water, acetic acid and sodium acetate (pH=4), dried over sodium sulfate and solvent evaporated. The resulting crude residue was purified by flash chromatography (0% to 30% ethyl acetate in hexane) to afford title compound 116 (0.265 g, quant.).

Step 2: (E)-2-(4-(2-chlorodibenzo[b,f][1,4]oxazepin-11-yl)piperazin-1-yl)-N-hydroxypyrimidine-5-carboxamide (117)

Using Procedure C (Table 1) with compound 116 the title compound 117 (0.2 g, 78%) was obtained as a brown solid. $^1$H NMR (400 MHz, DMSO-d$_6$) δ (ppm): 8.69 (s, 2H), 7.62 (dd, J=8.6, 2.4 Hz, 1H), 7.52 (d, J=2.3 Hz, 1H), 7.41 (d, J=8.8 Hz, 1H), 7.18 (d, J=7.8 Hz, 1H), 7.12-7.04 (m, 2H), 7.03-6.96 (m, 1H), 4.12-3.76 (m, 4H), 3.68-3.44 (m, 4H). LRMS (ESI): (calc) 450.12. (found) 451.1 (MH)+.

Scheme 25

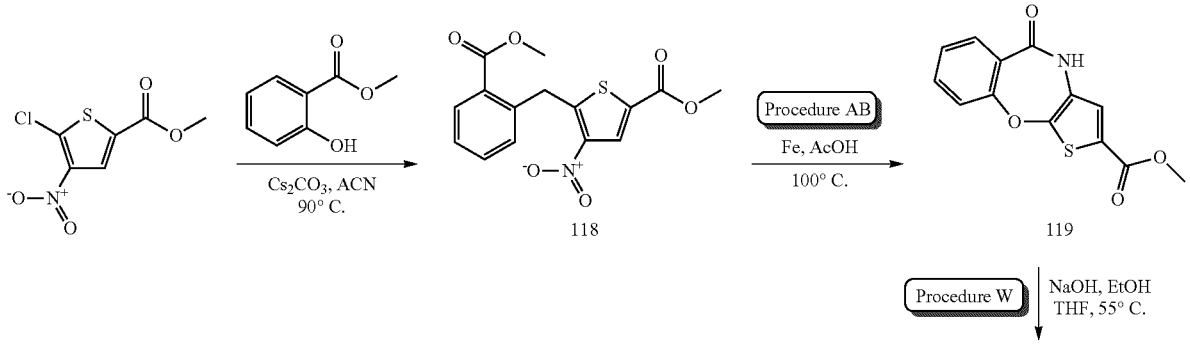

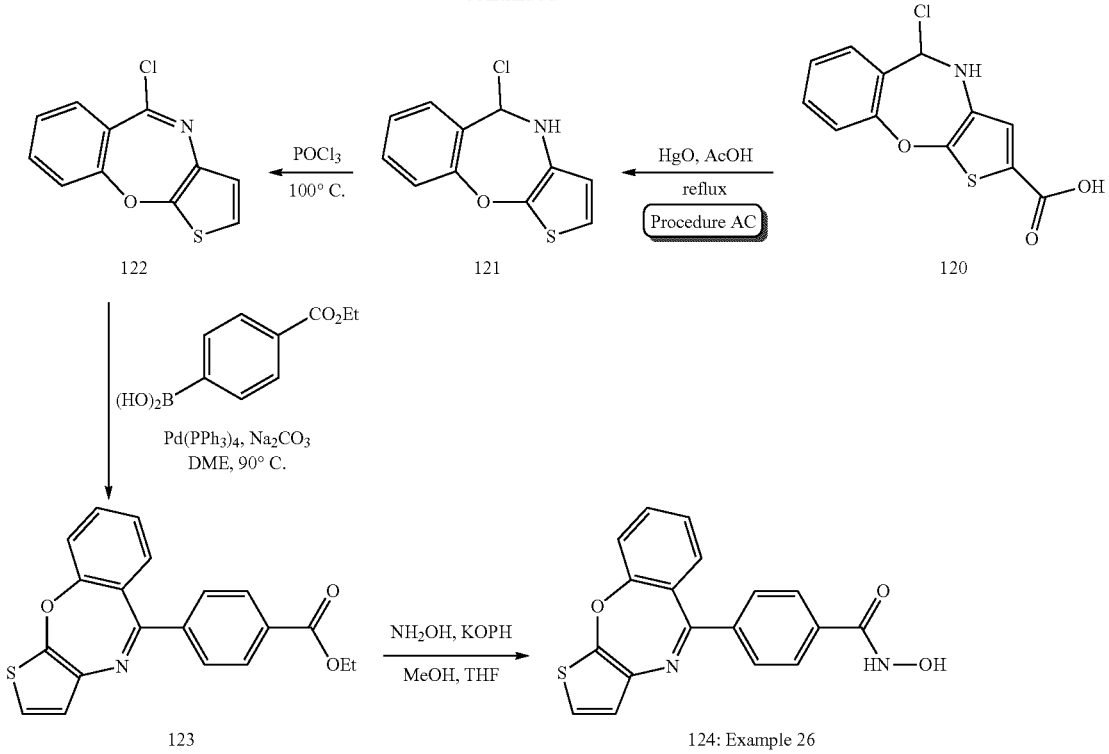

Example 26

(Z)-4-(benzo[f]thieno[2,3-b][1,4]oxazepin-5-yl)-N-hydroxybenzamide (124)

Step 1: methyl 5-(2-(methoxycarbonyl)phenoxy)-4-nitrothiophene-2-carboxylate (118)

Using Procedure I (Table 1) with methyl 5-chloro-4-nitrothiophene-2-carboxylate and methyl 2-hydroxybenzoate the title compound 118 (1.918 g, 93%) was obtained as an orange oil. LRMS (ESI): (calc) 337.03. (found) 338.0 (MH)+.

Step 2: methyl 5-oxo-4,5-dihydrobenzo[f]thieno[2,3-b][1,4]oxazepine-2-carboxylate (119)

To a stirring solution of compound 118 (1.918 g, 5.69 mmol) in acetic acid was added iron (2.223 g, 39.8 mmol) and the reaction mixture was stirred at 85° C. for 1 h then at 100° C. for 1 h. The mixture was cooled to room temperature, poured into 150 mL of ice-cold water and the resulting white precipitate was filtered to afford title compound 119 (1.261 g, 81%) as a beige solid. LRMS (ESI): (calc) 275.03. (found) 276.2 (MH)+.

Step 3: 5-oxo-4,5-dihydrobenzo[f]thieno[2,3-b][1,4]oxazepine-2-carboxylic acid (120)

To a stirring solution of compound 119 (0.856 g, 3.11 mmol) in ethanol (16 mL) and THF (8 mL) was added an aqueous solution of sodium hydroxide (5 mL, 31.3 mmol) and the resulting mixture was stirred at 55° C. for 2 h. The reaction mixture was solvent evaporated to one third volume, acidified with 3N HCl to pH 2 and the resulting white precipitate was filtered to afford 120 (0.801 g, 99%) as a beige solid. LRMS (ESI): (calc) 261.01. (found) 262.1 (MH)+.

Step 4: benzo[f]thieno[2,3-b][1,4]oxazepin-5(4H)-one (121)

To a stirring solution of compound 120 (0.801 g, 3.07 mmol) in acetic acid (30 mL) was added mercuric oxide (red) (0.664 g, 3.07 mmol) and the reaction mixture was stirred at reflux for 8 hours. The mixture was then cooled to room temperature and poured into ice-cold water (75 mL). The resulting solid was filtered and triturated in ethanol to afford title compound 121 (0.527 g, 79%) as a beige solid. LRMS (ESI): (calc) 217.02. (found) 217.9 (MH)+. $^1$H NMR (DMSO-$d_6$) δ (ppm): 10.45 (s, 1H), 7.80 (d, J=7.6 Hz, 1H), 7.59 (t, J=7.2 Hz, 1H), 7.33 (t, J=7.4 Hz, 1H), 7.25 (d, J=8.0 Hz, 1H), 6.99 (d, J=6.1 Hz, 1H), 6.63 (d, J=6.1 Hz, 1H).

Step 5: (E)-5-chlorobenzo[f]thieno[2,3-b][1,4]oxazepine (122)

Using Procedure A (Table 1) with compound 121 the title compound 122 was obtained as a brown oil and used crude for next step.

Step 6: (Z)-ethyl 4-(benzo[f]thieno[2,3-b][1,4]oxazepin-5-yl)benzoate (123)

Using Procedure B (Table 1) with compound 122 the title compound 123 (0.461 g, 55%) was obtained as a yellow foam. LRMS (ESI): (calc) 349.08. (found) 350.2 (MH)+. $^1$H NMR (DMSO-$d_6$) δ (ppm): 8.06 (d, J=8.2 Hz, 2H), 7.83 (d, J=8.4 Hz, 2H), 7.70-7.66 (m, 1H), 7.35 (dd, J=8.1, 1.1 Hz, 1H), 7.31 (dd, J=7.5, 1.1 Hz, 1H), 7.14 (dd, J=7.7, 1.7 Hz, 1H), 7.13 (d, J=6.1 Hz, 1H), 6.97 (dd, J=6.1, 0.4 Hz, 1H), 4.35 (q, J=7.1 Hz, 2H), 1.34 (t, J=7.1 Hz, 3H).

Step 7: (Z)-4-(benzo[f]thieno[2,3-b][1,4]oxazepin-5-yl)-N-hydroxybenzamide (124)
Using Procedure C (Table 1) with compound 123 the title compound 124 (0.366 g, 83%) was obtained as a yellow solid.
$^1$H NMR (DMSO-$d_6$) δ (ppm): 11.36 (s, 1H), 9.16 (s, 1H), 7.86 (d, J=8.4 Hz, 2H), 7.76 (d, J=8.4 Hz, 2H), 7.70-7.65 (m, 1H), 7.35-7.31 (m, 2H), 7.16-7.12 (m, 2H), 6.96 (d, J=6.1 Hz, 1H). LRMS (ESI): (calc) 336.06. (found) 337.28 (MH)+.
TABLE 1
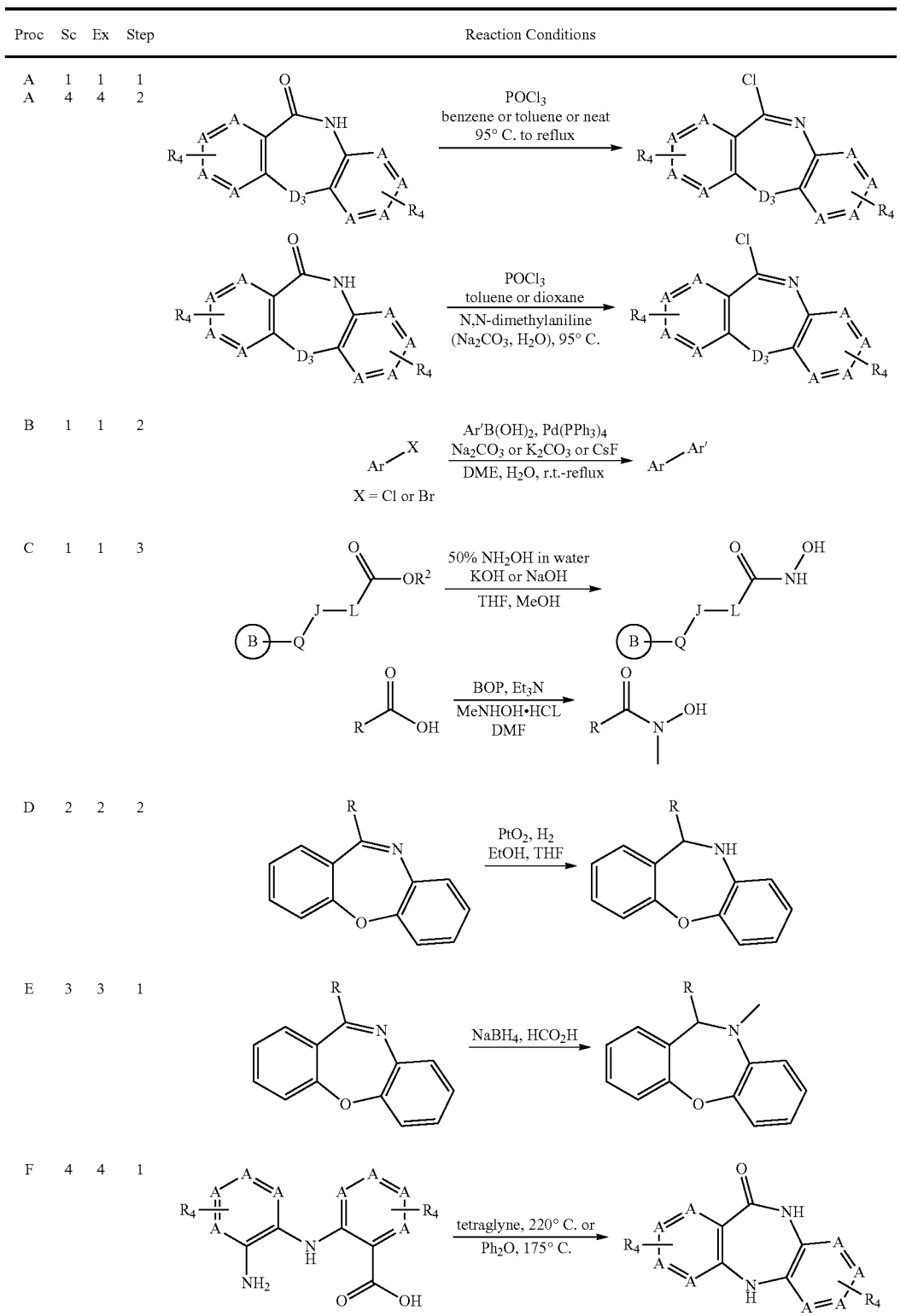

TABLE 1-continued

| Proc | Sc | Ex | Step | Reaction Conditions |
|---|---|---|---|---|
| G | 5 | 5 | 1 | |
| G | 19 | 20 | 3 | |
| G | 7 | 7 | 1 | |

R-NH₂ + Cl-C(O)-R' → R-NH-C(O)-R'
DIPEA or Et₃N, THF or EtOAc or DCM or neat, r.t.-160° C.

R-NH₂ + Cl-C(O)-R' → R-NH-C(O)-R'
Pyridine, DMAP, Benzene or Toluene, r.t.-90° C.

R-NH₂ + HO-C(O)-R' → R-NH-C(O)-R'
BOP, Et₃N, DMF

| H | 5 | 5 | 2 |

(2-hydroxybenzamide with chloro-heteroaryl) → tricyclic oxazepinone
NaH, DMF, 90-130° C. or MeONa, tetraglyme, 220° C. or NaH, dioxane reflux

| I | 17 | 17 | 1 |
| I | 6 | 6 | 1 |
| I | 8 | 8 | 7 |

Ar-F + RNH₂ → Ar-NH-R
RNH₂, DMSO or neat, r.t.-80° C.

Ar-X + ROH → Ar-O-R
Cs₂CO₃ or K₂CO₃, ACN, 80-90° C.
X = F or Cl

R'-CH₂-X + ROH → R'-CH₂-O-R
ROH, Cs₂CO₃, Ace or DMF, r.t.-60° C.
X = Br or Cl

| J | 6 | 6 | 2 |
| J | 12 | 12 | 2 |
| J | 19 | 20 | 2 |
| J | 18 | 19 | 2 |
| J | 22 | 23 | 2 |

R-NO₂ → R-NH₂
H₂, Pd(C) 10%, MeOH or EtOH or THF or EtOAc

R-NO₂ → R-NH₂
SnCl₂·2H₂O, EtOH, reflux

R-NO₂ → R-NH₂
NH₄Cl, Zn, MeOH, H₂O

Ar-Cl → Ar
H₂, Pd(C), NaOCHO, H₂O, 50° C.

Ar-Cl → Ar
H₂, Pd(C), EtOH

| K | 6 | 6 | 3 |

(aminoaryl + methyl ester aryl) → tricyclic lactam
AlMe₃, DCM (or toluene), r.t.-100° C.

| L | 7 | 7 | 2 |

R-O-CH₂-Ph → R-OH
33% HBr/ACOH

| M | 8 | 8 | 6 |

R-OMe → R-OH
BBr₃, DCM, -78° C. to r.t.

TABLE 1-continued

| Proc | Sc | Ex | Step | Reaction Conditions |
|---|---|---|---|---|
| N | 9 | 9 | 2 | R—NO$_2$ → R—NH$_2$; H$_2$, 45-65 PSI, Pd/C 10%, EtOH or MeOH or THF |
| O | 10 | 10 | 1 | Pyridine → Pyridine N-oxide; ReO$_3$, H$_2$O$_2$, DCM |
| P | 11 | 11 | 3 | R—S—R' → R—SO$_2$—R'; CrO$_3$, H$_5$IO$_6$, ACN or mCPBA, Et$_2$O, DCM |
| P | 13 | 13 | 1 | R—S—R' → R—S(O)—R'; H$_2$O$_2$, AcOH, DCM or H$_5$IO$_6$, FeCl$_3$, ACN |
| Q | 14 | 14 | 1 | R—COOH → R—COOMe; HCl and/or H$_2$SO$_4$, MeOH, 70-95° C. |
| R | 15 | 15 | 6 | Chloro-benzazepine → amino-benzazepine; R$_2$NH, toluene, reflux or R$_2$NH, DIPEA (or Et$_3$N) toluene, reflux. Ar—Cl → Ar—NR$_2$; R$_2$NH, HCl, EtOH, H$_2$O |
| S | 16 | 16 | 1 | R—COOH + R'NH$_2$ → R—C(O)NH—R'; (COCl)$_2$, DMF, pyridine DCM or benzene or (COCl)$_2$, DMF, Et$_3$N, THF |
| T | 17 | 17 | 4 | X = Cl or F; NaH, Pyridine Reflux or KHMDS, Toluene 120-140° C. |
| U | 19 | 20 | 4 | PPA or POCl$_3$, 100-145° C. |
| V | 21 | 22 | 3 | R—CHO → R—COOMe; HOC(CH$_3$)$_2$CN, Et$_3$N, KCN, MeOH, 40° C. |

TABLE 1-continued
| Proc | Sc | Ex | Step | Reaction Conditions |
|---|---|---|---|---|
| W | 22 | 23 | 5 | 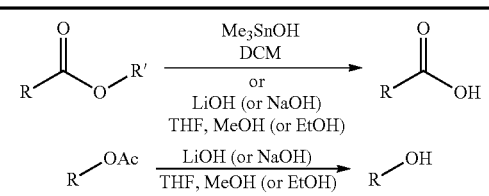 |
| W | 25 | 26 | 3 | |
| X | 22 | 23 | 6 | 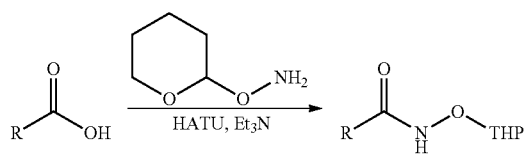 |
| Y | 22 | 23 | 7 | 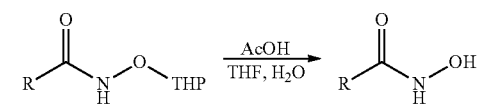 |
| Z | 23 | 24 | 2 | 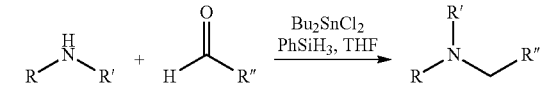 |
| AA | 24 | 25 | 1 | 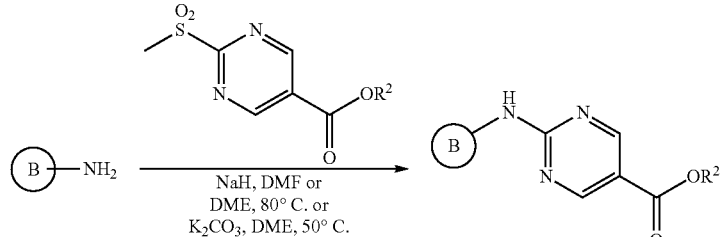 |
| AB | 25 | 26 | 2 | 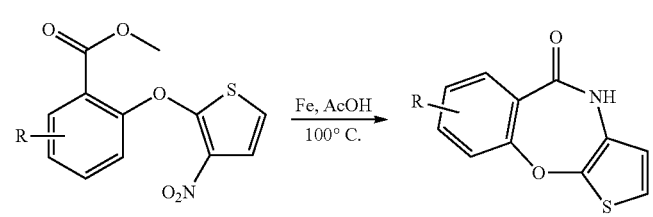 |
| AC | 25 | 26 | 4 | 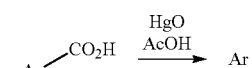 |
The compounds of the following table of examples (Table 2) are prepared starting from the corresponding starting material and following the preparative sequence (general procedure A to AC) indicated.

TABLE 2

| Ex | Cpd | Starting Material | Structure | Name | Characterization | Preparative sequence |
|---|---|---|---|---|---|---|
| 1 | 3 | | 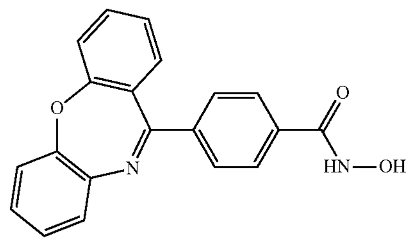 | (Z)-4-(dibenzo[b,f][1,4]oxazepin-11-yl)-N-hydroxybenzamide | $^1$H NMR (DMSO-d$_6$) δ (ppm): 11.37 (br s, 1H), 9.14 (br s, 1H), 7.86 (d, J = 8.8 Hz, 2H), 7.81 (d, J = 8.8 Hz, 2H), 7.66-7.62 (m, 1H), 7.43-7.39 (m, 2H), 7.32-7.25 (m, 4H), 7.17 (dd, J = 8.0, 1.6 Hz, 1H). LRMS (ESI): (calc) 330.1 (found) 331.4 (MH)+ | A, B, C |
| 2 | 6 | | 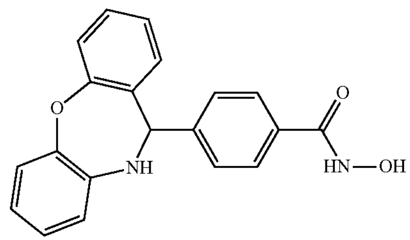 [SMILES: O=C(NO)c1ccc(C2Nc3ccccc3Oc3ccccc32)cc1] | 4-(10,11-dihydrodibenzo[b,f][1,4]oxazepin-11-yl)-N-hydroxybenzamide | (DMSO-d6) δ (ppm): 11.12 (s, 1H), 8.99 (s, 1H), 7.65 (d, J = 8.4 Hz, 2H), 7.45 (dd, J = 7.6, 1.8 Hz, 1H), 7.35-7.30 (m, 3H), 7.18 (td, J = 7.4, 1.2 Hz, 1H), 7.10 (dd, J = 8.0, 1.4 Hz, 1H), 6.89-6.75 (m, 4H), 6.52-6.48 (m, 1H), 5.51 (d, J = 6.0 Hz, 1H). LRMS(ESI): (calc) 332.12 (found) 333.19 (MH)+ | A, B, D, C |
| 3 | 8 | | 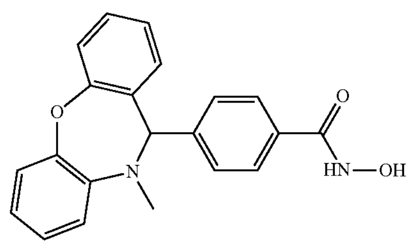 [SMILES: CN1c2ccccc2Oc2ccccc2C1c1ccc(C(=O)NO)cc1] | N-hydroxy-4-(10-methyl-10,11-dihydrodibenzo[b,f][1,4]oxazepin-11-yl)benzamide | (MeOD-d4) δ (ppm): 7.60 (d, J = 8.4 Hz, 2H), 7.43-7.39 (m, 1H), 7.35-7.29 (m, 2H), 7.20-7.13 (m, 5H), 7.09-7.05 (m, 1H), 6.94 (dd, J = 8.0 Hz, 1.6 Hz, 1H), 6.02 (s, 1H), 3.27 (s, 3H). LRMS(ESI): (calc) 346.13 (found) 347.28 (MH)+ | A, B, E, C |

TABLE 2-continued

| Ex | Cpd | Starting Material | Structure | Name | Characterization | Preparative sequence |
|---|---|---|---|---|---|---|
| 4 | 12 | | 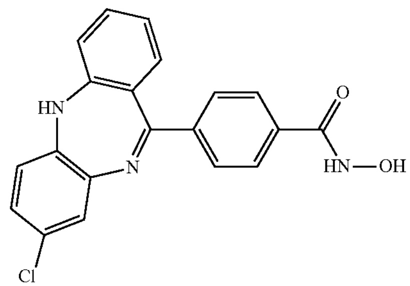 | (Z)-4-(8-chloro-5H-dibenzo[b,e][1,4]diazepin-11-yl)-N-hydroxybenzamide | (DMSO-d6) δ (ppm): 11.33 (s, 1H), 9.12 (s, 1H), 7.80 (d, J = 8.4 Hz, 2H), 7.64 (d, J = 8.4 Hz, 2H), 7.46 (s, 1H), 7.40-7.36 (m, 1H), 7.19 (d, J = 2.4 Hz, 1H), 7.10 (dd, J = 8.8, 2.8 Hz, 1H), 7.01-6.90 (m, 3H), 6.85 (dd, J = 7.6, 1.6 Hz, 1H), LRMS(ESI): MS (ESI): (calc) 363.08 (found) 364.22 (MH)+ | F, A, B, C |
| 5 | 17 | | 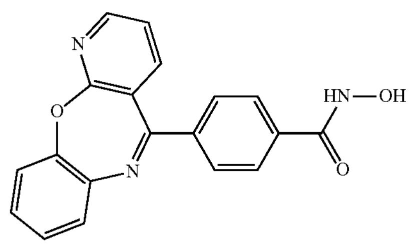 [SMILES: O=C(NO)c1ccc(C2=Nc3ccccc3Oc3ncccc32)cc1] | (Z)-4-(benzo[b]pyrido[3,2-f][1,4]oxazepin-5-yl)-N-hydroxybenzamide | (DMSO-d6) δ (ppm): 11.39 (s, 1H), 9.16 (s, 1H), 8.52 (dd, J = 5.2, 2.0 Hz, 1H), 7.88 (d, J = 8.4 Hz, 2H), 7.84 (d, J = 8.4 Hz, 2H), 7.75 (dd, J = 8.0, 2.0 Hz, 1H), 7.48-7.41 (m, 2H), 7.34-7.30 (m, 3H). LRMS(ESI): (calc) 331.12 (found) 332.18 (MH)+ | G, H, A, B, C |
| 6 | 23 | | 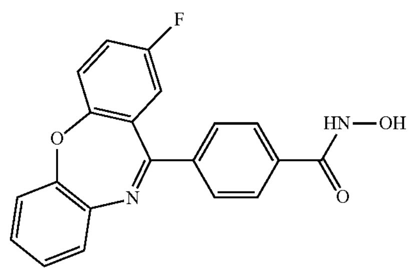 [SMILES: O=C(NO)c1ccc(C2=Nc3ccccc3Oc3ccc(F)cc32)cc1] | (Z)-4-(2-fluorodibenzo[b,f][1,4]oxazepin-11-yl)-N-hydroxybenzamide | (DMSO-d6) δ (ppm): 11.39 (s, 1H), 9.16 (s, 1H), 7.88 (d, J = 8.8 Hz, 2H), 7.85 (d, J = 8.8 Hz, 2H), 7.53-7.40 (m, 3H), 7.34-7.25 (m, 3H), 6.99 (dd, J = 8.6, 2.4 Hz, 1H). LRMS(ESI): (calc) 348.09 (found) 349.19 (MH)+ | I, J, K, A, B, C |

TABLE 2-continued

| Ex | Cpd | Starting Material | Structure | Name | Characterization | Preparative sequence |
|---|---|---|---|---|---|---|
| 7 | 29 | | 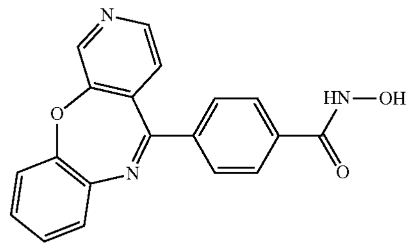 [SMILES: O=C(NO)c1ccc(C2=Nc3ccccc3Oc3cnccc32)cc1] | (Z)-4-(benzo[b]pyrido[4,3-f][1,4]oxazepin-5-yl)-N-hydroxybenzamide | (DMSO-d6) d(ppm) 1H: 11.41 (s, 1H), 9.19 (s, 1H), 8.78 (d, J = 0.4 Hz, 1H), 8.55 (d, J = 4.8 Hz, 1H), 7.92-7.87 (m, 4H), 7.50-7.48 (m, 1H), 7.42-7.31 (m, 3H), 7.22 (dd, J = 4.8, 0.4 Hz, 1H) LRMS(ESI): (calc) 331.32 (found) 332.15 (MH)+ | G, L, H, A, B, C |
| 8 | 37 | | 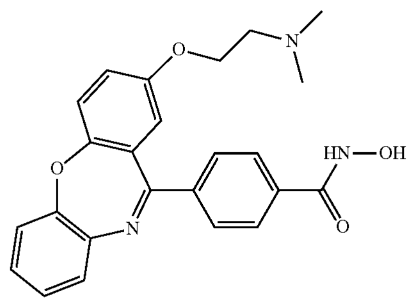 [SMILES: CN(C)CCOc1ccc2c(c1)C(c1ccc(C(=O)NO)cc1)=Nc1ccccc1O2] | (Z)-4-(2-(2-(dimethylamino)ethoxy)dibenzo[b,f][1,4]oxazepin-11-yl)-N-hydroxybenzamide | (MeOH-d4) d(ppm) 1H: 7.91-7.86 (m, 4H), 7.42-7.39 (m, 1H), 7.32-7.21 (m, 5H), 6.70 (d, J = 3.2 Hz, 1H), 4.11 (t, J = 5.2 Hz, 2H), 3.12 (t, J = 5.2 Hz, 2H), 2.61 (s, 6H) LRMS(ESI): (calc) 417.17 (found) 418.47 (MH)+ | I, J, K, A, B, M, I, C |
| 9 | 43 | | 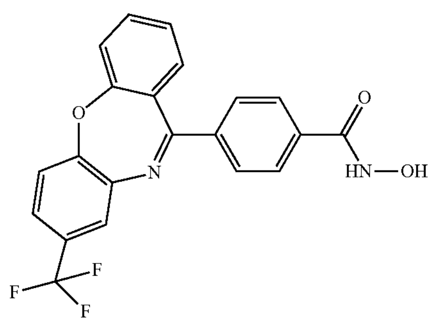 [SMILES: O=C(NO)c1ccc(C2=Nc3cc(C(F)(F)F)ccc3Oc3ccccc32)cc1] | (Z)-N-hydroxy-4-(8-(trifluoromethyl)dibenzo[b,f][1,4]oxazepin-11-yl)benzamide | (dmso) d(ppm) 1H: 11.38 (s, 1H), 9.17 (s, 1H), 7.95-7.84 (m, 4H), 7.76 (d, J = 1.6 Hz, 1H), 7.72-7.64 (m, 2H), 7.55 (d, J = 8.5 Hz, 1H), 7.48 (d, J = 7.8 Hz, 1H), 7.33 (t, J = 7.6 Hz, 1H), 7.21 (dd, J = 7.7 and 1.4 Hz, 1H) LRMS(ESI): (calc.) 398.1 (found) 399.2 (MH)+ | I, N, K, A, B, C |

TABLE 2-continued

| Ex | Cpd | Starting Material | Structure | Name | Characterization | Preparative sequence |
|---|---|---|---|---|---|---|
| 10 | 45 | | 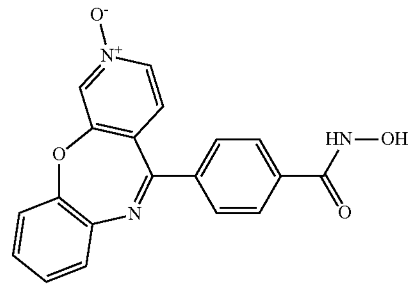 [SMILES: O=C(NO)c1ccc(C2=Nc3ccccc3Oc3c[n+]([O-])ccc32)cc1] | (Z)-5-(4-(hydroxycarbamoyl)phenyl)benzo[b]pyrido[4,3-f][1,4]oxazepine 2-oxide | (MeOH-$d_4$) δ (ppm): 8.51 (d, J = 1.8 Hz, 1H), 8.18 (dd, J = 6.8, 1.8 Hz, 1H), 7.94-7.89 (m, 4H), 7.51-7.49 (m, 1H), 7.37-7.31 (m, 3H), 7.26 (d, J = 6.7 Hz, 1H). LRMS(ESI): (calc) 347.09 (found) 348.1 (MH)+. | G, L, H, A, B, O, C |
| 11 | 49 | | 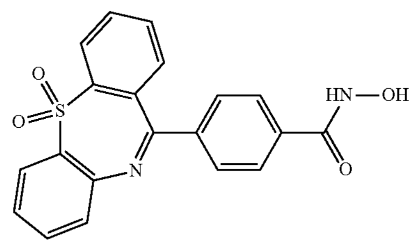 [SMILES: O=C(NO)c1ccc(C2=Nc3ccccc3S(=O)(=O)c3ccccc32)cc1] | | (DMSO-$d_6$) δ (ppm): 11.42 (s, 1H), 9.20 (s, 1H), 8.13-8.10 (m, 1H), 7.99 (dd, J = 8.0, 1.2 Hz, 1H), 7.93-7.83 (m, 6H), 7.81-7.77 (m, 1H), 7.63 (dd, J = 8.0, 0.8 Hz, 1H), 7.59-7.57 (m, 1H), 7.53-7.49 (m, 1H). LRMS(ESI): (calc) 378.40 (found) 379.1 (MH)+ | A, B, P, C |
| 12 | 55 | | 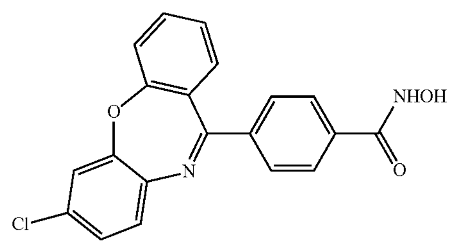 | (Z)-4-(7-chlorodibenzo[b,f][1,4]oxazepin-11-yl)-N-hydroxybenzamide | (DMSO-$d_6$) δ (ppm): 11.37 (s, 1H), 9.16 (s, 1H), 7.87 (d, J = 8.3 Hz, 2H), 7.82 (d, J = 8.2 Hz, 2H), 7.70-7.64 (m, 1H), 7.52-7.41 (m, 3H), 7.38-7.28 (m, 2H), 7.22-7.17 (m, 1H). LRMS(ESI): (calc) 364.06 (found) 365.1 (MH)+ | I, J, K, A, B, C |
| 13 | 57 | | 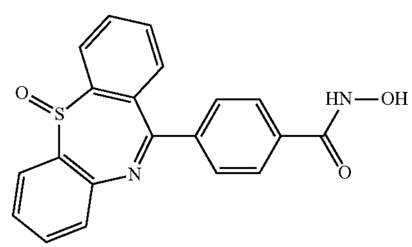 [SMILES: O=C(NO)c1ccc(C2=Nc3ccccc3S(=O)c3ccccc32)cc1] | | (DMSO-$d_6$) δ (ppm): 11.42 (s, 1H), 9.20 (s, 1H), 7.91-7.80 (m, 6H), 7.64-7.47 (m, 4H), 7.41 (d, J = 7.6 Hz, 1H), 7.37 (d, J = 8.0 Hz, 1H). LRMS(ESI): (calc) 362.07 (found) 363.3 (MH)+. | A, B, P, C |

TABLE 2-continued

| Ex | Cpd | Starting Material | Structure | Name | Characterization | Preparative sequence |
|---|---|---|---|---|---|---|
| 14 | 64 | | 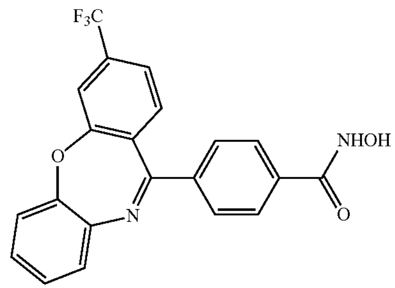 | (Z)-N-hydroxy-4-(3-(trifluoromethyl)dibenzo[b,f][1,4]oxazepin-11-yl)benzamide | (DMSO-$d_6$) δ (ppm): 11.39 (s, 1H), 9.17 (s, 1H), 7.94-7.82 (m, 5H), 7.66 (d, J = 7.8 Hz, 1H), 7.48-7.39 (m, 3H), 7.36-7.28 (m, 2H). LRMS(ESI): (calc) 398.09 (found) 399.4 (MH)+. | Q, I, J, K, A, B, C |
| 15 | 71 | | 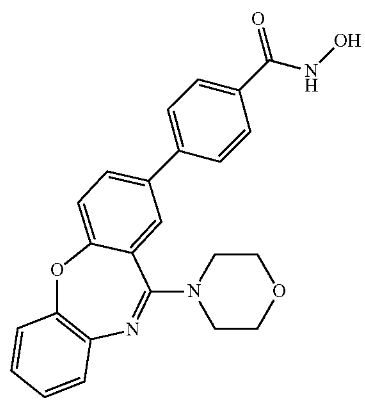 [SMILES: O=C(NO)c1ccc(-c2ccc3c(c2)C(N2CCOCC2)=Nc2ccccc2O3)cc1] | (E)-N-hydroxy-4-(11-morpholinodibenzo[b,f][1,4]oxazepin-2-yl)benzamide | (DMSO-$d_6$) δ (ppm): 11.28 (s, 1H), 9.08 (s, 1H), 7.90 (dd, J = 8.4, 2.0 Hz, 1H), 7.83 (d, J = 8.6 Hz, 2H), 7.73 (d, J = 8.6 Hz, 2H), 7.68 (d, J = 2.4 Hz, 1H), 7.47 (d, J = 8.4 Hz, 1H), 7.22 (dd, J = 8.0, 1.2 Hz, 1H), 7.12-7.06 (m, 2H), 7.03-6.99 (m, 1H), 3.08-3.07 (m, 4H), 3.55-3.54 (m, 4H). LRMS(ESI): (calc) 415.15 (found) 416.6 (MH)+. | I, B, J, K, A, R, C |
| 16 | 77 | | 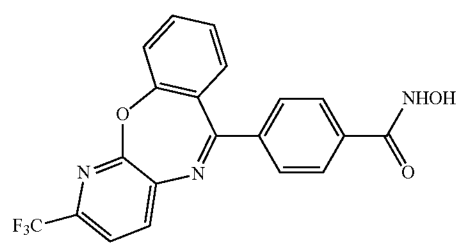 | (Z)-N-hydroxy-4-(2-(trifluoromethyl)benzo[f]pyrido[2,3-b][1,4]oxazepin-6-yl)benzamide | (DMSO-$d_6$) δ (ppm): 11.43 (s, 1H), 9.20 (s, 1H), 8.18 (d, J = 8.1 Hz, 1H), 7.97-7.86 (m, 5H), 7.78-7.72 (m, 1H), 7.55 (d, J = 8.0 Hz, 1H), 7.40 (t, J = 7.6 Hz, 1H), 7.29 (d, J = 6.6 Hz, 1H). LRMS(ESI): (calc) 399.08 (found) 400.4 (MH)+. | S, L, H, A, B, C |

TABLE 2-continued

| Ex | Cpd | Starting Material | Structure | Name | Characterization | Preparative sequence |
|---|---|---|---|---|---|---|
| 17 | 84a | cyclopropylamine + 2-fluoronitrobenzene | (structure) | (Z)-4-(11-cyclopropyl-11H-benzo[b]pyrido[2,3-e][1,4]diazepin-5-yl)-N-hydroxybenzamide | (DMSO-d₆) δ (ppm): 11.33 (s, 1H), 9.16 (s, 1H), 8.50-8.46 (m, 1H), 7.83 (d, J = 8.2 Hz, 2H), 7.68 (d, J = 8.2 Hz, 2H), 7.45-7.41 (m, 1H), 7.36 (d, J = 8.0 Hz, 1H), 7.27-7.21 (m, 2H), 7.20-7.11 (m, 2H), 3.05-3.48 (m, 1H), 0.95-0.80 (m, 2H), 0.51-0.45 (m, 1H), 0.31-0.23 (m, 1H). LRMS(ESI): (calc) 370.14 (found) 371.2 (MH)+. | I, N, G, T, A, B, C |
| 18a | 84b | cyclopropylamine + 2-fluoronitrobenzene | (structure) | (Z)-4-(5-cyclopropyl-5H-dibenzo[b,e][1,4]diazepin-11-yl)-N-hydroxybenzamide | (DMSO-d₆) δ (ppm): 11.31 (s, 1H), 9.14 (s, 1H), 7.81 (d, J = 8.5 Hz, 2H), 7.66 (d, J = 8.4 Hz, 2H), 7.55-7.49 (m, 1H), 7.46 (d, J = 7.9 Hz, 1H), 7.35-7.31 (m, 1H), 7.22-7.16 (m, 2H), 7.14-7.05 (m, 2H), 6.95-6.90 (m, 1H), 3.45-3.35 (m, 1H), 0.81-0.98 (m, 2H), 0.50-0.40 (m, 1H), 0.39-0.25 (m, 1H). LRMS(ESI): (calc) 369.2 (found) 370.5 (MH)+. | I, N, G, T, A, B, C |
| 18b | 84c | 2-fluoronitrobenzene + cyclopropylamine | (structure) | (Z)-4-(5-cyclopropyl-5H-dibenzo[b,e][1,4]diazepin-11-yl)-N-hydroxy-N-methylbenzamide | (DMSO-d₆) δ (ppm): 10.10 (s, 1H), 7.66 (d, J = 8.4 Hz, 2H), 7.63 (d, J = 8.4 Hz, 2H), 7.52 (t, J = 7.2 Hz, 1H), 7.45 (d, J = 8.0 Hz, 1H), 7.32 (d, J = 7.8 Hz, 1H), 7.23-7.15 (m, 2H), 7.14-7.06 (m, 2H), 6.94 (d, J = 7.8 Hz, 1H), 3.44-3.35 (m, 1H), 3.28 (s, 3H), 0.9-0.6 (m, 2H), 0.50-0.40 (m, 1H), 0.35-0.27 (m, 1H). LRMS(ESI): (calc) 383.16 (found) 384.5 (MH)+. | I, N, G, T, A, B, W, C |
| 19 | 89 | (structure) | (structure) | (Z)-4-(5H-dibenzo[b,e][1,4]diazepin-11-yl)-N-hydroxybenzamide | (DMSO-d₆) δ (ppm): 11.33 (s, 1H), 9.13 (s, 1H), 7.81 (d, J = 8.4 Hz, 2H), 7.65 (d, J = 8.4 Hz, 2H), 7.39-7.34 (m, 2H), 7.16 (dd, J = 7.6, 1.6 Hz, 1H), 7.09-6.91 (m, 5H), 7.85 (dd, J = 7.6, 1.2 Hz, 1H). LRMS(ESI): (calc) 329.12 (found) 330.4 (MH)+. | F, J, A, B, C |

TABLE 2-continued

| Ex | Cpd | Starting Material | Structure | Name | Characterization | Preparative sequence |
|---|---|---|---|---|---|---|
| 20 | 94 | (2-methoxy-4-fluorophenol) + (2-fluoro-1-nitrobenzene with F) | dibenzo[b,f][1,4]oxazepine with F and OMe substituents, linked to N-hydroxybenzamide | (Z)-4-(2-fluoro-4-methoxydibenzo[b,f][1,4]oxazepin-11-yl)-N-hydroxybenzamide | (CD₃OD) δ (ppm): 7.88 (s, 4H), 7.41 (m, 1H), 7.26 (m, 3H), 7.11 (dd, J = 2.8 Hz, 10.4 Hz, 1H), 6.38 (dd, J = 2.8 Hz, 8.4 Hz, 1H), 3.97 (s, 3H). LRMS(ESI): (calc) 378.10 (found) 377.3 (MH)−. | I, J, G, U, C |
| 21 | 100 | (2-methylthiophenol) + (2-fluoro-1-nitrobenzene) | dibenzo[b,f][1,4]oxazepine with S(O)Me substituent, linked to N-hydroxybenzamide | (Z)-N-hydroxy-4-(4-(methylsulfinyl)dibenzo[b,f][1,4]oxazepin-11-yl)benzamide | (CD₃OD) δ (ppm): 8.00 (d, J = 7.6 Hz, 1H), 7.87 (s, 4H), 7.52 (t, J = 8 Hz, 1H), 7.46 (m, 1H), 7.37 (d, J = 7.6 Hz, 1H), 7.31 (m, 3H), 3.06 (s, 3H). MS (m/z): 391.4 (M − H). | I, J, G, U, P, C |
| 22 | 104 | dibenzo[b,f][1,4]oxazepin-11(10H)-one | dibenzo[b,f][1,4]oxazepine linked to 3-fluoro-N-hydroxybenzamide | (E)-4-(dibenzo[b,f][1,4]oxazepin-11-yl)-3-fluoro-N-hydroxybenzamide | (DMSO-d₆) δ (ppm): 11.47 (s, 1H), 9.28 (s, 1H), 7.93 (t, J = 7.6 Hz, 1H), 7.79 (dd, J = 8.4, 1.6, 1H), 7.66-7.60 (m, 2H), 7.44-7.39 (m, 2H), 7.35-7.22 (m, 4H), 7.08 (d, J = 7.6 Hz, 1H). LRMS(ESI): (calc) 349.3 (found) 348.09 (MH)+. | A, B, V, C |
| 23 | 111 | 4-amino-2,6-dichloropyrimidine + indoline | pyrrolo-pyrimidine fused system linked to N-hydroxybenzamide | | (DMSO-d₆) δ (ppm): 11.3 (bs, 1H), 9.12 (bs, 1H), 8.29 (s, 1H), 8.02 (s, 1H), 7.78 (d, J = 8.4 Hz, 2H), 7.51 (d, J = 8.4 Hz, 2H), 7.25 (d, J = 7.2 Hz, 1H), 6.78 (t, J = 7.6 Hz, 1H), 6.52 (d, J = 7.6 Hz, 1H), 4.00 (t, J = 8.4 Hz, 2H), 2.94 (t, J = 8.4 Hz, 2H). LRMS(ESI): (calc) 357.12 (found) 356.4 (MH)+. | R, J, G, U, W, X, Y |

TABLE 2-continued

| Ex | Cpd | Starting Material | Structure | Name | Characterization | Preparative sequence |
|---|---|---|---|---|---|---|
| 24 | 115 | | 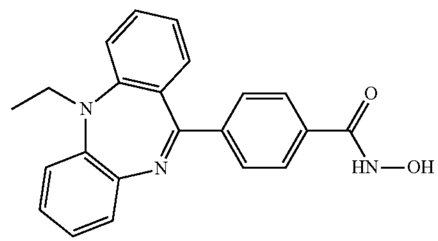 [SMILES: CCN1c2ccccc2N=C(c2ccc(C(=O)NO)cc2)c2ccccc21] | (Z)-4-(5-ethyl-5H-dibenzo[b,e][1,4]diazepin-11-yl)-N-hydroxybenzamide | (DMSO-d₆) δ (ppm): 7.83 (d, J = 8.8 Hz, 2H), 7.77 (d, J = 8.8 Hz, 2H), 7.49 (ddd, J = 8.2, 7.2, 1.6 Hz, 1H), 7.26 (dd, J = 1.6 Hz, 1H), 7.23-7.18 (m, 2H), 7.13-7.03 (m, 3H), 7.96 (dd, J = 7.6, 1.2, 1H), 3.83-3.68 (m, 2H), 1.24 (t, J = 6.8 Hz, 3H). LRMS(ESI): (calc) 357.15 (found) 358.3 (MH)+. | G, Z, U, C |
| 25 | 117 | | 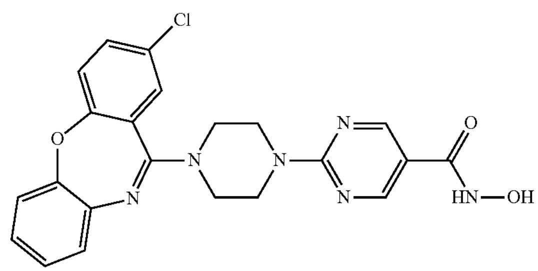 [SMILES: O=C(NO)c1cnc(N2CCN(C3=Nc4ccccc4Oc4ccc(Cl)cc43)CC2)nc1] | (E)-2-(4-(2-chlorodibenzo[b,f][1,4]oxazepin-11-yl)piperazin-1-yl)-N-hydroxypyrimidine-5-carboxamide | DMSO-d₆) δ (ppm): 8.69 (s, 2H), 7.62 (dd, J = 8.6, 2.4 Hz, 1H), 7.52 (d, J = 2.3 Hz, 1H), 7.41 (d, J = 8.8 Hz, 1H), 7.18 (d, J = 7.8 Hz, 1H), 7.12-7.04 (m, 2H), 7.03-6.96 (m, 1H), 4.12-3.76 (m, 4H), 3.68-3.44 (m, 4H). LRMS(ESI): (calc) 450.12 (found) 451.1 (MH)+. | AA, C |
| 26 | 124 | | 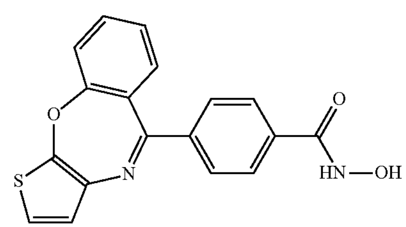 [SMILES: O=C(NO)c1ccc(C2=Nc3ccsc3Oc3ccccc32)cc1] | (Z)-4-(benzo[f]thieno[2,3-b][1,4]oxazepin-5-yl)-N-hydroxybenzamide | ¹H NMR (DMSO-d₆) δ (ppm): 11.36 (s, 1H), 9.16 (s, 1H), 7.86 (d, J = 8.4 Hz, 2H), 7.76 (d, J = 8.4 Hz, 2H), 7.70-7.65 (m, 1H), 7.35-7.31 (m, 2H), 7.16-7.12 (m, 2H), 6.96 (d, J = 6.1 Hz, 1H). LRMS(ESI): (calc) 336.06 (found) 337.28 (MH)+. | I, AB, W, AC, A, B, C |

TABLE 2-continued

| Ex | Cpd | Starting Material | Structure | Name | Characterization | Preparative sequence |
|---|---|---|---|---|---|---|
| 27 | 125 | 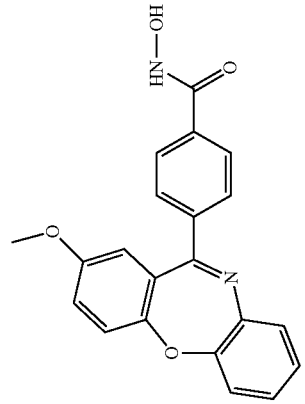 | 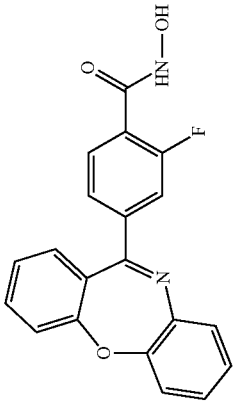 | (Z)-N-hydroxy-4-(2-methoxydibenzo[b,f][1,4]oxazepin-11-yl)benzamide | (DMSO-d6) d(ppm) 1H: 11.38 (s, 1H), 9.16 (s, 1H), 7.89 (s, 4H), 7.42-7.40 (m, 1H), 7.36 (d, J = 8.8 Hz, 1H), 7.32-7.25 (m, 3H), 7.21 (dd, J = 9.2, 3.4 Hz, 1H), 6.63 (d, J = 2.8 Hz, 1H), 3.65 (s, 3H) LRMS(ESI): (calc) 360.36 (found) 361.09 | I, J, K, A, B, C |
| 28 | 126 | 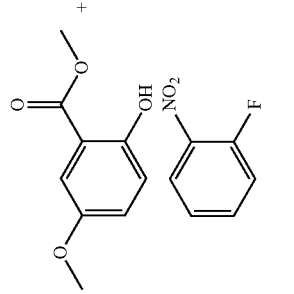 | 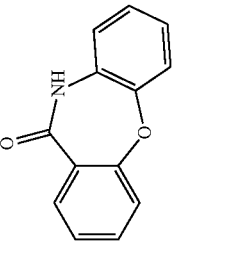 | (Z)-4-(dibenzo[b,f][1,4]oxazepin-11-yl)-2-fluoro-N-hydroxybenzamide | (DMSOD6) d(ppm) 1H: 11.12 (s, 1H), 9.32 (s, 1H), 7.70-7.63 (m, 3H), 7.59-7.56 (m, 1H), 7.45-7.41 (m, 2H), 7.38-7.25 (m, 4H), 7.22-7.19 (m, 1H) LRMS(ESI): (calc.) 348.1 (found) 349.2 (MH)+ | A, B, C |
| 29 | 127 | 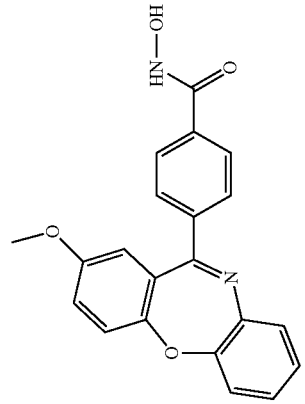 | 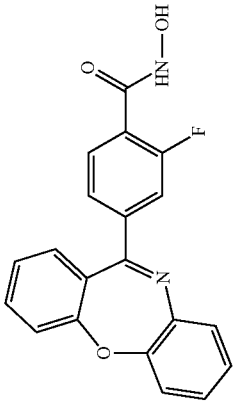 | (Z)-N-hydroxy-4-(3-methoxydibenzo[b,f][1,4]oxazepin-11-yl)benzamide | (MeOH-d4) δ (ppm): 7.85 (dd, J = 8.4 Hz, 10.2 Hz, 4H), 7.37 (m, 1H), 7.23 (m, 3H), 7.02 (d, J = 8.8 Hz, 1H), 6.90 (d, J = 2.4 Hz, 1H), 6.77 (dd, J = 2.4 Hz, 8.4 Hz, 1H), 3.86 (s, 3H). LRMS(ESI): (calc.) 360.11 (found) 359.00 (M)− | I, N, K, A, B, C |

TABLE 2-continued

| Ex | Cpd | Starting Material | Structure | Name | Characterization | Preparative sequence |
|---|---|---|---|---|---|---|
| 30 | 128 | (dibenzoxazepinone structure) | (hydroxamic acid dibenzoxazepine structure) | (Z)-3-(dibenzo[b,f][1,4]oxazepin-11-yl)-N-hydroxybenzamide | (MeOH-d₄) δ (ppm): 8.22 (t, J = 1.8 Hz, 1H), 7.96-7.86 (m, 2H), 7.60-7.54 (m, 2H), 7.45-7.40 (m, 1H), 7.36-7.32 (m, 1H), 7.28-7.16 (m, 4H), 7.10 (dd, J = 7.81.6 Hz, 1H). LRMS(ESI): (calc.) 330.3 (found) 331.4 (MH)+ | A, B, C |
| 31 | 129 | (methyl salicylate and fluoronitrotoluene) | (methyl-substituted dibenzoxazepine hydroxamic acid) | (Z)-N-hydroxy-4-(8-methyldibenzo[b,f][1,4]oxazepin-11-yl)benzamide | (DMSO-d₆) δ (ppm): 11.38 (s, 1H), 9.17 (s, 1H), 7.89 (d, J = 8.8 Hz, 2H), 7.82 (d, J = 8.8 Hz, 2H), 7.65-7.61 (m, 1H), 7.39 (dd, J = 8.4, 0.8 Hz, 1H), 7.29-7.15 (m, 4H), 7.07 (ddd, J = 8.2, 2.4, 0.8, 1H), 2.29 (s, 3H).). LRMS(ESI): (calc.) 344.12 (found) 345.4 (MH)+ | I, J, K, A, B, C |
| 32 | 130 | (methoxy salicylate and fluoronitrobenzene) | (methoxy-substituted dibenzoxazepine hydroxamic acid) | (Z)-N-hydroxy-4-(4-methoxydibenzo[b,f][1,4]oxazepin-11-yl)benzamide | (MeOH-d₄) δ (ppm): 7.86 (s, 4H), 7.39 (m, 1H), 7.26 (m, 4H), 7.14 (t, J = 8 Hz, 1H), 6.66 (d, J = 6.8 Hz, 1H), 3.96 (s, 3H), LRMS(ESI): (calc.) 360.11 (found) 359.2 (MH)− | I, J, K, A, B, C |

TABLE 2-continued

| Ex | Cpd | Starting Material | Structure | Name | Characterization | Preparative sequence |
|---|---|---|---|---|---|---|
| 33 | 131 | | 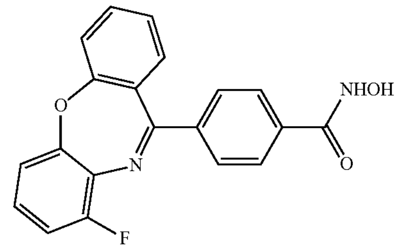 | (Z)-4-(9-fluorodibenzo[b,f][1,4]oxazepin-11-yl)-N-hydroxybenzamide | (DMSO-$d_6$) δ (ppm): 11.40 (m, 1H), 9.20 (m, 1H), 7.88 (d, J = 7.3 Hz, 2H), 7.82 (d, J = 7.2 Hz, 2H), 7.66 (t, J = 7.1 Hz, 1H), 7.43 (d, J = 8.0 Hz, 1H), 7.35-7.27 (m, 2H), 7.25-7.14 (m, 3H). LRMS(ESI): (calc.) 348.3 (found) 349.4 (MH)+ | I, N, K, A, B, C |
| 34 | 132 | | 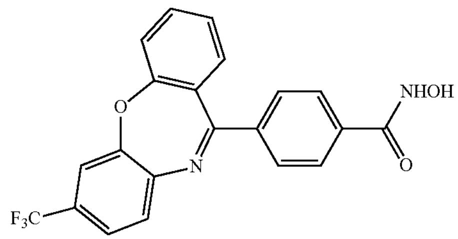 | (Z)-N-hydroxy-4-(7-(trifluoromethyl)dibenzo[b,f][1,4]oxazepin-11-yl)benzamide | (DMSO-$d_6$) δ (ppm): 11.39 (s, 1H), 9.17 (s, 1H), 7.93-7.82 (m, 4H), 7.76 (s, 1H), 7.72-7.58 (m, 3H), 7.53 (d, J = 8.0 Hz, 1H), 7.33 (t, J = 7.4 Hz, 1H), 7.22 (d, J = 7.2 Hz, 1H). LRMS(ESI): (calc.) 398.09 (found) 399.1 (MH)+ | I, J, K, A, B, C |
| 35 | 133 | | 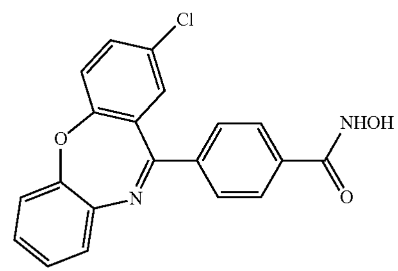 | (Z)-4-(2-chlorodibenzo[b,f][1,4]oxazepin-11-yl)-N-hydroxybenzamide | (DMSO-$d_6$) δ (ppm): 11.38 (s, 1H), 9.15 (s, 1H), 7.88 (d, J = 8.6 Hz, 2H), 7.84 (d, J = 8.4 Hz, 2H), 7.71 (dd, J = 8.6, 2.5 Hz, 1H), 7.47 (d, J = 8.6 Hz, 1H), 7.45-7.70 (m, 1H), 7.36-7.26 (m, 3H), 7.18 (d, J = 2.5 Hz, 1H). LRMS(ESI): (calc.) 364.06 (found) 365.3 (MH)+ | I, J, K, A, B, C |

TABLE 2-continued

| Ex | Cpd | Starting Material | Structure | Name | Characterization | Preparative sequence |
|---|---|---|---|---|---|---|
| 36 | 134 | | 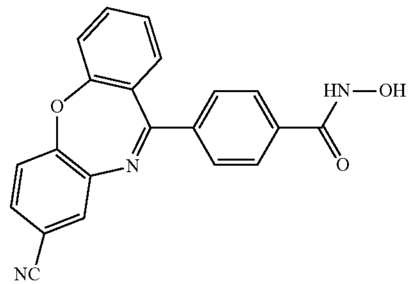 [SMILES: N#Cc1ccc2c(c1)N=C(c1ccc(C(=O)NO)cc1)c1ccccc1O2] | (Z)-4-(8-cyanodibenzo[b,f][1,4]oxazepin-11-yl)-N-hydroxybenzamide | (DMSO-d₆) δ (ppm): 11.41 (s, 1H), 9.18 (s, 1H), 7.93-7.85 (m, 5H), 7.79 (dd, J = 8.4, 2.0 Hz, 1H), 7.73-7.69 (m, 1H), 7.54 (d, J = 8.4 Hz, 1H), 7.49 (dd, J = 8.4 Hz, 1.2 Hz, 1H), 7.35 (td, J = 7.6, 1.2 Hz, 1H), 7.23 (dd, J = 7.6, 1.6 Hz, 1H), LRMS(ESI): (calc.) 355.10 (found) 356.2 (MH)+ | I, J, K, A, B, C |
| 37 | 135 | | 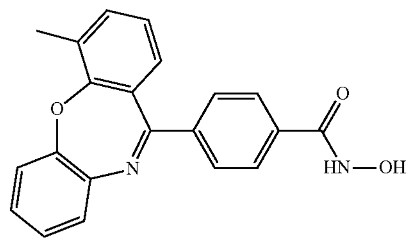 [SMILES: Cc1cccc2c1Oc1ccccc1N=C2c1ccc(C(=O)NO)cc1] | (Z)-N-hydroxy-4-(4-methyldibenzo[b,f][1,4]oxazepin-11-yl)benzamide | (CD₃OD) δ (ppm): 7.84 (s, 4H), 7.46 (d, J = 6.8 Hz, 1H), 7.41 (m, 1H), 7.28 (m, 3H), 7.10 (t, J = 7.6 Hz, 1H), 6.94 (d, J = 6.8 Hz, 1H), 2.55 (s, 3H). LRMS(ESI): (calc.) 344.12 (found) 343.2 (MH)− | I, J, K, A, B, C |
| 38 | 136 | | 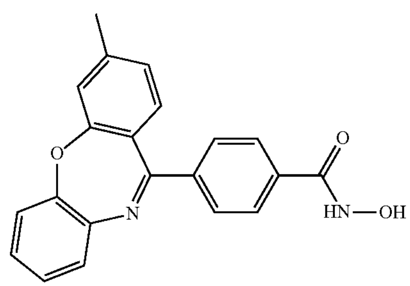 [SMILES: Cc1ccc2c(c1)Oc1ccccc1N=C2c1ccc(C(=O)NO)cc1] | (Z)-N-hydroxy-4-(3-methyldibenzo[b,f][1,4]oxazepin-11-yl)benzamide | (CD₃OD) δ (ppm): 7.85 (m, 4H), 7.38 (m, 1H), 7.24 (m, 3H), 7.17 (s, 1H), 7.02 (m, 2H), 2.40 (s, 3H). LRMS(ESI): (calc.) 344.12 (found) 343.3 (MH)− | I, J, K, A, B, C |

TABLE 2-continued

| Ex | Cpd | Starting Material | Structure | Name | Characterization | Preparative sequence |
|---|---|---|---|---|---|---|
| 39 | 137 | 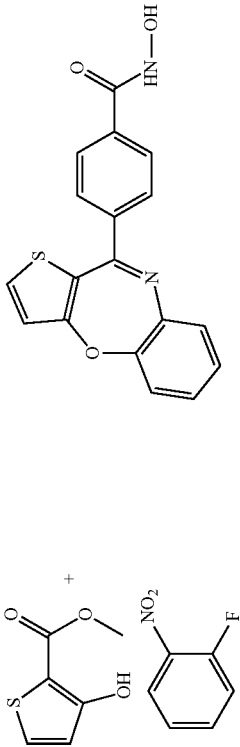 | 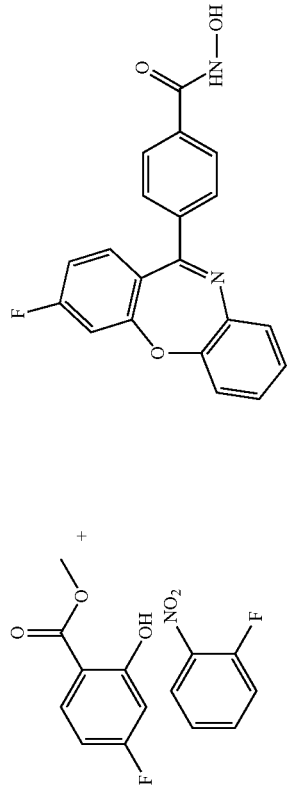 | (Z)-4-(benzo[b]thieno[2,3-f][1,4]oxazepin-10-yl)-N-hydroxybenzamide | (DMSO-d$_6$) δ (ppm): 11.40 (s, 1H), 9.18 (s, 1H), 7.99-7.96 (m, 3H), 7.88 (d, J = 8.4 Hz, 2H), 7.41 (dd, J = 7.6, 2.0 Hz, 1H), 7.36-7.27 (m, 2H), 7.18 (dd, J = 7.6, 1.2 Hz, 1H), 7.08 (d, J = 5.2 Hz, 1H). LRMS(ESI): (calc) 336.36 (found) 337.2 (MH)+ | I, J, K, A, B, C |
| 40 | 138 | 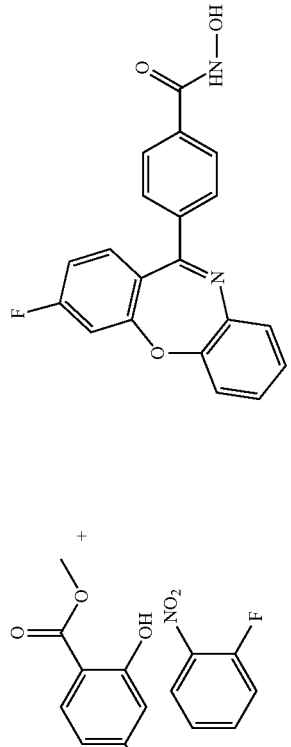 | 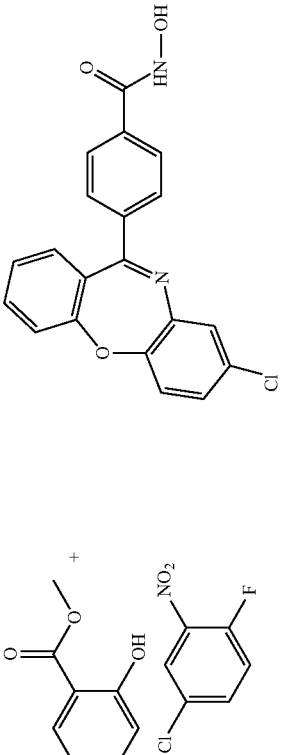 | (Z)-4-(3-fluorodibenzo[b,f][1,4]oxazepin-11-yl)-N-hydroxybenzamide | (DMSO-d$_6$) δ (ppm): 11.39 (s, 1H), 9.17 (s, 1H), 7.88 (d, J = 8.8 Hz, 2H), 7.83 (d, J = 8.8 Hz, 2H), 7.44-7.42 (m, 2H), 7.35-7.24 (m, 4H), 7.21-7.16 (td, J = 8.4 Hz, 1H). LRMS(ESI): (calc) 348.09 (found) 349.3 (MH)+ | I, J, K, A, B, C |
| 41 | 139 | 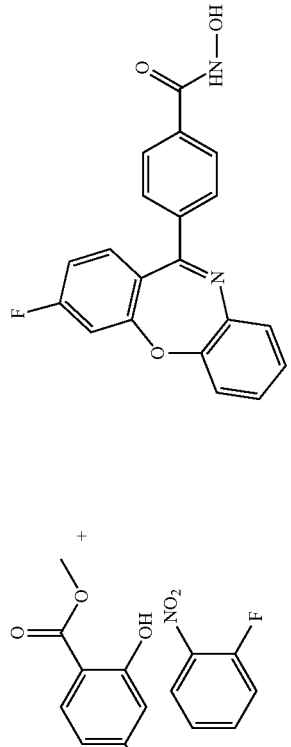 | 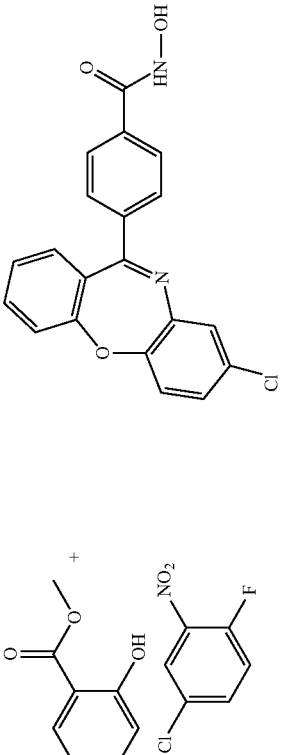 | (Z)-4-(8-chlorodibenzo[b,f][1,4]oxazepin-11-yl)-N-hydroxybenzamide | (CD$_3$OD) δ (ppm): 7.86 (s, 4H), 7.61 (m, 1H), 7.41 (s, 1H), 7.35 (d, J = 8 Hz, 1H), 7.26 (m, 3H), 7.18 (m, 1H). LRMS(ESI): (calc) 364.06 (found) 363.3 (MH)– | I, J, K, A, B, C |

TABLE 2-continued

| Ex | Cpd | Starting Material | Structure | Name | Characterization | Preparative sequence |
|---|---|---|---|---|---|---|
| 42 | 140 | | 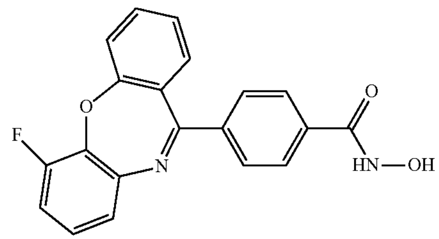 [SMILES: O=C(NO)c1ccc(C2=Nc3cccc(F)c3Oc3ccccc32)cc1] | (Z)-4-(6-fluorodibenzo[b,f][1,4]oxazepin-11-yl)-N-hydroxybenzamide | (DMSO-d₆) δ (ppm): 11.40 (s, 1H), 9.18 (s, 1H), 7.90 (d, J = 8.4 Hz, 2H), 7.84 (d, J = 8.4 Hz, 2H), 7.71-7.67 (m, 1H), 7.40 (d, J = 8.0 Hz, 1H), 7.35 (td, J = 7.6, 1.2 Hz, 1H), 7.29-7.22 (m, 4H). LRMS(ESI): (calc) 348.09 (found) 349.4 (MH)+ | I, J, K, A, B, C |
| 43 | 141 | | 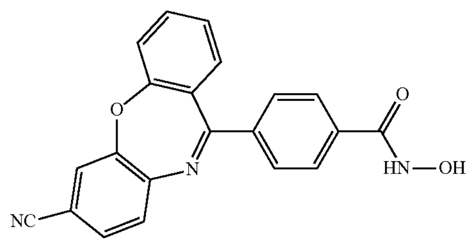 [SMILES: N#Cc1ccc2c(c1)Oc1ccccc1C(c1ccc(C(=O)NO)cc1)=N2] | (Z)-4-(7-cyanodibenzo[b,f][1,4]oxazepin-11-yl)-N-hydroxybenzamide | (DMSO-d₆) δ (ppm): 11.41 (s, 1H), 9.18 (s, 1H), 7.93 (d, J = 1.6 Hz, 1H), 7.90 (d, J = 8.8 Hz, 2H), 7.86 (d, J = 8.8 Hz, 2H), 7.77-7.70 (m, 2H), 7.58 (d, J = 8.4 Hz, 1H), 7.49 (dd, J = 8.0, 0.8 Hz, 1H), 7.35 (td, J = 7.6, 1.2 Hz, 1H), 7.24 (dd, J = 8.0, 1.6 Hz, 1H) LRMS(ESI): (calc) 355.10 (found) 356.4 (MH)+ | I, J, K, A, B, C |
| 44 | 142 | | 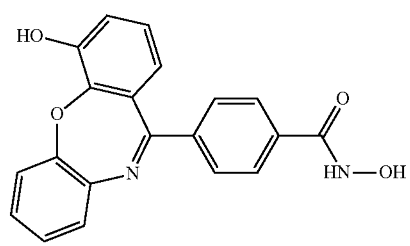 [SMILES: O=C(NO)c1ccc(C2=Nc3ccccc3Oc3c(O)cccc32)cc1] | (Z)-N-hydroxy-4-(4-hydroxydibenzo[b,f][1,4]oxazepin-11-yl)benzamide | (CD₃OD) δ (ppm): 7.86 (s, 4H), 7.41 (m, 2H), 7.25 (m, 2H), 7.11 (m, 1H), 7.02 (t, J = 8 Hz, 1H), 6.54 (m, 1H). LRMS(ESI): (calc) 346.10 (found) 345.3 (MH)− | I, J, K, A, B, M, C |

TABLE 2-continued

| Ex | Cpd | Starting Material | Structure | Name | Characterization | Preparative sequence |
|---|---|---|---|---|---|---|
| 45 | 143 | 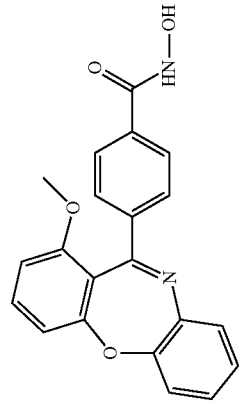 | 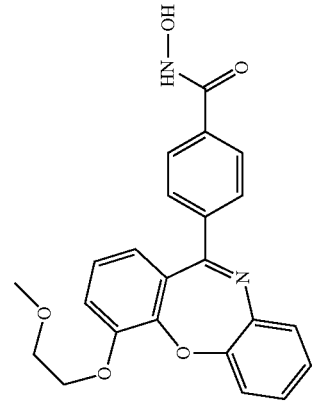 | (Z)-N-hydroxy-4-(1-methoxydibenzo[b,f][1,4]oxazepin-11-yl)benzamide | (DMSO-$d_6$) δ (ppm): 11.34 (s, 1H), 9.10 (s, 1H), 7.81 (d, J = 8.4 Hz, 2H), 7.70 (d, J = 8.4 Hz, 2H), 7.58 (t, J = 8.0 Hz, 1H), 7.38-7.36 (m, 1H), 7.29-7.21 (m, 3H), 7.03-6.99 (m, 2H), 3.47 (s, 3H). LRMS(ESI): (calc) 360.11 (found) 361.2 (MH)+ | Q, I, J, K, A, B, C |
| 46 | 144 | 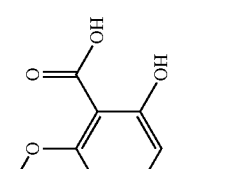 | 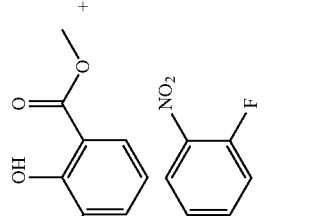 | (Z)-N-hydroxy-4-(4-(2-methoxyethoxy)dibenzo[b,f][1,4]oxazepin-11-yl)benzamide | (CD$_3$OD) δ (ppm): 7.84 (m, 4H), 7.22-7.41 (m, 5H), 7.13 (t, J = 8 Hz, 1H), 6.68 (d, J = 7.6 Hz, 1H), 4.27 (t, J = 4.4 Hz, 2H), 3.88 (t, J = 4.8 Hz, 2H), 3.51 (s, 3H). LRMS(ESI): (calc) 404.14 (found) 403.4 (MH)− | I, J, K, A, B, M, I, C |
| 47 | 145 | 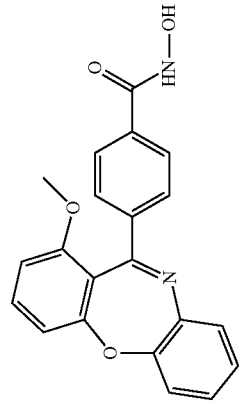 | 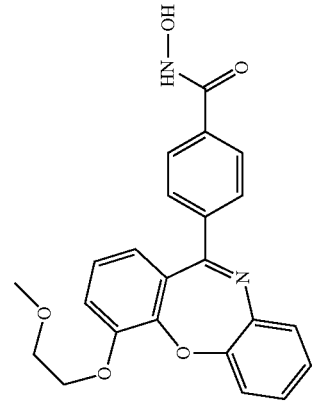 | (Z)-4-(1-fluorodibenzo[b,f][1,4]oxazepin-11-yl)-N-hydroxybenzamide | (DMSO-$d_6$) δ (ppm): 11.37 (s, 1H), 9.15 (s, 1H), 7.86 (d, J = 8.4 Hz, 2H), 7.81 (d, J = 8.4 Hz, 2H), 7.74-7.68 (m, 1H), 7.46-7.43 (m, 1H), 7.36-7.30 (m, 4H), 7.22 (t, J = 8.8 Hz, 1H). LRMS(ESI): (calc) 348.09 (found) 349.4 (MH)+ | I, J, K, A, B, C |

TABLE 2-continued

| Ex | Cpd | Starting Material | Structure | Name | Characterization | Preparative sequence |
|---|---|---|---|---|---|---|
| 48 | 146 | (methyl 2-hydroxy-3-methoxybenzoate) + (1-fluoro-2-nitrobenzene) | (dibenzo[b,f][1,4]oxazepine with 2-morpholinoethoxy substituent and N-hydroxybenzamide) | (Z)-N-hydroxy-4-(4-(2-morpholinoethoxy)dibenzo[b,f][1,4]oxazepin-11-yl)benzamide | (CD$_3$OD) δ (ppm): 7.87 (s, 4H), 7.10-7.40 (m, 6H), 6.69 (d, J = 7.6 Hz, 1H), 4.29 (s, 2H), 3.77 (s, 4H), 2.97 (s, 2H), 2.73 (s, 4H). LRMS(ESI): (calc) 459.18 (found) 458.6 (MH)− | I, J, K, A, B, M, I, C |
| 49 | 147 | (2-benzyloxybenzoic acid) + (2-chloro-3-nitropyridine) | (benzo[f]pyrido[2,3-b][1,4]oxazepine with N-hydroxybenzamide) | (Z)-4-(benzo[f]pyrido[2,3-b][1,4]oxazepin-6-yl)-N-hydroxybenzamide | (DMSO-d$_6$) δ (ppm): 11.41 (s, 1H), 9.18 (s, 1H), 8.19 (dd, J = 4.4, 1.6 Hz, 1H), 7.94 (dd, J = 7.6, 2.0 Hz, 1H), 7.90 (d, J = 8.4 Hz, 2H), 7.85 (d, J = 8.4 Hz, 2H), 7.73-7.69 (m, 1H), 7.47-7.42 (m, 2H), 7.35 (td, J = 7.8, 0.8 Hz, 1H), 7.24 (dd, J = 8.0, 1.6 Hz, 1H). LRMS(ESI): (calc) 331.10 (found) 332.4 (MH)+ | S, L, H, A, B, C |
| 50 | 148 | (2-hydroxy-thioanisole) + (1-fluoro-2-nitrobenzene) | (dibenzo[b,f][1,4]oxazepine with methylthio substituent and N-hydroxybenzamide) | (Z)-N-hydroxy-4-(4-(methylthio)dibenzo[b,f][1,4]oxazepin-11-yl)benzamide | (CD$_3$OD) δ (ppm): 7.86 (s, 4H), 7.42 (m, 3H), 7.26 (m, 2H), 7.20 (t, J = 8 Hz, 1H), 6.87 (d, J = 7.6 Hz, 1H), 3.30 (s, 3H). LRMS(ESI): (calc) 376.09 (found) 375.3 (MH)− | I, J, G, U, C |

TABLE 2-continued

| Ex | Cpd | Starting Material | Structure | Name | Characterization | Preparative sequence |
|---|---|---|---|---|---|---|
| 51 | 149 | 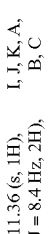 | 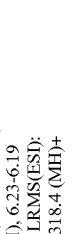 | (Z)-N-hydroxy-4-(4-(trifluoromethyl)dibenzo[b,f][1,4]oxazepin-11-yl)benzamide | (CD₃OD) δ (ppm): 7.81-7.93 (m, 5H), 7.37-7.47 (m, 3H), 7.27-7.32 (m, 3H). LRMS(ESI): (calc) 398.09 (found) 397.5 (MH)− | I, J, G, U, C |
| 52 | 150 |  | 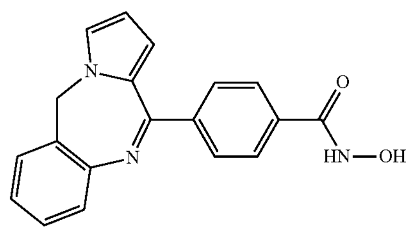 [SMILES: O=C(NO)c1ccc(C2=Nc3ccccc3Cn3cccc32)cc1] | (Z)-4-(5H-benzo[c]pyrrolo[1,2-a][1,4]diazepin-11-yl)-N-hydroxybenzamide | (DMSO-d₆) δ (ppm): 11.36 (s, 1H), 9.14 (s, 1H), 7.99 (d, J = 8.4 Hz, 2H), 7.86 (d, J = 8.4 Hz, 2H), 7.40-7.38 (m, 3H), 7.27-7.19 (m, 2H), 6.23-6.19 (m, 2H), 5.18 (s, 2H). LRMS(ESI): (calc) 317.12 (found) 318.4 (MH)+ | I, J, K, A, B, C |
| 53 | 151 |  | 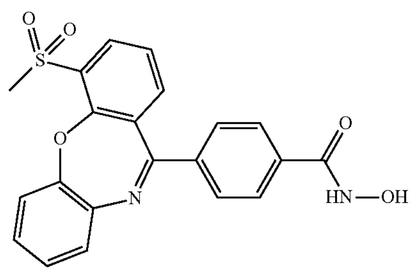 [SMILES: CS(=O)(=O)c1cccc2c1Oc1ccccc1N=C2c1ccc(C(=O)NO)cc1] | (Z)-N-hydroxy-4-(4-(methylsulfonyl)dibenzo[b,f][1,4]oxazepin-11-yl)benzamide | (CD3OD) δ (ppm): 8.19 (dd, J = 1.6 Hz, 7.6 Hz, 1H), 7.82 (q, J = 9.6 Hz, 4H), 7.68 (m, 1H), 7.46 (m, 3H), 7.30 (m, 2H), 3.51 (s, 3H). LRMS(ESI): (calc) 408.08 (found) 407.4 (MH)− | I, J, G, U, P, C |
| 54 | 152 | 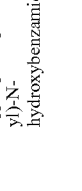 | 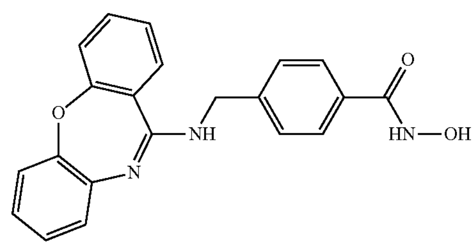 [SMILES: O=C(NO)c1ccc(CNC2=Nc3ccccc3Oc3ccccc32)cc1] | (E)-4-((dibenzo[b,f][1,4]oxazepin-11-ylamino)methyl)-N-hydroxybenzamide | (CD₃OD) δ (ppm): 7.75 (d, J = 8.4 Hz, 2H), 7.62-7.51 (m, 4H), 7.29-7.25 (m, 2H), 7.13-7.11 (m, 1H), 7.06-6.94 (m, 3H), 4.78 (s, 2H). LRMS(ESI): (calc) 359.13 (found) 360.5 (MH)+ | A, R, C |

| Ex | Cpd | Starting Material | Structure | Name | Characterization | Preparative sequence |
|---|---|---|---|---|---|---|
| 55 | 153 | (3-amino-2'-methoxy-4-trifluoromethyl diphenyl ether) + (methyl 4-chlorocarbonylbenzoate) | methoxy-trifluoromethyl dibenzoxazepine benzamide structure with HN-OH | (Z)-N-hydroxy-4-(4-methoxy-8-(trifluoromethyl)dibenzo[b,f][1,4]oxazepin-11-yl)benzamide | (CD₃OD) δ (ppm): 7.89 (dd, J = 8.4 Hz, 12.4 Hz, 4H), 7.69 (s, 1H), 7.55 (d, J = 8.4 Hz, 1H), 7.45 (d, J = 8.4 Hz, 1H), 7.32 (d, J = 7.6 Hz, 1H), 7.20 (t, J = 8.4 Hz, 1H), 6.71 (d, J = 8 Hz, 1H), 3.98 (s, 3H). LRMS(ESI): (calc) 428.10 (found) 427.3 (MH)− | G, U, C |
| 56 | 154 | 2-hydroxy-4-fluorobenzoic acid | morpholinodibenzoxazepine benzamide structure with NHOH | (Z)-N-hydroxy-4-(3-morpholinodibenzo[b,f][1,4]oxazepin-11-yl)benzamide | (DMSO-d₆) δ (ppm): 11.35 (s, 1H), 9.14 (s, 1H), 7.85 (d, J = 8.4 Hz, 2H), 7.79 (d, J = 8.2 Hz, 2H), 7.38-7.33 (m, 1H), 7.27-7.21 (m, 3H), 6.94 (d, J = 8.8 Hz, 1H), 6.90 (d, J = 2.4 Hz, 1H), 6.79 (dd, J = 8.9 and 2.5 Hz, 1H), 3.74-3.68 (m, 4H), 3.30-3.23 (m, 4H). LRMS(ESI): (calc) 415.15 (found) 416.5 (MH)+ | I, J, K, I, A, B, C |
| 57 | 155 | (2-hydroxyphenethyl) + (2-fluoro-nitrobenzene) | propyldibenzoxazepine benzamide structure with HN-OH | (Z)-N-hydroxy-4-(4-propyldibenzo[b,f][1,4]oxazepin-11-yl)benzamide | (CD₃OD) δ (ppm): 7.84 (m, 4H), 7.47 (d, J = 7.6 Hz, 1H), 7.40 (m, 1H), 7.26 (m, 3H), 7.13 (t, J = 7.6 Hz, 1H), 6.94 (d, J = 8 Hz, 1H), 2.93 (t, J = 7.6 Hz, 2H), 1.76 (m, 2H), 1.08 (t, J = 7.6 Hz, 3H). LRMS(ESI): (calc) 372.15 (found) 371.4 (MH)− | I, J, G, U, C |

TABLE 2-continued

| Ex | Cpd | Starting Material | Structure | Name | Characterization | Preparative sequence |
|---|---|---|---|---|---|---|
| 58 | 156 | | 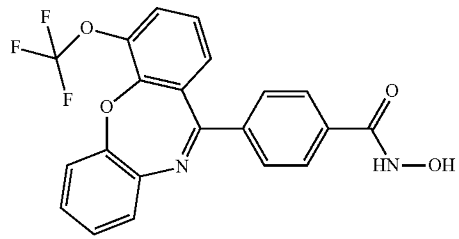 [SMILES: O=C(NO)c1ccc(C2=Nc3ccccc3Oc3c(OC(F)(F)F)cccc32)cc1] | (Z)-N-hydroxy-4-(4-(trifluoromethoxy)dibenzo[b,f][1,4]oxazepin-11-yl)benzamide | (CD₃OD) δ (ppm): 7.88 (s, 4H), 7.63 (d, J = 8.4 Hz, 1H), 7.45 (m, 1H), 7.23-7.33 (m, 4H), 7.16 (d, J = 8 Hz, 1H). LRMS(ESI): (calc) 414.08 (found) 413.4 (MH)− | I, J, G, U, C |
| 59 | 157 | | 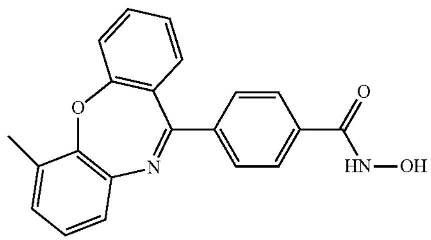 [SMILES: Cc1cccc2c1Oc1ccccc1C(c1ccc(C(=O)NO)cc1)=N2] | (Z)-N-hydroxy-4-(6-methyldibenzo[b,f][1,4]oxazepin-11-yl)benzamide | (DMSO-d₆) δ (ppm): 11.38 (s, 1H), 9.16 (s, 1H), 7.88 (d, J = 8.4 Hz, 2H), 7.81 (d, J = 8.4 Hz, 2H), 7.67-7.63 (m, 1H), 7.48 (d, J = 8.0 Hz, 1H), 7.30 (td, J = 7.6, 0.8 Hz, 1H), 7.25-7.13 (m, 4H), 2.48 (s, 3H). LRMS(ESI): (calc) 344.12 (found) 345.4 (MH)+ | I, J, G, U, C |
| 60 | 158 | | 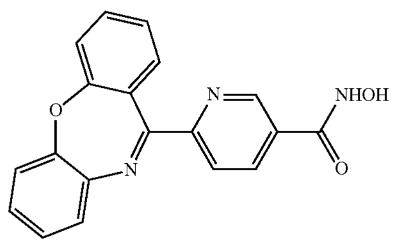 | (E)-6-(dibenzo[b,f][1,4]oxazepin-11-yl)-N-hydroxynicotinamide | (DMSO-d₆) δ (ppm): 11.54 (s, 1H), 9.33 (br s, 1H), 8.92 (s, 1H), 8.38 (d, J = 8.2 Hz, 1H), 8.32 (dd, J = 8.0, 1.7 Hz, 1H), 7.64-7.56 (m, 1H), 7.46 (d, J = 6.7 Hz, 1H), 7.39 (d, J = 8.0 Hz, 1H), 7.36-7.21 (m, 5H). LRMS(ESI): (calc) 331.10 (found) 332.4 (MH)+ | S, U, C |

TABLE 2-continued

| Ex | Cpd | Starting Material | Structure | Name | Characterization | Preparative sequence |
|---|---|---|---|---|---|---|
| 61 | 159 | | 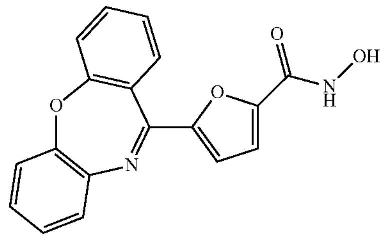 [SMILES: O=C(NO)c1ccc(C2=Nc3ccccc3Oc3ccccc32)o1] | (E)-5-(dibenzo[b,f][1,4]oxazepin-11-yl)-N-hydroxyfuran-2-carboxamide | (DMSO-d$_6$) δ (ppm): 11.37 (s, 1H), 9.27 (s, 1H), 7.69-7.65 (m, 1H), 7.60 (dd, J = 7.6, 1.6 Hz, 1H), 7.42-7.23 (m, 7H), 7.11 (d, J = 3.2 Hz, 1H). LRMS(ESI): (calc) 320.08 (found 321.3 (MH)+ | A, B, V, C |
| 62 | 160 | | 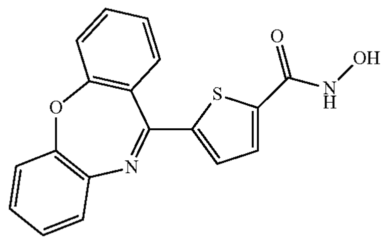 [SMILES: O=C(NO)c1ccc(C2=Nc3ccccc3Oc3ccccc32)s1] | (E)-5-(dibenzo[b,f][1,4]oxazepin-11-yl)-N-hydroxythiophene-2-carboxamide | ((CD$_3$OD) δ (ppm): 7.63-7.55 (m, 3H), 7.34-7.29 (m, 4H), 7.24-7.19 (m, 3H). LRMS(ESI): (calc) 336.06 (found) 337.4 (MH)+ | A, B, V, C |
| 63 | 161 | | 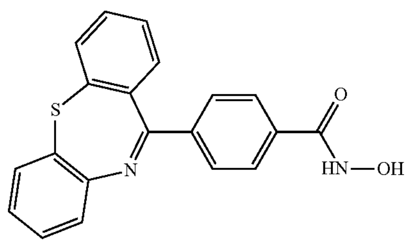 [SMILES: O=C(NO)c1ccc(C2=Nc3ccccc3Sc3ccccc32)cc1] | (Z)-4-(dibenzo[b,f][1,4]thiazepin-11-yl)-N-hydroxybenzamide | (DMSO-d6) δ (ppm): 11.37 (s, 1H), 9.15 (s, 1H), 7.86 (d, J = 8.8 Hz, 2H), 7.78 (d, J = 8.8 Hz, 2H), 7.62 (dd, J = 8.0, 1.0, 1H), 7.57-7.49 (m, 2H), 7.45-7.34 (m, 3H), 7.23-7.16 (m, 2H). LRMS(ESI): (calc) 346.08 (found) 347.24 (MH)+ | A, B, C |
| 64 | 162 | | 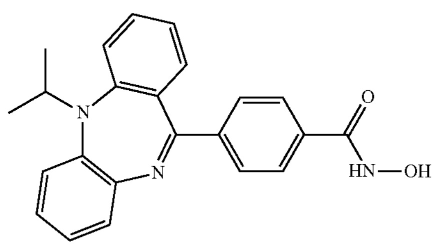 [SMILES: CC(C)N1c2ccccc2N=C(c2ccc(C(=O)NO)cc2)c2ccccc21] | (Z)-N-hydroxy-4-(5-isopropyl-5H-dibenzo[b,e][1,4]diazepin-11-yl)benzamide | (DMSO-d$_6$) δ (ppm): 11.35 (s, 1H), 9.15 (s, 1H), 7.86 (d, J = 8.4 Hz, 2H), 7.80 (d, J = 8.4 Hz, 2H), 7.54-7.50 (m, 1H), 7.32 (d, J = 7.6 Hz, 1H), 7.25 (d, J = 7.6 Hz, 1H), 7.22-7.18 (m, 2H), 7.15-7.09 (m, 2H), 7.02 (dd, J = 7.6, 1.2 Hz, 1H), 4.33-4.28 (m, 1H), 1.17 (t, J = 6.0 Hz, 3H), 1.09 (t, J = 6.0 Hz, 3H). LRMS (ESI): (calc) 371.16 (found) 372.5 (MH)+ | I, J, or N, G, T, A, B, C |

TABLE 2-continued

| Ex | Cpd | Starting Material | Structure | Name | Characterization | Preparative sequence |
|---|---|---|---|---|---|---|
| 65 | 163 | (2-fluoronitrobenzene + cyclopropylamine) | (structure) | (E)-4-((5-cyclopropyl-5H-dibenzo[b,e][1,4]diazepin-11-ylamino)methyl)-N-hydroxybenzamide | (DMSO-d$_6$) δ (ppm): 11.16 (s, 1H), 8.98 (s, 1H), 7.68 (d, J = 8.2 Hz, 2H), 7.57-7.49 (m, 1H), 7.48-7.34 (m, 5H), 7.22-7.16 (m, 1H), 7.18 (t, J = 5.4 Hz, 1H), 6.88-6.82 (m, 2H), 6.74-6.68 (m, 1H), 4.65-4.50 (m, 2H), 3.40-3.30 (m, 1H), 0.95-0.83 (m, 2H), 0.40-0.27 (m, 2H). LRMS(ESI): (calc) 398.17 (found) 399.5 (MH)+. | I, I, or N, G, T, A, R, C |
| 66 | 164 | (2-fluoro-4-nitrophenol + 2-fluoronitrobenzene) | (structure) | (Z)-4-(4-fluorodibenzo[b,f][1,4]oxazepin-11-yl)-N-hydroxybenzamide | (DMSO-d$_6$) δ (ppm): 11.39 (s, 1H), 9.19 (s, 1H), 7.89 (d, J = 8.8 Hz, 2H), 7.85 (d, J = 8.8 Hz, 2H), 7.66-7.62 (m, 1H), 7.48-7.46 (m, 4H), 7.01 (d, J = 7.6 Hz, 1H). LRMS(ESI): (calc) 348.09 (found) 349.4 (MH)+. | I, I, G, U, C |
| 67 | 165 | (2-fluoronitrobenzene + 2-methoxyethylamine) | (structure) | (Z)-N-hydroxy-4-(5-(2-methoxyethyl)-5H-dibenzo[b,e][1,4]diazepin-11-yl)benzamide | (DMSO-d$_6$) δ (ppm): 11.33 (s, 1H), 9.13 (s, 1H), 7.84 (d, J = 8.4 Hz, 2H), 7.72 (d, J = 8.4 Hz, 2H), 7.54-7.50 (m, 1H), 7.29-7.17 (m, 3H), 7.13-7.09 (m, 3H), 6.99 (dd, J = 7.6, 1.2, 1H), 3.97-3.91 (m, 1H), 3.82-3.76 (m, 1H), 3.52-3049 (m, 2H), 3.16 (s, 3H). LRMS(ESI): (calc) 387.16 (found) 388.5 (MH)+. | I, J or N, G, T, A, B, C |

| Ex | Cpd | Starting Material | Structure | Name | Characterization | Preparative sequence |
|---|---|---|---|---|---|---|
| 68 | 166 | [benzoic acid with ethylamine HCl] | [(E)-dibenzoxazepine linked via NH-CH2CH2-phenyl-C(O)NHOH] | (E)-4-(2-(dibenzo[b,f][1,4]oxazepin-11-ylamino)ethyl)-N-hydroxybenzamide | (DMSO-d6) δ (ppm): 8.29 (s, 0.65H, FA salt), 7.73 (d, J = 8.0 Hz, 2H), 7.63-7.59 (m, 1H), 7.50-7.45 (m, 3H), 7.32 (dd, J = 8.2, 1.0 Hz, 1H), 7.29 (dd, J = 7.6, 1.0 Hz, 1H), 7.23-7.10 (m, 4H), 3.85 (t, J = 7.2 Hz, 2H), 3.18 (t, J = 7.2 Hz, 2H). LRMS(ESI): (calc) 373.14 (found) 374.5 (MH)+. | Q, R, C |
| 69 | 167 | [4-fluoro-3-nitrobenzoic acid + methyl salicylate] | [pyridin-4-yl dibenzoxazepine-8-carboxamide with NHOH] | (Z)-N-hydroxy-11-(pyridin-4-yl)dibenzo[b,f][1,4]oxazepine-8-carboxamide | (MeOD) d(ppm) 1H: 8.71 (d, J = 5.9 Hz, 2H), 7.84-7.80 (m, 3H), 7.71-7.62 (m, 2H), 7.40-7.27 (m, 3H), 7.21-7.18 (m, 1H). LRMS(ESI): (calc) 331.10 (found) 332.2 (MH)+. | I, Q, J, K, A, B, C |
| 70 | 168 | [4-fluoro-3-nitrobenzoic acid + methyl salicylate] | [4-methylpiperazin-1-yl dibenzoxazepine-8-carboxamide with NHOH] | (E)-N-hydroxy-11-(4-methylpiperazin-1-yl)dibenzo[b,f][1,4]oxazepine-8-carboxamide | (MeOD) d(ppm) 1H: 7.56-7.51 (m, 1H), 7.48 (d, J = 2.1 Hz, 1H), 7.44-7.37 (m, 2H), 7.32-7.26 (m, 2H), 7.19 (d, J = 8.3 Hz, 1H), 3.58 (br s, 4H), 2.58 (br s, 4H), 2.36 (s, 3H). LRMS(ESI): (calc) 352.15 (found) 353.4 (MH)+. | I, Q, J, K, A, R, C |

TABLE 2-continued

| Ex | Cpd | Starting Material | Structure | Name | Characterization | Preparative sequence |
|---|---|---|---|---|---|---|
| 71 | 169 | 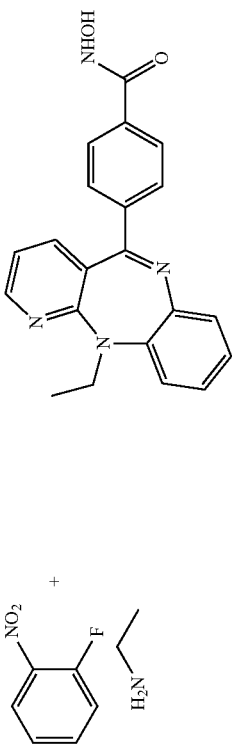 | 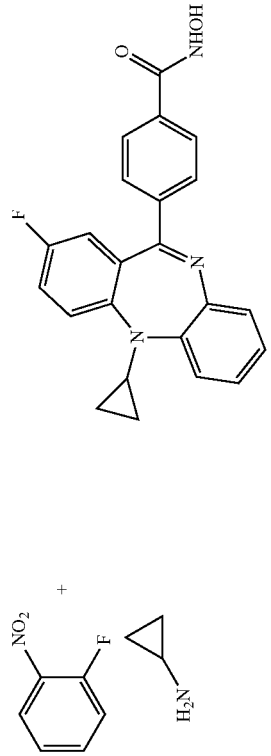 | (Z)-4-(11-ethyl-11H-benzo[b]pyrido[2,3-e][1,4]diazepin-5-yl)-N-hydroxybenzamide | ¹H NMR (DMSO-d₆) δ (ppm): 11.34 (br s, 1H), 9.15 (br s, 1H), 8.45 (dd, J = 4.7 and 1.8 Hz, 1H), 7.85 (d, J = 7.8 Hz, 2H), 7.72 (d, J = 8.4 Hz, 2H), 7.45 (dd, J = 7.5 and 1.8 Hz, 1H), 7.29 (dd, J = 7.6 and 1.6 Hz, 1H), 7.22 (td, J = 7.7 and 13.7 Hz, 1H), 7.19-7.08 (m, 3H), 4.08 (br s, 1H), 3.55 (br s, 1H), 1.15 (t, J = 6.9 Hz, 3H). LRMS(ESI): (calc) 358.14 (found) 359.2 (MH)+. | I, I, or N, G, T, A, B, C |
| 72 | 170 | 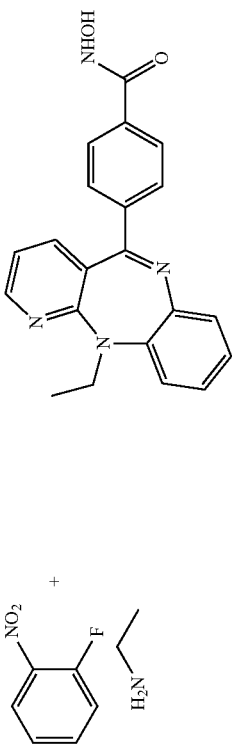 | 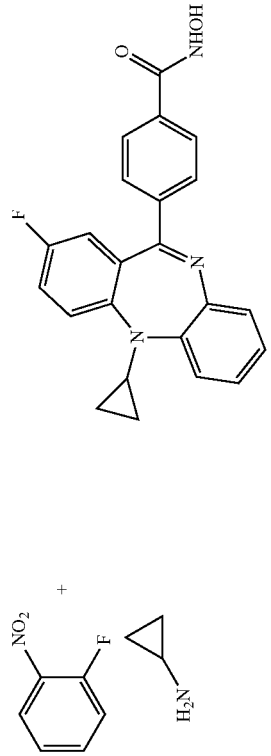 | (Z)-4-(5-cyclopropyl-2-fluoro-5H-dibenzo[b,e][1,4]diazepin-11-yl)-N-hydroxybenzamide | ¹H NMR (DMSO-d₆) δ (ppm): 11.33 (br s, 1H), 9.13 (br s, 1H), 7.83 (d, J = 8.2 Hz, 2H), 7.70 (d, J = 8.4 Hz, 2H), 7.49 (dd, J = 9.0 and 4.9 Hz, 1H), 7.40 (td, J = 8.5 and 2.9 Hz, 1H), 7.33 (d, J = 8.0 Hz, 1H), 7.25-7.17 (m, 2H), 7.11 (t, J = 7.0 Hz, 1H), 6.75 (dd, J = 9.0 and 2.9 Hz, 1H), 3.4 (m, 1H), 0.93-0.80 (m, 2H), 0.46-0.39 (m, 1H), 0.34-0.26 (m, 1H). LRMS(ESI): (calc) 387.14 (found) 388.5 (MH)+. | I, I, or N, G, T, A, B, C |
| 73 | 171 | 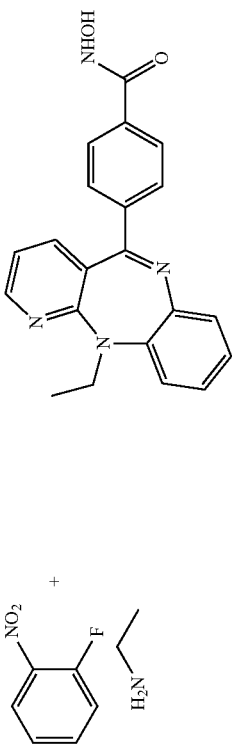 | 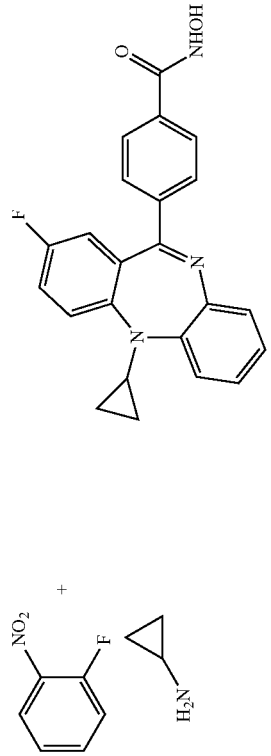 | (Z)-N-hydroxy-4-(11-isopropyl-11H-benzo[b]pyrido[2,3-e][1,4]diazepin-5-yl)benzamide | ¹H NMR (DMSO-d₆) δ (ppm): 11.3 (br s, 1H), 9.1 (br s, 1H), 8.50 (d, J = 3.3 Hz, 1H), 7.88 (d, J = 8.2 Hz, 2H), 7.78 (d, J = 8.2 Hz, 2H), 7.50 (d, J = 6.3 Hz, 1H), 7.29 (d, J = 7.4 HZ, 1H), 7.27-15 (m, 4H), 4.6-4.5 (m, 1H), 1.27 (d, J = 5.7 Hz, 3H), 1.14 (d, J = 5.9 Hz, 3H). LRMS(ESI): (calc) 372.16 (found) 373.2 (MH)+. | I, I, or N, G, T, A, B, C |

TABLE 2-continued

| Ex | Cpd | Starting Material | Name | Characterization | Preparative sequence |
|---|---|---|---|---|---|
| 75 | 172 | | (Z)-6-(4-(dibenzo[b,f][1,4]oxazepin-11-yl)benzamidooxy)-3,4,5-trihydroxytetrahydro-2H-pyran-2-carboxylic acid | ¹H NMR (MeOH-d₄) δ (ppm): 7.94 (d, J = 8.4 Hz, 2H), 7.87 (d, J = 8.4 Hz, 2H), 7.60 (ddd, J = 7.6, 7.2, 1.6 Hz, 1H), 7.43-7.41 (m, 1H), 7.35 (dd, J = 8.4, 0.8 Hz, 1H), 7.30-7.22 (m, 4H), 7.15 (dd, J = 7.6, 1.6 Hz, 1H), 4.81 (d, J = 7.6 Hz, 1H), 3.95 (d, J = 9.4 Hz, 1H), 3.59-3.44 (m, 3H). LRMS(ESI): (calc) 506.13 (found) 507.5 (MH)+. | G, U, W, G, W |
| 76 | 173 | | (Z)-N-hydroxy-4-(11-(3-morpholinopropyl)-11H-benzo[b]pyrido[2,3-e][1,4]diazepin-5-yl)benzamide | ¹H NMR (MeOH-d₄) δ (ppm)-formate salt: 8.43 (d, J = 4.3 Hz, 1H), 8.31 (s, 1H), 7.85 (d, J = 8.2 Hz, 2H), 7.78 (d, J = 8.2 Hz, 2H), 7.45 (d, J = 7.9 Hz, 1H), 7.33 (dd, J = 7.7 and 1.2 Hz, 1H), 7.28 (t, J = 9.0 Hz, 1H), 7.22-7.10 (m, 2H), 4.32-4.20 (m, 1H), 3.78-3.64 (m, 5H), 2.86-2.78 (m, 2H), 2.78-2.66 (m, 4H), 2.06-1.94 (m, 2H). LRMS(ESI): (calc) 457.21 (found) 458.5 (MH)+. | I, J, or N, G, T, A, B, C |
| 77 | 174 | | (Z)-N-hydroxy-4-(11-(2-morpholinoethyl)-11H-benzo[b]pyrido[2,3-e][1,4]diazepin-5-yl)benzamide | ¹H NMR (MeOH-d₄) δ (ppm)-formate salt: 8.44 (d, J = 4.3 Hz, 1H), 8.32-8.24 (m, 1H), 7.85 (d, J = 8.2 Hz, 2H), 7.79 (d, J = 8.2 Hz, 2H), 7.46 (d, J = 7.9 Hz, 1H), 7.33 (dd, J = 7.7 and 1.2 Hz, 1H), 7.28 (t, J = 9.0 Hz, 1H), 7.20 (d, J = 7.6 Hz, 1H), 7.18-7.12 (m, 2H), 4.60-4.50 (m, 1H), 3.92-3.82 (m, 1H), 3.66-3.58 (m, 4H), 3.05-2.96 (m, 2H), 2.90-2.78 (m, 4H). LRMS(ESI): (calc) 443.20 (found) 444.5 (MH)+. | I, J, or N, G, T, A, B, C |

TABLE 2-continued

| Ex | Cpd | Starting Material | Structure | Name | Characterization | Preparative sequence |
|---|---|---|---|---|---|---|
| 78 | 175 | (2-fluoro-nitrobenzene + cyclopropylmethylamine) | (structure shown) | (Z)-4-(11-(cyclopropylmethyl)-11H-benzo[b]pyrido[2,3-e][1,4]diazepin-5-yl)-N-hydroxybenzamide | ¹H NMR (DMSO-d₆) δ (ppm): 11.34 (s, 1H), 9.14 (s, 1H), 8.43 (dd, J = 5.1 and 1.8 Hz, 1H), 7.85 (d, J = 8.3 Hz, 2H), 7.71 (d, J = 8.4 Hz, 2H), 7.45 (dd, J = 7.7 and 1.8 Hz, 1H), 7.27 (dd, J = 7.4 and 1.4 Hz, 1H), 7.20 (td, J = 7.4 and 1.6 Hz, 1H), 7.18-7.09 (m, 3H), 4.10-4.00 (m, 1H), 3.40-3.20 (M, 1H), 1.13-1.04 (m, 1H), 0.44-0.31 (m, 2H), 0.30-0.15 (m, 2H). LRMS(ESI): (calc) 384.16 (found) 385.4 (MH)+. | I, J, or N, G, T, A, B, C |
| 79 | 176 | (2-fluoro-nitrobenzene + 2-morpholinoethylamine) | (structure shown) | (Z)-N-hydroxy-4-(5-(2-morpholinoethyl)-5H-dibenzo[b,e][1,4]diazepin-11-yl)benzamide | ¹H NMR (MeOH-d₄) δ (ppm)-formate salt: 8.26 (s, 1H), 7.87-7.49 (m, 4H), 7.56-7.50 (m, 1H), 7.31-7.21 (m, 3H), 7.18-7.09 (m, 3H), 7.01 (dd, J = 7.8 and 2.2 Hz, 1H), 4.12-3.95 (m, 2H), 3.60-3.55 (m, 4H), 2.99-2.83 (m, 2H), 2.82-2.70 (m, 4H). LRMS(ESI): (calc) 442.20 (found) 443.4 (MH)+. | I, J, or N, G, T, A, B, C |

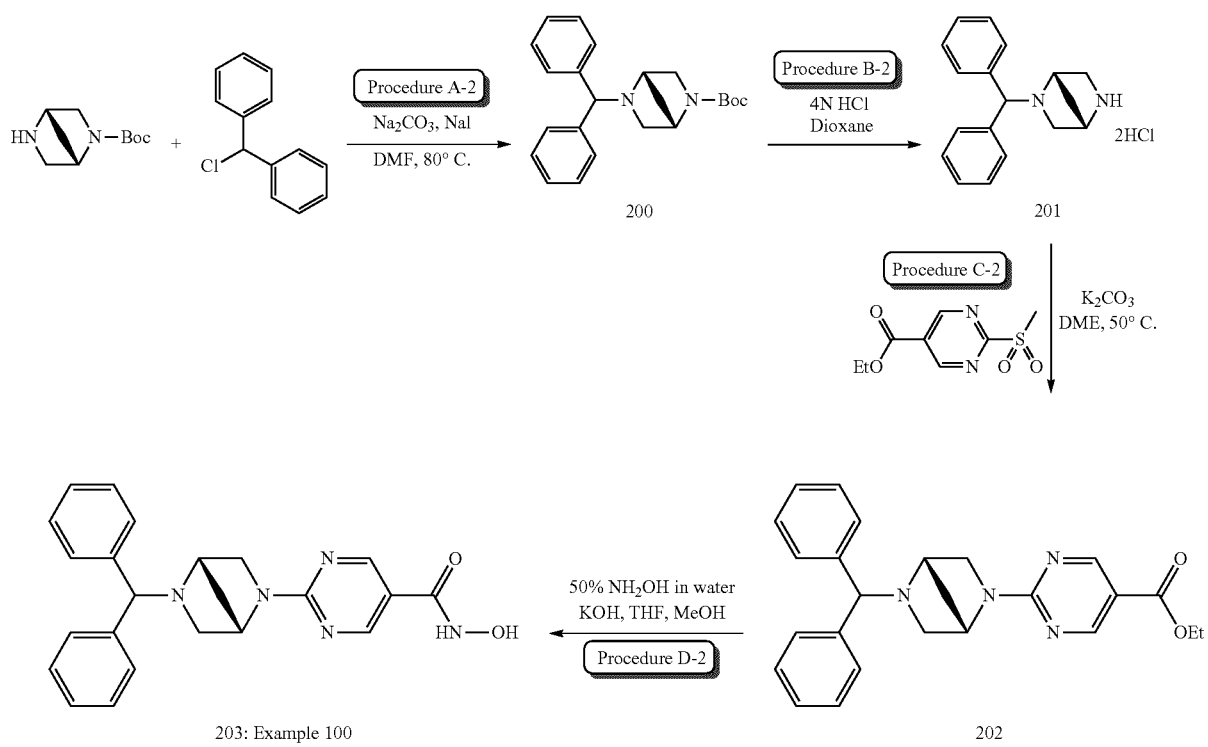

Scheme 30

Example 100

2-((1S,4S)-5-Benzhydryl-2,5-diazabicyclo[2.2.1]heptan-2-yl)-N-hydroxypyrimidine-5-carboxamide (203)

Step 1: (1S,4S)-tert-Butyl 5-benzhydryl-2,5-diazabicyclo[2.2.1]heptane-2-carboxylate (200)

To a stirred solution of chlorodiphenylmethane (0.39 g, 1.94 mmol) in DMF (5 mL) was added (1S,4S)-diazabicyclo[2,2,1]-heptane (0.5 g, 2.52 mmol), $Na_2CO_3$ (0.41 g, 3.88 mmol) and NaI (0.31 g, 2.04 mmol). The mixture was stirred for 2 h at 110° C., then cooled to room temperature and diluted with 75% AcOEt in Hexanes. The mixture was washed with water, brine, dried ($Na_2SO_4$), filtered and concentrated. The residue was purified by silica gel column chromatography with gradient of EtOAc (0-30%) in hexanes to afford 200 (0.5 g, 71%) as a beige solid. LRMS (ESI): (calc) 364.2. (found) 365.5 (MH)+.

Step 2: (1S,4S)-2-Benzhydryl-2,5-diazabicyclo[2.2.1]heptane2HCl (201)

A solution of compound 200 (0.5 g, 1.37 mmol) in 4N HCl in dioxane (5 mL) was stirred for 1 h at room temperature and then concentrated. The residue was purified by trituration with $Et_2O$ and filtered to afford 201 (0.24 g, 59%) as a beige solid. LRMS (ESI): (calc) 264.2. (found) 265.3 (MH)+.

Steps 3: ethyl 2-((1S,4S)-5-benzhydryl-2,5-diazabicyclo[2.2.1]heptan-2-yl)pyrimidine-5-carboxylate (202)

Title compound 201 (0.250 g, 0.741 mmol), ethyl 2-(methylsulfonyl)pyrimidine-5-carboxylate (0.122 g, 0.529 mmol), potassium carbonate (0.280 g, 2.645 mmol) and DME (5 mL) were combined. The reaction mixture was stirred at 50° C. for 2 hours. The mixture was cooled down and quench with water. The aqueous layer was extracted twice with ethyl acetate. The combined organic extracts were washed with brine, dried over sodium sulfate, filtered and evaporated. The crude was purified by flash chromatography eluting with 0% to 30% ethyl acetate in hexanes to afford title compound 202 (0.141 g, 64%). LRMS (ESI): (calc) 414.21. (found) 415.0 (MH)+.

Step 4: ((1S,4S)-5-Benzhydryl-2,5-diazabicyclo[2.2.1]heptan-2-yl)-N-hydroxypyrimidine-5-carboxamide (203)

Title compound 202 (0.140 g, 0.338 mmol), potassium hydroxide (4M, 0.34 mL), hydroxylamine (50% in water, 0.34 mL), MeOH (2 mL) and THF (2 mL) were combined and the reaction mixture was stirred for 1 hour. HCL 3N was added to adjust the pH to 8. After 15 minutes stirring, the solid was filtered and well dried to afford the title compound 203 (0.107 g, 79%) as a white powder. 1H NMR (DMSO-d6) δ (ppm): 7.80 (dd, J=8.0, 2.0 Hz, 1H), 7.61 (ddd, J=8.4, 6.8, 1.2 Hz, 1H), 7.46-7.41 (m, 3H), 7.38-7.30 (m, 3H), 3.62 (t, J=7.2 Hz, 2H), 2.06 (t, J=7.2 Hz, 2H), 1.61-1.51 (m, 4H), 1.44-1.28 (m, 4H). LRMS: (calc) 390.12. (found) 391.3 (MH)$^+$.

Scheme 31

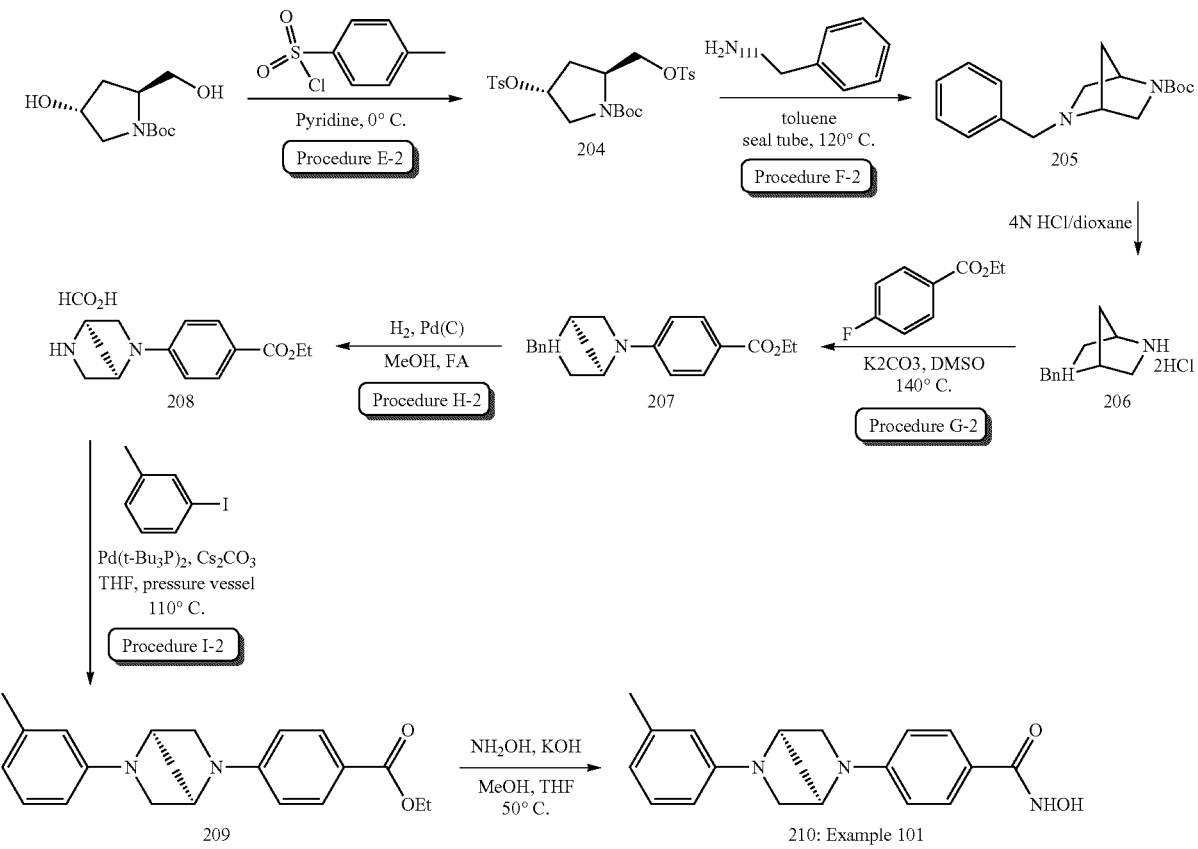

Example 101

N-hydroxy-4-((1R,4R)-5-m-tolyl-2,5-diazabicyclo[2.2.1]heptan-2-yl)benzamide (210)

Step 1: (2S,4R)-tert-butyl 4-(tosyloxy)-2-(tosyloxymethyl)pyrrolidine-1-carboxylate (204)

(2S,4R)-tert-butyl 4-hydroxy-2-(hydroxymethyl)pyrrolidine-1-carboxylate (5.40 g, 25.84 mmol) and 4-methylbenzene-1-sulfonyl chloride (14.22 g, 74.6 mmol) were combined in pyridine (50 mL) at 0° C. and store in the refrigerator for 3 days. The reaction mixture was concentrated to half the volume under vacuo and some water (~300 mL) was added slowly. The mixture was stirred 1 h until a white solid formed. The solid was filtered and dried on the pump on high-vacuum over night. The solid was recrystallized from MeOH (~20 ml) and water (few drops) to afford title compound 204 (6.40 g, 49%). LRMS: (calc) 525.15. (found) 426.4 (MH-Boc)$^+$.

Step 2: tert-butyl 5-benzyl-2,5-diazabicyclo[2.2.1]heptane-2-carboxylate (205)

A stirring solution of title compound 204 (3 g, 5.71 mmol) and benzylamine (1.78 mL, 16.27 mmol) in toluene (50 mL) was heated to 120° C. in a sealed tube for 18 h. The mixture was cooled down, refrigerated for 1 h and the PTSA formed was filtered off and rinsed with cold toluene. The filtrate was diluted with a diluted solution of bicarbonate in water (25 mL) and extracted with ethyl acetate (×3). The combined organic layers were washed with brine, dried over $Na_2SO_4$, filtered and concentrated. The crude was purified by flash chromatography: 40 g $SiO_2$, 0% to 100% ethyl acetate in hexanes over 30 min to afford title compound 205 (0.56 g, 36%). LRMS: (calc) 288.18. (found) 289.3 (MH)$^+$.

Step 3: 2-benzyl-2,5-diazabicyclo[2.2.1]heptane dihydrochloride (206)

Using Procedure B-2 (Table 3) with compound 205 the title compound 106 was obtained (0.5 g, 99%) as a beige solid foam. LRMS: (calc) 188.13. (found) 189.1 (MH)$^+$.

Step 4: ethyl 4-((1R,4R)-5-benzyl-2,5-diazabicyclo[2.2.1]heptan-2-yl)benzoate (207)

A stirring solution of title compound 206 (0.5 g, 1.914 mmol) and ethyl 4-fluorobenzoate (0.421 ml, 2.87 mmol) in DMSO (19.14 mL) was stirred at 140° C. overnight. The mixture was cooled down and poured over a diluted aqueous solution of bicarbonate and extracted with ethyl acetate (twice). The combined organic extracts were washed with brine, dried over $Na_2SO_4$, filtered and evaporated. The crude was purified by flash chromatography: 0% to 60% ethyl acetate in hexanes over 20 min on 20 g $SiO_2$ to afford title compound 207 (0.33 g, 51%) as beige oil. LRMS: (calc) 336.18. (found) 337.4 (MH)$^+$.

Step 5: ethyl 4-((1R,4R)-2,5-diazabicyclo[2.2.1]heptan-2-yl)benzoate formate (208)

Title compound 207 (0.32 g, 0.878 mmol) and Pd/C (0.093 g, 0.088 mmol) were combined in methanol (16.73 mL) and formic acid (0.836 mL). The reaction mixture was stirred at reflux for 2 h. The mixture was filtered and concentrated to afford title compound 208 (0.278 g, 99%) as a clear oil. LRMS: (calc) 246.14. (found) 247.3 (MH)+.

Step 6: ethyl 4-((1R,4R)-5-m-tolyl-2,5-diazabicyclo[2.2.1]heptan-2-yl)benzoate (109)

To a stirring solution of title compound 208 (0.145 g, 0.496 mmol), cesium carbonate (0.485 g, 1.488 mmol), bis(tri-t-butylphosphine)palladium (0) (0.013 g, 0.025 mmol) in THF (15 mL) was added 3-iodotoluene (0.083 mL, 0.645 mmol) and the resulting suspension was placed under N₂ and stirred at 110° C. overnight. The reaction was cooled, filtered through Celite® and washed with THF. The filtrate was evaporated to afford a brown residue. This residue was dissolved in DCM and purified by chromatography: 0% to 50% ethyl acetate in hexanes over 30 minutes to afford title compound 209 (110 mg, 66%) as an oil. LRMS: (calc) 336.18. (found) 337.5 (MH)+.

Step 7: N-hydroxy-4-((1R,4R)-5-m-tolyl-2,5-diazabicyclo[2.2.1]heptan-2-yl)benzamide (210)

Using Procedure D-2 (Table 3) with compound 209 the title compound 210 was obtained (50 mg, 47%) as grey solid. (MeOH-d₄) δ (ppm): 7.55 (d, J=8.8 Hz, 2H), 6.99 (t, J=7.6 Hz, 1H), 6.57 (d, J=8.8 Hz, 2H), 6.43 (d, J=7.5 Hz, 1H), 6.42-6.35 (m, 2H), 4.61 (s, 1H), 4.55 (s, 1H), 3.60 (t, J=9.0 Hz, 2H), 3.23 (d, J=9.0 Hz, 1H), 3.08 (d, J=8.8 Hz, 1H), 2.22 (s, 3H), 2.18-2.03 (m, 2H). LRMS: (calc) 323.16. (found) 324.4 (MH)+.

Example 102

N-hydroxy-2-((1S,4S)-5-(3-(trifluoromethyl)benzoyl)-2,5-diazabicyclo[2.2.1]heptan-2-yl)pyrimidine-5-carboxamide (214)

Step 1: (1S,4S)-tert-butyl 5-(5-(ethoxycarbonyl)pyrimidin-2-yl)-2,5-diazabicyclo[2.2.1]heptane-2-carboxylate (211)

Using Procedure C-2 (Table 3) with (1S,4S)-tert-butyl 2,5-diazabicyclo[2.2.1]heptane-2-carboxylate and ethyl 2-(methylsulfonyl)pyrimidine-5-carboxylate the title compound 211 was obtained (1.11 g, 63%) as white solid. ¹H NMR (400 MHz, CDCl₃) δ (ppm): 8.84-8.82 (m, 2H), 5.08 (s, 1H), 4.70-4.55 (m, 1H), 4.34 (q, J=7.1 Hz, 2H), 3.70-3.34 (m, 4H), 2.02-1.94 (m, 2H), 1.47-1.43 (m, 9H), 1.37 (t, J=7.1 Hz, 3H).

Step 2: ethyl 2-((1S,4S)-2,5-diazabicyclo[2.2.1]heptan-2-yl)pyrimidine-5-carboxylate (212)

Using Procedure B-2 (Table 3) with compound 211 the title compound 212 was obtained. LRMS: (calc) 248.13. (found) 249.2 (MH)+.

Step 3: ethyl 2-((1S,4S)-5-(3-(trifluoromethyl)benzoyl)-2,5-diazabicyclo[2.2.1]heptan-2-yl)pyrimidine-5-carboxylate (213)

To a stirring suspension of title compound 212 (160 mg, 0.562 mmol) in pyridine (3 mL) was added benzoyl chloride (0.10 mL, 0.674 mmol) drop wise. The reaction mixture was

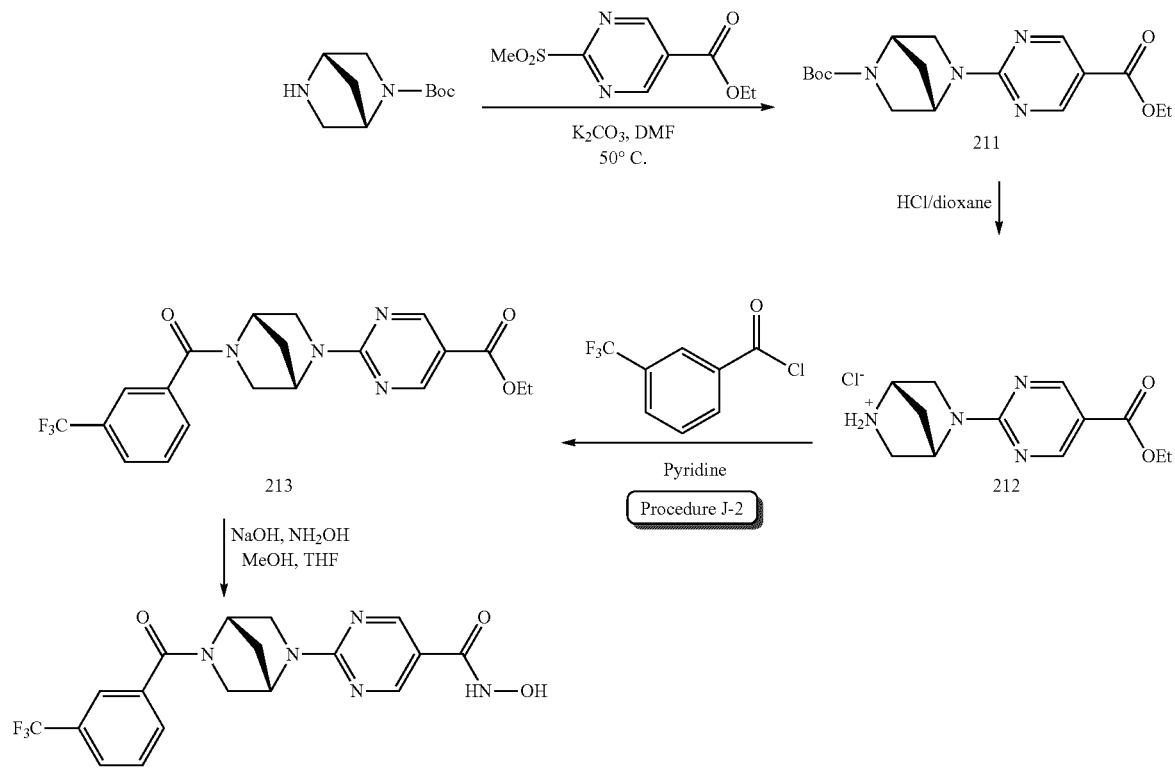

Scheme 32

214: Example 102 stirred overnight at room temperature then evaporated. The crude was purified by ISCO (10% to 90% ethyl acetate in hexanes) to afford title compound 213 (202 mg, 85%) as a white foam. LRMS: (calc) 420.14. (found) 421.2 (MH)+.

Step 4: N-hydroxy-2-((1S,4S)-5-(3-(trifluoromethyl) benzoyl)-2,5-diazabicyclo[2.2.1]heptan-2-yl)pyrimidine-5-carboxamide (214)

Using Procedure D-2 (Table 3) with compound 213 the title compound 214 was obtained (100 mg, 51%) as white solid. 1H NMR (CD3OD) δ (ppm) 1H, 8.70 (bs, 1H), 8.64 (bs, 1H), 7.62-7.85 (m, 4H), 5.20 (s, 1H), 5.10 (m, 1H), 4.53 (s, 1H), 3.56-3.80 (m, 3H), 2.13 (m, 2H). LRMS (ESI): (calc.) 407.1. (found) 406.3 (M)–.

Step 2: (1S,4S)-5-(3-(trifluoromethyl)phenyl)-5-aza-2-azoniabicyclo[2.2.1]heptane chloride (216)

Using Procedure B-2 (Table 3) with compound 215 the title compound 216 was obtained (7.17 g, 100%) as yellow solid. LRMS: (calc) 242.0. (found) 243.2 (MH)+.

Step 3: ethyl 2-((1S,4S)-5-(3-(trifluoromethyl)phenyl)-2,5-diazabicyclo[2.2.1]heptan-2-yl)thiazole-5-carboxylate (217)

A suspension of ethyl 2-bromothiazole-5-carboxylate (0.125 mL, 0.834 mmol), title compound 216 (425 mg, 1.525 mmol), and triethylamine (0.465 mL, 3.34 mmol) in dioxane (1.525 mL) was sonicated for 1 h. More THF (2 mL) was

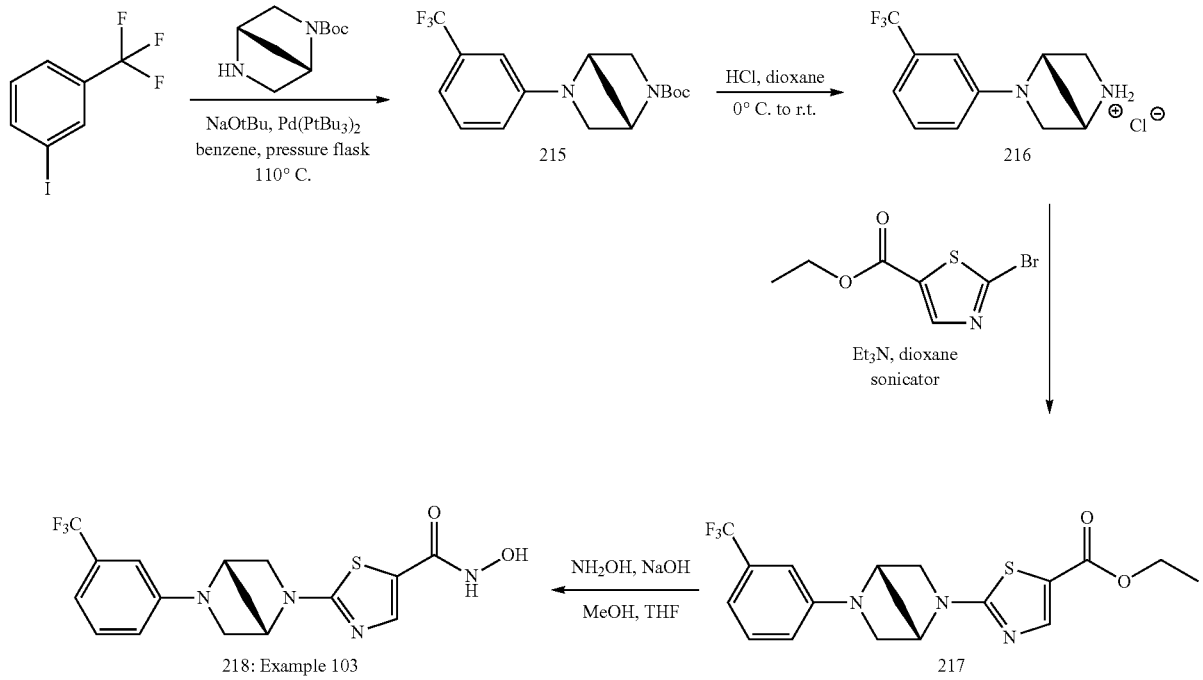

Scheme 33

Example 103

N-hydroxy-2-((1S,4S)-5-(3-(trifluoromethyl)phenyl)-2,5-diazabicyclo[2.2.1]heptan-2-yl)thiazole-5-carboxamide (218)

Step 1: (1S,4S)-tert-butyl 5-(3-(trifluoromethyl)phenyl)-2,5-diazabicyclo[2.2.1]heptane-2-carboxylate (215)

Using Procedure I-2 (Table 3) with 1-iodo-3-(trifluoromethyl)benzene and (1S,4S)-tert-butyl 2,5-diazabicyclo[2.2.1]heptane-2-carboxylate the title compound 215 was obtained (8.88 g, 70%) as white solid. LRMS: (calc) 342.16. (found) 343.3 (MH)+.

added and the mixture was sonicated for another 2 h. The mixture was partitioned between water and ethyl acetate and the organic layer was washed with water (×2) then with brine. The organic extract was dried (magnesium sulfate) and solvent evaporated. The residue was purified via ISCO (0-50% Hex/EtOAc; 40 g silica gel column) to obtain title compound 217 (316 mg, 95%) as a white foam. LRMS: (calc) 397.11. (found) 398.1 (MH)+.

Step 4: N-hydroxy-2-((1S,4S)-5-(3-(trifluoromethyl)phenyl)-2,5-diazabicyclo[2.2.1]heptan-2-yl)thiazole-5-carboxamide (218)

Using Procedure D-2 (Table 3) with compound 217 the title compound 218 was obtained (124 mg, 82%) as off-white solid. 1H NMR (CD3OD) δ (ppm): 7.66 (bs, 1H), 7.33 (t, J=8 Hz, 1H), 6.82-6.91 (m, 3H), 4.76 (s, 1H), 4.74 (s, 1H), 3.70 (dd, J=9.2 Hz, 18 Hz, 2H), 3.40 (d, J=9.6 Hz, 1H), 3.23 (d, J=9.2 Hz, 1H), 2.19 (s, 2H). LRMS (ESI): (calc.) 384.09. (found) 383.2 (M)–.

Scheme 34

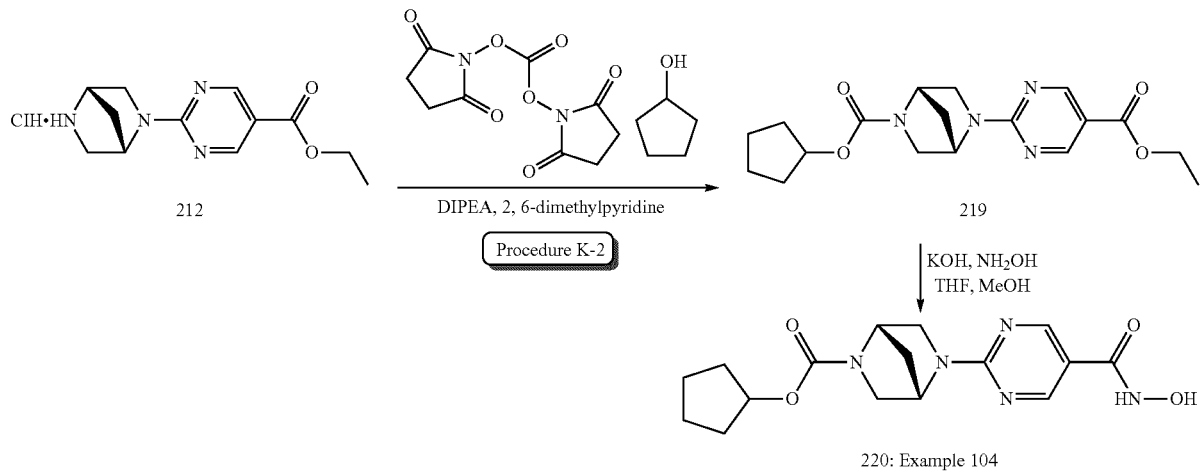

Example 104

(1S,4S)-cyclopentyl 5-(5-(hydroxycarbamoyl)pyrimidin-2-yl)-2,5-diazabicyclo[2.2.1]heptane-2-carboxylate (220)

Step 1: (1S,4S)-cyclopentyl 5-(5-(ethoxycarbonyl)pyrimidin-2-yl)-2,5-diazabicyclo[2.2.1]heptane-2-carboxylate (219)

To a solution of cyclopentanol (0.096 mL, 1.054 mmol) and DSC (0.225 g, 0.878 mmol) in ACN (3 mL) and DCM (3 mL) at 0° C. was added 2,6-lutidine (0.102 mL, 0.878 mmol). The mixture was stirred at room temperature, overnight. To the resulting mixture was added a solution of title compound 212 (0.25 g, 0.878 mmol) and DIPEA (0.306 mL, 1.756 mmol) in DCM. The mixture was stirred for 1 h at room temperature then at 45° C. overnight. More of the DCS solution substituting bases for DIPEA was made and the mixture was matured 4 h before adding to reaction mixture. The reaction mixture was stirred at 45° C. overnight then concentrated and purified by flash chromatography: 40 g SiO2, EA/H 0% to 50% over 20 min to afford title compound 219 (83 mg, 26%) as a clear oil that solidified upon standing. LRMS: (calc) 360.18. (found) 361.3 (MH)+. $^1$H NMR (CDCl$_3$, 400 MHz) δ (ppm): 8.84-8.83 (m, 2H), 5.10 (m, 2H), 4.73-4.58 (m, 1H), 4.34 (q, J=7.1 Hz, 2H), 3.72-3.35 (m, 4H), 2.00-1.60 (m, 10H), 1.37 (t, J=7.0 Hz, 3H).

Step 2: (1S,4S)-cyclopentyl 5-(5-(hydroxycarbamoyl)pyrimidin-2-yl)-2,5-diazabicyclo[2.2.1]heptane-2-carboxylate (220)

Using Procedure D-2 (Table 3) with compound 219 the title compound 220 was obtained (62 mg, 78%) as a white solid. $^1$H NMR (DMSO-d$_6$) δ (ppm): 11.07 (s, 1H), 9.00 (s, 1H), 8.65 (s, 2H), 4.93 (m, 2H), 4.49 (d, J=8.2 Hz, 1H), 3.60-3.50 (m, 1H), 3.49-3.25 (m, 2H), 3.24-3.10 (m, 1H), 1.93 (d, J=10.4 Hz, 2H), 1.85-1.40 (m, 8H). LRMS (ESI): (calc.) 347.2. (found) 348.3 (MH)+.

Scheme 35

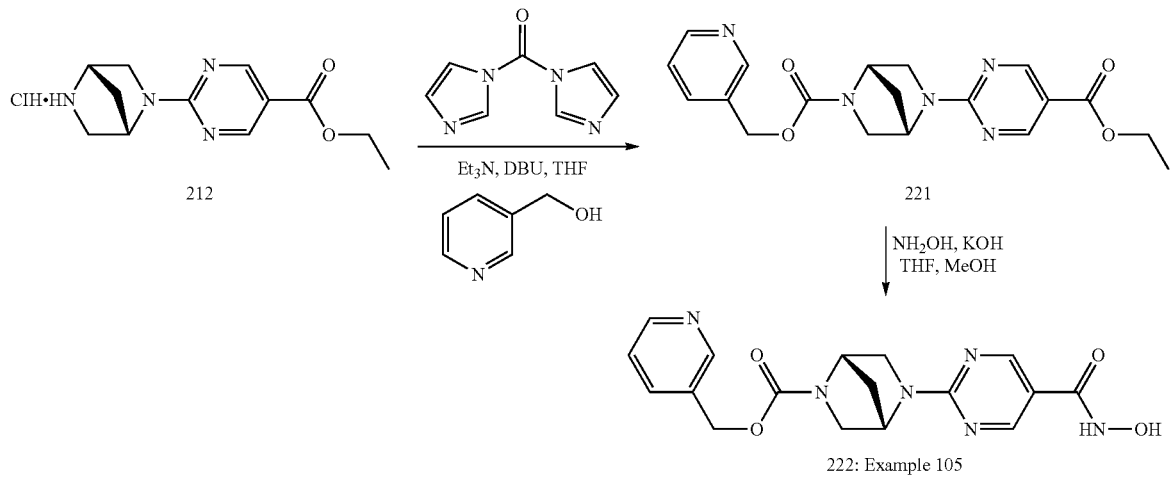

Example 105

(1S,4S)-pyridin-3-ylmethyl 5-(5-(hydroxycarbamoyl)pyrimidin-2-yl)-2,5-diazabicyclo[2.2.1]heptane-2-carboxylate (222)

Step 1: (1S,4S)-pyridin-3-ylmethyl 5-(5-(ethoxycarbonyl)pyrimidin-2-yl)-2,5-diazabicyclo[2.2.1]heptane-2-carboxylate (221)

To a solution of pyridin-3-ylmethanol (0.086 mL, 0.878 mmol) in THF (2.5 mL) was added N,N-carbonyldiimidazole (0.142 g, 0.878 mmol). After stirring for 1 h a solution of TEA (0.245 mL, 1.756 mmol), DBU (0.132 mL, 0.878 mmol) and the title compound 212 (0.25 g, 0.878 mmol) in THF (2.5 mL) was added. The reaction mixture was stirred overnight at 45° C. The mixture was cooled down and diluted with ethyl acetate. The organic layer was washed with water, brine, dried over $Na_2SO_4$, filtered and concentrated. The crude was purified by flash chromatography (twice): 40 SiO2, MeOH/EA 0% to 20% over 20 min to afford title compound 221 (80 mg, 24%) as an oil. 1H NMR (400 MHz, $CDCl_3$) δ (ppm): 8.81-8.77 (m, 2H), 8.60-8.57 (m, 2H), 7.83-7.76 (m, 1H), 7.42-7.35 (m, 1H), 5.21-5.05 (m, 1H), 5.21 (s, 2H), 4.79 (s, 1H), 4.72-4.64 (m, 1H), 4.31 (qd, J=7.1, 1.8 Hz, 2H), 3.69-3.41 (m, 3H), 1.98 (d, J=8.0 Hz, 2H), 1.34 (td, J=7.1, 2.5 Hz, 3H).

Step 2: (1S,4S)-pyridin-3-ylmethyl 5-(5-(hydroxycarbamoyl)pyrimidin-2-yl)-2,5-diazabicyclo[2.2.1]heptane-2-carboxylate (222)

Using Procedure D-2 (Table 3) with compound 221 the title compound 222 was obtained (30 mg, 39%) as a white solid. ¹H NMR (MeOD-d4) δ (ppm): 8.66 (s, 2H), 8.59 and 8.52 (2s, 1H), 8.50 and 8.46 (2d, J=4.5 Hz, 1H), 7.90 and 7.82 (2d, J=7.8 Hz, 1H), 7.50-7.39 (m, 1H), 5.21 (s, 1H), 5.07 (s, 1H), 5.20-5.08 (m, 1H), 4.69 (d, J=9.8 Hz, 1H), 3.66-3.36 (m, 4H), 2.05-1.99 (m, 2H) LRMS (ESI): (calc.) 370.1. (found) 371.2 (MH)+.

Scheme 36

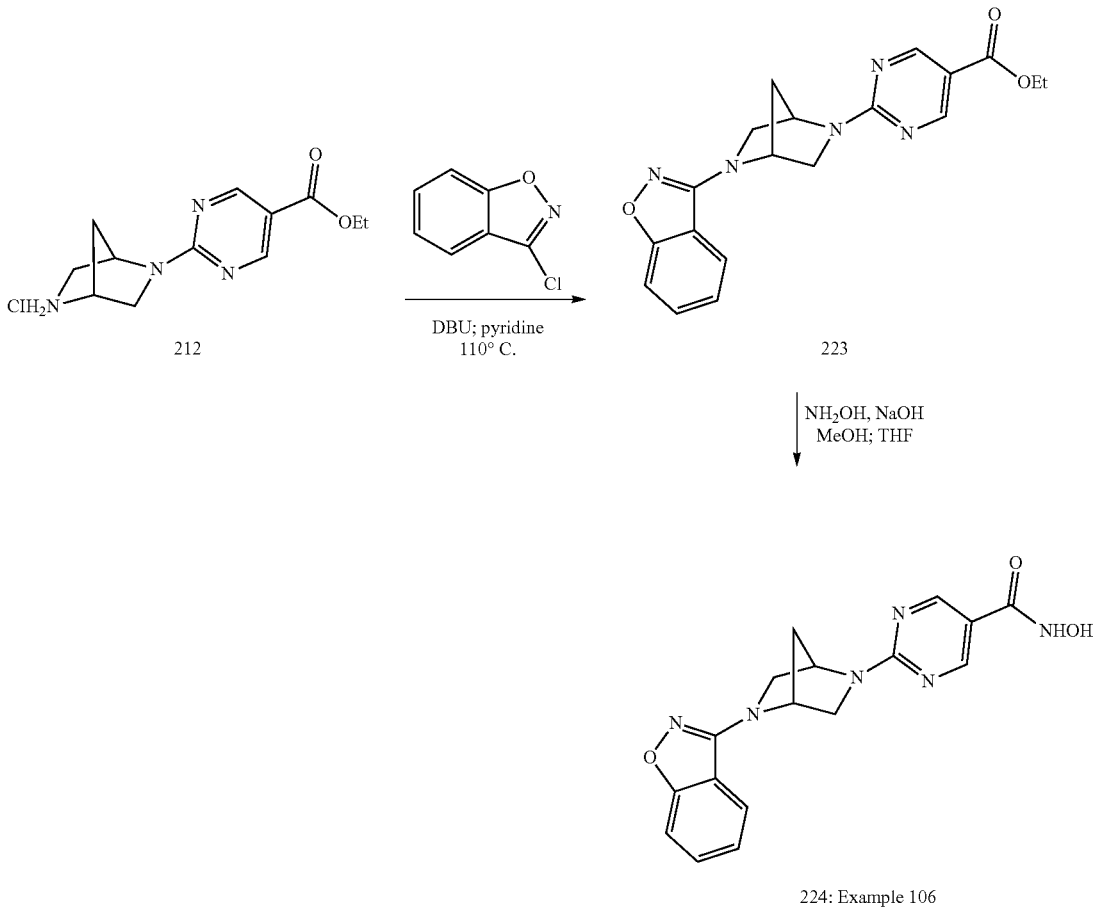

224: Example 106

Example 106

2-((1S,4S)-5-(benzo[d]isoxazol-3-yl)-2,5-diazabicyclo[2.2.1]heptan-2-yl)-N-hydroxypyrimidine-5-carboxamide (224)

Step 1: ethyl 2-((1S,4S)-5-(benzo[d]isoxazol-3-yl)-2,5-diazabicyclo[2.2.1]heptan-2-yl)pyrimidine-5-carboxylate (223)

Using Procedure G-2 (Table 3) with compound 212 the title compound 223 was obtained (53.6 mg, 21%) as a white solid. LRMS (ESI): (calc.) 365.15. (found) 366.3 (MH)+.

261

Step 2: 2-((1S,4S)-5-(benzo[d]isoxazol-3-yl)-2,5-diazabicyclo[2.2.1]heptan-2-yl)-N-hydroxypyrimidine-5-carboxamide (25)

Using Procedure D-2 (Table 1) with compound 223 the title compound 224 was obtained (35.6 mg, 69%) as an off-white solid. $^1$H NMR (400 MHz, CD$_3$OD) δ (ppm): 8.66 (s, 1H), 8.59 (s, 1H), 7.82 (d, J=8 Hz, 1H), 7.53 (t, J=7.6 Hz, 1H), 7.41 (d, J=8.4 Hz, 1H), 7.25 (t, J=7.6 Hz, 1H), 5.20 (s, 1H), 3.99 (d, J=9.2 Hz, 1H), 3.80 (d, J=10.8 Hz, 1H), 3.68 (m, 2H), 2.20 (dd, J=10 Hz, 13.6 Hz, 2H). LRMS (ESI): (calc.) 352.1. (found) 351.0 (M−H).

262

Step 2: methyl 2-fluoro-4-((1S,4S)-5-(3-(trifluoromethyl)phenyl)-2,5-diazabicyclo[2.2.1]heptan-2-yl)benzoate (226)

A stirring solution of title compound 225 (250 mg 0.657 mmol), 2N HCl in ether (1 mL, 2.00 mmol) and methanol (25 mL) was refluxed over the weekend. The mixture was concentrated and the residue was purified by chromatography: 20 g SiO$_2$, dry loaded on a samplet, 0% to 50% ethyl acetate in hexanes over 20 minutes to afford title compound 226 (120 mg, 46%) as a white foam. LRMS (ESI): (calc.) 394.13. (found) 395.3 (MH)+.

Scheme 37

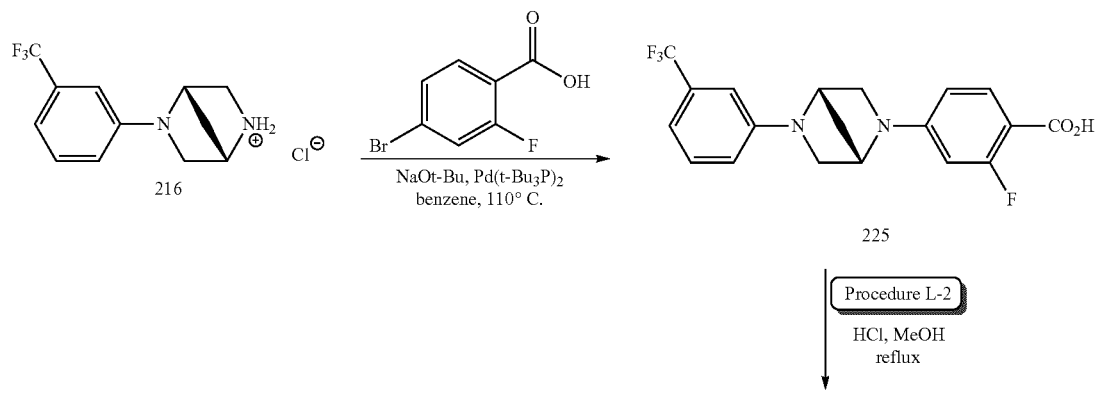

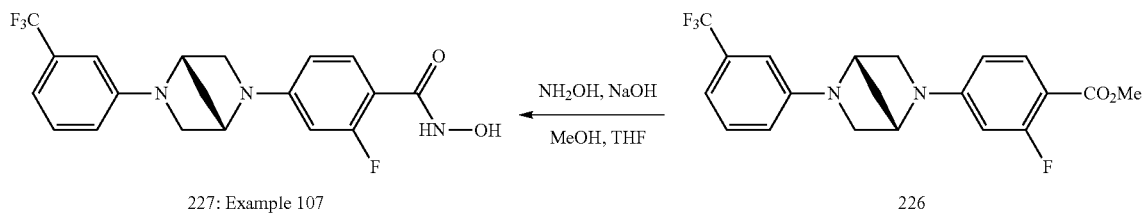

Example 107

2-fluoro-N-hydroxy-4-((1S,4S)-5-(3-(trifluoromethyl)phenyl)-2,5-diazabicyclo[2.2.1]heptan-2-yl)benzamide (227)

Step 1: 2-fluoro-4-((1S,4S)-5-(3-(trifluoromethyl)phenyl)-2,5-diazabicyclo[2.2.1]heptan-2-yl)benzoic acid (225)

Using Procedure I-2 (Table 3) with compound 216 and 4-bromo-2-fluorobenzoic acid the title compound 225 was obtained (250 mg, 75%) as a brown paste. LRMS (ESI): (calc.) 380.11. (found) 377.3 (M-3).

$^1$H NMR (CDCl$_3$, 400 MHz) δ (ppm): 7.77 (t, J=8.6 Hz, 1H), 7.28 (t, J=7.8 Hz, 1H), 6.92 (d, J=7.6 Hz, 1H), 6.71 (s, 1H), 6.67 (dd, J=8.3, 2.4 Hz, 1H), 6.28 (dd, J=8.9, 2.3 Hz, 1H), 6.17 (dd, J=14.1, 2.3 Hz, 1H), 4.56 (d, J=6.1 Hz, 2H), 3.84 (s, 3H), 3.69 (dd, J=8.7, 1.8 Hz, 1H) 3.63 (dd, J=9.0, 1.8 Hz, 1H), 3.30 (dd, J=9.0, 0.8 Hz, 1H), 3.22 (d, J=8.0 Hz, 1H), 2.20-2.13 (m, 2H).

Step 3: 2-fluoro-N-hydroxy-4-((1S,4S)-5-(3-(trifluoromethyl)phenyl)-2,5-diazabicyclo[2.2.1]heptan-2-yl)benzamide (227)

Using Procedure D-2 (Table 3) with compound 226 the title compound 227 was obtained (60 mg, 47%) as a white solid. $^1$H NMR (400 MHz, (DMSO-d$_6$) δ (ppm): 10.47 (s, 1H), 8.91 (s, 1H), 7.37 (t, J=8.6 Hz, 1H), 7.31 (t, J=7.9 Hz, 1H), 6.88-6.81 (m, 2H), 6.78 (s, 1H), 6.44 (s, 1H), 6.41 (s, 1H), 4.74 (d, J=13.7 Hz, 2H), 3.63-3.53 (m, 2H), 3.04 (d, J=9.4 Hz, 1H), 3.01 (d, J=9.2 Hz, 1H), 2.05 (s, 2H). LRMS (ESI): (calc.) 395.13. (found) 396.3 (MH)+.

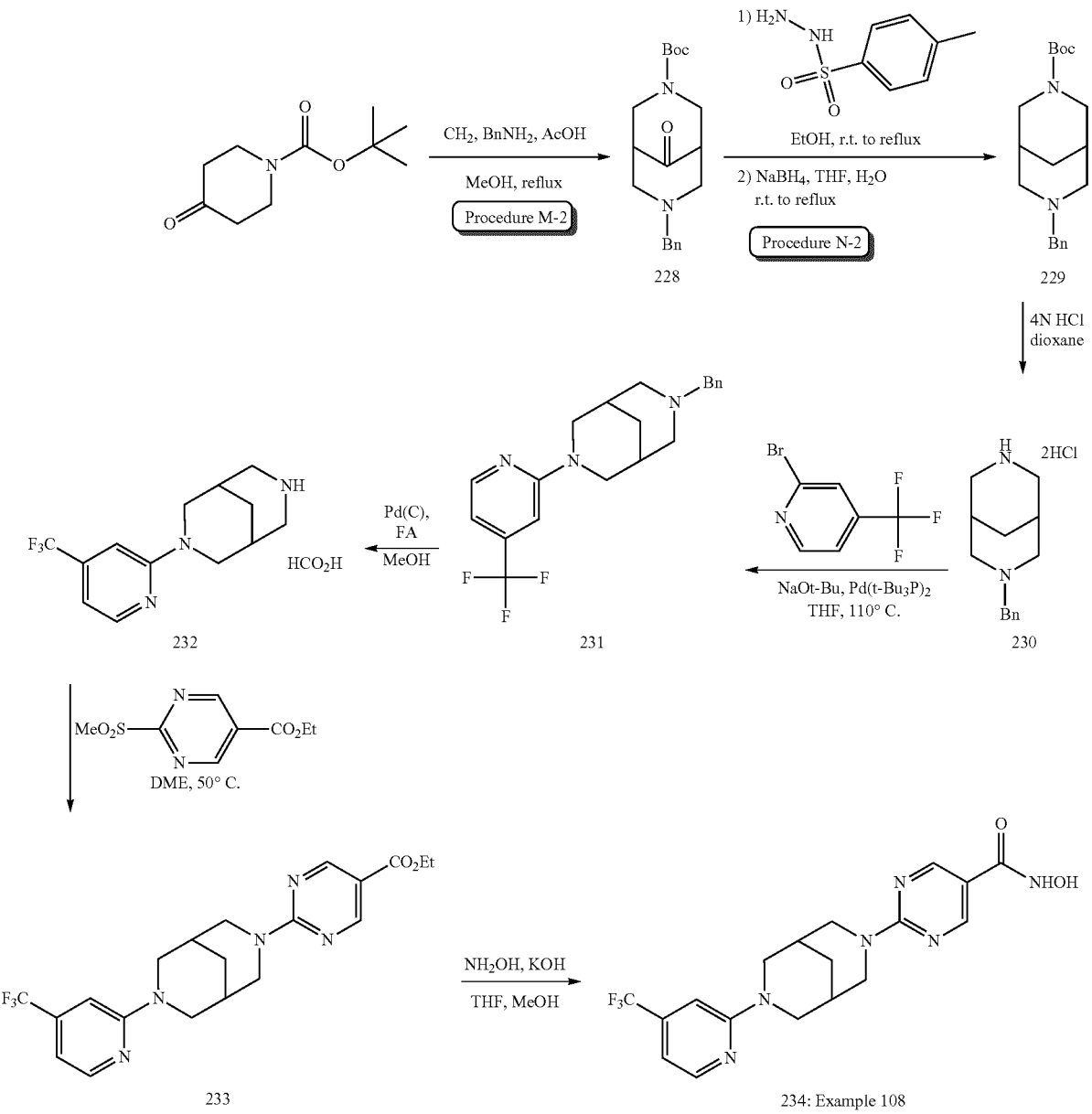

Scheme 38

Example 108

N-hydroxy-2-(7-(4-(trifluoromethyl)pyridin-2-yl)-3,7-diazabicyclo[3.3.1]nonan-3-yl)pyrimidine-5-carboxamide (234)

Step 1: tert-butyl 7-benzyl-9-oxo-3,7-diazabicyclo[3.3.1]nonane-3-carboxylate (29)

A solution of 1-Boc-4-piperidone (3 g, 15.06 mmol), benzylamine (1.73 mL, 15.81 mmol) and acetic acid (0.86 mL, 15.06 mmol) in MeOH (20 ml) was added a stirred suspension of paraformaldehyde (1 g) in MeOH (30 ml) at reflux. The mixture was stirred for 1 h and more paraformaldehyde (1 g) was added and the mixture was stirred for 4 h. The mixture was cooled and concentrated. The residue was dissolved in ether (40 mL) and 1M KOH solution (20 mL) was added. The layers were split and the aqueous mixture was extracted with ether four times. The combined organics were dried over $Na_2SO_4$ for 20 min, filtered and concentrated. The yellow residue was purified by flash chromatography: 0% to 50% EA/H over 20 min on 80 g $SiO_2$ to afford title compound 228 (5 g, 100%). LRMS (ESI): (calc.) 330.19. (found) 362.9 (MH+MeOH)+.

Step 2: tert-butyl 7-benzyl-3,7-diazabicyclo[3.3.1]nonane-3-carboxylate (229)

To a stirring solution of title compound 228 (3.6 g, 10.90 mmol) in EtOH (100 mL) was added p-toluenesulfanhydrazine (2.435 g, 13.07 mmol) at room temperature then the reaction mixture was heated at reflux for 2 h. The mixture was cooled to room temperature and concentrated. The residue was dissolved in THF (60 mL) and water (15 mL) and NaBH₄ (4.12 g, 109 mmol) was added portionwise at 0° C. over 5 min (effervescence). The reaction mixture was stirred for 30 minutes at room temperature then 3 h at reflux. The mixture was cooled, water was added and the mixture was extracted with Et₂O (4 times). The organic extracts were dried over Na₂SO₄, filtered and concentrated. Purified residue by flash chromatography: 40 g SiO₂, 0% to 50% EA/hexanes over 30 min. to afford title compound 229 (1.35 g, 27%). LRMS (ESI): (calc.) 316.22. (found) 317.5 (MH)+.

Step 3: 3-benzyl-3,7-diazabicyclo[3.3.1]nonane dihydrochloride (230)

Using Procedure B-2 (Table 3) with compound 229 the title compound 230 was obtained (1.54 g, 100%) as light pink foam. LRMS (ESI): (calc.) 216.16. (found) 217.3 (MH)+.
¹H NMR (CDCl₃) δ (ppm): 7.72-7.71 (m, 2H), 7.44-7.41 (m, 3H), 4.46 (s, 2H), 3.51-3.46 (m, 4H), 2.67 (s, 4H), 2.55 (m, 2H), 2.12-2.00 (m, 2H).

Step 4: 3-benzyl-7-(4-(trifluoromethyl)pyridin-2-yl)-3,7-diazabicyclo[3.3.1]nonane (231)

Using Procedure I-2 (Table 3) with compound 230 the title compound 231 was obtained (0.41 g, 66%). LRMS (ESI): (calc.) 361.18. (found) 362.4 (MH)+. ¹H NMR (400 MHz, DMSO-d₆) δ (ppm): 8.30 (d, J=5.1, 1H), 7.12-7.04 (m, 3H), 6.88-6.86 (m, 3H), 6.76 (d, J=4.9 Hz, 1H), 4.37-4.15 (m, 2H), 3.23 (s, 2H), 3.15 (dd, J=12.9, 2.3 Hz, 2H), 2.84 (d, J=10.8 Hz, 2H), 2.20 (d, J=11.0 Hz, 2H), 1.99 (s, 2H), 1.78 (m, 1H), 1.64 (m, 1H).

Step 5: 3-(4-(trifluoromethyl)pyridin-2-yl)-3,7-diazabicyclo[3.3.1]nonane formate (232)

Using Procedure H-2 (Table 3) with compound 231 the title compound 232 was obtained (0.36 g, 80%) as a clear oil. LRMS (ESI): (calc.) 271.13. (found) 272.3 (MH)+.
¹H NMR (CDCl₃) δ (ppm): 8.38 (d, J=5.1 Hz, 1H), 8.04 (s, 3H), 7.06 (s, 1H), 6.98 (d, J=5.1 Hz, 1H), 4.40 (d, J=12.7 Hz, 2H), 3.65 (d, J=13.1 Hz, 2H), 3.35 (d, J=13.1 Hz, 2H), 3.14 (d, J=12.5 Hz, 2H), 2.34 (s, 2H), 2.04-1.93 (m, 1H), 1.74 (dd, J=17.5, 5.0 Hz, 1H).

Step 6: ethyl 2-(7-(4-(trifluoromethyl)pyridin-2-yl)-3,7-diazabicyclo[3.3.1]nonan-3-yl)pyrimidine-5-carboxylate (233)

Using Procedure C-2 (Table 3) with compound 232 the title compound 233 was obtained (0.28 g, 76%) as clear oil. LRMS (ESI): (calc.) 421.17. (found) 422.6 (MH)+.
¹H NMR (CDCl₃) δ (ppm): 8.52 (s, 2H), 8.07 (d, J=5.5 Hz, 1H), 6.59 (s, 1H), 6.50 (d, J=5.3 Hz, 1H), 5.18 (d, J=14.1 Hz, 2H), 4.47 (d, J=13.1 Hz, 2H), 4.25 (q, J=7.1 Hz, 2H), 3.32-3.20 (m, 4H), 2.18 (s, 2H), 2.11-1.97 (m, 2H), 1.32 (t, J=7.1 Hz, 3H).

Step 7: N-hydroxy-2-(7-(4-(trifluoromethyl)pyridin-2-yl)-3,7-diazabicyclo[3.3.1]nonan-3-yl)pyrimidine-5-carboxamide (234)

Using Procedure D-2 (Table 3) with compound 233 the title compound 234 was obtained (0.18 g, 64%) as a white solid. ¹H NMR (400 MHz, DMSO-d₆) δ (ppm): 10.82 (s, 1H), 8.88 (s, 1H), 8.36 (s, 2H), 8.01 (d, J=5.1 Hz, 1H), 6.68 (s, 1H), 6.45 (d, J=5.1 Hz, 1H), 4.88 (d, J=23.3 Hz, 2H), 4.46 (d, J=22.9 Hz, 2H), 3.14 (d, J=23.3 Hz, 2H), 3.05 (d, J=23.1 Hz, 2H), 2.07 (s, 2H), 2.00-1.90 (m, 2H). LRMS (ESI): (calc.) 408.15. (found) 409.6 (MH)+.

Scheme 39

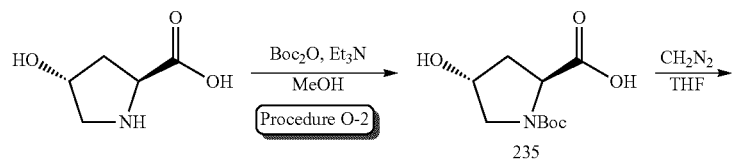

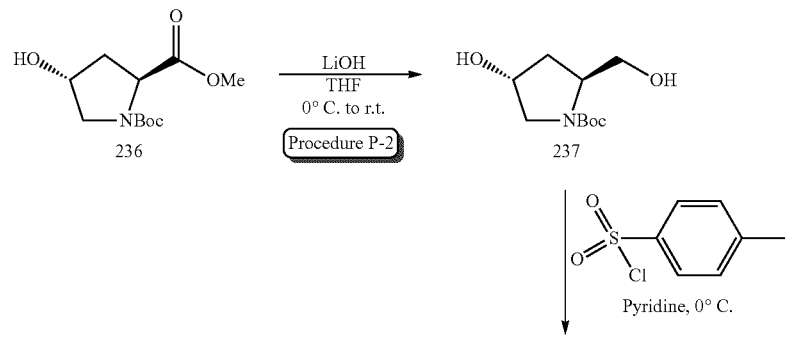

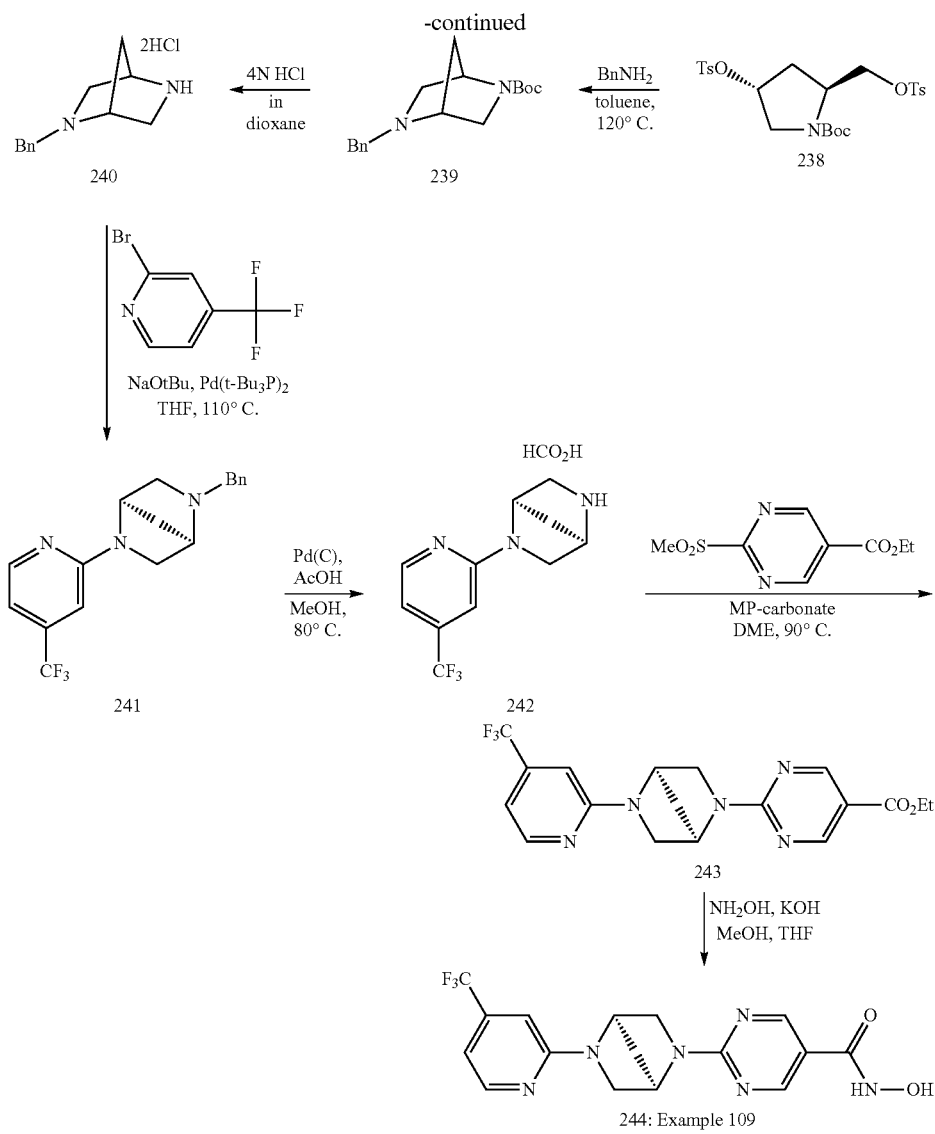

244: Example 109

Example 109

N-hydroxy-2-((1R,4R)-5-(4-(trifluoromethyl)pyridin-2-yl)-2,5-diazabicyclo[2.2.1]heptan-2-yl)pyrimidine-5-carboxamide (244)

Step 1: (2S,4R)-1-(tert-butoxycarbonyl)-4-hydroxypyrrolidine-2-carboxylic acid (235)

To a suspension of trans-D-hydroxyproline (3 g, 22.88 mmol) in Et$_3$N (6 mL) and MeOH (30 mL) was added Boc anhydride (5.49 g, 25.2 mmol). The mixture was stirred at 40° C. until a clear solution was obtained. The mixture was then concentrated, diluted with 1N NaOH (20 mL), washed with hexanes, acidified with 3N HCl, salted and extracted with copious amounts of ethyl acetate (four times). Organics were dried over Na$_2$SO$_4$ and concentrated to afford title compound 235 (5.2 g, 98%) as a white foam. LRMS (ESI): (calc.) 231.11. (found) 230.2 (MH)−.

Step 2: (2S,4R)-1-tert-butyl 2-methyl 4-hydroxypyrrolidine-1,2-dicarboxylate (236)

To a solution of compound 235 (5.2 g, 22.49 mmol) in THF (50 mL) was added diazomethane (38.5 mL, 27.0 mmol, 0.7M) dropwise until yellow color persists. The mixture was concentrated to afford title compound 236 (5.3 g, 96%) as a clear oil. $^1$H NMR (400 MHz, CDCl$_3$) δ (ppm): 4.50-4.47 (m, 1H), 4.44 (t, J=7.7 Hz, 1H), 3.76-3.43 (m, 2H), 3.73 (s, 3H), 2.33-2.22 (m, 1H), 2.11-2.03 (m, 1H), 1.91 (m, 1H), 1.45-1.41 (m, 9H). LRMS (ESI): (calc.) 245.13. (found) 146.0 (M-Boc+H)+.

Step 3: (2S,4R)-tert-butyl 4-hydroxy-2-(hydroxymethyl)pyrrolidine-1-carboxylate (237)

To a solution of compound 236 (6.4 g, 26.09 mmol) in THF (80 mL) at 0° C. was added a solution of LiBH$_4$ (2.063 g, 94.76 mmol) in one shot. The suspension was stirred at 0° C. for 1 h then at room temperature overnight. The mixture was cooled to 0° C. and water (52 mL) then 6N HCl (20 mL) were added. The layers were separated and the aqueous layer was extracted with ethyl acetate (3×70 mL). The combined organics were washed with 2N NaOH, 2N HCl and brine (20 mL each). The organic layers were dried over $Na_2SO_4$ filtered and concentrated to afford title compound 237 (5.4 g, 95%) as clear oil. LRMS (ESI): (calc.) 217.13. (found) 256.3 (M+K).

Step 4: (2S,4R)-tert-butyl 4-(tosyloxy)-2-(tosyloxymethyl)pyrrolidine-1-carboxylate (238)

Using Procedure E-2 (Table 3) with compound 237 the title compound 238 was obtained (6.4 g, 49%) as a white solid. LRMS (ESI): (calc.) 525.15. (found) 426.4 (M-Boc+H).

Step 5: (1R,4R)-tert-butyl 5-benzyl-2,5-diazabicyclo[2.2.1]heptane-2-carboxylate (239)

Using Procedure F-2 (Table 3) with compound 238 the title compound 239 was obtained (0.7 g, 26%). LRMS (ESI): (calc.) 288.18. (found) 289.3 (MH)+.

Step 6: (1R,4R)-2-benzyl-2,5-diazabicyclo[2.2.1]heptane (240)

Using Procedure B-2 (Table 3) with compound 239 the title compound 240 was obtained (0.59 g, 93%) as beige solid.

Step 7: (1R,4R)-2-benzyl-5-(4-(trifluoromethyl)pyridin-2-yl)-2,5-diazabicyclo[2.2.1]heptane (241)

Using Procedure I-2 (Table 3) with compound 240 the title compound 241 was obtained (0.32 g, 84%). LRMS (ESI): (calc.) 333.15. (found) 334.5 (MH)+.

Step 8: (1R,4R)-2-(4-(trifluoromethyl)pyridin-2-yl)-2,5-diazabicyclo[2.2.1]heptane formate (242)

Using Procedure H-2 (Table 3) with compound 241 the title compound 242 was obtained (0.30 g, 100%) as clear oil. LRMS (ESI): (calc.) 243.10. (found) 244.2 (MH)+.

Step 9: ethyl 2-((1R,4R)-5-(4-(trifluoromethyl)pyridin-2-yl)-2,5-diazabicyclo[2.2.1]heptan-2-yl)pyrimidine-5-carboxylate (243)

Using Procedure C-2 (Table 3) with compound 242 the title compound 243 was obtained (0.21 g, 70%) as a white solid. LRMS (ESI): (calc.) 393.14. (found) 394.5 (MH)+. $^1$H NMR ($CDCl_3$) δ (ppm): 8.81 (d, J=5.5 Hz, 2H), 8.23 (d, J=5.3 Hz, 1H), 6.73 (d, J=5.3 Hz, 1H), 6.49 (s, 1H), 5.24 (s, 1H), 5.10 (s, 1H), 4.31 (q, J=7.1 Hz, 2H), 3.75-3.68 (m, 3H), 3.43 (d, J=9.4 Hz, 1H), 2.13 (s, 2H), 1.34 (t, J=7.1 Hz, 3H).

Step 10: N-hydroxy-2-((1R,4R)-5-(4-(trifluoromethyl)pyridin-2-yl)-2,5-diazabicyclo[2.2.1]heptan-2-yl)pyrimidine-5-carboxamide (244)

Using Procedure D-2 (Table 3) with compound 243 the title compound 244 was obtained (0.15 g, 71%) as a yellow solid. $^1$H NMR (400 MHz, DMSO-$d_6$) δ (ppm): 11.06 (s, 1H), 9.00 (s, 1H), 8.67 (s, 1H), 8.62 (s, 1H), 8.27 (d, J=5.2 Hz, 1H), 6.81 (d, J=5.1 Hz, 1H), 6.73 (s, 1H), 5.08 (s, 1H), 5.05 (s, 1H), 3.70-3.60 (m, 2H), 3.46 (d, J=10.6 Hz, 1H), 3.40-3.30 (m, 1H), 2.18-2.00 (m, 2H). LRMS (ESI): (calc.) 380.12. (found) 381.4 (MH)+.

Scheme 40

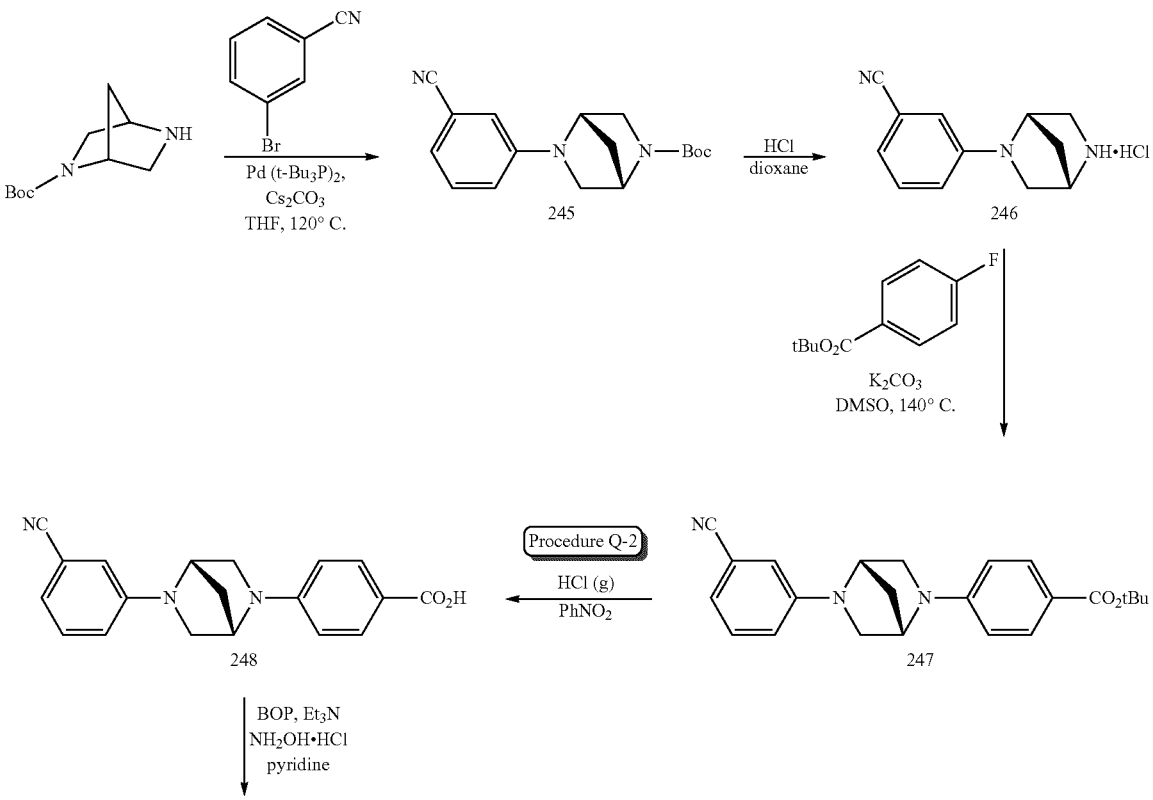

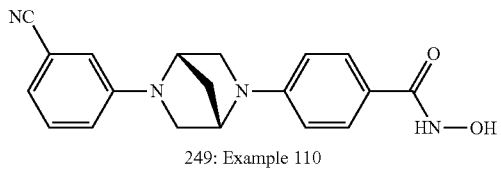

249: Example 110

Example 110

4-((1S,4S)-5-(3-cyanophenyl)-2,5-diazabicyclo[2.2.1]heptan-2-yl)-N-hydroxybenzamide (249)

Step 1: (1S,4S)-tert-butyl 5-(3-cyanophenyl)-2,5-diazabicyclo[2.2.1]heptane-2-carboxylate (245)

Using Procedure I-2 (Table 3) with (1R,4R)-tert-butyl 2,5-diazabicyclo[2.2.1]heptane-2-carboxylate and 3-bromobenzonitrile the title compound 245 was obtained (2.4 g, 79%) as an off-white paste. LRMS (ESI): (calc.) 299.16. (found) 300.3 (MH)+.

Step 2: 3-((1S,4S)-2,5-diazabicyclo[2.2.1]heptan-2-yl)benzonitrile hydrochloride (246)

Using Procedure B-2 (Table 3) with compound 245 the title compound 246 was obtained (1.85 g, 98%) as a white solid. LRMS (ESI): (calc.) 199.11. (found) 200.2 (MH)+.

Step 3: tert-butyl 4-((1S,4S)-5-(3-cyanophenyl)-2,5-diazabicyclo[2.2.1]heptan-2-yl)benzoate (247)

Using Procedure G-2 (Table 3) with compound 246 the title compound 247 was obtained (0.45 g, 33%) as a clear oil. LRMS (ESI): (calc.) 375.19. (found) 376.5 (MH)+.
$^1$H NMR (DMSO-d$_6$) δ (ppm): 7.65 (d, J=9.2 Hz, 2H), 7.28 (dd, J=8.4, 7.4 Hz, 1H), 7.01 (s, 1H), 6.96 (d, J=7.6 Hz, 1H), 6.89 (dd, J=8.4, 2.2 Hz, 1H), 6.60 (d, J=8.6 Hz, 2H), 4.75 (s, 2H), 3.59 (dt, J=10, 2.5 Hz, 2H), 3.08 (d, J=9.6 Hz, 1H), 3.02 (d, J=9.4 Hz, 1H), 2.08 (s, 2H), 1.48 (s, 9H).

Step 4: 4-((1S,4S)-5-(3-cyanophenyl)-2,5-diazabicyclo[2.2.1]heptan-2-yl)benzoic acid (248)

To a saturated mixture of HCl (gas) and nitromethane (25 mL) was added title compound 247 (0.85 g, 2.264 mmol). The clear solution was stirred 2 h then concentrated. The beige residue was triturated with ether overnight and filtered to afford title compound 248 (315 mg, 39%) as a beige solid. LRMS (ESI): (calc.) 319.13. (found) 320.3 (MH)+.

Step 5: 4-((1S,4S)-5-(3-cyanophenyl)-2,5-diazabicyclo[2.2.1]heptan-2-yl)-N-hydroxybenzamide (249)

Title compound 248 (0.21 g, 0.590 mmol) and BOP (0.287 g, 0.649 mmol) were combined and pyridine (5.90 ml) was added. The mixture was stirred 15 min. Hydroxylamine hydrochloride (0.045 g, 0.649 mmol) was added and the mixture was stirred at room temperature overnight. The mixture was concentrated, water and 3N HCl were added (to reach pH=5). This aqueous mixture was extracted twice with ethyl acetate. The combined organic extracts were washed with brine, dried over Na$_2$SO$_4$, filtered and concentrated. The residue was dissolved in THF (3 mL) and MeOH (3 mL), 4M KOH (0.3 ml) was added and the homogenous mixture was concentrated partially. The resulting aq. solution was diluted with water and 3N HCl (0.4 ml) was added. The precipitate was filtered, washed with water and ether and pumped on Hi-Vac overnight to afford title compound 249 (0.18 g, 91%) as a pink solid. $^1$H NMR (400 MHz, DMSO-d$_6$) δ (ppm): 10.81 (s, 1H), 8.70 (d, J=1.8 Hz, 1H), 7.56 (d, J=8.7 Hz, 2H), 7.27 (t, J=7.9 Hz, 1H), 7.01 (s, 1H), 6.95 (d, J=7.6 Hz, 1H), 6.88 (d, J=8.6 Hz, 1H), 6.58 (d, J=8.6 Hz, 2H), 4.73 (d, J=5.1 Hz, 2H), 3.57 (d, J=9.4 Hz, 2H), 3.03 (t, J=10.1 Hz, 2H), 2.06 (s, 2H). LRMS (ESI): (calc.) 334.1. (found) 333.4 (MH)−.

The general procedures A-2 to Q-2 used to synthesize compounds of this invention are described in the Table 3. A specific example of each general procedure is provided in the indicated step of a particular example. It is realized that substrates and methods may be modified and/or adapted by those of skill in the art in order to facilitate the synthesis of the compounds within the scope of the present invention.

TABLE 3

| Proc | Sc | Ex | Step | Reaction Conditions |
|---|---|---|---|---|
| A-2 | 30 | 100 | 1 | Ar–Cl $\xrightarrow{\text{HNR}_2,\ \text{Na}_2\text{CO}_3,\ \text{NaI}}_{\text{DMF, 80° C.}}$ Ar–NR$_2$ |
| B-2 | 30 | 100 | 2 | R$_2$NBoc $\xrightarrow{\text{HCl/dioxane}}$ R$_2$NH |

TABLE 3-continued
| Proc | Sc | Ex | Step | Reaction Conditions |
|---|---|---|---|---|
| C-2 | 30 | 100 | 3 | 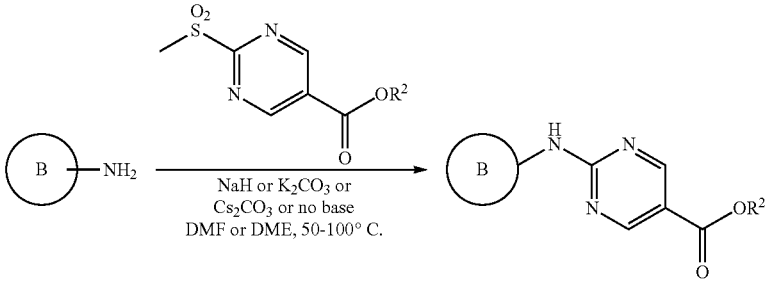 |
| D-2 | 30 | 100 | 4 | 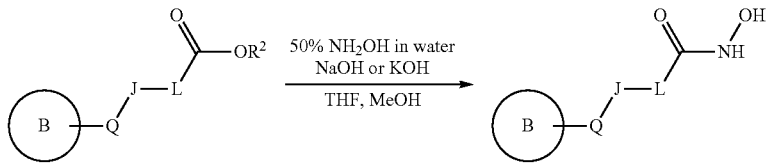 |
| E-2 | 31 | 101 | 1 | 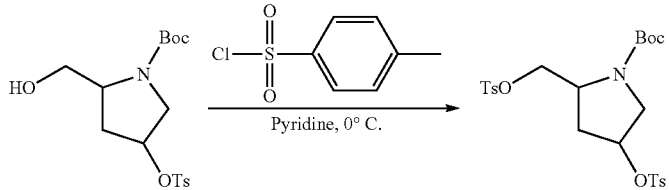 [SMILES: Cc1ccc(S(=O)(=O)OC2CC(CO)N(C(=O)OC(C)(C)C)C2)cc1 ; Cc1ccc(S(=O)(=O)Cl)cc1 ; Cc1ccc(S(=O)(=O)OCC2CC(OS(=O)(=O)c3ccc(C)cc3)CN2C(=O)OC(C)(C)C)cc1] |
| F-2<br>F-2 | 31<br>39 | 101<br>109 | 2<br>5 | 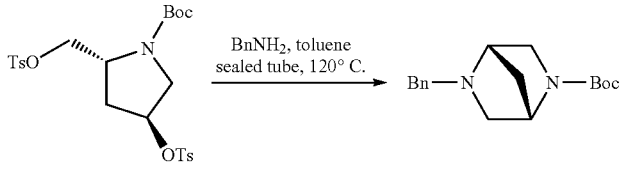 |
| G-2<br>G-2 | 31<br>36 | 101<br>106 | 4<br>1 | 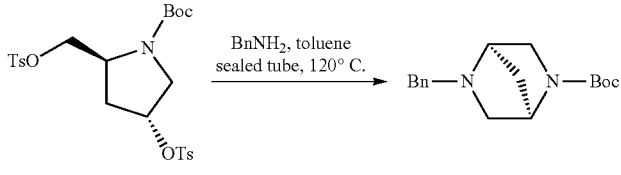<br>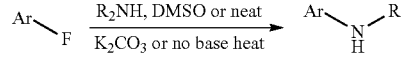 |
| H-2 | 31 | 101 | 5 | 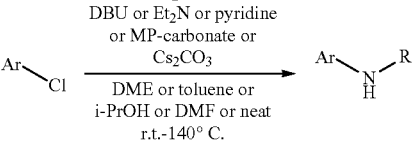 |

TABLE 3-continued

| Proc | Sc | Ex | Step | Reaction Conditions |
|---|---|---|---|---|
| I-2 | 31 | 101 | 6 | ArX + R$_2$NH → Ar—NR$_2$<br>Pd(tBu$_3$P)$_2$, Cs$_2$CO$_3$, THF, pressure vessel, 110° C.<br>or<br>Pd(tBu$_3$P)$_2$, NaOtBu, toluene or benzene or THF, pressure vessel, 110° C.<br>or<br>Et$_3$N, dioxane, sonicator |
| J-2 | 32 | 102 | 3 | R—NH$_2$ + R'C(O)Cl → R—NH—C(O)—R'<br>DIPEA or Et$_3$N or NaHCO$_3$ or Pyridine (DMAP)<br>THF or DCM or benzene or toluene<br>0–160° C. |
| K-2<br>K-2 | 34<br>35 | 104<br>105 | 1<br>1 | R$_2$NH + R'OH + N,N'-disuccinimidyl carbonate → R$_2$N—C(O)—OR'<br>Et$_3$N or DIPEA and 2,6-lutidine<br><br>R$_2$NH + R'OH + CDI (1,1'-carbonyldiimidazole) → R$_2$N—C(O)—OR'<br>Et$_3$N, DBU |
| L-2 | 37 | 107 | 2 | R—C(O)OH → R—C(O)OMe<br>HCl and/or H$_2$SO$_4$, MeOH, 70–95° C.<br>or CH$_2$N$_2$, THF |
| M-2 | 38 | 108 | 1 | N-Boc-piperidin-4-one → Boc/Bn bis-azabicyclic ketone<br>H2CO, BnNH2, AcOH, MeOH, reflux |
| N-2 | 38 | 108 | 2 | 1) EtOH, reflux; H$_2$N-NH-Ts<br>2) NaBH$_4$, THF, water, 0° C. to reflux |
| O-2 | 39 | 109 | 1 | R$_2$NH → R$_2$NBoc<br>Boc$_2$O, Et$_3$N, MeOH, 40° C. |

TABLE 3-continued
| Proc | Sc | Ex | Step | Reaction Conditions |
|---|---|---|---|---|
| P-2 | 39 | 109 | 3 | RCOOMe $\xrightarrow{\text{LiBH4, THF}}_{\text{0° C. to r.t.}}$ RCH$_2$OH |
| Q-2 | 40 | 110 | 4 | 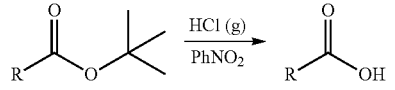 |
The examples described in Table 4 were prepared following the preparative sequences (general procedures A-1 to Q-2) as indicated in Table 3 or other preparative sequence(s) from Table 1 and/or Table 5.

TABLE 4

| Ex | Cpd | Structure | Name | Characterization |
|---|---|---|---|---|
| 100 | 203 | 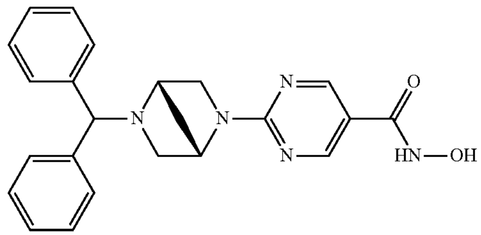 [SMILES: O=C(NO)c1cnc(N2C[C@@H]3C[C@H]2CN3C(c2ccccc2)c2ccccc2)nc1] | 2-((1S,4S)-5-benzhydryl-2,5-diazabicyclo[2.2.1]heptan-2-yl)-N-hydroxypyrimidine-5-carboxamide | $^1$H NMR (DMSO-d$_6$) δ (ppm): 7.80 (dd, J = 8.0, 2.0 Hz, 1H), 7.61 (ddd, J = 8.4, 6.8, 1.2 Hz, 1H), 7.46-7.41 (m, 3H), 7.38-7.30 (m, 3H), 3.62 (t, J = 7.2 Hz, 2H), 2.06 (t, J = 7.2 Hz, 2H), 1.61-1.51 (m, 4H), 1.44-1.28 (m, 4H), LRMS: (calc) 390.12 (found) 391.3 (MH)$^+$. |
| 101 | 210 | 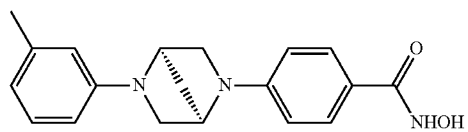 | N-hydroxy-4-((1R,4R)-5-m-tolyl-2,5-diazabicyclo[2.2.1]heptan-2-yl)benzamide | (MeOH-d$_4$) δ 7.55 (d, J = 8.8 Hz, 2H), 6.99 (t, J = 7.6 Hz, H), 6.57 (d, J = 8.8 Hz, 2H), 6.45 (d, J = 7.5 Hz, 1H), 6.42-6.35 (m, 2H), 4.61 (s, 1H), 4.55 (s, 1H), 3.60 (t, J = 9.0 Hz, 2H), 3.23 (d, J = 9.0 Hz, 1H), 3.08 (d, J = 8.8 Hz, 1H), 2.22 (s, 3H), 2.18-2.03 (m, 2H). MS (m/z): 324.4 (M + H). |
| 102 | 214 | 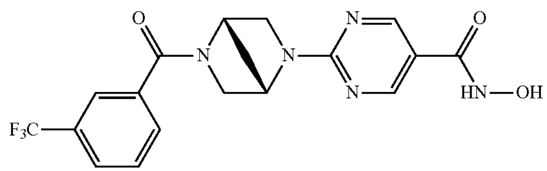 [SMILES: O=C(NO)c1cnc(N2C[C@@H]3C[C@H]2CN3C(=O)c2cccc(C(F)(F)F)c2)nc1] | N-hydroxy-2-((1S,4S)-5-(3-(trifluoromethyl)benzoyl)-2,5-diazabicyclo[2.2.1]heptan-2-yl)pyrimidine-5-carboxamide | (CD$_3$OD) d(ppm) 1H: 8.70 (bs, 1H), 8.64 (bs, 1H), 7.62-7.85 (m, 4H), 5.20 (s, 1H), 5.10 (m, 1H), 4.53 (s, 1H), 3.56-3.80 (m, 3H), 2.13 (m, 2H), LRMS(ESI): (calc.) 407.1 (found) 406.3 (M)− |
| 103 | 218 | 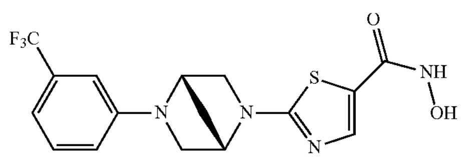 [SMILES: O=C(NO)c1cnc(N2C[C@@H]3C[C@H]2CN3c2cccc(C(F)(F)F)c2)s1] | N-hydroxy-2-((1S,4S)-5-(3-(trifluoromethyl)phenyl)-2,5-diazabicyclo[2.2.1]heptan-2-yl)thiazole-5-carboxamide | (CD$_3$OD) d(ppm) 1H: 7.66 (bs, 1H), 7.33 (t, J = 8 Hz, 1H), 6.82-6.91 (m, 3H), 4.76 (s, 1H), 4.74 (s, 1H), 3.70 (dd, J = 9.2 Hz, 18 Hz, 2H), 3.40 (d, J = 9.6 Hz, 1H), 3.23 (d, J = 9.2 Hz, 1H), 2.19 (s, 2H). LRMS(ESI): (calc.) 384.0 (found) 383.2 (M)− |
| 104 | 220 | 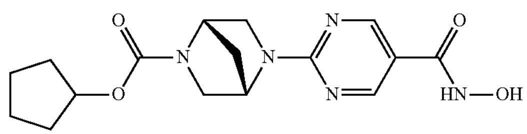 [SMILES: O=C(NO)c1cnc(N2C[C@@H]3C[C@H]2CN3C(=O)OC2CCCC2)nc1] | (1S,4S)-cyclopentyl 5-(5-(hydroxycarbamoyl)pyrimidin-2-yl)-2,5-diazabicyclo[2.2.1]heptane-2-carboxylate | $^1$H NMR (DMSO-d$_6$) δ (ppm): 11.07 (s, 1H), 9.00 (s, 1H), 8.65 (s, 2H), 4.93 (m, 2H), 4.49 (d, J = 8.2 Hz, 1H), 3.60-3.50 (m, 1H), 3.49-3.25 (m, 2H), 3.24-3.10 (m, 1H), 1.93 (d, J = 10.4 Hz, 2H), 1.85-1.40 (m, 8H) LRMS(ESI): (calc.) 347.2 (found) 348.3 (MH)+. |

TABLE 4-continued

| Ex | Cpd | Structure | Name | Characterization |
|---|---|---|---|---|
| 105 | 222 | 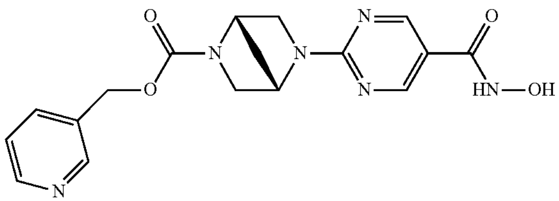 [SMILES: O=C(NO)c1cnc(N2C[C@@H]3C[C@H]2CN3C(=O)OCc2cccnc2)nc1] | (1S,4S)-pyridin-3-ylmethyl 5-(5-(hydroxycarbamoyl)pyrimidin-2-yl)-2,5-diazabicyclo[2.2.1]heptane-2-carboxylate | (MeOD-d4) d(ppm) 1H: 8.66 (s, 2H), 8.59 and 8.52 (2s, 1H), 8.50 and 8.46 (2d, J = 4.5 Hz, 1H), 7.90 and 7.82 (2d, J = 7.8 Hz, 1H), 7.50-7.39 (m, 1H), 5.21 (s, 1H), 5.07 (s, 1H), 5.20-5.08 (m, 1H), 4.69 (d, J = 9.8 Hz, 1H), 3.66-3.36 (m, 4H), 2.05-1.99 (m, 2H) LRMS(ESI): (calc.) 370.1 (found) 371.2 (MH)+ |
| 106 | 224 | 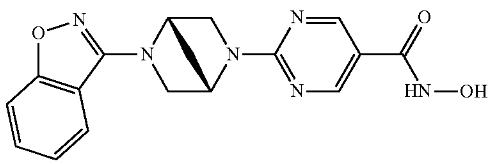 [SMILES: O=C(NO)c1cnc(N2C[C@@H]3C[C@H]2CN3c2noc3ccccc23)nc1] | 2-((1S,4S)-5-(benzo[d]isoxazol-3-yl)-2,5-diazabicyclo[2.2.1]heptan-2-yl)-N-hydroxypyrimidine-5-carboxamide | (CD3OD) d(ppm) 1H: 8.66 (s, 1H), 8.59 (s, 1H), 7.82 (d, J = 8 Hz, 1H), 7.53 (t, J = 7.6 Hz, 1H), 7.41 (d, J = 8.4 Hz, 1H), 7.25 (t, J = 7.6 Hz, 1H), 5.20 (s, 1H), 3.99 (d, J = 9.2 Hz, 1H), 3.80 (d, J = 10.8 Hz, 1H), 3.68 (m, 2H), 2.20 (dd, J = 10 Hz, 13.6 Hz, 2H) LRMS(ESI): (calc.) 352.13 (found) 351.0 (M)− |
| 107 | 227 | 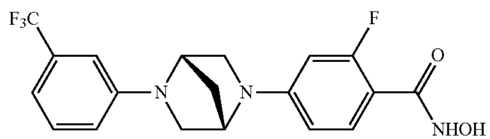 | 2-fluoro-N-hydroxy-4-((1S,4S)-5-(3-(trifluoromethyl)phenyl)-2,5-diazabicyclo[2.2.1]heptan-2-yl)benzamide | (DMSO-d6) δ (ppm): 10.47 (s, 1H), 8.91 (s, 1H), 7.37 (t, J = 8.6 Hz, 1H), 7.31 (t, J = 7.9 Hz, 1H), 6.88-6.81 (m, 2H), 6.78 (s, 2H), 6.44 (s, 1H), 6.41 (s, 1H), 4.74 (d, J = 13.7 Hz, 2H), 3.63-3.53 (m, 2H), 3.04 (d, J = 9.4 Hz, 1H), 3.01 (d, J = 9.2 Hz, 1H), 2.05 (s, 2H). MS (m/z): 396.3 (M + H). |
| 108 | 234 | 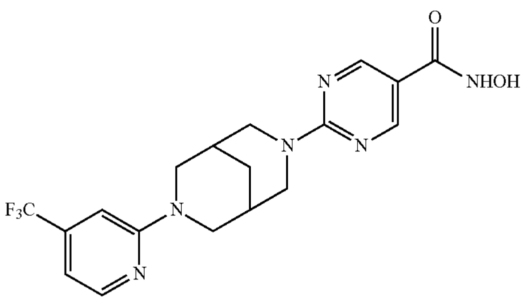 | N-hydroxy-2-(7-(4-(trifluoromethyl)pyridin-2-yl)-3,7-diazabicyclo[3.3.1]nonan-3-yl)pyrimidine-5-carboxamide | (DMSO-d6) δ (ppm): 10.82 (s, 1H), 8.88 (s, 1H), 8.36 (s, 2H), 8.01 (d, J = 5.1 Hz, 1H), 6.68 (s, 1H), 6.45 (d, J = 5.1 Hz, 1H), 4.88 (d, J = 23.3 Hz, 2H), 4.46 (d, J = 22.9 Hz, 2H), 3.14 (d, J = 23.3 Hz, 2H), 3.05 (d, J = 23.1 Hz, 2H), 2.07 (s, 2H), 2.00-1.90 (m, 2H). MS (m/z): 409.6 (M + H). |
| 109 | 244 | 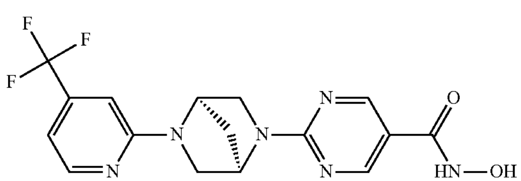 [SMILES: O=C(NO)c1cnc(N2C[C@H]3C[C@@H]2CN3c2cc(C(F)(F)F)ccn2)nc1] | N-hydroxy-2-((1R,4R)-5-(4-(trifluoromethyl)pyridin-2-yl)-2,5-diazabicyclo[2.2.1]heptan-2-yl)pyrimidine-5-carboxamide | (DMSO-d6) δ (ppm): 11.06 (s, 1H), 9.00 (s, 1H), 8.67 (s, 1H), 8.62 (s, 1H), 8.27 (d, J = 5.2 Hz, 1H), 6.81 (d, J = 5.1 Hz, 1H), 6.73 (s, 1H), 5.08 (s, 1H), 5.05 (s, 1H), 3.70-3.60 (m, 2H), 3.46 (d, J = 10.6 Hz, 1H), 3.40-3.30 (m, 1H), 2.18-2.00 (m, 2H). MS (m/z): 381.4 (M + H). |

| Ex | Cpd | Structure | Name | Characterization |
|---|---|---|---|---|
| 110 | 249 | 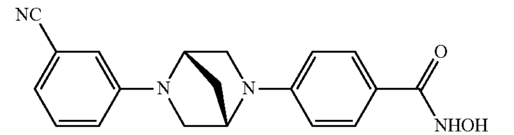 | 4-((1S,4S)-5-(3-cyanophenyl)-2,5-diazabicyclo[2.2.1]heptan-2-yl)-N-hydroxybenzamide | (dmso-d6) δ (ppm) 1H: 10.81 (s, 1H), 8.70 (d, J = 1.8 Hz, 1H), 7.56 (d, J = 8.7 Hz, 2H), 7.27 (t, J = 7.9 Hz, 1H), 7.01 (s, 1H), 6.95 (d, J = 7.6 Hz, 1H), 6.88 (d, J = 8.6 Hz, 1H), 6.58 (d, J = 8.6 Hz, 2H), 4.73 (d, J = 5.1 Hz, 2H), 3.57 (d, J = 9.4 Hz, 2H), 3.03 (t, J = 10.1 Hz, 2H), 2.06 (s, 2H). LRMS(ESI): (calc.) 334.1 (found) 333.4 (MH)− |
| 111 | 250 | 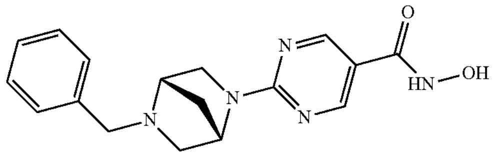 [SMILES: O=C(NO)c1cnc(N2C[C@@H]3C[C@H]2CN3Cc2ccccc2)nc1] | 2-((1S,4S)-5-benzyl-2,5-diazabicyclo[2.2.1]heptan-2-yl)-N-hydroxypyrimidine-5-carboxamide | (DMSO-d6) δ (ppm): 11.03 (s, 0.9H), 8.98 (s, 0.9H), 8.62 (d, J = 13.5 Hz, 2H), 7.32-7.24 (m, 4H), 7.22-7.16 (m, 1H), 4.78 (s, 1H), 3.68 (s, 2H), 3.64 (d, J = 11.0 Hz, 1H), 3.56 (s, 1H), 3.39-3.32 (m, 1H), 2.89-2.80 (m, 1H), 2.44 (d, J = 9.4 Hz, 1H), 1.92 (d, J = 10.4 Hz, 1H), 1.77 (d, J = 9.4 Hz, 1H). LRMS: (calc.) 325.15 (found) 326.4 (MH)+. |
| 112 | 251 | 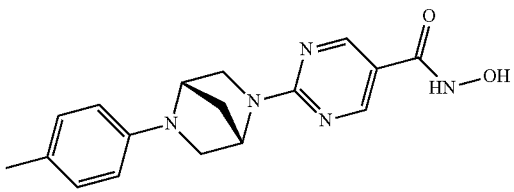 [SMILES: Cc1ccc(N2C[C@@H]3C[C@H]2CN3c2ncc(C(=O)NO)cn2)cc1] | N-hydroxy-2-((1S,4S)-5-p-tolyl-2,5-diazabicyclo[2.2.1]heptan-2-yl)pyrimidine-5-carboxamide | (DMSO-d6) δ (ppm): 11.0 (br s, 0.5H), 9.0 (br s, 0.4H), 8.62 (s, 1H), 8.56 (s, 1H), 6.92 (d, J = 8.2 Hz, 2H), 6.48 (d, J = 8.4 Hz, 2H), 4.97 (s, 1H), 4.56 (s, 1H), 3.55-3.51 (m, 1H), 3.51-3.45 (m, 2H), 2.90 (d, J = 8.8 Hz, 1H), 2.12 (s, 3H), 2.03 (m, 2H). LRMS: (calc.) 325.2 (found) 324.3 (MH)+. |
| 113 | 252 | 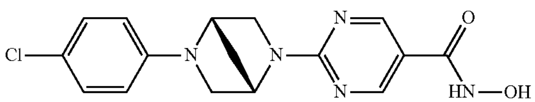 | 2-((1S,4S)-5-(4-chlorophenyl)-2,5-diazabicyclo[2.2.1]heptan-2-yl)-N-hydroxypyrimidine-5-carboxamide | (DMSO-d6) δ (ppm): 11.03 (s, 1H), 8.99 (s, 1H), 8.63 (s, 1H), 8.58 (s, 1H), 7.12 (dd, J = 7.0, 2.2 Hz, 2H), 6.60 (dd, J = 8.1, 3.3 Hz, 2H), 5.00 (s, 1H), 4.62 (s, 1H), 3.26 (dd, J = 9.0, 1.7 Hz, 1H), 3.55 (dd, J = 10.8, 1.6 Hz, 1H), 3.46 (d, J = 10.6 Hz, 1H), 2.95 (d, J = 9.0 Hz, 1H), 2.05 (s, 2H). LRMS(ESI): (calc.) 345.1 (found) 346.1 (MH)+ |
| 114 | 253 | 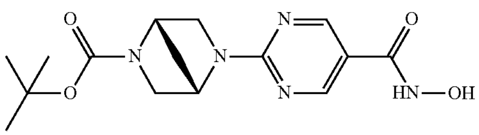 | (1S,4S)-tert-butyl 5-(5-(hydroxycarbamoyl)pyrimidin-2-yl)-2,5-diazabicyclo[2.2.1]heptane-2-carboxylate | (DMSO-d6) δ (ppm): 11.09 (s, 1H), 9.03 (s, 1H), 8.64 (s, 2H), 4.91 (s, 1H), 4.45 (d, J = 11.7 Hz, 1H), 3.60-3.30 (m, 3H), 3.14 (d, J = 9.7 Hz, 1H), 1.93 (s, 1H), 1.90 (s, 1H), 1.38 (s, 5H), 1.33 (s, 4H). LRMS(ESI): (calc.) 335.16 (found) 336.3 (MH) |
| 115 | 254 | 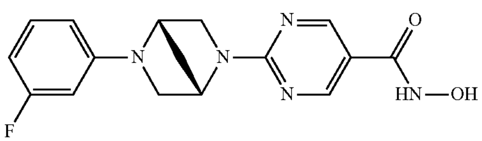 | 2-((1S,4S)-5-(3-fluorophenyl)-2,5-diazabicyclo[2.2.1]heptan-2-yl)-N-hydroxypyrimidine-5-carboxamide | (DMSO-d6) δ (ppm): 11.03 (s, 1H), 8.98 (s, 1H), 8.64 (s, 1H), 8.59 (s, 1H), 7.20-7.07 (m, 1H), 6.45-6.31 (m, 3H), 5.01 (s, 1H), 4.65 (s, 1H), 3.63-3.61 (m, 1H), 3.58-3.54 (m, 1H), 3.7 (d, J = 10.8 Hz, 1H), 2.99 (d, J = 9.2 Hz, 1H), 2.05 (s, 2H). LRMS(ESI): (calc.) 329.13 (found) 330.2 (MH)+ |
| 116 | 255 | 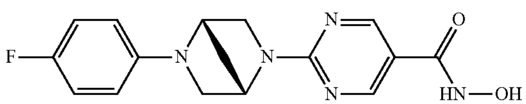 | 2-((1S,4S)-5-(4-fluorophenyl)-2,5-diazabicyclo[2.2.1]heptan-2-yl)-N-hydroxypyrimidine-5-carboxamide | (DMSO-d6) δ (ppm): 11.02 (s, 1H), 8.98 (s, 1H), 8.63 (s, 1H), 8.57 (s, 1H), 6.96 (t, J = 8.9 Hz, 2H), 6.62-6.55 (m, 2H), 4.99 (s, 1H), 4.59 (s, 1H), 3.63 (dd, J = 8.8, 1.6 Hz, 1H), 3.56-3.53 (m, 1H), 3.47 (d, J = 10.5 Hz, 1H), 2.92 (d, J = 9.0 Hz, 1H), 2.05 (s, 2H). LRMS(ESI): (calc.) 329.1 (found) 330.2 (MH)+ |

TABLE 4-continued

| Ex | Cpd | Structure | Name | Characterization |
|---|---|---|---|---|
| 117 | 256 | 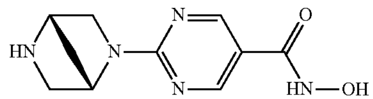 [SMILES: O=C(NO)c1cnc(N2C[C@@H]3C[C@H]2CN3)nc1] | 2-((1S,4S)-2,5-diazabicyclo[2.2.1]heptan-2-yl)-N-hydroxypyrimidine-5-carboxamide | (DMSO-d6) δ (ppm): 11.17 (br s, 0.5H), 9.79 (s, 1H), 9.19 (s, 1H), 8.71 (s, 2H), 5.00 (s, 1H), 4.64 (s, 1H), 3.79 (d, J = 11.7 Hz, 1H), 3.58 (d, J = 11.5 Hz, 1H), 3.38-3.22 (m, 1H), 3.20-3.10 (m, 1H), 2.11 (d, J = 10.6 Hz, 1H), 1.93 (d, J = 10.8 Hz, 1H) LRMS(ESI): (calc.) 235.1 (found) 236.1 (MH)+ |
| 118 | 257 | 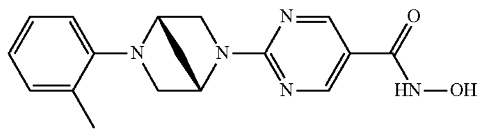 | N-hydroxy-2-((1S,4S)-5-o-tolyl-2,5-diazabicyclo[2.2.1]heptan-2-yl)pyrimidine-5-carboxamide | (DMSO-d6) δ (ppm): 11.02 (s, 1H), 8.97 (s, 1H), 8.61 (d, J = 4.7 Hz, 2H), 7.05-6.98 (m, 2H), 6.82 (d, J = 8.3 Hz, 1H), 6.71 (t, J = 7.3 Hz, 1H), 4.96 (s, 1H), 4.34 (s, 1H), 3.73 (d, J = 10.9 Hz, 1H), 3.67-3.61 (m, 1H), 3.60-3.54 (m, 1H), 3.03 (d, J = 9.0 Hz, 1H), 2.16 (s, 3H), 2.06-1.96 (m, 2H). LRMS(ESI): (calc.) 326.15 (found) 326.3 (MH)+ |
| 119 | 258 | 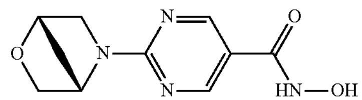 | 2-((1S,4S)-2-oxa-5-azabicyclo[2.2.1]heptan-5-yl)-N-hydroxypyrimidine-5-carboxamide | (DMSO-d6) δ (ppm): 11.06 (s, 1H), 8.99 (s, 1H), 8.64 (s, 2H), 4.98 (s, 1H), 4.67 (s, 1H), 3.80-3.76 (d, 1H), 3.63 (d, J = 7.2 Hz, 1H), 3.51-3.46 (m, 1H), 3.39 (d, J = 11.4 Hz, 1H), 1.92 (d, J = 9.8 Hz, 1H), 1.86 (d, J = 10.0 Hz, 1H). LRMS(ESI): (calc.) 236.1 (found) 237.1 (MH)+ |
| 120 | 259 | 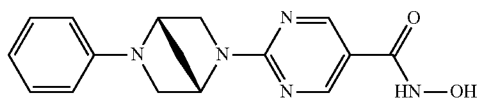 | N-hydroxy-2-((1S,4S)-5-phenyl-2,5-diazabicyclo[2.2.1]heptan-2-yl)pyrimidine-5-carboxamide | (DMSO-d6) δ (ppm): 11.01 (s, 1H), 8.97 (s, 1H), 8.63 (s, 1H), 8.57 (s, 1H), 7.12 (t, J = 7.9 Hz, 2H), 6.62-6.54 (m, 3H), 5.00 (s, 1H), 4.62 (s, 1H), 3.63 (dd, J = 8.9, 1.5 Hz, 1H), 3.58-3.53 (m, 1H), 3.49 (d, J = 10.5 Hz, 1H), 2.97 (d, J = 9.0 Hz, 1H), 2.05 (s, 2H). LRMS(ESI): (calc.) 311.14 (found) 312.3 (MH)+ |
| 121 | 260 | 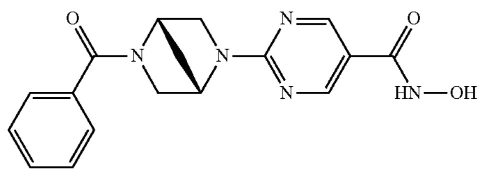 [SMILES: O=C(NO)c1cnc(N2C[C@@H]3C[C@H]2CN3C(=O)c2ccccc2)nc1] | 2-((1S,4S)-5-benzoyl-2,5-diazabicyclo[2.2.1]heptan-2-yl)-N-hydroxypyrimidine-5-carboxamide | (MeOD-d4) δ (ppm): 8.69-8.62 (m, 2H), 7.52-7.40 (m, 5H), 5.17 (s, 0.5H), 5.05 (s, 0.5H), 4.57 (s, 0.5H), 3.79-3.74 (m, 3H), 3.64 (d, J = 10.8 Hz, 0.5H) 3.55 (d, J = 11.35 Hz, 0.5H), 3.35-3.30 (m, 0.5H), 2.15-2.04 (m, 2H) LRMS(ESI): (calc.) 339.1 (found) 338.3 (M–) |
| 122 | 261 | 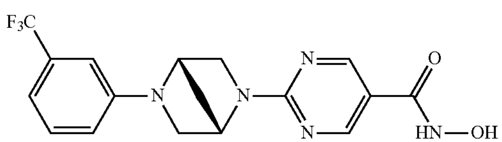 | N-hydroxy-2-((1S,4S)-5-(3-(trifluoromethyl)phenyl)-2,5-diazabicyclo[2.2.1]heptan-2-yl)pyrimidine-5-carboxamide | (DMSO-d6) δ (ppm): 11.0 (bs, 1H), 8.98 (bs, 1H), 8.63 (s, 1H), 8.58 (s, 1H), 7.31 (t, J = 8 Hz, 1H), 6.88 (s, 1H), 6.86 (s, 1H), 6.81 (s, 1H), 5.03 (s, 1H), 4.76 (s, 1H), 3.69 (d, J = 1.2 Hz, 1H), 3.60 (d, J = 10.8 Hz, 1H), 3.45 (d, J = 10.8 Hz, 1H), 3.03 (d, J = 9.2 Hz, 1H), 2.07 (s, 2H). LRMS(ESI): (calc.) 379.1 (found) 378.2 (M–) |
| 123 | 262 | 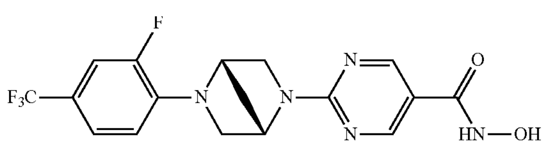 [SMILES: O=C(NO)c1cnc(N2C[C@@H]3C[C@H]2CN3c2ccc(C(F)(F)F)cc2F)nc1] | 2-((1S,4S)-5-(2-fluoro-4-(trifluoromethyl)phenyl)-2,5-diazabicyclo[2.2.1]heptan-2-yl)-N-hydroxypyrimidine-5-carboxamide | (DMSO-d6) δ (ppm): 11.0 (bs, 1H), 8.98 (bs, 1H), 8.63 (s, 1H), 8.60 (s, 1H), 7.42 (d, J = 14 Hz, 1H), 7.30 (d, J = 8.8 Hz, 1H), 6.92 (t, J = 8.8 Hz, 1H), 5.00 (s, 1H), 4.72 (s, 1H), 3.84 (d, J = 8 Hz, 1H), 3.60 (s, 2H), 3.20 (m, 2H), 2.06 (s, 2H). LRMS(ESI): (calc.) 397.1 (found) 396.2 (M)– |

| Ex | Cpd | Structure | Name | Characterization |
|---|---|---|---|---|
| 124 | 263 | 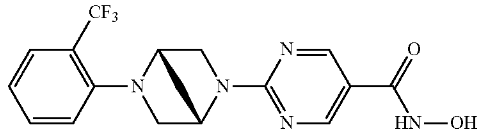 [SMILES: O=C(NO)c1cnc(N2C[C@@H]3C[C@H]2CN3c2ccccc2C(F)(F)F)nc1] | N-hydroxy-2-((1S,4S)-5-(2-(trifluoromethyl)phenyl)-2,5-diazabicyclo[2.2.1]heptan-2-yl)pyrimidine-5-carboxamide | (DMSO-d6) δ (ppm): 11.0 (bs, 1H), 8.97 (bs, 1H), 8.62 (s, 2H), 7.53 (d, J = 7.2 Hz, 1H), 7.44 (t, J = 7.2 Hz, 1H), 7.13 (d, J = 8.4 Hz, 1H), 6.90 (t, J = 7.6 Hz, 1H), 5.00 (s, 1H), 4.48 (s, 1H), 3.71 (m, 2H), 3.61 (m, 1H), 3.07 (d, J = 9.2 Hz, 1H), 2.05 (s, 2H). LRMS(ESI): (calc.) 379.1 (found) 378.1 (M)– |
| 125 | 264 | 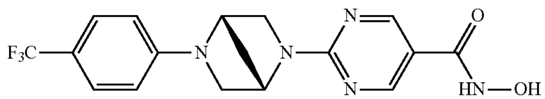 | N-hydroxy-2-((1S,4S)-5-(4-(trifluoromethyl)phenyl)-2,5-diazabicyclo[2.2.1]heptan-2-yl)pyrimidine-5-carboxamide | (DMSO-d6) δ (ppm): 11.0 (bs, 1H), 8.98 (bs, 1H), 8.64 (s, 1H), 8.59 (s, 1H), 7.42 (d, J = 8.4 Hz, 2H), 6.72 (d, J = 8.4 Hz, 2H), 5.04 (s, 1H), 4.75 (s, 1H), 3.66 (d, J = 8.8 Hz, 1H), 3.59 (d, J = 10 Hz, 1H), 3.46 (d, J = 10 Hz, 1H), 3.08 (d, J = 9.2 Hz, 1H), 2.06 (s, 2H). LRMS(ESI): (calc.) 379.1 (found) 378.1 (M)– |
| 126 | 265 | 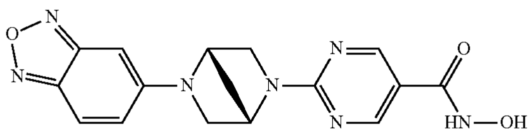 [SMILES: O=C(NO)c1cnc(N2C[C@@H]3C[C@H]2CN3c2ccc3nsnc3c2)nc1] | 2-((1S,4S)-5-(benzo[c][1,2,5]oxadiazol-5-yl)-2,5-diazabicyclo[2.2.1]heptan-2-yl)-N-hydroxypyrimidine-5-carboxamide | (DMSO-d6) δ (ppm): 11.0 (bs, 1H), 8.98 (bs, 1H), 8.65 (s, 1H), 8.60 (s, 1H), 7.82 (d, J = 9.6 Hz, 1H), 7.44 (bs, 1H), 6.46 (bs, 1H), 5.08 (s, 1H), 4.94 (bs, 1H), 3.73-3.54 (m, 2H), 2.11 (m, 2H). LRMS(ESI): (calc.) 353.1 (found) 352.2 (M)– |
| 127 | 266 | 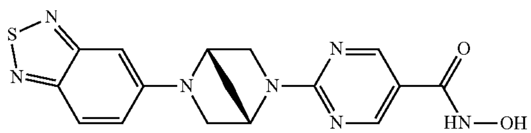 | 2-((1S,4S)-5-(benzo[c][1,2,5]thiadiazol-5-yl)-2,5-diazabicyclo[2.2.1]heptan-2-yl)-N-hydroxypyrimidine-5-carboxamide | (DMSO-d6) δ (ppm): 11.0 (bs, 1H), 8.98 (bs, 1H), 8.65 (s, 1H), 8.58 (s, 1H), 7.82 (d, J = 9.6 Hz, 1H), 7.44 (bs, 1H), 6.82 (s, 1H), 5.08 (s, 1H), 4.91 (s, 1H), 3.76 (d, J = 8 Hz, 1H), 3.65 (d, J = 10.8 Hz, 1H), 3.55 (d, J = 10.8 Hz, 1H), 3.23 (d, J = 8 Hz, 1H), 2.12 (s, 2H). LRMS(ESI): (calc.) 369.1 (found) 368.2 (M)– |
| 128 | 267 | 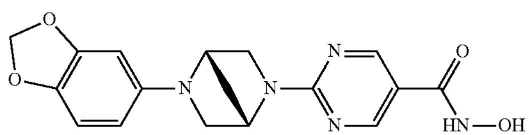 [SMILES: O=C(NO)c1cnc(N2C[C@@H]3C[C@H]2CN3c2ccc3c(c2)OCO3)nc1] | 2-((1S,4S)-5-(benzo[d][1,3]dioxol-5-yl)-2,5-diazabicyclo[2.2.1]heptan-2-yl)-N-hydroxypyrimidine-5-carboxamide | (DMSO-d6) δ (ppm): 11.0 (bs, 1H), 8.9 (bs, 1H), 8.62 (s, 1H), 8.57 (s, 1H), 6.69 (d, J = 8.4 Hz, 1H), 6.36 (d, J = 2.4 Hz, 1H), 5.96 (dd, J = 2.4 Hz, 8.4 Hz, 1H), 5.83 (d, J = 5.6 Hz, 2H), 4.95 (s, 1H), 4.52 (s, 1H), 3.59 (d, J = 8.8 Hz, 1H), 3.50 (s, 2H), 2.88 (d, J = 8.8 Hz, 1H), 2.02 (s, 2H). LMRS(ESI): (calc.) 355.1 (found) 353.9 (M)– |
| 129 | 268 | 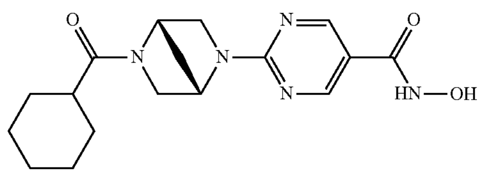 [SMILES: O=C(NO)c1cnc(N2C[C@@H]3C[C@H]2CN3C(=O)C2CCCCC2)nc1] | 2-((1S,4S)-5-(cyclohexanecarbonyl)-2,5-diazabicyclo[2.2.1]heptan-2-yl)-N-hydroxypyrimidine-5-carboxamide | MeOD-d4) δ (ppm):8.67 (s, 2H), 5.12 (d, J = 10.2 Hz, 1H), 3.63 (dd, J = 10.8, 1.9 Hz, 0.5H), 3.72 (d, J = 18.0 Hz, 1H), 3.58-3.48 (m, 2H), 3.37 (d, J = 11.3 Hz, 0.5H), 2.64-2.58 (m, 0.5H), 2.33-2.30 (m, 0.5H), 2.12-1.97 (m, 2H), 1.82-1.66 (m, 5H), 1.57-1.19 (m, 6H). LRMS(ESI): (calc.) 345.2 (found) 344.3 (M)– |

TABLE 4-continued

| Ex | Cpd | Structure | Name | Characterization |
|---|---|---|---|---|
| 130 | 269 | 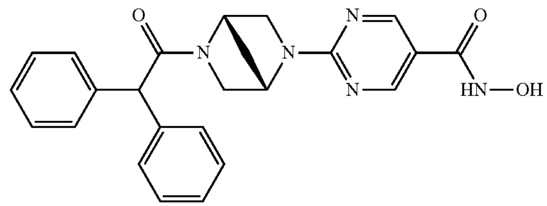 [SMILES: O=C(NO)c1cnc(N2C[C@@H]3C[C@H]2CN3C(=O)C(c2ccccc2)c2ccccc2)nc1] | 2-((1S,4S)-5-(2,2-diphenylacetyl)-2,5-diazabicyclo[2.2.1]heptan-2-yl)-N-hydroxypyrimidine-5-carboxamide | (DMSO-d6) δ (ppm): 11.00 (s, 1H), 9.02 (m, 1H), 8.62 (s, 1H), 8.59 (s, 0.5H), 8.51 (s, 0.5H), 7.34-7.14 (m, 7H), 7.13-7.06 (m, 2.5H), 7.02-6.97 (m, 0.5H), 5.51 (s, 0.5H), 5.06 (s, 0.5H), 4.93 (d, J = 8.1 Hz, 1H), 4.82 (d, J = 7.5 Hz, 1H), 3.60-3.10 (m, 4H), 1.95 and 1.85 (AB d, J = 10.0 Hz, 2H). LRMS(ESI): (calc.) 429.2 (found) 430.3 (MH)+ |
| 131 | 270 | 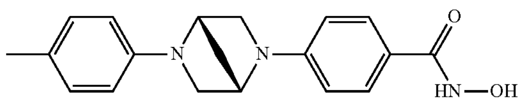 | N-hydroxy-4-((1S,4S)-5-p-tolyl-2,5-diazabicyclo[2.2.1]heptan-2-yl)benzamide | (DMSO-d6) δ (ppm): 10.79 (s, 1H), 8.70 (s, 1H), 7.53 (d, J = 8.8 Hz, 2H), 6.90 (d, J = 8.2 Hz, 2H), 6.54 (d, J = 8.6 Hz, 2H), 6.45 (d, J = 8.4 Hz, 2H), 4.64 (s, 1H), 4.54 (s, 1H), 3.54 (t, J = 7.9 Hz, 2H), 3.04 (d, J = 9.2 Hz, 1H), 2.89 (d, J = 8.8 Hz, 2H), 2.12 (s, 3H), 2.07-1.99 (m, 2H). LRMS(ESI): (calc.) 323.2 (found) 324.3 (MH)+ |
| 132 | 271 | 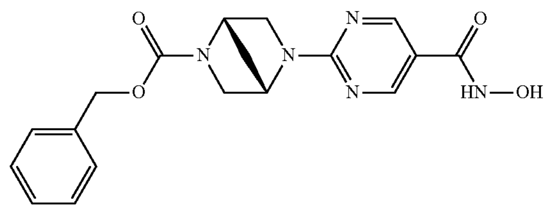 [SMILES: O=C(NO)c1cnc(N2C[C@@H]3C[C@H]2CN3C(=O)OCc2ccccc2)nc1] | (1S,4S)-benzyl 5-(5-(hydroxycarbamoyl)pyrimidin-2-yl)-2,5-diazabicyclo[2.2.1]heptane-2-carboxylate | (dmso-d6) d(ppm) 1H: 11.10 (s, 1H), 8.99 (s, 1H), 8.65 (s, 2H), 7.39-7.22 (m, 5H), 5.10-5.00 (m, 2H), 4.94 (s, 1H), 4.57 (d, J = 10.7 Hz, 1H), 3.60-3.30 (m, 4H), 2.0-1.80 (m, 2H) LRMS(ESI): (calc.) 369.1 (found) 370.3 (MH)+ |
| 133 | 272 | 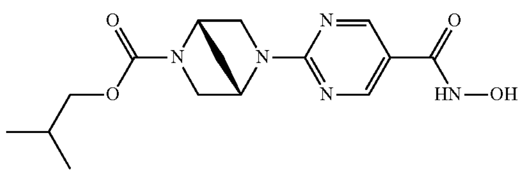 [SMILES: CC(C)COC(=O)N1C[C@@H]2C[C@H]1CN2c1ncc(C(=O)NO)cn1] | (1S,4S)-isobutyl 5-(5-(hydroxycarbamoyl)pyrimidin-2-yl)-2,5-diazabicyclo[2.2.1]heptane-2-carboxylate | (dmso-d6) d(ppm) 1H: 11.07 (s, 1H), 9.01 (s, 1H), 8.65 (s, 2H), 5.00-4.90 (m, 1H), 4.53 (s, 1H), 3.82-3.70 (s, 2H), 3.56 (t, J = 11.0 Hz, 1H), 3.50-3.39 (m, 2H), 3.50-3.30 (m, 1H), 1.96 (s, 1H), 1.93 (s, 1H), 1.91-1.70 (m, 1H), 0.88 (d, J = 6.7 Hz, 3H), 0.79 (d, J = 6.6 Hz, 3H) LRMS(ESI): (calc.) 335.2 (found) 336.3 (MH)+ |
| 134 | 273 | 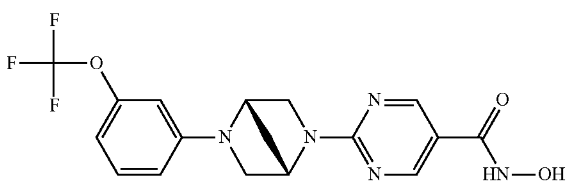 [SMILES: O=C(NO)c1cnc(N2C[C@@H]3C[C@H]2CN3c2cccc(OC(F)(F)F)c2)nc1] | N-hydroxy-2-((1S,4S)-5-(3-(trifluoromethoxy)phenyl)-2,5-diazabicyclo[2.2.1]heptan-2-yl)pyrimidine-5-carboxamide | (CD3OD) d(ppm) 1H: 8.65 (s, 1H), 8.59 (s, 1H), 7.20 (t, J = 8.4 Hz, 1H), 6.59 (d, J = 8.4 Hz, 1H), 6.51 (d, J = 8.4 Hz, 1H), 6.45 (s, 1H), 5.14 (s, 1H), 4.64 (s, 1H), 3.63-3.70 (m, 3H), 3.12 (d, J = 8.8 Hz, 1H), 2.14 (d, J = 10 Hz, 13.2 Hz, 2H) LRMS(ESI): (calc.) 395.12 (found) 394.17 (M)− |
| 135 | 274 | 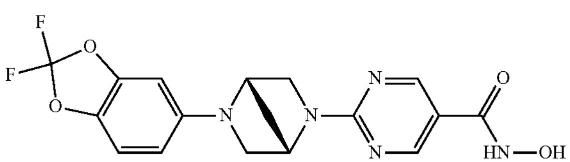 [SMILES: O=C(NO)c1cnc(N2C[C@@H]3C[C@H]2CN3c2ccc3c(c2)OC(F)(F)O3)nc1] | 2-((1S,4S)-5-(2,2-difluorobenzo[d][1,3]dioxol-5-yl)-2,5-diazabicyclo[2.2.1]heptan-2-yl)-N-hydroxypyrimidine-5-carboxamide | (CD3OD) d(ppm) 1H: 8.65 (s, 1H), 8.59 (s, 1H), 6.96 (d, J = 8.4 Hz, 1H), 6.55 (s, 1H), 6.30 (d, J = 8.8 Hz, 1H), 5.13 (s, 1H), 4.59 (s, 1H), 3.70 (d, J = 9.2 Hz, 1H), 3.63 (s, 2H), 3.07 (d, J = 8.8 Hz, 1H), 2.14 (dd, J = 9.2 Hz, 17.2 Hz, 2H) LRMS(ESI): (calc.) 391.1 (found) 390.1 (M)− |

TABLE 4-continued

| Ex | Cpd | Structure | Name | Characterization |
|---|---|---|---|---|
| 136 | 275 | 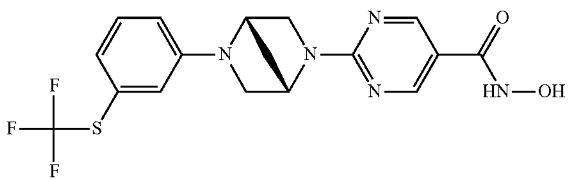 [SMILES: O=C(NO)c1cnc(N2C[C@@H]3C[C@H]2CN3c2cccc(SC(F)(F)F)c2)nc1] | N-hydroxy-2-((1S,4S)-5-(3-(trifluoromethylthio)phenyl)-2,5-diazabicyclo[2.2.1]heptan-2-yl)pyrimidine-5-carboxamide | (CD3OD) d(ppm) 1H: 8.65 (s, 1H), 8.58 (s, 1H), 7.24 (t, J = 7.6 Hz, 1H), 6.91 (d, J = 7.6 Hz, 1H), 6.86 (s, 1H), 6.78 (d, J = 7.6 Hz, 1H), 5.15 (s, 1H), 4.67 (s, 1H), 3.60-3.72 (m, 3H), 3.13 (d, J = 8.8 Hz, 1H), 2.14 (dd, J = 10 Hz, 13.2 Hz, 2H) LRMS(ESI): (calc.) 411.1 (found) 410.2 (M)− |
| 137 | 276 | 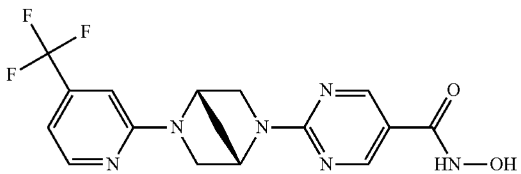 | N-hydroxy-2-((1S,4S)-5-(4-(trifluoromethyl)pyridin-2-yl)-2,5-diazabicyclo[2.2.1]heptan-2-yl)pyrimidine-5-carboxamide | (CD3OD) d(ppm) 1H: 8.66 (s, 1H), 8.61 (s, 1H), 8.22 (d, J = 5.2 Hz, 1H), 6.78 (d, J = 5.2 Hz, 1H), 6.73 (s, 1H), 5.20 (s, 1H), 5.05 (s, 1H), 3.72 (d, J = 11.2 Hz, 2H), 3.60 (d, J = 10.8 Hz, 1H), 3.41 (d, J = 9.6 Hz, 1H), 2.15 (s, 2H) LRMS(ESI): (calc.) 380.1 (found) 379.2 (M)− |
| 138 | 277 | 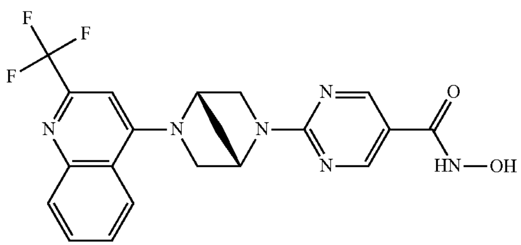 [SMILES: O=C(NO)c1cnc(N2C[C@@H]3C[C@H]2CN3c2cc(C(F)(F)F)nc3ccccc23)nc1] | N-hydroxy-2-((1S,4S)-5-(2-(trifluoromethyl)quinolin-4-yl)-2,5-diazabicyclo[2.2.1]heptan-2-yl)pyrimidine-5-carboxamide | (CD3OD) d(ppm) 1H: 8.63 (bs, 2H), 8.23 (d, J = 8.8 Hz, 1H), 7.96 (d, J = 8.8 Hz, 1H), 7.70 (t, J = 7.2 Hz, 1H), 7.51 (t, J = 7.2 Hz, 1H), 6.96 (s, 1H), 5.23 (s, 1H), 5.04 (s, 1H), 4.42 (d, J = 9.2 Hz, 1H), 3.98 (d, J = 10.8 Hz, 1H), 3.85 (d, J = 10.8 Hz, 1H), 3.65 (d, J = 9.2 Hz, 1H), 2.28 (dd, J = 10 Hz, 22 Hz, 2H) LRMS(ESI): (calc.) 430.14 (found) 429.15 (M)− |
| 139 | 278 | 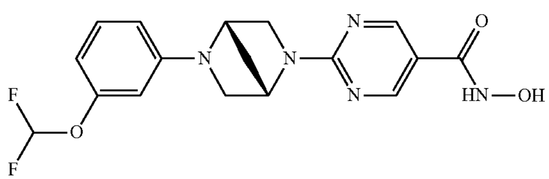 [SMILES: O=C(NO)c1cnc(N2C[C@@H]3C[C@H]2CN3c2cccc(OC(F)F)c2)nc1] | 2-((1S,4S)-5-(3-(difluoromethoxy)phenyl)-2,5-diazabicyclo[2.2.1]heptan-2-yl)-N-hydroxypyrimidine-5-carboxamide | (CD3OD) d(ppm) 1H: 8.65 (s, 1H), 8.58 (s, 1H), 7.14 (t, J = 8 Hz, 1H), 6.73 (t, J = 74.5 Hz, 1H), 6.47 (d, J = 6.4 Hz, 1H), 6.38 (d, J = 6.4 Hz, 1H), 6.33 (s, 1H), 5.13 (s, 1H), 4.62 (s, 1H), 3.69 (d, J = 8.8 Hz, 1H), 3.63 (s, 2H), 3.12 (d, J = 8.8 Hz, 1H), 2.12 (dd, J = 10 Hz, 14 Hz, 2H) LRMS(ESI): (calc.) 377.13 (found) 376.24 (M)− |
| 140 | 279 | 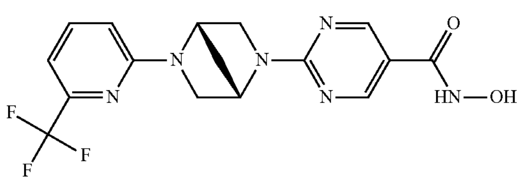 [SMILES: O=C(NO)c1cnc(N2C[C@@H]3C[C@H]2CN3c2cccc(C(F)(F)F)n2)nc1] | N-hydroxy-2-((1S,4S)-5-(6-(trifluoromethyl)pyridin-2-yl)-2,5-diazabicyclo[2.2.1]heptan-2-yl)pyrimidine-5-carboxamide | (CD3OD) d(ppm) 1H: 8.66 (s, 1H), 8.60 (s, 1H), 7.62 (t, J = 8.2 Hz, 1H), 6.92 (d, J = 7.2 Hz, 1H), 6.96 (d, J = 8.2 Hz, 1H), 5.18 (s, 1H), 5.05 (s, 1H), 3.69 (m, 2H), 3.60 (d, J = 10.8 Hz, 1H), 3.40 (d, J = 9.6 Hz, 1H), 2.13 (s, 2H) LRMS(ESI): (calc.) 380.12 (found) 379.24 (M)− |

TABLE 4-continued

| Ex | Cpd | Structure | Name | Characterization |
|---|---|---|---|---|
| 141 | 280 | 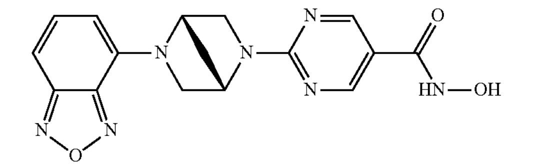 [SMILES: O=C(NO)c1cnc(N2C[C@@H]3C[C@H]2CN3c2cccc3nonc23)nc1] | 2-((1S,4S)-5-(benzo[c][1,2,5]oxadiazol-4-yl)-2,5-diazabicyclo[2.2.1]heptan-2-yl)-N-hydroxypyrimidine-5-carboxamide | (CD3OD) d(ppm) 1H: 8.67 (s, 1H), 8.59 (s, 1H), 7.28 (t, J = 7.6 Hz, 1H), 6.98 (d, J = 8.8 Hz, 1H), 6.13 (d, J = 7.6 Hz, 1H), 5.45 (s, 1H), 5.23 (s, 1H), 3.95 (d, J = 8.8 Hz, 1H), 3.74 (dd, J = 10.8 Hz, 23 Hz, 2H), 3.51 (d, J = 10 Hz, 1H), 2.23 (q, J = 11.2 Hz, 2H) LRMS(ESI): (calc.) 353.1 (found) 352.0 (M)− |
| 142 | 281 | 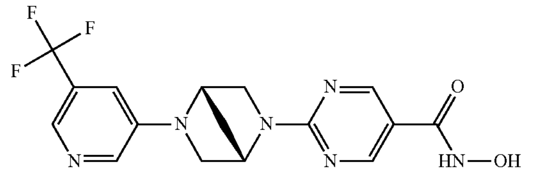 | N-hydroxy-2-((1S,4S)-5-(5-(trifluoromethyl)pyridin-3-yl)-2,5-diazabicyclo[2.2.1]heptan-2-yl)pyrimidine-5-carboxamide | (CD3OD) d(ppm) 1H: 8.66 (s, 1H), 8.60 (s, 1H), 8.18 (s, 1H), 8.06 (s, 1H), 7.26 (s, 1H), 5.21 (s, 1H), 4.83 (s, 1H), 3.76 (m, 2H), 3.60 (d, J = 10.8 Hz, 1H), 3.25 (d, J = 9.2 Hz, 1H), 2.18 (s, 2H) LRMS(ESI): (calc.) 380.1 (found) 379.0 (M)− |
| 143 | 282 | 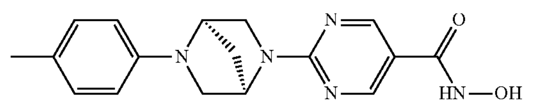 [SMILES: Cc1ccc(N2C[C@H]3C[C@@H]2CN3c2ncc(C(=O)NO)cn2)cc1] | N-hydroxy-2-((1S,4R)-5-p-tolyl-2,5-diazabicyclo[2.2.1]heptan-2-yl)pyrimidine-5-carboxamide | (dmso-d6) d(ppm) 1H: 11.02 (s, 1H), 9.00 (s, 1H), 8.62 (s, 1H), 8.57 (s, 1H), 6.94 (d, J = 8.0 Hz, 2H), 6.49 (d, J = 8.2 Hz, 2H), 4.97 (s, 1H), 4.56 (s, 1H), 3.61 (d, J = 8.6 Hz, 1H), 3.53 and 3.48 (ab d, J = 10.7 Hz, 2H), 2.90 (d, J = 9.0 Hz, 1H), 2.13 (s, 3H), 2.10-2.00 (m, 2H) LRMS(ESI): (calc.) 325.2 (found) 326.2 (MH)+ |
| 144 | 283 | 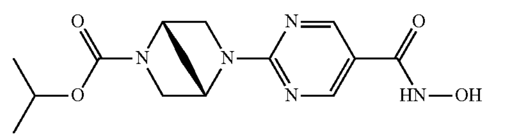 [SMILES: CC(C)OC(=O)N1C[C@@H]2C[C@H]1CN2c1ncc(C(=O)NO)cn1] | (1S,4S)-isopropyl 5-(5-(hydroxycarbamoyl)pyrimidin-2-yl)-2,5-diazabicyclo[2.2.1]heptane-2-carboxylate | (dmso-d6) d(ppm) 1H: 11.06 (s, 1H), 9.00 (s, 1H), 8.65 (s, 2H), 4.93 (d, J = 5.2 Hz, 1H), 4.80-4.68 (m, 1H), 4.50 (d, J = 14.3 Hz, 1H), 3.60-3.50 (m, 1H), 3.45-3.38 (m, 2H), 3.22-3.15 (m, 2H), 1.95 (s, 1H), 1.92 (s, 1H), 1.22-1.08 (m, 6H) LRMS(ESI): (calc.) 321.1 (found) 322.2 (MH)+ |
| 145 | 284 | 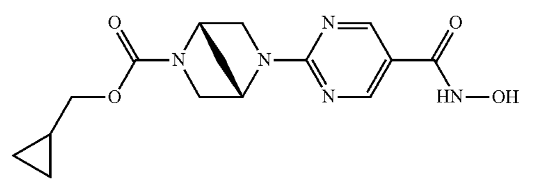 [SMILES: O=C(NO)c1cnc(N2C[C@@H]3C[C@H]2CN3C(=O)OCC2CC2)nc1] | (1S,4S)-cyclopropylmethyl 5-(5-(hydroxycarbamoyl)pyrimidin-2-yl)-2,5-diazabicyclo[2.2.1]heptane-2-carboxylate | (dmso-d6) d(ppm) 1H: 11.07 (s, 1H), 9.01 (s, 1H), 8.66 (s, 2H), 4.95 (d, J = 5.1 Hz, 1H), 4.53 (s, 1H), 3.90-3.70 (m, 2H), 3.56 (t, J = 9.5 Hz, 1H), 3.50-3.40 (m, 2H), 3.21 (t, J = 10.5 Hz, 1H), 1.97 (s, 1H), 1.94 (s, 1H), 1.15-0.95 (m, 1H), 0.55-0.49 (m, 2H), 0.48-0.46 (m, 2H) LRMS(ESI): (calc.) 333.1 (found) 334.2 (MH)+ |
| 146 | 285 | 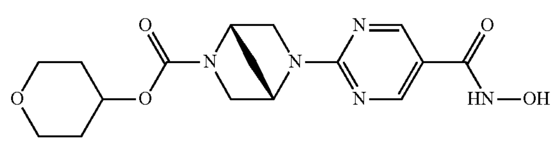 [SMILES: O=C(NO)c1cnc(N2C[C@@H]3C[C@H]2CN3C(=O)OC2CCOCC2)nc1] | (1S,4S)-tetrahydro-2H-pyran-4-yl 5-(5-(hydroxycarbamoyl)pyrimidin-2-yl)-2,5-diazabicyclo[2.2.1]heptane-2-carboxylate | (dmso-d6) d(ppm) 1H: 11.07 (s, 1H), 9.01 (s, 1H), 8.65 (s, 2H), 4.94 (d, J = 7.4 Hz, 1H), 4.54 (s, 1H), 4.78-4.65 (m, 1H), 4.54 (d, J = 8.6 Hz, 1H), 3.82-363 (m, 2H), 3.56 (t, J = 10.4 Hz, 1H), 3.50-3.35 (m, 4H), 3.26-3.15 (m, 1H), 1.95 (d, J = 12.8 Hz, 2H), 1.90-1.70 (m, 2H), 1.60-1.40 (m, 2H) LRMS(ESI): (calc.) 363.2 (found) 364.2 (MH)+ |

TABLE 4-continued

| Ex | Cpd | Structure | Name | Characterization |
|---|---|---|---|---|
| 147 | 286 | 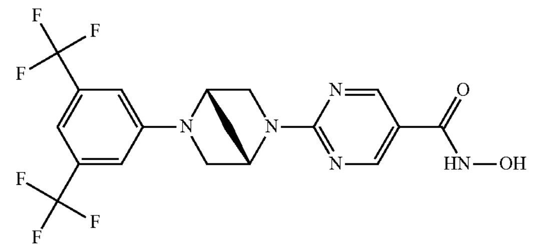 [SMILES: O=C(NO)c1cnc(N2C[C@@H]3C[C@H]2CN3c2cc(C(F)(F)F)cc(C(F)(F)F)c2)nc1] | 2-((1S,4S)-5-(3,5-bis(trifluoromethyl)phenyl)-2,5-diazabicyclo[2.2.1]heptan-2-yl)-N-hydroxypyrimidine-5-carboxamide | (CD3OD) d(ppm) 1H: 8.66 (s, 1H), 8.60 (s, 1H), 7.06 (m, 3H), 5.20 (s, 1H), 4.82 (s, 1H), 3.75 (m, 2H), 3.60 (d, J = 10.8 Hz, 1H), 3.21 (d, J = 9.2 Hz, 1H), 2.17 (m, 2H) LRMS(ESI): (calc.) 447.11 (found) 446.45 (M)− |
| 148 | 287 | 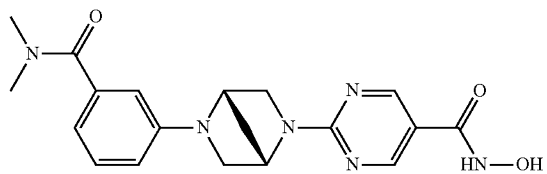 [SMILES: CN(C)C(=O)c1cccc(N2C[C@@H]3C[C@H]2CN3c2ncc(C(=O)NO)cn2)c1] | 2-((1S,4S)-5-(3-(dimethylcarbamoyl)phenyl)-2,5-diazabicyclo[2.2.1]heptan-2-yl)-N-hydroxypyrimidine-5-carboxamide | (CD3OD) d(ppm) 1H: 8.64 (s, 1H), 8.57 (s, 1H), 7.22 (t, J = 8 Hz, 1H), 6.64 (m, 3H), 5.12 (s, 1H), 4.65 (s, 1H), 3.70 (d, J = 8.4 Hz, 1H), 3.63 (s, 2H), 3.12 (d, J = 8.8 Hz, 1H), 3.06 (s, 3H), 2.96 (s, 3H), 2.13 (m, 2H). MS (m/z): 381.0 (M − H). |
| 149 | 288 | 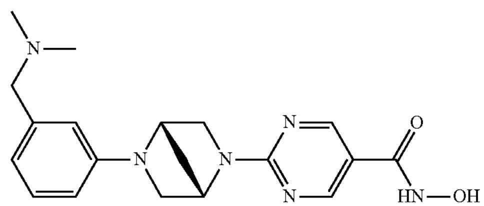 [SMILES: CN(C)Cc1cccc(N2C[C@@H]3C[C@H]2CN3c2ncc(C(=O)NO)cn2)c1] | 2-((1S,4S)-5-(3-((dimethylamino)methyl)phenyl)-2,5-diazabicyclo[2.2.1]heptan-2-yl)-N-hydroxypyrimidine-5-carboxamide | (CD3OD) d(ppm) 1H: 8.64 (s, 1H), 8.57 (s, 1H), 7.24 (t, J = 8 Hz, 1H), 6.72 (m, 3H), 5.13 (s, 1H), 4.65 (s, 1H), 4.15 (s, 2H), 3.70 (d, J = 8.4 Hz, 1H), 3.63 (s, 2H), 3.12 (d, J = 8.8 Hz, 1H), 2.72 (s, 6H), 2.13 (m, 2H). MS (m/z): 369.5 (M + H) |
| 150 | 289 | 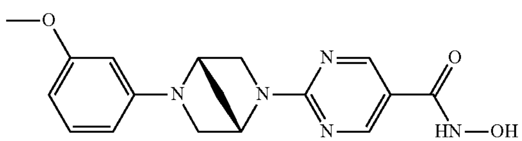 [SMILES: COc1cccc(N2C[C@@H]3C[C@H]2CN3c2ncc(C(=O)NO)cn2)c1] | N-hydroxy-2-((1S,4S)-5-(3-methoxyphenyl))-2,5-diazabicyclo[2.2.1]heptan-2-yl)pyrimidine-5-carboxamide | (CD3OD) d(ppm) 1H: 8.64 (s, 1H), 8.57 (s, 1H), 7.04 (t, J = 8.4 Hz, 1H-artifact from sovent), 6.22 (m, 2H), 6.13 (s, 1H), 5.10 (s, 1H), 4.59 (s, 1H), 3.72 (s, 3H), 3.66 (m, 3H), 3.09 (d, J = 8.8 Hz, 2H), 2.12 (dd, J = 9.6 Hz, 18.4 Hz, 2H). LRMS(ESI): (calc.) 341.15 (found) 340.28 (M)− |
| 151 | 290 | 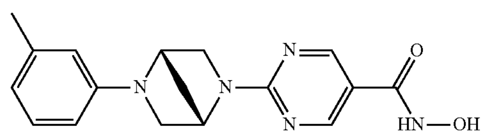 [SMILES: Cc1cccc(N2C[C@@H]3C[C@H]2CN3c2ncc(C(=O)NO)cn2)c1] | N-hydroxy-2-((1S,4S)-5-m-tolyl-2,5-diazabicyclo[2.2.1]heptan-2-yl)pyrimidine-5-carboxamide | (CD3OD) d(ppm) 1H: 8.64 (s, 1H), 8.57 (s, 1H), 7.02 (t, J = 7.6 Hz, 1H-artifact from solvent), 6.42 (m, 3H), 5.10 (s, 1H), 4.59 (s, 1H), 3.66 (m, 3H), 3.09 (d, J = 8.8 Hz, 2H), 2.24 (s, 3H), 2.12 (dd, J = 9.6 Hz, 27.2 Hz, 2H). MS (m/z): 324.3 (M − H) |
| 152 | 291 | 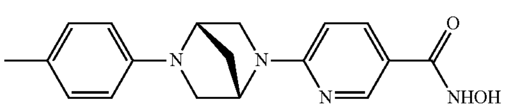 | N-hydroxy-6-((1S,4S)-5-p-tolyl-2,5-diazabicyclo[2.2.1]heptan-2-yl)nicotinamide | (DMSO-d6) δ (ppm): 10.87 (s, 1H), 8.82 (s, 1H), 8.40 (s, 1H), 7.75 (dd, J = 9.0, 2.3 Hz, 1H), 6.91 (d, J = 8.2 Hz, 2H), 6.47 (d, J = 8.5 Hz, 2H), 4.90 (s, 1H), 4.56 (s, 1H), 3.58 (d, J = 7.6 Hz, 1H), 3.49 (d, J = 8.6 Hz, 1H), 3.4-3.2 (m, 1H), 2.88 (d, J = 9.0 Hz, 1H), 2.12 (s, 3H), 2.10-2.00 (m, 2H). MS (m/z): 323.4 (M − H) |

TABLE 4-continued

| Ex | Cpd | Structure | Name | Characterization |
|---|---|---|---|---|
| 153 | 292 | (structure) | N-hydroxy-5-((1S,4S)-5-(3-(trifluoromethyl)phenyl)-2,5-diazabicyclo[2.2.1]heptan-2-yl)pyrazine-2-carboxamide | (DMSO-d$_6$) δ (ppm): 10.99 (s, 1H), 8.87 (s, 1H), 8.48 (s, 1H), 7.94 (s, 1H), 7.32 (t, J = 7.9 Hz, 1H), 6.87 (d, J = 8.0 Hz, 1H), 6.82 (s, 1H), 5.10 (s, 1H), 4.83 (s, 1H), 3.70-3.59 (m, 2H), 3.44 (d, J = 10.2 Hz, 1H), 3.08 (d, J = 9.2 Hz, 1H), 2.13-2.02 (m, 2H). MS (m/z): 380.3 (M + H) |
| 154 | 293 | (structure) | N-hydroxy-2-((1S,4S)-5-(pyrrolidine-1-carbonyl)-2,5-diazabicyclo[2.2.1]heptan-2-yl)pyrimidine-5-carboxamide | (DMSO-d$_6$) δ (ppm): 11.06 (s, 1H), 8.99 (s, 1H), 8.64 (s, 2H), 4.91 (s, 1H), 4.40 (s, 1H), 3.67 (d, J = 10.5 Hz, 1H), 3.57-3.47 (m, 2H), 3.30-3.19 (m, 2H), 3.17-3.09 (m, 3H), 1.87 (q, J = 9.7 Hz, 2H), 1.80-1.59 (m, 4H). MS (m/z): 333.4 (M + H) |
| 155 | 294 | (structure) | N-hydroxy-2-((1S,4S)-5-(4-(trifluoromethyl)pyrimidin-2-yl)-2,5-diazabicyclo[2.2.1]heptan-2-yl)pyrimidine-5-carboxamide | (CD3OD) d(ppm) 1H: 8.87 (s, 1H), 8.62 (s, 1H), 8.54 (s, 1H), 6.90 (d, J = 5.2 Hz, 1H), 5.19 (s, 1H), 5.16 (s, 1H), 3.72 (m, 2H), 3.60 (m, 2H), 2.15 (s, 2H). MS (m/z): 380.35 (M − H). |
| 156 | 295 | (structure) | N-hydroxy-6-((1S,4S)-5-(3-(trifluoromethyl)phenyl)-2,5-diazabicyclo[2.2.1]heptan-2-yl)pyrimidine-5-carboxamide | (DMSO-d$_6$) δ (ppm): 11.34 (s, 1H), 8.98 (s, 1H), 7.71 (d, J = 9.2 Hz, 1H), 7.32 (t, J = 7.9 Hz, 1H), 7.04 (br s, 1H), 6.87 (d, J = 6.4 Hz, 2H), 6.82 (s, 1H), 5.10 (br s, 1H), 4.83 (s, 1H), 3.72-3.60 (m, 2H), 3.44 (br s, 1H), 3.07 (d, J = 9.2 Hz, 1H), 2.15-2.05 (m, 2H). MS (m/z): 380.4 (M + H) |
| 157 | 296 | (structure) | N-hydroxy-2-((1R,4R)-5-m-tolyl-2,5-diazabicyclo[2.2.1]heptan-2-yl)pyrimidine-5-carboxamide | (DMSO-d$_6$) δ (ppm): 11.01 (s, 1H), 8.98 (s, 1H), 8.63 (s, 1H), 8.62 (s, 1H), 7.02-6.90 (m, 1H), 6.43-6.35 (m, 3H), 4.98 (s, 1H), 4.59 (s, 1H), 3.62 (dd, J = 8.9 and 1.6 Hz, 1H), 3.60-3.44 (m, 2H), 2.94 (d, J = 9.0 Hz, 1H), 2.18 (s, 3H), 2.04 (s, 2H). MS (m/z): 326.4 (M + H) |
| 158 | 297 | (structure) | N-hydroxy-2-((1S,4S)-5-(3-(pentafluorosulfanyl)phenyl)-2,5-diazabicyclo[2.2.1]heptan-2-yl)pyrimidine-5-carboxamide | (CD3OD) δ (ppm): 8.66 (s, 1H), 8.59 (s, 1H), 7.31 (t, J = 8 Hz, 1H), 7.03 (d, J = 8 Hz, 1H), 6.94 (s, 1H), 6.84 (d, J = 8.4 Hz, 1H), 5.16 (s, 1H), 4.70 (s, 1H), 3.73 (d, J = 8.8 Hz, 1H), 3.66 (q, J = 10.8 Hz, 2H), 3.14 (d, J = 8.8 Hz, 1H), 2.17 (q, J = 10 Hz, 2H). MS (m/z): 436.4 (M − H). |

| Ex | Cpd | Structure | Name | Characterization |
|---|---|---|---|---|
| 159 | 298 | 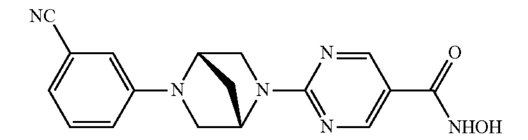 | 2-((1S,4S)-5-(3-cyanophenyl)-2,5-diazabicyclo[2.2.1]heptan-2-yl)-N-hydroxypyrimidine-5-carboxamide | (DMSO-d$_6$) δ (ppm): 11.04 (s, 1H), 9.00 (s, 1H), 8.64 (s, 1H), 8.59 (s, 1H), 7.29 (t, J = 8.0 Hz, 1H), 7.04 (d, J = 7.4 Hz, 1H), 6.92 (d, J = 8.4 Hz, 1H), 5.04 (s, 1H), 4.74 (s, 1H), 3.64 (d, J = 6.8 Hz, 1H), 3.57 (d, J = 9.6 Hz, 1H), 3.45 (d, J = 11.0 Hz, 1H), 3.04 (d, J = 9.2 Hz, 1H), 2.10-2.00 (m, 2H). MS (m/z): 337.4 (M + H). |
| 160 | 299 | 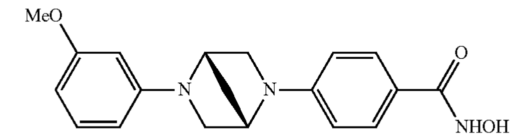 | N-hydroxy-4-((1S,4S)-5-(3-methoxyphenyl)-2,5-diazabicyclo[2.2.1]heptan-2-yl)benzamide | (DMSO-d$_6$) δ (ppm): 11.19 (s, 1H), 10.79 (s, 1H), 7.54 (d, J = 8.6 Hz, 2H), 6.98 (t, J = 8.1 Hz, 1H), 6.55 (d, J = 8.6 Hz, 2H), 6.18-6.11 (m, 2H), 6.08-6.04 (m, 1H), 4.65 (s, 1H), 4.58 (s, 1H), 3.65 (s, 3H), 3.54 (d, J = 8.2 Hz, 2H), 3.06 (d, J = 9.2 Hz, 1H), 2.95 (d, J = 9.0 Hz, 1H), 2.07-1.98 (m, 2H). MS (m/z): 340.5 (M + H). |
| 161 | 300 | 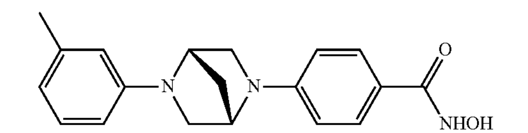 | N-hydroxy-4-((1S,4S)-5-m-tolyl-2,5-diazabicyclo[2.2.1]heptan-2-yl)benzamide | (DMSO-d$_6$) δ (ppm): 10.79 (s, 1H), 8.70 (s, 1H), 7.54 (d, J = 8.6 Hz, 2H), 6.98 (t, J = 7.4 Hz, 1H), 6.55 (d, J = 8.6 Hz, 2H), 6.41-6.33 (m, 3H), 4.65 (s, 1H), 4.57 (s, 1H), 3.55 (d, J = 8.8 Hz, 2H), 3.05 (d, J = 9.0 Hz, 1H), 2.93 (d, J = 8.8 Hz, 1H), 2.17 (s, 3H), 2.07-1.98 (m, 2H). MS (m/z): 324.4 (M + H). |
| 162 | 301 | 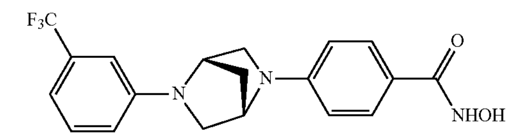 | N-hydroxy-4-((1S,4S)-5-(3-(trifluoromethyl)phenyl)-2,5-diazabicyclo[2.2.1]heptan-2-yl)benzamide | (DMSO-d$_6$) δ (ppm): 10.80 (s, 1H), 8.70 (s, 1H), 7.55 (d, J = 8.6 Hz, 2H), 7.30 (t, J = 8.0 Hz, 1H), 6.84 (d, J = 7.0 Hz, 2H), 6.78 (s, 1H), 6.58 (d, J = 8.6 Hz, 2H), 4.75 (s, 1H), 4.72 (s, 1H), 3.60 (t, J = 7.9 Hz, 2H), 3.03 (d, J = 9.5 Hz, 2H), 2.06 (s, 2H). MS (m/z): 378.5 (M + H). |
| 163 | 302 | 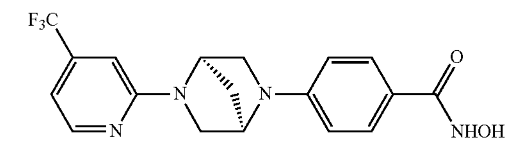 | N-hydroxy-4-((1R,4R)-5-(4-(trifluoromethyl)pyridin-2-yl)-2,5-diazabicyclo[2.2.1]heptan-2-yl)benzamide | (DMSO-d$_6$) δ (ppm): 10.83 (s, 1H), 8.73 (s, 1H), 8.24 (d, J = 5.3 Hz, 1H), 7.57 (d, J = 8.8 Hz, 2H), 6.78 (d, J = 5.0 Hz, 2H), 6.60 (d, J = 8.6 Hz, 2H), 5.02 (s, 1H), 4.75 (s, 1H), 3.63 (d, J = 7.8 Hz, 1H), 3.59 (d, J = 9.0 Hz, 1H), 3.40-3.30 (m, 1H), 3.05 (d, J = 9.2 Hz, 1H), 2.06 (s, 2H). MS (m/z): 379.5 (M + H). |
| 164 | 303 | 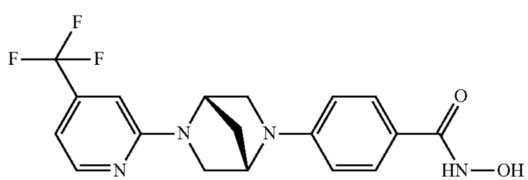 [SMILES: O=C(NO)c1ccc(N2C[C@@H]3C[C@H]2CN3c2cc(C(F)(F)F)ccn2)cc1] | N-hydroxy-4-((1S,4S)-5-(4-(trifluoromethyl)pyridin-2-yl)-2,5-diazabicyclo[2.2.1]heptan-2-yl)benzamide | (dmso-d6) δ (ppm) 1H: 10.83 (s, 1H), 8.73 (s, 1H), 8.24 (d, J = 5.3 Hz, 1H), 7.57 (d, J = 8.8 Hz, 2H), 6.78 (d, J = 5.0 Hz, 2H), 6.60 (d, J = 8.6 Hz, 2H), 5.02 (s, 1H), 4.75 (s, 1H), 3.63 (d, J = 7.8 Hz, 1H), 3.59 (d, J = 9.0 Hz, 1H), 3.40-3.30 (m, 1H), 3.05 (d, J = 9.2 Hz, 1H), 2.06 (s, 2H). LRMS(ESI): (calc.) 378.13 (found) 379.1 (MH)+ |

TABLE 4-continued

| Ex | Cpd | Structure | Name | Characterization |
|---|---|---|---|---|
| 165 | 304 | 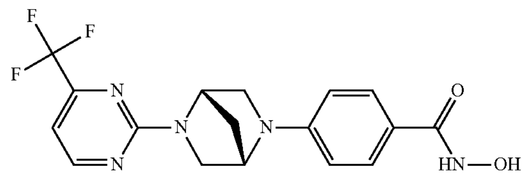 [SMILES: O=C(NO)c1ccc(N2C[C@@H]3C[C@H]2CN3c2nccc(C(F)(F)F)n2)cc1] | N-hydroxy-4-((1S,4S)-5-(4-(trifluoromethyl)pyrimidin-2-yl)-2,5-diazabicyclo[2.2.1]heptan-2-yl)benzamide | ¹H NMR (DMSO-d₆) δ (ppm): 10.83 (s, 1H), 8.71 (s, 1H), 8.63 (dd, J = 25.5, 4.3 Hz, 1H), 7.59 (d, J = 8.8 Hz, 2H), 6.99 (d, J = 4.9 Hz, 1H), 6.63 (d, J = 8.6 Hz, 2H), 5.05 (s, 0.5H), 4.97 (s, 0.5H), 4.74 (s, 1H), 3.68 (d, J = 9.0 Hz, 1H), 3.59 (t, J = 8.4 Hz, 1H), 3.52-3.35 (m, 1H), 3.15-3.05 (m, 1H), 2.15-2.05 (m, 2H). |
| 166 | 305 | 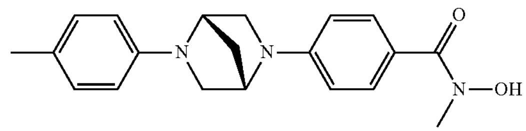 [SMILES: Cc1ccc(N2C[C@@H]3C[C@H]2CN3c2ccc(C(=O)N(C)O)cc2)cc1] | N-hydroxy-N-methyl-4-((1S,4S)-5-p-tolyl-2,5-diazabicyclo[2.2.1]heptan-2-yl)benzamide | ¹H NMR (DMSO-d₆) δ (ppm): 9.77 (s, 1H), 7.53 (d, J = 8.8 Hz, 2H), 6.91 (d, J = 8.2 Hz, 2H), 6.52 (d, J = 8.6 Hz, 2H), 6.47 (d, J = 8.4 Hz, 2H), 4.64 (s, 1H), 4.55 (s, 1H), 3.55 (t, J = 7.6 Hz, 2H), 3.18 (s, 3H), 3.06 (d, J = 9.0 Hz, 1H), 2.92 (d, J = 8.8 Hz, 1H), 2.13 (s, 3H), 2.08-2.00 (m, 2H). MS (m/z): 338.4 (M + H). |
| 167 | 306 | 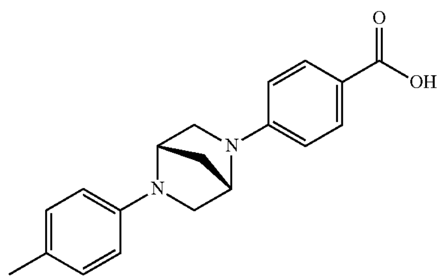 | 4-((1S,4S)-5-p-tolyl-2,5-diazabicyclo[2.2.1]heptan-2-yl)benzoic acid | ¹H NMR (DMSO-d₆) δ (ppm): 7.65 (d, J = 9.8 Hz, 2H), 6.90 (d, J = 8.2 Hz, 2H), 6.54 (d, J = 8.2 Hz, 2H), 6.45 (d, J = 8.4 Hz, 2H), 4.66 (s, 1H), 4.55 (s, 1H), 3.54 (t, J = 8.3 Hz, 2H), 3.07 (d, J = 9.2 Hz, 1H), 2.90 (d, J = 8.8 Hz, 1H), 2.11 (s, 3H), 2.04-1.98 (m, 2H). MS (m/z): 304.4 (M + H) |
| 168 | 307 | 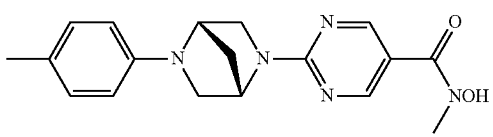 | N-hydroxy-N-methyl-2-((1S,4S)-5-p-tolyl-2,5-diazabicyclo[2.2.1]heptan-2-yl)pyrimidine-5-carboxamide | (DMSO) (ppm) 1H: 10.18 (s, 1H), 8.68 (s, 1H), 8.62 (s, 1H), 6.95 (d, J = 8.2 Hz, 2H), 6.52 (d, J = 8.2 Hz, 2H), 5.00 (s, 1H), 4.59 (s, 1H), 3.64 (d, J = 8.2 Hz, 1H), 3.60-3.47 (m, 2H), 3.21 (s, 3H), 2.94 (d, J = 9.0 Hz, 2H), 2.18 (s, 3H), 2.12-2.03 (m, 2H). LRMS(ESI): (calc.) 339.2 (found) 340.4 (MH)+ |
| 169 | 308 | 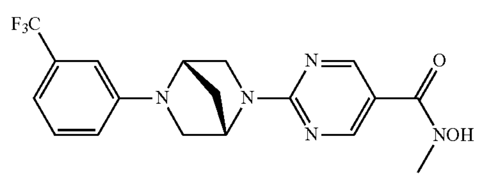 | N-hydroxy-N-methyl-2-((1S,4S)-5-(3-(trifluoromethyl)phenyl)-2,5-diazabicyclo[2.2.1]heptan-2-yl)pyrimidine-5-carboxamide | (MeOD) (ppm) 1H: 8.76 (s, 1H), 8.70 (s, 1H), 7.31 (t, J = 7.9 Hz, 1H), 6.88 (d, J = 7.6 Hz, 1H), 6.83 (d, J = 8.4 Hz, 1H), 6.80 (s, 1H), 5.15 (s, 1H), 4.70 (s, 1H), 3.72 (dd, J = 9.0 and 1.6 Hz, 1H), 3.70-3.49 (m, 2H), 3.31 (s, 3H), 3.14 (d, J = 9.0 Hz, 1H), 2.21-2.10 (m, 2H). LRMS(ESI): 393.1 (calc.) 394.4 (MH)+ (found) |

Scheme 50

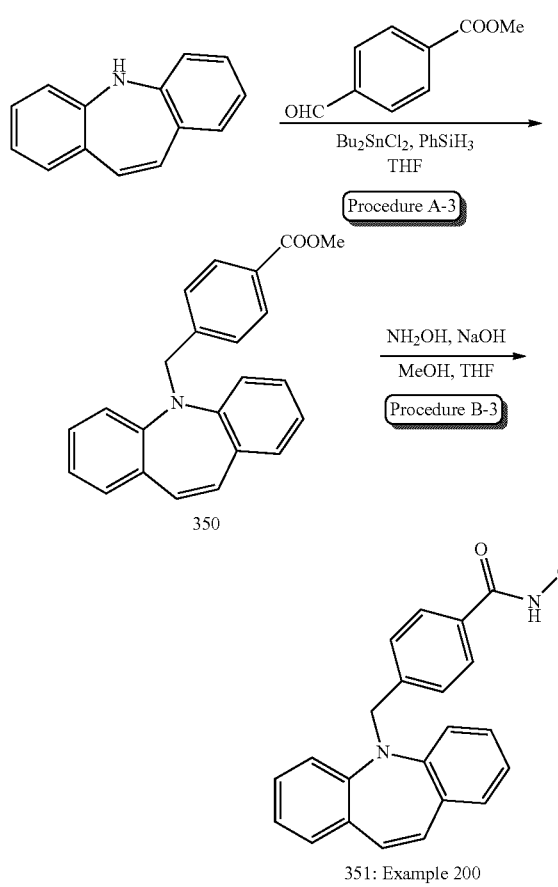

Example 200

(Z)-4-((5H-dibenzo[b,f]azepin-5-yl)methyl)-N-hydroxybenzamide (351)

Step 1: (Z)-methyl 4-((5H-dibenzo[b,f]azepin-5-yl)methyl)benzoate (350)

(Z)-5H-Dibenzo[b,f]azepine (100 mg, 0.52 mmol), dibutyltin dichloride (54 mg, 0.16 mmol) and methyl 4-formylbenzoate (260 mg, 1.60 mmol) were stirred in THF (2 mL) for 30 minutes. Phenylsilane was added and the reaction mixture was stirred for 3 days. The solvent was evaporated and the residue was purified by flash chromatography (0% to 40% EtOAc in hexanes). The fractions containing some product were washed with $Na_2S_2O_4$. The layers were split and the organic layer was evaporated to afford title compound 350 (147 mg, 83%) as a yellow solid.

Step 2: (Z)-4-((5H-dibenzo[b,f]azepin-5-yl)methyl)-N-hydroxybenzamide (351)

Title compound 350 (147 mg, 0.43 mmol), hydroxylamine (50% in water, 6 mL) and sodium hydroxide (138 mg, 3.40 mmol) were stirred in methanol (3 mL) and THF (3 mL) at room temperature overnight. The organic solvent was evaporated and the precipitate was filtered off and washed with a little bit of cold methanol to afford title compound 351 (39 mg, 26%) as a yellow solid. $^1$H NMR (DMSO-$d_6$) δ (ppm): 11.06 (s, 1H), 8.96 (s, 1H), 7.57 (d, J=8.4 Hz, 2H), 7.47 (d, J=8.4 Hz, 2H), 7.21 (td, J=1.6 and 7.2 Hz, 2H), 7.18-7.13 (m, 2H), 7.10 (dd, J=1.6 and 7.6 Hz, 2H), 6.6 (td, J=1.2 and 7.2 Hz, 2H), 6.85 (s, 2H), 5.00 (s, 2H). LRMS: 342.1 (calc). 343.2 (found).

Scheme 51

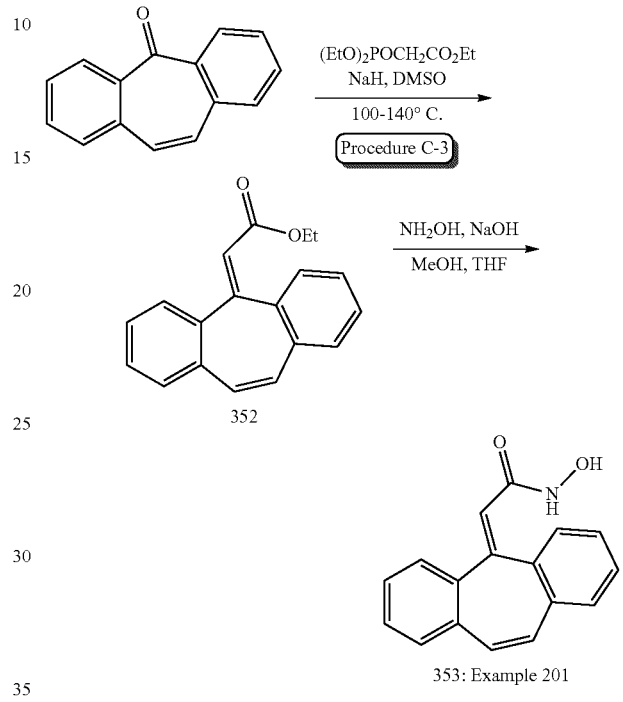

Example 201

Compound (353)

Step 1: Compound (352)

To a suspension of sodium hydride (0.55 g, 14.0 mmol, 60% in oil, washed with hexanes) in DMSO (20 mL) was added a solution of ethyl 2-(diethoxyphosphoryl)acetate (2.8 mL, 14.0 mmol) in DMSO (5 mL). The mixture was stirred for 30 minutes. A solution of the ketone (2.5 g, 12.1 mmol) in DMSO (20 mL) was added and the reaction mixture was stirred at 100° C. for 30 hours. The reaction mixture was cooled down to room temperature and poured into an ice-water mixture and stirred vigorously for 1 hour. The precipitate was then filtered and dried to afford title compound 352 (2.75 g, 82% crude yield) as a beige solid. MS (m/z): 277.0 (M+H).

Step 2: Compound (353)

Using Procedure B-3 (Table 5) with compound 352 the title compound 353 was obtained (220 mg, 75%) as a yellow solid. $^1$H NMR (DMSO-$d_6$) δ (ppm): 10.7-10.4 (1H, br s), 8.9-8.7 (1H, br s), 7.44-7.25 (8H, m), 6.99 and 6.91 (2H, AB doublet, J=12.1 Hz), 5.75 (1H, s). MS (m/z): 264.0 (M+H).

Scheme 52

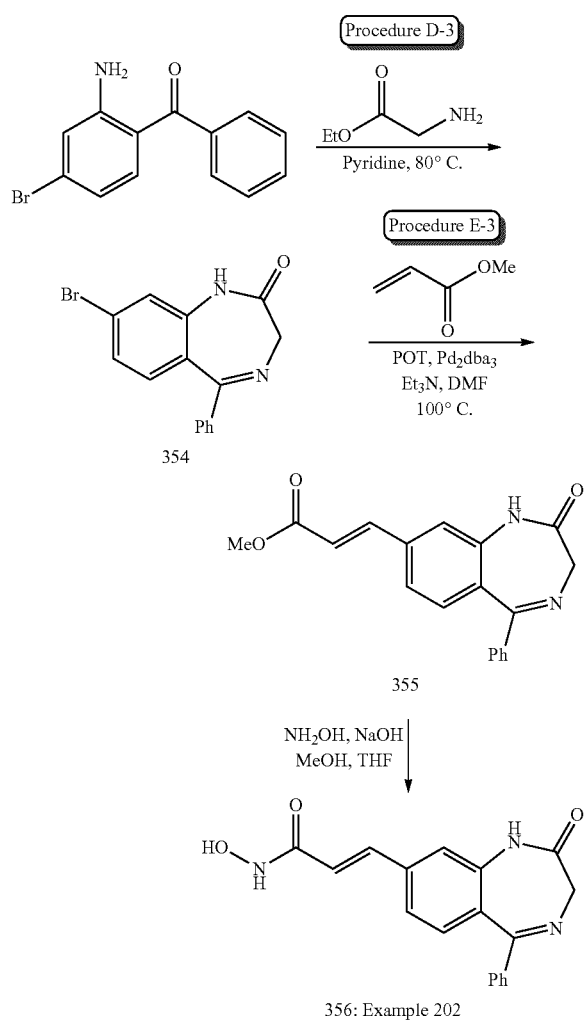

was partitioned between ethyl acetate and water. The 2 layers were split and the aqueous layer was extracted with 2 other portions of ethyl acetate. The combined organic layers were washed with brine, dried over MgSO4, filtered and evaporated. The crude product was purified by flash chromatography (50% to 65% ethyl acetate in hexanes) to afford title compound 355 (135 mg, 33%) as a light yellow solid. $^1$H NMR (DMSO-$d_6$) δ (ppm): 10.56 (s, 1H), 7.77 (d, J=8.4 Hz, 2H), 7.68 (d, J=16.0 Hz, 1H), 7.58-7.54 (m, 1H), 7.49 (d, J=8.4 Hz, 2H), 7.24 (d, J=6.4 Hz, 2H), 7.16 (td, J=7.5, 1.0 Hz, 1H), 6.70 (d, J=16.2 Hz, 1H), 4.12 (s, 2H), 3.72 (s, 3H).

Step 3: (E)-N-hydroxy-3-4Z)-2-oxo-5-phenyl-2,3-dihydro-1H-benzo[e][1,4]diazepin-8-yl)acrylamide (356)

Using Procedure B-3 (Table 5) with compound 355 the title compound 356 was obtained (20 mg, 24%) as a yellow solid. $^1$H NMR (DMSO-$d_6$) δ (ppm): 10.54 (s, 1H), 7.61-7.53 (m, 3H), 7.50-7.44 (m, 3H), 7.26-7.22 (m, 2H), 7.17 (td, J=7.2, 1.0 Hz, 1H), 6.51 (d, J=5.9 Hz, 1H), 4.12-4.01 (br s, 2H). MS (m/z): 322.2 (M+H).

Scheme 53

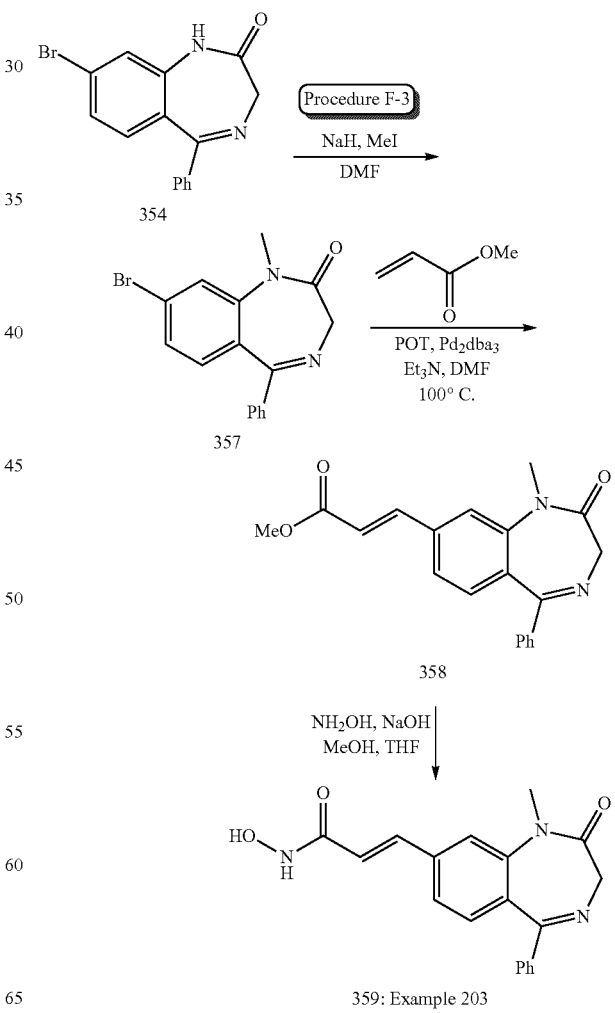

Example 202

(E)-N-hydroxy-3-((Z)-2-oxo-5-phenyl-2,3-dihydro-1H-benzo[e][1,4]diazepin-8-yl)acrylamide (356)

Step 1: (Z)-8-bromo-5-phenyl-1H-benzo[e][1,4]diazepin-2(3H)-one (354)

(2-Amino-4-bromophenyl)(phenyl)methanone (1.75 g, 10 mmol), ethyl 2-aminoacetate (2.23 g, 16 mmol) and pyridine (40 mL) were stirred together at 80° C. for about 3 days. The pyridine was evaporated and the residue was triturated in 5% methanol in ethyl acetate to afford title compound 354 (1.6 g, 51%) as a yellow solid.

Step 2: (E)-methyl 3-((Z)-2-oxo-5-phenyl-2,3-dihydro-1H-benzo[e][1,4]diazepin-8-yl)acrylate (355)

Title compound 354 (400 mg, 1.28 mmol), methyl acrylate (132 mg, 1.54 mmol), Pd2(dba)3 (16 mg, 0.038 mmol), POT (24 mg, 0.07 mmol) and triethylamine (0.446 mL, 3.2 mmol) were mixed in DMF (15 mL). The mixture was degassed with nitrogen for 5 minutes and the reaction mixture was heated to 100° C. for 2 hours. The DMF was removed and the residue

Example 203

(E)-N-hydroxy-3-((Z)-1-methyl-2-oxo-5-phenyl-2,3-dihydro-1H-benzo[e][1,4]diazepin-8-yl)acrylamide (359)

Step 1: (Z)-8-bromo-1-methyl-5-phenyl-1H-benzo[e][1,4]diazepin-2(3H)-one (357)

Title compound 354 (3.1 g, 11.8 mmol), sodium hydride (565 mg, 14.14 mmol) and methyliodide (0.88 mL, 14.14 mmol) were stirred together in DMF (60 mL) at room temperature for 6 hours. DMF was removed and the residue was partitioned in EtOAc and water. The organic layer was dried, filtered and evaporated. The crude product was purified by flash chromatography (3:1 to 1:2 hexane:ethyl acetate) to afford title compound 357 (2.3 g, 60%) as a white solid.

Step 2: (E)-methyl 3-((Z)-1-methyl-2-oxo-5-phenyl-2,3-dihydro-1H-benzo[e][1,4]diazepin-8-yl)acrylate (358)

Using Procedure E-3 (Table 5) with compound 357 the title compound 358 was obtained (380 mg, 45%) as a light brown solid. $^1$H NMR (DMSO-$d_6$) δ (ppm): 7.78 (d, J=8.2 Hz, 2H), 7.69 (d, J=16.0 Hz, 1H), 7.67-7.63 (m, 1H), 7.58-7.55 (m, 3H), 7.26-7.25 (m, 2H), 6.71 (d, J=16.0 Hz, 1H), 4.56 (d, J=10.8 Hz, 1H), 3.73 (d, J=10.0 Hz, 1H), 3.72 (s, 3H), 3.30 (s, 3H).

Step 3: (E)-N-hydroxy-3-((Z)-1-methyl-2-oxo-5-phenyl-2,3-dihydro-1H-benzo[e][1,4]diazepin-8-yl)acrylamide (359)

Using Procedure B-3 (Table 5) with compound 358 the title compound 359 was obtained (60 mg, 17%) as a beige solid. $^1$H NMR (CD$_3$OD) δ (ppm): 7.70-7.56 (m, 7H), 7.29 (d, J=4.1 Hz, 2H), 6.55 (d, J=15.8 Hz, 1H), 4.63 (d, J=10.8 Hz, 1H), 3.83 (d, J=10.8 Hz, 1H), 3.43 (s, 3H). MS (m/z): 336.1 (M+H).

Scheme 54

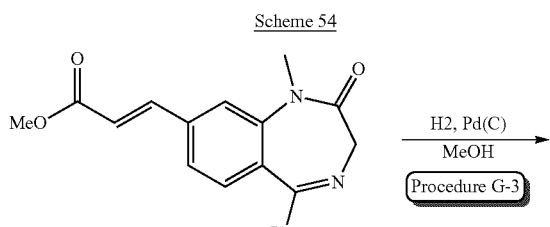

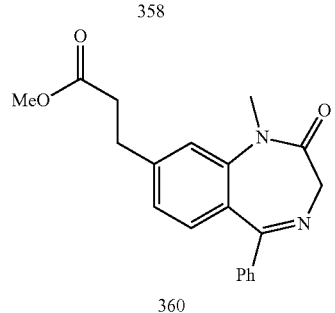

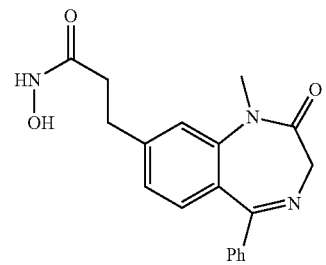

361: Example 204

Example 204

(Z)-N-hydroxy-3-(1-methyl-2-oxo-5-phenyl-2,3-dihydro-1H-benzo[e][1,4]diazepin-8-yl)propanamide (361)

Step 1: (Z)-methyl 3-(1-methyl-2-oxo-5-phenyl-2,3-dihydro-1H-benzo[e][1,4]diazepin-8-yl)propanoate (360)

Title compound 358 (410 mg, 1.23 mmol) was dissolved in methanol (30 mL) and Pd(C) (250 mg) was added. The reaction mixture was stirred under hydrogen atmosphere for 2 hours. The catalyst was filtered off and the filtrate was evaporated to afford title compound 360 (370 mg, 90%) as a clear oil. 1H NMR (DMSO-d6) δ (ppm): 7.65-7.61 (m, 1H), 7.55 (d, J=8.0 Hz, 1H), 7.44 (d, J=8.4 Hz, 2H), 7.28-7.22 (m, 4H), 4.51 (d, J=10.6 Hz, 1H), 3.69 (d, J=10.8 Hz, 1H), 3.56 (s, 3H), 3.29 (s, 3H), 2.88 (t, J=7.5 Hz, 2H), 2.64 (t, J=7.5 Hz, 2H).

Step 2: (Z)-N-hydroxy-3-(1-methyl-2-oxo-5-phenyl-2,3-dihydro-1H-benzo[e][1,4]diazepin-8-yl)propanamide (361)

Using Procedure B-3 (Table 5) with compound 360 the title compound 361 was obtained (50 mg, 14%) as a clear oil. 1H NMR (CD$_3$OD) δ (ppm): 7.68-7.63 (m, 1H), 7.56 (d, J=8.2 Hz, 1H), 7.45 (d, J=8.4 Hz, 2H), 7.29-7.23 (m, 4H), 4.58 (d, J=11.0 Hz, 1H), 3.79 (d, J=11.0 Hz, 1H), 3.42 (s, 3H), 2.97 (t, J=7.6 Hz, 2H), 2.40 (t, J=7.8 Hz, 2H). MS (m/z): 338.2 (M+H).

Scheme 55

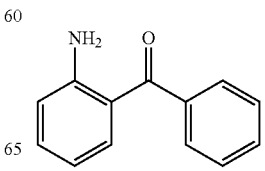

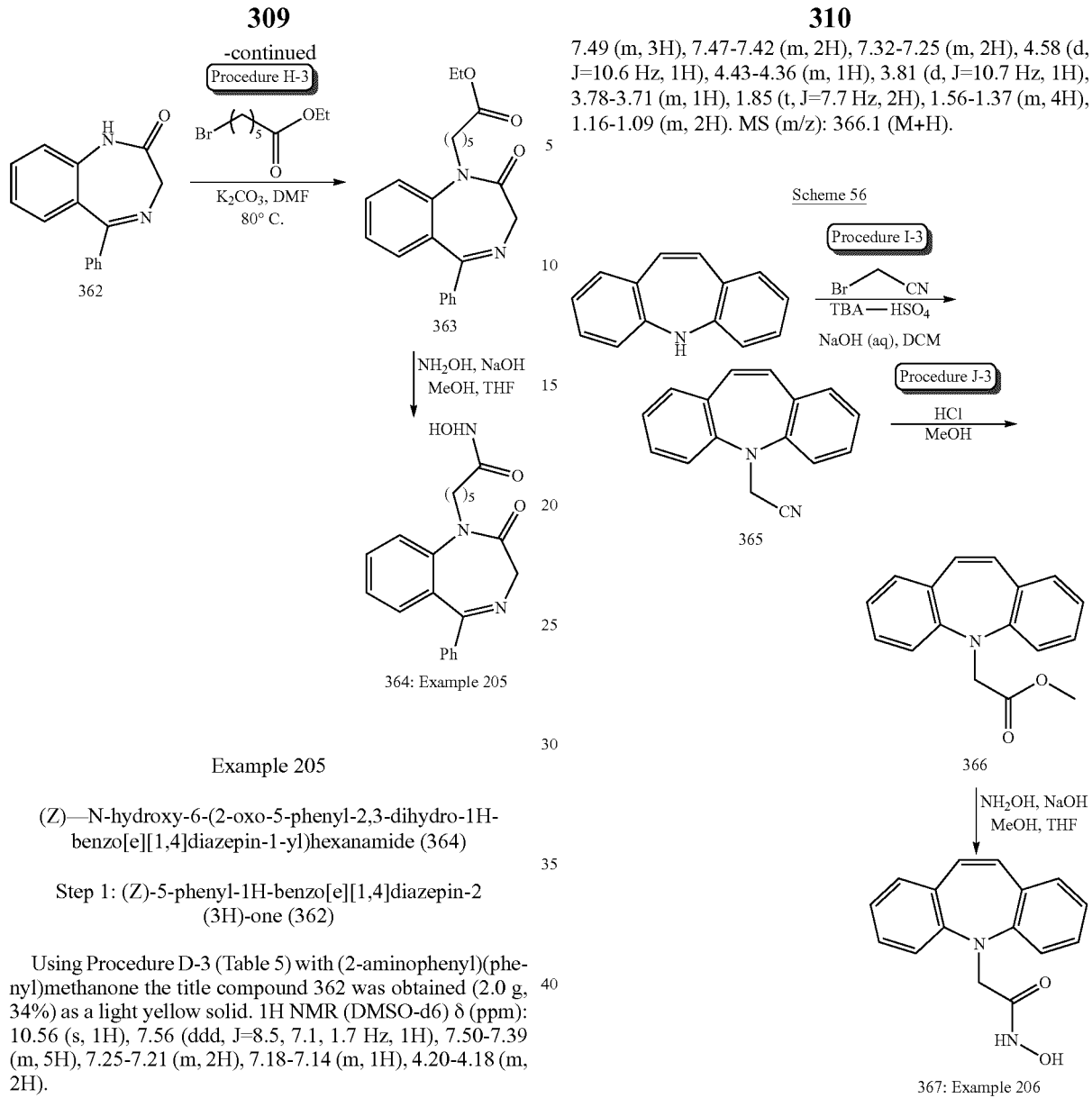

7.49 (m, 3H), 7.47-7.42 (m, 2H), 7.32-7.25 (m, 2H), 4.58 (d, J=10.6 Hz, 1H), 4.43-4.36 (m, 1H), 3.81 (d, J=10.7 Hz, 1H), 3.78-3.71 (m, 1H), 1.85 (t, J=7.7 Hz, 2H), 1.56-1.37 (m, 4H), 1.16-1.09 (m, 2H). MS (m/z): 366.1 (M+H).

Example 205

(Z)—N-hydroxy-6-(2-oxo-5-phenyl-2,3-dihydro-1H-benzo[e][1,4]diazepin-1-yl)hexanamide (364)

Step 1: (Z)-5-phenyl-1H-benzo[e][1,4]diazepin-2(3H)-one (362)

Using Procedure D-3 (Table 5) with (2-aminophenyl)(phenyl)methanone the title compound 362 was obtained (2.0 g, 34%) as a light yellow solid. 1H NMR (DMSO-d6) δ (ppm): 10.56 (s, 1H), 7.56 (ddd, J=8.5, 7.1, 1.7 Hz, 1H), 7.50-7.39 (m, 5H), 7.25-7.21 (m, 2H), 7.18-7.14 (m, 1H), 4.20-4.18 (m, 2H).

Step 2: (Z)-ethyl 6-(2-oxo-5-phenyl-2,3-dihydro-1H-benzo[e][1,4]diazepin-1-yl)hexanoate (363)

Title compound 362 (400 mg, 1.69 mmol), ethyl 6-bromohexanoate (0.3 mL, 1.69 mmol) and potassium carbonate (584 mg, 4.23 mmol) were mixed in DMF (20 mL) and the reaction mixture was heated to 80° C. for 24 hours. The DMF was removed and the residue was partitioned between water and ethyl acetate. The 2 layers were split and the aqueous layer was extracted with 2 other portions of ethyl acetate. The combined organic layers were washed with brine, dried, filtered and evaporated. The crude product was purified by flash chromatography (2:1 to 1:2, hexanes:ethyl acetate) to afford title compound 363 (400 mg, 63%) as a clear oil.

Step 3: (Z)—N-hydroxy-6-(2-oxo-5-phenyl-2,3-dihydro-1H-benzo[e][1,4]diazepin-1-yl)hexanamide (364)

Using Procedure B-3 (Table 5) with compound 363 the title compound 364 was obtained (100 mg, 26%) as a yellow oily solid. ¹H NMR (CD₃OD) δ (ppm): 7.69-7.61 (m, 2H), 7.55-

Example 206

(Z)-2-(5H-dibenzo[b,f]azepin-5-yl)-N-hydroxyacetamide (367)

Step 1: (Z)-2-(5H-dibenzo[b,f]azepin-5-yl)acetonitrile (365)

(Z)-5H-dibenzo[b,f]azepine (0.1 g, 0.5 mmol), tetrabutylammonium sulfate (0.35 g, 1.0 mmol), 2-bromoacetonitrile (0.4 mL, 5.0 mmol) and 50% aqueous sodium hydroxide (1 mL) were mixed in DCM (1 mL) and the reaction mixture was stirred for 5 days. The mixture was diluted in water and the aqueous layer was extracted with DCM (2 times). The combined organic layers were dried over sodium sulfate, filtered and concentrated. The crude product was purified by flash chromatography (0% to 50% ethyl acetate in hexanes) to afford title compound 365 (60 mg, 50%). ¹H NMR (CDCl₃) δ (ppm): 7.36-7.31 (m, 2H), 7.26-7.23 (m, 2H), 7.17-7.11 (m, 4H), 6.76 (s, 2H), 4.47 (s, 2H).

Step 2: (Z)-methyl 2-(5H-dibenzo[b,f]azepin-5-yl) acetate (366)

To title compound 365 (60 mg, 0.26 mmol) was added conc HCl and methanol and the reaction mixture was stirred for 5 hours. The mixture was concentrated and the residue was partitioned between sodium bicarbonate and ethyl acetate. The layers were split and the aqueous layer was extracted another time with ethyl acetate. The combined organic layers were evaporated to afford title compound 366 (40 mg, 58% crude yield). MS (m/z): 266.0 (M+H).

Step 3: (Z)-2-(5H-dibenzo[b,f]azepin-5-yl)-N-hydroxyacetamide (367)

Using Procedure B-3 (Table 5) with compound 366 the title compound 367 was obtained (30 mg, 24%) as beige solid. $^1$H NMR (CDCl$_3$) δ (ppm): 7.28 (2H, t, J=7.1 Hz), 7.16-7.11 (4H, m), 7.04 (2H, t, J=7.1 Hz), 6.83 (2H, s), 4.42 (2H, s). MS (m/z): 267.0 (M+H).

Example 207

Compound (370)

Step 1: Compound (368)

Ketone (3.0 g, 14.4 mmol), hydroxylamine hydrochloride (3.0 g) and pyridine (3 mL) were mixed in ethanol (3 mL) and the reaction mixture was refluxed for 4 hours. The ethanol and the pyridine were evaporated and the residue was diluted with water. The aqueous layer was extracted twice with ethyl acetate. The combined organic layers were washed with brine, dried over sodium sulfate, filtered and concentrated. The residue was purified by trituration in ethyl acetate (15 mL) and hexanes (5 mL), filtered, washed with hexanes and dried to afford title compound 368 (1.2 g, 46%) as brown solid. MS (m/z): 223 (M+H).

Step 2: Compound (369)

Title compound 368 (100 mg, 0.45 mmol), potassium carbonate (187 mg, 1.35 mmol) and methyl 8-bromooctanoate (0.14 mL, 0.67 mmol) were mixed in acetone (1 mL) and the reaction mixture was heated to 40° C. for 4 hours. The mixture was cooled down and concentrated. PS trisamine (0.3 g) and DCM were added to the residue and the mixture was stirred for 3 hours. The mixture was filtered and concentrated to afford crude title compound 369 that was used directly to next step.

Step 3: Compound (370)

Using Procedure B-3 (Table 5) with compound 369 the title compound 370 was obtained (67 mg, 39% for 2 steps). (CD$_3$OD) δ (ppm): 7.51 (dd, J=7.8, 1.5 Hz, 1H), 7.30-7.25 (m, 4H), 7.24-7.15 (m, 2H), 7.13 (d, J=7.6 Hz, 1H), 4.13 (t, J=6.5 Hz, 2H), 3.12-3.00 (m, 4H), 2.06 (t, J=7.5 Hz, 2H), 1.67-1.56 (m, 4H), 1.40-1.20 (m, 6H). MS (m/z): 381.2 (M+H).

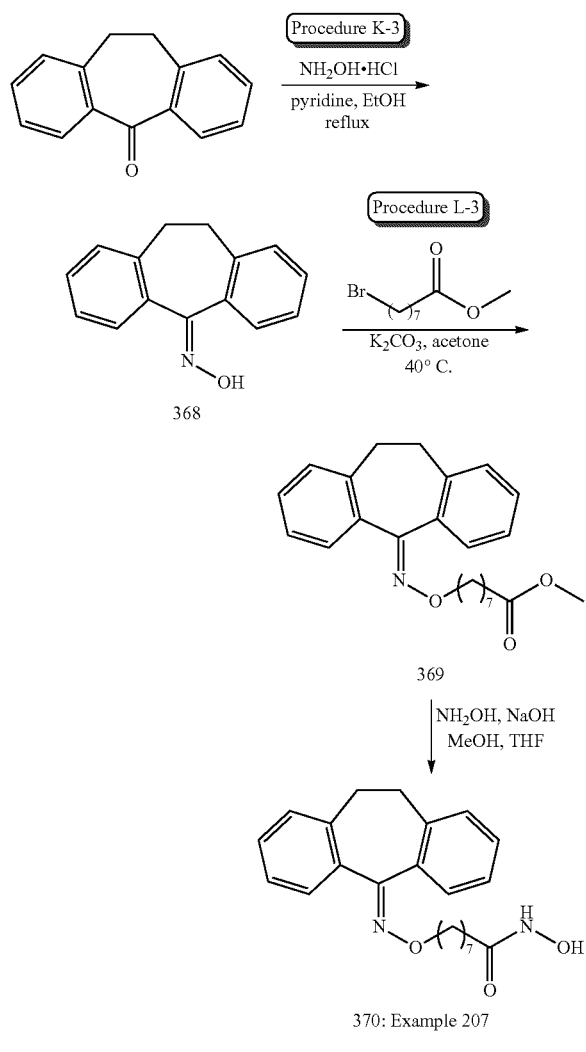

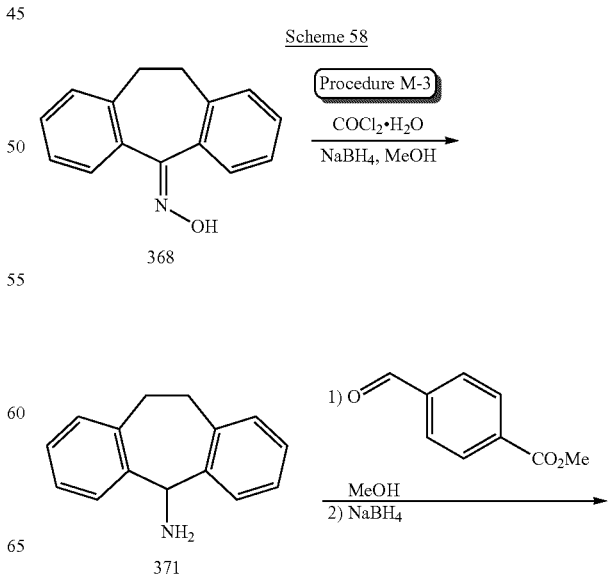

313 -continued

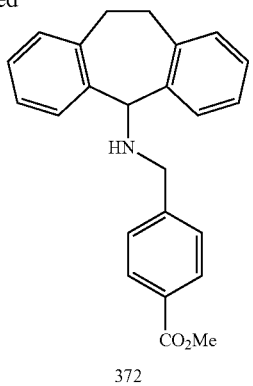

372

| NH₂OH, NaOH
| MeOH, THF
↓

373: Example 208

314

Example 208

Compound (373)

Step 1: Compound (371)

Title compound 368 (50 mg, 0.224 mmol) and phosgene (107 mg, 0.448) were dissolved in methanol (5 mL). Sodium borohydride (8.5 mg, 2.24 mmol) was added portion wise and the reaction mixture was stirred for 5 minutes. The mixture was diluted with ethyl acetate. The organic layer was washed with a solution of 5% NaOH in water (twice), water and brine, dried over sodium sulfate, falterer and evaporated to afford title compound 371.

Step 2: Compound (372)

Using Procedure A-3 (Table 5) with compound 371 the title compound 372 was obtained (295 mg, 83%).

Step 3: Compound (373)

To a solution of potassium hydroxide (232 mg, 4.13 mmol) in methanol (10 mL) was added the hydroxylamine hydrochloride (287 mg, 4.13 mmol) followed by a solution of title compound 372 (295 mg, 0.826 mmol) in THF (5 mL). The reaction mixture was stirred at r.t. for 1 hour. The mixture was acidified with 40% HCl to reach pH=2. The precipitate was filtered and the solid was triturated in water, then in methanol and hexanes to afford title compound 373 (65 mg, 22%) as an off-white solid. $^1$H NMR (MeOH-$d_4$) δ (ppm): 7.80 (d, J=8.4 Hz, 2H), 7.53 (d, J=8.4 Hz, 2H), 7.42-7.38 (m, 4H), 7.33-7.27 (m, 4H), 5.49 (br s, 1H), 4.20 (s, 2H), 3.44-3.42 (m, 2H), 3.08 (m, 2H). MS (m/z): 359.1 (M+H).

Scheme 59

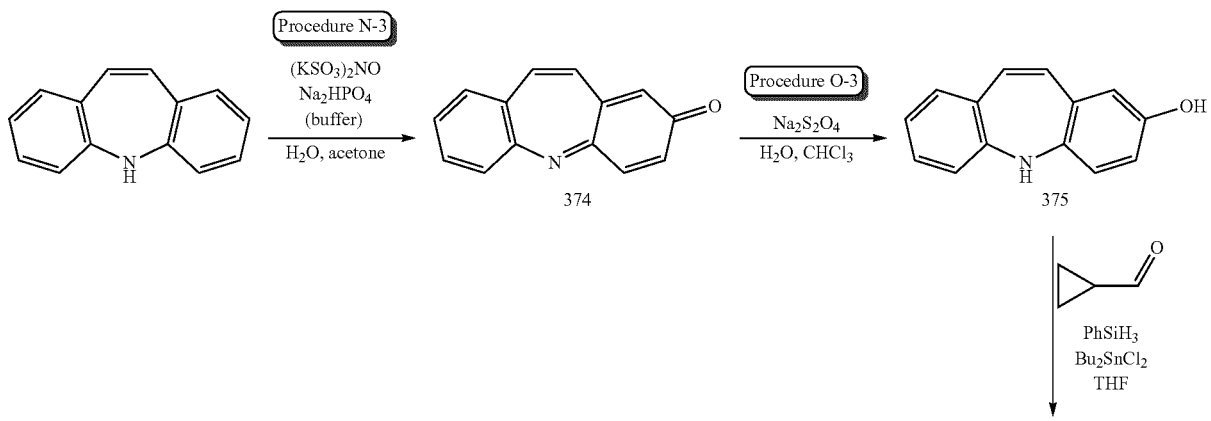

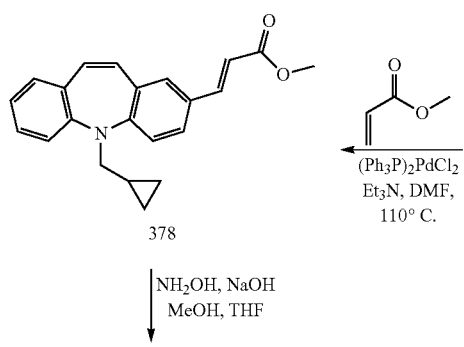
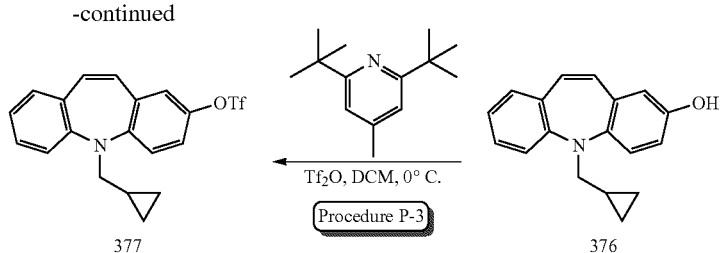

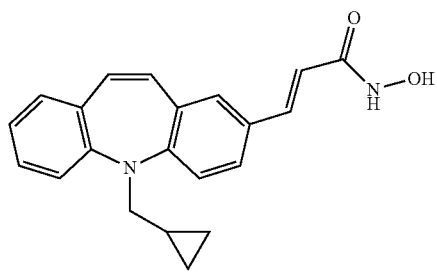

379: Example 209

Example 209

(E)-3-((Z)-5-(cyclopropylmethyl)-5H-dibenzo[b,f]azepin-2-yl)-N-hydroxyacrylamide (379)

Step 1: (4aZ,10Z)-2H-dibenzo[b,f]azepin-2-one (374)

To a solution of Na$_2$HPO$_4$ (2.5 g, 9.32 mmol) in water (95 mL) was added (KSO$_3$)$_2$NO (1.8 g, 12.7 mmol). This solution was added to a solution of the (Z)-5H-dibenzo[b,f]azepine (0.5 g, 2.59 mmol) in acetone (50 mL). This reaction mixture was stirred at 4° C. over night. The solid was filtered and the filtrate was evaporated. The residue was dissolved in ether and water. The 2 layers were split. The organic layer and the solid were mixed and evaporated. The crude product was purified by flash chromatography to afford title compound 374 (170 mg, 34%). MS (m/z): 207 (M+H). Step 2: (Z)-5H-dibenzo[b,f]azepin-2-ol (375)

Title compound 374 (170 mg, 0.82 mmol) was solubilized in CHCl$_3$ (5 mL) and a saturated solution of Na$_2$S$_2$O$_4$ in water was added (20 mL). The mixture was stirred for 3 hours. The 2 layers were split and the organic layer was dried over sodium sulfate, filtered and evaporated to afford title compound 375 (110 mg, 65%). MS (m/z): 209.9 (M+H).

Step 3: (Z)-5-(cyclopropylmethyl)-5H-dibenzo[b,f]azepin-2-ol (376)

Using Procedure A-3 (Table 5) with compound 375 the title compound 376 was obtained (40 mg, 64%).

Step 4: (Z)-5-(cyclopropylmethyl)-5H-dibenzo[b,f]azepin-2-yl trifluoromethanesulfonate (377)

Title compound 376 (90 mg, 0.34 mmol) and 2,6-di-tert-butyl-4-methylpyridine (105 mg, 0.44 mmol) were solubilized in THF (0.5 mL). This solution was added to a solution of trifluoromethanesulfonic anhydride (74 μL, 0.44 mmol) in THF (0.5 mL) at 0° C. The flask was rinsed with THF (2×0.5 mL). The reaction mixture was stirred at r.t. for 3 hours. More trifluoromethanesulfonic anhydride (15 μL) was added and the mixture was stirred for 1 hour. A saturated aqueous solution of sodium bicarbonate was added and the mixture was stirred for 5 minutes prior to the extraction with DCM (2 times). The combined organic layers were evaporated and the residue was purified by flash chromatography (0% to 20% EtOAc in hexanes) to afford title compound 377 (190 mg) mixed with some base. MS (m/z): 396.1 (M+H).

Step 5: (E)-methyl 3-((Z)-5-(cyclopropylmethyl)-5H-dibenzo[b,f]azepin-2-yl)acrylate (378)

Using Procedure E-3 (Table 5) with compound 377 the title compound 378 was obtained (50 mg, 44%). MS (m/z): 332 (M+H). $^1$H NMR (CDCl$_3$) δ (ppm): 7.38 (d, J=16.0 Hz, 1H), 7.18 (dd, J=8.2, 2.2 Hz, 1H), 7.05-6.97 (m, 2H), 6.84-6.75 (m, 4H), 6.53 (d, J=11.3 Hz, 1H), 6.46 (d, J=11.3 Hz, 1H), 6.97 (d, J=16.0 Hz, 1H), 3.57 (s, 3H), 3.37 (d, J=4.7 Hz, 2H), 0.83-0.79 (m, 1H), 0.24-0.19 (m, 2H), 0.04-0.00 (m, 2H).

Step 6: (E)-3-4Z)-5-(cyclopropylmethyl)-5H-dibenzo[b,f]azepin-2-yl)-N-hydroxyacrylamide (379)

Using Procedure B-3 (Table 5) with compound 378 the title compound 379 was obtained (7 mg, 14%). $^1$H NMR (CD$_3$OD) δ (ppm): 7.5-7.4 (2H, m), 7.25-7.2 (2H, m), 7.05-7.0 (3H, m), 6.99-9.93 (1H, m), 6.75-6.65 (2H, observed 2d), 6.33 (1H, d, J=15.7 Hz), 3.57 (2H, d, J=6.4 Hz), 1.05-0.95 (1H, m), 0.45-0.37 (2H, m), 0.25-0.18 (2H, m). MS (m/z): 333.1 (M+H).

Scheme 60

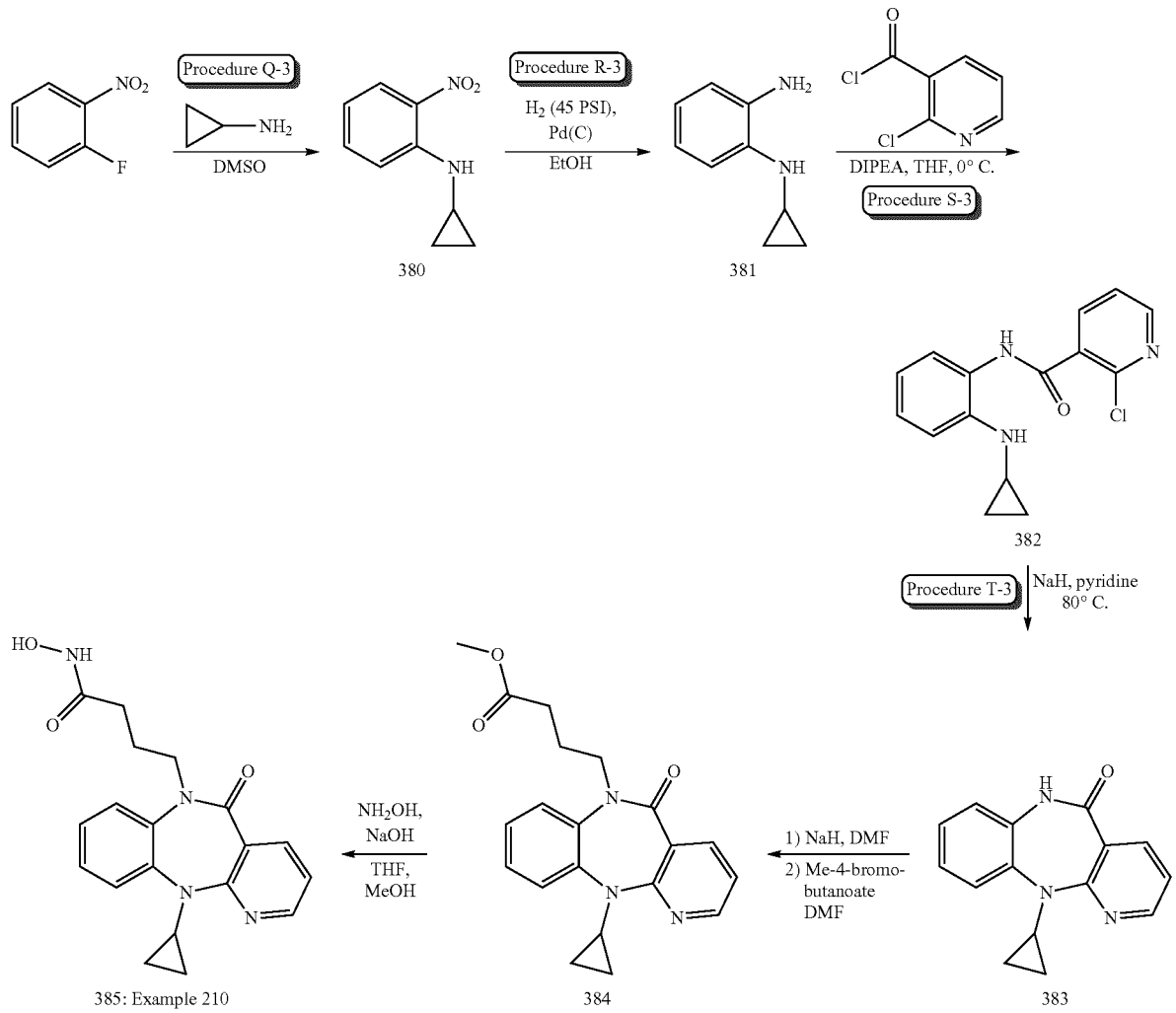

Example 210

4-(11-cyclopropyl-5-oxo-5H-benzo[b]pyrido[2,3-e][1,4]diazepin-6(11H)-yl)-N-hydroxybutanamide (385)

Step 1: N-cyclopropyl-2-nitroaniline (380)

1-fluoro-2-nitrobenzene (1.85 mL, 175 mmol) and cyclopropanamine (2.43 mL, 35 mmol) were stirred in DMSO for 3 hours. Water was added (250 mL) and the mixture was extracted with ether (2×250 mL). The combined organic extracts were washed with brine, dried over sodium sulfate, filtered and evaporated to afford title compound 380 (3.1 g, 99%) as an orange oil. MS (m/z): 178.9 (M+H). $^1$H NMR (CDCl$_3$) δ (ppm): 8.15 (dd, J=8.6, 1.6 Hz, 1H), 8.09 (s, 1H), 7.49-7.45 (m, 1H), 7.32 (dd, J=8.6, 1.4 Hz, 1H), 6.72-6.67 (m, 1H), 2.60-2.58 (m, 1H), 0.94-0.89 (m, 2H), 0.68-0.64 (m, 2H).

Step 2: N1-cyclopropylbenzene-1,2-diamine (381)

Title compound 380 (3.1 g, 17.4 mmol) and palladium on charcoal 10% (0.3 g, 10% w/w) were mixed in ethanol (100 mL) and the reaction mixture was stirred under 45 PSI of hydrogen for 4 hours. The mixture was filtered to remove the catalyst and the filtrate was evaporated to afford title compound 381 as black oil that was used without further purification. MS (m/z): 148.9 (M+H).

Step 3: 2-chloro-N-(2-(cyclopropylamino)phenyl)nicotinamide (382)

To a solution of title compound 381 (0.83 g, 5.84 mmol) and diisopropylethylamine (1.02 mL, 0.74 mmol) in THF (50 mL) was added a solution of 2-chloronicotinoyl chloride (1.03 g, 5.84 mmol) in THF at 0° C. The reaction mixture was stirred over night and concentrated. To the residue was added a saturated solution of bicarbonate (3 mL) and this aqueous layer was extracted with DCM (2×). The combined organic layers were washed with brine, dried over sodium sulfate, filtered and evaporated. The solid was triturated in DCM (3 mL) and filtered. The filtrate was evaporated and purified by flash chromatography (0% to 80% ethyl acetate in hexanes). The 2 solids were mixed to afford title compound 382 (1.1 g, 65%) as a white solid. MS (m/z): 288.0 (M+H).

Step 4: 11-cyclopropyl-6,11-dihydro-5H-benzo[b] pyrido[2,3-e][1,4]diazepin-5-one (383)

Title compound 382 (0.7 g, 2.4 mmol), sodium hydride (0.292 g, 7.3 mmol) and pyridine (20 mL) were stirred together at 80° C. for 5 hours then at room temperature over week-end. The reaction mixture was then poured into an ice-water mixture and stirred for 1 hour. The beige solid was filtered and the filtrate was extracted with ethyl acetate (2 times). The combined organic extracts were dried and concentrated. The residue was purified by flash chromatography (10-70% ethyl acetate in hexanes). The 2 solids were mixed together to afford title compound 383 (0.51 g, 85%) as a beige solid. MS (m/z): 251.9 (M+H).

Step 5: methyl 4-(11-cyclopropyl-5-oxo-5H-benzo [b]pyrido[2,3-e][1,4]diazepin-6(11H)-yl)butanoate (384)

Using Procedure H-3 (Table 5) with compound 383 the title compound 384 was obtained (50 mg, 71%). MS (m/z): 352 (M+H). $^1$H NMR (CDCl$_3$) δ (ppm): 8.38 (dd, J=4.8, 2.1 Hz, 1H), 8.04 (dd, J=7.6, 2.0 Hz, 1H), 7.47 (dd, J=7.9, 1.8 Hz, 1H), 7.24-7.13 (m, 3H), 7.02 (dd, J=7.6, 4.7 Hz, 1H), 4.68-4.61 (m, 1H), 3.69-3.54 (m, 2H), 3.60 (s, 3H), 2.31-2.26 (m, 2H), 1.96 (sept., J=6.9 Hz, 1H), 1.77-1.69 (m, 1H), 1.07-1.02 (m, 1H), 0.93-0.87 (m, 1H), 0.66-0.60 (m, 1H), 0.51-0.45 (m, 1H).

Step 6: 4-(11-cyclopropyl-5-oxo-5H-benzo[b]pyrido [2,3-e][1,4]diazepin-6(11H)-yl)-N-hydroxybutanamide (385)

Using Procedure B-3 (Table 5) with compound 384 the title compound 385 was obtained (24 mg, 49%). $^1$H NMR (CD$_3$OD) δ (ppm): 8.36 (1H, dd, J=4.9, 1.7 Hz), 8.00 (1H, dd, J=7.6, 1.7 Hz), 7.52 (1H, dd, J=8.1, 1.3 Hz), 7.38 (1H, dd, J=8.0, 1.1 Hz), 7.26 (1H, td, J=7.8, 1.3 Hz), 7.23-7.17 (1H, td observed), 7.12 (1H, dd, J=7.6, 4.9 Hz), 4.58-4.48 (1H, m), 3.76-3.68 (1H, m), 3.60-3.55 (1H, m), 2.06 (2H, t, J=7.6 Hz), 1.95-1.80 (1H, m), 1.79-1.73 (1H, m), 1.05-0.87 (2H, m), 0.60-0.42 (2H, m). MS (m/z): 353.1 (M+H).

Scheme 61

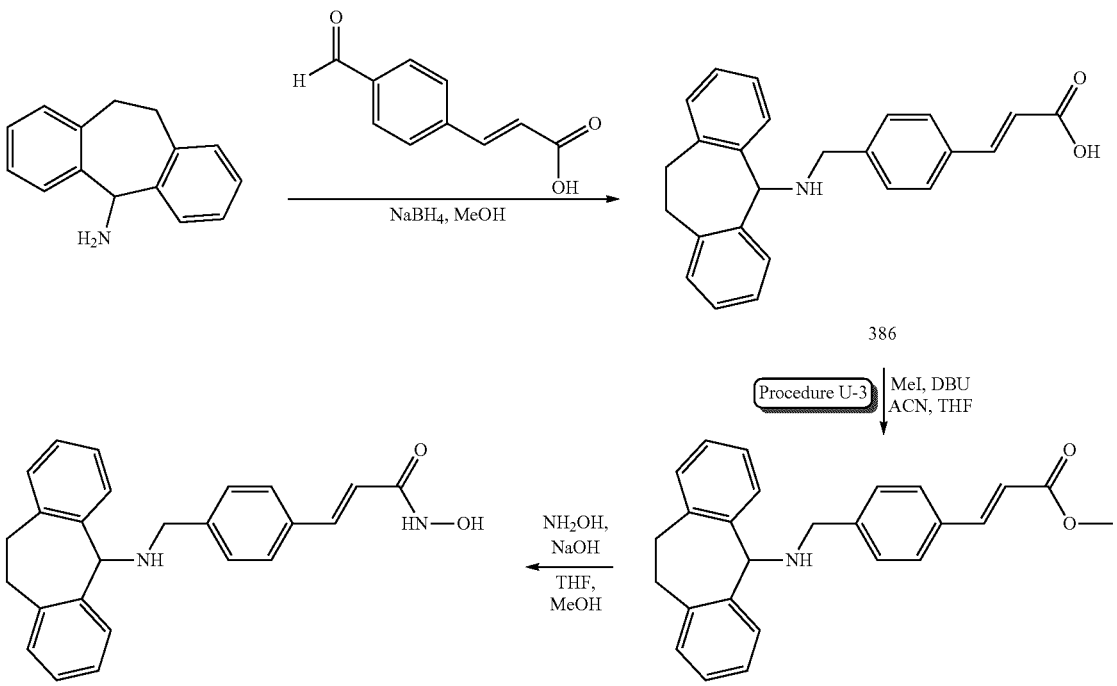

Example 211

Compound (388)

Step 1: Compound (386)

Using Procedure A-3 (Table 5) with starting amine the title compound 386 was obtained (71 mg, 40%). $^1$H NMR (CD$_3$OD) δ (ppm): 7.61-7.53 (3H, m), 7.35 (2H, d, J=8.2 Hz), 7.28-7.14 (8H, m), 6.48 (1H, d, J=15.9 Hz), 5.05 (1H, s), 3.84 (2H, s), 3.65-3.52 (2H, m), 3.03-2.93 (2H, m). MS (m/z): 368 (M−H).

Step 2: Compound (387)

Title compound 386 (71 mg, 0.19 mmol), DBU (30 μL, 0.20 mmol) and methyl iodide (12 μL, 0.20 mmol) were stirred in acetonitrile (1 mL) for 30 minutes. More DBU and methyl iodide were added and the reaction mixture was stirred over week-end. The mixture was concentrated and the residue was partitioned between saturated solution of bicarbonate and ethyl acetate. The aqueous layer was extracted with another portion of ethyl acetate. The combined organic layers were washed with brine, dried over sodium sulfate, filtered and evaporated to afford crude compound 387 that was used directly for next step.

Step 3: Compound (388)
Using Procedure B-3 (Table 5) with compound 387 the title compound 388 was obtained (50 mg, 50%). $^1$H NMR (CD$_3$OD) δ (ppm): 7.70-7.55 (3H, m), 7.47 (2H, d, J=7.8 Hz), 7.42-7.34 (4H, m), 7.33-7.21 (5H, m), 6.56 (1H, d, J=15.9 Hz), 5.49 (1H, br s), 4.16 (1H, br s), 3.50-3.36 (2H, m), 3.25-2.98 (2H, m). MS (m/z): 385.1 (M+H).
Scheme 62
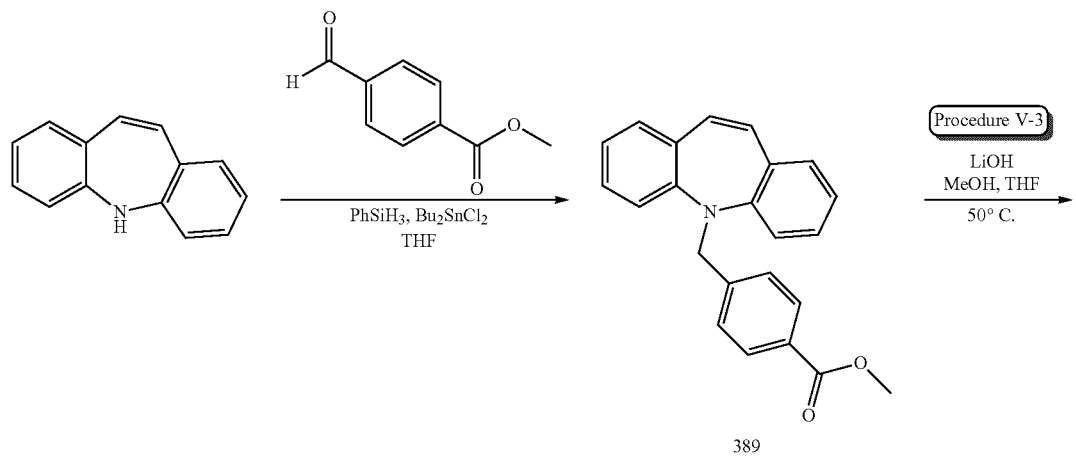
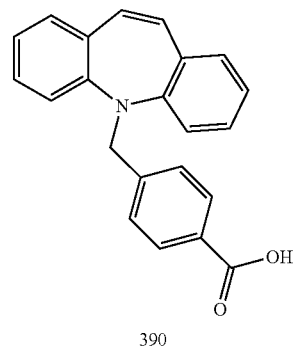
390
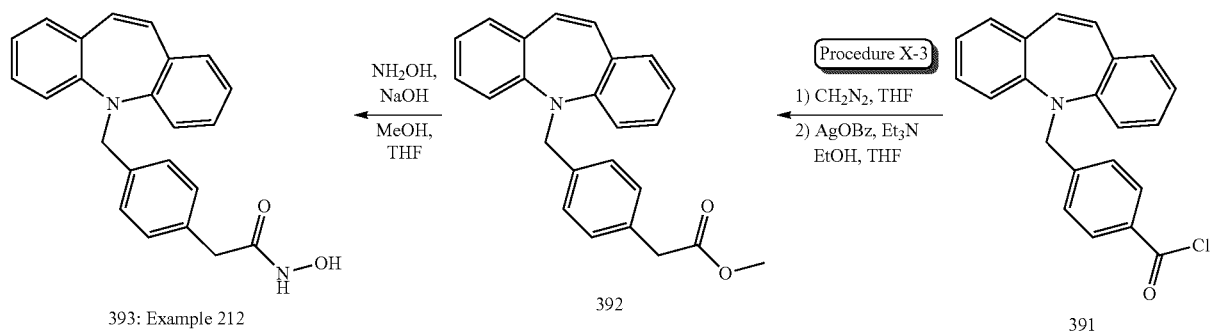

Example 212

(Z)-2-(4-((5H-dibenzo[b,f]azepin-5-yl)methyl)phenyl)-N-hydroxyacetamide (393)

Step 1: (Z)-methyl 4-((5H-dibenzo[b,f]azepin-5-yl)methyl)benzoate (389)

Using Procedure A-3 (Table 5) with (Z)-5H-dibenzo[b,f]azepine the title compound 389 was obtained (1.9 g mg, 100%). MS (m/z): 342.0 (M+H).

Step 2: (Z)-methyl 4-((5H-dibenzo[b,f]azepin-5-yl)methyl)benzoate (390)

Title compound 389 (1.0 g, 2.93 mmol) and lithium hydroxide (2N in water, 10 mL) were stirred in a mixture of THF (20 mL) and methanol (20 mL) over night. The reaction mixture was then heated to 50° C. for 3 hours. The solvent were evaporated and the residue was acidified to pH=4-5 with 3N HCl. The solid was filtered, washed with water and dried. The mother liquor was extracted with ethyl acetate (3 times). The combined organic layers were washed with brine, dried over sodium sulfate, filtered and evaporated. The residue was triturated in ether and the 2 solids were mixed together to afford title compound 390 (0.71 g, 74%) as a brown solid. $^1$H NMR (DMSO-$d_6$) δ (ppm): 7.74 (2H, d, J=7.8 Hz), 7.48 (2H, d, J=7.6 Hz), 7.22-7.05 (6H, m), 6.98-6.91 (2H, m), 6.83 (2H, s), 5.00 (2H, s). MS (m/z): 326.1 (M−H).

Step 3: (Z)-4((5H-dibenzo[b,f]azepin-5-yl)methyl)benzoyl chloride (391)

The title compound 390 (0.72 g, 2.2 mmol) and the oxalyl chloride (0.58 mL, 6.6 mmol) were mixed in DCM (10 mL) and few drops of DMF was added. The reaction mixture was stirred for 30 minutes and the solvent was evaporated (and stripped with toluene twice) to afford title compound 391 that was used crude for next step.

Step 4: (Z)-methyl 2-(4-((5H-dibenzo[b,f]azepin-5-yl)methyl)phenyl)acetate (392)

The nitroso methyl urea (4.3 g, 42 mmol) was combined with potassium hydroxide (40% in water, 7.75 mL) in ether at 0° C. The reaction mixture was stirred for 30 minutes and cooled to −78° C. The organic phase was decanted to afford a solution of diazomethane in ether. To half of this solution at 0° C. was added the title compound 391 (2.2 mmol) in THF (20 mL) and this reaction mixture was stirred at 0° C. for 2 hours. The excess of diazomethane was evaporated (flow of air) and a saturated solution of bicarbonate was added. This mixture was extracted with ethyl acetate (2 times). The combined organic extracts were washed with brine, dried over sodium sulfate, filtered and evaporated. The residue was purified by flash chromatography (0% to 50% ethyl acetate in hexanes) to afford title compound 392 (0.40 g, 50%) as a solid. MS (m/z): 356.1 (M+H).

Step 5: (Z)-2-(4-((5H-dibenzo[b,f]azepin-5-yl)methyl)phenyl)-N-hydroxyacetamide (393)

Using Procedure B-3 (Table 5) with compound 392 the title compound 393 was obtained (40 mg, 36%) as a yellow solid. $^1$H NMR (DMSO-$d_6$) δ (ppm): 10.57 (1H, s), 8.74 (1H, s), 7.31 (2H, d, J=8.2 Hz), 7.19 (2H, td, J=7.2, 1.6 Hz), 7.11 (2H, d, J=7.2 Hz), 7.10-7.04 (4H, m), 6.92 (2H, m), 6.81 (2H, s), 4.89 (2H, s), 3.13 (2H, s). MS (m/z): 357.1 (M+H).

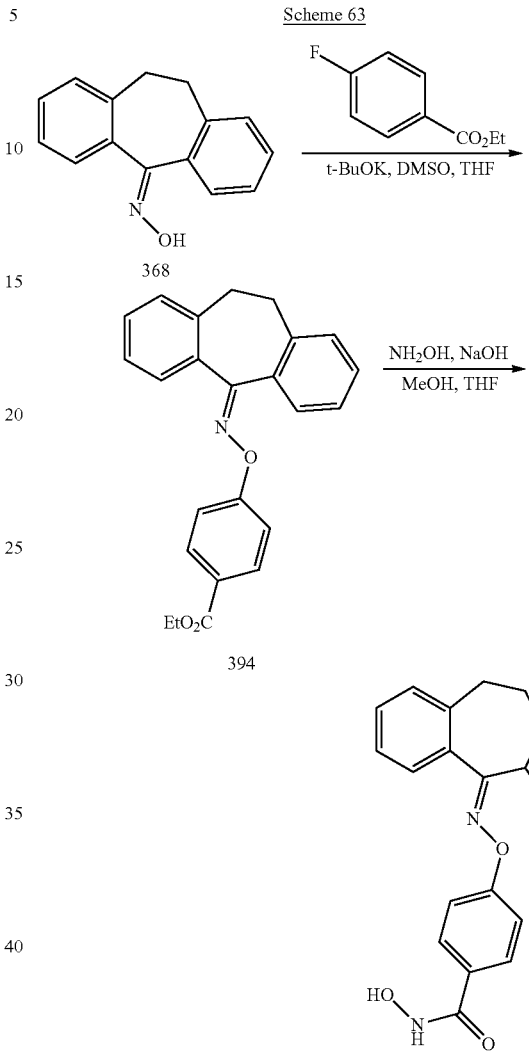

Scheme 63

Example 213

Compound (395)

Step 1: Compound (394)

Title compound 368 (0.26 g, 1.16 mmol) and potassium tert-butoxide (0.143 g, 1.17 mmol) were stirred in THF (1 mL) for 20 minutes. A solution of ethyl 4-fluorobenzoate (0.171 mL, 1.16 mmol) in DMSO (0.3 mL) was added. The reaction mixture was stirred 1 hour at room temperature, 1 hour at 50° C. and 2 hours at 75° C. The mixture was diluted with ethyl acetate. This organic layer was washed with water (3 times) and brine, dried over sodium sulfate, filtered and evaporated. The crude was purified by flash chromatography (0% to 30% ethyl acetate in hexanes) to afford title compound 394 (0.1 g, 23%). MS (m/z): 372 (M+H).

Step 2: Compound (395)

Using Procedure B-3 (Table 5) with compound 394 the title compound 395 was obtained (71 mg, 73%) as a white solid. $^1$H NMR (DMSO-d$_6$) δ (ppm): 11.13 (1H, s), 8.94 (1H, s), 7.74 (2H, d, J=8.8 Hz), 7.67 (1H, d, J=7.4 Hz), 7.42-7.34 (4H, m), 7.32-7.26 (2H, m), 7.26-7.19 (3H, m), 3.21-2.99 (4H, m). MS (m/z): 359.0 (M+H).

Scheme 64

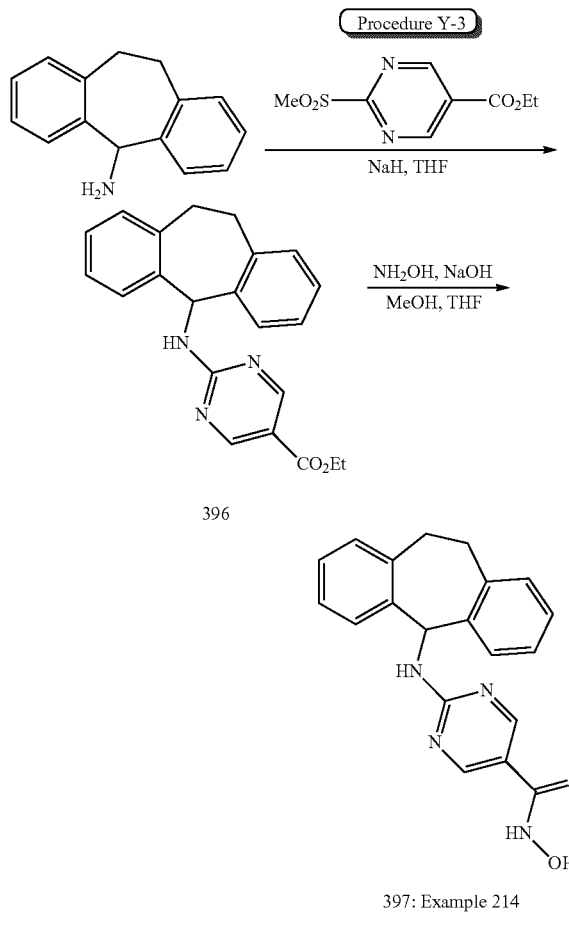

396

397: Example 214

Example 214

Compound (397)

Step 1: Compound (396)

The amine (0.4 g, 1.9 mmol) and the sodium hydride (60% in oil, 84 mg, 2.1 mmol) were stirred in THF (2 mL) for 1 hour. To this mixture at 0° C. was added a suspension of ethyl 2-(methylsulfonyl)pyrimidine-5-carboxylate (0.754 g, 1.9 mmol) in THF (1 mL). The reaction mixture was stirred at room temperature for 1 hour. Some water was added and the solid was filtered and discard. The filtrate was extracted with ethyl acetate (2 times). The combined organic extracts were washed with brine, dried over sodium sulfate, filtered and evaporated. The crude was purified by flash chromatography (0% to 100% ethyl acetate in hexanes) then with HPLC to afford title compound 396 (15 mg, 2.5% yield) as a white solid. MS (m/z): 360.1 (M+H).

Step 2: Compound (397)

Using Procedure B-3 (Table 5) with compound 396 the title compound 397 was obtained (8 mg, 57%) as a white solid. $^1$H NMR (MeOD) δ (ppm): 8.62 (2H,$), 7.44 (2H, d, J=7.1 Hz), 7.17-7.09 (6H, m), 6.66 (1H, s), 3.38-3.30 (2H, m), 3.28-3.18 (2H, m). MS (m/z): 345.1 (M−H).

Scheme 65

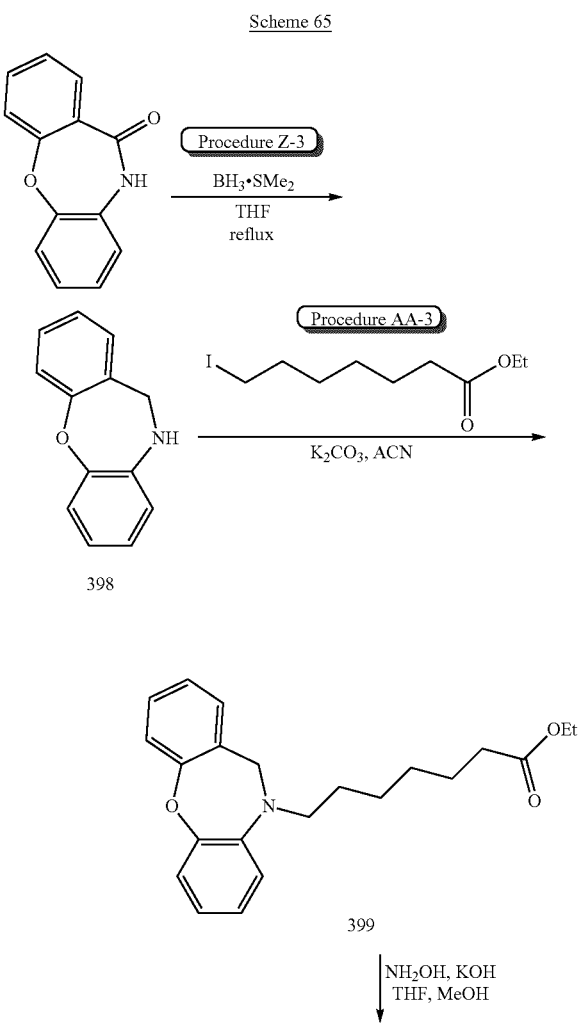

398

399

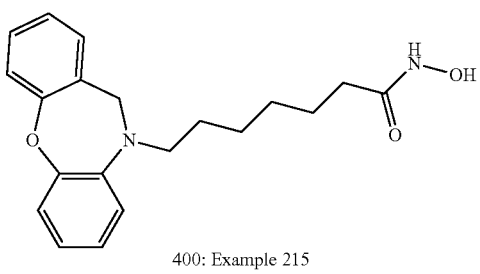

400: Example 215

Example 215

7-(dibenzo[b,f][1,4]oxazepin-10(11H)-yl)-N-hydroxyheptanamide (400)

Step 1: 10,11-dihydrodibenzo[b,f][1,4]oxazepine (398)

Dibenzo[b,f][1,4]oxazepin-11(10H)-one (1.001 g, 4.7 mmol) was dissolved in THF (20 mL) and the borane (2M in THF, 20 mL, 40.0 mmol) was added. The reaction mixture was refluxed for 3 hours. The mixture was cooled down to room temperature and an excess of ethanol was added to quench the reaction. The resulting mixture was refluxed for 2 hours. The mixture was cooled down and concentrated in vacuo. The residue was dissolved in ethyl acetate and the organic layer was washed with water and brine, dried over sodium sulfate, filtered and evaporated to afford title compound 398 (0.945 g, quantitative). MS (m/z): 198.1 (M+H). $^1$H NMR (CD$_3$OD) δ (ppm): 7.29-7.19 (m, 2H), 7.16-7.04 (m, 2H), 7.01-6.99 (m, 1H), 6.82-6.78 (m, 1H), 6.63-6.59 (m, 2H), 4.88 (s, 1H), 4.39 (s, 2H). MS (m/z): 198.1 (M+H).

Step 2: ethyl 7-(dibenzo[b,f][1,4]oxazepin-10(11H)-yl)heptanoate (399)

Title compound 398 (0.304 g, 1.54 mmol) was dissolved in acetonitrile (5.0 mL) and the ethyl 7-iodoheptanoate (0.613 g, 2.16 mmol) and the potassium carbonate (0.639 g, 4.62 mmol) were added. The reaction mixture was stirred at 70° C. for 60 hours. The mixture was cooled down and diluted with ethyl acetate. The organic phase was washed with water and brine, dried over sodium sulfate, filtered and evaporated. The residue was purified by flash chromatography with 10% ethyl acetate in hexanes to afford title compound 399 (201 mg, 37%). MS (m/z): 354.2 (M+H).

Step 3: 7-(dibenzo[b,f][1,4]oxazepin-10(11H)-yl)-N-hydroxyheptanamide (400)

Using Procedure B-3 (Table 5) with compound 399 the title compound 400 was obtained (21 mg, 10%) as an oil. $^1$H NMR (400 MHz, CD$_3$OD) δ (ppm): 7.71 (m, 1H), 7.60 (t, J=8.0 Hz, 1H), 7.52-7.48 (m, 2H), 7.43 (d, J=7.8 Hz, 1H), 7.39-7.36 (m, 2H), 7.27 (t, J=7.4 Hz, 1H), 5.01 (s, 2H), 3.56 (t, J=8.0 Hz, 2H), 2.15 (br s, 2H), 1.73-1.70 (m, 2H), 1.59-1.55 (m, 2H), 1.31 (br s, 4H). MS (m/z): 341.1 (M+H).

Scheme 66

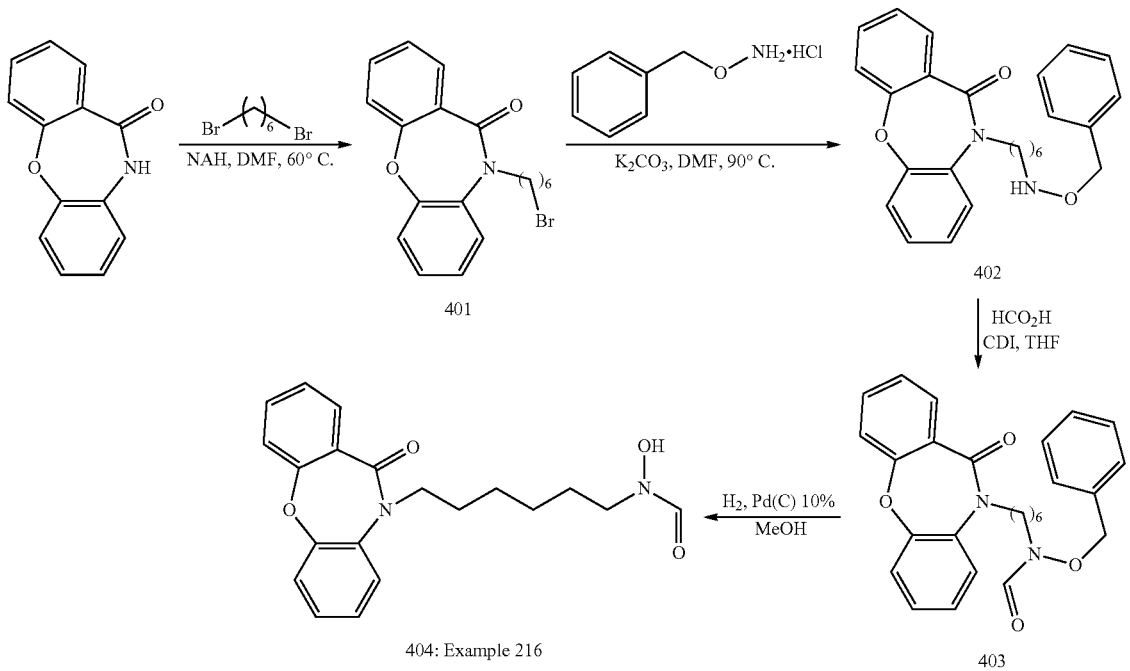

404: Example 216

Example 216

N-hydroxy-N-(6-(11-oxodibenzo[b,f][1,4]oxazepin-10(11H)-yl)hexyl)formamide (404)

Step 1: 10-(6-bromohexyl)dibenzo[b,f][1,4]oxazepin-11(10H)-one (401)

Using Procedure H-3 (Table 5) with dibenzo[b,f][1,4]oxazepin-11(10H)-one the title compound 401 was obtained (740 mg, 83%) as a colorless oil. MS (m/z): 374.1 (M+H).

Step 2: 10-(6-(benzyloxyamino)hexyl)dibenzo[b,f][1,4]oxazepin-11(10H)-one (402)

Using Procedure I-3 (Table 5) with compound 401 the title compound 402 was obtained (648 mg, 79%) as a colorless oil. MS (m/z): 417.3 (M+H).

Step 3: N-(benzyloxy)-N-(6-(11-oxodibenzo[b,f][1,4]oxazepin-10(1H)-yl)hexyl)formamide (403)

1,1'-Carbonyldiimidazole (1.26 g, 7.8 mmol) was dissolved in THF (15 mL) and the mixture was cooled at 0° C.

Title compound 402 (0.646 g, 1.56 mmol) and formic acid in solution in THF (5 mL) was added. The reaction mixture was stirred at room temperature for 3 hours then diluted in ethyl acetate. The organic phase was washed with a saturated aqueous solution of bicarbonate, water and brine, then evaporated. The residue was purified by flash chromatography (30-50% ethyl acetate in hexanes) to afford title compound 403 (348 mg, 50%) as a colorless oil. MS (m/z): 445.2 (M+H).

Step 4: N-hydroxy-N-(6-(11-oxodibenzo[b,f][1,4] oxazepin-10(11H)-yl)hexyl)formamide (404)

Title compound 403 (348 mg, 0.783 mmol) was dissolved in methanol (10 mL). The 10% palladium on charcoal (120 mg, 33% by wt) was added. The reaction mixture was stirred for 3 hours under 1 atmosphere of hydrogen at room temperature. The reaction mixture was filtered to remove the catalyst and the filtrate was evaporated. The residue was partitioned between ethyl acetate and water. The organic layer was dried over sodium sulfate, filtered and evaporated to afford title compound 404 (18 mg, 6%) as a white solid. $^1$H NMR (CD$_3$OD) δ (ppm): 8.24, 7.89 (2s, rotamers, 1H), 7.74 (d, J=7.6 Hz, 1H), 7.54-7.46 (m, 2H), 7.33 (dt, J=7.4, 2.0 Hz, 1H), 7.28-7.21 (m, 4H), 4.19 (br s, 2H), 3.50 (t, J=6.8 Hz, 1H), 3.44 (t, J=6.8 Hz, 1H), 1.70-1.55 (m, 4H), 1.44-1.29 (m, 4H). MS (m/z): 355.2 (M+H).

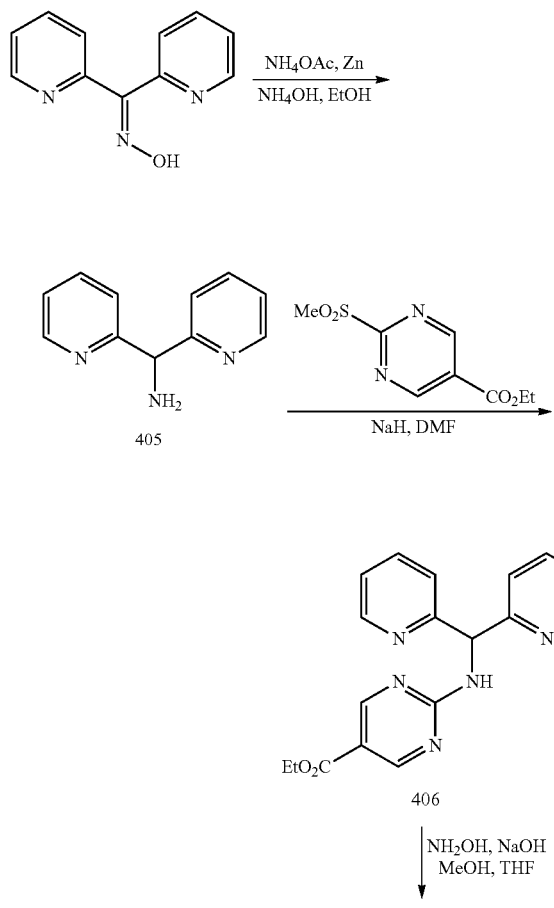

Scheme 67

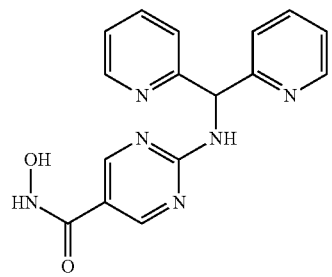

407: Example 217

Example 217

2-(dipyridin-2-ylmethylamino)-N-hydroxypyrimidine-5-carboxamide (407)

Step 1: dipyridin-2-ylmethanamine (405)

Dipyridin-2-ylmethanone oxime (500 mg, 2.510 mmol) and ammonium acetate were solubilized in ethanol and the mixture was reflux for 3 hours adding portion of zinc at 0 h, 1 h and 2 h. The reaction mixture was cooled down to room temperature and stirred over night. The pH was adjusted to 12 with sodium hydroxide and the mixture was filtered through celite. The mixture was diluted with ethyl acetate and the organic layer was washed with brine, dried over magnesium sulfate, filtered and evaporated to afford title compound 405 (282 mg, 61%) as a light yellow oil. MS (m/z): 186.2 (M+H). $^1$H NMR (CDCl$_3$) δ (ppm): 8.50-8.49 (m, 2H), 7.56 (td, J=7.7, 1.8 Hz, 2H), 7.33 (dt, J=8.0, 0.9 Hz, 2H), 7.08 (ddd, J=7.4, 4.9, 1.2 Hz, 2H), 5.26 (s, 1H), 2.38 (s, 2H).

Step 2: ethyl 2-(dipyridin-2-ylmethylamino)pyrimidine-5-carboxylate (406)

Using Procedure Y-3 (Table 5) with compound 405 the title compound 406 was obtained (27 mg, 10%) as a yellow solid. MS (m/z): 336.2 (M+H).

Step 3: 2-(dipyridin-2-ylmethylamino)-N-hydroxypyrimidine-5-carboxamide (407)

Using Procedure B-3 (Table 5) with compound 406 the title compound 407 was obtained (8 mg, 31%) as a yellow solid. $^1$H NMR (CD$_3$OD) δ (ppm): 8.65 (bs, 2H), 8.54 (d, J=4.8 Hz, 2H), 7.79 (dt, J=2 Hz, 7.6 Hz, 2H), 7.56 (d, J=7.6 Hz, 2H), 7.31 (dd, J=2 Hz, 6.8 Hz, 2H), 6.43 (s, 1H). MS (m/z): 323.4 (M+H).

Scheme 68

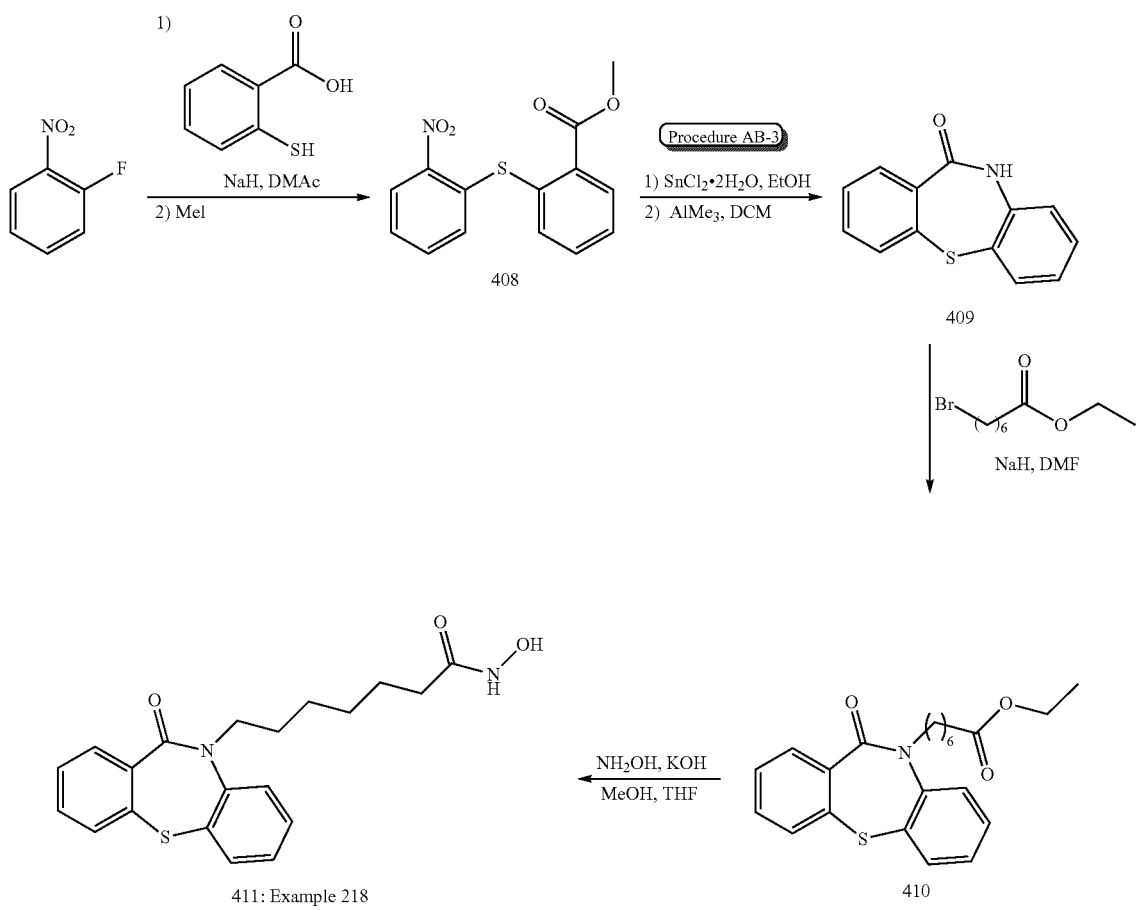

Example 218

N-hydroxy-7-(11-oxodibenzo[b,f][1,4]thiazepin-10(11H)-yl)heptanamide (411)

Step 1: methyl 2-(2-nitrophenylthio)benzoate (408)

A solution of 2-mercaptobenzoic acid (6.0 g, 39.0 mmol) in dimethylacetamide (20 mL) was added to a suspension of sodium hydride (60% in oil, 3.1 g, 77.5 mmol) in dimethylacetamide (15 mL). The mixture was stirred for 5 minutes and 1-fluoro-2-nitrobenzene (5.0 g, 35.5 mmol) was added. The reaction mixture was heated at 80° C. for one hour. The mixture was cooled down to room temperature and methyl iodide (7.3 mL, 117.15 mmol) was added. The reaction mixture was stirred at room temperature 16 hours. The mixture was then poor into water and extracted with a mixture of 75% ethyl acetate in hexanes (3 times). The combined organic layers were washed with water and brine, dried over sodium sulfate, filtered and evaporated. The residue was dissolved in a minimum amount of dichloromethane and hexanes was added to precipitate the product. The solid was filtered and dried to afford title compound 408 (7.81 g, 76%) as a yellow solid. MS (m/z): 312.2 (M+H).

Step 2: dibenzo[b,f][1,4]thiazepin-11(10H)-one (409)

Using Procedure J (Table 1) with compound 408 followed by procedure K (Table 1), the title compound 409 was obtained (1.15 g, 40%) as a white solid. MS (m/z): 228.2 (M+H). $^1$H NMR (DMSO-$d_6$) δ (ppm): 10.70 (s, 1H), 7.68 (ddd, J=7.4, 1.9, 0.5 Hz, 1H), 7.57-7.42 (m, 4H), 7.36 (ddd, J=8.0, 7.3, 1.5 Hz, 1H), 7.23 (dd, J=8.0, 1.2 Hz, 1H), 7.15 (td, J=7.5, 1.4 Hz, 1H).

Step 3: ethyl 7-(11-oxodibenzo[b,f][1,4]thiazepin-10(11H)-yl)heptanoate (410)

Title compound 409 (0.403 g, 1.77 mmol) was dissolved in DMF (5.0 mL) and sodium hydride (60% in oil, 0.0.086 g, 2.13 mmol) was added. The reaction mixture was stirred at 50° C. for 30 minutes. Ethyl 7-bromoheptanoate (0.631 g, 2.66 mmol) was added and the reaction mixture was stirred at 50° C. for 16 hours. The mixture was cooled down to room temperature and quenched with water. The aqueous layer was extracted 3 times with at mixture of 75% ethyl acetate in hexanes. The combined organic extracts were washed with water and brine, dried over sodium sulfate, filtered and evaporated. The residue was purified by flash chromatography (30% ethyl acetate in hexanes) to afford title compound 410 (470 mg, 69%). MS (m/z): 384.4 (M+H).

Step 4: N-hydroxy-7-(11-oxodibenzo[b,f][1,4]thiazepin-10(11H)-yl)heptanamide (411)

Using Procedure B-3 (Table 5) with compound 410 the title compound 411 was obtained (220 mg, 48%) as a white solid. $^1$H NMR (CD$_3$OD) δ (ppm): 7.63-7.59 (m, 2H), 7.52-7.46 (m, 2H), 7.42-7.34 (m, 3H), 7.19 (td, J=7.4, 1.4 Hz, 1H), 4.70 (dt, J=13.7, 1.4 Hz, 1H), 3.67 (ddd, J=13.7, 7.4, 5.9 Hz, 1H), 2.04 (t, J=7.0 Hz, 2H), 1.65-1.52 (m, 4H), 1.44-1.22 (m, 4H). MS (m/z): 371.4 (M+H).

Scheme 69

Procedure AC-3

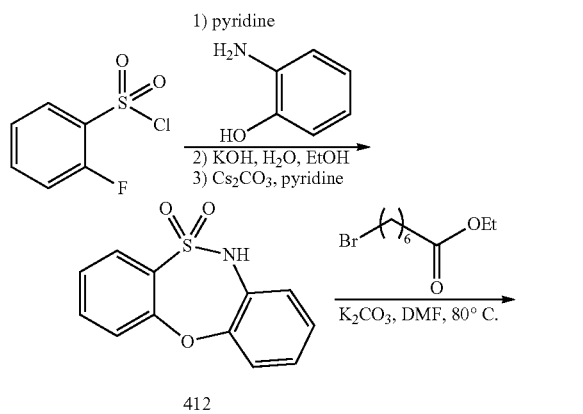

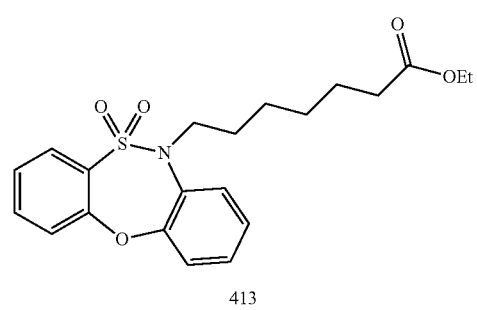
413

NH$_2$OH, KOH
MeOH, THF

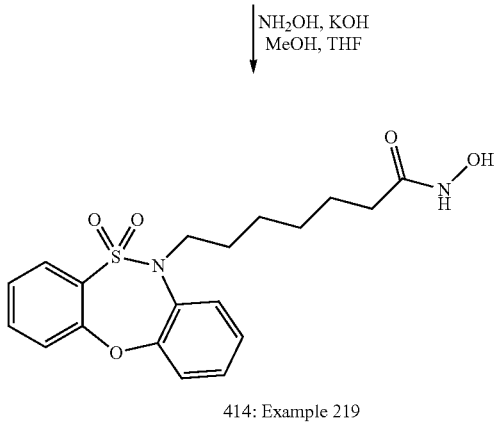
414: Example 219

Example 219

Compound (414)

Step 1: Compound (414)

2-Aminophenol (0.676 g, 6.2 mmol) was dissolved in pyridine (4.0 mL) and the 2-fluorobenzene-1-sulfonyl chloride (1.80 mL, 13.6 mmol) was added. The reaction mixture was stirred at room temperature for 20 hours then 10% HCl (20 mL) was added and the mixture was stirred at room temperature 24 hours. The mixture was diluted with ethyl acetate (and a bit of methanol). The organic layer was washed with 10% HCl (5 times), brine, dried over sodium sulfate, filtered and evaporated. The residue was dissolved in ethanol (20 mL) and potassium hydroxide in water (4M, 6 mL) was added. This reaction mixture was stirred at 100° C. in a sealed tube for 24 hours. The mixture was cooled down to room temperature and the pH was adjusted to pH=2 with 10% HCl. The aqueous layer was extracted twice with ethyl acetate. The combined organic layers were washed with water and brine, dried over sodium sulfate, filtered and evaporated. The residue was diluted with pyridine and cesium carbonate was added (2.02 g, 6.2 mmol). The reaction mixture was stirred at 130° C. for 36 hours. The mixture was cooled down to room temperature and the pH was adjusted to pH=2 with 3N HCl. The aqueous layer was extracted with ethyl acetate (3×). The combined organic extracts were washed with water and brine, dried over sodium sulfate, filtered and evaporated. The crude was purified by flash chromatography (40% ethyl acetate in hexanes) then triturated in a mixture of 30% ethyl acetate in hexanes to afford title compound 412 (685 mg, 45%) as a white solid. MS (m/z): 246.0 (M−H). $^1$H NMR (DMSO-d$_6$) δ (ppm): 10.88 (s, 1H), 7.78 (dd, J=7.7, 1.5 Hz, 1H), 7.72 (ddd, J=8.1, 7.4, 1.7 Hz, 1H), 7.51 (dd, J=8.2, 0.8 Hz, 1H), 7.42 (td, J=7.6, 1.2 Hz, 1H), 7.39-7.35 (m, 1H), 7.20-7.15 (m, 2H), 7.08-7.05 (m, 1H).

Step 2: Compound (413)

Using Procedure H-3 (Table 5) with compound 412 the title compound 413 was obtained (536 mg, 94%) as a white solid. MS (m/z): 404.2 (M+H). $^1$H NMR (DMSO-d$_6$) δ (ppm): 7.80 (dd, J=7.9, 1.7 Hz, 1H), 7.68 (ddd, J=8.4, 7.2, 1.8 Hz, 1H), 7.50-7.43 (m, 4H), 7.40-7.33 (m, 2H), 4.02 (q, J=7.1 Hz, 2H), 3.56 (t, J=7.1 Hz, 2H), 2.22 (t, J=7.4 Hz, 2H), 1.49-1.40 (m, 4H), 1.33-1.18 (m, 4H), 1.15 (t, J=7.1 Hz, 3H).

Step 3: (414)

Using Procedure B-3 (Table 5) with compound 413 the title compound 414 was obtained (439 mg, 85%) as a white solid. $^1$H NMR (CD$_3$OD) δ (ppm): 7.80 (dd, J=8.0, 2.0 Hz, 1H), 7.61 (ddd, J=8.4, 6.8, 1.2 Hz, 1H), 7.46-7.41 (m, 3H), 7.38-7.30 (m, 3H), 3.62 (t, J=7.2 Hz, 2H), 2.06 (t, J=7.2 Hz, 2H), 1.61-1.51 (m, 4H), 1.44-1.28 (m, 4H). MS (m/z): 391.3 (M+H).

Scheme 70

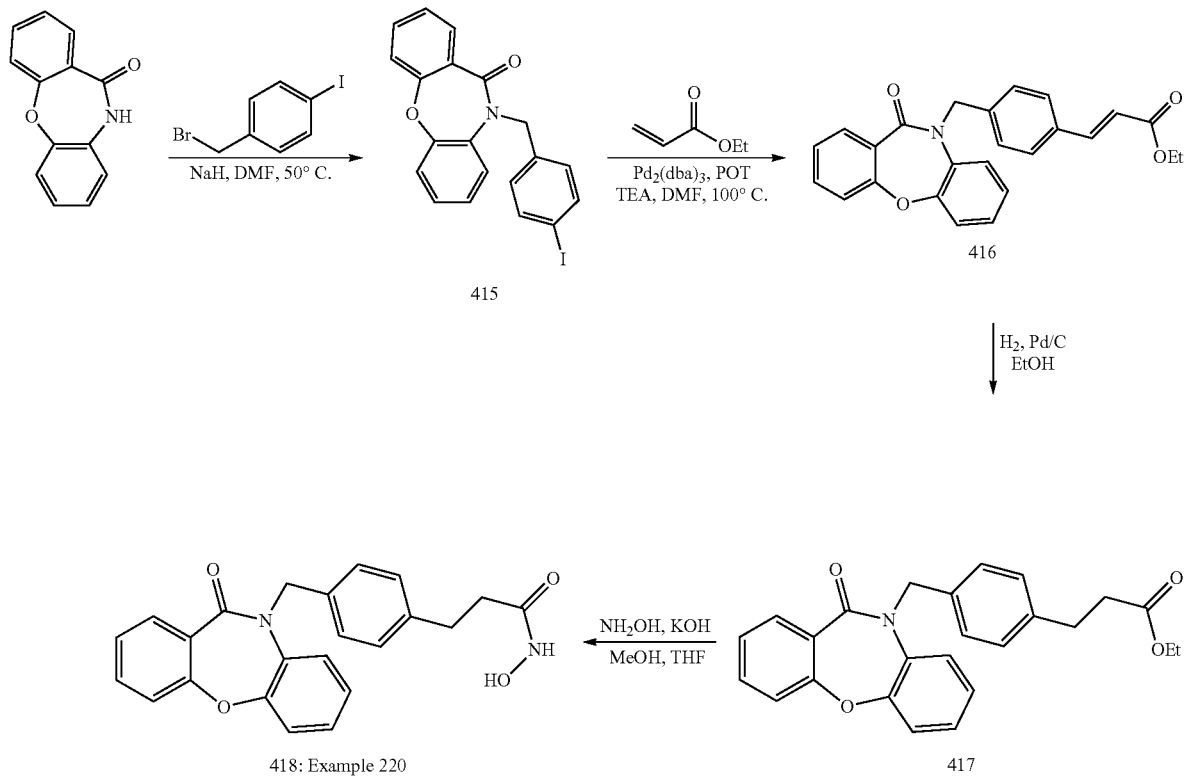

Example 220

N-hydroxy-3-(4-((11-oxodibenzo[b,f][1,4]oxazepin-10(11H)-yl)methyl)phenyl)propanamide (418)

Step 1: 10-(4-iodobenzyl)dibenzo[b,f][1,4]oxazepin-11(10H)-one (415)

Using Procedure H-3 (Table 5) with dibenzo[b,f][1,4]oxazepin-11(10H)-one and 1-(bromomethyl)-4-iodobenzene the title compound 415 was obtained (1.92 g, 78%) as beige foam. MS (m/z): 500 (M−H). $^1$H NMR (CD$_3$OD) δ (ppm): 7.81 (dd, J=8.0, 1.8 Hz, 1H), 7.64 (d, J=8.4 Hz, 2H), 7.55 (td, J=7.8, 1.8 Hz, 1H), 7.38-7.36 (m, 1H), 7.31-7.27 (m, 3H), 7.19-7.12 (m, 2H), 7.10 (d, J=8.4 Hz, 2H), 5.33 (s, 2H).

Step 2: (E)-ethyl 3-(4-((11-oxodibenzo[b,f][1,4]oxazepin-10(11H)-yl)methyl)phenyl)acrylate (416)

Using Procedure E-3 (Table 5) with compound 415 the title compound 416 was obtained (743 mg, 78%) as pink foam. MS (m/z): 400.4 (M+H).

Step 3: ethyl 3-(4-((11-oxodibenzo[b,f][1,4]oxazepin-10(11H)-yl)methyl)phenyl)propanoate (417)

Compound 416 (0.364 g, 0.912 mmol) was dissolved in ethanol (10.0 mL) and the palladium on charcoal (0.037 g, 10% w/w) was added. The reaction mixture was stirred over 1 atmosphere of hydrogen at room temperature for 1 hour. The catalyst was filtered and the filtrate was concentrated to afford title compound 417 (346 mg, 95%) that was used crude for next step. MS (m/z): 402.4 (M+H).

Step 4: N-hydroxy-3-(4-((11-oxodibenzo[b,f][1,4]oxazepin-10(11H)-yl)methyl)phenyl)propanamide (418)

Using Procedure B-3 (Table 5) with compound 417 the title compound 418 was obtained (132 mg, 40%) as a white solid. $^1$H NMR (DMSO-d$_6$) δ (ppm): 10.33 (s, 1H), 8.68 (s, 1H), 7.74 (dd, J=7.6, 1.6 Hz, 1H), 7.60-7.56 (m, 1H), 7.48-7.44 (m, 1H), 7.36-7.28 (m, 3H), 7.19-7.10 (m, 6H), 5.31 (s, 2H), 2.73 (t, J=7.2 Hz, 2H), 2.20 (t, J=7.2 Hz, 2H). MS (m/z): 389.4 (M+H).

Scheme 71

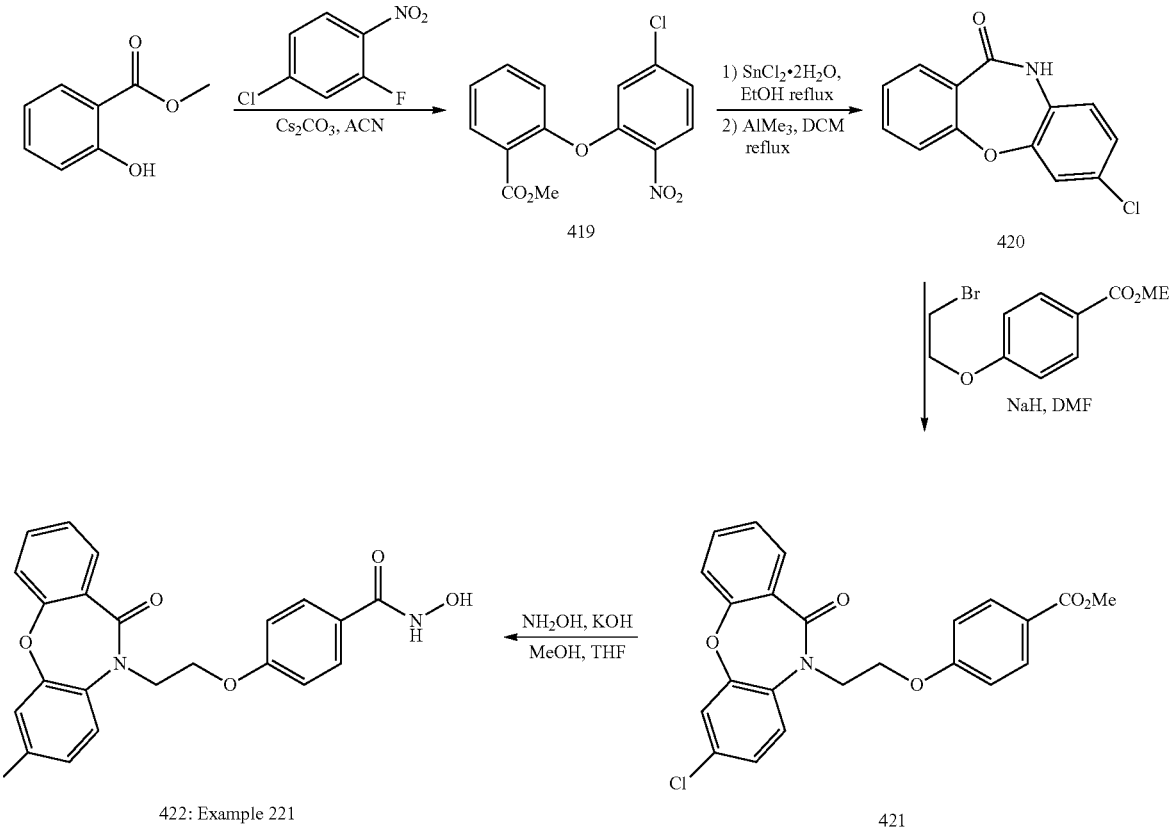

Example 221

4-(2-(7-chloro-11-oxodibenzo[b,f][1,4]oxazepin-10(11H)-yl)ethoxy)-N-hydroxybenzamide (421)

Step 1: methyl 2-(5-chloro-2-nitrophenoxy)benzoate (419)

Methyl 2-hydroxybenzoate (2.75 mL, 21.3 mmol) and 4-chloro-2-fluoro-1-nitrobenzene (1.85 g, 10.6 mmol) were dissolved in acetonitrile (25.0 mL). The cesium carbonate (6.94 g, 21.3 mmol) was added and the reaction mixture was stirred at 80° C. for 24 hours. The mixture was cooled down to room temperature then poor into ethyl acetate. The organic layer was washed with water and brine, dried over sodium sulfate, filtered and evaporated. The crude was purified by flash chromatography (10-30% ethyl acetate in hexanes) to afford title compound 419 (2.55 g, 78%). MS (m/z): 308.2 (M+H). $^1$H NMR (DMSO-$d_6$) δ (ppm): 8.14 (d, J=8.8 Hz, 1H), 7.98 (dd, J=7.8, 1.6 Hz, 1H), 7.74 (ddd, J=8.1, 7.4, 1.8 Hz, 1H), 7.47 (td, J=7.6, 1.2 Hz, 1H), 7.39 (dd, J=8.8, 2.2 Hz, 1H), 7.36 (dd, J=8.3, 1.1 Hz, 1H), 6.88 (d, J=2.0 Hz, 1H), 3.69 (s, 3H).

Step 2: 7-chlorodibenzo[b,f][1,4]oxazepin-11(10H)-one (420)

Using Procedure AB-3 (Table 5) with compound 419 the title compound 420 was obtained (200 mg, 10%) as white solid. MS (m/z): 246.1 (M+H). $^1$H NMR (DMSO-$d_6$) δ (ppm): 10.63 (s, 1H), 7.77 (dd, J=7.8, 1.6 Hz, 1H), 7.64 (ddd, 8.2, 7.3, 1.8 Hz, 1H), 7.51 (d, J=2.3 Hz, 1H), 7.38 (dd, J=8.1, 0.9 Hz, 1H), 7.34 (td, J=7.5, 1.2 Hz, 1H), 7.28 (dd, J=8.6, 2.3 Hz, 1H), 7.17 (d, J=8.6 Hz, 1H).

Step 3: methyl 4-(2-(7-chloro-11-oxodibenzo[b,f][1,4]oxazepin-10(11H)-yl)ethoxy)benzoate (421)

Using Procedure H-3 (Table 5) with compound 420 the title compound 421 was obtained (189 mg, 56%) as white solid. MS (m/z): 424.4 (M+H).

Step 4: 4-(2-(7-chloro-11-oxodibenzo[b,f][1,4]oxazepin-10(11H)-yl)ethoxy)-N-hydroxybenzamide (422)

Using Procedure B-3 (Table 5) with compound 421 the title compound 422 was obtained (55 mg, 29%) as white solid. $^1$H NMR (DMSO-$d_6$) δ (ppm): 11.04 (s, 1H), 8.90 (s, 1H), 7.74-7.71 (m, 2H), 7.68 (d, J=8.8 Hz, 2H), 7.61-7.57 (m, 2H), 7.39-7.36 (m, 2H), 7.32 (td, J=7.4, 1.2 Hz, 1H), 6.91 (d, J=8.8 Hz, 2H), 4.42 (br s, 2H), 4.30 (t, J=5.2 Hz, 2H). MS (m/z): 447.4 (M+Na).

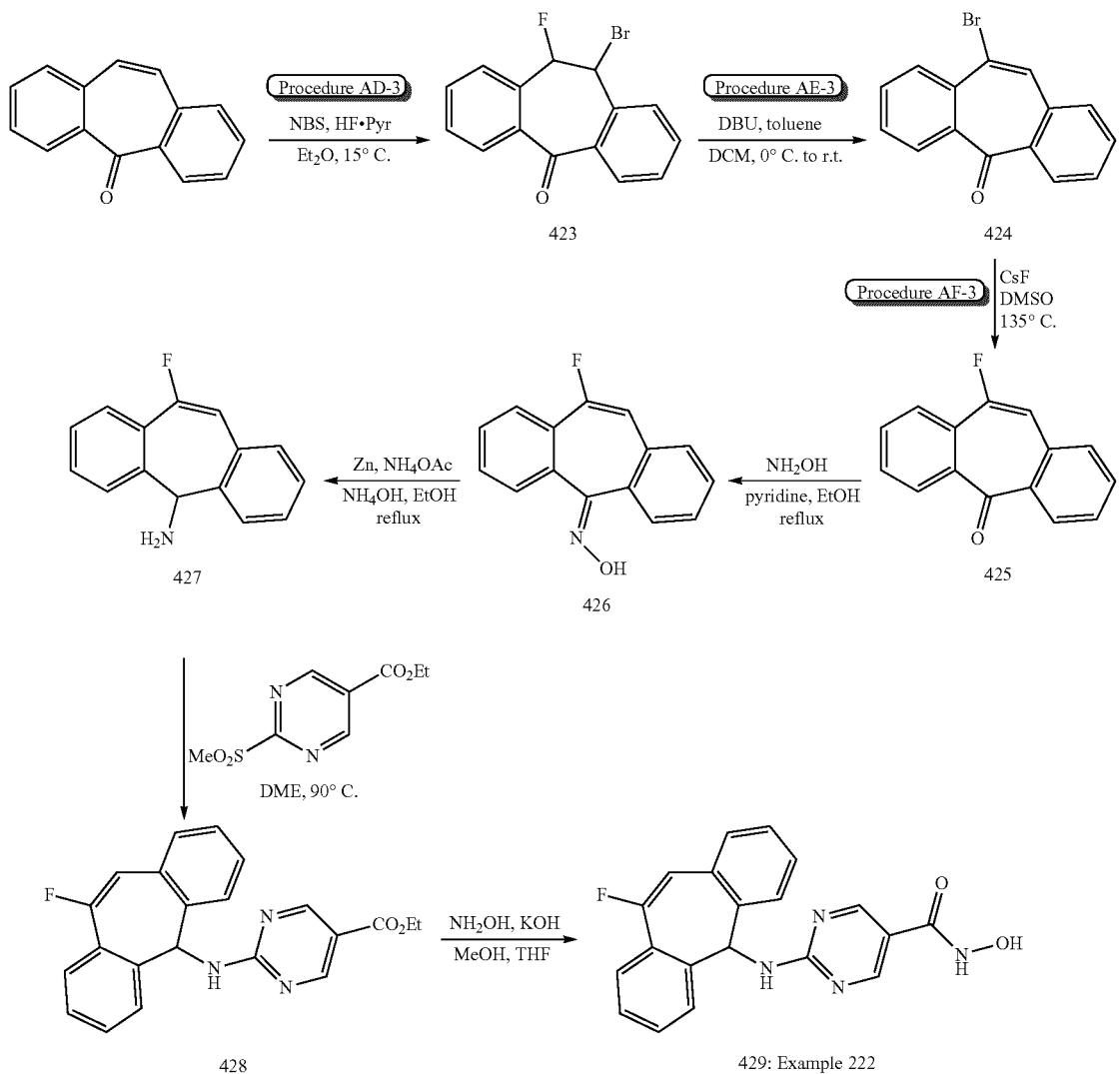

Example 222

Compound (429)

Step 1: Compound (423)

The fluoric acid-pyridine (70%, 20 mL) was combined with ether (20 mL) (in a plastic vessel) and the mixture was cooled to 0° C. The N-bromosuccinimide (2.5 g, 14 mmol) was added followed by 5-dibenzosuberenone 2.06 g, 10 mmol). The reaction mixture was stirred at 15-20° C. for about 5 hours then poor over ice-water (100 mL) mixture. The aqueous layer was washed with water, saturated aqueous solution of bicarbonate (until it stay basic), water and brine. The organic layer was let evaporated on the bench overnight. The needle that formed were filtered and washed with a bit of ether to afford title compound 423 (2.06 g, 69%) as beige solid.

Step 2: Compound (424)

Title compound 423 (2.0 g, 6.6 mmol) was dissolved in toluene (20 mL) and dichloromethane (2 mL) and the mixture was cooled to 0° C. The DBU was added and the reaction mixture was stirred at room temperature for 2 hours. The mixture was diluted with ethyl acetate. The organic layer was washed with 1N HCl (2 times), water and brine, dried over sodium sulfate, filtered and evaporated to afford title compound 424 (1.3 g, 88%) as a white solid. MS (m/z): 285.2 (M+H).

Step 3: Compound (425)

Title compound 424 (3.60 g, 12.63 mmol) was dissolved in DMSO (50 mL) and cesium fluoride (13.43 g, 88.38 mmol) was added. The reaction mixture was stirred at 135° C. for 5 hours. The mixture was poured over water and extracted with ether. The combined organic layers were washed with water and brine, dried over sodium sulfate, filtered and evaporated. The crude was purified by flash chromatography (0% to 20% ethyl acetate in hexanes) to afford title compound 425 (260 mg, 9%).

Step 4: Compound (426)

Using Procedure K-3 (Table 5) with compound 425 the title compound 426 was obtained and used crude for next step.

Step 5: Compound (427)

Using Procedure M-3 (Table 5) with compound 426 the title compound 427 was obtained (300 mg, 85% for 2 steps). MS (m/z): 209.1 (M-NH$_2$).

Step 6: Compound (428)

Using Procedure Y-3 (Table 5) with compound 427 the title compound 428 was obtained (200 mg, 63%). $^1$H NMR (CDCl$_3$) δ (ppm): 8.86-8.68 (m, 2H), 7.78-7.29 (m, 8H), 6.93 (d, J=20.3 Hz, 1H), 6.45-6.43 (m, 2H), 4.31 (q, J=7.0 Hz, 2H), 1.34 (t, J=7.0 Hz, 3H).

Step 7: Compound (429)

Using Procedure B-3 (Table 5) with compound 428 the title compound 429 was obtained (121 mg, 49%) as white solid. $^1$H NMR (DMSO-d$_6$) δ (ppm): 9.46 (s, 0.1H), 8.58 (br s, 2H), 7.80 (d, J=7.8 HZ, 1H), 7.73 (d, J=7.8 Hz, 1H), 7.63 (d, J=7.6 Hz, 1H), 7.56 (t, J=7.5 Hz, 1H), 7.43 (d, J=7.6 Hz, 1H), 7.39 (t, J=7.6 Hz, 2H), 7.27 (d, J=7.4 Hz, 1H), 7.21 (d, J=21.7 Hz, 1H), 5.92 (s, 1H). MS (m/z): 361.4 (M−H).

Step 2: benzo[b]pyrido[3,2-f][1,4]oxazepin-5(6H)-one (431)

Title compound 430 (3.65 g, 14.7 mmol) was dissolved in DMF (25.0 mL) and sodium hydroxide powder (0.706 g, 17.7 mmol) was added. The reaction mixture was stirred at 130° C. for 5 hours. The mixture was cooled down to room temperature and ice cooled water was added. The precipitate was filtered. The solid was triturated in ethanol to afford title compound 431 (1.798 g, 58%) as a white solid. $^1$H NMR (DMSO-d$_6$) δ (ppm): 10.75 (s, 1H), 8.50 (dd, J=4.8, 2.1 Hz, 1H), 8.27 (dd, J=7.6, 2.0 Hz, 1H), 7.46 (dd, J=7.5, 4.8 Hz, 1H), 7.34 (dd, J=7.8, 1.2 Hz, 1H), 7.25-7.14 (m, 3H). MS (m/z): 213.2 (M+H).

Step 3: methyl 4-(2-(5-oxobenzo[b]pyrido[3,2-f][1,4]oxazepin-6(5H)-yl)ethoxy)benzoate (432)

Using Procedure H-3 (Table 5) with compound 431 the title compound 432 was obtained (0.360 g, 92%). MS (m/z): 391.3 (M+H).

Scheme 73

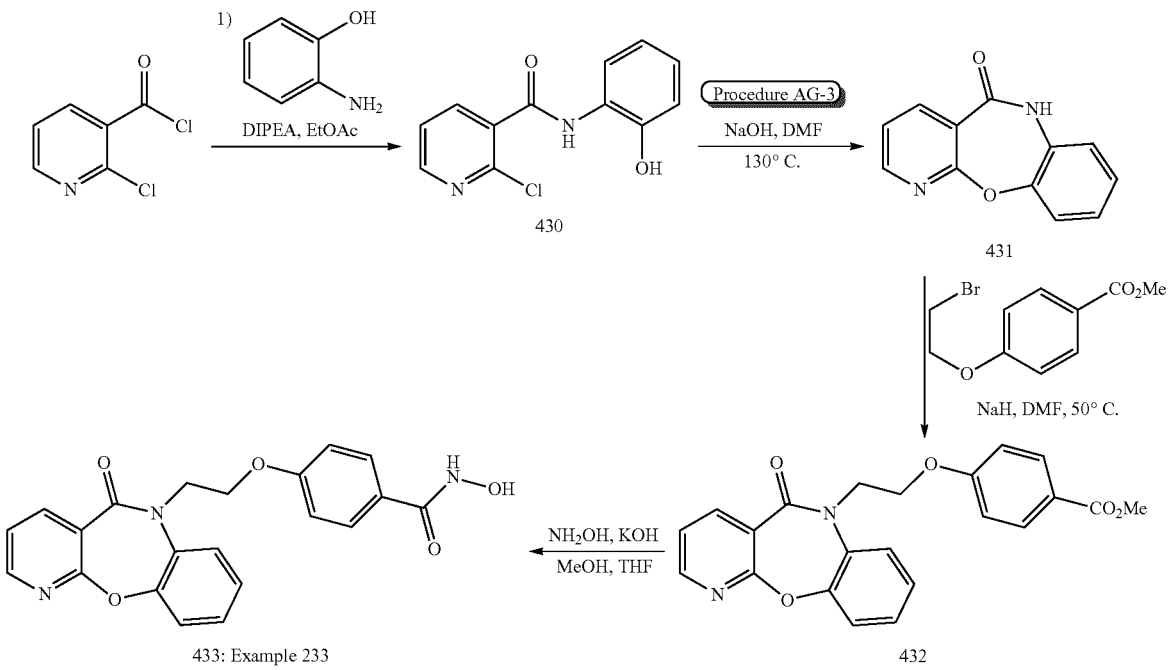

Example 223

N-hydroxy-4-(2-(5-oxobenzo[b]pyrido[3,2-f][1,4]oxazepin-6(5H)-yl)ethoxy)benzamide (433)

Step 1: N-hydroxy-4-(2-(5-oxobenzo[b]pyrido[3,2-f][1,4]oxazepin-6(5H)-yl)ethoxy)benzamide (430)

Using Procedure S-3 (Table 5) with compound 2-chloronicotinoyl chloride and 2-aminophenol the title compound 430 was obtained (3.69 g, 81%). MS (m/z): 249.2 (M+H).

Step 4: N-hydroxy-4-(2-(5-oxobenzo[b]pyrido[3,2-f][1,4]oxazepin-6(5H)-yl)ethoxy)benzamide (433)

Using Procedure B-3 (Table 5) with compound 432 the title compound 433 was obtained (27 mg, 8%). $^1$H NMR (DMSO-d$_6$) δ (ppm): 11.05 (s, 1H), 8.90 (s, 1H), 8.46 (dd, J=4.8, 2.0 Hz, 1H), 8.23 (dd, J=7.6, 1.6 Hz, 1H), 7.72 (dd, J=8.0, 1.6 Hz, 1H), 7.67 (d, J=9.2 Hz, 2H), 7.44 (dd, J=7.6, 4.4 Hz, 1H), 7.39-7.25 (m, 3H), 6.90 (d, J=9.2 Hz, 2H), 4.47 (m, 2H), 4.32 (t, J=5.2 Hz, 2H). MS (m/z): 392.3 (M+H).

Scheme 74

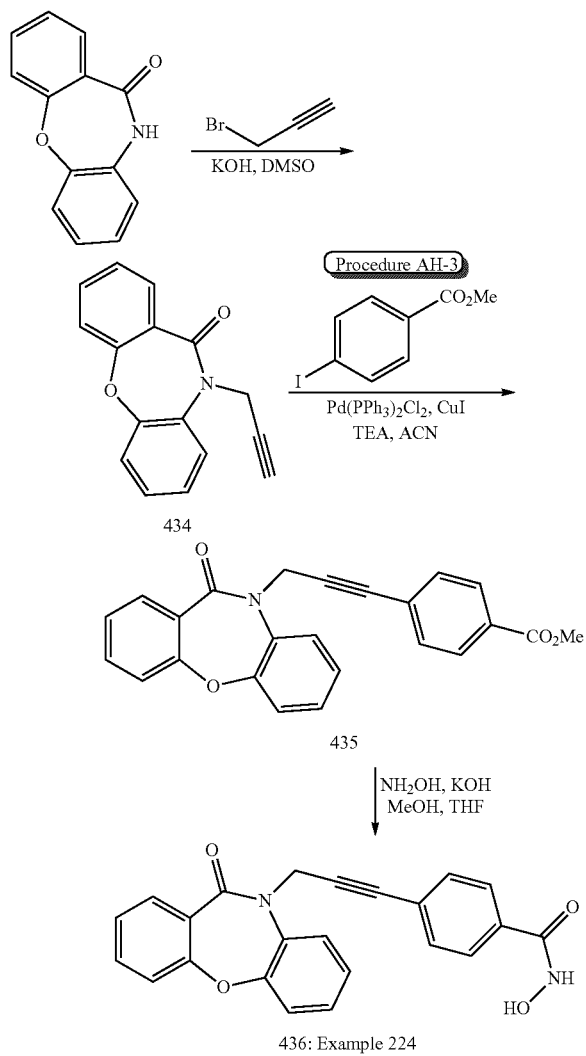

Example 224

N-hydroxy-4-(3-(11-oxodibenzo[b,f][1,4]oxazepin-10(11H)-yl)prop-1-ynyl)benzamide (436)

Step 1: 10-(prop-2-ynyl)dibenzo[b,f][1,4]oxazepin-11(10H)-one (434)

Using Procedure H-3 (Table 5) with dibenzo[b,f][1,4]oxazepin-11(10H)-one and 3-bromoprop-1-yne the title compound 85 was obtained (1.58 g, 89%) as an off-white solid. $^1$H NMR (DMSO-d$_6$) δ (ppm): 7.76 (ddd, J=7.5, 1.7, 0.4 Hz, 1H), 7.65 (dd, J=8.0, 1.7 Hz, 1H), 7.61 (ddd, J=8.2, 7.2, 1.8 Hz, 1H), 7.41 (dd, J=7.8, 1.6 Hz, 1H), 7.37 (ddd, J=8.2, 1.0, 0.4 Hz, 1H), 7.34-7.24 (m, 3H), 4.83 (d, J=2.3 Hz, 2H), 3.31 (t, J=2.3 Hz, 1H). MS (m/z): 250.0 (M+H)

Step 2: methyl 4-(3-(11-oxodibenzo[b,f][1,4]oxazepin-10(11H)-yl)prop-1-ynyl)benzoate (435)

The title compound 434 (0.310 g, 1.24 mmol) and the methyl 4-iodobenzoate (0.390 g, 1.48 mmol) were stirred in acetonitrile (10.0 mL). Copper iodide (24 mg, 0.124 mmol) and dichlorobis(triphenylphosphine)palladium (87 mg, 0.124 mmol) were added followed by triethylamine (0.44 mL, 3.11 mmol). The reaction mixture was stirred at room temperature for 4 hours. The mixture was poor into ethyl acetate and the organic layer was washed with water and brine, dried over sodium sulfate, filtered and evaporated. The crude was purified by flash chromatography (10-30% ethyl acetate in hexanes) to afford title compound 435 (285 mg, 60%) as a light brown solid. MS (m/z): 384.3 (M+H).

Step 3: N-hydroxy-4-(3-(11-oxodibenzo[b,f][1,4]oxazepin-10(11H)-yl)prop-1-ynyl)benzamide (436)

Using Procedure B-3 (Table 5) with compound 435 the title compound 436 was obtained (185 mg, 66%) as a white solid. $^1$H NMR (DMSO-d$_6$) δ (ppm): 11.30 (s, 1H), 9.11 (s, 1H), 7.79 (dd, J=8.0, 1.6 Hz, 1H), 7.74-7.72 (m, 3H), 7.64-7.59 (m, 1H), 7.47-7.26 (m, 7H), 5.11 (s, 2H) LRMS (ESI): (calc) 384.11. (found) 385.16 (MH)+

Scheme 75

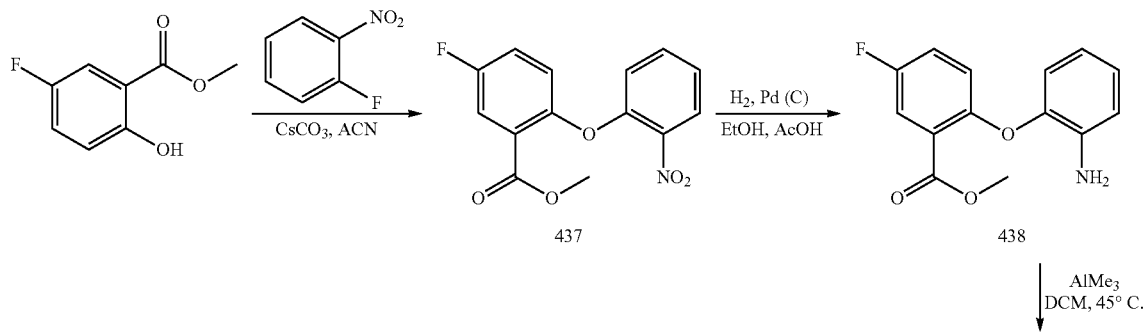

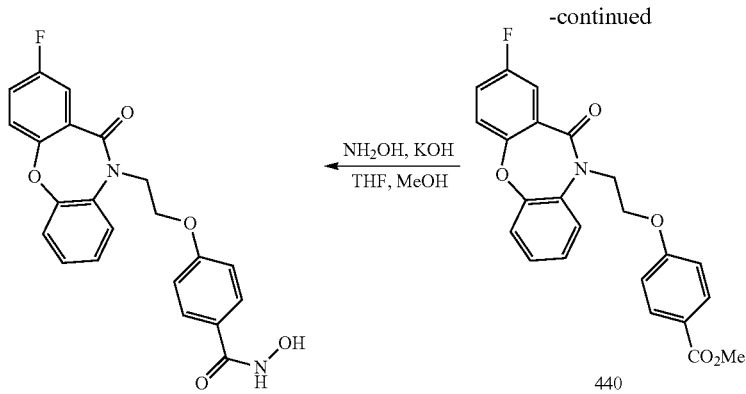

441: Example 225

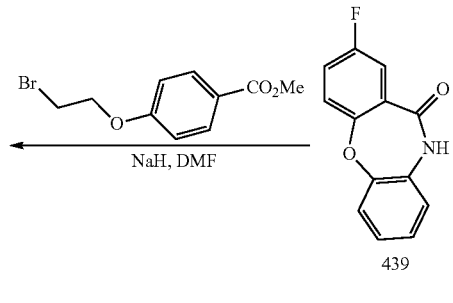

440

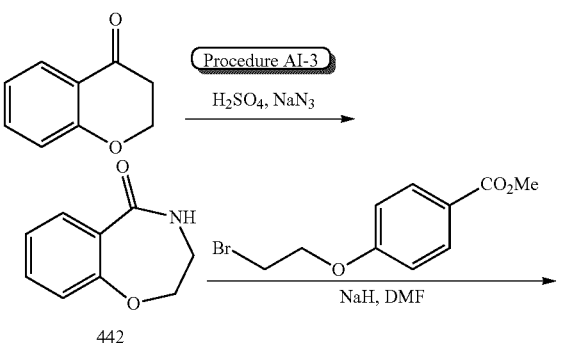

439

Example 225

4-(2-(2-fluoro-11-oxodibenzo[b,f][1,4]oxazepin-10 (11H)-yl)ethoxy)-N-hydroxybenzamide (441)

Step 1: methyl 5-fluoro-2-(2-nitrophenoxy)benzoate (437)

Using the procedure described in Scheme 71, step 1, with methyl 5-fluoro-2-hydroxybenzoate and 1-fluoro-2-nitrobenzene the title compound 437 was obtained (3.49 g, 84%) as a white solid. $^1$H NMR (DMSO-$d_6$) δ (ppm): 8.06 (dd, J=8.1, 1.7 Hz, 1H), 7.74 (dd, J=8.8, 3.3 Hz, 1H), 7.63-7.58 (m, 2H), 7.38 (dd, J=9.0, 4.5 Hz, 1H), 7.29 (ddd, J=8.3, 7.3, 1.1 Hz, 1H), 6.88 (dd, J=8.5, 1.0 Hz, 1H), 3.67 (s, 3H). MS (m/z): 292.2 (M+H).

Steps 2 and 3: 2-fluorodibenzo[b,f][1,4]oxazepin-11 (10H)-one (438 and 439)

Title compound 437 (3.48 g, 11.9 mmol) was dissolved in ethanol (30.0 mL), acetic acid (1.0 mL) and THF (10 mL). The palladium on charcoal was added and the reaction mixture was stirred under 1 atmosphere of hydrogen during 20 hours. The catalyst was filtered and the filtrate was evaporated. The residue was diluted in ether and the organic layer was washed with sodium bicarbonate saturated solution, water and brine then concentrated to afford title compound 438 (2.95 g, 95%) as a beige solid. MS (m/z): 262.3 (M+H).

The solid 438 (1.51 g, 5.78 mmol) was dissolved in dichloromethane (20.0 mL) and the mixture was cooled to 0° C. The trimethylaluminium (2M in tol., 3.2 mL, 6.38 mmol) was added drop wise. The reaction mixture was allowed to warm to room temperature then heated to 45° C. for 48 hours. The mixture was cooled down to room temperature and some water was added slowly. This mixture was diluted with dichloromethane. This organic layer was washed with 10% HCl (2 times), water and saturated aqueous solution of sodium bicarbonate, dried over sodium sulfate, filtered and evaporated. The crude was triturated in 30% ethyl acetate in hexanes to afford title compound 439 (1.05 g, 79%) as a white solid. $^1$H NMR (DMSO-$d_6$) δ (ppm): 10.68 (s, 1H), 7.51-7.46 (m, 2H), 7.44-7.39 (m, 1H), 7.34 (ddd, J=7.6, 1.5, 0.6 Hz, 1H), 7.22-7.12 (m, 3H). MS (m/z): 230.1 (M+H).

Step 4: methyl 4-(2-(2-fluoro-11-oxodibenzo[b,f][1, 4]oxazepin-10(11H)-yl)ethoxy)benzoate (440)

Using Procedure H-3 (Table 5) with compound 439 the title compound 440 was obtained (0.344 g, 64%) as a white foam. MS (m/z): 408.3 (M+H).

Step 5: 4-(2-(2-fluoro-11-oxodibenzo[b,f][1,4]oxazepin-10(11H)-yl)ethoxy)-N-hydroxybenzamide (441)

Using Procedure B-3 (Table 5) with compound 440 the title compound 441 was obtained (210 mg, 62%) as a white solid. $^1$H NMR (DMSO-$d_6$) δ (ppm): 11.05 (s, 1H), 8.90 (s, 1H), 7.70-7.65 (m, 3H), 7.49-7.38 (m, 4H), 7.33-7.23 (m, 2H), 6.89 (d, J=9.0 Hz, 2H), 4.45 (br s, 2H), 4.31 (t, J=5.2 Hz, 2H). MS (m/z): 409.3 (M+H).

Scheme 76

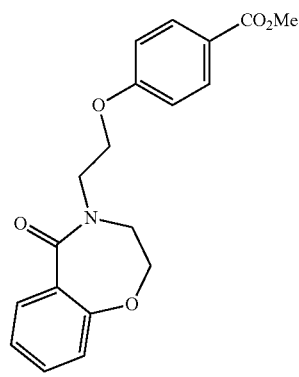

443

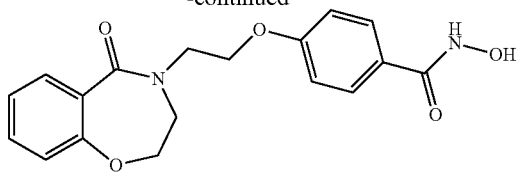

444: Example 226

Example 226

N-hydroxy-4-(2-(5-oxo-2,3-dihydrobenzo[f][1,4]oxazepin-4(5H)-yl)ethoxy)benzamide (444)

Step 1: 3,4-dihydrobenzo[f][1,4]oxazepin-5(2H)-one (442)

The chroman-4-one (5.0 g, 33.8 mmol) was dissolved in sulfuric acid (10 mL) and the mixture was cooled at 0° C. Sodium azide (2.88 g, 44.3 mmol) was added portionwise followed by some sulfuric acid (5 mL). The reaction mixture was stirred at room temperature over night. The mixture was then pour into ice-water and basified to pH=7 with potassium hydroxide pellets. This aqueous layer was extracted with ether (twice).

The combined organic layer was washed with water and brine, dried over magnesium sulfate, filtered and evaporated. The crude was purified by flash chromatography (50% to 100% ethyl acetate in hexanes) to afford title compound 442 (2.47 g, 45%) as a white solid. 1H NMR (DMSO-d6) δ (ppm): 8.33 (s, 1H), 7.76 (dd, J=7.8, 2.0 Hz, 1H), 7.45 (ddd, J=7.6, 7.2, 2.0 Hz, 1H), 7.12 (ddd, J=7.8, 7.2, 1.2 Hz, 1H), 7.01 (dd, J=8.3, 1.1 Hz, 1H), 4.27 (dd, J=5.4, 4.4 Hz, 2H), 3.30 (dd, J=9.5, 5.5 Hz, 2H). MS (m/z): 164.0 (M+H).

Step 2: methyl 4-(2-(5-oxo-2,3-dihydrobenzo[f][1,4]oxazepin-4(5H)-yl)ethoxy)benzoate (443)

Using Procedure H-3 (Table 5) with compound 442 the title compound 443 was obtained (300 mg, 59%) as a white solid. MS (m/z): 342.3 (M+H).

Step 3: N-hydroxy-4-(2-(5-oxo-2,3-dihydrobenzo[f][1,4]oxazepin-4(5H)-yl)ethoxy)benzamide (444)

Using Procedure B-3 (Table 5) with compound 443 the title compound 444 was obtained (256 mg, 87%) as a white solid. $^1$H NMR (DMSO-d$_6$) δ (ppm): 11.08 (s, 1H), 8.92 (s, 1H), 7.73 (d, J=8.8 Hz, 2H), 7.64 (dd, J=7.6, 1.6 Hz, 1H), 7.48-7.44 (m, 1H), 7.16 (td, J=7.6, 1.2 Hz, 1H), 7.05-7.01 (m, 3H), 4.36 (t, J=4.7 Hz, 2H), 4.23 (t, J=5.7 Hz, 2H), 3.92 (t, J=5.5 Hz, 2H), 3.64 (t, J=5.1 Hz, 2H). MS (m/z): 343.2 (M+H).

Scheme 77

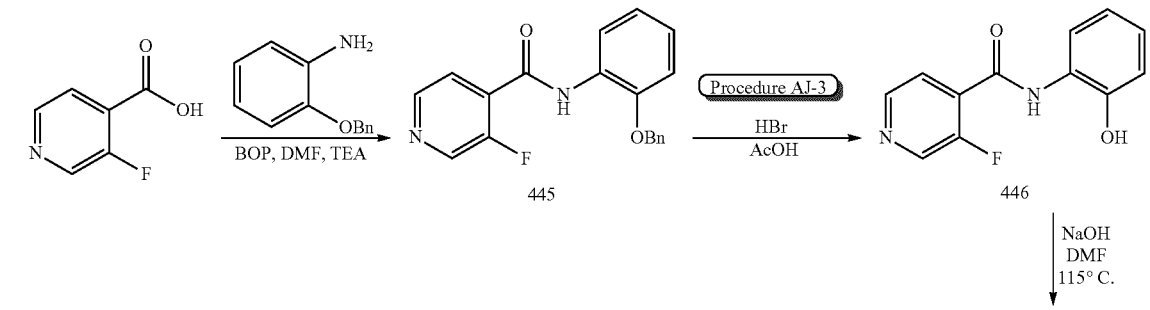

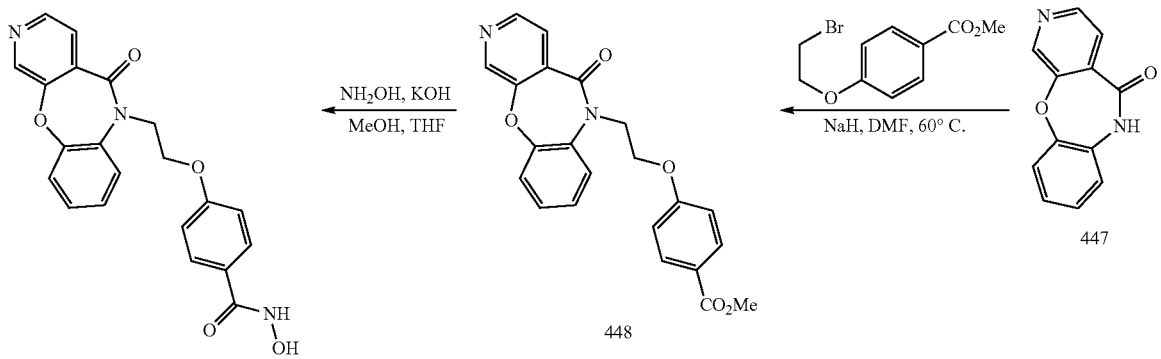

449: Example 227

Example 227

N-hydroxy-4-(2-(5-oxobenzo[b]pyrido[4,3-f][1,4]oxazepin-6(5H)-yl)ethoxy)benzamide (449)

Step 1:
N-(2-(benzyloxy)phenyl)-3-fluoroisonicotinamide (445)

Using Procedure S-3 (Table 5) with 3-fluoroisonicotinic acid and 2-(benzyloxy)aniline the title compound 96 was obtained (4.01 g, 88%) as a white solid. MS (m/z): 323.2 (M+H).

Step 2:
3-fluoro-N-(2-hydroxyphenyl)isonicotinamide (446)

Title compound 445 (1.99 g, 6.18 mmol) was dissolved in the solution of HBr (33% in AcOH, 15.0 mL) and acetic acid (10.0 mL). The reaction mixture was stirred at room temperature for 4 hours. The mixture was diluted with water and basified with solid sodium bicarbonate until alkaline. More water was added to dissolve the salt and the aqueous layer was extracted with ethyl acetate (twice). The combined organic layers were washed with water and brine, dried over sodium sulfate, filtered and evaporated. The residue was triturated in 30% ethyl acetate in hexanes to afford title compound 446 (1.21 g, 84%) as a beige-yellow solid. $^1$H NMR (DMSO-$d_6$) δ (ppm): 10.02 (s, 1H), 9.75 (s, 1H), 8.75 (d, J=2.0 Hz, 1H), 8.59 (dd, J=4.8, 1.3 Hz, 1H), 7.94 (dd, J=8.0, 1.6 Hz, 1H), 7.76 (dd, J=6.1, 4.9 Hz, 1H), 7.03 (ddd, J=8.0, 7.4, 1.6 Hz, 1H), 6.92 (dd, J=8.0, 1.4 Hz, 1H), 6.84 (td, J=7.6, 1.3 Hz, 1H). MS (m/z): 233.2 (M+H).

Step 3:
benzo[b]pyrido[4,3-f][1,4]oxazepin-5(6H)-one (447)

Using Procedure AG-3 (Table 5) with compound 446 the title compound 447 was obtained (940 mg, 93%) as beige solid. MS (m/z): 213.1 (M+H).

Step 4: methyl 4-(2-(5-oxobenzo[b]pyrido[4,3-f][1,4]oxazepin-6(5H)-yl)ethoxy)benzoate (448)

Using Procedure H-3 (Table 5) with compound 447 the title compound 448 was obtained (530 mg, 63%) as a white solid. MS (m/z): 391.3 (M+H).

Step 5: N-hydroxy-4-(2-(5-oxobenzo[b]pyrido[4,3-f][1,4]oxazepin-6(5H)-yl)ethoxy)benzamide (449)

Using Procedure B-3 (Table 5) with compound 448 the title compound 449 was obtained (35 mg, 26%) as a white solid. $^1$H NMR (DMSO-$d_6$) δ (ppm): 11.06 (s, 1H), 8.92 (s, 1H), 8.71 (s, 1H), 8.54 (d, J=4.8 Hz, 1H), 7.72 (dd, J=8.4, 1.8 Hz, 1H), 7.69-7.66 (m, 3H), 7.44 (dd, J=8.0, 1.8 Hz, 1H), 7.35-7.26 (m, 2H), 6.89 (d, J=8.8 Hz, 2H), 4.48-4.47 (m, 2H), 4.32 (t, J=5.4 Hz, 2H). MS (m/z): 392.3 (M+H).

Scheme 78

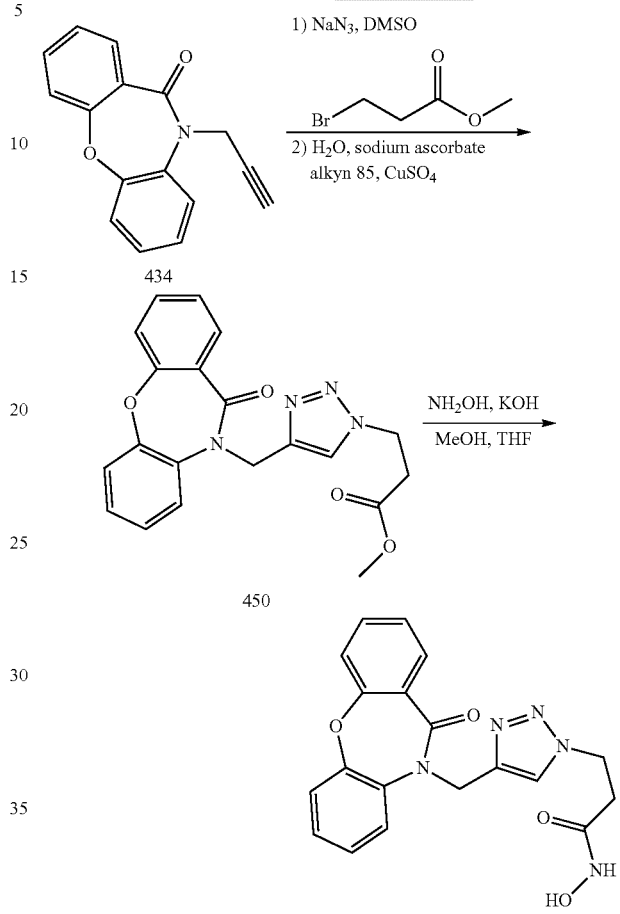

Example 228 methyl 3-(4-((11-oxodibenzo[b,f][1,4]oxazepin-10(11H)-yl)methyl)-1H-1,2,3-triazol-1-yl)propanoate (451)

Step 1: methyl 3-(4-((11-oxodibenzo[b,f][1,4]oxazepin-10(11H)-yl)methyl)-1H-1,2,3-triazol-1-yl)propanoate (450)

Methyl 3-bromopropanoate (0.227 g, 1.37 mmol) was dissolved in a solution of sodium azide in DMSO (0.5M, 2.7 mL, 1.37 mmol). The reaction mixture was stirred at room temperature for 3 hours. Water (3.0 mL), followed by sodium ascorbate (0.027 g, 0.137 mmol), followed by compound 434 (0.340 g, 1.37 mmol), followed by copper sulfate (1M, 0.27 mL, 0.274 mmol) were added. The reaction mixture was stirred at room temperature for 3 hours. The gummy solid formed was dissolved in a minimum of DCM and the mixture was pour into ethyl acetate (150 mL). The organic layer was washed with water (2 times) and brine, dried over sodium sulfate, filtered and evaporated. The crude was purified by flash chromatography (100% ethyl acetate) to afford title compound 450 (160 mg, 31%) as a colorless oil. MS (m/z): 379.3 (M+H).

351

Step 2: methyl 3-(4-((11-oxodibenzo[b,f][1,4]ox-azepin-10(11H)-yl)methyl)-1H-1,2,3-triazol-1-yl) propanoate (451)

Using Procedure B-3 (Table 5) with compound 450 the title compound 451 was obtained (44 mg, 28%) as a white solid. $^1$H NMR (CD$_3$OD) δ (ppm): 7.97 (s, 1H), 7.79 (dd, J=8.4, 1.8 Hz, 1H), 7.68-7.65 (m, 1H), 7.56-7.52 (m, 1H), 7.32-7.20 (m, 5H), 5.28 (s, 2H), 4.69 (t, J=6.8 Hz, 2H), 2.71 (t, J=6.8 Hz, 2H). MS (m/z): 380.3 (M+H).

Scheme 79

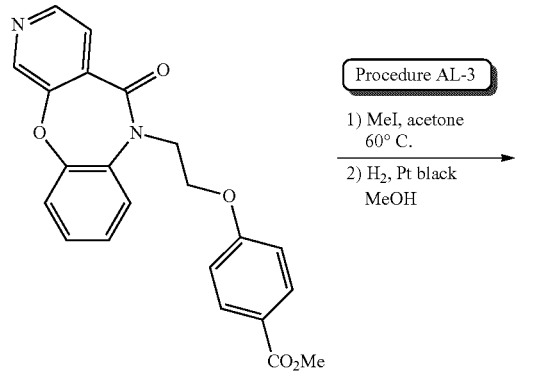

448

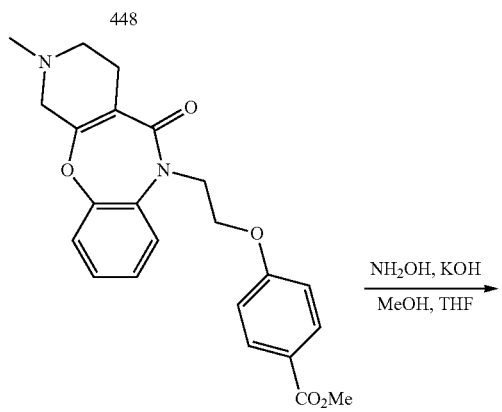

452

352

Example 229

N-hydroxy-4-(2-(2-methyl-5-oxo-1,2,3,4-tetrahydrobenzo[b]pyrido[4,3-f][1,4]oxazepin-6(5H)-yl) ethoxy)benzamide (453)

Step 1: methyl 4-(2-(2-methyl-5-oxo-1,2,3,4-tetrahydrobenzo[b]pyrido[4,3-f][1,4]oxazepin-6(5H)-yl) ethoxy)benzoate (452)

Title compound 448 (0.249 g, 0.638 mmol) was solubilized in acetone (15.0 mL) and the methyl iodide (2.0 mL) was added. The reaction mixture was stirred in a sealed tube at 60° C. for 18 hours. The mixture was cooled down and evaporated. The residue was dissolved in methanol (15 mL) and Pt black (55 mg) was added. The reaction mixture was stirred over 55PSI of hydrogen for 3 hours. The catalyst was filtered and the filtrate was evaporated. The crude was purified by flash chromatography (75-100% ethyl acetate in hexanes with 1.5% of ammonium hydroxide) to afford title compound 452 (133 mg, 51%). $^1$H NMR (DMSO-d$_6$) δ (ppm): 7.89 (d, J=8.2 Hz, 2H), 7.54 (d, J=8.0 Hz, 1H), 7.26 (t, J=7.7 Hz, 1H), 7.19 (t, J=7.7 Hz, 1H), 7.07 (dd, J=7.4, 1.2 Hz, 1H), 6.88 (d, J=8.2 Hz, 2H), 4.38 (t, J=4.9 Hz, 2H), 4.31 (t, J=4.9 Hz, 2H), 3.84 (s, 3H), 3.17 (s, 2H), 2.52-2.51 (m, 2H), 2.44 (m, 2H), 2.36 (s, 3H). MS (m/z): 409.4 (M+H).

Step 2: N-hydroxy-4-(2-(2-methyl-5-oxo-1,2,3,4-tetrahydrobenzo[b]pyrido[4,3-f][1,4]oxazepin-6 (5H)-yl)ethoxy)benzamide (453)

Using Procedure B-3 (Table 5) with compound 452 the title compound 453 was obtained (45 mg, 36%) as a white solid. $^1$H NMR (CD$_3$OD) δ (ppm): 7.65 (d, J=8.8 Hz, 2H), 7.55 (dd, J=8.0, 1.2 Hz, 1H), 7.27 (td, J=7.6, 1.6 Hz, 1H), 7.20 (td, J=8.0, 1.6 Hz, 1H), 7.10 (dd, J=8.0, 1.6 Hz, 1H), 6.87 (d, J=8.8 Hz, 2H), 4.38 (t, J=5.2 Hz, 2H), 4.30 (t, J=5.2 Hz, 2H), 3.34-3.33 (m, 2H), 2.68 (t, J=5.8 Hz, 2H), 2.48 (br s, 5H). MS (m/z): 410.4 (M+H).

Scheme 80

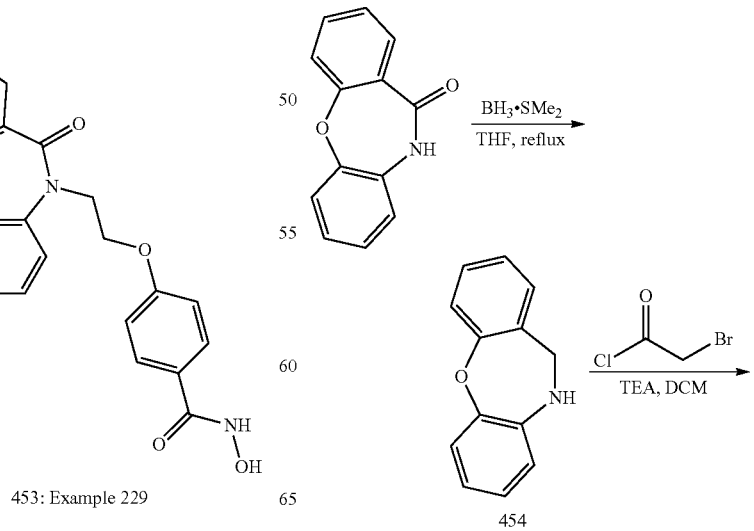

453: Example 229

353

-continued

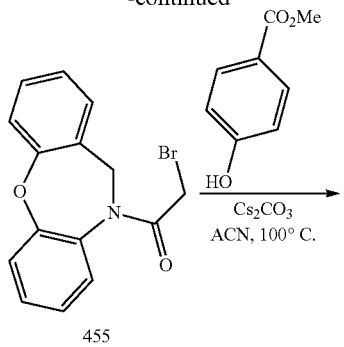

354

Step 3: methyl 4-(2-(dibenzo[b,f][1,4]oxazepin-10(11H)-yl)-2-oxoethoxy)benzoate (456)

Title compound 455 (0.890 g, 2.81 mmol) and the methyl 4-hydroxybenzoate (0.512 g, 3.37 mmol) were dissolved in acetonitrile (10.0 mL) and the cesium carbonate (1.83 g, 5.62 mmol) was added. The reaction mixture was stirred at 100° C. in a sealed tube for 4 hours. The mixture was cooled down to room temperature and diluted with ethyl acetate. The organic layer was washed with water (2 times) and brine, dried over sodium sulfate, filtered and evaporated. The crude was purified by flash chromatography (30-40% ethyl acetate in hexanes) to afford title compound 456 (355 mg, 32%) as white foam. MS (m/z): 390.3 (M+H).

Step 4: 4-(2-(dibenzo[b,f][1,4]oxazepin-10(11H)-yl)-2-oxoethoxy)-N-hydroxybenzamide (457)

Using Procedure B-3 (Table 5) with compound 456 the title compound 457w as obtained (305 mg, 89%) as a white solid. $^1$H NMR (DMSO-$d_6$) δ (ppm): 11.03 (s, 1H), 8.90 (s, 1H), 7.70 (d, J=7.6 Hz, 1H), 7.59 (d, J=8.8 Hz, 2H), 7.47-7.41 (m, 2H), 7.30-7.22 (m, 4H), 7.10-7.06 (m, 1H), 6.75 (d, J=8.8 Hz, 2H), 5.01-4.66 (m, 4H). MS (m/z): 391.1 (M+H).

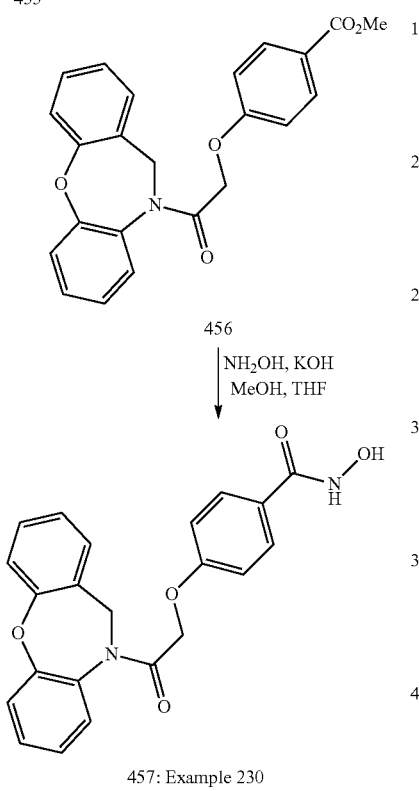

Example 230

4-(2-(dibenzo[b,f][1,4]oxazepin-10(11H)-yl)-2-oxo-ethoxy)-N-hydroxybenzamide (457)

Step 1: 10,11-dihydrodibenzo[b,f][1,4]oxazepine (454)

Using Procedure Z-3 (Table 5) with dibenzo[b,f][1,4]oxazepin-11(10H)-one the title compound 454 was obtained (2.075 g, 100%) as beige solid. $^1$H NMR (CD$_3$OD) δ (ppm): 7.29-7.19 (m, 2H), 7.16-7.04 (m, 2H), 7.01-6.99 (m, 1H), 6.82-6.78 (m, 1H), 6.63-6.59 (m, 2H), 4.88 (s, 1H), 4.39 (s, 2H). MS (m/z): 198.1 (M+H).

Step 2: 2-bromo-1-(dibenzo[b,f][1,4]oxazepin-10(11H)-yl)ethanone (455)

Using Procedure S-3 (Table 5) with compound 454 the title compound 455 was obtained (900 mg, 88%) as brown oil. MS (m/z): 318.1 (M+H).

Scheme 81

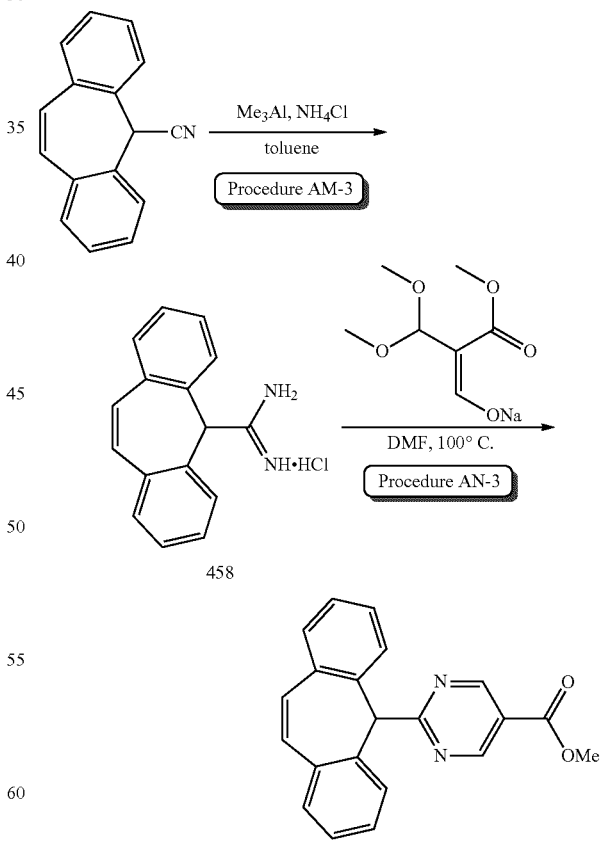

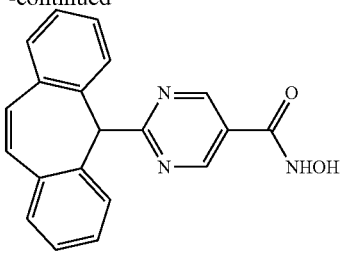

460: Example 231

Example 231

Compound (460)

Step 1: Compound (458)

To a suspension of ammonium chloride (0.976 g, 18.242 mmol) in toluene (2.5 mL) was added trimethylaluminium (2M in toluene, 9.1 mL, 18.242 mmol). This mixture was stirred for 1 hour and then added to a solution of the cyano compound (2.000 g, 9.121 mmol) in toluene (2.5 mL). The reaction mixture was heated at 80° C. for 3 hours. The mixture was cooled down to room temperature and poured into a suspension of $SiO_2$ in chloroform. The mixture was stirred for 5 minutes, filtered and washed with methanol (100 mL). The filtrate was evaporated to afford title compound 458 (2.3 g, 100%) as beige solid. MS (m/z): 236.2 (M+2H).

Step 2: Compound (459)

Title compound 458 (0.500 g, 1.833 mmol), sodium (Z)-2-(dimethoxymethyl)-3-methoxy-3-oxoprop-1-en-1-olate (0.418 g, 2.108 mmol) and dimethylformamide (4 mL) were combined and stirred at 100° C. for 1 hour. Water was added and the precipitate was filtered. The solid was purified by flash chromatography (0-30% ethyl acetate in hexanes) to afford title compound 459 (200 mg, 34%) as a white solid. $^1$H NMR (CDCl$_3$) δ (ppm): 8.77 (s, 2H), 7.51-7.36 (m, 8H), 6.92 (s, 2H), 3.83 (s, 3H). MS (m/z): 330.2 (M+H).

Step 3: Compound (460)

Using Procedure B-3 (Table 5) with compound 459 the title compound 460 was obtained (240 mg, 136%) as a white solid. $^1$H NMR (DMSO-d$_6$) δ (ppm): 11.06 (s, 1H), 9.06 (s, 1H), 8.59 (s, 2H), 7.58-7.47 (m, 6H), 7.40-7.31 (m, 2H), 7.01 (s, 2H).

Scheme 82

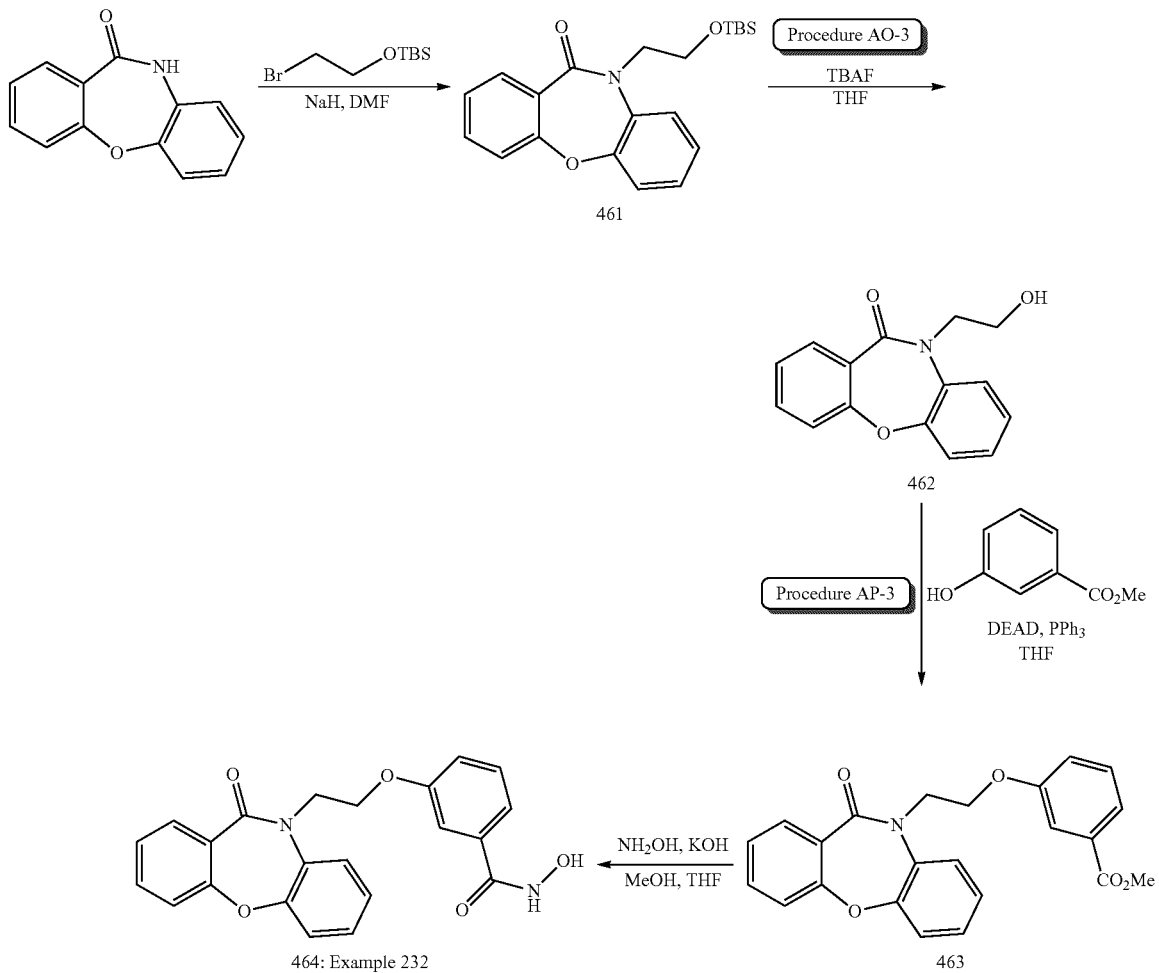

Example 232

N-hydroxy-3-(2-(11-oxodibenzo[b,f][1,4]oxazepin-10(11H)-yl)ethoxy)benzamide (464)

Step 1: 10-(2-(tert-butyldimethylsilyloxy)ethyl)dibenzo[b,f][1,4]oxazepin-11(10H)-one (461)

Using Procedure H-3 (Table 5) with dibenzo[b,f][1,4]oxazepin-11(10H)-one and (2-bromoethoxy)(tert-butyl)dimethylsilane the title compound 461 was obtained (4.35 g, 100%) as a colorless oil. MS (m/z): 370.4 (M+H).

Step 2: 10-(2-hydroxyethyl)dibenzo[b,f][1,4]oxazepin-11(10H)-one (462)

Title compound 461 (4.29 g, 11.6 mmol) was dissolved in THF (30.0 mL) and tetrabutylammonium fluoride (1M in THF, 13.4 mL, 13.4 mmol) was added. The reaction mixture was stirred at room temperature for 1 hour. The mixture was evaporated to ⅓ of the volume and then poured in ether. The organic layer was washed with water and brine, dried over sodium sulfate, filtered and evaporated. The crude was purified by flash chromatography (50-70% ethyl acetate in hexanes) to afford title compound 462 (2.51 g, 85%) as a white solid. MS (m/z): 256.1 (M+H).

Step 3: methyl 3-(2-(11-oxodibenzo[b,f][1,4]oxazepin-10(11H)-yl)ethoxy)benzoate (463)

Title compound 462 (0.300 g, 1.18 mmol), methyl 3-hydroxybenzoate (0.179 g, 1.18 mmol) and triphenylphosphine (0.401 g, 1.53 mmol) were dissolved in THF (5 mL) then diethylazodicarboxylate (0.222 mL, 1.41 mmol) was added. The reaction mixture was stirred at room temperature for 3 hours. The solvent was evaporated to provide title compound 463.

Step 4: N-hydroxy-3-(2-(11-oxodibenzo[b,f][1,4]oxazepin-10(11H)-yl)ethoxy)benzamide (464)

Using Procedure B-3 (Table 5) with compound 463 the title compound 464 was obtained (18 gm, 11%) as a white solid. $^1$H NMR (CD$_3$OD) δ (ppm): 7.77 (dd, J=8.0, 1.8 Hz, 1H), 7.67 (dd, J=7.8, 1.8 Hz, 1H), 7.58-7.53 (m, 1H), 7.38-7.22 (m, 8H), 7.09-7.04 (m, 1H), 4.59-4.51 (br s, 2H), 4.42 (t, J=5.3 Hz, 2H). MS (m/z): 389.2 (M–H).

Scheme 83

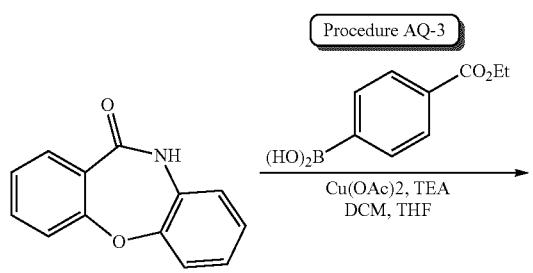

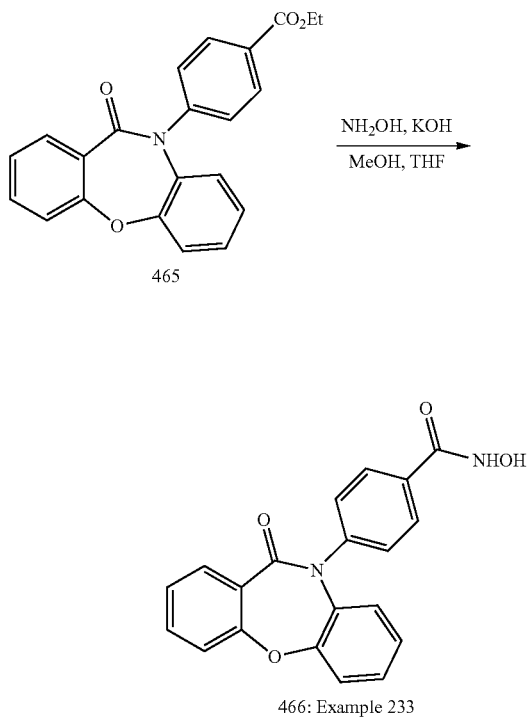

Example 233

N-hydroxy-4-(11-oxodibenzo[b,f][1,4]oxazepin-10(11H)-yl)benzamide (466)

Step 1: ethyl 4-(11-oxodibenzo[b,f][1,4]oxazepin-10(11H)-yl)benzoate (465)

To a suspension of dibenzo[b,f][1,4]oxazepin-11(10H)-one (0.623 g, 2.95 mmol) in THF (10.0 mL), dichloromethane (10.0 mL) and triethylamine (2.0 mL, 14.7 mmol) was added diacetoxycopper (0.587 g, 3.25 mmol) followed by 4-(ethoxycarbonyl)phenylboronic acid (1.15 g, 5.91 mmol). The reaction mixture was stirred at room temperature for 5 days. It was diluted with ethyl acetate and this organic layer was washed with 10% HCl (2 times), water and brine, dried over sodium sulfate, filtered and evaporated. The crude was purified by flash chromatography (a 1$^{st}$ one with 20% ethyl acetate in hexanes and second one with 0.5% methanol in dichloromethane) to afford title compound 465 (248 mg, 23%) as a white solid. MS (m/z): 360.3 (M+H).

Step 2: N-hydroxy-4-(11-oxodibenzo[b,f][1,4]oxazepin-10(11H)-yl)benzamide (466)

Using Procedure B-3 (Table 5) with compound 465 the title compound 466 was obtained (40 mg, 17%) as a pink solid. $^1$H NMR (DMSO-d$_6$) δ (ppm): 11.33 (s, 1H), 9.14 (s, 1H), 7.87 (d, J=8.8 Hz, 2H), 7.81 (dd, J=8.0, 2.0 Hz, 1H), 7.66-7.62 (m, 1H), 7.51-7.43 (m, 4H), 7.36 (td, J=7.8, 0.8 Hz, 1H), 7.22 (td, J=7.4, 1.6 Hz, 1H), 7.11 (td, J=7.8, 1.6 Hz, 1H), 6.76 (dd, J=8.0, 1.6 Hz, 1H). MS (m/z): 347.2 (M+H).

Scheme 84

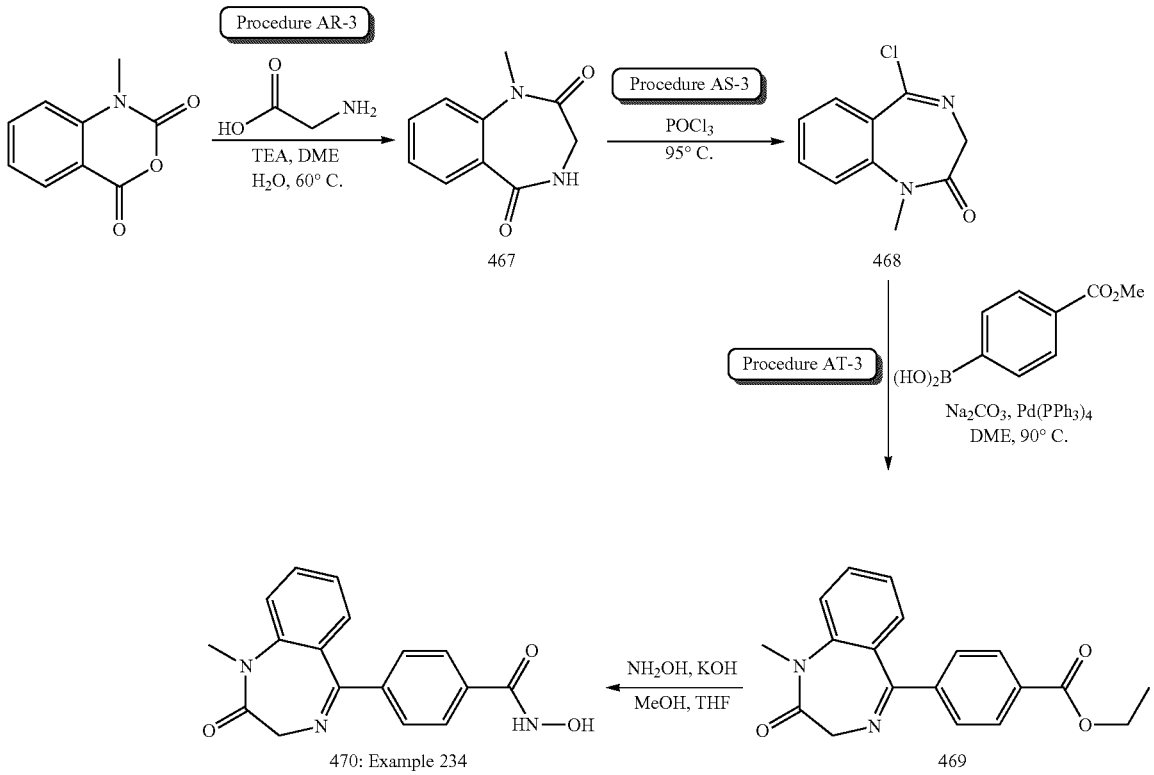

Example 234

(Z)—N-hydroxy-4-(1-methyl-2-oxo-2,3-dihydro-1H-benzo[e][1,4]diazepin-5-yl)benzamide (470)

Step 1: 1-methyl-3,4-dihydro-1H-benzo[e][1,4]diazepine-2,5-dione (467)

1-Methyl-1H-benzo[d][1,3]oxazine-2,4-dione (11.0 g, 62.1 mmol) and 2-aminoacetic acid (5.13 g, 68.3 mmol) were dissolved in DME (60 mL) and water (20 mL) and triethylamine was added. The reaction mixture was stirred at 60° C. for 4 hours. The mixture was concentrated in vacuo to get a light tan heavy oily residue that was dissolved in acetic acid (75 mL). This mixture was refluxed 4 hours then cooled down to room temperature. The solvent was evaporated to get a tan heavy oil. The oil was allowed to stand at room temperature overnight in ether (50 mL). The beige crystalline solid was filtered and washed with ether. The solid was then triturated in ether to afford title compound 467 (7.95 g, 67%) as a beige crystalline solid. $^1$H NMR (DMSO-$d_6$) δ (ppm): 8.70 (s, 1H), 7.70 (d, J=7.6 Hz, 1H), 7.60 (t, J=7.2 Hz, 1H), 7.42 (d, J=8.0 Hz, 1H), 7.32 (t, J=7.5 Hz, 1H), 3.75-3.72 (m, 1H), 3.51-3.46 (m, 1H), 3.28 (s, 3H). MS (ESI): 190.90 (MH)+

Step 2: (E)-5-chloro-1-methyl-1H-benzo[e][1,4]diazepin-2(3H)-one (468)

The title compound 467 (1.54 g, 8.10 mmol) was heated in phosphorus oxychloride (15 mL) at 95° C. for 2 hours. The reaction mixture was then cooled to room temperature and excess of phosphorus oxychloride was removed under reduced pressure. The black oil was dissolved in ethyl acetate and the organic phase was washed with sodium bicarbonate (saturated solution) and brine, dried over sodium sulfate, filtered and concentrated to afford crude title compound 468 that was used as such for the next step. MS (ESI): 209.12 (MH)+.

Step 3: (Z)-ethyl 4-(1-methyl-2-oxo-2,3-dihydro-1H-benzo[e][1,4]diazepin-5-yl)benzoate (469)

Title compound 468 (1.69 g, 8.10 mmol) was dissolve in DME (50 mL) and 4-(methoxycarbonyl)phenylboronic acid (1.47 g, 7.58 mmol) was added followed by tetrakis(triphenylphosphine)palladium (0) (0.301 g, 0.260 mmol) and then sodium carbonate (2M in water, 12 mL, 24.00 mmol). The reaction mixture was stirred at 90° C. for 1 h, cooled at room temperature and poured into ethyl acetate. The organic layer was washed with water and brine, dried over sodium sulfate, filtered and concentrated. The crude was purified by flash chromatography (10% ethyl acetate in hexanes) to afford title compound 469 (1.41 g, 54%) as a red foam. MS (ESI): 323.42 (MH)+.

Step 4: (Z)—N-hydroxy-4-(1-methyl-2-oxo-2,3-dihydro-1H-benzo[e][1,4]diazepin-5-yl)benzamide (470)

Using Procedure B-3 (Table 5) with compound 469 the title compound 470 was obtained (323 mg, 24%) as a pink solid. $^1$H NMR (DMSO-$d_6$) δ (ppm): 11.33 (s, 1H), 9.12 (s, 1H), 7.81 (d, J=8.4 Hz, 2H), 7.69-7.65 (m, 1H), 7.62-7.58 (m, 3H), 7.31-7.23 (m, 2H), 4.59 (d, J=10.4 Hz, 1H), 3.76 (d, J=10.4 Hz, 1H), 3.32 (s, 3H). MS (m/z): 310.3 (M+H).

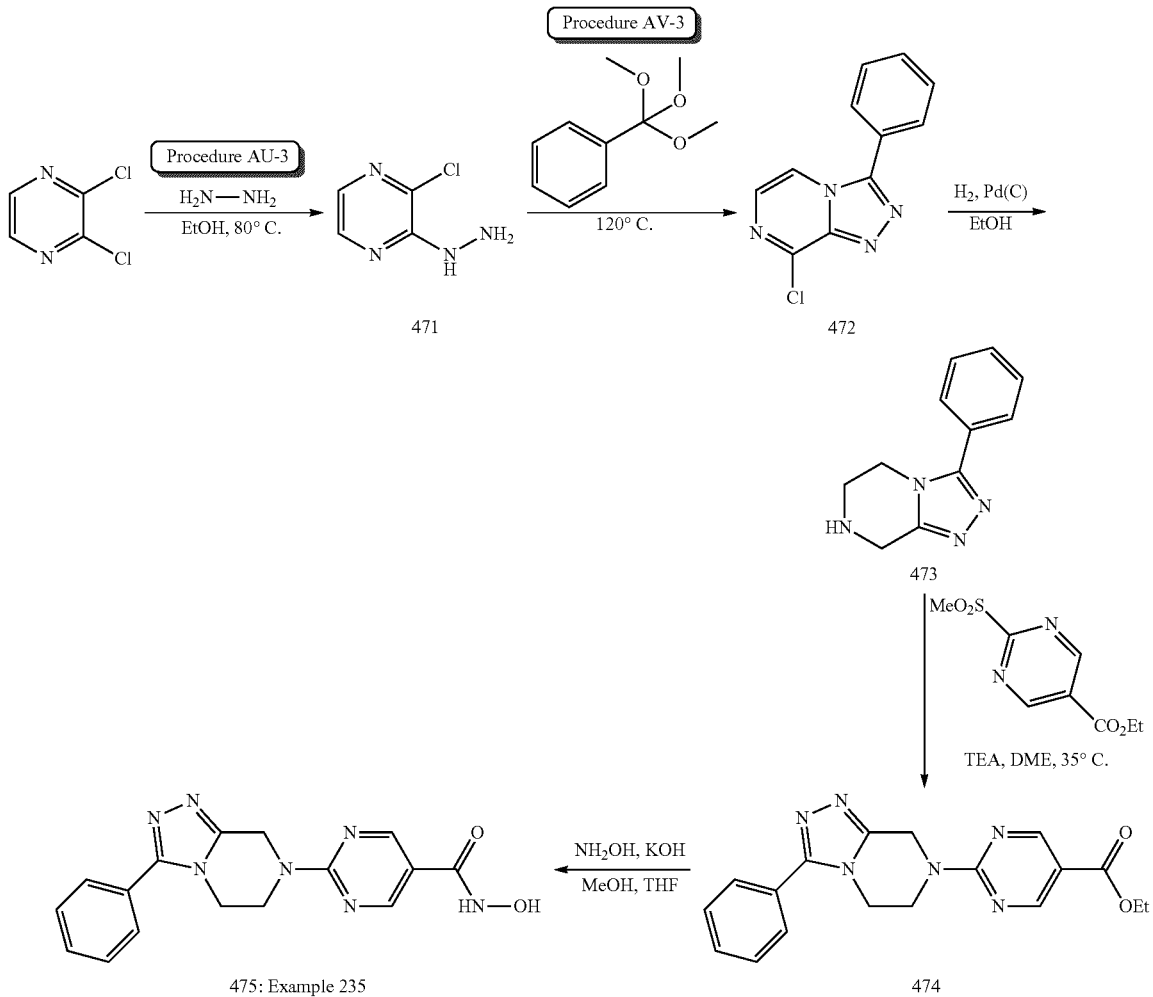

Example 235

N-hydroxy-2-(3-phenyl-5,6-dihydro-[1,2,4]triazolo[4,3-a]pyrazin-7(8H)-yl)pyrimidine-5-carboxamide (475)

Step 1: 2-chloro-3-hydrazinylpyrazine (471)

2,3-Dichloropyrazine (2 g, 13.42 mmol), hydrazine (1.324 g, 26.8 mmol) and ethanol (40 ml) were combined and the reaction mixture was stirred at 80° C. for 1.5 h. The mixture was cooled to room temperature and the yellow flakes were filtered off. The solid was washed with a small amount of water and dried. The mother liquor was concentrated to afford a yellow solid triturated with a small amount of water and dried. The 2 solids were combined to afford title product 471 (1.15 g, 59%) as yellow solid. MS (m/z): 145.0 (M+H).

Step 2: 8-chloro-3-phenyl-[1,2,4]triazolo[4,3-a]pyrazine (472)

Title compound 471 (0.8 g, 5.53 mmol) and Trimethyl orthobenzoate (5 mL, 29.1 mmol) were combined and the reaction mixture was stirred at 120° C. for 3 h. The mixture was cooled to room temperature and the solid was filtered and washed with hexanes to afford title compound 472 (1.35 g, 100%) as a beige solid. MS (m/z): 231.1 (M+H)

Step 3: 3-phenyl-5,6,7,8-tetrahydro-[1,2,4]-triazolo[4,3-a]pyrazine (473)

Title compound 472 (310 mg, 1.34 mmol) was dissolved in EtOH (25 mL) and 10% Pd/C (75 mg, 25% w/w) was added. The reaction mixture was stirred under 1 atmosphere of hydrogen over night. The catalyst was filtered and the filtrate was evaporated to afford title compound 473 (269 mg, 100%). MS (m/z): 201.1 (M+H).

Step 4: ethyl 2-(3-phenyl-5,6-dihydro-[1,2,4]triazolo[4,3-a]pyrazin-7(8H)-yl)pyrimidine-5-carboxylate (474)

Using Procedure Y-3 (Table 5) with compound 473 the title compound 474 was obtained (85 mg, 18%) as a clear oil. MS (m/z): 353.5 (M+3).

Step 5: N-hydroxy-2-(3-phenyl-5,6-dihydro-[1,2,4]triazolo[4,3-a]pyrazin-7(8H)-yl)pyrimidine-5-carboxamide (475)

Using Procedure B-3 (Table 5) with compound 474 the title compound 475 was obtained (85 mg, 93%) as a white solid. $^1$H NMR (DMSO-$d_6$) δ (ppm): 11.19 (s, 1H), 9.09 (s, 1H), 8.79 (s, 2H), 7.78-7.77 (m, 2H), 7.76-7.75 (m, 3H), 5.20-5.15 (m, 2H), 4.35-4.20 (m, 4H). MS (m/z): 338.4 (M+H).

poured over water. The aqueous was basified with conc. NH$_4$OH (exotherm) at 0° C. Water was added until everything was dissolved. The mixture was extracted with ethyl acetate (×4). The organics were washed with brine, died over Na$_2$SO$_4$, filtered and concentrated to a brown paste. The residue was purified by flash chromatography (0% to 70% ethyl acetate in hexanes) to afford title compound 478 (0.9 g, 32%) as a brown solid. MS (m/z): 189.1 (M+H).

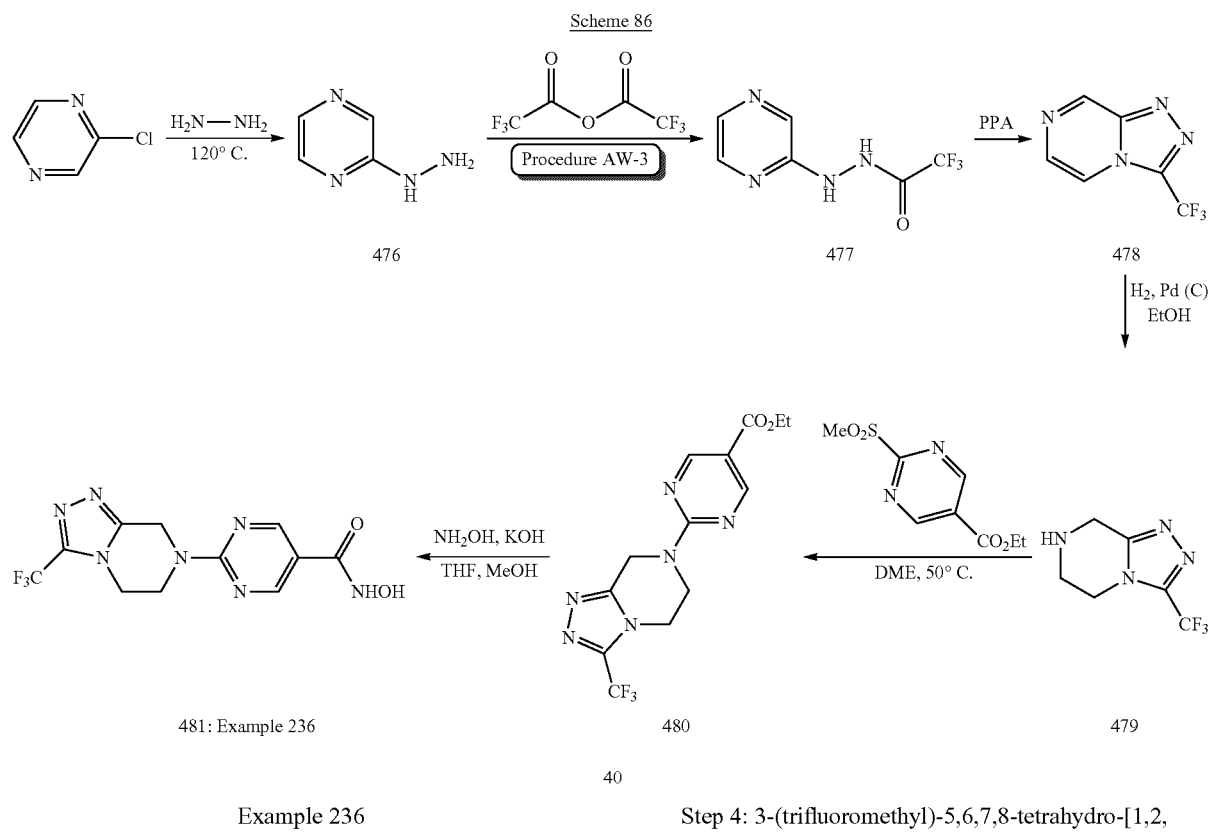

Scheme 86

Example 236

N-hydroxy-2-(3-(trifluoromethyl)-5,6-dihydro-[1,2,4]triazolo[4,3-a]pyrazin-7(8H)-yl)pyrimidine-5-carboxamide (481)

Step 1: 2-hydrazinylpyrazine (476)

Using Procedure AU-3 (Table 5) with 2-chloropyrazine the title compound 476 was obtained (4.4 g, 46%) as a yellow solid. MS (m/z): 111.0 (M+H).

Step 2: 2,2,2-trifluoro-N'-(pyrazin-2-yl)acetohydrazide (477)

In a 100 ml RB, trifluoroacetic anhydride (15 mL, 106 mmol) was added slowly to title compound 476 (1.7 g, 15.44 mmol) at 0° C. (exotherm). The mixture was stirred at room temperature for 2 h then concentrated to give compound 477 as a red paste that was used crude for next step (>3.5 g).

Step 3: 3-(trifluoromethyl)-[1,2,4]-triazolo[4,3-a]pyrazine (478)

To title compound 477 (3.12 g, 15.14 mmol) was added PPA (15 mL). The mixture was heated to 150° C. for 1 h then

Step 4: 3-(trifluoromethyl)-5,6,7,8-tetrahydro-[1,2,4]-triazolo[4,3-a]pyrazine (479)

Using Procedure G-3 (Table 5) with compound 478 the title compound 479 (crude) was obtained (130 mg, 89%) as a brown oil. MS (m/z): 193.1 (M+H).

Step 5: ethyl 2-(3-(trifluoromethyl)-5,6-dihydro-[1,2,4]-triazolo[4,3-a]pyrazin-7(8H)-yl)pyrimidine-5-carboxylate (480)

Using Procedure Y-3 (Table 5) with compound 479 the title compound 480 was obtained (550 mg, 49%) as a beige solid. MS (m/z): 343.4 (M+H).

Step 6: N-hydroxy-2-(3-(trifluoromethyl)-5,6-dihydro-[1,2,4]-triazolo[4,3-a]pyrazin-7(8H)-yl)pyrimidine-5-carboxamide (481)

Using Procedure B-3 (Table 5) with compound 480 the title compound 481 was obtained (198 mg, 59%) as a white solid. $^1$H NMR (DMSO-$d_6$) δ (ppm): 11.19 (s, 1H), 9.10 (s, 1H), 8.77 (s, 2H), 5.20 (s, 2H), 4.32 (t, J=5.1 Hz, 2H), 4.25 (t, J=4.9 Hz, 2H). MS (m/z): 330.2 (M+H).

Scheme 87

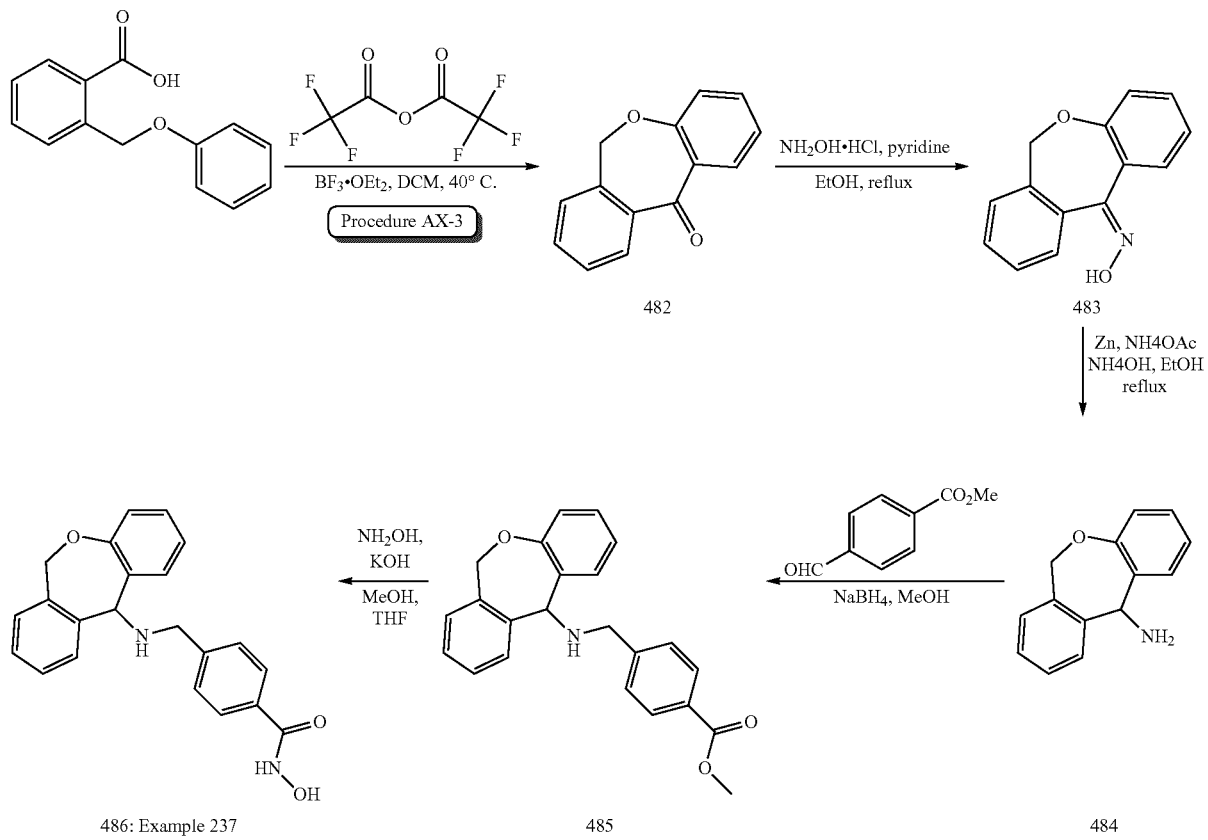

Example 237

4-((6,11-dihydrodibenzo[b, e]oxepin-11-ylamino)methyl)-N-hydroxybenzamide (486)

Step 1: dibenzo[b,e]oxepin-11(6H)-one (482)

The 2-(phenoxymethyl)benzoic acid (22.18 g, 97 mmol) was dissolved in DCM (200 mL) and trifluoroacetic anhydride (20.59 mL, 146 mmol) was added, followed by a catalytic amount of borontrifluoride etherate (2.22 mL, 17.5 mmol). The reaction mixture was heated at 40° C. for 2 hours. The solution was then washed with water, sodium bicarbonate (saturated solution) and water. The organic phases was dried over sodium sulfate, filtered and concentrated under reduced pressure. The crude product was purified on silica gel (10-20% ethyl acetate in hexanes) to afford title compound 482 (19.937 g, 98%) as a light pink solid. MS (m/z): 211.1 (M+H).

Step 2: (E)-dibenzo[b,e]oxepin-11(6H)-one oxime (483)

Using Procedure K-3 (Table 5) with compound 482 the title compound 483 was obtained (4.458 g, 40%) as a white solid. MS (m/z): 226.2 (M+H).

Step 3: 6,11-dihydrodibenzo[b,e]oxepin-11-amine (484)

Using Procedure M-3 (Table 5) with compound 483 the title compound 484 was obtained (2.87 g, 100%) as a yellow oil. MS (m/z): 212.2 (M+H).

Step 4: methyl 4-((6,11-dihydrodibenzo[b,e]oxepin-11-ylamino)methyl)benzoate (485)

Using Procedure A-3 (Table 5) with compound 484 the title compound 485 was obtained (1.436 g, 93%) as a yellow oil. $^1$H NMR (DMSO-$d_6$) δ (ppm): 7.89 (d, J=8.2 Hz, 2H), 7.44 (d, J=8.2 Hz, 2H), 7.37-7.14 (m, 5H), 6.93-6.78 (m, 2H), 6.44 (d, J=12.3 Hz, 1H), 4.91 (d, J=12.1 Hz, 1H), 4.65 (d, J=2.9 Hz, 1H), 3.83 (d, J=0.4 Hz, 3H), 3.69 (t, J=6.7 Hz, 2H), 3.19-3.14 (m, 1H). MS (m/z): 360.4 (M+H).

Step 5: 4-((6,11-dihydrodibenzo[b,e]oxepin-11-ylamino)methyl)-N-hydroxybenzamide (486)

Using Procedure B-3 (Table 5) with compound 485 the title compound 486 was obtained (56 m g, 4%) as a light pink solid. $^1$H NMR (DMSO-$d_6$) δ (ppm): 11.14 (s, 1H), 8.99 (s, 1H), 7.70-7.68 (d, J=7.6 Hz, 2H), 7.38-7.23 (m, 6H), 7.18-7.14 (m, 2H), 6.87 (t, J=7.0 Hz, 1H), 6.78 (d, J=7.6 Hz, 1H), 6.44 (d, J=12.4 Hz, 1H), 4.91 (d, J=12.4 Hz, 1H), 4.65 (d, J=2.8 Hz, 1H), 3.63 (d, J=5.6 Hz, 2H), 3.07 (br s, 1H). MS (m/z): 361.4 (M+H).

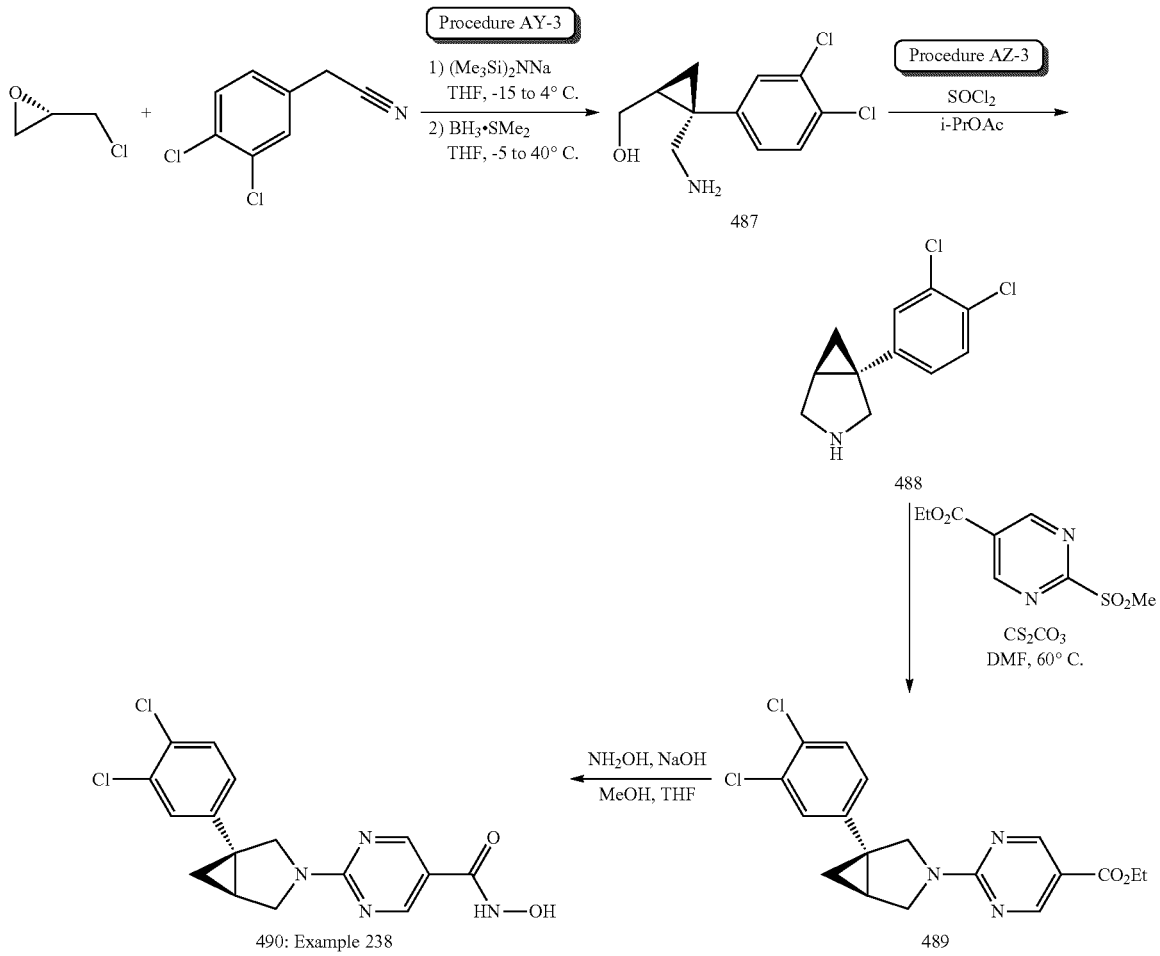

Example 238

2-((1R,5S)-1-(3,4-dichlorophenyl)-3-azabicyclo [3.1.0]hexan-3-yl)-N-hydroxypyrimidine-5-carboxamide (490)

Step 1: ((1S,2R)-2-(aminomethyl)-2-(3,4-dichlorophenyl)cyclopropyl)methanol (487)

To a solution of 2-(3,4-Dichlorophenyl)acetonitrile (3.5 g, 18.81 mmol) and (S)-(+)-Epichlorohydrin (1.877 ml, 23.99 mmol) in tetrahydrofuran (18.5 mL) at −15° C. (dry ice/ethanol/water bath, internal temp monitored with thermocouple) under atmosphere of N2 was added sodium bis(trimethylsilyl)amide (16.5 mL, 33.0 mmol) dropwise over 3 hours. The reaction mixture was stirred for additional 3 hours at −15° C., then, overnight at 4° C. (cold room). The mixture was cooled to −5° C. and borane-methyl sulfide complex (4.4 mL, 44.0 mmol) was added over 2 hours via syringe pump. The reaction mixture was then gradually warmed to 40° C. over 3 hours. After aging 1.5 hours at 40° C., the reaction mixture was cooled to 20-25° C. and slowly quenched into a 2N HCl solution (27.7 L). The quenched mixture was then stirred for 1 h at 40° C. Ammonium hydroxide concentrated (6.3 L) was added and the aqueous layer was discarded. i-PrOAc (18.5 L) and 5% dibasic sodium phosphate (18.5 L) were charged. The organic phase was then washed with saturated brine (18.5 L), dried over magnesium sulfate, filtered and evaporated to afford title compound 487 (4.63 g, 100%).

Step 2: (1R,5S)-1-(3,4-dichlorophenyl)-3-azabicyclo [3.1.0]hexane (488)

Title compound 487 (4.63 g, 18.81 mmol) was dissolved in isopropyl acetate (24.5 mL). The above crude amino alcohol solution in isopropyl acetate was slowly subsurface-added to a solution of thionyl chloride (1.61 ml, 22.06 mmol) in isopropyl acetate (17.5 mL) at ambient temperature over 2 hours. After aging additional 1-5 h, 5.0 N sodium hydroxide (16.4 mL) was added over 1 hour while the batch temperature was maintained at <30° C. with external cooling. The two-phase reaction mixture was stirred for 1 hour at ambient temperature to allow pH to stabilize (usually to 8.5-9.0) with sodium hydroxide pH titration. The organic phase was washed with 40% aqueous isopropanol (21 mL) followed by water (10.5 mL). Concentrated HCl (1.69 mL) was added. The aqueous isopropyl acetate was azeotropically concentrated in vacuum to ca. 24.5 mL. Methylcyclohexane (17.5 mL) was added dropwise over 2 hours. Compound did not crystallize out. The pH was adjusted to neutral and organic layer was separated. The organic layer was washed with water and brine, dried over magnesium sulfate, filtered and evaporated. The residue was purified by ISCO (EtOAc to 60% MeOH in EtOAc, 40 g silica column) to afford title compound 488 (1.8 g, 42%) as a thick yellow oil. ¹H NMR (CD₃OD) δ (ppm): 7.44 (d, J=8.4 Hz, 1H), 7.41 (d, J=2.2 Hz, 1H), 7.18 (dd, J=8.4, 2.2 Hz, 1H), 3.31-3.30 (m, 2H), 3.23-3.17 (m, 2H), 1.97-1.93 (m, 1H), 1.20-1.04 (m, 2H). MS (m/z)=228.15 (M+H)

Step 3: ethyl 2-((1R,5S)-1-(3,4-dichlorophenyl)-3-azabicyclo[3.1.0]hexan-3-yl)pyrimidine-5-carboxylate (489)

Using Procedure Y-3 (Table 5) with compound 488 the title compound 489 was obtained (176 mg, 43%) as a yellow solid. MS (m/z): 378.5 (M+H).

Step 4: 2-((1R,5S)-1-(3,4-dichlorophenyl)-3-azabicyclo[3.1.0]hexan-3-yl)-N-hydroxypyrimidine-5-carboxamide (490)

Using Procedure B-3 (Table 5) with compound 489 the title compound 490 was obtained (132 mg, 78%) as a white solid. ¹H NMR (CD₃OD) δ (ppm): 8.67 (s, 2H), 7.46 (m, 2H), 7.23 (dd, J=2.4 Hz, 8.4 Hz, 1H), 4.31 (d, J=11.2 Hz, 1H), 4.07 (d, J=11.2 Hz, 1H), 3.76 (d, J=11.2 Hz, 2H), 2.14 (quin, J=4 Hz, 1H), 1.22 (m, 1H), 0.90 (t, J=4.8 Hz, 1H). MS (m/z): 363.4 (M−H).

Example 239

(Z)-4-(7-bromo-2-oxo-2,3-dihydro-1H-thieno[2,3-e][1,4]diazepin-5-yl)-N-hydroxybenzamide (495)

Step 1: methyl 4-(2-aminothiophene-3-carbonyl)benzoate (491)

Triethylamine (1.331 mL, 9.55 mmol) was added with stirring to a solution of methyl 4-(2-cyanoacetyl)benzoate (4.85 g, 23.87 mmol) and 1,4-dithiane-2,5-diol (1.817 g, 11.93 mmol) in dimethylformamide (10 mL), to give a yellow solution. After 15 min, the solution was heated to 60° C. for 2 hours and stirred at room temperature overnight. Water (50 mL), ethyl acetate (50 mL), and glacial acetic acid (ca. 1-3 mL) were added to the oily residue until the organic layer became clear. After separation of the organic layer and further extraction of the aqueous layer with ethyl acetate (50 mL), the combined organic layers were washed subsequently with 5% aqueous NaHCO₃ and H₂O, dried over anhydrous MgSO₄. The solvent was removed and the residue was purified via ISCO (0-50% EtOAc/Hexanes; 80 g silica gel column) to afford title compound 491 (3.7 g, 59%) as a yellow solid. MS (m/z): 357.4 (M+H).

Scheme 89

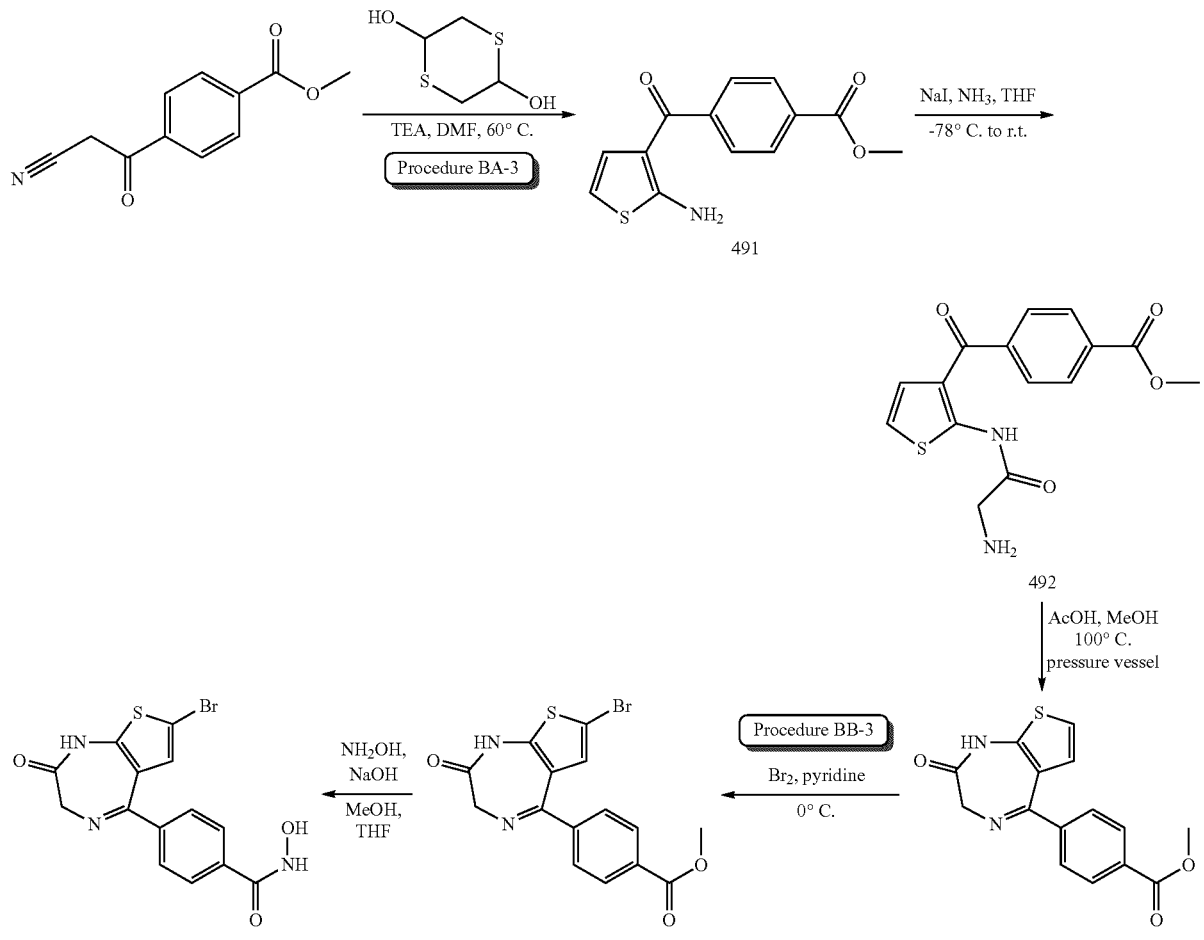

Step 2: methyl 4-(2-(2-aminoacetamido)thiophene-3-carbonyl)benzoate (492)

In a 100 mL round-bottomed flask was dissolved title compound 491 (1 g, 2.96 mmol) and sodium iodide (0.533 g, 3.55 mmol) in tetrahydrofuran (20 mL) to give a yellow suspension. The mixture was heated at reflux for 2 hours. The mixture was cooled to −78° C. A Dewar-type condenser was attached and filled with dry ice/acetone Ammonia was introduced as a gas and about 30 mL was condensed into the flask. The reaction mixture was left to warm up to room temperature over the weekend. The solvent was removed in vacuo and the residue was purified via ISCO (50-100% EtOAc/Hexanes; 40 g silica gel column) to obtain product as a tan powder. The solid was purified by suspending it in 1:1 dichloromethane/ether and filtering to afford title compound 492 (265 mg, 28%) as a tan powder which was sufficiently pure for the next step. MS (m/z): 319.3 (M+H).

Step 3: (Z)-methyl 4-(2-oxo-2,3-dihydro-1H-thieno[2,3-e][1,4]diazepin-5-yl)benzoate (493)

In a 75 mL pressure flask was suspended compound 492 (0.265 g, 0.832 mmol) and acetic acid (0.071 mL, 1.249 mmol) in methanol (20 mL) to give a yellow suspension. The reaction mixture was heated at 100° C. overnight. The solvent was removed to afford title compound 493 (250 mg, 100%) as a tan powder. MS (m/z): 301.3 (M+H).

Step 4: (Z)-methyl 4-(7-bromo-2-oxo-2,3-dihydro-1H-thieno[2,3-e][1,4]diazepin-5-yl)benzoate (494)

In a 20 mL dram screw-cap vial with septum was dissolved compound 493 (0.140 g, 0.466 mmol) in pyridine (3 mL) to give an orange solution. The mixture was cooled to 0° C. and bromine (0.029 mL, 0.559 mmol) was added dropwise. The reaction mixture was left to stir at 0° C. for 1 hour. The mixture was quenched with saturated thiosulfate solution and extracted with ethyl acetate. The organic layer was washed several times with water, then brine, dried over magnesium sulfate, filtered and evaporated. The residue was suspended in ether and filtered to afford title compound 494 (101 mg, 57%) as a tan solid. MS (m/z): 379.33 (M+H).

Step 5: (Z)-4-(7-bromo-2-oxo-2,3-dihydro-1H-thieno[2,3-e][1,4]diazepin-5-yl)-N-hydroxybenzamide (495)

Using Procedure B-3 (Table 5) with compound 494 the title compound 495 was obtained (40 mg, 40%) as a tan solid. $^1$H NMR (CD$_3$OD) δ (ppm): 7.84 (d, J=8.4 Hz, 2H), 7.66 (d, J=8.4 Hz, 2H), 6.85 (s, 1H), 4.36 (s, 2H). MS (m/z): 378.2 (M−H).

Scheme 90

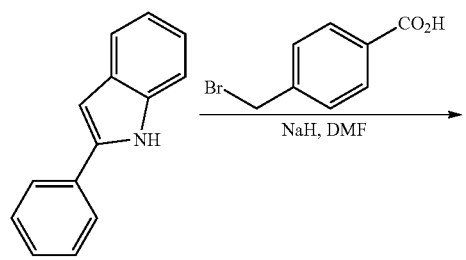

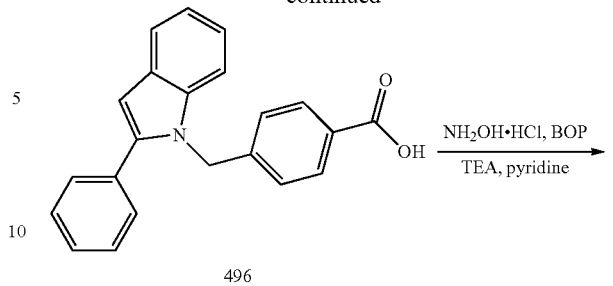

496

497: Example 240

Example 240

N-hydroxy-4-((2-phenyl-1H-indol-1-yl)methyl)benzamide (497)

Step 1: 4-((2-phenyl-1H-indol-1-yl)methyl)benzoic acid (496)

Using Procedure H-3 (Table 5) with 2-phenyl-1H-indole and 4-(bromomethyl)benzoic acid the title compound 496 was obtained (332 mg, 22%) as a tan solid. $^1$H NMR (DMSO-d$_6$) δ (ppm): 7.78 (d, J=8.2 Hz, 2H), 7.61 (dd, J=7.0, 1.7 Hz, 1H), 7.50-7.41 (m, 5H), 7.34 (d, J=8.2 Hz, 1H), 7.14-7.06 (m, 2H), 6.93 (d, J=8.2 Hz, 2H), 6.67 (d, J=0.8 Hz, 1H), 5.51 (s, 2H). MS (m/z)=326.2 (M−H).

Step 2: N-hydroxy-4((2-phenyl-1H-indol-1-yl)methyl)benzamide (497)

Title compound 496 (332 mg, 1.014 mmol), hydroxylamine hydrochloride (85 mg, 1.217 mmol), BOP (583 mg, 1.318 mmol), triethylamine (0.424 mL, 3.04 mmol) and pyridine (7 mL) were stirred together at room temperature for 1 hour. All solvents were then removed under reduced pressure, and the residue was diluted with ethyl acetate and brine. Following extraction with ethyl acetate, the combined organic layers were dried with anhydrous sodium sulfate, filtered, and concentrated. The residue was then purified by column chromatography on silica gel using 50-100% EtOAc/hexanes as the eluent to afford title compound 497 (0.058 g, 17%) as a white solid. $^1$H NMR (CD$_3$OD) δ (ppm): 7.66-7.62 (m, 3H), 7.50-7.38 (m, 5H), 7.28-7.23 (m, 1H), 7.17-7.08 (m, 2H), 7.03 (d, J=8.4 Hz, 2H), 6.65 (d, J=0.6 Hz, 1H), 5.51 (s, 2H). MS (m/z): 343.5 (M+H).

Scheme 91

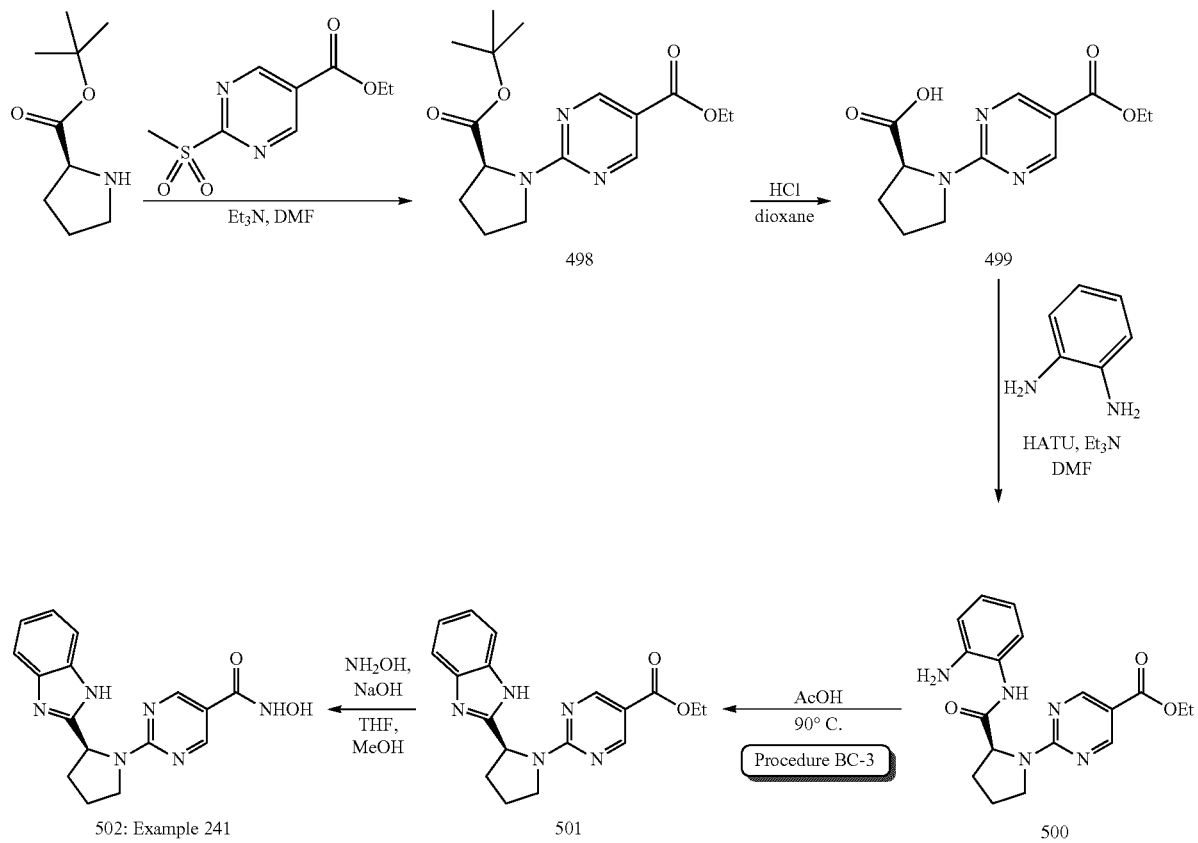

Example 241

(S)-2-(2-(1H-benzo[d]imidazol-2-yl)pyrrolidin-1-yl)-N-hydroxypyrimidine-5-carboxamide (502)

Step 1: (S)-ethyl 2-(2-(tert-butoxycarbonyl)pyrrolidin-1-yl)pyrimidine-5-carboxylate (498)

Using Procedure Y-3 (Table 5) with (S)-tert-butyl pyrrolidine-2-carboxylate and ethyl 2-(methylsulfonyl)pyrimidine-5-carboxylate the title compound 498 was obtained (278 mg, 66%). MS (m/z): 322.3 (M+H).

Step 2: (S)-1-(5-(ethoxycarbonyl)pyrimidin-2-yl)pyrrolidine-2-carboxylic acid (499)

HCl in dioxane (3 mL) was added to compound 498 (278 mg, 0.865 mmol) and the reaction mixture was stirred overnight. The reaction was then concentrated to afford compound 499 which was used without further purification. MS (m/z): 266.2 (M+H).

Step 3: (S)-ethyl 2-(2-(2-aminophenylcarbamoyl)pyrrolidin-1-yl)pyrimidine-5-carboxylate (500)

Using Procedure S-3 (Table 5) with compound 499 the title compound 500 was obtained (117 mg, 51%).

Step 4: (S)-ethyl 2-(2-(1H-benzo[d]imidazol-2-yl)pyrrolidin-1-yl)pyrimidine-5-carboxylate (501)

AcOH (2 mL) was added to compound 500 (117 mg, 0.329 mmol) and the solution was heated at 90° C. for 30 minutes. The solvent was evaporated under reduced pressure. The residue was then partitioned between ethyl acetate and water and the pH adjusted to pH=10. The organic phase was separated, dried over sodium sulfate, filtered and concentrated under reduced pressure. The residue was purified by silica gel column chromatography eluting with 50-100% EtOAc in hexanes to afford title compound 501 (72 mg, 65%). MS (m/z): 338.4 (M+H).

Step 5: (S)-2-(2-(1H-benzo[d]imidazol-2-yl)pyrrolidin-1-yl)-N-hydroxypyrimidine-5-carboxamide (502)

Using Procedure B-3 (Table 5) with compound 501 the title compound 502 was obtained (17 mg, 25%). $^1$H NMR (CD$_3$OD) δ (ppm): 8.72 (bs, 1H), 8.50 (bs, 1H), 7.46 (s, 2H), 7.17 (m, 2H), 5.48 (d, J=8.0 Hz, 1H), 4.04 (m, 1H), 3.79 (m, 1H), 2.53 (m, 1H), 2.28 (m, 1H), 2.14 (m, 2H). MS (m/z): 325.3 (M+H).

The general procedures A-3 to BC-3 used to synthesize compounds of this invention are described in the Table 5. A specific example of each general procedure is provided in the indicated step of a particular example. It is realized that substrates and methods may be modified and/or adapted by those of skill in the art in order to facilitate the synthesis of the compounds within the scope of the present invention.

TABLE 5
| Proc | Sc | Ex | Step | Reaction Conditions |
|---|---|---|---|---|
| A-3 | 50 | 200 | 1 | 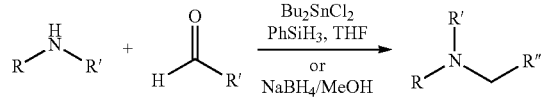 |
| B-3 | 50 | 200 | 2 | 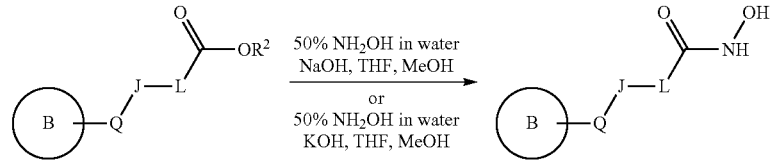 |
| C-3 | 51 | 201 | 1 | 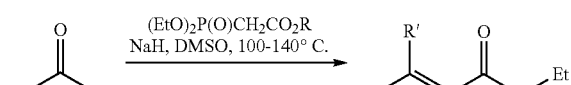 |
| D-3 | 52 | 202 | 1 | 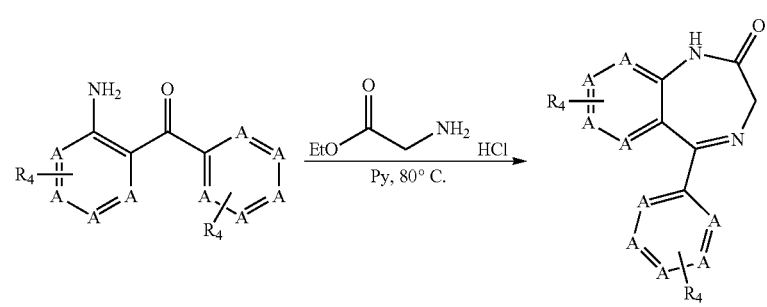 |
| E-3 | 52 | 202 | 2 | 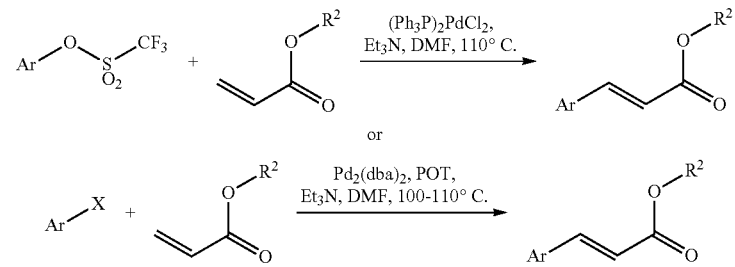 |
| F-3 | 53 | 203 | 1 |  |
| G-3 | 54 | 204 | 1 | 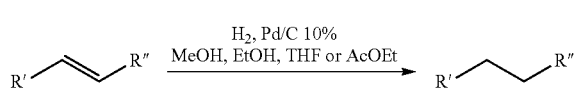 |
| H-3 | 55 | 205 | 2 | 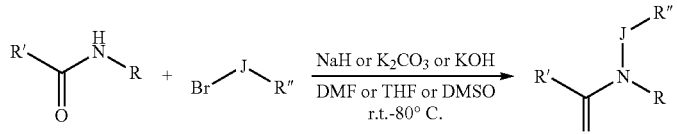 |

TABLE 5-continued

| Proc | Sc | Ex | Step | Reaction Conditions |
|---|---|---|---|---|
| I-3 | 56 | 206 | 1 | R′–CH₂–Br + HNR₂, K₂CO₃, DMF, 90° C. → R′–CH₂–NR₂<br><br>R′–CH₂–Br + R₂NH, TBA-HSO₄, NaOH (aq), DCM → R′–CH₂–NR₂<br>or<br>R₂NH, NaOH, DMF |
| J-3 | 56 | 206 | 2 | R–CH₂–CN + HCl / MeOH → R–CH₂–C(=O)–O–CH₃ |
| K-3 | 57 | 207 | 1 | R–C(=O)–R′ + NH₂OH·HCl, Pyridine, EtOH, reflux → R′–C(=N–OH)–R′ |
| L-3 | 57 | 207 | 2 | R=N–OH + R′–CH₂–Br, K₂CO₃, acetone, 40° C. → R=N–O–CH₂–R′ |
| M-3 | 58 | 208 | 1 | R=N–OH + COCl₂·H₂O, NaBH₄, MeOH or NH₄OAc, Zn, NH₄OH, EtOH → R–NH₂ |
| N-3 | 59 | 209 | 1 | Dibenz[b,f]azepine + (KSO₃)₂NO, Na₂HPO₄, H₂O, acetone → iminoquinone |
| O-3 | 59 | 209 | 2 | iminoquinone + Na₂S₂O₄, H₂O / CHCl₃ → hydroxy-dibenzazepine |
| P-3 | 59 | 209 | 4 | R–OH + 2,6-di-tert-butyl-4-methylpyridine, Tf₂O, DCM, 0 °C → R–OTf |
| Q-3 | 60 | 210 | 1 | Ar–X + RNH₂, DMSO or neat → Ar–NH–R (X = F or Cl)<br>or<br>Ar–F + RSH, NaH, DMAc → Ar–S–R<br>or<br>Ar–F + ROH, Cs₂CO₃, ACN → Ar–O–R<br>or<br>R′–CH₂–Br + ROH, Cs₂CO₃, ACN, 100° C. → R′–CH₂–O–R |

TABLE 5-continued
| Proc | Sc | Ex | Step | Reaction Conditions |
|---|---|---|---|---|
| R-3 | 60 | 210 | 2 | 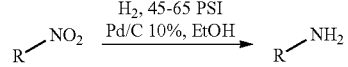 |
| S-3 | 60 | 210 | 3 | 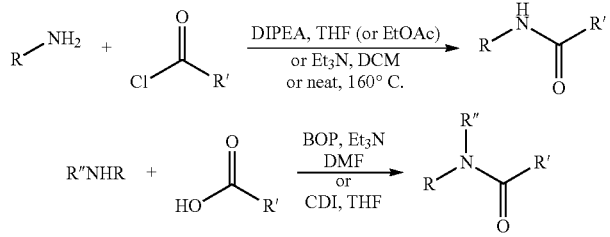 |
| T-3 | 60 | 210 | 4 | 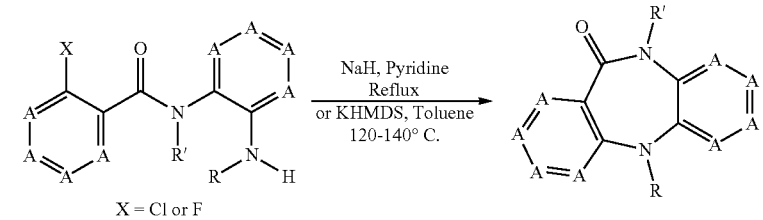 |
| U-3 | 61 | 211 | 2 |  |
| V-3 | 62 | 212 | 2 | 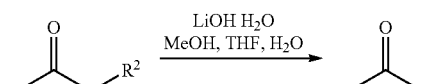 |
| W-3 | 62 | 212 | 3 | 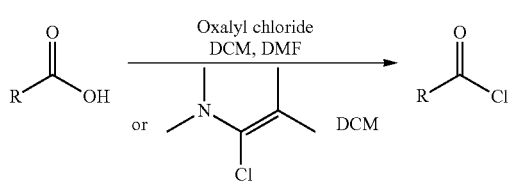 |
| X-3 | 62 | 212 | 4 | 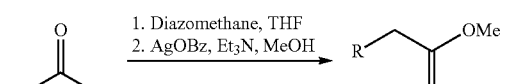 |
| Y-3 | 64 | 214 | 1 | 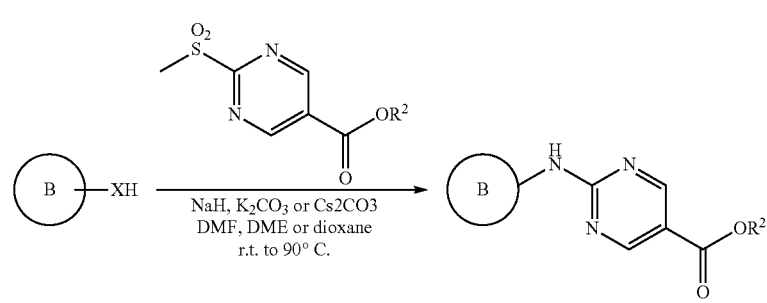 |

TABLE 5-continued

| Proc | Sc | Ex | Step | Reaction Conditions |
|---|---|---|---|---|
| | | | | (scheme: B=N-OH + methylsulfonyl pyrimidine ester → B=N-O-pyrimidine ester; NaH, DMF, r.t. or DME, 80° C. or $K_2CO_3$, DME, 50° C.) |
| Z-3 | 65 | 215 | 1 | lactam → cyclic amine; $BH_3 \cdot SMe_2$, THF, reflux |
| AA-3 | 65 | 215 | 2 | R-NH-R' + I-J-L-C(O)-OR² or Br-J-L-C(O)-OR² → R'-N(R)-J-L-C(O)-OR²; $K_2CO_3$, $CH_3CN$ (or acetone) |
| AB-3 | 68 | 218 | 2 | nitro diaryl ester → lactam; 1. $SnCl_2$, $2H_2O$, EtOH or $H_2$, Pd(C), EtOH, AcOH; 2. $AlMe_3$, DCM (or tol) 45-100° C. |
| AC-3 | 69 | 219 | 1 | sulfonyl chloride + aminophenol → dibenzoxathiazepine dioxide; 1) Pyridine; 2) KOH, $H_2O$, EtOH |
| AD-3 | 72 | 222 | 1 | cis-alkene → fluorobromide; NBS, HF-pyridine, $Et_2O$, 15° C. |
| AE-3 | 72 | 222 | 2 | fluorobromide → vinyl bromide; DBU, toluene, DCM, 0° C. to r.t. |
| AF-3 | 72 | 222 | 3 | vinyl bromide → vinyl fluoride; CsF, DMSO, 135° C. |

TABLE 5-continued
| Proc | Sc | Ex | Step | Reaction Conditions |
|---|---|---|---|---|
| AG-3 | 73 | 223 | 2 | 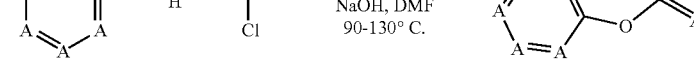 |
| AH-3 | 74 | 224 | 2 | 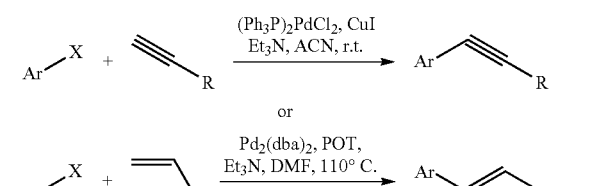 |
| AI-3 | 76 | 226 | 1 | 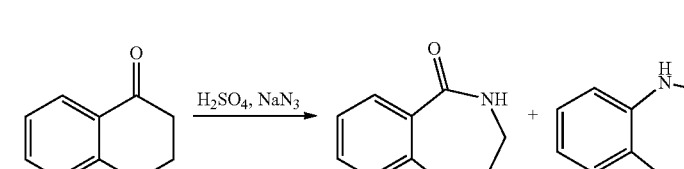 |
| AJ-3 | 77 | 227 | 2 | 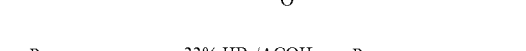 |
| AK-3 | 78 | 228 | 1 | 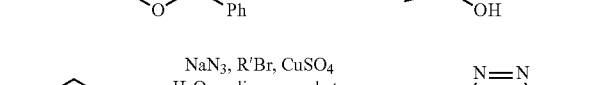 |
| AL-3 | 79 | 229 | 1 | 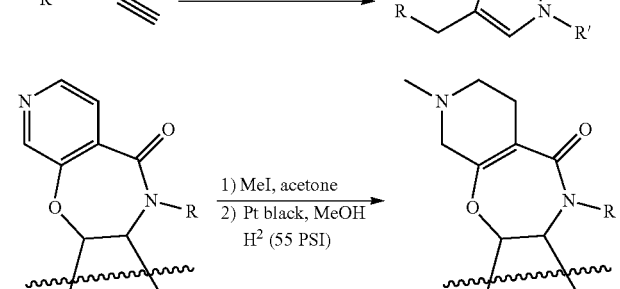 |
| AM-3 | 81 | 231 | 1 |  |
| AN-3 | 81 | 231 | 2 | 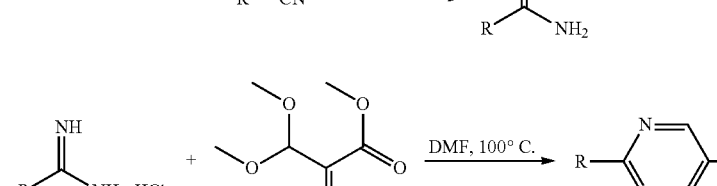 |
| AO-3 | 82 | 232 | 2 |  |
| AP-3 | 82 | 232 | 3 | 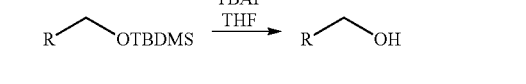 |

TABLE 5-continued
| Proc | Sc | Ex | Step | Reaction Conditions |
|---|---|---|---|---|
| AQ-3 | 83 | 233 | 1 | 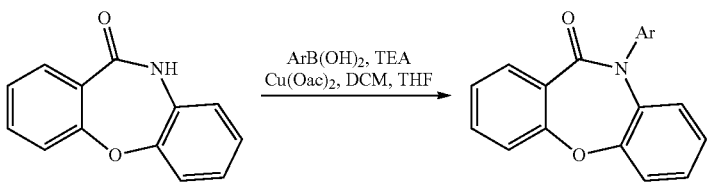 |
| AR-3 | 84 | 234 | 1 | 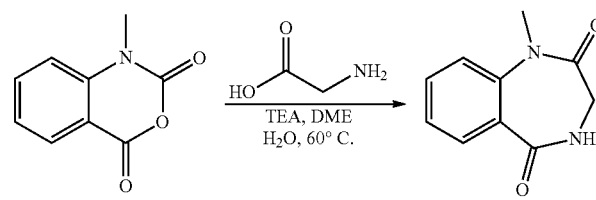 |
| AS-3 | 84 | 234 | 2 | 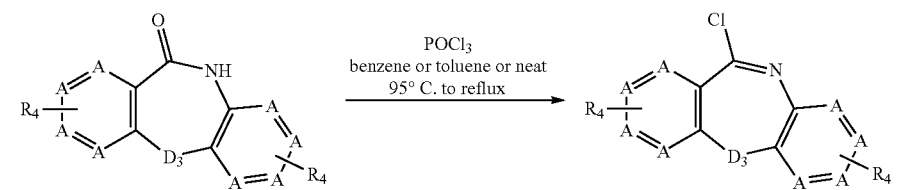 |
| AT-3 | 84 | 234 | 3 | 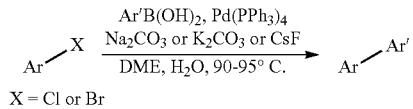 |
| AU-3 | 85 | 235 | 1 | 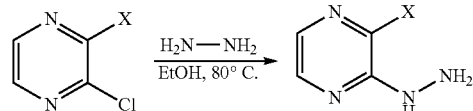 |
| AV-3 | 85 | 235 | 2 | 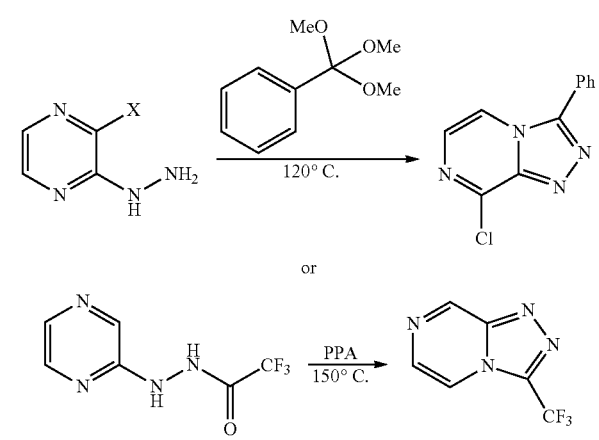 |
| AW-3 | 86 | 236 | 2 | 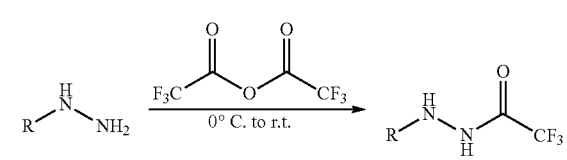 |
| AX-3 | 87 | 237 | 1 | 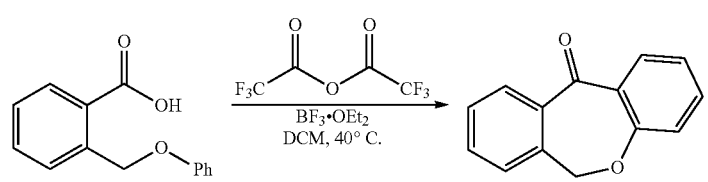 |

TABLE 5-continued

| Proc | Sc | Ex | Step | Reaction Conditions |
|---|---|---|---|---|
| AY-3 | 88 | 238 | 1 | 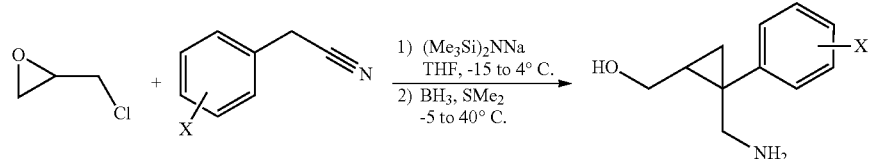 |
| AZ-3 | 88 | 238 | 2 | 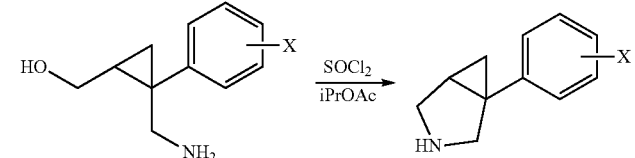 |
| BA-3 | 89 | 239 | 1 | 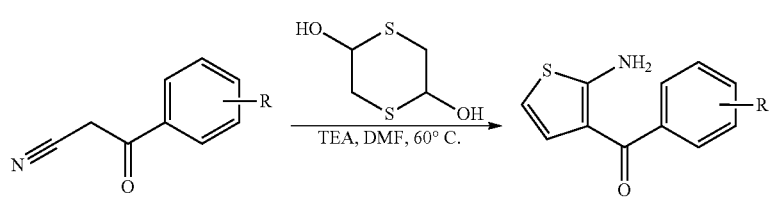 |
| BB-3 | 89 | 239 | 4 | 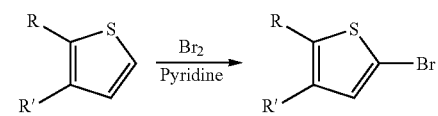 |
| BC-3 | 91 | 241 | 4 | 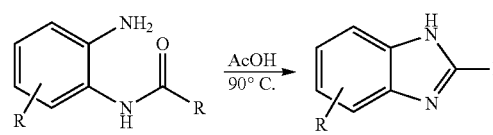 |

The examples described in Table 6 were prepared following the preparative sequences (general procedures A-3 to BC-3) indicated in Table 5 or using a preparative sequence(s) already described (for example, Table 1 and/or Table 3).

TABLE 6

| Ex | Cpd | Structure | Name | Characterization |
|---|---|---|---|---|
| 200 | 351 | 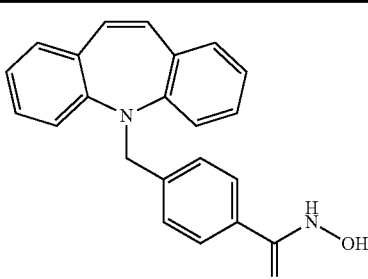 | (Z)-4-((5H-dibenzo[b,f]azepin-5-yl)methyl)-N-hydroxybenzamide | (DMSO-d6) δ (ppm): 11.06 (s, 1H), 8.96 (s, 1H), 7.57 (d, J = 8.4 Hz, 2H), 7.47 (d, J = 8.4 Hz, 2H), 7.21 (td, J = 1.6 and 7.2 Hz, 2H), 7.18-7.13 (m, 2H), 7.10 (dd, J = 1.6 and 7.6 Hz, 2H), 6.6 (td, J = 1.2 and 7.2 Hz, 2H), 6.85 (s, 2H), 5.00 (s, 2H), LRMS: 342.1 (calc) 343.2 (found) |
| 201 | 353 | 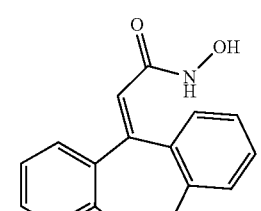 | | $^1$H NMR (DMSO-d$_6$) δ (ppm): 10.7-10.4 (1H, br s), 8.9-8.7 (1H, br s), 7.44-7.25 (8H, m), 6.99 and 6.91 (2H, AB doublet, J = 12.1 Hz), 5.75 (1H, s). MS (m/z): 264.0 (M + H). |

TABLE 6-continued

| Ex | Cpd | Structure | Name | Characterization |
|---|---|---|---|---|
| 202 | 356 | 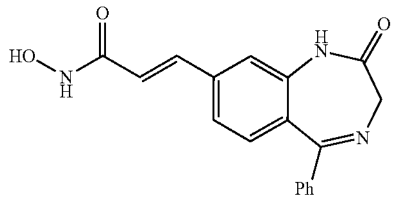 [SMILES: O=C(/C=C/c1ccc2c(c1)NC(=O)CN=C2c1ccccc1)NO] | ε-N-hydroxy-3-((Z)-2-oxo-5-phenyl-2,3-dihydro-1H-benzo[e][1,4]diazepin-8-yl)acrylamide | ¹H NMR (DMSO-d₆) δ (ppm)-formate salt: 10.54 (s, 1H), 7.61-7.53 (m, 3H), 7.50-7.44 (m, 3H), 7.26-7.22 (m, 2H), 7.17 (td, J = 7.2, 1.0 Hz, 1H), 6.51 (d, J = 5.9 Hz, 1H), 4.12-4.01 (br s, 2H). MS (m/z): 322.2 (M + H) |
| 203 | 359 | 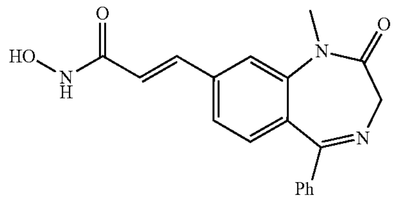 [SMILES: CN1C(=O)CN=C(c2ccccc2)c2ccc(/C=C/C(=O)NO)cc21] | ε-N-hydroxy-3-((Z)-1-methyl-2-oxo-5-phenyl-2,3-dihydro-1H-benzo[e][1,4]diazepin-8-yl)acrylamide | ¹H NMR (CD₃OD) δ (ppm)-formate salt: 7.70-7.56 (m, 7H), 7.29 (d, J = 4.1 Hz, 2H), 6.55 (d, J = 15.8 Hz, 1H), 4.63 (d, J = 10.8 Hz, 1H), 3.83 (d, J = 10.8 Hz, 1H), 3.43 (s, 3H). MS (m/z): 336.1 (M + H). |
| 204 | 361 | 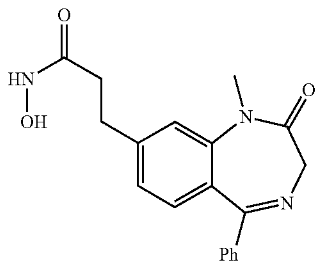 [SMILES: CN1C(=O)CN=C(c2ccccc2)c2ccc(CCC(=O)NO)cc21] | (Z)-N-hydroxy-3-(1-methyl-2-oxo-5-phenyl-2,3-dihydro-1H-benzo[e][1,4]diazepin-8-yl)propanamide | (MeOD) d(ppm): 7.68-7.63 (m, 1H), 7.56 (d, J = 8.2 Hz, 1H), 7.45 (d, J = 8.4 Hz, 2H), 7.29-7.23 (m, 4H), 4.58 (d, J = 11.0 Hz, 1H), 3.79 (d, J = 11.0 Hz, 1H), 3.42 (s, 3H), 2.97 (t, J = 7.6 Hz, 2H), 2.40 (t, J = 7.8 Hz, 2H). MS (m/z): 338.2 (M + H) |
| 205 | 364 | 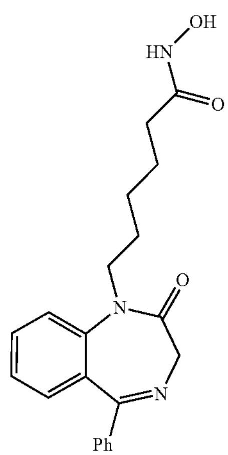 [SMILES: O=C(CCCCCN1C(=O)CN=C(c2ccccc2)c2ccccc21)NO] | (Z)-N-hydroxy-6-(2-oxo-5-phenyl-2,3-dihydro-1H-benzo[e][1,4]diazepin-1-yl)hexanamide | (CD₃OD) δ (ppm): 7.69-7.61 (m, 2H), 7.55-7.49 (m, 3H), 7.47-7.42 (m, 2H), 7.32-7.25 (m, 2H), 4.58 (d, J = 10.6 Hz, 1H), 4.43-4.36 (m, 1H), 3.81 (d, J = 10.7 Hz, 1H), 3.78-3.71 (m, 1H), 1.85 (t, J = 7.7 Hz, 2H), 1.56-1.37 (m, 4H), 1.16-1.09 (m, 2H). MS (m/z): 366.1 (M + H). |
| 206 | 367 | 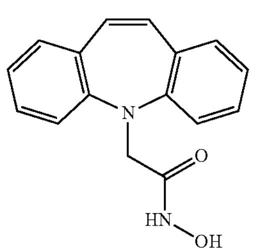 [SMILES: O=C(CN1c2ccccc2C=Cc2ccccc21)NO] | (Z)-2-(5H-dibenzo[b,f]azepin-5-yl)-N-hydroxyacetamide | (CDCl₃) δ (ppm): 7.28 (2H, t, J = 7.1 Hz), 7.16-7.11 (4H, m), 7.04 (2H, t, J = 7.1 Hz), 6.83 (2H, s), 4.42 (2H, s). MS (m/z): 267.0 (M + H). |
| 207 | 370 | 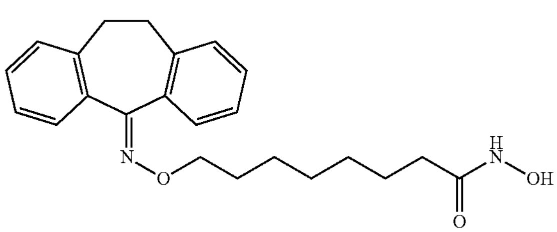 [SMILES: O=C(CCCCCCCON=C1c2ccccc2CCc2ccccc21)NO] | | (CDCl₃) δ (ppm): 7.51 (dd, J = 7.8, 1.5 Hz, 1H), 7.30-7.25 (m, 4H), 7.24-7.15 (m, 2H), 7.13 (d, J = 7.6 Hz, 1H), 4.13 (t, J = 6.5 Hz, 2H), 3.12-3.00 (m, 4H), 2.06 (t, J = 7.5 Hz, 2H), 1.67-1.56 (m, 4H), 1.40-1.20 (m, 6H). MS (m/z): 381.2 (M + H). |

TABLE 6-continued

| Ex | Cpd | Structure | Name | Characterization |
|---|---|---|---|---|
| 208 | 373 | 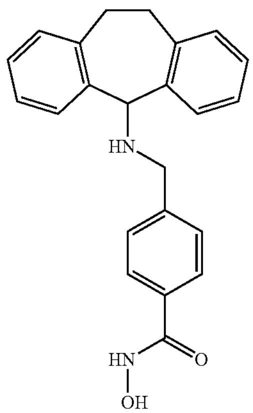 [SMILES: O=C(NO)c1ccc(CNC2c3ccccc3CCc3ccccc32)cc1] | | (MeOH-d₄) δ (ppm): 7.80 (d, J = 8.4 Hz, 2H), 7.53 (d, J = 8.4 Hz, 2H), 7.42-7.38 (m, 4H), 7.33-7.27 (m, 4H), 5.49 (br s, 1H), 4.20 (s, 2H), 3.44-3.42 (m, 2H), 3.08 (m, 2H). MS (m/z): 359.1 (M + H). |
| 209 | 379 | 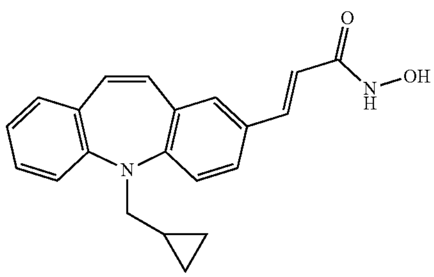 [SMILES: O=C(/C=C/c1ccc2c(c1)C=Cc1ccccc1N2CC1CC1)NO] | ε-3-((Z)-5-(cyclopropylmethyl)-5H-dibenzo[b,f]azepin-2-yl)-N-hydroxyacrylamide | (CD₃OD) δ (ppm): 7.5-7.4 (2H, m), 7.25-7.2 (2H, m), 7.05-7.0 (3H, m), 6.99-9.93 (1H, m), 6.75-6.65 (2H, observed 2d), 6.33 (1H, d, J = 15.7 Hz), 3.57 (2H, d, J = 6.4 Hz), 1.05-0.95 (1H, m), 0.45-0.37 (2H, m), 0.25-0.18 (2H, m). MS (m/z): 333.1 (M + H). |
| 210 | 385 | 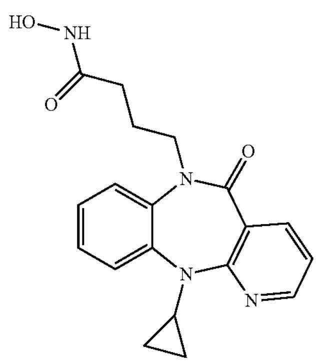 [SMILES: O=C(CCCN1C(=O)c2cccnc2N(C2CC2)c2ccccc21)NO] | 4-(11-cyclopropyl-5-oxo-5H-benzo[b]pyrido[2,3-e][1,4]diazepin-6(11H)-yl)-N-hydroxybutanamide | (CD₃OD) δ (ppm): 8.36 (1H, dd, J = 4.9, 1.7 Hz), 8.00 (1H, dd, J = 7.6, 1.7 Hz), 7.52 (1H, dd, J = 8.1, 1.3 Hz), 7.38 (1H, dd, J = 8.0, 1.1 Hz), 7.26 (1H, td, J = 7.8, 1.3 Hz), 7.23-7.17 (1H, td observed), 7.12 (1H, dd, J = 7.6, 4.9 Hz), 4.58-4.48 (1H, m), 3.76-3.68 (1H, m), 3.60-3.55 (1H, m), 2.06 (2H, t, J = 7.6 Hz), 1.95-1.80 (1H, m), 1.79-1.73 (1H, m), 1.05-0.87 (2H, m), 0.60-0.42 (2H, m). MS (m/z): 353.1 (M + H). |
| 211 | 388 | 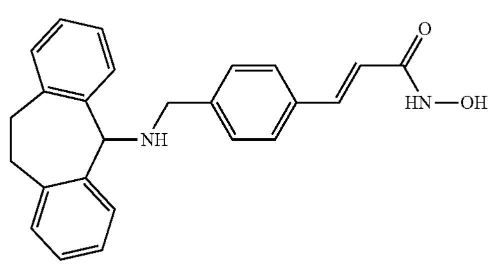 [SMILES: O=C(/C=C/c1ccc(CNC2c3ccccc3CCc3ccccc32)cc1)NO] | | (CD₃OD) δ (ppm): 7.70-7.55 (3H, m), 7.47 (2H, d, J = 7.8 Hz), 7.42-7.34 (4H, m), 7.33-7.21 (5H, m), 6.56 (1H, d, J = 15.9 Hz), 5.49 (1H, br s), 4.16 (1H, br s), 3.50-3.36 (2H, m), 3.25-2.98 (2H, m). MS (m/z): 385.1 (M + H). |

TABLE 6-continued

| Ex | Cpd | Structure | Name | Characterization |
|---|---|---|---|---|
| 212 | 393 | 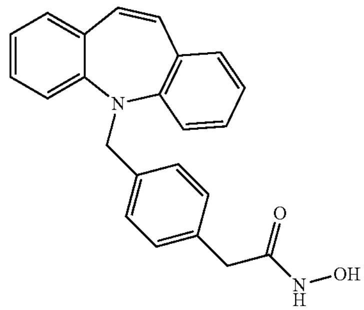 [SMILES: O=C(Cc1ccc(CN2c3ccccc3C=Cc3ccccc32)cc1)NO] | (Z)-2-(4-((5H-dibenzo[b,f]azepin-5-yl)methyl)phenyl)-N-hydroxyacetamide | (dmso) δ (ppm): 10.57 (1H, s), 8.74 (1H, s), 7.31 (2H, d, J = 8.2 Hz), 7.19 (2H, td, J = 7.2, 1.6 Hz), 7.11 (2H, d, J = 7.2 Hz), 7.10-7.04 (4H, m), 6.92 (2H, m), 6.81 (2H, s), 4.89 (2H, s), 3.13 (2H, s). MS (m/z): 357.1 (M + H) |
| 213 | 395 | 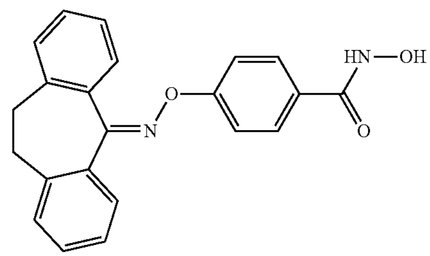 [SMILES: O=C(NO)c1ccc(ON=C2c3ccccc3CCc3ccccc32)cc1] | | (DMSO-d$_6$) δ (ppm): 11.13 (1H, s), 8.94 (1H, s), 7.74 (2H, d, J = 8.8 Hz), 7.67 (1H, d, J = 7.4 Hz), 7.42-7.34 (4H, m), 7.32-7.26 (2H, m), 7.26-7.19 (3H, m), 3.21-2.99 (4H, m). MS (m/z): 359.0 (M + H). |
| 214 | 397 | 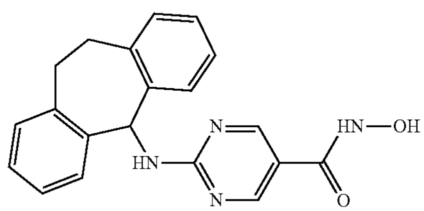 [SMILES: O=C(NO)c1cnc(NC2c3ccccc3CCc3ccccc32)nc1] | | $^1$H NMR (MeOD) δ (ppm): 8.62 (2H, s), 7.44 (2H, d, J = 7.1 Hz), 7.17-7.09 (6H, m), 6.66 (1H, s), 3.38-3.30 (2H, m), 3.28-3.18 (2H, m). MS (m/z): 345.1 (M − H). |
| 215 | 400 | 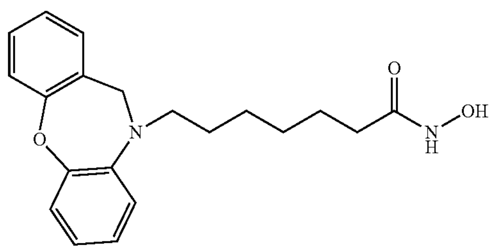 [SMILES: O=C(CCCCCCN1Cc2ccccc2Oc2ccccc21)NO] | 7-(dibenzo[b,f][1,4]oxazepin-10(11H)-yl)-N-hydroxyheptanamide | $^1$H NMR (400 MHz, CD$_3$OD) δ (ppm): 7.71 (m, 1H), 7.60 (t, J = 8.0 Hz, 1H), 7.52-7.48 (m, 2H), 7.43 (d, J = 7.8 Hz, 1H), 7.39-7.36 (m, 2H), 7.27 (t, J = 7.4 Hz, 1H), 5.01 (s, 2H), 3.56 (t, J = 8.0 Hz, 2H), 2.15 (br s, 2H), 1.73-1.70 (m, 2H), 1.59-1.55 (m, 2H), 1.31 (br s, 4H). MS (m/z): 341.1 (M + H). |
| 216 | 404 | 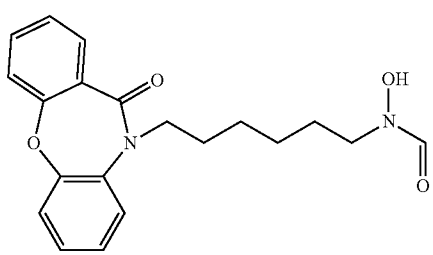 [SMILES: O=CN(O)CCCCCCN1C(=O)c2ccccc2Oc2ccccc21] | N-hydroxy-N-(6-(11-oxodibenzo[b,d][1,4]oxazepin-10(11H)-yl)hexyl)formamide | $^1$H NMR (CD$_3$OD) δ (ppm): 8.24, 7.89 (2s, rotamers, 1H), 7.74 (d, J = 7.6 Hz, 1H), 7.54-7.46 (m, 2H), 7.33 (dt, J = 7.4, 2.0 Hz, 1H), 7.28-7.21 (m, 4H), 4.19 (br s, 2H), 3.50 (t, J = 6.8 Hz, 1H), 3.44 (t, J = 6.8 Hz, 1H), 1.70-1.55 (m, 4H), 1.44-1.29 (m, 4H). MS (m/z): 355.2 (M + H). |
| 217 | 407 | 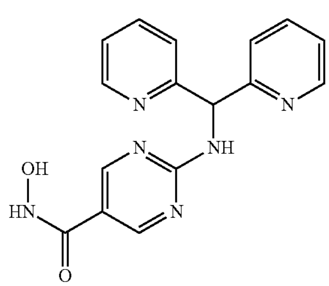 [SMILES: O=C(NO)c1cnc(NC(c2ccccn2)c2ccccn2)nc1] | 2-(dipyridin-2-ylmethylamino)-N-hydroxypyrimidine-5-carboxamide | $^1$H NMR (CD$_3$OD) δ (ppm): 8.65 (bs, 2H), 8.54 (d, J = 4.8 Hz, 2H), 7.79 (dt, J = 2 Hz, 7.6 Hz, 2H), 7.56 (d, J = 7.6 Hz, 2H), 7.31 (dd, J = 2 Hz, 6.8 Hz, 2H), 6.43 (s, 1H)... MS (m/z): 323.4 (M + H). |

TABLE 6-continued

| Ex | Cpd | Structure | Name | Characterization |
|---|---|---|---|---|
| 218 | 411 | 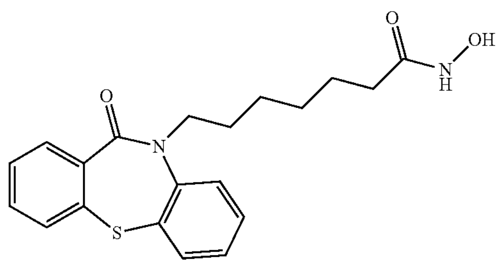 [SMILES: O=C(CCCCCCN1C(=O)c2ccccc2Sc2ccccc21)NO] | N-hydroxy-4-(11-oxodibenzo[b,f][1,4]thiazepin-10(11H)-yl)heptanamide | $^1$H NMR (CD$_3$OD) δ (ppm): 7.63-7.59 (m, 2H), 7.52-7.46 (m, 2H), 7.42-7.34 (m, 3H), 7.19 (td, J = 7.4, 1.4 Hz, 1H), 4.70 (dt, J = 13.7, 1.4 Hz, 1H), 3.67 (ddd, J = 13.7, 7.4, 5.9 Hz, 1H), 2.04 (t, J = 7.0 Hz, 2H), 1.65-1.52 (m, 4H), 1.44-1.22 (m, 4H). MS (m/z): 371.4 (M + H). |
| 219 | 414 | 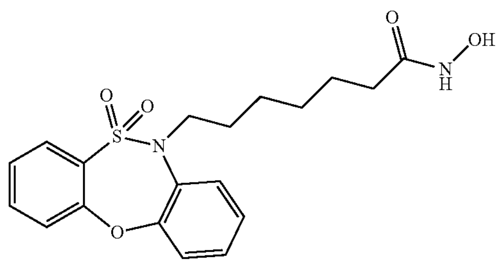 [SMILES: O=C(CCCCCCN1c2ccccc2Oc2ccccc2S1(=O)=O)NO] | | $^1$H NMR (CD$_3$OD) δ (ppm): 7.80 (dd, J = 8.0, 2.0 Hz, 1H), 7.61 (ddd, J = 8.4, 6.8, 1.2 Hz, 1H), 7.46-7.41 (m, 3H), 7.38-7.30 (m, 3H), 3.62 (t, J = 7.2 Hz, 2H), 2.06 (t, J = 7.2 Hz, 2H), 1.61-1.51 (m, 4H), 1.44-1.28 (m, 4H). MS (m/z): 391.3 (M + H). |
| 220 | 418 | 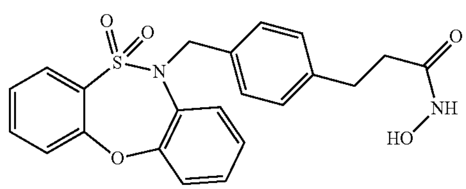 [SMILES: O=C(CCc1ccc(CN2c3ccccc3Oc3ccccc3S2(=O)=O)cc1)NO] | N-hydroxy-3-(4-((11-oxodibenzo[b,f][1,4]oxazepin-10(11H)-yl)methyl)phenyl)propanamide | $^1$H NMR (DMSO-d$_6$) δ (ppm): 10.33 (s, 1H), 8.68 (s, 1H), 7.74 (dd, J = 7.6, 1.6 Hz, 1H), 7.60-7.56 (m, 1H), 7.48-7.44 (m, 1H), 7.36-7.28 (m, 3H), 7.19-7.10 (m, 6H), 5.31 (s, 2H), 2.73 (t, J = 7.2 Hz, 2H), 2.20 (t, J = 7.2 Hz, 2H). MS (m/z): 389.4 (M + H). |
| 221 | 422 | 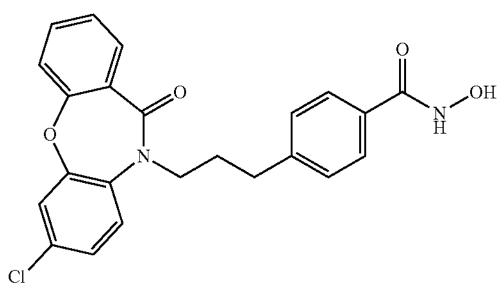 [SMILES: O=C(NO)c1ccc(CCCN2C(=O)c3ccccc3Oc3cc(Cl)ccc32)cc1] | 4-(2-(7-chloro-11-oxodibenzo[b,f][1,4]oxazepin-10(11H)-yl)ethoxy)-N-hydroxybenzamide | $^1$H NMR (DMSO-d$_6$) δ (ppm): 11.04 (s, 1H), 8.90 (s, 1H), 7.74-7.71 (m, 2H), 7.68 (d, J = 8.8 Hz, 2H), 7.61-7.57 (m, 2H), 7.39-7.36 (m, 2H), 7.32 (td, J = 7.4, 1.2 Hz, 1H), 6.91 (d, J = 8.8 Hz, 2H), 4.42 (br s, 2H), 4.30 (t, J = 5.2 Hz, 2H). MS (m/z): 447.4 (M + Na). |
| 222 | 429 | 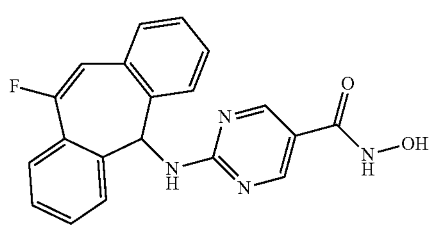 [SMILES: O=C(NO)c1cnc(NC2c3ccccc3C=C(F)c3ccccc32)nc1] | | $^1$H NMR (DMSO-d$_6$) δ (ppm): 9.46 (s, 0.1H), 8.58 (br s, 2H), 7.80 (d, J = 7.8 HZ, 1H), 7.73 (d, J = 7.8 Hz, 1H), 7.63 (d, J = 7.6 Hz, 1H), 7.56 (t, J = 7.5 Hz, 1H), 7.43 (d, J = 7.6 Hz, 1H), 7.39 (t, J = 7.6 Hz, 2H), 7.27 (d, J = 7.4 Hz, 1H), 7.21 (d, J = 21.7 Hz, 1H), 5.92 (s, 1H)... MS (m/z): 361.4 (M − H). |
| 223 | 433 | 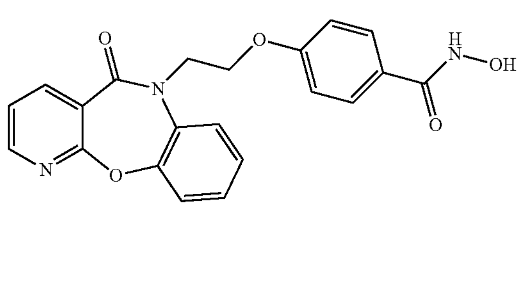 [SMILES: O=C(NO)c1ccc(OCCN2C(=O)c3cccnc3Oc3ccccc32)cc1] | N-hydroxy-4-(2-(5-oxobenzo[b]pyrido[3,2-f][1,4]oxazepin-6(5H)-yl)ethoxy)benzamide | $^1$H NMR (DMSO-d$_6$) δ (ppm): 11.05 (s, 1H), 8.90 (s, 1H), 8.46 (dd, J = 4.8, 2.0 Hz, 1H), 8.23 (dd, J = 7.6, 1.6 Hz, 1H), 7.72 (dd, J = 8.0, 1.6 Hz, 1H), 7.67 (d, J = 9.2 Hz, 2H), 7.44 (dd, J = 7.6, 4.4 Hz, 1H), 7.39-7.25 (m, 3H), 6.90 (d, J = 9.2 Hz, 2H), 4.47 (m, 2H), 4.32 (t, J = 5.2 Hz, 2H). MS (m/z): 392.3 (M + H). |

TABLE 6-continued

| Ex | Cpd | Structure | Name | Characterization |
|---|---|---|---|---|
| 224 | 436 | 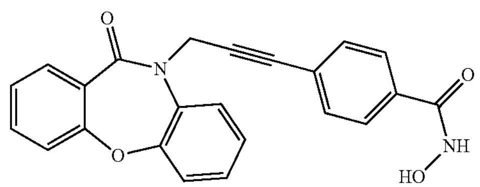 [SMILES: O=C(NO)c1ccc(C#CCN2C(=O)c3ccccc3Oc3ccccc32)cc1] | N-hydroxy-4-(3-(11-oxodibenzo[b,f][1,4]oxazepin-10(11H)-yl)prop-1-ynyl)benzamide | $^1$H NMR (DMSO-d$_6$) δ (ppm): 11.30 (s, 1H), 9.11 (s, 1H), 7.79 (dd, J = 8.0, 1.6 Hz, 1H), 7.47-7.72 (m, 3H), 7.64-7.59 (m, 1H), 7.47-7.26 (m, 7H), 5.11 (s, 2H) LRMS(ESI): (calc) 384.11 (found) 385.16 (MH)+ |
| 225 | 441 | 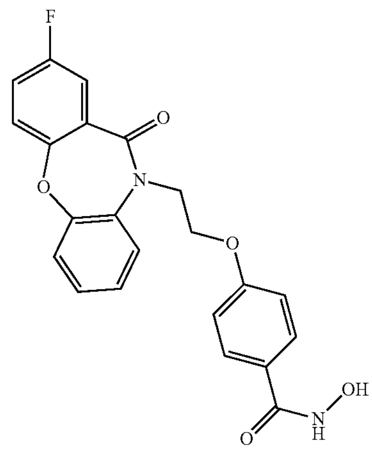 [SMILES: O=C(NO)c1ccc(OCCN2C(=O)c3cc(F)ccc3Oc3ccccc32)cc1] | 4-(2-(2-fluoro-11-oxodibenzo[b,f][1,4]oxazepin-10(11H)-yl)ethoxy)-N-hydroxybenzamide | $^1$H NMR (DMSO-d$_6$) δ (ppm): 11.05 (s, 1H), 8.90 (s, 1H), 7.70-7.65 (m, 3H), 7.49-7.38 (m, 4H), 7.33-7.23 (m, 2H), 6.89 (d, J = 9.0 Hz, 2H), 4.45 (br s, 2H), 4.31 (t, J = 5.2 Hz, 2H). MS (m/z): 409.3 (M + H). |
| 226 | 444 | 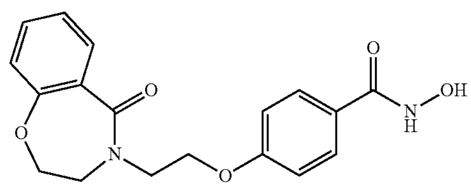 [SMILES: O=C(NO)c1ccc(OCCN2CCOc3ccccc3C2=O)cc1] | N-hydroxy-4-(2-(5-oxo-2,3-dihydrobenzo[f][1,4]oxazepin-4(5H)-yl)ethoxy)benzamide | $^1$H NMR (DMSO-d$_6$) δ (ppm): 11.08 (s, 1H), 8.92 (s, 1H), 7.73 (d, J = 8.8 Hz, 2H), 7.64 (dd, J = 7.6, 1.6 Hz, 1H), 7.48-7.44 (m, 1H), 7.16 (td, J = 7.6, 1.2 Hz, 1H), 7.05-7.01 (m, 3H), 4.36 (t, J = 4.7 Hz, 2H), 4.23 (t, J = 5.7 Hz, 2H), 3.92 (t, J = 5.5 Hz, 2H), 3.64 (t, J = 5.1 Hz, 2H). MS (m/z): 343.2 (M + H). |
| 227 | 449 | 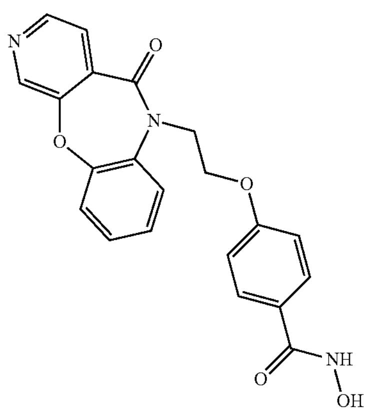 [SMILES: O=C(NO)c1ccc(OCCN2C(=O)c3ccncc3Oc3ccccc32)cc1] | N-hydroxy-4-(2-(5-oxobenzo[b]pyrido[4,3-f][1,4]oxazepin-6(5H)-yl)ethoxy)benzamide | $^1$H NMR (DMSO-d$_6$) δ (ppm): 11.06 (s, 1H), 8.92 (s, 1H), 8.71 (s, 1H), 8.54 (d, J = 4.8 Hz, 1H), 7.72 (dd, J = 8.4, 1.8 Hz, 1H), 7.69-7.66 (m, 3H), 7.44 (dd, J = 8.0, 1.8 Hz, 1H), 7.35-7.26 (m, 2H), 6.89 (d, J = 8.8 Hz, 2H), 4.48-4.47 (m, 2H), 4.32 (t, J = 5.4 Hz, 2H). MS (m/z): 392.3 (M + H). |
| 228 | 451 | 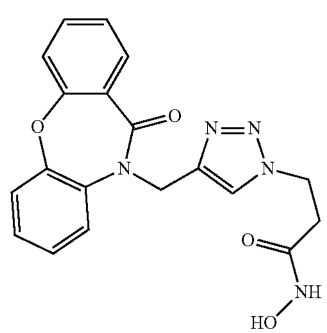 [SMILES: O=C(CCn1cc(CN2C(=O)c3ccccc3Oc3ccccc32)nn1)NO] | N-hydroxy-3-(4-((11-oxodibenzo[b,f][1,4]oxazepin-10(11H)-yl)methyl)-1H-1,2,3-triazol-1-yl)propanamide | $^1$H NMR (CD$_3$OD) δ (ppm): 7.97 (s, 1H), 7.79 (dd, J = 8.4, 1.8 Hz, 1H), 7.68-7.65 (m, 1H), 7.56-7.52 (m, 1H), 7.32-7.20 (m, 5H), 5.28 (s, 2H), 4.69 (t, J = 6.8 Hz, 2H), 2.71 (t, J = 6.8 Hz, 2H). MS (m/z): 380.3 (M + H). |

TABLE 6-continued

| Ex | Cpd | Structure | Name | Characterization |
|---|---|---|---|---|
| 229 | 453 | 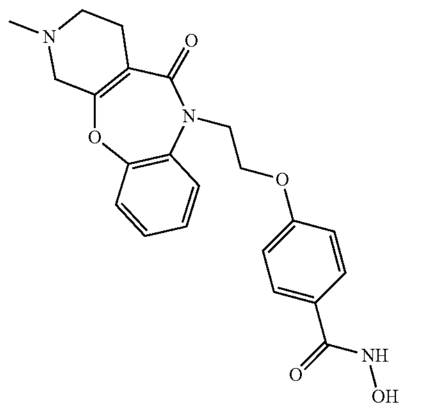 [SMILES: CN1CCC2=C(C1)Oc1ccccc1N(CCOc1ccc(C(=O)NO)cc1)C2=O] | N-hydroxy-4-(2-(2-methyl-5-oxo-1,2,3,4-tetrahydrobenzo[b]pyrido[4,3-f][1,4]oxazepin-6(5H)-yl)ethoxy)benzamide | ¹H NMR (CD₃OD) δ (ppm): 7.65 (d, J = 8.8 Hz, 2H), 7.55 (dd, J = 8.0, 1.2 Hz, 1H), 7.27 (td, J = 7.6, 1.6 Hz, 1H), 7.20 (td, J = 8.0, 1.6 Hz, 1H), 7.10 (dd, J = 8.0, 1.6 Hz, 1H), 6.87 (d, J = 8.8 Hz, 2H), 4.38 (t, J = 5.2 Hz, 2H), 4.30 (t, J = 5.2 Hz, 2H), 3.34-3.33 (m, 2H), 2.68 (t, J = 5.8 Hz, 2H), 2.48 (br s, 5H). MS (m/z): 410.4 (M + H). |
| 230 | 457 | 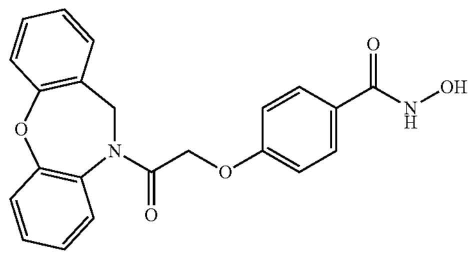 [SMILES: O=C(NO)c1ccc(OCC(=O)N2Cc3ccccc3Oc3ccccc32)cc1] | 4-(2-(dibenzo[b,d][1,4]oxazepin-10(11H)-yl)-2-oxoethoxy)-N-hydroxybenzamide | ¹H NMR (DMSO-d₆) δ (ppm): 11.03 (s, 1H), 8.90 (s, 1H), 7.70 (d, J = 7.6 Hz, 1H), 7.59 (d, J = 8.8 Hz, 2H), 7.47-7.41 (m, 2H), 7.30-7.22 (m, 4H), 7.10-7.06 (m, 1H), 6.75 (d, J = 8.8 Hz, 2H), 5.01-4.66 (m, 4H). MS (m/z): 391.1 (M + H). |
| 231 | 460 | 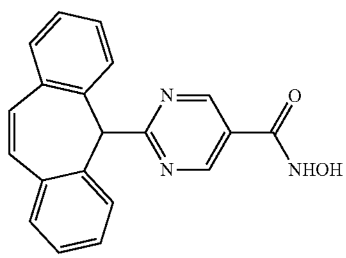 | | ¹H NMR (DMSO-d₆) δ (ppm): 11.06 (s, 1H), 9.06 (s, 1H), 8.59 (s, 2H), 7.58-7.47 (m, 6H), 7.40-7.31 (m, 2H), 7.01 (s, 2H). |
| 232 | 464 | 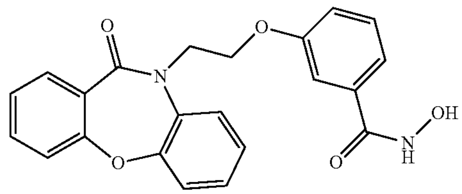 [SMILES: O=C(NO)c1cccc(OCCN2C(=O)c3ccccc3Oc3ccccc32)c1] | N-hydroxy-3-(2-(11-oxodibenzo[b,f][1,4]oxazepin-10(11H)-yl)ethoxy)benzamide | ¹H NMR (CD₃OD) δ (ppm): 7.77 (dd, J = 8.0, 1.8 Hz, 1H), 7.67 (dd, J = 7.8, 1.8 Hz, 1H), 7.58-7.53 (m, 1H), 7.38-7.22 (m, 8H), 7.09-7.04 (m, 1H), 4.59-4.51 (br s, 2H), 4.42 (t, J = 5.3 Hz, 2H). MS (m/z): 389.2 (M − H). |
| 233 | 466 | 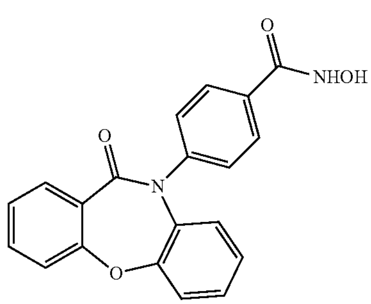 | N-hydroxy-4-(11-oxodibenzo[b,f][1,4]oxazepin-10(11H)-yl)benzamide | ¹H NMR (DMSO-d₆) δ (ppm): 11.33 (s, 1H), 9.14 (s, 1H), 7.87 (d, J = 8.8 Hz, 2H), 7.81 (dd, J = 8.0, 2.0 Hz, 1H), 7.66-7.62 (m, 1H), 7.51-7.43 (m, 4H), 7.36 (td, J = 7.8, 0.8 Hz, 1H), 7.22 (td, J = 7.4, 1.6 Hz, 1H), 7.11 (td, J = 7.8, 1.6 Hz, 1H), 6.76 (dd, J = 8.0, 1.6 Hz, 1H). MS (m/z): 347.2 (M + H). |
| 234 | 470 | 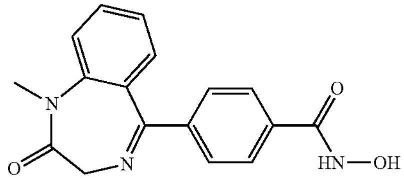 [SMILES: CN1C(=O)CN=C(c2ccc(C(=O)NO)cc2)c2ccccc21] | (Z)-N-hydroxy-4-(1-methyl-2-oxo-2,3-dihydro-1H-benzo[e][1,4]diazepan-5-yl)benzamide | ¹H NMR (DMSO-d₆) δ (ppm): 11.33 (s, 1H), 9.12 (s, 1H), 7.81 (d, J = 8.4 Hz, 2H), 7.69-7.65 (m, 1H), 7.62-7.58 (m, 3H), 7.31-7.23 (m, 2H), 4.59 (d, J = 10.4 Hz, 1H), 3.76 (d, J = 10.4 Hz, 1H), 3.32 (s, 3H). MS (m/z): 310.3 (M + H). |

TABLE 6-continued

| Ex | Cpd | Structure | Name | Characterization |
|---|---|---|---|---|
| 235 | 475 | 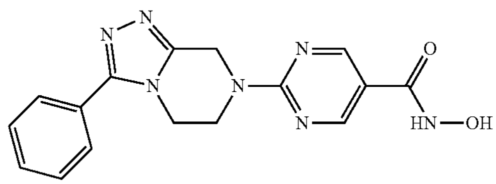 [SMILES: O=C(NO)c1cnc(N2CCn3c(nnc3-c3ccccc3)C2)nc1] | N-hydroxy-2-(3-phenyl-5,6-dihydro-[1,2,4]triazolo[4,3-a]pyrazin-7(8H)-yl)pyrimidine-5-carboxamide | $^1$H NMR (DMSO-d$_6$) δ (ppm): 11.19 (s, 1H), 9.09 (s, 1H), 8.79 (s, 2H), 7.78-7.77 (m, 2H), 7.76-7.75 (m, 3H), 5.20-5.15 (m, 2H), 4.35-4.20 (m, 4H). MS (m/z): 338.4 (M + H). |
| 236 | 481 | 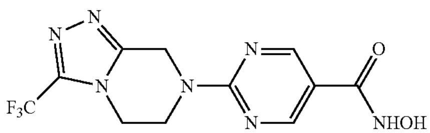 | N-hydroxy-2-(3-(trifluoromethyl)-5,6-dihydro-[1,2,4]triazolo[4,3-a]pyrazin-7(8H)-yl)pyrimidine-5-carboxamide | $^1$H NMR (DMSO-d$_6$) δ (ppm): 11.19 (s, 1H), 9.10 (s, 1H), 8.77 (s, 2H), 5.20 (s, 2H), 4.32 (t, J = 5.1 Hz, 2H), 4.25 (t, J = 4.9 Hz, 2H)... MS (m/z): 330.2 (M + H). |
| 237 | 486 | 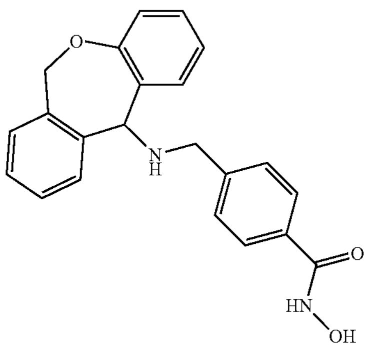 [SMILES: O=C(NO)c1ccc(CNC2c3ccccc3COc3ccccc32)cc1] | 4-((6,11-dihydrodibenzo[b,e]oxepin-11-ylamino)methyl)-N-hydroxybenzamide | $^1$H NMR (DMSO-d$_6$) δ (ppm): 11.14 (s, 1H), 8.99 (s, 1H), 7.70-7.68 (d, J = 7.6 Hz, 2H), 7.38-7.23 (m, 6H), 7.18-7.14 (m, 2H), 6.87 (t, J = 7.0 Hz, 1H), 6.78 (d, J = 7.6 Hz, 1H), 6.44 (d, J = 12.4 Hz, 1H), 4.91 (d, J = 12.4 Hz, 1H), 4.65 (d, J = 2.8 Hz, 1H), 3.63 (d, J = 5.6 Hz, 2H), 3.07 (br s, 1H). MS (m/z): 361.4 (M + H). |
| 238 | 490 | 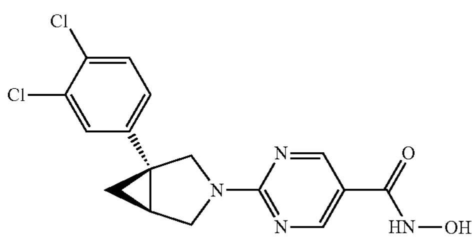 [SMILES: O=C(NO)c1cnc(N2C[C@H]3C[C@@]3(c3ccc(Cl)c(Cl)c3)C2)nc1] | 2-((1R,5S)-1-(3,4-dichlorophenyl)-3-azabicyclo[3.1.0]hexan-3-yl)-N-hydroxypyrimidine-5-carboxamide | $^1$H NMR (CD$_3$OD) δ (ppm): 8.67 (s, 2H), 7.46 (m, 2H), 7.23 (dd, J = 2.4 Hz, 8.4 Hz, 1H), 4.31 (d, J = 11.2 Hz, 1H), 4.07 (d, J = 11.2 Hz, 1H), 3.76 (d, J = 11.2 Hz, 2H), 2.14 (quin, J = 4 Hz, 1H), 1.22 (m, 1H), 0.90 (t, J = 4.8 Hz, 1H). MS (m/z): 363.4 (M − H). |
| 239 | 495 | 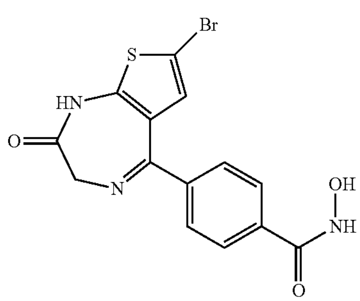 [SMILES: O=C1CN=C(c2ccc(C(=O)NO)cc2)c2cc(Br)sc2N1] | (Z)-4-(7-bromo-2-oxo-2,3-dihydro-1H-thieno[2,3-e][1,4]diazepin-5-yl)-N-hydroxybenzamide | $^1$H NMR (CD$_3$OD) δ (ppm): 7.84 (d, J = 8.4 Hz, 2H), 7.66 (d, J = 8.4 Hz, 2H), 6.85 (s, 1H), 4.36 (s, 2H). MS (m/z): 378.2 (M − H). |
| 240 | 497 | 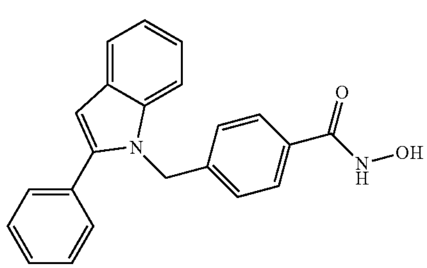 [SMILES: O=C(NO)c1ccc(Cn2c(-c3ccccc3)cc3ccccc32)cc1] | N-hydroxy-4-((2-phenyl-1H-indol-1-yl)methyl)benzamide | $^1$H NMR (CD$_3$OD) δ (ppm): 7.66-7.62 (m, 3H), 7.50-7.38 (m, 5H), 7.28-7.23 (m, 1H), 7.17-7.08 (m, 2H), 7.03 (d, J = 8.4 Hz, 2H), 6.65 (d, J = 0.6 Hz, 1H), 5.51 (s, 2H). MS (m/z): 343.5 (M + H). |

TABLE 6-continued

| Ex | Cpd | Structure | Name | Characterization |
|---|---|---|---|---|
| 241 | 502 | 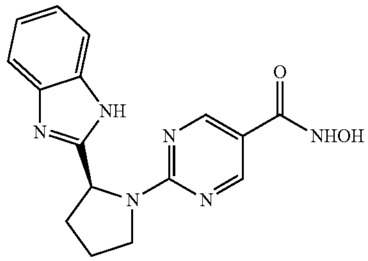 | (S)-2-(2-(1H-benzo[d]imidazol-2-yl)pyrrolidin-1-yl)-N-hydroxypyrimidine-5-carboxamide | ¹H NMR (CD₃OD) δ (ppm): 8.72 (bs, 1H), 8.50 (bs, 1H), 7.46 (s, 2H), 7.17 (m, 2H), 5.48 (d, J = 8.0 Hz, 1H), 4.04 (m, 1H), 3.79 (m, 1H), 2.53 (m, 1H), 2.28 (m, 1H), 2.14 (m, 2H). MS (m/z): 325.3 (M + H). |
| 242 | 504 | 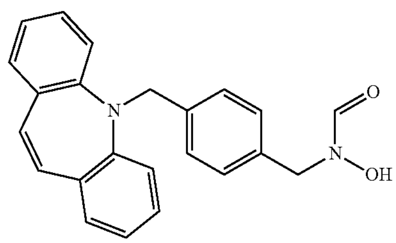 [SMILES: O=CN(O)Cc1ccc(CN2c3ccccc3C=Cc3ccccc32)cc1] | (Z)-N-(4-((5H-dibenzo[b,f]azepin-5-yl)methyl)benzyl)-N-hydroxyformamide | ¹H NMR (CD₃OD) δ (ppm): 8.29 (s, 0.5H), 8.10 (s, 0.5H), 7.46 (t, J = 8.6 Hz, 2H), 7.18-7.12 (m, 4H), 7.09 (d, J = 7.6 Hz, 2H), 7.04 (dd, J = 7.7 and 1.4 Hz, 2H), 6.93 (td, J = 7.4 and 0.8 Hz, 2H), 6.90 (s, 2H), 4.95 (d, J = 3.0 Hz, 2H), 4.58 (s, 1H), 4.53 (s, 1H). MS (m/z): 357.3 (M + H). |
| 243 | 505 | 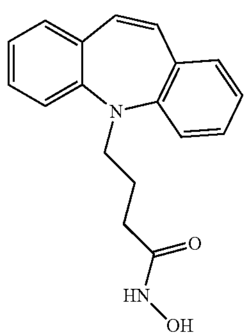 [SMILES: O=C(CCCN1c2ccccc2C=Cc2ccccc21)NO] | (Z)-4-(5H-dibenzo[b,f]azepin-5-yl)-N-hydroxybutanamide | ¹H NMR (CD₃OD) δ (ppm): 7.27-7.22 (2H, m), 7.05 (4H, dd, J = 7.7, 1.8 Hz), 6.99-6.95 (2H, m), 6.73 (2H, s), 3.74 (2H, t, J = 6.7 Hz), 2.16 (2H, t, J = 7.4 Hz), 1.83-1.79 (2H, m). MS (m/z): 295.1 (M + H). |
| 244 | 506 | 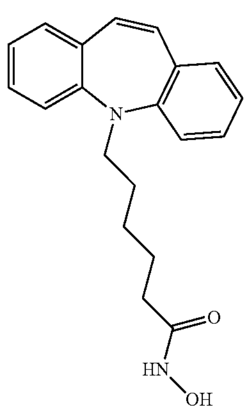 [SMILES: O=C(CCCCCN1c2ccccc2C=Cc2ccccc21)NO] | (Z)-6-(5H-dibenzo[b,f]azepin-5-yl)-N-hydroxyhexanamide | ¹H NMR (CD₃OD) δ (ppm): 7.25-7.19 (2H, m), 7.03-6.98 (4H, m), 6.95-6.91 (2H, m), 6.67 (2H, s), 3.65 (2H, t, J = 6.7 Hz), 1.97 (2H, t, J = 7.6 Hz), 1.55-1.45 (4H, m), 1.4-1.3 (2H, m). MS (m/z): 323.1 (M + H). |

TABLE 6-continued

| Ex | Cpd | Structure | Name | Characterization |
|---|---|---|---|---|
| 245 | 507 | 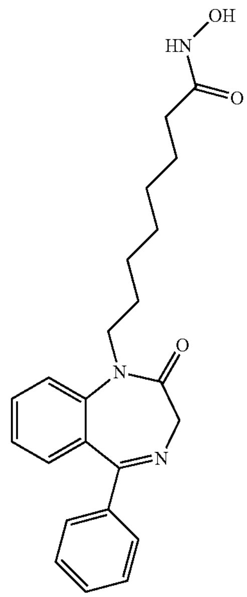 [SMILES: O=C(CCCCCCCN1C(=O)CN=C(c2ccccc2)c2ccccc21)NO] | (Z)-N-hydroxy-8-(2-oxo-5-phenyl-2,3-dihydro-1H-benzo[e][1,4]diazepin-1-yl)octanamide | $^1$H NMR (CD$_3$OD) δ (ppm): 7.69-7.62 (m, 2H), 7.56-7.50 (m, 3H), 7.47-7.43 (m, 2H), 7.33-7.27 (m, 2H), 4.59 (d, J = 10.6 Hz, 1H), 4.48-4.41 (m, 1H), 3.83 (d, J = 10.6 Hz, 1H), 3.78-3.71 (m, 1H), 1.91 (t, J = 6.3 Hz, 2H), 1.52-1.49 (m, 1H), 1.39 (quintet, J = 7.6 Hz, 3H), 1.18-1.03 (m, 6H). MS (m/z): 394.2 (M + H). |
| 246 | 508 | 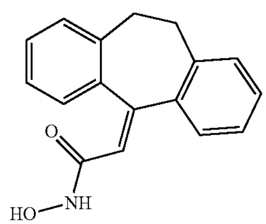 [SMILES: O=C(C=C1c2ccccc2CCc2ccccc21)NO] | | $^1$H NMR (CD$_3$OD) δ (ppm): 7.37-7.26 (1H, m), 7.26-7.40 (7H, m), 6.11 (1H, s), 3.26-2.90 (4H, br m). MS (m/z): 266.0 (M + H). |
| 247 | 509 | 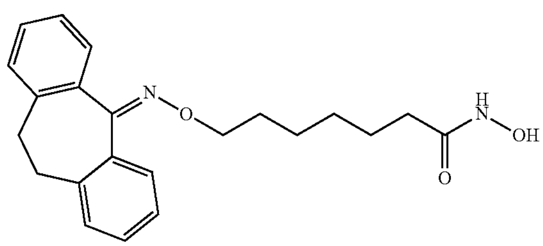 [SMILES: O=C(CCCCCCON=C1c2ccccc2CCc2ccccc21)NO] | | $^1$H NMR (CD$_3$OD) δ (ppm): 7.49 (d, J = 7.7 Hz, 1H), 7.30-7.12 (m, 7H), 4.12 (t, J = 6.5 Hz, 2H), 3.18-3.00 (m, 4H), 2.05 (t, J = 7.4 Hz, 2H), 1.75-1.55 (m, 4H), 1.42-1.22 (m, 4H). MS (m/z): 367.1 (M + H). |
| 248 | 510 | 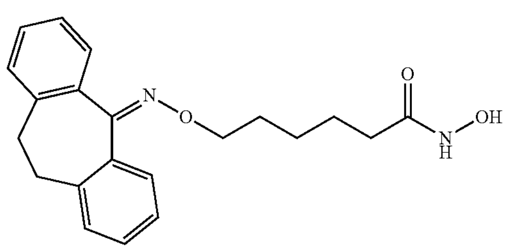 [SMILES: O=C(CCCCCON=C1c2ccccc2CCc2ccccc21)NO] | | $^1$H NMR (CD$_3$OD) δ (ppm): 7.27 (d, J = 6.9 Hz, 1H), 7.35-7.12 (m, 7H), 4.14 (t, J = 6.4 Hz, 2H), 3.18-3.00 (m, 4H), 2.07 (t, J = 7.5 Hz, 2H), 1.75-1.55 (m, 4H), 1.42-1.32 (m, 2H). MS (m/z): 353.1 (M + H). |
| 249 | 511 | 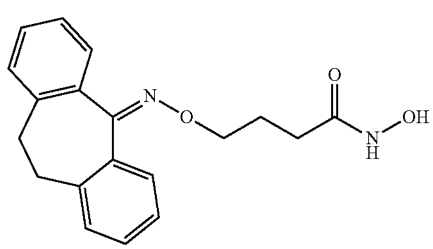 [SMILES: O=C(CCCON=C1c2ccccc2CCc2ccccc21)NO] | | $^1$H NMR (CD$_3$OD) δ (ppm): 7.55 (1H, dd, J = 7.7, 1.2 Hz), 7.35-7.2 (6H, m), 7.19-7.10 (1H, m), 4.18 (2H, t, J = 5.3 Hz), 3.16-3.05 (4H, m), 2.26-2.16 (2H, m), 2.10-1.98 (2H, m). MS (m/z): 325.0 (M + H). |

TABLE 6-continued

| Ex | Cpd | Structure | Name | Characterization |
|---|---|---|---|---|
| 250 | 512 | 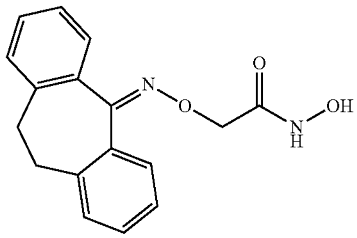 [SMILES: O=C(CON=C1c2ccccc2CCc2ccccc21)NO] | | ¹H NMR (CD₃OD) δ (ppm): 7.52 (dd, J = 7.8, 1.4 Hz, 1H), 7.46 (d, J = 7.5 Hz, 1H), 7.30-7.22 (m, 3H), 7.21-7.15 (m, 3H), 4.53 (s, 2H), 3.18-3.02 (m, 4H). MS (m/z): 297.0 (M + H). |
| 251 | 513 | 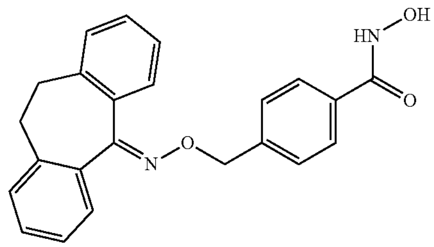 [SMILES: O=C(NO)c1ccc(CON=C2c3ccccc3CCc3ccccc32)cc1] | | ¹H NMR (DMSO-d₆) δ (ppm): 7.69 (2H, d, J = 8.2 Hz), 7.40 (1H, dd, J = 7.7, 1.3 Hz), 7.33-7.12 (9H, m), 5.16 (2H, s), 3.06-2.95 (4H, m). MS (m/z): 373.1 (M + H). |
| 252 | 514 | 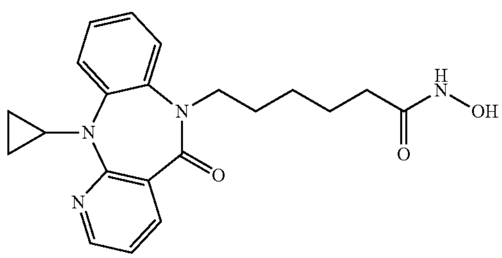 [SMILES: O=C(CCCCCN1C(=O)c2cccnc2N(C2CC2)c2ccccc21)NO] | 6-(11-cyclopropyl-5-oxo-5H-benzo[b]pyrido[2,3-e][1,4]diazepin-6(11H)-yl)-N-hydroxyhexanamide | ¹H NMR (CD₃OD) δ (ppm): 8.36 (dd, J = 4.7, 1.8 Hz, 1H), 8.00 (dd, J = 7.6, 2.0 Hz, 1H), 7.52 (dd, J = 8.0, 1.3 Hz, 1H), 7.37 (dd, J = 8.0, 1.6 Hz, 1H), 7.30-7.17 (m, 2H), 7.14-7.10 (m, 1H), 4.62-4.52 (m, 1H), 3.70-3.55 (m, 2H), 2.05-2.00 (m, 2H), 1.62-1.38 (m, 4H), 1.33-1.20 (m, 2H), 1.08-0.97 (m, 2H), 0.60-0.50 (m, 1H), 0.40-0.30 (m, 1H). MS (m/z): 381.2 (M + H). |
| 253 | 515 | 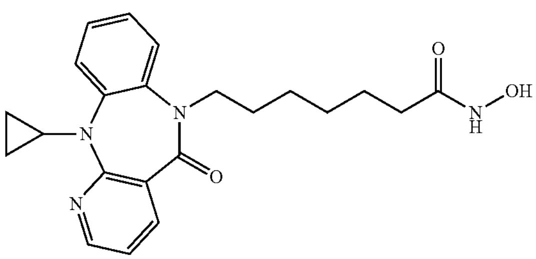 [SMILES: O=C(CCCCCCN1C(=O)c2cccnc2N(C2CC2)c2ccccc21)NO] | 7-(11-cyclopropyl-5-oxo-5H-benzo[b]pyrido[2,3-e][1,4]diazepin-6(11H)-yl)-N-hydroxyheptanamide | ¹H NMR (CD₃OD) δ (ppm): 8.37 (dd, J = 4.6, 2.0 Hz, 1H), 8.00 (dd, J = 7.9, 2.1 Hz, 1H), 7.52 (dd, J = 8.2, 1.4 Hz, 1H), 7.36 (dd, J = 8.1, 1.6 Hz, 1H), 7.30-7.17 (m, 2H), 7.14-7.10 (m, 1H), 4.65-4.52 (m, 1H), 3.70-3.55 (m, 2H), 2.02 (t, J = 7.4 Hz, 2H), 1.60-1.45 (m, 3H), 1.44-1.33 (m, 1H), 1.32-1.16 (m, 4H), 1.08-0.87 (m, 2H), 0.60-0.50 (m, 1H), 0.42-0.35 (m, 1H). MS (m/z): 395.1 (M + H). |
| 254 | 516 | 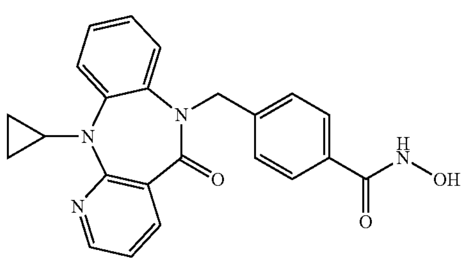 [SMILES: O=C(NO)c1ccc(CN2C(=O)c3cccnc3N(C3CC3)c3ccccc32)cc1] | 4-((11-cyclopropyl-5-oxo-5H-benzo[b]pyrido[2,3-e][1,4]diazepin-6(11H)-yl)methyl-N-hydroxybenzamide | ¹H NMR (CD₃OD) δ (ppm): 8.42-8.38 (m, 1H), 8.10-8.04 (m, 1H), 7.63 (d, J = 8.2 Hz, 2H), 7.47-7.40 (m, 2H), 7.30 (d, J = 8.3 Hz, 2H), 7.22-7.10 (m, 3H), 5.82 (d, J = 15.7 Hz, 1H), 5.00-4.80 (m, 1H), 3.61-3.50 (m, 1H), 1.03-0.97 (m, 1H), 0.88-0.80 (m, 1H), 0.60-0.54 (m, 1H), 0.23-00.17 (m, 1H). MS (m/z): 401.0 (M + H). |
| 256 | 518 | 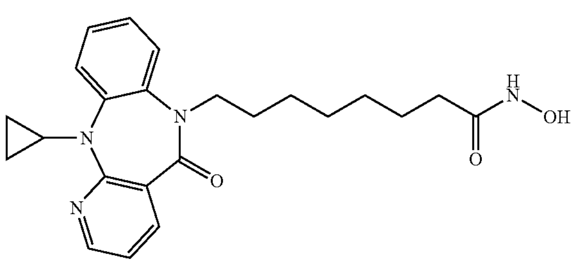 [SMILES: O=C(CCCCCCCN1C(=O)c2cccnc2N(C2CC2)c2ccccc21)NO] | 8-(11-cyclopropyl-5-oxo-5H-benzo[b]pyrido[2,3-e][1,4]diazepin-6(11H)-yl)-N-hydroxyoctanamide | ¹H NMR (CD₃OD) δ (ppm): 8.36 (dd, J = 5.9, 2.0 Hz, 1H), 8.00 (dd, J = 7.6, 2.0 Hz, 1H), 7.52 (dd, J = 8.1, 1.5 Hz, 1H), 7.36 (dd, J = 7.9, 1.6 Hz, 1H), 7.30-7.17 (m, 2H), 7.14-7.10 (m, 1H), 4.65-4.57 (m, 1H), 3.66-3.57 (m, 2H), 2.05-2.01 (m, 2H), 1.62-1.18 (m, 11H), 1.08-0.90 (m, 2H), 0.56-0.50 (m, 1H), 0.42-0.38 (m, 1H). MS (m/z): 409.1 (M + H). |

TABLE 6-continued

| Ex | Cpd | Structure | Name | Characterization |
|---|---|---|---|---|
| 257 | 519 | 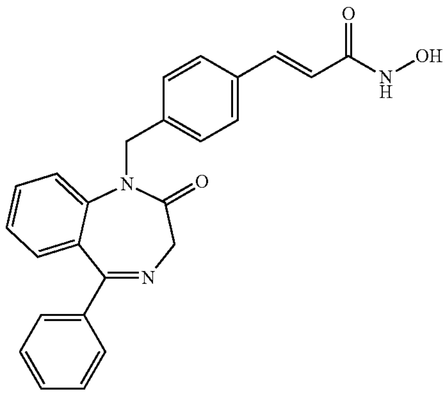 [SMILES: O=C(/C=C/c1ccc(CN2C(=O)CN=C(c3ccccc3)c3ccccc32)cc1)NO] | (E)-N-hydroxy-3-(4-(((Z)-2-oxo-5-phenyl-2,3-dihydro-1H-benzo[e][1,4]diazepin-1-yl)methyl)phenyl)acrylamide | $^1$H NMR (DMSO-d$_6$) δ (ppm): 7.65 (d, J = 7.6 Hz, 1H), 7.57-7.53 (m, 1H), 7.51-7.46 (m, 1H), 7.39 (t, J = 7.8 Hz, 2H), 7.34-7.28 (m, 5H), 7.21-7.17 (m, 1H), 7.17-7.10 (m, 1H), 6.99 (d, J = 8.0 Hz, 2H), 6.32 (d, J = 15.8 Hz, 1H), 5.45 (d, J = 16.0 Hz, 1H), 4.93 (d, J = 16.0 Hz, 1H), 4.62 (d, J = 10.4 Hz, 1H), 3.83 (d, J = 10.4 Hz, 1H). MS (m/z): 412.2 (M + H). |
| 258 | 520 | 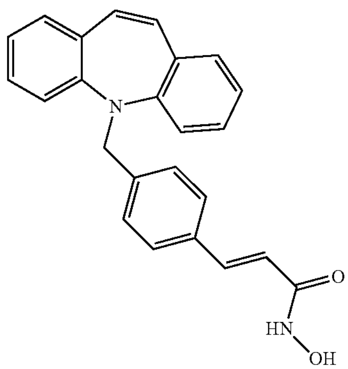 [SMILES: O=C(/C=C/c1ccc(CN2c3ccccc3C=Cc3ccccc32)cc1)NO] | (E)-3-(4-(((Z)-5H-dibenzo[b,f]azepin-5-yl)methyl)phenyl)-N-hydroxyacrylamide | $^1$H NMR (CD$_3$OD) δ (ppm): 7.48 (1H, d, J = 1.5 Hz), 7.45 (2H, d, J = 10.0 Hz), 7.35 (2H, d, J = 8.0 Hz), 7.19-7.13 (2H, m), 7.08 (2H, d, J = 7.6 Hz), 7.05 (2H, dd, J = 7.6, 1.6 Hz), 6.92 (2H, td, J = 7.4, 0.9 Hz), 6.79 (2H, s), 6.34 (1H, d, J = 15.9 Hz), 4.96 (2H, s). MS (m/z): 369.2 (M + H). |
| 259 | 521 | 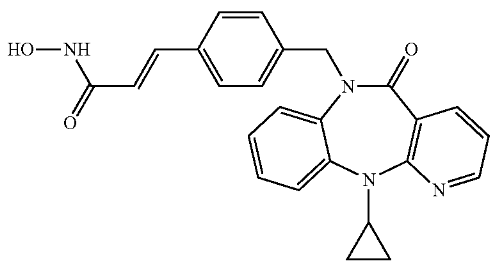 [SMILES: O=C(/C=C/c1ccc(CN2C(=O)c3cccnc3N(C3CC3)c3ccccc32)cc1)NO] | (E)-3-(4-((11-cyclopropyl-5-oxo-5H-benzo[b]pyrido[2,3-e][1,4]diazepin-6(11H)-yl)methyl)phenyl)-N-hydroxyacrylamide | $^1$H NMR (CD$_3$OD) δ (ppm): 8.41-8.36 (1H, m), 8.07 (1H, d, J = 7.6, 1.8 Hz), 7.49 (1H, d, J = 15.8 Hz), 7.46-7.40 (4H, m), 7.26-7.10 (5H, m), 6.40 (1H, d, J = 15.8 Hz), 5.80 (1H, d, J = 15.4 Hz), 4.84 (1H, d, J = 15.7 Hz), 3.60-3.50 (1H, m), 1.02-0.92 (1H, m), 0.84-0.74 (1H, m), 0.58-0.48 (1H, m), 0.16-0.06 (1H, m). MS (m/z): 427.2 (M + H). |
| 260 | 522 | 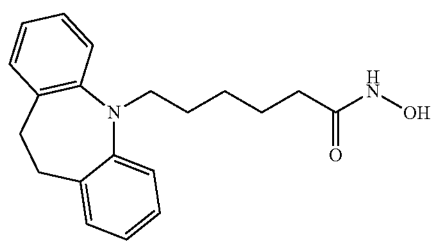 [SMILES: O=C(CCCCCN1c2ccccc2CCc2ccccc21)NO] | 6-(10,11-dihydro-5H-dibenzo[b,f]azepin-5-yl)-N-hydroxyhexanamide | $^1$H NMR (CDCl$_3$) δ (ppm): 7.11-7.02 (m, 6H), 6.87 (t, J = 7.4 Hz, 2H), 3.60 (t, J = 6.6 Hz, 2H), 1.87-1.77 (m, 2H), 3.10 (s, 4H), 1.51-1.33 (m, 4H), 1.26-1.14 (m, 2H). MS (m/z): 325.2 (M + H). |
| 261 | 523 | 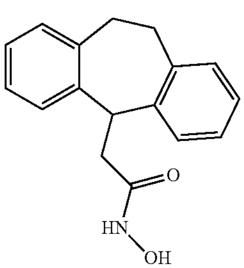 [SMILES: O=C(CC1c2ccccc2CCc2ccccc21)NO] | | $^1$H NMR (CD$_3$OD) δ (ppm): 7.23-7.19 (2H, m), 7.11-7.06 (6H, m), 4.65 (1H, t, J = 7.8 Hz), 3.4-3.31 (2H, m), 3.05-2.98 (2H, m), 2.80 (2H, d, J = 7.8 Hz). |

TABLE 6-continued

| Ex | Cpd | Structure | Name | Characterization |
|---|---|---|---|---|
| 262 | 524 | 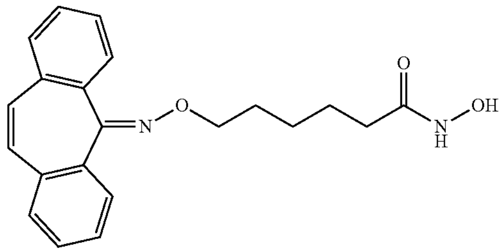 [SMILES: O=C(CCCCCON=c1c2ccccc2ccc2ccccc12)NO] | | ¹H NMR (CD₃OD) δ (ppm): 7.55-7.53 (m, 2H), 7.45-7.36 (m, 6H), 6.93 (s, 2H), 4.16-4.02 (m, 2H), 2.06 (t, J = 7.2 Hz, 2H), 1.68-1.57 (m, 4H), 1.39-1.31 (m, 2H). MS (m/z): 351.0 (M + H). |
| 263 | 525 | 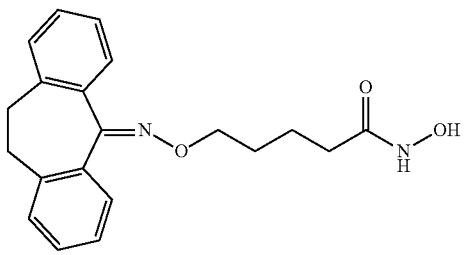 [SMILES: O=C(CCCCON=C1c2ccccc2CCc2ccccc21)NO] | | ¹H NMR (CD₃OD) δ (ppm): 7.53-7.51 (m, 1H), 7.32-7.14 (m, 7H), 4.16 (t, J = 5.6 Hz, 2H), 3.12-3.04 (m, 4H), 2.12-2.09 (m, 2H), 1.68 (br s, 4H). MS (m/z): 339.2 (M + H). |
| 264 | 526 | 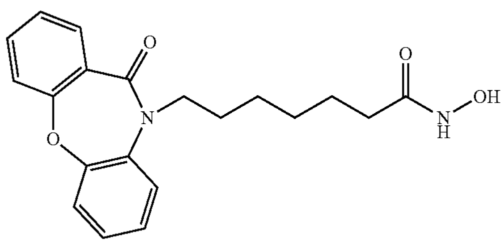 [SMILES: O=C(CCCCCCN1C(=O)c2ccccc2Oc2ccccc21)NO] | N-hydroxy-7-(11-oxodibenzo[b,f][1,4]oxazepin-10(11H)-yl)heptanamide | ¹H NMR (CD₃OD) δ (ppm): 7.75-7.23 (m, 1H), 7.54-7.50 (m, 1H), 7.46 (dd, J = 7.8, 1.6 Hz, 1H), 7.32 (dd, J = 7.4, 2.2 Hz, 1H), 7.28-7.20 (m, 4H), 4.18 (br s, 2H), 2.04 (t, J = 7.4 Hz, 2H), 1.70-1.53 (m, 4H), 1.41-1.28 (m, 4H). MS (m/z): 355.2 (M + H). |
| 265 | 527 | 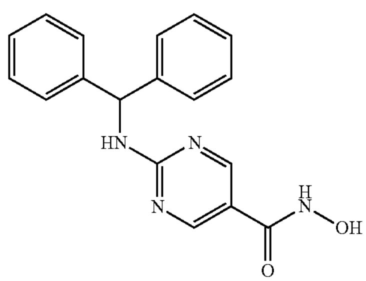 [SMILES: O=C(NO)c1cnc(NC(c2ccccc2)c2ccccc2)nc1] | 2-(benzhydrylamino)-N-hydroxypyrimidine-5-carboxamide | ¹H NMR (DMSO-d₆) δ (ppm): 11.01 (s, 1H), 8.99 (s, 1H), 8.77 (d, J = 9.4 Hz, 1H), 8.61 (s, 2H), 7.38 (d, J = 7.4 Hz, 4H), 7.31 (t, J = 7.5 Hz, 4H), 7.22 (t, J = 7.3 Hz, 2H), 6.43 (d, J = 9.2 Hz, 1H). MS (m/z): 319.2 (M − H). |
| 266 | 528 | 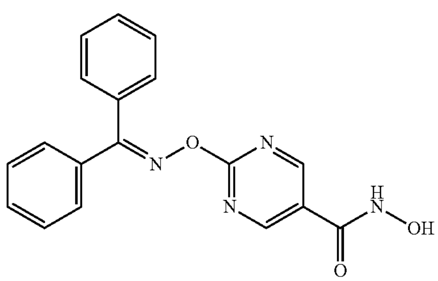 [SMILES: O=C(NO)c1cnc(ON=C(c2ccccc2)c2ccccc2)nc1] | 2-(diphenylmethyleneamino-oxy)-N-hydroxypyrimidine-5-carboxamide | ¹H NMR (DMSO-d₆) δ (ppm): 11.3 (s, 1H), 8.64 (s, 2H), 7.26-7.4 (m, 10H), 6.42 (s, 1H). |
| 267 | 529 | 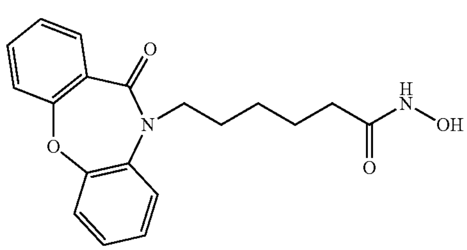 [SMILES: O=C(CCCCCN1C(=O)c2ccccc2Oc2ccccc21)NO] | N-hydroxy-6-(11-oxodibenzo[b,f][1,4]oxazepin-10(11H)-yl)hexanamide | ¹H NMR (CD₃OD) δ (ppm): 7.73 (dd, J = 8.2, 2.0 Hz, 1H), 7.54-7.45 (m, 2H), 7.31 (dd, J = 7.4, 2.2 Hz, 1H), 7.27-7.19 (m, 4H), 4.17 (br s, 2H), 2.05 (t, J = 7.0 Hz, 2H), 1.71-1.57 (m, 4H), 1.41-1.34 (m, 2H). MS (m/z): 341.1 (M + H). |

TABLE 6-continued

| Ex | Cpd | Structure | Name | Characterization |
|---|---|---|---|---|
| 268 | 530 | 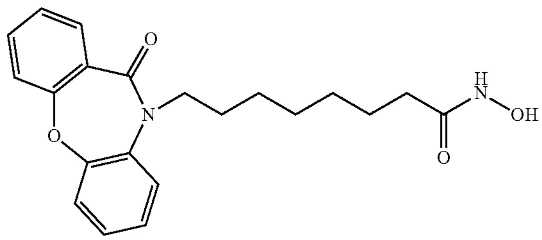 [SMILES: O=C(CCCCCCCN1C(=O)c2ccccc2Oc2ccccc21)NO] | N-hydroxy-8-(11-oxodibenzo[b,f][1,4]oxazepin-10(11H)-yl)octanamide | ¹H NMR (CD₃OD) δ (ppm): 7.73 (dd, J = 8.0, 1.8 Hz, 1H), 7.53-7.45 (m, 2H), 7.33-7.20 (m, 5H), 4.18 (br s, 2H), 2.05 (t, J = 7.4 Hz, 2H), 1.68-1.54 (m, 4H), 1.33-1.29 (m, 6H). MS (m/z): 369.2 (M + H). |
| 269 | 531 | 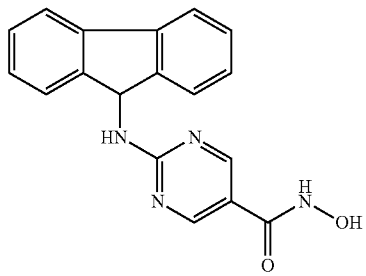 [SMILES: O=C(NO)c1cnc(NC2c3ccccc3-c3ccccc32)nc1] | 2-(9H-fluoren-9-ylamino)-N-hydroxypyrimidine-5-carboxamide | ¹H NMR (DMSO-d₆) δ (ppm): 8.68 (br s, 2H), 8.23 (d, J = 8.8 Hz, 1H), 7.85 (d, J =7.7 Hz, 2H), 7.47 (d, J = 7.4 Hz, 2H), 7.40 (t, J = 7.5 Hz, 2H), 7.28 (t, J = 7.4 Hz, 2H), 6.33 (m, 1H). MS (m/z): 319.2 (M + H). |
| 270 | 532 | 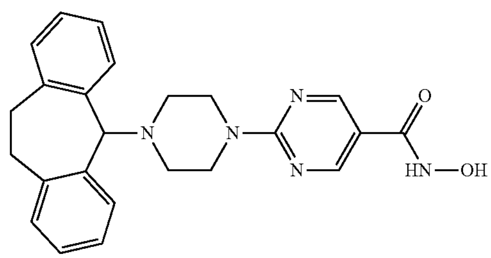 [SMILES: O=C(NO)c1cnc(N2CCN(C3c4ccccc4CCc4ccccc43)CC2)nc1] | | ¹H NMR (DMSO-d₆) δ (ppm): 11.05 (br s, 1H), 8.99 (br s, 1H), 8.62 (s, 2H), 7.22-7.04 (m, 8H), 4.05 (s, 1H), 4.01-3.90 (m, 2H), 3.72 (s, 4H), 2.82-2.70 (m, 2H), 2.29-2.20 (m, 4H). MS (m/z): 414.2 (M + H). LRMS: 415.2 (calc), 414.2 (MH)– |
| 271 | 533 | 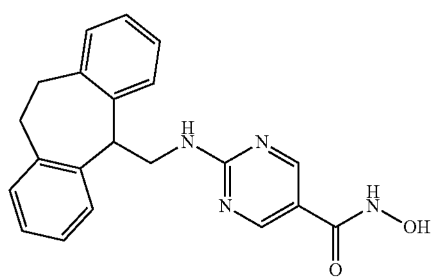 [SMILES: O=C(NO)c1cnc(NCC2c3ccccc3CCc3ccccc32)nc1] | | ¹H NMR (CD₃OD) δ (ppm): 8.64 (m, 1H), 8.49 (m, 1H), 7.06-7.17 (m, 8H), 4.40 (t, J = 8 Hz, 1H), 4.00 (d, J = 8 Hz, 2H), 3.44 (m, 2H), 2.96 (m, 2H). MS (m/z): 359.3 (M – H). |
| 272 | 534 | 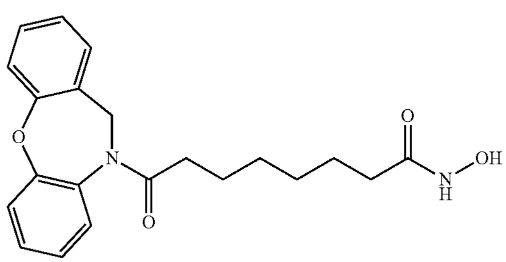 [SMILES: O=C(CCCCCCC(=O)N1Cc2ccccc2Oc2ccccc21)NO] | 8-(dibenzo[b,f][1,4]oxazepin-10(11H)-yl)-N-hydroxy-8-oxooctanamide | ¹H NMR (CD₃OD) δ (ppm): 7.44-7.38 (m, 2H), 7.36-7.31 (m, 1H), 7.30-7.14 (m, 4H), 7.04 (t, J = 7.4 Hz, 1H), 6.00-5.20 (m, 1H), 4.50-4.00 (m, 1H), 2.28-2.18 (m, 2H), 1.99 (t, J = 7.5 Hz, 2H), 1.56-1.40 (m, 4H), 1.22-1.08 (m, 4H). MS (m/z): 369.4 (M + H). |
| 273 | 535 | 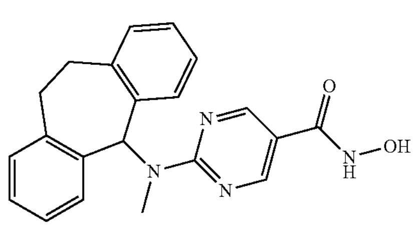 [SMILES: CN(c1ncc(C(=O)NO)cn1)C1c2ccccc2CCc2ccccc21] | | ¹H NMR (DMSO-d₆) δ (ppm): 8.71 (s, 2H), 7.37 (s, 1H), 7.31 (d, J = 7.0 Hz, 2H), 7.20-7.13 (m, 6H), 3.30-3.17 (m, 2H), 3.02-2.94 (m, 2H), 2.90 (s, 3H). MS (m/z): 359.3 (MH)–. |

TABLE 6-continued

| Ex | Cpd | Structure | Name | Characterization |
|---|---|---|---|---|
| 274 | 536 | 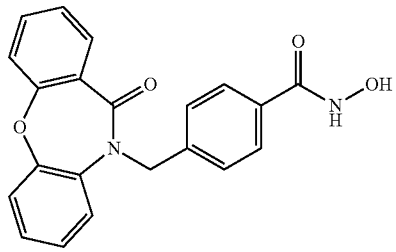 [SMILES: O=C(NO)c1ccc(CN2C(=O)c3ccccc3Oc3ccccc32)cc1] | N-hydroxy-4-((11-oxodibenzo[b,f][1,4]oxazepin-10(11H)-yl)methyl)benzamide | $^1$H NMR (CD$_3$OD) δ (ppm): 7.81-7.79 (m, 1H), 7.69 (dt, J = 8.4, 2.0 Hz, 2H), 7.58-7.53 (m, 1H), 7.42-7.36 (m, 3H), 7.31-7.27 (m, 3H), 7.18-7.12 (m, 2H), 5.43 (s, 2H). MS (m/z): 361.3 (M + H). |
| 275 | 537 | 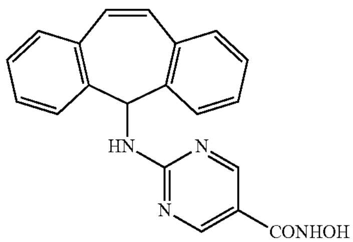 | | $^1$H NMR (DMSO-d$_6$) δ (ppm): 11.01 (s, 1H), 8.99 (s, 1H), 8.68-8.51 (m, 2H), 7.72 (d, J = 7.8 Hz, 2H), 7.42-7.38 (m, 4H), 7.29-7.24 (m, 4H), 5.95 (br s, 1H). MS (m/z): 343.5 (M − H). |
| 276 | 538 | 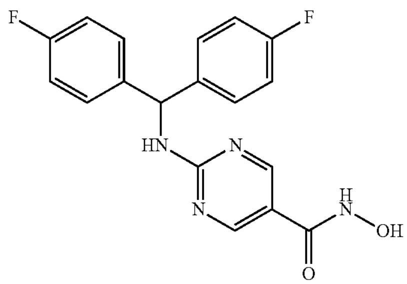 [SMILES: O=C(NO)c1cnc(NC(c2ccc(F)cc2)c2ccc(F)cc2)nc1] | 2-(bis(4-fluorophenyl)methylamino)-N-hydroxypyrimidine-5-carboxamide | $^1$H NMR (CD$_3$OD) δ (ppm): 8.62 (s, 2H) ,7.32 (m, 4H), 7.04 (t, J = 8.4 Hz, 4H), 6.40 (s, 1H). MS (m/z): 355.3 (M − H). |
| 277 | 539 | 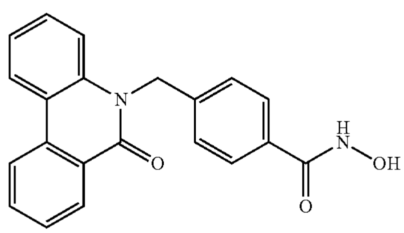 [SMILES: O=C(NO)c1ccc(Cn2c(=O)c3ccccc3c3ccccc32)cc1] | N-hydroxy-4-((6-oxophenanthridin-5(6H)-yl)methyl)benzamide | $^1$H NMR (DMSO-d$_6$) δ (ppm) 11.05 (br s, 1H), 9.00 (br s, 1H), 8.58 (d, J = 8.2 Hz, 1H), 8.52 (d, J = 7.3 Hz, 1H), 8.45-8.40 (m, 1H), 7.94-7.86 (m, 1H), 7.73-7.62 (m, 3H), 7.49-7.43 (m, 1H), 7.40-7.34 (m, 1H), 7.34-7.28 (m, 1H), 7.28-7.23 (m, 2H), 5.66 (s, 2H). MS (m/z): 343.3 (MH)−. |
| 278 | 540 | 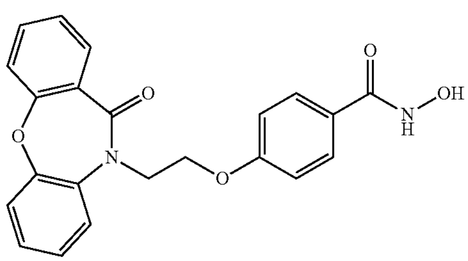 [SMILES: O=C(NO)c1ccc(OCCN2C(=O)c3ccccc3Oc3ccccc32)cc1] | N-hydroxy-4-(2-(11-oxodibenzo[b,f][1,4]oxazepin-10(11H)-yl)ethoxy)benzamide | $^1$H NMR (DMSO-d$_6$) δ (ppm) 11.06 (s, 1H), 8.91 (s, 1H), 7.73-7.66 (m, 4H), 7.59-7.54 (m, 1H), 7.39-7.21 (m, 5H), 6.91 (d, J = 9.0 Hz, 2H), 4.45 (br s, 2H), 4.33 (t, J = 5.5 Hz, 2H). MS (m/z): 413.4 (M + Na). |
| 279 | 541 | 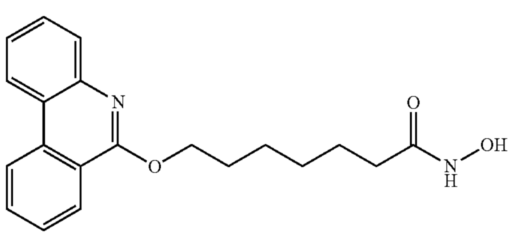 [SMILES: O=C(CCCCCCOc1nc2ccccc2c2ccccc12)NO] | N-hydroxy-7-(phenanthridin-6-yloxy)heptanamide | $^1$H NMR (DMSO-d$_6$) δ (ppm) 10.33 (s, 1H), 8.73 (d, J = 8.2 Hz, 1H), 8.66 (br s, 1H), 8.62 (d, J = 8.3 Hz, 1H), 8.29 (d, J = 7.6 Hz, 1H), 7.95-7.88 (m, 1H), 7.80-7.70 (m, 2H), 7.68-7.60 (m, 1H), 7.54-7.48 (m, 1H), 4.55 (t, J = 16.4 Hz, 2H), 1.95 (t, J = 7.2 Hz, 2H), 1.91-1.81 (m, 2H), 1.58-1.45 (m, 4H), 1.42-1.30 (m, 2H). MS (m/z): 339.4 (M + H). |

TABLE 6-continued

| Ex | Cpd | Structure | Name | Characterization |
|---|---|---|---|---|
| 280 | 542 | 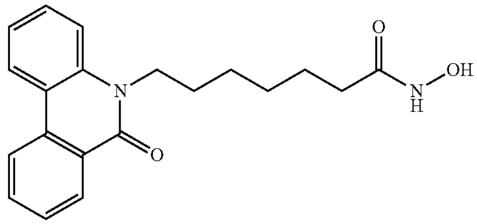 [SMILES: O=C(CCCCCCn1c(=O)c2ccccc2c2ccccc21)NO] | N-hydroxy-7-(6-oxophenanthridin-5(6H)-yl)heptanamide | ¹H NMR (CDCl₃) δ (ppm): 9.47 (s, 1H), 8.51 (d, J = 7.9 Hz, 1H), 8.28 (t, J = 8.6 Hz, 2H), 7.80-7.72 (m, 1H), 7.62-7.51 (m, 2H), 7.39 (d, J = 8.4 Hz, 1H), 7.32 (t, J = 7.5 Hz, 1H), 4.38 (t, J = 7.3 Hz, 2H), 2.22 (t, J = 7.0 Hz, 2H), 1.86-1.62 (m, 4H), 1.52-1.42 (m, 4H). MS (m/z): 337.4 (MH)–. |
| 281 | 543 | 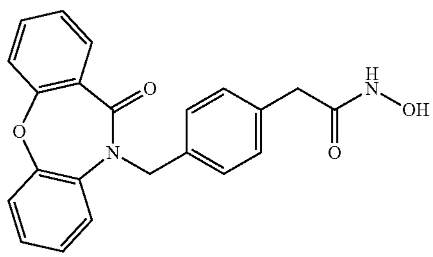 [SMILES: O=C(Cc1ccc(CN2C(=O)c3ccccc3Oc3ccccc32)cc1)NO] | N-hydroxy-2-(4-((11-oxodibenzo[b,f][1,4]oxazepin-10(11H)-yl)methyl)phenyl)acetamide | ¹H NMR (DMSO-d₆) δ (ppm): 10.62 (s, 1H), 8.79 (s, 1H), 7.76 (dd, J = 8.0, 1.6 Hz, 1H), 7.59 (ddd, J = 8.0, 7.2, 1.6 Hz, 1H), 7.49-7.46 (m, 1H), 7.38-7.30 (m, 3H), 7.21-7.14 (m, 6H), 5.33 (s, 2H), 3.22 (s, 2H). MS (m/z): 397.4 (M + Na). |
| 282 | 544 | 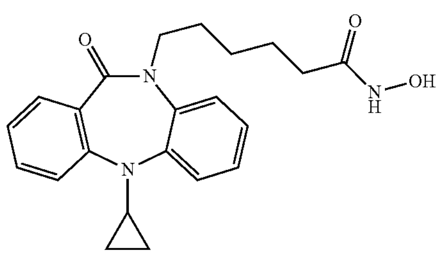 [SMILES: O=C(CCCCCN1C(=O)c2ccccc2N(C2CC2)c2ccccc21)NO] | 6-(5-cyclopropyl-11-oxo-5H-dibenzo[b,e][1,4]diazepin-10(11H)-yl)-N-hydroxyhexanamide | 7.70 (d, J = 7.6 Hz, 1H), 7.42-7.35 (m, 2H), 7.28 (d, J = 8.4 Hz, 1H), 7.25-7.00 (m, 4H), 4.65-4.55 (m, 1H), 3.63-3.53 (m, 1H), 3.25-3.05 (m, 1H), 2.20-2.05 (m, 2H), 1.76-1.40 (m, 4H), 1.39-1.10 (m, 2H), 1.00-0.08 (m, 2H), 0.07-0.05 (m, 1H), 0.05-0.04 (m, 1H). MS (m/z): 378.4 (MH)– |
| 283 | 545 | 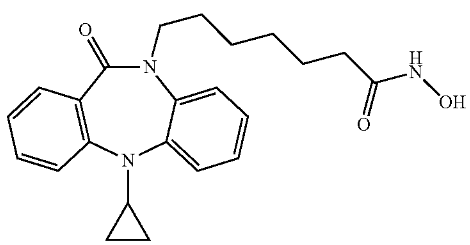 [SMILES: O=C(CCCCCCN1C(=O)c2ccccc2N(C2CC2)c2ccccc21)NO] | 7-(5-cyclopropyl-11-oxo-5H-dibenzo[b,e][1,4]diazepin-10(11H)-yl)-N-hydroxyheptanamide | 7.70 (d, J = 7.6 Hz, 1H), 7.37 (t, J = 7.5 Hz, 2H), 7.25-7.02 (m, 5H), 4.78-4.60 (m, 1H), 3.46-3.60 (m, 1H), 3.27-3.18 (m, 1H), 2.18-1.95 (m, 2H), 1.80-1.01 (m, 8H), 1.00-0.82 (m, 2H), 0.65-0.59 (m, 1H), 0.58-0.43 (m, 1H). MS (m/z): 392.5 (MH)– |
| 284 | 546 | 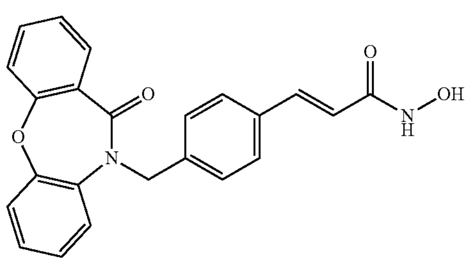 [SMILES: O=C(/C=C/c1ccc(CN2C(=O)c3ccccc3Oc3ccccc32)cc1)NO] | (E)-N-hydroxy-3-(4-((11-oxodibenzo[b,f][1,4]oxazepin-10(11H)-yl)methyl)phenyl)acrylamide | ¹H NMR (DMSO-d₆) δ (ppm): 10.75 (s, 1H), 9.04 (s, 1H), 7.77 (dd, J = 8.0, 1.6 Hz, 1H), 7.63-7.58 (m, 1H), 7.51-7.30 (m, 9H), 7.21-7.15 (m, 2H), 6.40 (d, J = 15.6 Hz, 1H), 5.38 (s, 2H). MS (m/z): 387.3 (M + H). |
| 285 | 547 | 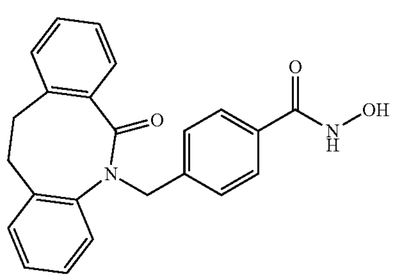 [SMILES: O=C(NO)c1ccc(CN2C(=O)c3ccccc3CCc3ccccc32)cc1] | N-hydroxy-4-((6-oxo-11,12-dihydrodibenzo[b,f]azocin-5(6H)-yl)methyl)benzamide | ¹H NMR (DMSO-d₆) δ (ppm): 11.21 (s, 1H), 9.03 (s, 1H), 7.69 (d, J = 8.4 Hz, 2H), 7.33 (d, J = 8.4 Hz, 2H), 7.16-6.95 (m, 8H), 5.26 (d, J = 14.4 Hz, 1H), 4.77 (d, J = 14.4 Hz, 1H), 3.19-3.11 (m, 1H), 2.90-2.83 (m, 1H), 2.71-2.55 (m, 2H). MS (m/z): 373.2 (M + H). |

TABLE 6-continued

| Ex | Cpd | Structure | Name | Characterization |
|---|---|---|---|---|
| 287 | 549 | 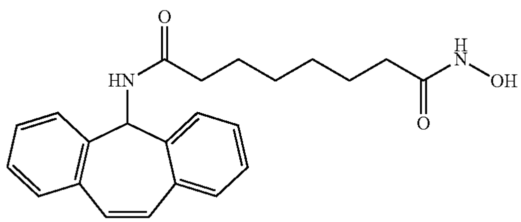 [SMILES: O=C(CCCCCCC(=O)NC1c2ccccc2C=Cc2ccccc21)NO] | | $^{1}$H NMR (DMSO-d$_{6}$) δ (ppm): 7.56 (d, J = 7.4 Hz, 2H), 7.42-7.36 (m, 4H), 7.28-7.26 (m, 2H), 7.17 (s, 2H), 5.63 (s, 1H), 2.26 (br s, 2H), 1.90 (t, J = 7.4 Hz, 2H), 1.52-1.36 (m, 4H), 1.30-1.10 (m, 4H). MS (m/z): 377.5 (M − H). |
| 288 | 550 | 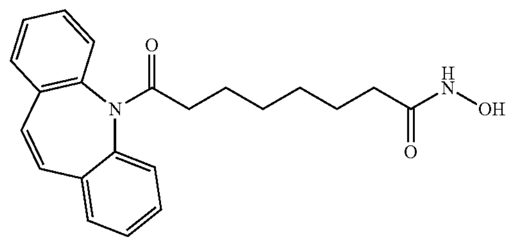 [SMILES: O=C(CCCCCCC(=O)N1c2ccccc2C=Cc2ccccc21)NO] | (Z)-8-(5H-dibenzo[b,f]azepin-5-yl)-N-hydroxy-8-oxooctanamide | $^{1}$H NMR (DMSO-d$_{6}$) δ (ppm): 10.28 (s, 1H), 8.64 (s, 1H), 7.59-7.31 (m, 8H), 7.02 (s, 2H), 2.19-2.10 (m, 1H), 1.84 (t, J = 7.4 Hz, 2H), 1.81-1.71 (m, 1H), 1.40-1.20 (m, 4H), 1.15-0.99 (m, 4H). MS (m/z): 363.4 (M − H). |
| 289 | 551 | 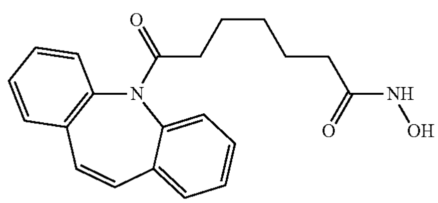 [SMILES: O=C(CCCCCC(=O)N1c2ccccc2C=Cc2ccccc21)NO] | (Z)-7-(5H-dibenzo[b,f]azepin-5-yl)-N-hydroxy-7-oxoheptanamide | $^{1}$H NMR (DMSO-d$_{6}$) δ (ppm): 10.28 (s, 1H), 8.63 (s, 1H), 7.60-7.30 (m, 8H), 7.03 (s, 2H), 2.21-2.09 (m, 1H), 1.82 (t, J = 7.4 Hz, 2H), 1.79-1.69 (m, 1H), 1.41-1.24 (m, 4H), 1.09-0.85 (m, 2H). MS (m/z): 351.4 (M + H). |
| 290 | 552 | 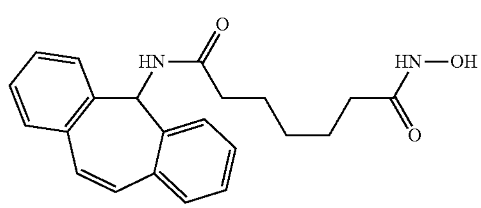 [SMILES: O=C(CCCCCC(=O)NC1c2ccccc2C=Cc2ccccc21)NO] | | $^{1}$H NMR (DMSO-d$_{6}$) δ (ppm): 10.33 (s, 1H), 8.69 (s, 1H), 7.56 (d, J = 7.6 Hz, 2H), 7.43-7.35 (m, 4H), 7.29-7.23 (m, 2H), 7.17 (s, 2H), 5.63 (s, 1H), 2.34-2.18 (m, 2H), 1.90 (t, J = 7.5 Hz, 2H), 1.54-1.40 (m, 4H), 1.25-1.11 (m, 2H). MS (m/z): 363.4 (M − H). |
| 291 | 553 | 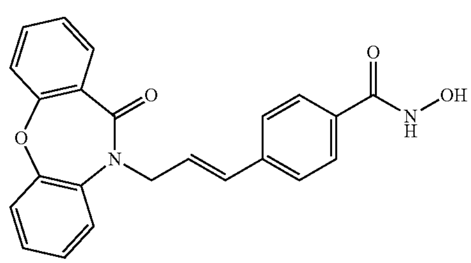 [SMILES: O=C(NO)c1ccc(/C=C/CN2C(=O)c3ccccc3Oc3ccccc32)cc1] | (E)-N-hydroxy-4-(3-(11-oxodibenzo[b,f][1,4]oxazepin-10(11H)-yl)prop-1-enyl)benzamide | $^{1}$H NMR (DMSO-d$_{6}$) δ (ppm): 11.20 (s, 1H), 9.00 (s, 1H), 7.76 (dd, J = 7.6, 1.6 Hz, 1H), 7.69 (d, J = 8.4 Hz, 2H), 7.62-7.55 (m, 2H), 7.48 (d, J = 8.4 Hz, 2H), 7.41-7.20 (m, 5H), 6.65 (d, J = 16.0 Hz, 1H), 6.53 (dt, J = 16.0, 4.4 Hz, 1H), 4.86 (d, J = 4.4 Hz, 2H). MS (m/z) 387.2 (M + H). |
| 292 | 554 | 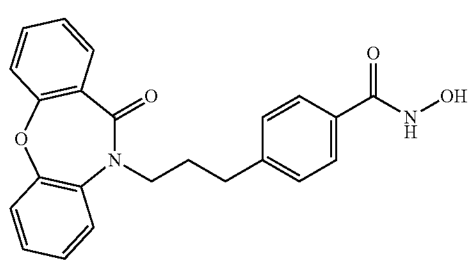 [SMILES: O=C(NO)c1ccc(CCCN2C(=O)c3ccccc3Oc3ccccc32)cc1] | N-hydroxy-4-(3-(11-oxodibenzo[b,f][1,4]oxazepin-10(11H)-yl)propyl)benzamide | $^{1}$H NMR (DMSO-d$_{6}$) δ (ppm): 11.13 (s, 1H), 8.97 (s, 1H), 7.71 (dd, J = 8.0, 2.0 Hz, 2H), 7.63 (d, J = 8.4 Hz, 2H), 7.59-7.54 (m, 1H), 7.43-7.40 (m, 1H), 7.35 (dd, J = 8.0, 0.8 Hz, 1H), 7.31-7.22 (m, 3H), 7.17 (d, J = 8.4 Hz, 2H), 4.12 (br s, 2H), 2.62 (t, J = 7.6 Hz, 2H), 1.92-1.86 (m, 2H). MS (m/z): 389.3 (M + H). |

TABLE 6-continued

| Ex | Cpd | Structure | Name | Characterization |
|---|---|---|---|---|
| 293 | 555 | 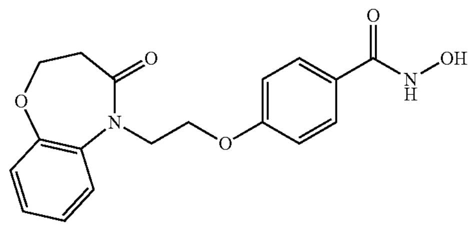 [SMILES: O=C(NO)c1ccc(OCCN2C(=O)CCOc3ccccc32)cc1] | N-hydroxy-4-(2-(4-oxo-3,4-dihydrobenzo[b][1,4]oxazepin-5(2H)-yl)ethoxy)benzamide | $^1$H NMR (DMSO-d$_6$) δ (ppm): 11.05 (s, 1H), 8.90 (s, 1H), 7.67 (d, J = 8.8 Hz, 2H), 7.58-7.55 (m, 1H), 7.28-7.21 (m, 2H), 7.14-7.12 (m, 1H), 6.87 (d, J = 8.8 Hz, 2H), 4.45 (t, J = 6.8 Hz, 2H), 4.18-4.15 (m, 2H), 4.10-4.07 (m, 2H), 2.53 (t, J = 6.8 Hz, 2H). MS (m/z): 343.3 (M + H). |
| 294 | 556 | 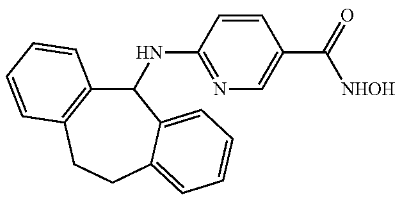 | | $^1$H NMR (DMSO-d$_6$) δ (ppm): 10.87 (s, 1H), 8.82 (s, 1H), 8.34 (d, J = 2.0 Hz, 1H), 8.13 (d, J = 8.4 Hz, 1H), 7.73 (dd, J = 7.3, 2.3 Hz, 1H), 7.45-7.40 (m, 2H), 7.18-7.06 (m, 6H), 6.81-6.75 (m, 2H), 3.23 (s, 4H). MS (m/z): 346.2 (M + H). |
| 295 | 557 | 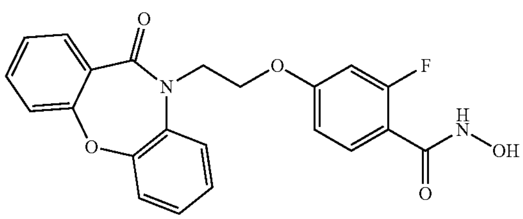 [SMILES: O=C(NO)c1ccc(OCCN2C(=O)c3ccccc3Oc3ccccc32)cc1F] | 2-fluoro-N-hydroxy-4-(2-(11-oxodibenzo[b,f][1,4]oxazepin-10(11H)-yl)ethoxy)benzamide | $^1$H NMR (CD$_3$OD) δ (ppm): 7.72 (d, J = 8.0 Hz, 1H), 7.62-7.56 (m, 2H), 7.49 (t, J = 7.4 Hz, 1H), 7.29-7.17 (m, 5H), 6.74 (d, J = 8.8 Hz, 1H), 6.68 (d, J = 12.7 Hz, 1H), 4.49 (br s, 2H), 4.38-4.34 (m, 2H). MS (m/z): 409.2 (M + H). |
| 296 | 558 | 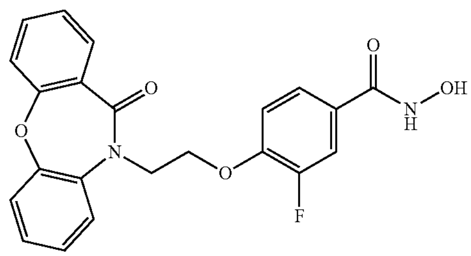 [SMILES: O=C(NO)c1ccc(OCCN2C(=O)c3ccccc3Oc3ccccc32)c(F)c1] | 3-fluoro-N-hydroxy-4-(2-(11-oxodibenzo[b,f][1,4]oxazepin-10(11H)-yl)ethoxy)benzamide | $^1$H NMR (CD$_3$OD) δ (ppm): 7.75-7.71 (m, 2H), 7.54-7.46 (m, 3H), 7.31-7.15 (m, 6H), 4.51 (s, 4H). MS (m/z): 409.2 (M + H). |
| 297 | 559 | 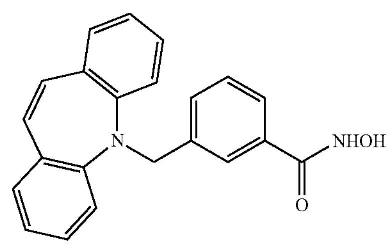 | (Z)-3-((5H-dibenzo[b,f]azepin-5-yl)methyl)-N-hydroxybenzamide | $^1$H NMR (CD$_3$OD) δ (ppm): 7.90-7.86 (m, 1H), 7.70-7.65 (m, 1H), 7.51-7.46 (m, 1H), 7.28 (t, J = 7.6 Hz, 1H), 7.23-7.06 (m, 6H), 6.98-6.93 (m, 2H), 6.83 (s, 2H), 5.03 (s, 2H). MS (m/z): 343.4 (M + H). |
| 298 | 560 | 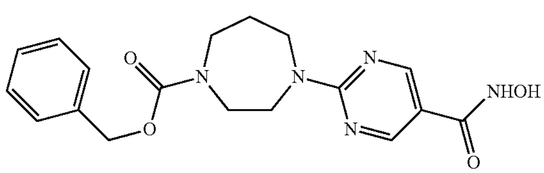 | benzyl 4-(5-(hydroxycarbamoyl)pyrimidin-2-yl)-1,4-diazepane-1-carboxylate | $^1$H NMR (DMSO-d$_6$) δ (ppm): 11.05 (s, 1H), 9.05 (s, 1H), 8.65 (s, 2H), 7.33-7.17 (m, 5H), 5.74 (s, 1H), 5.01 (s, 1H), 3.93-3.83 (m, 2H), 3.82-3.70 (m, 2H), 3.62 (t, J = 5.9 Hz, 1H), 3.56 (t, J = 5.6 Hz, 1H), 3.45-3.30 (m, 2H), 1.8-1.68 (m, 2H). MS (m/z): 372.4 (M + H). |
| 299 | 561 | 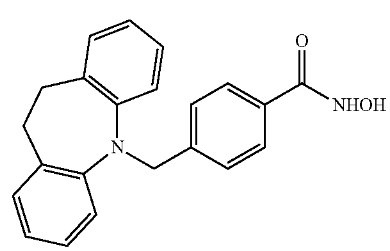 | 4-((10,11-dihydro-5H-dibenzo[b,f]azepin-5-yl)methyl)-N-hydroxybenzamide | $^1$H NMR (CD$_3$OD) δ (ppm): 7.62 (d, J = 8.2 Hz, 2H), 7.53 (d, J = 8.4 Hz, 2H), 7.19-7.02 (m, 6H), 6.92-6.84 (m, 2H), 5.03 (s, 2H), 3.24 (s, 4H). MS (m/z): 345.4 (M + H). |

TABLE 6-continued

| Ex | Cpd | Structure | Name | Characterization |
|---|---|---|---|---|
| 300 | 562 | 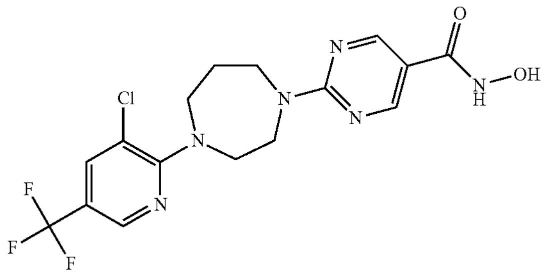 [SMILES: O=C(NO)c1cnc(N2CCCN(c3ncc(C(F)(F)F)cc3Cl)CC2)nc1] | 2-(4-(3-chloro-5-(trifluoromethyl)pyridin-2-yl)-1,4-diazepan-1-yl)-N-hydroxypyrimidine-5-carboxamide | $^1$H NMR (CD$_3$OD) δ (ppm): 8.64 (s, 1H), 8.59 (s, 1H), 8.25 (s, 1H), 7.81 (s, 1H), 4.10 (t, J = 5.6 Hz, 2H), 4.01 (t, J = 5.6 Hz, 2H), 3.87 (t, J = 5.6 Hz, 2H), 3.81 (t, J = 5.6 Hz, 2H), 2.08 (m, 2H). MS (m/z) 415.4 (M − H). |
| 301 | 563 | 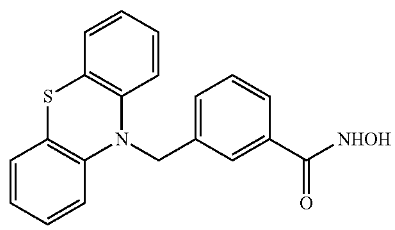 | 3-((10H-phenothiazin-10-yl)methyl)-N-hydroxybenzamide | $^1$H NMR (DMSO-d$_6$) δ (ppm): 11.25 (br s, 1H), 9.08 (br s, 1H), 7.84-7.80 (m, 1H), 7.64-7.59 (m, 1H), 7.50-7.39 (m, 2H), 7.22-7.07 (m, 4H), 6.98-6.92 (m, 2H), 6.86-6.80 (m, 2H), 5.21 (s, 2H). MS (m/z): 349.4 (M + H). |
| 302 | 564 | 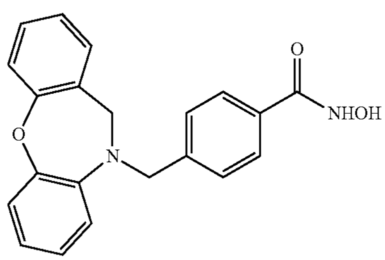 | 4-(dibenzo[b,f][1,4]oxazepin-10(11H)-ylmethyl)-N-hydroxybenzamide | $^1$H NMR (CD$_3$OD) δ (ppm): 7.79-7.73 (m, 2H), 7.52-7.46 (m, 2H), 7.34-7.28 (m, 1H), 7.23-7.18 (m, 1H), 7.16-7.07 (m, 3H), 6.96-6.77 (m, 3H), 4.46 (s, 2H), 4.42 (s, 2H). MS (m/z): 347.4 (M + H). |
| 303 | 565 | 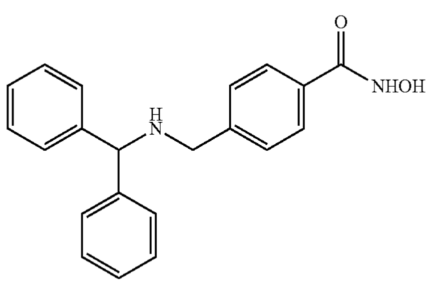 | 4-((benzhydrylamino)methyl)-N-hydroxybenzamide | $^1$H NMR (CD$_3$OD) δ (ppm): 7.77-7.72 (m, 2H), 7.46-7.40 (m, 6H), 7.35-7.30 (m, 4H), 7.26-7.21 (m, 2H), 4.82 (s, 1H), 3.78 (s, 2H). MS (m/z): 333.4 (M + H). |
| 304 | 566 | 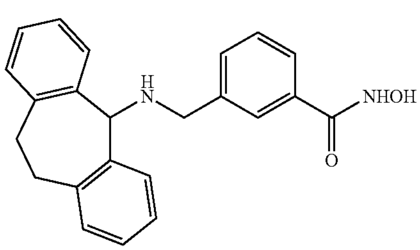 | | $^1$H NMR (CD$_3$OD) δ (ppm): 7.73-7.70 (m, 1H), 7.65-7.61 (m, 1H), 7.52-7.48 (m, 1H), 7.44 (t, J = 7.6 Hz, 1H), 7.29-7.24 (m, 2H), 7.22-7.11 (m, 6H), 4.89 (s, 1H), 3.82-3.67 (m, 4H), 3.04-2.90 (m, 2H). MS (m/z): 359.5 (M + H). |

TABLE 6-continued

| Ex | Cpd | Structure | Name | Characterization |
|---|---|---|---|---|
| 305 | 567 | 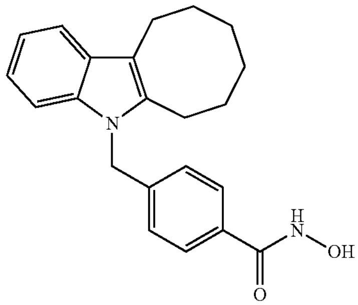 [SMILES: O=C(NO)c1ccc(Cn2c3c(c4ccccc42)CCCCCC3)cc1] | 4-((6,7,8,9,10,11-hexahydro-5H-cycloocta[b]indol-5-yl)methyl)-N-hydroxybenzamide | $^1$H NMR (CD$_3$OD) δ (ppm): 7.44-7.40 (m, 1H), 7.34-7.25 (m, 4H), 7.21-7.18 (m, 1H), 6.67 (d, J = 8.2 Hz, 2H), 3.19 (dd, J = 31.7, 13.9 Hz, 2H), 2.98-2.90 (m, 1H), 2.74 (dt, J = 12.9, 4.7 Hz, 1H), 2.63-2.54 (m, 1H), 2.32 (dt, J = 14.7, 4.1 Hz, 1H), 2.22-2.16 (m, 1H), 1.86-1.67 (m, 2H), 1.55-1.29 (m, 3H), 1.04-0.95 (m, 1H), 0.80-0.70 (m, 1H). MS (m/z): 349.5 (M + H). |
| 306 | 568 | 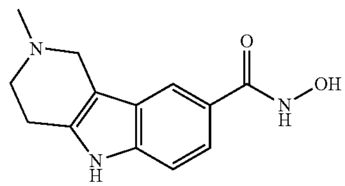 [SMILES: CN1CCc2[nH]c3ccc(C(=O)NO)cc3c2C1] | N-hydroxy-2-methyl-2,3,4,5-tetrahydro-1H-pyrido[4,3-b]indole-8-carboxamide | $^1$H NMR (DMSO-d$_6$) δ (ppm): 11.08 (s, 1H), 10.98 (br s, 1H), 8.18 (s, 1H), 7.80 (s, 1H), 7.45 (dd, J = 8.5, 1.6 Hz, 1H), 7.27 (d, J = 8.4 Hz, 1H), 3.61 (s, 2H), 2.84-2.76 (m, 4H), 2.47 (s, 3H). MS (m/z): 246.3 (M + H). |
| 307 | 569 | 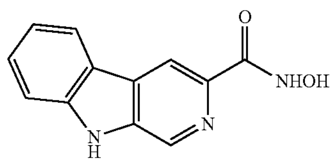 | N-hydroxy-9H-pyrido[3,4-b]indole-3-carboxamide | $^1$H NMR (DMSO-d$_6$) δ (ppm): 11.97 (s, 1H), 11.28 (s, 1H), 9.02 (s, 1H), 8.89 (s, 1H), 8.83 (s, 1H), 8.43 (d, J = 7.6 Hz, 1H), 7.72-7.60 (m, 2H), 7.36-7.31 (m, 1H), MS (m/z): 228.2 (M + H). |
| 308 | 570 | 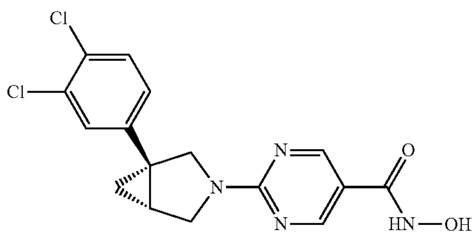 [SMILES: O=C(NO)c1cnc(N2C[C@@H]3C[C@]3(c3ccc(Cl)c(Cl)c3)C2)nc1] | 2-((1S,5R)-1-(3,4-dichlorophenyl)-3-azabicyclo[3.1.0]hexan-3-yl)-N-hydroxypyrimidine-5-carboxamide | $^1$H NMR (CD$_3$OD) δ (ppm): 8.67 (s, 2H), 7.46 (m, 2H), 7.23 (dd, J = 2.4 Hz, 8.4 Hz, 1H), 4.31 (d, J = 11.2 Hz, 1H), 4.07 (d, J = 11.2 Hz, 1H), 3.76 (d, J = 11.2 Hz, 2H), 2.14 (quin, J = 4 Hz, 1H), 1.22 (m, 1H), 0.90 (t, J = 4.8 Hz, 1H). MS (m/z): 363.5 (M − H). |
| 309 | 571 | 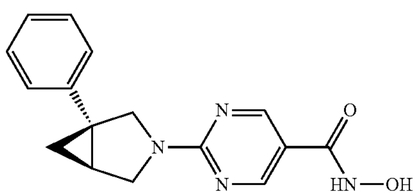 [SMILES: O=C(NO)c1cnc(N2C[C@H]3C[C@@]3(c3ccccc3)C2)nc1] | N-hydroxy-2-((1R,5S)-1-phenyl-3-azabicyclo[3.1.0]hexan-3-yl)pyrimidine-5-carboxamide | $^1$H NMR (DMSO-d$_6$) δ (ppm): 8.67 (s, 2H), 7.21-7.33 (m, 5H), 4.31 (d, J = 11.2 Hz, 1H), 4.05 (d, J = 11.2 Hz, 1H), 3.76 (m, 2H), 2.10 (quin, J = 4 Hz, 1H), 1.18 (m, 1H), 0.84 (t, J = 4.4 Hz, 1H). MS (m/z): 295.4 (M − H). |
| 310 | 572 | 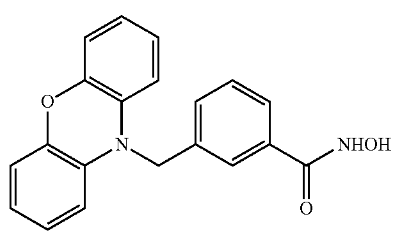 | 3-((10H-phenoxazin-10-yl)methyl)-N-hydroxybenzamide | $^1$H NMR (DMSO-d$_6$) δ (ppm): 11.28 (s, 1H), 9.06 (s, 1H), 7.76 (s, 1H), 7.67-7.61 (m, 1H), 7.47-7.42 (m, 2H), 6.81-6.57 (m, 6H), 6.51 (dd, J = 7.8, 1.4 Hz, 2H), 4.95 (s, 2H). MS (m/z): 331.5 (M − H). |
| 311 | 573 | 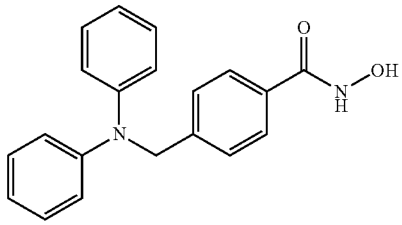 [SMILES: O=C(NO)c1ccc(CN(c2ccccc2)c2ccccc2)cc1] | 4-((diphenylamino)methyl)-N-hydroxybenzamide | $^1$H NMR (DMSO-d$_6$) δ (ppm): 11.13 (s, 1H), 9.00 (s, 1H), 7.67 (d, J = 8.2 Hz, 2H), 7.39 (d, J = 8.4 Hz, 2H), 7.26-7.21 (m, 4H), 7.04 (dd, J = 8.6, 1.0 Hz, 4H), 6.93-6.89 (m, 2H), 5.05 (s, 2H). MS (m/z): 319.4 (M + H). |

TABLE 6-continued

| Ex | Cpd | Structure | Name | Characterization |
|---|---|---|---|---|
| 312 | 574 | 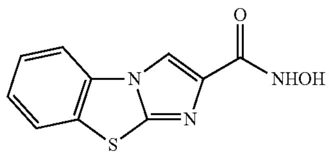 | | $^1$H NMR (CD$_3$OD) δ (ppm): 11.98 (br s, 1H), 9.03 (br s, 1H), 8.89 (s, 1H), 8.20-8.14 (m, 1H), 8.11-8.05 (m, 1H), 7.64-7.57 (m, 1H), 7.53-7.46 (m, 1H). MS (m/z): 234.2 (M + H). |
| 313 | 575 | 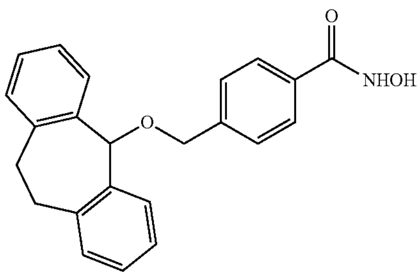 | | $^1$H NMR (CD$_3$OD) δ (ppm): 7.77-7.72 (m, 2H), 7.42 (d, J = 8.4 Hz, 2H), 7.37-7.33 (m, 2H), 7.28-7.16 (m, 6H), 5.47 (s, 1H), 4.55 (s, 2H), 3.66-3.56 (m, 2H), 3.04-2.94 (m, 2H). MS (m/z): 358.4 (M − H). |
| 314 | 576 | 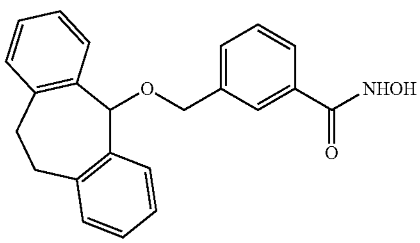 | | $^1$H NMR (CD$_3$OD) δ (ppm): 7.75-7.71 (m, 1H), 7.70-7.65 (m, 1H), 7.53-7.42 (m, 2H), 7.36 (d, J = 7.8 Hz, 2H), 7.28-7.16 (m, 6H), 5.48 (s, 1H), 4.54 (s, 2H), 3.67-3.57 (m, 2H), 3.04-2.93 (m, 2H). MS (m/z): 358.3 (M − H). |
| 315 | 577 | 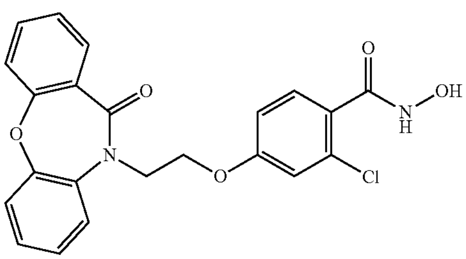 [SMILES: O=C(NO)c1ccc(OCCN2C(=O)c3ccccc3Oc3ccccc32)cc1Cl] | 2-chloro-N-hydroxy-4-(2-(11-oxodibenzo[b,f][1,4]oxazepin-10(11H)-yl)erthoxy)benzamide | $^1$H NMR (CD$_3$OD) δ (ppm): 7.74 (dd, J = 8.0, 1.8 Hz, 1H), 7.59 (dd, J = 7.8, 1.8 Hz, 1H), 7.54-7.49 (m, 1H), 7.34-7.20 (m, 6H), 6.95 (d, J = 2.4 Hz, 1H), 6.87 (dd, J = 8.6, 2.4 Hz, 1H), 4.51 (br s, 2H), 4.38 (t, J = 5.1 Hz, 2H). MS (m/z): 425.4 (M + H). |
| 316 | 578 | 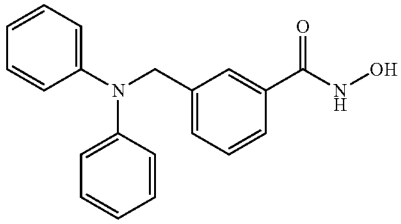 [SMILES: O=C(NO)c1cccc(CN(c2ccccc2)c2ccccc2)c1] | 3-((diphenylamino)methyl)-N-hydroxybenzamide | $^1$H NMR (DMSO-d$_6$) δ (ppm): 11.20 (br s, 1H), 9.01 (br s, 1H), 7.74 (s, 1H), 7.56 (d, J = 7.6 Hz, 1H), 7.45 (d, J = 7.9 Hz, 1H), 7.37 (t, J = 7.6 Hz, 1H), 7.27-7.21 (m, 4H), 7.06-7.02 (m, 4H), 6.91 (t, J = 7.2 Hz, 2H), 5.04 (s, 2H). MS (m/z): 319.2 (M + H). |
| 319 | 581 | 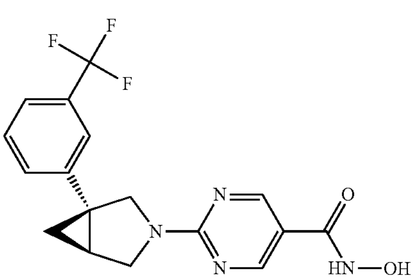 [SMILES: O=C(NO)c1cnc(N2C[C@H]3C[C@@]3(c3cccc(C(F)(F)F)c3)C2)nc1] | N-hydroxy-2-((1R,5S)-1-(3-(trifluoromethyl)phenyl)-3-azabicyclo[3.1.0]hexan-3-yl)pyrimidine-5-carboxamide | $^1$H NMR (CD$_3$OD) δ (ppm): 8.68 (s, 2H), 7.54 (m, 4H), 4.38 (d, J = 11.2 Hz, 1H), 4.08 (d, J = 11.6 Hz, 1H), 3.80 (m, 2H), 2.19 (m, 1H), 1.24 (m, 1H), 0.93 (t, J = 4.8 Hz, 1H). MS (m/z): 363.2 (M − H). |

TABLE 6-continued

| Ex | Cpd | Structure | Name | Characterization |
|---|---|---|---|---|
| 321 | 583 | 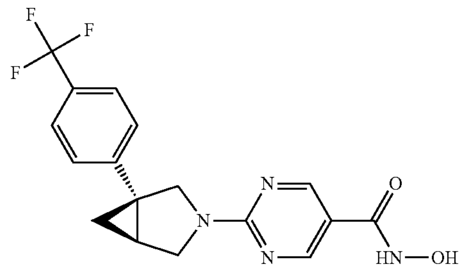 [SMILES: O=C(NO)c1cnc(N2C[C@H]3C[C@@]3(c3ccc(C(F)(F)F)cc3)C2)nc1] | N-hydroxy-2-((1R,5S)-1-(4-(trifluoromethyl)phenyl)-3-azabicyclo[3.1.0]hexan-3-yl)pyrimidine-5-carboxamide | $^1$H NMR (CD$_3$OD) δ (ppm): 8.68 (s, 2H), 7.62 (d, J = 8.2 Hz, 2H), 7.46 (d, J = 8.2 Hz, 2H), 4.37 (d, J = 10.8 Hz, 1H), 4.09 (d, J = 11.6 Hz, 1H), 3.85 (d, J = 11.2 Hz, 1H), 3.77 (dd, J = 4 Hz, 11.2 Hz, 1H), 2.22 (m, 1H), 1.26 (m, 1H), 0.95 (t, J = 4.8 Hz, 1H). MS (m/z): 363.3 (M − H). |
| 322 | 584 | 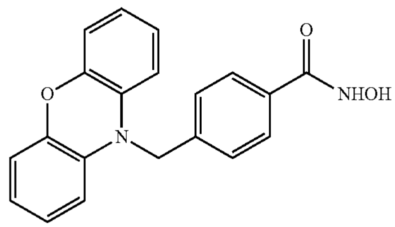 | 4-((10H-phenoxazin-10-yl)methyl)-N-hydroxybenzamide | $^1$H NMR (MeOD-d4) (ppm) 1H: 7.78-7.73 (m, 2H), 7.46-7.42 (m, 2H), 6.77-6.68 (m, 6H), 6.45-6.40 (m, 2H), 4.98 (s, 2H). LRMS(ESI): (calc.) 332.4 (found) 331.3 (M − H+) |
| 323 | 585 | 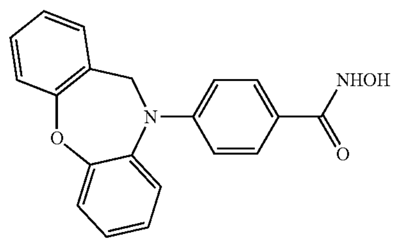 | 4-(dibenzo[b,f][1,4]oxazepin-10(11H)-yl)-N-hydroxybenzamide | $^1$H NMR (DMSO-d$_6$) δ (ppm): 10.88 (s, 1H), 8.80 (s, 1H), 7.52 (d, J = 8.8 Hz, 2H), 7.39-7.28 (m, 4H), 7.25-7.18 (m, 2H), 7.09-6.99 (m, 2H), 6.74 (d, J = 8.8 Hz, 2H), 4.98 (S, 2H). LRMS(ESI): (calc.) 332.12 (found) 333.4 (MH)+ |
| 324 | 586 | 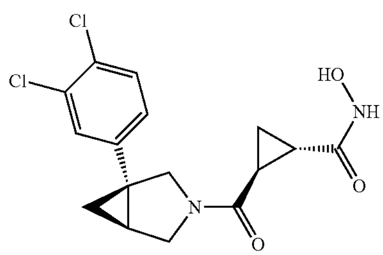 [SMILES: O=C(NO)[C@H]1C[C@@H]1C(=O)N1C[C@H]2C[C@@]2(c2ccc(Cl)c(Cl)c2)C1] | (1S,2S)-2-((1R,5S)-1-(3,4-dichlorophenyl)-3-azabicyclo[3.1.0]hexane-3-carbonyl)-N-hydroxycyclopropanecarboxamide | $^1$H NMR (CD3OD) (ppm) 1H: [Both diastereomers, 28H total] 7.41-7.46 (m, 4H), 7.16-7.21 (m, 2H), 4.21-4.31 (m, 1H), 4.07-4.11 (m, 1H), 3.82-4.02 (m, 4H), 3.55 (m, 2H), 2.2-2.29 (m, 2H), 2.10 (m, 1H), 2.03 (m, 1H), 1.95 (m, 2H), 1.25-1.35 (m, 4H), 1.19 (m, 2H), 0.86 (m, 2H). LRMS(ESI): (calc.) 354.05 (found) 353.27 (M)− |
| 325 | 587 | 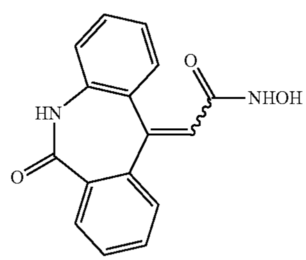 | (Z and E)-N-hydroxy-2-(6-oxo-5H-dibenzo[b,e]azepin-11(6H)-ylidene)acetamide | $^1$H NMR (DMSO-d$_6$) δ (ppm): 10.77 (s, 1H), 10.50 and 10.49 (2s, 1H), 8.95 (brs, 1H), 7.81 and 7.78 (2d, J = 7.5 Hz, 1H), 6.62 (t, J = 7.5 Hz, 0.5H), 7.48 (t, J = 7.1 Hz, 1H), 7.45-7.39 (m, 0.5H), 7.36-7.21 (m, 3H), 7.19-7.09 (m, 1.5H), 7.05 (t, J = 7.5 Hz, 0.5H), 6.07 (s, 0.5H), 6.01 (s, 0.5H). LRMS(ESI): (calc.) 280.1 (found) 281.2 (MH)+ |
| 326 | 588 | 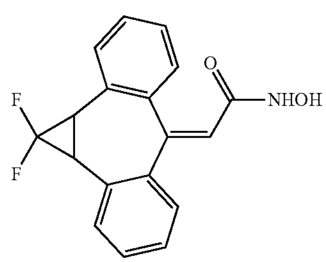 | | $^1$H NMR (DMSO-d$_6$) δ (ppm): 10.67 (s, 1H), 8.91 (s, 1H), 7.36-7.08 (m, 8H), 6.05 (s, 1H), 3.55-3.40 (m, 2H). LRMS(ESI): (calc.) 313.1 (found) 314.3 (MH)+ |

TABLE 6-continued

| Ex | Cpd | Structure | Name | Characterization |
|---|---|---|---|---|
| 327 | 589 | 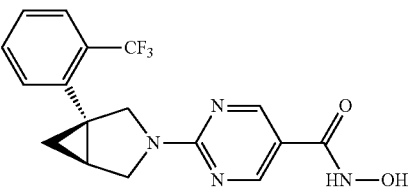 [SMILES: O=C(NO)c1cnc(N2C[C@H]3C[C@@]3(c3ccccc3C(F)(F)F)C2)nc1] | | ¹H NMR (CD3OD) (ppm) 1H: 8.66 (bs, 2H), 7.70 (m, 2H), 7.61 (t, J = 7.6 Hz, 1H), 7.47 (t, J = 7.6 Hz, 1H), 4.22 (d, J = 11.2 Hz, 1H), 4.07 (d, J = 11.6 Hz, 1H), 3.87 (dd, J = 4 Hz, 11.2 Hz, 1H), 3.53 (d, J = 11.6 Hz, 1H) 2.09 (m, 1H), 1.27 (m, 1H), 0.908 (t, J = 4.8 Hz, 1H). LRMS(ESI): (calc.) 364.11 (found) 363.26 (M)– |
| 328 | 590 | 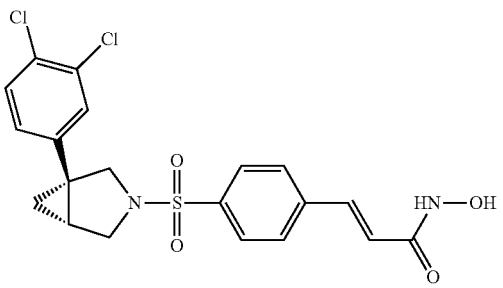 [SMILES: O=C(/C=C/c1ccc(S(=O)(=O)N2C[C@@H]3C[C@]3(c3ccc(Cl)c(Cl)c3)C2)cc1)NO] | (E)-3-(4-((1S,5R)-1-(3,4-dichlorophenyl)-3-azabicyclo[3.1.0]hexan-3-ylsulfonyl)phenyl)-N-hydroxyacrylamide | ¹H NMR (CD3OD) (ppm) 1H: 7.80 (dd, J = 8 Hz, 29.2 Hz, 4H), 7.60 (d, J = 15.6 Hz, 1H), 7.38 (d, J = 8.4 Hz, 1H), 7.30 (s, 1H), 7.06 (d, J = 8.4 Hz, 1H), 6.60 (d, J = 15.6 Hz, 1H), 3.86 (d, J = 9.2 Hz, 1H), 3.60 (d, J = 9.2 Hz, 1H), 3.23 (d, J = 9.6 Hz, 2H), 1.92 (m, 1H), 0.98 (m, 2H). LRMS(ESI): (calc.) 452.04 (found) 451.27 (M)– |

Compositions

In a second aspect, the invention provides compositions comprising an inhibitor of histone deacetylase according to the invention and a pharmaceutically acceptable carrier, excipient, or diluent. Compounds of the invention may be formulated by any method known in the art and may be prepared for administration by any route, including, without limitation, parenteral, oral, sublingual, transdermal, topical, intranasal, intratracheal, or intrarectal. In certain preferred embodiments, compounds of the invention are administered intravenously in a hospital setting. In certain other preferred embodiments, administration may preferably be by the oral route. The compositions may be in any form, including but not limited to, liquid solutions or suspensions; for oral administration, formulations may be in the form of tablets or capsules; and for intranasal formulations, in the form of powders, nasal drops or aerosols. The compositions of the invention may be administered systemically or locally.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, or other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term "pharmaceutically acceptable salts" is intended to mean salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate). As used herein, the term "salt" is also meant to encompass complexes, such as with an alkaline metal or an alkaline earth metal.

The active compound is included in the pharmaceutically acceptable carrier or diluent in an amount sufficient to deliver an inhibition effective amount without causing serious toxic effects. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

In certain preferred embodiments of the second aspect of the invention, the composition further comprises an antisense oligonucleotide that inhibits the expression of a histone deacetylase gene. The combined use of a nucleic acid level inhibitor (e.g., antisense oligonucleotide) and a protein level inhibitor (i e, inhibitor of histone deacetylase enzyme activity) results in an improved inhibitory effect, thereby reducing the amounts of the inhibitors required to obtain a given inhibitory effect as compared to the amounts necessary when either is used individually. The antisense oligonucleotide according to this aspect of the invention is complementary to regions of RNA or double-stranded DNA that encode one or more of, for example, HDAC-1, HDAC-2, HDAC-3, HDAC-4, HDAC-5, HDAC-6, HDAC-7, HDAC-8, HDAC-9, HDAC-10 and HDAC-11 (see e.g., GenBank Accession Number U50079 for HDAC-1, GenBank Accession Number U31814 for HDAC-2, and GenBank Accession Number U75697 for HDAC-3).

Inhibition of Histone Deacetylase

In a third aspect, the present invention provides a method of inhibiting histone deacetylase, comprising contacting the histone deacetylase with an inhibition effective amount of an inhibitor of histone deacetylase of the present invention.

In another embodiment of the third aspect, the invention provides a method of inhibiting histone deacetylase in a cell, comprising contacting the cell in which inhibition of histone deacetylase is desired with an inhibition effective amount of an inhibitor of histone deacetylase, or composition thereof, according to the present invention.

Because compounds of the invention inhibit histone deacetylase, they are useful research tools for in vitro study histone deacetylases and their role in biological processes.

Measurement of the enzymatic activity of a histone deacetylase can be achieved using known methodologies. For Example, Yoshida et al., *J. Biol. Chem.*, 265: 17174-17179 (1990), describes the assessment of histone deacetylase enzymatic activity by the detection of acetylated histones in trichostatin A treated cells. Taunton et al., *Science*, 272: 408-411 (1996), similarly describes methods to measure histone deacetylase enzymatic activity using endogenous and recombinant HDAC-1.

In some preferred embodiments, the histone deacetylase inhibitor interacts with and reduces the activity of all histone deacetylases in a cell. In some other preferred embodiments according to this aspect of the invention, the histone deacetylase inhibitor interacts with and reduces the activity of fewer than all histone deacetylases in the cell. In certain preferred embodiments, the inhibitor interacts with and reduces the activity of one histone deacetylase (e.g., HDAC-1), but does not interact with or reduce the activities of other histone deacetylases (e.g., HDAC-2, HDAC-3, HDAC-4, HDAC-5, HDAC-6, HDAC-7, HDAC-8, HDAC-9, HDAC-10 and HDAC-11).

The term "inhibition effective amount" is meant to denote a dosage sufficient to cause inhibition of histone deacetylase activity in a cell, which cell can be in a multicellular organism. The multicellular organism can be a plant or an animal, preferably a mammal, more preferably a human. If in a multicellular organism, the method according to this aspect of the invention comprises administering to the organism a compound or composition according to the present invention. Administration may be by any route, including, without limitation, parenteral, oral, sublingual, transdermal, topical, intranasal, intratracheal, or intrarectal. In certain particularly preferred embodiments, compounds of the invention are administered intravenously in a hospital setting. In certain other preferred embodiments, administration may preferably be by the oral route.

In certain preferred embodiments of the third aspect of the invention, the method further comprises contacting a histone deacetylase enzyme or a cell expressing histone deacetylase activity with an antisense oligonucleotide that inhibits the expression of a histone deacetylase gene. The combined use of a nucleic acid level inhibitor (e.g., antisense oligonucleotide) and a protein level inhibitor (i e, inhibitor of histone deacetylase enzyme activity) results in an improved inhibitory effect, thereby reducing the amounts of the inhibitors required to obtain a given inhibitory effect as compared to the amounts necessary when either is used individually. The antisense oligonucleotides according to this aspect of the invention are complementary to regions of RNA or double-stranded DNA that encode, for example, HDAC-1, HDAC-2, HDAC-3, HDAC-4, HDAC-5, HDAC-6, HDAC-7, HDAC-8, HDAC-9, HDAC-10 and HDAC-11 (see e.g., GenBank Accession Number U50079 for HDAC-1, GenBank Accession Number U31814 for HDAC-2, and GenBank Accession Number U75697 for HDAC-3).

For purposes of the invention, the term "oligonucleotide" includes polymers of two or more deoxyribonucleosides, ribonucleosides, or 2'-substituted ribonucleoside residues, or any combination thereof. Preferably, such oligonucleotides have from about 6 to about 100 nucleoside residues, more preferably from about 8 to about 50 nucleoside residues, and most preferably from about 12 to about 30 nucleoside residues. The nucleoside residues may be coupled to each other by any of the numerous known internucleoside linkages. Such internucleoside linkages include without limitation phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate and sulfone internucleoside linkages. In certain preferred embodiments, these internucleoside linkages may be phosphodiester, phosphotriester, phosphorothioate, or phosphoramidate linkages, or combinations thereof. The term oligonucleotide also encompasses such polymers having chemically modified bases or sugars and/or having additional substituents, including without limitation lipophilic groups, intercalating agents, diamines and adamantane.

For purposes of the invention the term "2'-substituted ribonucleoside" includes ribonucleosides in which the hydroxyl group at the 2' position of the pentose moiety is substituted to produce a 2'-O-substituted ribonucleoside. Preferably, such substitution is with a lower alkyl group containing 1-6 saturated or unsaturated carbon atoms, or with an aryl or allyl group having 2-6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups. The term "2'-substituted ribonucleoside" also includes ribonucleosides in which the 2'-hydroxyl group is replaced with an amino group or with a halo group, preferably fluoro.

Particularly preferred antisense oligonucleotides utilized in this aspect of the invention include chimeric oligonucleotides and hybrid oligonucleotides.

For purposes of the invention, a "chimeric oligonucleotide" refers to an oligonucleotide having more than one type of internucleoside linkage. One preferred example of such a chimeric oligonucleotide is a chimeric oligonucleotide comprising a phosphorothioate, phosphodiester or phosphorodithioate region, preferably comprising from about 2 to about 12 nucleotides, and an alkylphosphonate or alkylphosphonothioate region (see e.g., Pederson et al. U.S. Pat. Nos. 5,635,377 and 5,366,878). Preferably, such chimeric oligonucleotides contain at least three consecutive internucleoside linkages selected from phosphodiester and phosphorothioate linkages, or combinations thereof.

For purposes of the invention, a "hybrid oligonucleotide" refers to an oligonucleotide having more than one type of nucleoside. One preferred example of such a hybrid oligonucleotide comprises a ribonucleotide or 2'-substituted ribonucleotide region, preferably comprising from about 2 to about 12 2'-substituted nucleotides, and a deoxyribonucleotide region. Preferably, such a hybrid oligonucleotide contains at least three consecutive deoxyribonucleosides and also contains ribonucleosides, 2'-substituted ribonucleosides, preferably 2'-O-substituted ribonucleosides, or combinations thereof (see e.g., Metelev and Agrawal, U.S. Pat. No. 5,652, 355).

The exact nucleotide sequence and chemical structure of an antisense oligonucleotide utilized in the invention can be varied, so long as the oligonucleotide retains its ability to inhibit expression of the gene of interest. This is readily determined by testing whether the particular antisense oligonucleotide is active. Useful assays for this purpose include quantitating the mRNA encoding a product of the gene, a Western blotting analysis assay for the product of the gene, an activity assay for an enzymatically active gene product, or a soft agar growth assay, or a reporter gene construct assay, or an in vivo tumor growth assay, all of which are known in the art, or are as described in detail in this specification or in, for example, Ramchandani et al. (1997) *Proc. Natl. Acad. Sci. USA* 94: 684-689.

Antisense oligonucleotides utilized in the invention may conveniently be synthesized on a suitable solid support using well known chemical approaches, including H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG) (see, e.g., Pon, R. T. (1993) *Methods in Molec. Biol.* 20: 465-496).

Particularly preferred oligonucleotides have nucleotide sequences of from about 13 to about 35 nucleotides which include the nucleotide sequences shown in Table 44. Yet additional particularly preferred oligonucleotides have nucleotide sequences of from about 15 to about 26 nucleotides which include the nucleotide sequences shown in Table 7.

istration of the antisense oligonucleotide. The mammal may receive one or more dosages of the HDAC inhibitor of the present invention prior to receiving one or more dosages of antisense oligonucleotide.

In certain other preferred embodiments of the present invention, the HDAC inhibitor of the present invention may be administered together with another HDAC inhibitor known in the art or which will be discovered. Administration of such HDAC inhibitor(s) may be done sequentially or concurrently. In certain preferred embodiments of the present invention the composition comprises an HDAC inhibitor of the present invention and/or an antisense oligonucleotide and/or another HDAC inhibitor known in the art or which will be discovered. The active ingredients of such compositions preferably act synergistically to produce a therapeutic effect.

In certain embodiments, the known HDAC inhibitor is selected from the group consisting of, but not limited to, trichostatin A, depudecin, trapoxin, suberoylanilide hydroxamic acid, FR901228, MS-27-275, CI-994 sodium butyrate, MGCD0103, and those compounds found in WO 2003/024448, WO 2004/069823, WO 2001/038322, U.S. Pat. No. 6,541,661, WO 01/70675, WO 2004/035525 and WO 2005/030705.

The following examples are intended to further illustrate certain preferred embodiments of the invention, and are not intended to limit the scope of the invention.

TABLE 7

| Oligo | Target | Accession Number | Nucleotide Position | Sequence | position within Gene | Seq ID No. |
|---|---|---|---|---|---|---|
| HDAC1 AS1 | Human HDAC1 | U50079 | 1585-1604 | 5'-GAAACGTGAGGGACTCAGCA-3' | 3'-UTR | Seq ID No: 1 |
| HDAC1 AS2 | Human HDAC1 | U50079 | 1565-1584 | 5'-GGAAGCCAGAGCTGGAGAGG-3' | 3'-UTR | Seq ID No: 2 |
| HDAC2 AS | Human HDAC2 | U31814 | 1643-1622 | 5'-GCTGAGCTGTTCTGATTTGG-3' | 3'-UTR | Seq ID No: 3 |
| HDAC3 AS | Human HDAC3 | AF039703 | 1276-1295 | 5'-CGCTTTCCTTGTCATTGACA-3' | 3'-UTR | Seq ID No: 4 |
| HDAC4 AS1 | Human HDAC4 | AB006626 | 514-33 | 5-GCTGCCTGCCGTGCCCACCC-3' | 5'-UTR | Seq ID No: 5 |
| HDAC4 AS2 | Human HDAC4 | AB006626 | 7710-29 | 5'-TACAGTCCATGCAACCTCCA-3' | 3'-UTR | Seq ID No: 6 |
| HDAC5 AS | Human HDAC5 | AF039691 | 2663-2682 | 5'-CTTCGGTCTCACCTGCTTGG-3' | 3'-UTR | Seq ID No: 7 |
| HDAC6 AS | Human HDAC6 | AJ011972 | 3791-3810 | 5'-CAGGCTGGAATGAGCTACAG-3' | 3'-UTR | Seq ID No: 8 |
| HDAC7 AS | Human HDAC7 | AF239243 | 2896-2915 | 5'-CTTCAGCCAGGATGCCCACA-3' | 3'-UTR | Seq ID No: 9 |
| HDAC8 AS1 | Human HDAC8 | AF230097 | 51-70 | 5'-CTCCGGCTCCTCCATCTTCC-3' | 5'-UTR | Seq ID No: 10 |
| HDAC8 AS2 | Human HDAC8 | AF230097 | 1328-1347 | 5'-AGCCAGCTGCCACTTGATGC-3' | 3'-UTR | Seq ID No: 11 |

In certain preferred embodiments of the invention, the antisense oligonucleotide and the HDAC inhibitor of the present invention are administered separately to a mammal, preferably a human. For example, the antisense oligonucleotide may be administered to the mammal prior to administration to the mammal of the HDAC inhibitor of the present invention. The mammal may receive one or more dosages of antisense oligonucleotide prior to receiving one or more dosages of the HDAC inhibitor of the present invention.

In another embodiment, the HDAC inhibitor of the present invention may be administered to the mammal prior to admin-

ASSAY EXAMPLES

Assay Example 1

Inhibition of Histone Deacetylase Enzymatic Activity

The following protocol is used to assay the compounds of the invention. In the assay, the buffer used is 25 mM HEPES, pH 8.0, 137 mM NaCl, 2.7 mM KCl, 1 mM $MgCl_2$ and the substrate is Boc-Lys(Ac)-AMC in a 50 mM stock solution in DMSO. The enzyme stock solution is 4.08 µg/mL in buffer.

The compounds are pre-incubated (2 µl in DMSO diluted to 13 µl in buffer for transfer to assay plate) with enzyme (20 µl of 4.08 mg/ml) for 10 minutes at room temperature (35 µl pre-incubation volume). The mixture is pre-incubated for 5 minutes at room temperature. The reaction is started by bringing the temperature to 37° C. and adding 16 µl substrate. Total reaction volume is 50 µl. The reaction is stopped after 20 minutes by addition of 50 µl developer, prepared as directed by Biomol (Fluor-de-Lys developer, Cat. # KI-105). A plate is incubated in the dark for 10 minutes at room temperature before reading ($\lambda_{Ex}$=360 nm, $\lambda_{Em}$=470 nm, Cutoff filter at 435 nm).

All compounds exemplified have an $IC_{50}$ value less than or equal to 10 µM against one or more of HDAC-1, HDAC-2, HDAC-3, HDAC-4, HDAC-5, HDAC-6, HDAC-7, HDAC-8, HDAC-9, HDAC-10 and HDAC-11. Tables 8, 9 and 10 show selected examples. In the Tables 8, 9 and 10, A≤0.05 µM; 0.05 µM≤B≤0.1 µM; 0.1 µM<C≤1 µM; and 1 µM<D≤10 µM.

Assay Example 2

Whole-Cell Histone Deacetylase (HDAC) Inhibition Assay in Primary Mouse Cortical Cultures Primary neocortical cultures are established through the dissection of the neocortex from E17 embryos harvested from time-pregnant Balb/C mice. Following dissection, the neocortical tissue specimens undergo digestion by incubation at 37° C. for 10 minutes in dissection medium (1×HBSS/10 mM HEPES/1 mM Sodium Pyruvate) supplemented with (0.25%) Trypsin and (0.1%) DNase I. Digested tissue is washed and resuspended in plating medium (NeuroBasal/10% HS/0.5 mM L-Glutamine (Invitrogen Corporation)) for trituration. Additional plating medium is added, and the contents are passed over a 70 um cell-strainer. The cell-density is quantified using a hemacytometer, and dilutions are made to allow for the plating of 50000 cells/well/100 uL in 96-well PDL-coated plates. Plates are incubated for 4-5 hours in 37° C./5% $CO_2$-incubator, after which time the entire volume is exchanged to feeding medium (NeuroBasal/2% B-27 Serum-free supplement/0.5 mM L-Glutamine/1% Penicillin-Streptomycin (Invitrogen Corporation)). The cultures undergo two 50% fresh feeding medium exchanges at 3 days in vitro (DIV3), and again at DIV7.

Compounds for testing are resuspended in dimethyl sulphoxide (DMSO), and further diluted in DMSO for a ten-point dose-response curve, with appropriate controls. Each master plate is assayed in triplicate. 3.5 uL/well of the master dilution plate is transferred to a 96-well round-bottom daughter plate, to which 175 uL/well of warmed feeding medium is added and thoroughly mixed. Three DIV9 culture plates are leveled to 50 uL/well, onto which each has overlaid 50 uL/well of the diluted daughter plate. The plates are returned to the 37° C./5% $CO_2$-incubator for 16-18 hours.

The next step of the assay involves the exposure of a HDAC colorimetric substrate, comprising an acetylated lysine side chain, to the compound-treated neuronal cultures. Based on the ability of the compound to inhibit HDAC activity in the neuronal cultures, the substrate is deacetylated by HDACs, and subsequently sensitized. A 7.5 mM BOC-Lys(Ac)-AMC (Bachem Bioscience, Inc.) substrate solution is prepared by making a 1:1 dilution of 15 mM BOC-Lys(Ac)-AMC with HDAC Assay Buffer (25 mM Tris-Cl/137 mM NaCl/2.7 mM KCl/1 mM $MgCl_2$). Compound-incubated culture plates are again leveled to 50 uL/well and 2 uL/well of 7.5 mM BOC-Lys (Ac)-AMC substrate is added and thoroughly mixed. Plates are returned to the 37° C./5% $CO_2$-incubator for 1 hour.

The final addition to the culture plates entails treatment with a Fluor de Lys™-based developer (BIOMOL Research Laboratories, Inc.) to produce a fluorophore, which is analyzed using a spectrophotometer. The developer solution (1× Fluor de Lys™/1% NP-40/1 uM TSA in HDAC Buffer Solution) is prepared, and 50 uL/well is added to each of the wells of the culture plates. Trichostatin A is typically added as an "inhibitor stop" for class I and II HDACs. The plates are returned to the 37° C./5% $CO_2$-incubator for 10-15 minutes, after which time, they are removed and set in the dark at room temperature for 5-10 minutes. The plates are read, and the results used to determine the percent HDAC activity of each compound compared to DMSO controls, and subsequently, used to calculate the corresponding $IC_{50}$ values.

Assay Example 3

Ex Vivo Histone Acetylation Analysis Via Western Blotting of Mouse Liver and Striatal Tissues from Mice Orally-Dosed with Histone Deacetylase (HDAC) Inhibitors Pre-weighed liver and striatal specimens are transferred from −80° C. to wet-ice to be processed for tissue-homogenization. For the liver specimens, a 20-fold excess of chilled 1×XT LDS (Bio-Rad Laboratories, Inc.) sample buffer is added over the weight of each individual liver sample, and a 10-fold excess over the weight of the striatal samples. After adding 1.0 mm Zirconia-Silica beads (BioSpec Products, Inc.) to each sample, the tubes are loaded into the Mini-Beadbeater™ (BioSpec Products, Inc.), the liver samples are homogenized for 4 minutes, and the striatal samples for 3 minutes.

Rescued homogenates are then heated at 95° C. for 10-15 minutes, vortexed briefly, and centrifuged at 13200 rpm for 4 minutes. Samples are diluted 1:10, and 20×XT Reducing agent (Bio-Rad Laboratories, Inc.) is added in preparation for loading.

15 uL of each diluted sample is loaded in CRITERION™ 4-12% Bis-Tris gels (Bio-Rad Laboratories, Inc.) and run at 150V (constant) in a 1×XT MES buffer system (Bio-Rad Laboratories, Inc.) until the dye-front reaches the bottom.

Immobilon-FL PVDF-membranes (Millipore Corporation) are briefly activated in Methanol, hydrated in $diH_2O$, and then equilibrated in chilled 1× Tris-Glycine transfer buffer (Bio-Rad Laboratories, Inc.) supplemented with 10% Methanol until the transfer-sandwiches are ready to be assembled. Gels are removed from the cartridges and equilibrated for 15 minutes in chilled transfer buffer. Transfer-sandwiches are assembled, loaded into the CRITERION™ Blotter System, and transferred for 40 minutes at 100V (constant).

PVDF-membranes are removed, rinsed briefly in $diH_2O$, and then blocked for 1 hour in 1:1 dilution (in PBS) of Odyssey Blocking Buffer solution (LI-COR Bioscience, Inc.).

Primary antibody solution is prepared as follows: Into 40 mL of 1:1 diluted Odyssey Blocking Buffer is added 4 uL of anti-Actin (AC-15) antibody (Sigma-Aldrich Co.), 8 uL of anti-Acetylated H2A antibody (Millipore Corporation) and 20 uL of anti-Acetylated H4 antibody (Millipore Corporation). PVDF membranes are incubated in primary antibody solution overnight at 4° C.

Membranes are washed 4×5 minutes in TBS-T (Sigma-Aldrich Co.). Secondary antibody solution is prepared as follows: Into 40 mL of TBS-T solution, supplemented with 0.02% SDS (Sigma-Aldrich Co.), is added 4 uL of goat anti-rabbit IRDye800 antibody (Rockland, Inc.) and 4 uL of goat anti-mouse AlexaFluor 680 antibody (Invitrogen Corporation). PVDF membranes are incubated in secondary antibody solution, protected from light, for 1 h at room temperature. Membranes are washed 4×5 minutes in TBS-T, followed by 2×2 minute washes in PBS solution.

PVDF membranes are scanned using LI-COR/Odyssey Infrared Imaging System. Induced acetylation of Histone 2A or Histone 4 is calculated for each sample by dividing the integrated intensity of the designated acetylated histone band by the integrated intensity of the actin band from the same sample, correcting for loading variability. The individually normalized sample values from each treatment group, assayed in triplicate, are then averaged and plotted as a relative Histone 2A or Histone 4 acetylation level.

Assay Example 3

Whole-Cell Histone Deacetylase (HDAC) Inhibition Assay in Normal Human Astrocyte Cultures Normal human astrocyte cultures (Lonza, Inc.) are passaged using standard passaging techniques. Pelleted cells are resuspended in Astrocyte Growth Medium (Astrocyte Basal Medium/3% FBS/1% L-Glutamine/0.1% Ascorbic acid/0.1% rhEGF/0.25% Insulin/0.1% Gentamycin Sulfate-Amphotericin; (Lonza, Inc.)). The cell density is quantified using a hemacytometer, and dilutions are made to allow for the plating of 10000 cells/well/100 uL into 96-well flat-bottomed TC-treated plates. The cultures plates are incubated at 37° C./5% $CO_2$ overnight.

Compounds for testing are resuspended in dimethyl sulphoxide (DMSO), and further diluted in DMSO for a ten-point dose-response curve, with appropriate controls. Each master plate is assayed in triplicate. 3.5 uL/well of the master dilution plate is transferred to a 96-well round-bottom daughter plate, to which 175 uL/well of warmed Astrocyte Growth Medium is added and thoroughly mixed. Three culture plates are leveled to 50 uL/well, onto which each has overlaid 50 uL/well of the diluted daughter plate. The plates are returned to the 37° C./5% $CO_2$-incubator for 16-18 hours.

The next step of the assay involves the exposure of a HDAC colorimetric substrate, comprising an acetylated lysine side chain, to the compound-treated human astrocyte cultures. Based on the ability of the compound to inhibit HDAC activity in the human astrocyte cultures, the substrate is deacetylated by HDACs, and subsequently sensitized. A 7.5 mM BOC-Lys(Ac)-AMC (Bachem Bioscience, Inc.) substrate solution is prepared by making a 1:1 dilution of 15 mM BOC-Lys(Ac)-AMC with HDAC Assay Buffer (25 mM Tris-Cl/137 mM NaCl/2.7 mM KCl/1 mM $MgCl_2$). Compound-incubated culture plates are again leveled to 50 uL/well and 2 uL/well of 7.5 mM BOC-Lys (Ac)-AMC substrate is added and thoroughly mixed. Plates are returned to the 37° C./5% $CO_2$-incubator for 1 hour.

The final addition to the culture plates entails treatment with a Fluor de Lys™-based developer (BIOMOL Research Laboratories, Inc.) to produce a fluorophore, which is analyzed using a spectrophotometer. The developer solution (1× Fluor de Lys™/1% NP-40/1 uM TSA in HDAC Buffer Solution) is prepared, and 50 uL/well is added to each of the wells of the culture plates. Trichostatin A is typically added as an "inhibitor stop" for class I and II HDACs. The plates are returned to the 37° C./5% $CO_2$-incubator for 10-15 minutes, after which time, they are removed and set in the dark at room temperature for 5-10 minutes. The plates are read, and the results are used to determine the percent HDAC activity of each compound compared to DMSO controls, and subsequently, used to calculate the corresponding IC50 values.

The activity ($IC_{50}$ μM) of selected compounds in the above-mentioned neuronal cell based assay are shown in Tables 8, 9 and 10. In the Tables 8, 9 and 10, W≤1 μM; 1<X≤5 μM; 5<Y≤15 μM; and 15<Z.

TABLE 8

| | HDAC Inhibition ($IC_{50}$ μM) | |
|---|---|---|
| Compound Name | HDAC Enzyme | WC mouse cortical neurons |
| (E)-2-(4-(2-chlorodibenzo[b,f][1,4]oxazepin-11-yl)piperazin-1-yl)-N-hydroxypyrimidine-5-carboxamide | A | Y |
| (Z)-4-(dibenzo[b,f][1,4]oxazepin-11-yl)-N-hydroxybenzamide | A | W |
| (Z)-4-(dibenzo[b,f][1,4]thiazepin-11-yl)-N-hydroxybenzamide | C | — |
| 4-(10,11-dihydrodibenzo[b,f][1,4]oxazepin-11-yl)-N-hydroxybenzamide | A | X |
| N-hydroxy-4-(10-methyl-10,11-dihydrodibenzo[b,f][1,4]oxazepin-11-yl)benzamide | C | Y |
| (Z)-4-(8-chloro-5H-dibenzo[b,e][1,4]diazepin-11-yl)-N-hydroxybenzamide | B | X |
| (Z)-4-(benzo[b]pyrido[3,2-f][1,4]oxazepin-5-yl)-N-hydroxybenzamide | B | X |
| (Z)-4-(2-fluorodibenzo[b,f][1,4]oxazepin-11-yl)-N-hydroxybenzamide | A | X |
| (Z)-N-hydroxy-4-(2-methoxydibenzo[b,f][1,4]oxazepin-11-yl)benzamide | C | Y |
| (Z)-4-(benzo[b]pyrido[4,3-f][1,4]oxazepin-5-yl)-N-hydroxybenzamide | C | W |
| (Z)-4-(2-(2-(dimethylamino)ethoxy)dibenzo[b,f][1,4]oxazepin-11-yl)-N-hydroxybenzamide | n/d | Z |
| (Z)-N-hydroxy-4-(8-(trifluoromethyl)dibenzo[b,f][1,4]oxazepin-11-yl)benzamide | C | Y |
| (Z)-4-(dibenzo[b,f][1,4]oxazepin-11-yl)-2-fluoro-N-hydroxybenzamide | C | Y |

TABLE 8-continued

| Compound Name | HDAC Inhibition (IC$_{50}$ µM) HDAC Enzyme | WC mouse cortical neurons |
|---|---|---|
| (Z)-5-(4-(hydroxycarbamoyl)phenyl)benzo[b]pyrido[4,3-f][1,4]oxazepine 2-oxide | C | Y |
| (Z)-N-hydroxy-4-(3-methoxydibenzo[b,f][1,4]oxazepin-11-yl)benzamide | C | X |
| (Z)-3-(dibenzo[b,f][1,4]oxazepin-11-yl)-N-hydroxybenzamide | C | Z |
| (Z)-N-hydroxy-4-(8-methyldibenzo[b,f][1,4]oxazepin-11-yl)benzamide | B | X |
| (Z)-N-hydroxy-4-(4-methoxydibenzo[b,f][1,4]oxazepin-11-yl)benzamide | B | X |
| [structure: dibenzothiepine S,S-dioxide with N-hydroxybenzamide] | D | Y |
| (Z)-4-(9-fluorodibenzo[b,f][1,4]oxazepin-11-yl)-N-hydroxybenzamide | B | X |
| (Z)-N-hydroxy-4-(7-(trifluoromethyl)dibenzo[b,f][1,4]oxazepin-11-yl)benzamide | C | Z |
| (Z)-4-(7-chlorodibenzo[b,f][1,4]oxazepin-11-yl)-N-hydroxybenzamide | C | Y |
| (Z)-4-(2-chlorodibenzo[b,f][1,4]oxazepin-11-yl)-N-hydroxybenzamide | A | Y |
| [structure: dibenzothiepine S-oxide with N-hydroxybenzamide] | C | X |
| (E)-N-hydroxy-11-(4-methylpiperazin-1-yl)dibenzo[b,f][1,4]oxazepine-8-carboxamide | C | n/d |
| (Z)-4-(8-cyanodibenzo[b,f][1,4]oxazepin-11-yl)-N-hydroxybenzamide | B | X |
| (Z)-N-hydroxy-4-(4-methyldibenzo[b,f][1,4]oxazepin-11-yl)benzamide | B | X |
| (Z)-N-hydroxy-4-(3-methyldibenzo[b,f][1,4]oxazepin-11-yl)benzamide | A | X |
| (Z)-N-hydroxy-11-(pyridin-4-yl)dibenzo[b,f][1,4]oxazepine-8-carboxamide | C | n/d |
| (Z)-4-(benzo[b]thieno[2,3-f][1,4]oxazepin-10-yl)-N-hydroxybenzamide | A | X |
| (Z)-4-(3-fluorodibenzo[b,f][1,4]oxazepin-11-yl)-N-hydroxybenzamide | C | Z |
| (Z)-4-(8-chlorodibenzo[b,f][1,4]oxazepin-11-yl)-N-hydroxybenzamide | C | Y |
| (Z)-N-hydroxy-4-(3-(trifluoromethyl)dibenzo[b,f][1,4]oxazepin-11-yl)benzamide | B | Z |
| (Z)-4-(6-fluorodibenzo[b,f][1,4]oxazepin-11-yl)-N-hydroxybenzamide | B | Y |
| (Z)-4-(7-cyanodibenzo[b,f][1,4]oxazepin-11-yl)-N-hydroxybenzamide | A | Y |
| (Z)-N-hydroxy-4-(4-hydroxydibenzo[b,f][1,4]oxazepin-11-yl)benzamide | B | W |
| (Z)-N-hydroxy-4-(1-methoxydibenzo[b,f][1,4]oxazepin-11-yl)benzamide | C | Z |
| (Z)-N-hydroxy-4-(4-(2-methoxyethoxy)dibenzo[b,f][1,4]oxazepin-11-yl)benzamide | A | X |

TABLE 8-continued

| Compound Name | HDAC Inhibition (IC$_{50}$ μM) | |
|---|---|---|
| | HDAC Enzyme | WC mouse cortical neurons |
| (E)-N-hydroxy-4-(11-morpholinobenzo[b,f][1,4]oxazepin-2-yl)benzamide | A | Z |
| (Z)-4-(1-fluorodibenzo[b,f][1,4]oxazepin-11-yl)-N-hydroxybenzamide | A | Y |
| (Z)-N-hydroxy-4-(2-(trifluoromethyl)benzo[f]pyrido[2,3-b][1,4]oxazepin-6-yl)benzamide | B | Y |
| (Z)-4-(11-cyclopropyl-11H-benzo[b]pyrido[2,3-e][1,4]diazepin-5-yl)-N-hydroxybenzamide | A | W |
| (Z)-4-(5-cyclopropyl-5H-dibenzo[b,e][1,4]diazepin-11-yl)-N-hydroxybenzamide | C | X |
| (Z)-4-(5H-dibenzo[b,e][1,4]diazepin-11-yl)-N-hydroxybenzamide | C | X |
| (Z)-N-hydroxy-4-(4-(2-morpholinoethoxy)dibenzo[b,f][1,4]oxazepin-11-yl)benzamide | A | W |
| (Z)-4-(benzo[f]pyrido[2,3-b][1,4]oxazepin-6-yl)-N-hydroxybenzamide | A | X |
| (Z)-4-(2-fluoro-4-methoxydibenzo[b,f][1,4]oxazepin-11-yl)-N-hydroxybenzamide | A | X |
| (Z)-N-hydroxy-4-(4-(methylthio)dibenzo[b,f][1,4]oxazepin-11-yl)benzamide | A | X |
| (Z)-N-hydroxy-4-(4-(trifluoromethyl)dibenzo[b,f][1,4]oxazepin-11-yl)benzamide | A | Z |
| (Z)-N-hydroxy-4-(4-(methylsulfinyl)dibenzo[b,f][1,4]oxazepin-11-yl)benzamide | B | X |
| (Z)-4-(5H-benzo[e]pyrrolo[1,2-a][1,4]diazepin-11-yl)-N-hydroxybenzamide | A | X |
| (Z)-N-hydroxy-4-(4-(methylsulfonyl)dibenzo[b,f][1,4]oxazepin-11-yl)benzamide | A | X |
| (E)-4-((dibenzo[b,f][1,4]oxazepin-11-ylamino)methyl)-N-hydroxybenzamide | A | W |
| (Z)-N-hydroxy-4-(4-methoxy-8-(trifluoromethyl)dibenzo[b,f][1,4]oxazepin-11-yl)benzamide | C | Y |
| (Z)-N-hydroxy-4-(3-morpholinodibenzo[b,f][1,4]oxazepin-11-yl)benzamide | C | Y |
| (Z)-N-hydroxy-4-(4-propyldibenzo[b,f][1,4]oxazepin-11-yl)benzamide | C | Z |
| (Z)-N-hydroxy-4-(4-(trifluoromethoxy)dibenzo[b,f][1,4]oxazepin-11-yl)benzamide | C | Z |
| (Z)-N-hydroxy-4-(6-methyldibenzo[b,f][1,4]oxazepin-11-yl)benzamide | C | Y |
| (E)-4-(dibenzo[b,f][1,4]oxazepin-11-yl)-3-fluoro-N-hydroxybenzamide | D | Y |
| (E)-6-(dibenzo[b,f][1,4]oxazepin-11-yl)-N-hydroxynicotinamide | C | Y |
| (E)-5-(dibenzo[b,f][1,4]oxazepin-11-yl)-N-hydroxyfuran-2-carboxamide | D | Z |
|  | C | Y |
| (E)-5-(dibenzo[b,f][1,4]oxazepin-11-yl)-N-hydroxythiophene-2-carboxamide | A | X |
| (Z)-4-(5-ethyl-5H-dibenzo[b,e][1,4]diazepin-11-yl)-N-hydroxybenzamide | B | X |
| (Z)-4-(5-cyclopropyl-5H-dibenzo[b,e][1,4]diazepin-11-yl)-N-hydroxy-N-methylbenzamide | D | n/d |
| (Z)-N-hydroxy-4-(5-isopropyl-5H-dibenzo[b,e][1,4]diazepin-11-yl)benzamide | A | W |
| (E)-4-((5-cyclopropyl-5H-dibenzo[b,e][1,4]diazepin-11-ylamino)methyl)-N-hydroxybenzamide | C | Y |
| (Z)-4-(4-fluorodibenzo[b,f][1,4]oxazepin-11-yl)-N-hydroxybenzamide | C | Y |
| (Z)-N-hydroxy-4-(5-(2-methoxyethyl)-5H-dibenzo[b,e][1,4]diazepin-11-yl)benzamide | C | X |

TABLE 8-continued

| Compound Name | HDAC Inhibition (IC$_{50}$ μM) | |
|---|---|---|
| | HDAC Enzyme | WC mouse cortical neurons |
| (E)-4-(2-(dibenzo[b,f][1,4]oxazepin-11-ylamino)ethyl)-N-hydroxybenzamide | C | Y |
| (Z)-4-(11-ethyl-11H-benzo[b]pyrido[2,3-e][1,4]diazepin-5-yl)-N-hydroxybenzamide | A | W |
| (Z)-4-(5-cyclopropyl-2-fluoro-5H-dibenzo[b,e][1,4]diazepin-11-yl)-N-hydroxybenzamide | B | X |
| (Z)-N-hydroxy-4-(11-isopropyl-11H-benzo[b]pyrido(2,3-e][1,4]diazepin-5-yl)benzamide | A | W |
| (Z)-4-(benzo[f]thieno[2,3-b][1,4]oxazepin-5-yl)-N-hydroxybenzamide | C | X |
| (Z)-6-(4-(dibenzo[b,f][1,4]oxazepin-11-yl)benzamidooxy)-3,4,5-trihydroxytetrahydro-2H-pyran-2-carboxylic acid | — | Z |
| (Z)-N-hydroxy-4-(11-(3-morpholinopropyl)-11H-benzo[b]pyrido[2,3-e][1,4]diazepin-5-yl)benzamide | C | X |
| (Z)-N-hydroxy-4-(11-(2-morpholinoethyl)-11H-benzo[b]pyrido[2,3-e][1,4]diazepin-5-yl)benzamide | B | X |
| (Z)-4-(11-(cyclopropylmethyl)-11H-benzo[b]pyrido[2,3-e][1,4]diazepin-5-yl)-N-hydroxybenzamide | D | n/d |
| (Z)-N-hydroxy-4-(5-(2-morpholinoethyl)-5H-dibenzo[b,e][1,4]diazepin-11-yl)benzamide | C | n/d |

TABLE 9

| Compound Name | HDAC Inhibition (IC$_{50}$ μM) | |
|---|---|---|
| | HDAC Enzyme | WC mouse cortical neurons |
| 2-((1S,4S)-5-benzyl-2,5-diazabicyclo[2.2.1]heptan-2-yl)-N-hydroxypyrimidine-5-carboxamide | C | X |
| N-hydroxy-2-((1S,4S)-5-p-tolyl-2,5-diazabicyclo[2.2.1]heptan-2-N-yl)pyrimidine-5-carboxamide | A | W |
| 2-((1S,4S)-5-benzhydryl-2,5-diazabicyclo[2.2.1]heptan-2-yl)-N-hydroxypyrimidine-5-carboxamide | A | X |
| 2-((1S,4S)-5-(4-chlorophenyl)-2,5-diazabicyclo[2.2.1]heptan-2-yl)-N-hydroxy-pyrimidine-5-carboxamide | A | W |
| (1S,4S)-tert-butyl 5-(5-(hydroxycarbamoyl)pyrimidin-2-yl)-2,5-diazabicyclo[2.2.1]heptane-2-carboxylate | A | W |
| 2-((1S,4S)-5-(3-fluorophenyl)-2,5-diazabicyclo[2.2.1]heptan-2-yl)-N-hydroxy-pyrimidine-5-carboxamide | A | W |
| 2-((1S,4S)-5-(4-fluorophenyl)-2,5-diazabicyclo[2.2.1]heptan-2-yl)-N-hydroxy-pyrimidine-5-carboxamide | B | W |
| 2-((1S,4S)-2,5-diazabicyclo[2.2.1]heptan-2-yl)-N-hydroxypyrimidine-5-carboxamide | C | Y |
| N-hydroxy-2-((1S,4S)-5-o-tolyl-2,5-diazabicyclo[2.2.1]heptan-2-yl)pyrimidine-5-carboxamide | B | X |
| 2-(2-oxa-5-azabicyclo[2.2.1]heptan-5-yl)-N-hydroxypyrimidine-5-carboxamide | C | X |
| N-hydroxy-2-((1S,4S)-5-phenyl-2,5-diazabicyclo[2.2.1]heptan-2-yl)pyrimidine-5-carboxamide | B | W |
| 2-((1S,4S)-5-benzoyl-2,5-diazabicyclo[2.2.1]heptan-2-yl)-N-hydroxypyrimidine-5-carboxamide | A | W |
| N-hydroxy-2-((1S,4S)-5-(3-(trifluoromethyl)phenyl)-2,5-diazabicyclo[2.2.1]heptan-2-yl)pyrimidine-5-carboxamide | A | W |
| 2-((1S,4S)-5-(2-fluoro-4-(trifluoromethyl)phenyl)-2,5-diazabicyclo[2.2.1]heptan-2-yl)-N-hydroxypyrimidine-5-carboxamide | A | X |
| N-hydroxy-2-((1S,4S)-5-(2-(trifluoromethyl)phenyl)-2,5-diazabicyclo[2.2.1]heptan-2-yl)pyrimidine-5-carboxamide | C | X |
| N-hydroxy-2-((1S,4S)-5-(4-(trifluoromethyl)phenyl)-2,5-diazabicyclo[2.2.1]heptan-2-yl)pyrimidine-5-carboxamide | A | X |
| 2-((1S,4S)-5-(benzo[c][1,2,5]oxadiazol-5-yl)-2,5-diazabicyclo[2.2.1]heptan-2-yl)-N-hydroxypyrimidine-5-carboxamide | A | W |
| 2-((1S,4S)-5-(benzo[c][1,2,5]thiadiazol-5-yl)-2,5-diazabicyclo[2.2.1]heptan-2-yl)-N-hydroxypyrimidine-5-carboxamide | A | W |

TABLE 9-continued

| Compound Name | HDAC Inhibition (IC$_{50}$ μM) | |
|---|---|---|
| | HDAC Enzyme | WC mouse cortical neurons |
| N-hydroxy-2-((1S,4S)-5-(3-(trifluoromethyl)benzoyl)-2,5-diazabicyclo[2.2.1]heptan-2-yl)pyrimidine-5-carboxamide | B | X |
| 2-((1S,4S)-5-(benzo[d][1,3]dioxol-5-yl)-2,5-diazabicyclo[2.2.1]heptan-2-yl)-N-hydroxypyrimidine-5-carboxamide | A | W |
| 2-((1S,4S)-5-(cyclohexanecarbonyl)-2,5-diazabicyclo[2.2.1]heptan-2-yl)-N-hydroxypyrimidine-5-carboxamide | n/d | X |
| 2-((1S,4S)-5-(2,2-diphenylacetyl)-2,5-diazabicyclo[2.2.1]heptan-2-yl)-N-hydroxy-pyrimidine-5-carboxamide | B | X |
| N-hydroxy-4-((1S,4S)-5-p-tolyl-2,5-diazabicyclo[2.2.1]heptan-2-yl)benzamide | C | X |
| N-hydroxy-2-((1S,4S)-5-(3-(trifluoromethyl)phenyl)-2,5-diazabicyclo[2.2.1]heptan-2-yl)thiazole-5-carboxamide | A | X |
| (1S,4S)-benzyl 5-(5-(hydroxycarbamoyl)pyrimidin-2-yl)-2,5-diazabicyclo[2.2.1]heptane-2-carboxylate | A | W |
| (1S,4S)-isobutyl 5-(5-(hydroxycarbamoyl)pyrimidin-2-yl)-2,5-diazabicyclo[2.2.1]heptane-2-carboxylate | A | W |
| N-hydroxy-2-((1S,4S)-5-(3-(trifluoromethoxy)phenyl)-2,5-diazabicyclo[2.2.1]heptan-2-yl)pyrimidine-5-carboxamide | A | W |
| 2-((1S,4S)-5-(2,2-difluorobenzo[d][1,3]dioxol-5-yl)-2,5-diazabicyclo[2.2.1]heptan-2-yl)-N-hydroxypyrimidine-5-carboxamide | A | X |
| N-hydroxy-2-((1S,4S)-5-(3-(trifluoromethylthio)phenyl)-2,5-diazabicyclo[2.2.1]heptan-2-yl)pyrimidine-5-carboxamide | A | X |
| N-hydroxy-2-((1S,4S)-5-(4-(trifluoromethyl)pyridin-2-yl)-2,5-diazabicyclo[2.2.1]heptan-2-yl)pyrimidine-5-carboxamide | A | W |
| N-hydroxy-2-((1S,4S)-5-(2-(trifluoromethyl)quinolin-4-yl)-2,5-diazabicyclo[2.2.1]heptan-2-yl)pyrimidine-5-carboxamide | A | W |
| 2-((1S,4S)-5-(3-(difluoromethoxy)phenyl)-2,5-diazabicyclo[2.2.1]heptan-2-yl)-N-hydroxypyrimidine-5-carboxamide | A | W |
| N-hydroxy-2-((1S,4S)-5-(6-(trifluoromethyl)pyridin-2-yl)-2,5-diazabicyclo[2.2.1]heptan-2-yl)pyrimidine-5-carboxamide | A | W |
| (1S,4S)-cyclopentyl 5-(5-(hydroxycarbamoyl)pyrimidin-2-yl)-2,5-diazabicyclo[2.2.1]heptane-2-carboxylate | A | W |
| 2-((1S,4S)-5-(benzo[c][1,2,5]oxadiazol-4-yl)-2,5-diazabicyclo[2.2.1]heptan-2-yl)-N-hydroxypyrimidine-5-carboxamide | A | W |
| N-hydroxy-2-((1S,4S)-5-(5-(trifluoromethyl)pyridin-3-yl)-2,5-diazabicyclo[2.2.1]heptan-2-yl)pyrimidine-5-carboxamide | A | W |
| N-hydroxy-2-((1R,4R)-5-p-tolyl-2,5-diazabicyclo[2.2.1]heptan-2-yl)pyrimidine-5-carboxamide | A | W |
| (1S,4S)-isopropyl 5-(5-(hydroxycarbamoyl)pyrimidin-2-yl)-2,5-diazabicyclo[2.2.1]heptane-2-carboxylate | A | W |
| (1S,4S)-pyridin-3-ylmethyl 5-(5-(hydroxycarbamoyl)pyrimidin-2-yl)-2,5-diazabicyclo[2.2.1]heptane-2-carboxylate | A | W |
| (1S,4S)-cyclopropylmethyl 5-(5-(hydroxycarbamoyl)pyrimidin-2-yl)-2,5-diazabicyclo[2.2.1]heptane-2-carboxylate | A | W |
| (1S,4S)-tetrahydro-2H-pyran-4-yl 5-(5-(hydroxycarbamoyl)pyrimidin-2-yl)-2,5-diazabicyclo[2.2.1]heptane-2-carboxylate | A | W |
| 2-((1S,4S)-5-(3,5-bis(trifluoromethyl)phenyl)-2,5-diazabicyclo[2.2.1]heptan-2-yl)-N-hydroxypyrimidine-5-carboxamide | A | X |
| 2-((1S,4S)-5-(benzo[d]isoxazol-3-yl)-2,5-diazabicyclo[2.2.1]heptan-2-yl)-N-hydroxypyrimidine-5-carboxamide | A | W |
| 2-((1S,4S)-5-(3-(dimethylcarbamoyl)phenyl)-2,5-diazabicyclo[2.2.1]heptan-2-yl)-N-hydroxypyrimidine-5-carboxamide | A | W |
| 2-((1S,4S)-5-(3-((dimethylamino)methyl)phenyl)-2,5-diazabicyclo[2.2.1]heptan-2-yl)-N-hydroxypyrimidine-5-carboxamide | A | W |
| N-hydroxy-2-((1S,4S)-5-(3-methoxyphenyl)-2,5-diazabicyclo[2.2.1]heptan-2-yl)pyrimidine-5-carboxamide | A | W |
| N-hydroxy-2-((1S,4S)-5-m-tolyl-2,5-diazabicyclo[2.2.1]heptan-2-yl)pyrimidine-5-carboxamide | A | W |
| N-hydroxy-6-(5-p-tolyl-2,5-diazabicyclo[2.2.1]heptan-2-yl)nicotinamide | A | W |
| N-hydroxy-5-((1S,4S)-5-(3-(trifluoromethyl)phenyl)-2,5-diazabicyclo[2.2.1]heptan-2-yl)pyrazine-2-carboxamide | C | Y |
| 2-fluoro-N-hydroxy-4-(1S,4S)-5-(3-(trifluoromethyl)phenyl)-2,5-diazabicyclo[2.2.1]heptan-2-yl)benzamide | C | Y |
| N-hydroxy-2-((1S,4S)-5-(pyrrolidine-1-carbonyl)-2,5-diazabicyclo[2.2.1]heptan-2-yl)pyrimidine-5-carboxamide | B | W |
| N-hydroxy-2-((1S,4S)-5-(4-(trifluoromethyl)pyrimidin-2-yl)-2,5-diazabicyclo[2.2.1]heptan-2-yl)pyrimidine-5-carboxamide | A | W |
| N-hydroxy-6-((1S,4S)-5-(3-(trifluoromethyl)phenyl)-2,5-diazabicyclo[2.2.1]heptan-2-yl)pyridazine-3-carboxamide | C | Y |
| N-hydroxy-2-(7-(4-(trifluoromethyl)pyridin-2-yl)-3,7-diazabicyclo[3.3.1]nonan-3-yl)pyrimidine-5-carboxamide | C | Z |
| N-hydroxy-2-((1R,4R)-5-(4-(trifluoromethyl)pyridin-2-yl)-2,5-diazabicyclo[2.2.1]heptan-2-yl)pyrimidine-5-carboxamide | A | W |

TABLE 9-continued

| Compound Name | HDAC Inhibition (IC$_{50}$ μM) | |
|---|---|---|
| | HDAC Enzyme | WC mouse cortical neurons |
| N-hydroxy-2-((1R,4R)-5-m-tolyl-2,5-diazabicyclo[2.2.1]heptan-2-yl)pyrimidine-5-carboxamide | B | W |
| [structure: pentafluorosulfanyl-phenyl-diazabicyclo-pyrimidine-hydroxamide] | A | X |
| 2-(5-(3-cyanophenyl)-2,5-diazabicyclo[2.2.1]heptan-2-yl)-N-hydroxypyrimidine-5-carboxamide | A | W |
| N-hydroxy-4-(5-(3-methoxyphenyl)-2,5-diazabicyclo[2.2.1]heptan-2-yl)benzamide | C | X |
| N-hydroxy-4-(5-m-tolyl-2,5-diazabicyclo[2.2.1]heptan-2-yl)benzamide | C | X |
| N-hydroxy-4-((1S,4S)-5-(3-(trifluoromethyl)phenyl)-2,5-diazabicyclo[2.2.1]heptan-2-yl)benzamide | C | X |
| N-hydroxy-4-((1S,4S)-5-(4-(trifluoromethyl)pyridin-2-yl)-2,5-diazabicyclo[2.2.1]heptan-2-yl)benzamide | C | X |
| 4-((1S,4S)-5-(3-cyanophenyl)-2,5-diazabicyclo[2.2.1]heptan-2-yl)-N-hydroxybenzamide | C | X |
| N-hydroxy-4-((1R,4R)-5-m-tolyl-2,5-diazabicyclo[2.2.1]heptan-2-yl)benzamide | C | X |
| N-hydroxy-4-((1R,4R)-5-(4-(trifluoromethyl)pyridin-2-yl)-2,5-diazabicyclo[2.2.1]heptan-2-yl)benzamide | D | Y |
| N-hydroxy-4-((1S,4S)-5-(4-(trifluoromethyl)pyrimidin-2-yl)-2,5-diazabicyclo[2.2.1]heptan-2-yl)benzamide | n/d | X | n/d = Not Determined

TABLE 10

| Compound Name | HDAC Inhibition (IC$_{50}$ μM) | |
|---|---|---|
| | HDAC Enzyme | WC mouse cortical neurons |
| (Z)-4-((5H-dibenzo[b,f]azepin-5-yl)methyl)-N-hydroxybenzamide | A | Y |
| [structure: dibenzoazepinylidene-N-hydroxyacetamide] | C | n/d |
| (Z)-4-(5H-dibenzo[b,f]azepin-5-yl)-N-hydroxybutanamide | D | Y |
| (E)-N-hydroxy-3-((Z)-2-oxo-5-phenyl-2,3-dihydro-1H-benzo[e][1,4]diazepin-8-yl)acrylamide | B | X |
| (E)-N-hydroxy-3-((Z)-1-methyl-2-oxo-5-phenyl-2,3-dihydro-1H-benzo[e][1,4]diazepin-8-yl)acrylamide | C | X |
| (Z)-6-(5H-dibenzo[b,f]azepin-5-yl)-N-hydroxyhexanamide | A | X |
| (Z)-N-hydroxy-3-(1-methyl-2-oxo-5-phenyl-2,3-dihydro-1H-benzo[e][1,4]diazepin-8-yl)propanamide | C | Y |
| (Z)-N-hydroxy-6-(2-oxo-5-phenyl-2,3-dihydro-1H-benzo[e][1,4]diazepin-1-yl)hexanamide | C | X |
| (Z)-N-hydroxy-8-(2-oxo-5-phenyl-2,3-dihydro-1H-benzo[e][1,4]diazepin-1-yl)octanamide | C | X |

TABLE 10-continued

| Compound Name | HDAC Inhibition (IC$_{50}$ μM) | |
|---|---|---|
| | HDAC Enzyme | WC mouse cortical neurons |
| [structure] | D | n/d |
| (Z)-2-(5H-dibenzo[b,f]azepin-5-yl)-N-hydroxyacetamide | D | n/d |
| [structure] | C | X |
| [structure] | C | X |
| [structure] | C | Y |
| [structure] | C | Y |

TABLE 10-continued

| Compound Name | HDAC Inhibition (IC$_{50}$ μM) | |
|---|---|---|
| | HDAC Enzyme | WC mouse cortical neurons |
| *[structure: dibenzosuberane with CH-NH-CH2-C6H4-C(O)NHOH]* | A | Y |
| *[structure: dibenzosuberone oxime O-CH2-C6H4-C(O)NHOH]* | C | Y |
| (E)-3-((Z)-5-(cyclopropylmethyl)-5H-dibenzo[b,f]azepin-2-yl)-N-hydroxyacrylamide | C | Y |
| 4-(11-cyclopropyl-5-oxo-5H-benzo[b]pyrido[2,3-e][1,4]diazepin-6(11H)-yl)-N-hydroxybutanamide | D | n/d |
| 6-(11-cyclopropyl-5-oxo-5H-benzo[b]pyrido[2,3-e][1,4]diazepin-6(11H)-yl)-N-hydroxyhexanamide | C | X |
| 7-(11-cyclopropyl-5-oxo-5H-benzo[b]pyrido[2,3-e][1,4]diazepin-6(11H)-yl)-N-hydroxyheptanamide | B | X |
| 4-((11-cyclopropyl-5-oxo-5H-benzo[b]pyrido[2,3-e][1,4]diazepin-6(11H)-yl)methyl)-N-hydroxybenzamide | C | Y |
| 8-(11-cyclopropyl-5-oxo-5H-benzo[b]pyrido[2,3-e][1,4]diazepin-6(11H)-yl)-N-hydroxyoctanamide | C | W |
| (E)-N-hydroxy-3-(4-(((Z)-2-oxo-5-phenyl-2,3-dihydro-1H-benzo[e][1,4]diazepin-1-yl)methyl)phenyl)acrylamide | B | X |
| (E)-3-(4-(((Z)-5H-dibenzo[b,f]azepin-5-yl)methyl)phenyl)-N-hydroxyacrylamide | B | X |
| *[structure: dibenzosuberane-CH-NH-CH2-C6H4-CH=CH-C(O)NHOH]* | B | Y |
| (E)-3-(4-((11-cyclopropyl-5-oxo-5H-benzo[b]pyrido[2,3-e][1,4]diazepin-6(11H)-yl)methyl)phenyl)-N-hydroxyacrylamide | A | W |
| (Z)-2-(4-((5H-dibenzo[b,f]azepin-5-yl)methyl)phenyl)-N-hydroxyacetamide | C | Y |

TABLE 10-continued

| Compound Name | HDAC Inhibition (IC$_{50}$ µM) | |
|---|---|---|
| | HDAC Enzyme | WC mouse cortical neurons |
| 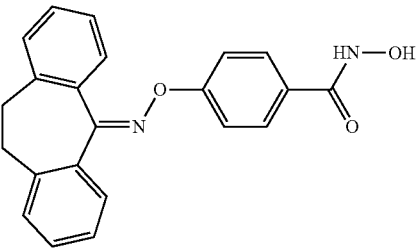 [SMILES: O=C(NO)c1ccc(ON=C2c3ccccc3CCc3ccccc32)cc1] | C | Y |
| 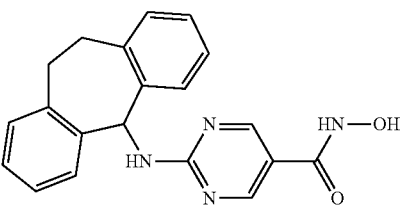 [SMILES: O=C(NO)c1cnc(NC2c3ccccc3CCc3ccccc32)nc1] | A | n/d |
| 6-(10,11-dihydro-5H-dibenzo[b,f]azepin-5-yl)-N-hydroxyhexanamide | A | X |
| (Z)-5-(5H-dibenzo[b,f]azepin-5-yl)-N-hydroxypentanamide | C | Y |
| (Z)-7-(5H-dibenzo[b,f]azepin-5-yl)-N-hydroxyheptanamide | A | X |
| 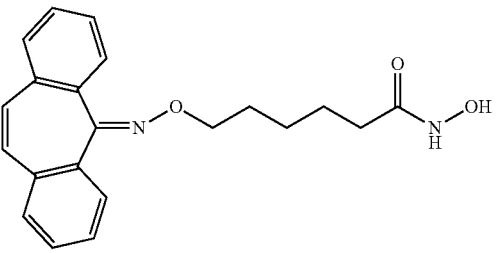 [SMILES: O=C(CCCCCON=c1c2ccccc2ccc2ccccc12)NO] | C | Y |
| 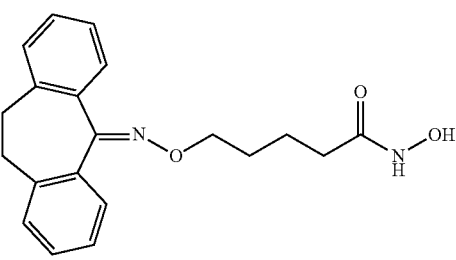 [SMILES: O=C(CCCCON=C1c2ccccc2CCc2ccccc21)NO] | C | Y |
| N-hydroxy-7-(11-oxodibenzo[b,f][1,4]oxazepin-10(11H)-yl)heptanamide | A | W |
| 7-(dibenzo[b,f][1,4]oxazepin-10(11H)-yl)-N-hydroxyheptanamide | C | Z |
| 2-(benzhydrylamino)-N-hydroxypyrimidine-5-carboxamide | A | W |
| 2-(diphenylmethyleneaminooxy)-N-hydroxypyrimidine-5-carboxamide | D | Y |
| N-hydroxy-6-(11-oxodibenzo[b,f][1,4]oxazepin-10(11H)-yl)hexanamide | A | W |
| N-hydroxy-8-(11-oxodibenzo[b,f][1,4]oxazepin-10(11H)-yl)octanamide | B | X |
| 2-(9H-fluoren-9-ylamino)-N-hydroxypyrimidine-5-carboxamide | C | Y |

TABLE 10-continued

| Compound Name | HDAC Inhibition (IC$_{50}$ μM) | |
|---|---|---|
| | HDAC Enzyme | WC mouse cortical neurons |
| 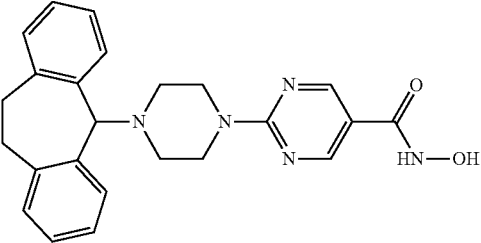 [SMILES: O=C(NO)c1cnc(N2CCN(C3c4ccccc4CCc4ccccc43)CC2)nc1] | C | Y |
| N-hydroxy-N-(6-(11-oxodibenzo[b,f][1,4]oxazepin-10(11H)-yl)hexyl)formamide | A | n/d |
| 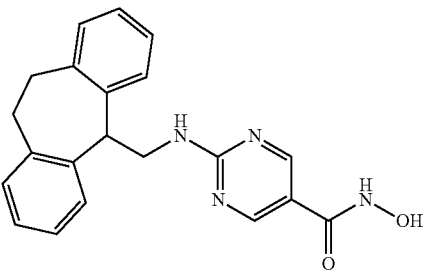 [SMILES: O=C(NO)c1cnc(NCC2c3ccccc3CCc3ccccc32)nc1] | A | Y |
| 2-(dipyridin-2-ylmethylamino)-N-hydroxypyrimidine-5-carboxamide | — | W |
| 8-(dibenzo[b,f][1,4]oxazepin-10(11H)-yl)-N-hydroxy-8-oxooctanamide | C | X |
| N-hydroxy-7-(11-oxodibenzo[b,f][1,4]thiazepin-10(11H)-yl)heptanamide | A | W |
| 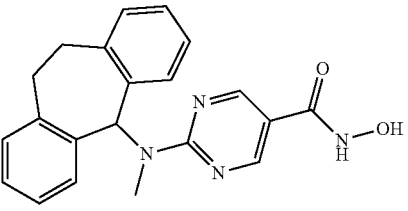 [SMILES: CN(c1ncc(C(=O)NO)cn1)C1c2ccccc2CCc2ccccc21] | A | X |
| N-hydroxy-4-((11-oxodibenzo[b,f][1,4]oxazepin-10(11H)-yl)methyl)benzamide | A | W |
| 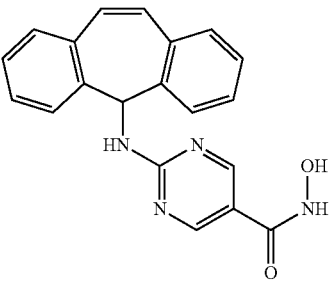 [SMILES: O=C(NO)c1cnc(NC2c3ccccc3C=Cc3ccccc32)nc1] | A | W |
| 2-(bis(4-fluorophenyl)methylamino)-N-hydroxypyrimidine-5-carboxamide | A | n/d |
| N-hydroxy-4-((6-oxophenanthridin-5(6H)-yl)methyl)benzamide | A | W |
| N-hydroxy-4-(2-(11-oxodibenzo[b,f][1,4]oxazepin-10(11H)-yl)ethyloxodibenzo[b,f][1,4]oxazepin-10(11H)-yl)ethoxy)benzamide | A | W |
| N-hydroxy-7-(phenanthridin-6-yloxy)heptanamide | A | Y |
| N-hydroxy-7-(6-oxophenanthridin-5(6H)-yl)heptanamide | A | W |

TABLE 10-continued

| Compound Name | HDAC Inhibition (IC$_{50}$ μM) | |
|---|---|---|
| | HDAC Enzyme | WC mouse cortical neurons |
| N-hydroxy-2-(4-((11-oxodibenzo[b,f][1,4]oxazepin-10(11H)-yl)methyl)phenyl)acetamide | C | X |
| 6-(5-cyclopropyl-11-oxo-5H-dibenzo[b,e][1,4]diazepin-10(11H)-yl)-N-hydroxyhexanamide | C | X |
| 7-(5-cyclopropyl-11-oxo-5H-dibenzo[b,e][1,4]diazepin-10(11H)-yl)-N-hydroxyheptanamide | C | X |
| *[dibenzoxathiazepine sulfone-N-hexanoyl hydroxamic acid structure]* | C | X |
| (E)-N-hydroxy-3-(4-((11-oxodibenzo[b,f][1,4]oxazepin-10(11H)-yl)methyl)phenyl)acrylamide | A | X |
| N-hydroxy-3-(4-((11-oxodibenzo[b,f][1,4]oxazepin-10(11H)-yl)methyl)phenyl)propanamide | C | X |
| N-hydroxy-4-((6-oxo-11,12-dihydrodibenzo[b,f]azocin-5(6H)-yl)methyl)benzamide | C | X |
| 4-(2-(7-chloro-11-oxodibenzo[b,f][1,4]oxazepin-10(11H)-yl)ethylchloro-11-oxodibenzo[b,f][1,4]oxazepin-10(11H)-yl)ethoxy)-N-hydroxybenzamide | A | X |
| 2-(bis(4-fluorophenyl)methoxy)-N-hydroxypyrimidine-5-carboxamide | C | Z |
| *[dibenzosuberyl-amino diamide hydroxamic acid structure]* | C | X |
| (Z)-8-(5H-dibenzo[b,f]azepin-5-yl)-N-hydroxy-8-oxooctanamide | C | Y |
| (Z)-7-(5H-dibenzo[b,f]azepin-5-yl)-N-hydroxy-7-oxoheptanamide | A | W |
| *[dibenzosuberyl-amino hydroxamic acid structure]* | C | X |
| *[fluoro-dibenzosuberyl-aminopyrimidine hydroxamic acid structure]* | A | W |
| N-hydroxy-4-(2-(5-oxobenzo[b]pyrido[3,2-f][1,4]oxazepin-6(5H)-yl)ethyloxobenzo[b]pyrido[3,2-f][1,4]oxazepin-6(5H)-yl)ethoxy)benzamide | A | W |
| (E)-N-hydroxy-4-(3-(11-oxodibenzo[b,f][1,4]oxazepin-10(11H)-yl)prop-1-ynyl)benzamide | B | W |
| N-hydroxy-4-(3-(11-oxodibenzo[b,f][1,4]oxazepin-10(11H)-yl)propyl)benzamide | B | W |

TABLE 10-continued

| Compound Name | HDAC Inhibition (IC$_{50}$ µM) | |
|---|---|---|
| | HDAC Enzyme | WC mouse cortical neurons |
| N-hydroxy-4-(3-(11-oxodibenzo[b,f][1,4]oxazepin-10(11H)-yl)prop-1-ynyl)benzamide | A | X |
| 4-(2-(2-fluoro-11-oxodibenzo[b,f][1,4]oxazepin-10(11H)-yl)ethylfluoro-11-oxodibenzo[b,f][1,4]oxazepin-10(11H)-yl)ethoxy)-N-hydroxybenzamide | A | W |
| N-hydroxy-4-(2-(5-oxo-2,3-dihydrobenzo[f][1,4]oxazepin-4(5H)-yl)ethyloxo-2,3-dihydrobenzo[f][1,4]oxazepin-4(5H)-yl)ethoxy)benzamide | A | X |
| N-hydroxy-4-(2-(4-oxo-3,4-dihydrobenzo[b][1,4]oxazepin-5(2H)-yl)ethyloxo-3,4-dihydrobenzo[b][1,4]oxazepin-5(2H)-yl)ethoxy)benzamide | A | W |
| N-hydroxy-4-(2-(5-oxobenzo[b]pyrido[4,3-f][1,4]oxazepin-6(5H)-yl)ethyloxobenzo[b]pyrido[4,3-f][1,4]oxazepin-6(5H)-yl)ethoxy)benzamide | A | W |
| N-hydroxy-3-(4-((11-oxodibenzo[b,f][1,4]oxazepin-10(11H)-yl)methyl)-1H-1,2,3-triazol-1-yl)propanamide | C | X |
| N-hydroxy-4-(2-(2-methyl-5-oxo-1,2,3,4-tetrahydrobenzo[b]pyrido[4,3-f][1,4]oxazepin-6(5H)-yl)ethylmethyl-5-oxo-1,2,3,4-tetrahydrobenzo[b]pyrido[4,3-f][1,4]oxazepin-6(5H)-yl)ethoxy)benzamide | A | W |
| 4-(2-(dibenzo[b,f][1,4]oxazepin-10(11H)-yl)-2-oxoethyldibenzo[b,f][1,4]oxazepin-10(11H)-yl)-2-oxoethoxy)-N-hydroxybenzamide | C | X |
| 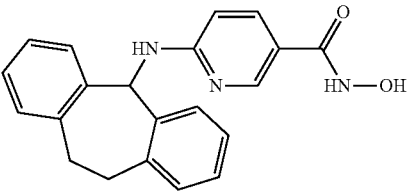 [SMILES: O=C(NO)c1ccc(NC2c3ccccc3CCc3ccccc32)nc1] | A | W |
| 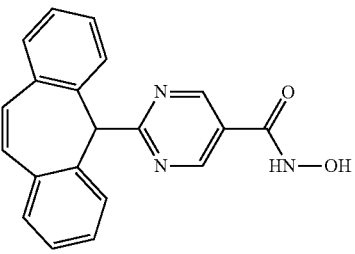 [SMILES: O=C(NO)c1cnc(C2c3ccccc3C=Cc3ccccc32)nc1] | C | Z |
| 2-fluoro-N-hydroxy-4-(2-(11-oxodibenzo[b,f][1,4]oxazepin-10(11H)-yl)ethyloxodibenzo[b,f][1,4]oxazepin-10(11H)-yl)ethoxy)benzamide | B | n/d |
| N-hydroxy-3-(2-(11-oxodibenzo[b,f][1,4]oxazepin-10(11H)-yl)ethyloxodibenzo[b,f][1,4]oxazepin-10(11H)-yl)ethoxy)benzamide | C | Z |
| 3-fluoro-N-hydroxy-4-(2-(11-oxodibenzo[b,f][1,4]oxazepin-10(11H)-yl)ethyloxodibenzo[b,f][1,4]oxazepin-10(11H)-yl)ethoxy)benzamide | B | W |
| 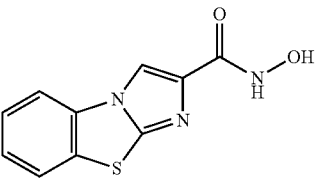 [SMILES: O=C(NO)c1cn2c(n1)sc1ccccc12] | C | n/d |
| N-hydroxy-4-(11-oxodibenzo[b,f][1,4]oxazepin-10(11H)-yl)benzamide | C | Z |
| (Z)-3-((5H-dibenzo[b,f]azepin-5-yl)methyl)-N-hydroxybenzamide | C | n/d |
| benzyl 4-(5-(hydroxycarbamoyl)pyrimidin-2-yl)-1,4-diazepane-1-carboxylate | B | X |

TABLE 10-continued

| Compound Name | HDAC Inhibition (IC$_{50}$ μM) | |
|---|---|---|
| | HDAC Enzyme | WC mouse cortical neurons |
| *[structure: dibenzosuberyl-O-CH2-C6H4-C(O)NHOH (para)]* | C | n/d |
| 4-((10,11-dihydro-5H-dibenzo[b,f]azepin-5-yl)methyl)-N-hydroxybenzamide | A | n/d |
| 2-(4-(3-chloro-5-(trifluoromethyl)pyridin-2-yl)-1,4-diazepan-1-yl)-N-hydroxypyrimidine-5-carboxamide | A | Y |
| *[structure: dibenzosuberyl-O-CH2-C6H4-C(O)NHOH (meta)]* | C | n/d |
| (S)-2-(2-(1H-benzo[d]imidazol-2-yl)pyrrolidin-1-yl)-N-hydroxypyrimidine-5-carboxamide | C | n/d |
| 2-chloro-N-hydroxy-4-(2-(11-oxodibenzo[b,f][1,4]oxazepin-10(11H)-yl)ethyloxodibenzo[b,f][1,4]oxazepin-10(11H)-yl)ethoxy)benzamide | D | n/d |
| (Z)-N-hydroxy-4-(1-methyl-2-oxo-2,3-dihydro-1H-benzo[e][1,4]diazepin-5-yl)benzamide | C | Y |
| 3-((10H-phenothiazin-10-yl)methyl)-N-hydroxybenzamide | C | n/d |
| 4-(dibenzo[b,f][1,4]oxazepin-10(11H)-ylmethyl)-N-hydroxybenzamide | A | n/d |
| 4-((benzhydrylamino)methyl)-N-hydroxybenzamide | A | n/d |
| *[structure: dibenzosuberyl-NH-CH2-C6H4-C(O)NHOH (meta)]* | C | n/d |
| N-hydroxy-2-(3-phenyl-5,6-dihydro-[1,2,4]triazolo[4,3-a]pyrazin-7(8H)-yl)pyrimidine-5-carboxamide | A | X |
| 4-((6,7,8,9,10,11-hexahydro-5H-cycloocta[b]indol-5-yl)methyl)-N-hydroxybenzamide | C | n/d |
| N-hydroxy-2-(3-(trifluoromethyl)-5,6-dihydro-[1,2,4]triazolo[4,3-a]pyrazin-7(8H)-yl)pyrimidine-5-carboxamide | B | X |
| N-hydroxy-2-methyl-2,3,4,5-tetrahydro-1H-pyrido[4,3-b]indole-8-carboxamide | D | n/d |
| N-hydroxy-9H-pyrido[3,4-b]indole-3-carboxamide | D | n/d |
| 4-((6,11-dihydrodibenzo[b,e]oxepin-11-ylamino)methyl)-N-hydroxybenzamide | C | n/d |
| 2-((1R,5S)-1-(3,4-dichlorophenyl)-3-azabicyclo[3.1.0]hexan-3-yl)-N-hydroxypyrimidine-5-carboxamide | C | n/d |
| 2-((1S,5R)-1-(3,4-dichlorophenyl)-3-azabicyclo[3.1.0]hexan-3-yl)-N-hydroxypyrimidine-5-carboxamide | C | n/d |

TABLE 10-continued

| Compound Name | HDAC Enzyme | WC mouse cortical neurons |
|---|---|---|
| N-hydroxy-2-((1R,5S)-1-phenyl-3-azabicyclo[3.1.0]hexan-3-yl)pyrimidine-5-carboxamide | C | n/d |
| N-hydroxy-4-((2-phenyl-1H-indol-1-yl)methyl)benzamide | C | n/d |
| 3-((10H-phenoxazin-10-yl)methyl)-N-hydroxybenzamide | D | n/d |
| (Z)-4-(7-bromo-2-oxo-2,3-dihydro-1H-thieno[2,3-c][1,4]diazepin-5-yl)-N-hydroxybenzamide | C | n/d |
| 4-((diphenylamino)methyl)-N-hydroxybenzamide | C | n/d |
| 3-((diphenylamino)methyl)-N-hydroxybenzamide | D | n/d |
| (Z)-N-(5H-dibenzo[b,f]azepin-5-yl)methyl)benzyl)-N-hydroxyformamide | C | n/d |
| N-hydroxy-2-((1R,5S)-1-(3-(trifluoromethyl)phenyl)-3-azabicyclo[3.1.0]hexan-3-yl)pyrimidine-5-carboxamide | C | n/d |
| N-hydroxy-2-((1R,5S)-1-(4-(trifluoromethyl)phenyl)-3-azabicyclo[3.1.0]hexan-3-yl)pyrimidine-5-carboxamide | C | n/d | n/d = Not Determined

Assay Example 4

In Vivo *Drosophila* Fly Assay for Treatment of Huntington's Disease

The present invention discloses methods and pharmaceutical compositions for treating polyglutamine (polyQ) expansion diseases. In certain preferred embodiments, the disease is selected from the group consisting of Huntington's Disease (HD), Dentatorubralpallidoluysian atrophy (DRPLA), spinal and bulbar muscular atrophy (SBMA), and five spinocerebellar ataxias (SCA1, SCA2, SCA3/MJD (Machado-Joseph Disease), SCA6 and SCA7).

The suitability of a compound for treatment of a polyglutamine (polyQ) expansion diseases can be assessed in any of a number of animal models. For example, mice transgenic for an expanded polyglutamine repeat mutant of ataxin-1 develop ataxia typical of spinocerebellar ataxia type 1 (SCA-I) are known (Burright et al., 1995, Cell 82: 937-948; Lorenzetti et al., 2000, Hum. Mol. Genet. 9: 779-785; Watase, 2002, Neuron 34: 905-919), and can be used to determine the efficacy of a given compound in the treatment or prevention of neurodegenerative disease. Additional animal models, for example, for Huntington's disease (see, e.g., Mangiarini et al., 1996, Cell 87: 493-506, Lin et al., 2001, Hum. Mol. Genet. 10: 137-144), can be used to evaluate the efficacy of the compounds of the present invention in a similar manner.

Animal models are not limited to mammalian models. For example, *Drosophila* strains provide accepted models for a number of neurodegenerative disorders.

The *Drosophila* Huntington's Disease assay used to screen compounds of the present invention followed that of WO 2007/002497, which is hereby incorporated by reference in its entirety.

*Drosohila melanogaster* Fly Production:

Briefly, parental (model and driver) lines are maintained in sufficient quantities to provide virgins and males for assay crosses as well as perpetuating the lines. Disease model flies are maintained with the disease genes "silent", functionally linked to a UAS enhancer element. The "driver" lines contain a GAL4 element under the control of a tissue-specific promoter. These are crossed together to generate the assay flies which have tissue-specific (i.e. CNS) expression of the disease gene(s).

Weekly assay crosses are set up with sufficient virgins and males to generate enough assay embryos for sorting. Approximately 50,000 males and 75,000 virgins are crossed in population cages. Embryos are collected for an eight hour window two days later. The embryos are then sorted onto 16 mm assay vials containing regular fly media and allowed to develop. Flies containing both the GAL4 driver element and the disease gene(s) are detected by the presence of GFP, a fluorescing protein. Approximately 10 assay flies eclose per vial, the optimal number for the behavioral assay. Once the flies eclose, they are transferred onto assay vials containing liquid *Drosophila* food. Similarly, control crosses are set up with virgins of the driver and males from a non-disease UAS line. Throughout fly production and the assay days, all flies are maintained at constant temperature and humidity, with preset light cycle, optimized for the particular lines and crosses.

Quality control (QC) for the parental lines is carried out weekly by collecting a sample of random male flies from each line. Single-fly PCR is carried out to ascertain the presence of the GAL4 or UAS element. If greater than 5% of the individuals lack the appropriate element, the assay cross is aborted. A second form of QC is also carried out to ensure that the GAL4 element is able to drive expression of a transgene. A sample of individual "driver" virgins is crossed to UAS-GFP males. Their progeny are visually checked for GFP expression in the appropriate tissues. Lack of GFP in greater than 4% of the crosses results in the assay being aborted.

Compound Handling and Dosing:

Test compounds are weighed out and dissolved in DMSO at stock concentrations 100× what is desired in the assay and arrayed into 96-well master plates, including wells for DMSO-only controls and the positive control(s). A single well is reserved for a colored dye used to ensure proper orientation of compounds during drug dispensing and fly transfer. Replicate daughter plates for each day of the assay are stamped out. The plates are bar coded and stored at −20 C until used for the assay.

For a particular assay day, the plates are thawed and a robotic liquid handler is used to dilute the test compound into the liquid fly food and dispense the mixture into the assay vials. For Huntington Disease (HD) models, eight replicates per single treatment (one compound, one concentration) are dispensed. Fresh test compound treated media is made daily during an assay.

Automated Behavioral Assay:

On the day the assay flies eclose (emerge from larvae; assay Day 0) they are transferred to the test compound treated vials. On assay Day 1, the flies are transferred onto clean test compound treated vials one hour before assay time. They are then placed in the assay machine to acclimate to the appropriate climate conditions.

The assay machine is an environmentally-enclosed and controlled robot that can maintain user-set temperature and humidity. The machine can hold up to sixteen 96-vial racks in four quadrants, for a total of 1536 vials. There are four camera stations, which hold four vials each and a CCD camera for movie capture. A robotic arm carries a gripper which picks up four vials at a time, places them in a designated camera station, taps the vials to stimulate fly climbing behavior, then moves onto the next rack to pick up four vials into the next camera station, etc. For HD assays, each vial is recorded four times for 7.5 seconds, the recording starting after the vials are tapped.

After the assay run, the racks of flies are returned to the warm rooms at the designated temperature and humidity. This process is repeated for all days of the assay (10 for HD assays).

The movies are then "tracked"; using a number of parameters given in the TrackingServer custom application, movement of the flies in each movie is converted into a tracking file. Each tracking file is then processed by the scoring server, converting the movement of the flies into a number of measurements for each movie for each individual vial for a particular trial day. The measurements for each movie are outputted as a .CSV file.

Analysis and Hit Determination:

Examples of metrics are included below:
(1) xpos: The average of all the x-positions of all detected regions (i.e. flies) before 7.5 seconds in the tracking file.
(2) xspeed: The average of all the x-speeds of all detected regions before 7.5 seconds in the tracking file.
(3) speed: The average of all the speeds of all detected regions before 7.5 seconds in the tracking file.
(4) turning: The average of all turning angles of all detected regions before 7.5 seconds. The turning is determined by the angle between a speed vector and the previous one.
(5) stumbling: The average of all stumbling angles of all detected regions before 7.5 seconds. The stumbling is determined by the angle between a speed vector and the orientation of the corresponding region.
(6) size: The average area of all detected regions.
(7) tcount: The total number of trajectories.
(8) pcount: The total number of detected regions.
(9) tlength: The total sum of all trajectory lengths.
(10) crosshigh: The number of trajectories that cross or start above a certain high threshold
(11) crosslow: The number of trajectories that cross or start above a certain high threshold
(12) fcount: The maximum number of detected regions in any one frame. Used as an estimate of the number of flies in the video.

The particular spectrum of metrics to detect improvement in behavior of a treated disease fly vs. an untreated disease fly differs from disease model to disease model. Metrics are chosen based on the dynamic range of i) the difference between untreated disease and positive control and ii) the difference between untreated disease and non-disease. For the Huntington's disease screening model, speed is the best metric. Summary metrics for performance are used to determine effect sizes of treatments vs. control. The summary metrics used for the HD model are "early speed", the average speed for days 1-7 and "late speed", the average speed for days 8-10. These day ranges were chosen based on the shape of the speed curves and the t-statistic for all different day ranges. Toxicity for a compound treatment is determined by fly loss throughout the assay.

The effect sizes for the performance metrics are calculated for the different treatments by dividing the value for the metric by the pooled standard deviation for the assay. Certain systematic variations in the data can be modeled and integrated into the analysis. For example, a linear statistical model for rack position or drug dispense order can be applied to correct the effect sizes. A final assessment of assay and data quality is done by the experimenters.

For test compound treatments, a multiple repeat strategy is used to define compound hits. Statistical power is set to decrease the number of false positives and to increase the number of true positives. A threshold of effect size is set for each of three assays per treatment. A treatment below threshold for the first or second pass is not run in a third pass without convincing rationale. For current screening with the HD model, the effect size threshold for a hit after three passes is >0.4 early speed (effect size) or >0.6 late speed (effect size). Strong hits are defined are effect sizes of >0.8 early speed and >1.2 late speed. Effect size is defined as the difference between DMSO-carrier control and test compound divided by the pooled standard deviation in the whole assay (preferred test compounds have early effect size>0.4 or late effect size>0.6; more preferred test compounds have early effect size>0.6 or late effect size>1.2). TSA was used as a HDAC positive control.

| STRUCTURE | Speed 1 to 7 (concentration) | | | | |
| --- | --- | --- | --- | --- | --- |
| | 30 uM | 100 uM | 150 uM | 200 uM | 300 uM |
| 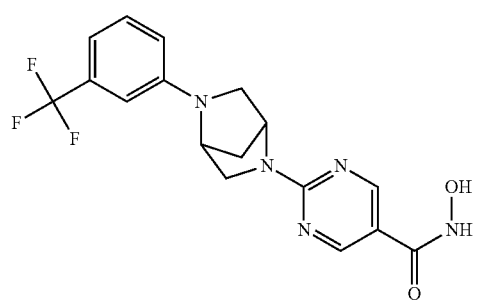 [SMILES: O=C(NO)c1cnc(N2CC3CC2CN3c2cccc(C(F)(F)F)c2)nc1] | 0.02 | 0.48 | | | 0.506 |

-continued

| Structure | | | |
|---|---|---|---|
| 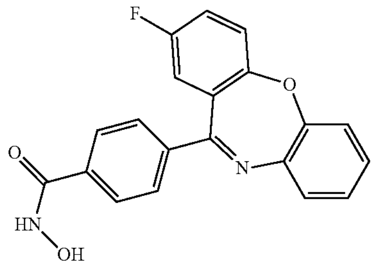 [SMILES: O=C(NO)c1ccc(C2=Nc3ccccc3Oc3ccc(F)cc32)cc1] | 0.118 | −0.004 | 0.444 |
| 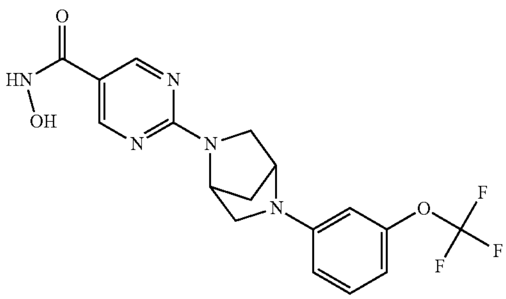 [SMILES: O=C(NO)c1cnc(N2CC3CC2CN3c2cccc(OC(F)(F)F)c2)nc1] | 0.05 | −0.01 | 0.68 |
| 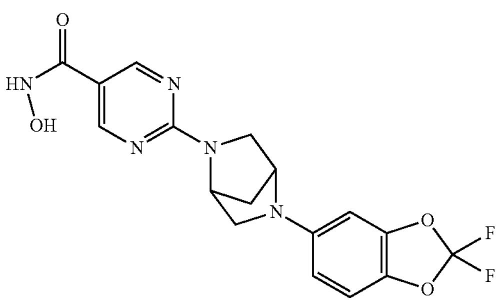 [SMILES: O=C(NO)c1cnc(N2CC3CC2CN3c2ccc3c(c2)OC(F)(F)O3)nc1] | 0.28 | 0.64 | 0.66 |
| 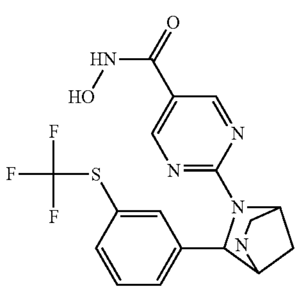 [SMILES: O=C(NO)c1cnc(N2C3CNC(C3)C2c2cccc(SC(F)(F)F)c2)nc1] | 0.63 | 0.38 | 0.03 |
| 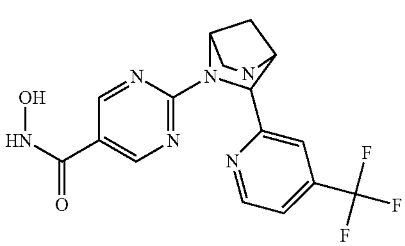 [SMILES: O=C(NO)c1cnc(N2C3CNC(C3)C2c2cc(C(F)(F)F)ccn2)nc1] | 0.468 | 0.82 | 0.3 |
| 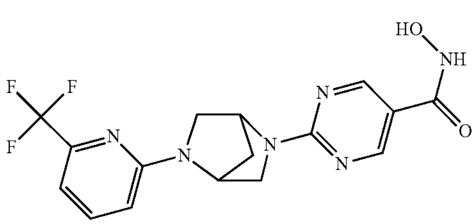 [SMILES: O=C(NO)c1cnc(N2CC3CC2CN3c2cccc(C(F)(F)F)n2)nc1] | 0.781 | 0.549 | 0.411 |

-continued
| STRUCTURE | | | |
|---|---|---|---|
| 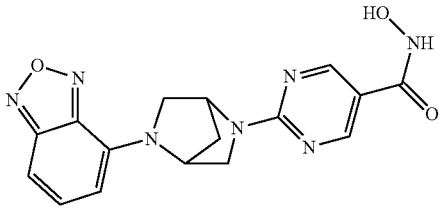 [SMILES: O=C(NO)c1cnc(N2CC3CC2CN3c2cccc3nonc23)nc1] | 0.84 | | 0.68 |
| 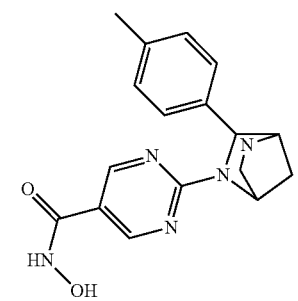 [SMILES: Cc1ccc(C2C3CC(CN3)N2c2ncc(C(=O)NO)cn2)cc1] | −0.007 | 0.046 | 0.829 |
| 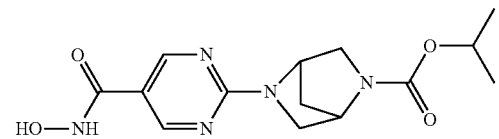 [SMILES: CC(C)OC(=O)N1CC2CC1CN2c1ncc(C(=O)NO)cn1] | 0.495 | 0.33 | −0.469 |
| 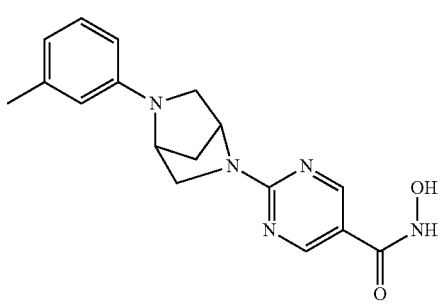 [SMILES: Cc1cccc(N2CC3CC2CN3c2ncc(C(=O)NO)cn2)c1] | 0.493 | 0.588 | 0.412 |
| | Speed 8 to 10 (concentration) | | | | |
|---|---|---|---|---|---|
| STRUCTURE | 30 uM | 100 uM | 150 uM | 200 uM | 300 uM |
| 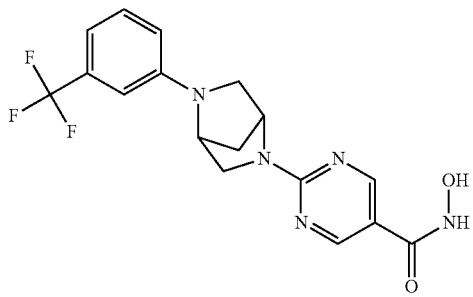 [SMILES: O=C(NO)c1cnc(N2CC3CC2CN3c2cccc(C(F)(F)F)c2)nc1] | −0.14 | 0.3 | | | −0.112 |
| 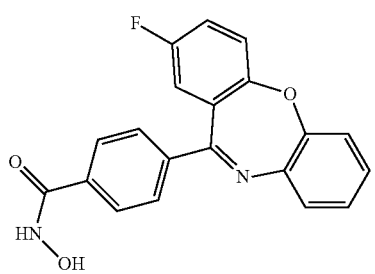 [SMILES: O=C(NO)c1ccc(C2=Nc3ccccc3Oc3ccc(F)cc32)cc1] | −0.108 | 0.139 | | | 0.47 |

-continued
| | | | |
|---|---|---|---|
| 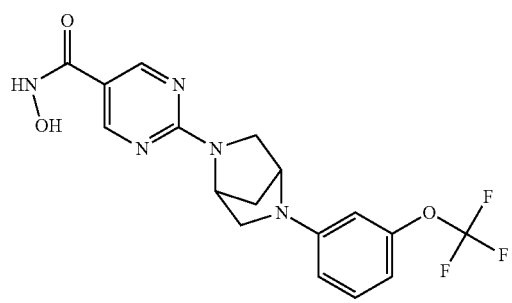 [SMILES: O=C(NO)c1cnc(N2CC3CC2CN3c2cccc(OC(F)(F)F)c2)nc1] | 0.15 | 0.16 | 0.35 |
| 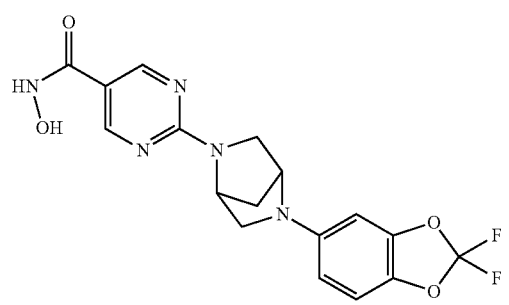 [SMILES: O=C(NO)c1cnc(N2CC3CC2CN3c2ccc3c(c2)OC(F)(F)O3)nc1] | 0.22 | 0.46 | 0.58 |
| 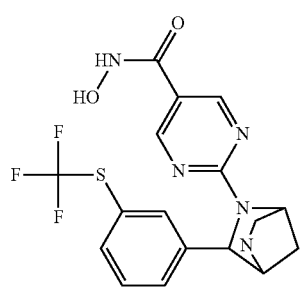 [SMILES: O=C(NO)c1cnc(N2C3CNC(C3)C2c2cccc(SC(F)(F)F)c2)nc1] | 0.28 | 0.02 | −0.29 |
| 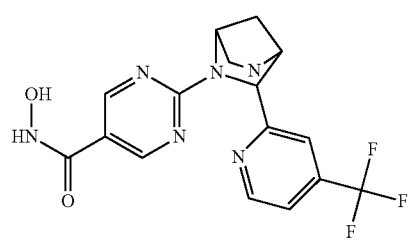 [SMILES: O=C(NO)c1cnc(N2C3CNC(C3)C2c2cc(C(F)(F)F)ccn2)nc1] | 0.087 | 0.82 | 0.54 |
| 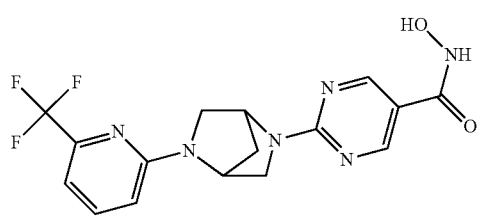 [SMILES: O=C(NO)c1cnc(N2CC3CC2CN3c2cccc(C(F)(F)F)n2)nc1] | 0.291 | 0.376 | 0.471 |
| 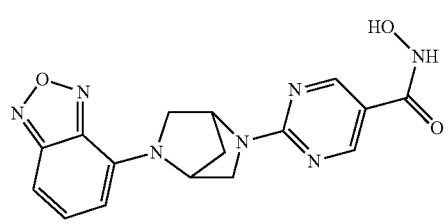 [SMILES: O=C(NO)c1cnc(N2CC3CC2CN3c2cccc3nonc23)nc1] | | 0.26 | 0.5 |

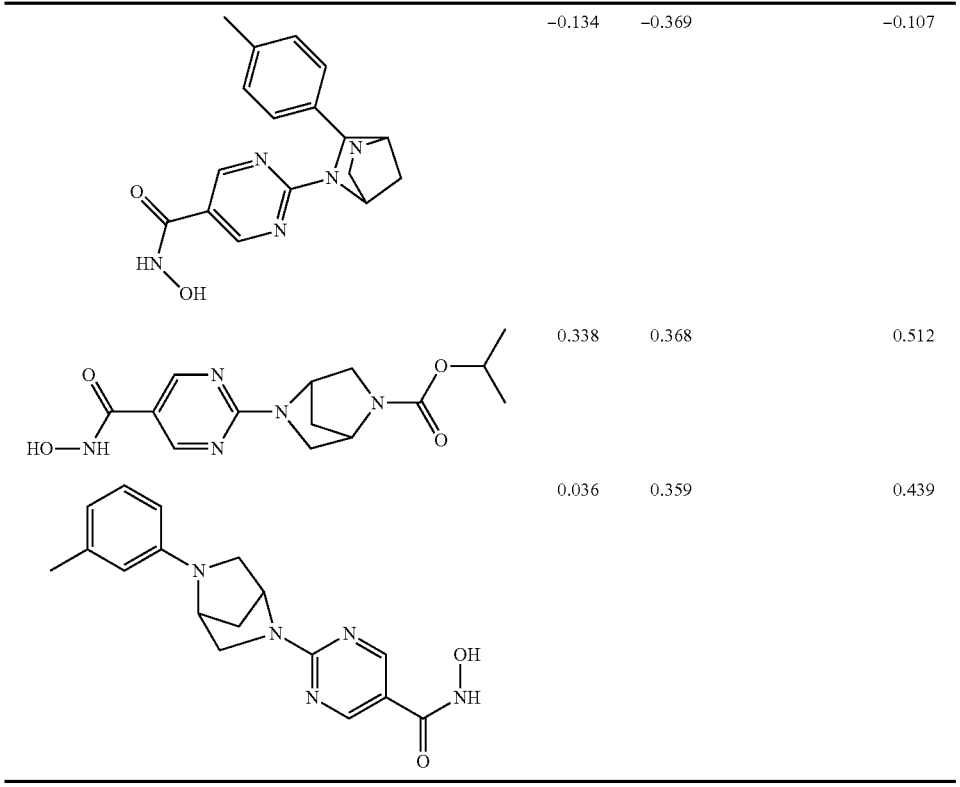

Compounds according to the present invention are able to cross the blood brain barrier in treated mice and inhibit a histone deacetylase in a cell thereacross, thereby increasing histone acetylation in the brain.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method of inhibiting histone deacetylase, comprising contacting the histone deacetylase with a pharmaceutical composition comprising:
   i) (Z)-4-(dibenzo[b,f][1,4]oxazepin-11-yl)-N-hydroxybenzamide, or a pharmaceutically acceptable salt thereof; and
   ii) a pharmaceutically acceptable carrier, excipient, or diluent.

2. A method of inhibiting histone deacetylase, comprising contacting the histone deacetylase with (Z)-4-(dibenzo[b,f][1,4]oxazepin-11-yl)-N-hydroxybenzamide, or a pharmaceutically acceptable salt thereof.

* * * * *

SEQUENCE LISTING

```
<160> NUMBER OF SEQ ID NOS: 11

<210> SEQ ID NO 1
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-1

<400> SEQUENCE: 1
gaaacgtgag ggactcagca                                              20

<210> SEQ ID NO 2
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-1

<400> SEQUENCE: 2
ggaagccaga gctggagagg                                              20
```

<210> SEQ ID NO 3
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-2

<400> SEQUENCE: 3
gctgagctgt tctgatttgg                                                   20

<210> SEQ ID NO 4
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-3

<400> SEQUENCE: 4
cgctttcctt gtcattgaca                                                   20

<210> SEQ ID NO 5
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-4

<400> SEQUENCE: 5
gctgcctgcc gtgcccaccc                                                   20

<210> SEQ ID NO 6
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-4

<400> SEQUENCE: 6
tacagtccat gcaacctcca                                                   20

<210> SEQ ID NO 7
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-5

<400> SEQUENCE: 7
cttcggtctc acctgcttgg                                                   20

<210> SEQ ID NO 8
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-6

<400> SEQUENCE: 8
caggctggaa tgagctacag                                                   20

```
<210> SEQ ID NO 9
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-7

<400> SEQUENCE: 9
cttcagccag gatgcccaca                                                    20

<210> SEQ ID NO 10
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-8

<400> SEQUENCE: 10
ctccggctcc tccatcttcc                                                    20

<210> SEQ ID NO 11
<211> LENGTH: 20
<212> TYPE: DNA
<213> ORGANISM: Artificial
<220> FEATURE:
<223> OTHER INFORMATION: Synthetic; antisense oligonucleotide targeted
      to human HDAC-8

<400> SEQUENCE: 11
agccagctgc cacttgatgc                                                    20
```